United States Patent
Maynard et al.

(10) Patent No.: US 6,423,704 B2
(45) Date of Patent: *Jul. 23, 2002

(54) SUBSTITUTED 4-(1H-BENZIMIDAZOL-2-YL) [1,4]DIAZEPANES USEFUL FOR THE TREATMENT OF ALLERGIC DISEASES

(75) Inventors: George D. Maynard, Clinton, CT (US); Tieu-Binh Le, Bridgewater, NJ (US)

(73) Assignee: Aventis Pharmaceuticals Inc., Bridgewater, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 09/739,741

(22) Filed: Dec. 18, 2000

Related U.S. Application Data

(63) Continuation-in-part of application No. 09/513,847, filed on Oct. 29, 1997, now Pat. No. 6,194,406, which is a continuation-in-part of application No. 08/736,411, filed on Oct. 24, 1996, now abandoned.
(60) Provisional application No. 60/070,907, filed on Dec. 20, 1995.

(51) Int. Cl.$^7$ ..................... A61K 31/551; C07D 403/14

(52) U.S. Cl. .................. 514/218; 540/575; 540/596

(58) Field of Search .................. 514/218; 540/575, 540/596

(56) References Cited

U.S. PATENT DOCUMENTS

| | | |
|---|---|---|
| 3,282,947 A | 11/1966 | Grogan |
| 3,862,173 A | 1/1975 | Carr |
| 4,254,129 A | 3/1981 | Carr |
| 4,254,130 A | 3/1981 | Carr |
| 4,285,958 A | 8/1981 | Carr |
| 4,550,116 A | 10/1985 | Soto |
| 4,598,079 A | 7/1986 | Beyerle |
| 4,666,905 A | 5/1987 | Downs |
| 4,835,161 A | 5/1989 | Janssens |
| 4,908,372 A | 3/1990 | Carr |
| 4,960,776 A | 10/1990 | Walsh |
| 4,988,689 A | 1/1991 | Janssens |
| 5,023,256 A | 6/1991 | Roberto |
| 5,064,850 A | 11/1991 | Carr |
| 5,166,136 A | 11/1992 | Ward |
| 5,182,399 A | 1/1993 | Kane |
| 5,212,187 A | 5/1993 | Alisch |
| 5,214,040 A | 5/1993 | Cuberes-Altisent |
| 5,236,921 A | 8/1993 | Emonds-Alt |
| 5,272,150 A | 12/1993 | Janssens |
| 5,317,020 A | 5/1994 | Emonds-Alt |
| 5,322,850 A | 6/1994 | Orjales-Venero |
| 5,340,822 A | 8/1994 | Emonds-Alt |
| 5,371,093 A | 12/1994 | Carr |
| 5,411,971 A | 5/1995 | Emonds-Alt |
| 5,606,065 A | 2/1997 | Emonds-Alt |
| 6,194,406 B1 * | 2/2001 | Kane et al. ................. 514/218 |

FOREIGN PATENT DOCUMENTS

| | | |
|---|---|---|
| AU | 1591692 | 5/1991 |
| AU | 1490995 | 9/1995 |
| DE | 2601262 | 7/1976 |
| EP | 0145037 | 6/1985 |
| EP | 0184257 | 6/1986 |
| EP | 0282133 | 9/1988 |
| EP | 0378254 | 7/1990 |
| EP | 0428434 | 11/1990 |
| EP | 0512902 | 5/1991 |
| EP | 0482539 | 10/1991 |
| EP | 0464927 | 1/1992 |
| EP | 0533344 | 8/1992 |
| EP | 0559538 | 3/1993 |
| EP | 0699668 | 5/1994 |
| EP | 0714891 | 11/1995 |
| FR | 0517589 | 6/1991 |
| JP | 4297492 | 2/1991 |
| WO | 9300330 | 1/1973 |

(List continued on next page.)

OTHER PUBLICATIONS

Barnes, et al., TIPS 11:185–189 (5/90).
Ichinose, et al., The Lancet 340:1248–1251 (Nov. 21, 1992).
Hagiwara, et al., "Studies on Neurokinin Antagonists 2.", Journal of Medicinal Chemistry, vol. 35, No. 17, 3184–3191, 1992.
Hagiwara, et al., Studies on Neurokinin Antagonists 1., J. Med. Chem. 35, 2015–2025, 1992.
Janssens, et al., J. Med. Chem. 28:1934–1943, (1985).
Janssens, et al., Drug Development Research 8:27–36, (1986).
Jannssens, et al., J. Med. Chem.,28(12):1925–1933, (1985).
Iemura, et al., Chem. Pharm. Bull., 37(4):967–972, (1989).

(List continued on next page.)

*Primary Examiner*—Charanjit S. Aulakh
(74) *Attorney, Agent, or Firm*—Julie Anne Knight; Lawrence L. Martin

(57) ABSTRACT

The present invention relates to novel 4-(1H-benzimidazol-2-yl)[1,4]diazepane derivatives of formula (1):

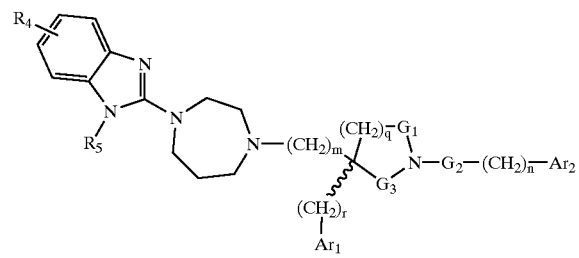

formula (1)

and stereoisomers thereof, and pharmaceutically acceptable salts thereof which are useful as histamine receptor antagonists and tachykinin receptor antagonist. Such antagonists are useful in the treatment of allergic rhinitis, including seasonal rhinitis and sinusitis; inflammatory bowel diseases, including Crohn's disease and ulcerative colitis; asthma; bronchitis; and emesis.

27 Claims, No Drawings

FOREIGN PATENT DOCUMENTS

| | | |
|---|---|---|
| WO | 9206086 | 10/1990 |
| WO | 9222569 | 6/1991 |
| WO | 9314113 | 1/1992 |
| WO | 9201687 | 2/1992 |
| WO | 9201697 | 2/1992 |
| WO | 9407495 | 4/1994 |
| WO | 9426735 | 11/1994 |
| WO | 9606094 | 2/1996 |
| WO | 9719074 | 5/1997 |
| WO | 9722604 | 6/1997 |
| WO | 9730989 | 8/1997 |
| WO | 9730990 | 8/1997 |
| WO | 9730991 | 8/1997 |

OTHER PUBLICATIONS

Janssens, et al., J. Med. Chem., 28(12):1943–1947, (1985).
Carr et al., The J. Organic Chem., 55(4):1399–1401, (1990).
Iemura, et al., Chem. Pharm. Bull., 37(4):962–966, (1989).
Maynard, Biorganic and Medicinal Chemistry Letters, vol. 3 (4), 753–756, 1993.
Wahlgren, J. Heterocyclic Chem., 26, 541–543, 1989.
Iemura, Chem. Pharm. Bull., 37(4), 967–972, 1989.
Iemura, J. Heterocyclic Che., 24, 31–37, 1987.
Daijiro Hagiwara et. al., "Design of a Novel Dipeptide Substance P Antagoinst FK888 and Its PharmacologicalProfile", Fujisawa Pharmacetucial Co., Ltd.
Iemura, et al., J. Med. Chem., 29(7):1178–1183, (1986).
Hagiwara, et al., Studies on Neurokinin Antagonists 3., J. Med. Chem, 36, 2266–2278, 1993.
Emonds–Alt, et al., Life Sciences, 56(1):27–32, (1995).
Melloni, et al., Eur. J. Med. Chem., 26, 207–213 (1991).
Kucharczyk, et al., J. Med. Chem., 36.1654–1661 (1993).

* cited by examiner

SUBSTITUTED 4-(1H-BENZIMIDAZOL-2-YL)[1,4]DIAZEPANES USEFUL FOR THE TREATMENT OF ALLERGIC DISEASES

This application is a continuation-in-part of U.S. application Ser. No. 09/513,847, filed Oct. 29, 1997, now U.S. Pat No. 6,194,406, which is a continuation-in-part of U.S. application Ser. No. 08/736,411, filed Oct. 24, 1996, now abandoned, which claims the benefit of U.S. Provisional application serial No. 60/070,907, filed Dec. 20, 1995.

The present invention relates to novel substituted 4-(1H-benzimidazol-2-yl)[1,4]diazepane derivatives (herein referred to as a compound or compounds of formula (1)) and their use as histamine receptor antagonists and tachykinin receptor antagonists. Such antagonists are useful in the treatment of asthma; bronchitis; inflammatory bowel diseases, including Crohn's disease and ulcerative colitis; allergic rhinitis, including seasonal rhinitis and sinusitis; allergies; and emesis.

The compounds of the present invention are useful in their pharmacological activities, such as histamine receptor antagonism and tachykinin receptor antagonism. Antagonism of histamine responses can be elicited through blocking of histamine receptors. Antagonism of tachykinin responses can be elicited through blocking of tachykinin receptors. One object of the present invention is to provide new and useful antagonists of histamine. A further object of the present invention is to provide new and useful antagonists of tachykinins. A particular object of the present invention are those compounds that exhibit both histamine and tachykinin receptor antagonism.

SUMMARY OF THE INVENTION

The present invention provides novel substituted 4-(1H-benzimidazol-2-yl)[1,4]diazepane derivatives of the formula:

formula (1)

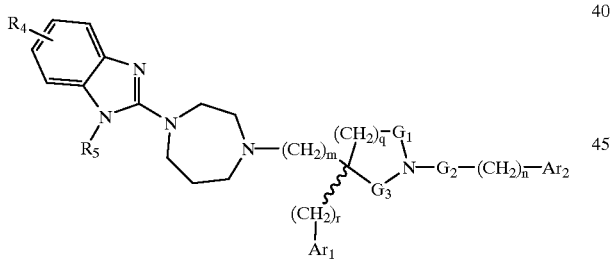

wherein
m is 2 or 3;
n is 0 or 1;
q is 1 or 2;
r is 0 or 1;
$G_1$ is —$CH_2$— or —C(O)—;
$G_2$ is —$CH_2$—, —CH($CH_3$)— or —C(O)—;
$G_3$ is —$CH_2$— or —C(O)—;
$Ar_1$ is a radical chosen from the group consisting of

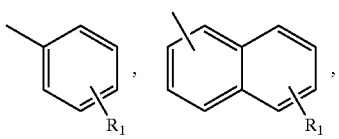

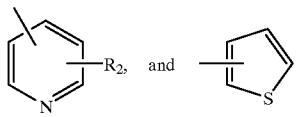

wherein
$R_1$ is from 1 to 3 substituents each independently chosen from the group consisting of hydrogen, halogen, hydroxy, —$CF_3$, $C_1$–$C_6$ alkyl, and $C_1$–$C_6$ alkoxy;
$R_2$ is from 1 to 2 substituents each independently chosen from the group consisting of hydrogen, halogen, $C_1$–$C_6$ alkyl, and $C_1$–$C_6$ alkoxy;
$Ar_2$ is a radical selected from the group consisting of

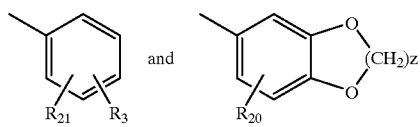

wherein
z is 1 or 2;
$R_{20}$ is from 1 to 2 substituents each independently chosen from the group consisting of hydrogen, hydroxy, halogen, $C_1$–$C_6$ alkyl, and $C_1$–$C_6$ alkoxy;
$R_3$ is from 1 to 3 substituents each independently chosen from the group consisting of hydrogen, hydroxy, halogen, —$OCF_3$, $C_1$–$C_6$ alkyl, $C_1$–$C_6$ alkoxy, —$(CH_2)_dS(O)_bR_{22}$, —$(CH_2)_eCN$, —$O(CH_2)_cCO_2R_{23}$, —$NH_2$, —NHC(O)$CH_3$, —NHSO$_2$CH$_3$ wherein c is an integer from 1 to 5; b is 0, 1, or 2; d is 0 or 1; e is 0 or 1; $R_{22}$ is $C_1$–$C_4$ alkyl; and $R_{23}$ is hydrogen or $C_1$–$C_4$ alkyl;
$R_{21}$ is hydrogen or a radical chosen from the group consisting of

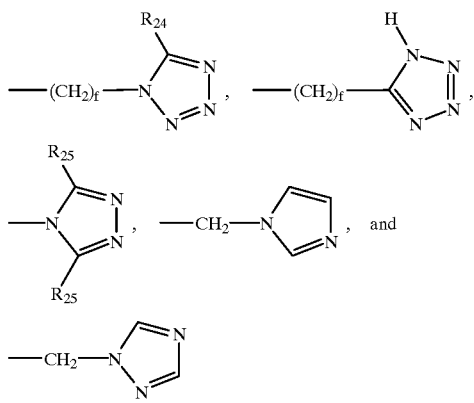

wherein
f is 0 or 1;
$R_{25}$ is hydrogen or —$CH_3$;
$R_{24}$ is selected from the group consisting of hydrogen, $C_1$–$C_4$ alkyl, —$CF_3$, phenyl, S(O)$_x$R$_{26}$, and $CH_2$N($CH_3$)$_2$ wherein x is 0, 1, or 2; $R_{26}$ is $C_1$–$C_4$ alkyl;
$R_4$ is from 1 to 2 substituents each independently chosen from the group consisting of hydrogen, halogen, —$CF_3$, $C_1$–$C_6$ alkyl, and $C_1$–$C_6$ alkoxy;
$R_5$ is chosen from the group consisting of hydrogen, $C_1$–$C_4$ alkyl, —$(CH_2)_w$—O—$(CH_2)_tCO_2R_8$, —$(CH_2)_jCN$, —$(CH_2)_uCO_2R_6$, —$(CH_2)_uC(O)NR_{16}R_{17}$, —$(CH_2)_uC(O)$
$CH_3$, —$(CH_2)_pAr_3$, —$(CH_2)_w$—O—$R_7$,
—$CH_2CH=CHCF_3$, —$(CH_2)_2CH=CH_2$,
—$CH_2CH=CH_2$, —$CH_2CH=CHCH_3$,
—$CH_2CH=CHCH_2CH_3$, —$CH_2CH=C(CH_3)_2$, and
—$(CH_2)_gS(O)_kR_{19}$, wherein
w is an integer from 2 to 5;
t is an integer from 1 to 3;
j is an integer from 1 to 5;
u is an integer from 1 to 5;
p is an integer from 1 to 4;
g is 2 or 3;
k is 0, 1, or 2;
$R_8$ is hydrogen or $C_1$–$C_4$ alkyl;
$R_6$ is hydrogen or $C_1$–$C_4$ alkyl;
$R_{16}$ is hydrogen or $C_1$–$C_4$ alkyl;
$R_{17}$ is hydrogen or $C_1$–$C_4$ alkyl;
$R_{19}$ is $C_1$–$C_4$ alkyl or a radical of the formula

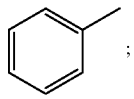

$Ar_3$ is a radical chosen from the group consisting of

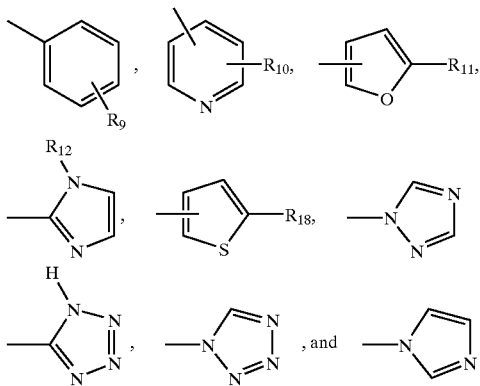

wherein
$R_9$ is from 1 to 3 substituents each independently chosen from the group consisting of hydrogen, halogen, —$CF_3$, $C_1$–$C_6$ alkyl, $C_1$–$C_6$ alkoxy, and —$CO_2R_{13}$ wherein $R_{13}$ is chosen from the group consisting of hydrogen and $C_1$–$C_4$ alkyl;
$R_{10}$ is from 1 to 2 substituents each independently chosen from the group consisting of hydrogen, halogen, $C_1$–$C_6$ alkyl, and $C_1$–$C_6$ alkoxy;
$R_{11}$ is chosen from the group consisting of hydrogen, —$CH_3$, and —$CH_2OH$;
$R_{12}$ is chosen from the group consisting of hydrogen, $C_1$–$C_4$ alkyl, and benzyl;
$R_{18}$ is chosen from the group consisting of hydrogen, halogen, —$CH_3$, and —$CH_2OH$;
$R_7$ is hydrogen, $C_1$–$C_4$ alkyl, —$(CH_2)_y$—$CF_3$, —$CH_2CN$ or a radical chosen from the group consisting of

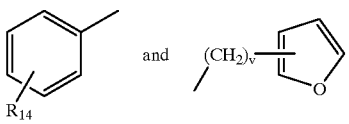

wherein
v is an integer from 1 to 3;
y is an integer from 0 to 2;
$R_{14}$ is chosen from the group consisting of hydrogen, halogen, $C_1$–$C_4$ alkyl, and. —$CO_2R_{15}$ wherein $R_{15}$ is hydrogen or $C_1$–$C_4$ alkyl;
provided that when $G_1$ is —C(O)— then $G_2$ is either —$CH_2$— or —$CH(CH_3)$— and $G_3$ is —$CH_2$—;
further provided that when $G_2$ is —C(O)— then $G_1$ is —$CH_2$— and $G_3$ is —$CH_2$—;
still further provided that when $G_3$ is —C(O)— then $G_1$ is —$CH_2$— and $G_2$ is either —$CH_2$— or —$CH(CH_3)$—;
or stereoisomers, or pharmaceutically acceptable salts thereof.

As is appreciated by one of ordinary skill in the art the compounds of the formula (1) may exist as stereoisomers depending on the nature of the substituents present. Any reference in this application to one of the compounds of the formula (1) is meant to encompass either specific stereoisomers or a mixture of stereoisomers. Where indicated, the compounds follow the designation of (+)- and (−)- or (R)- and (S)- or (E)- and (Z)- for the stereochemistry of compounds represented by formula (1). It is specifically recognized that in the substituted 3-aryl-3-((1H-benzimidazol-2-yl)[1,4]diazepan-1-yl)alkyl)pyrrolidines, substituted 3-arylmethyl-3-((1H-benzimidazol-2-yl)[1,4]diazepan-1-yl) alkyl)pyrrolidines, substituted 3-aryl-3-((1H-benzimidazol-2-yl)[1,4]diazepan-1-yl)alkyl)piperidines, and substituted 3-arylmethyl-3-((1H-benzimidazol-2-yl)[1,4]diazepan-1-yl) alkyl)piperidines; the 3-position of the pyrrolidine or piperidine is asymmetric, and may be in the (R)- or (S)-configuration, or may be a mixture thereof. It is specifically recognized that compounds of formula (1) in which $G_2$ is —$CH(CH_3)$— are asymetric at the methyl bearing carbon and may be in the (R)- or (S)-configuration, or may be a mixture thereof. It is specifically recognized that compounds of formula (1) in which $R_5$ is —$CH_2CH=CHCF_3$, —$CH_2CH=CHCH_3$, and —$CH_2CH=CHCH_2CH_3$ may exist as stereoisomers and may be in the (E)- or (Z)-configuration, or may be a mixture thereof.

The specific stereoisomers can be prepared by stereospecific synthesis using enantiomerically or geometrically pure or enantiomerically or geometrically enriched starting materials. The specific stereoisomers of either starting materials or products can be resolved and recovered by techniques known in the art, such as chromatography on chiral stationary phases, enzymatic resolution, or fractional recrystallization of addition salts formed by reagents used for that purpose. Useful methods of resolving and recovering specific stereoisomers are know in the art and described in *Stereochemistry of Organic Compounds*, E. L. Eliel and S. H. Wilen, Wiley (1994) and *Enantiomers, Racemates, and Resolutions*, J. Jacques, A. Collet, and S. H. Wilen, Wiley (1981).

As is appreciated by one of ordinary skill in the art some of the compounds of the formula (1) may exist as tautomers. Any reference in this application to one of the tautomers of compounds of the formula (1) is meant to encompass every tautomeric form and mixtures thereof.

As used in this application:

a) the term "halogen" refers to a fluorine atom, chlorine atom, bromine atom, or iodine atom;
b) the term "$C_1$–$C_6$ alkyl" refers to a branched or straight chained alkyl radical containing from 1 to 6 carbon atoms, such as methyl, ethyl, n-propyl, isopropyl, n-butyl, sec-butyl, isobutyl, t-butyl, pentyl, hexyl, cyclopentyl, cyclohexyl, etc;
c) the term "$C_1$–$C_6$ alkoxy" refers to a straight or branched alkoxy group containing from 1 to 6 carbon atoms, such as methoxy, ethoxy, n-propoxy, isopropoxy, n-butoxy, isobutoxy, t-butoxy, pentoxy, hexoxy, cyclopentoxy, cyclohexoxy, etc;
d) the designations —C(O)— or —(O)C— refer to a carbonyl group of the formula:

e) the designation "⌇⌇⌇" refers to a bond for which the stereochemistry is not designated;
f) as used in the examples and preparations, the following terms have the meanings indicated: "kg" refers to kilograms, "g" refers to grams, "mg" refers to milligrams, "$\mu$g" refers to micrograms, "mol" refers to moles, "mmol" refers to millimoles, "nmole" refers to nanomoles, "L" refers to liters, "mL" or "ml" refers to milliliters, "$\mu$L" refers to microliters, "° C." refers to degrees Celsius, "$R_f$" refers to retention factor, "mp" refers to melting point, "dec" refers to decomposition, "bp" refers to boiling point, "mm of Hg" refers to pressure in millimeters of mercury, "cm" refers to centimeters, "nm" refers to nanometers, "$[\alpha]^{20}_D$" refers to specific rotation of the D line of sodium at 20° C. obtained in a 1 decimeter cell, "c" refers to concentration in g/mL, "THF" refers to tetrahydrofuran, "DMF" refers to dimethylformamide, "brine" refers to a saturated aqueous sodium chloride solution, "M" refers to molar, "mM" refers to millimolar, "$\mu$M" refers to micromolar, "nM" refers to nanomolar, "psi" refers to pounds per square inch, "TLC" refers to thin layer chromatography, "HPLC" refers to high performance liquid chromatography, "HRMS" refers to high resolution mass spectrum, "lb" refers to pounds, "gal" refers to gallons, "L.O.D." refers to loss on drying, "$\mu$Ci" refers to microcuries, "i.p." refers to intraperitoneally, "i.v." refers to intravenously, and "DPM" refers to disintegrations per minute;
g) the designation

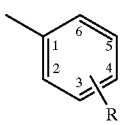

refers to a phenyl or a substituted phenyl and it is understood that the radical is attached at the 1-position and the substituent or substituents represented by R can be attached in any of the 2, 3, 4, 5, or 6 positions;

h) the designation

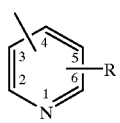

refers to a pyridine, substituted pyridine, pyridyl or substituted pyridyl and it is understood that the radical can be attached at either the 2-position, the 3-position, or the 4-position, it is further understood that when the radical is attached at the 2-position the substituent or substituents represented by R can be attached in any of the 3, 4, 5, or 6 positions, that when the radical is attached at the 3-position the substituent or substituents represented by R can be attached in any of the 2, 4, 5, or 6 positions, and that when the radical is attached at the 4-position the substituent or substituents represented by R can be attached in any of the 2, 3, 5, or 6 positions;
i) the designation

refers to a thiophene or thienyl and it is understood that the radical is attached at the 2 or 3-positions;
j) the designation

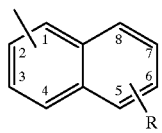

refers to a naphthalene, substituted naphthalene, naphthyl or substituted naphthyl and it is understood that the radical can be attached at either the 1-position or the 2-position, it is further understood that when the radical is attached at the 1-position the substituent or substituents represented by R can be attached in any of the 2, 3, 4, 5, 6, 7, or 8 positions and that when the radical is attached at the 2-position the substituent or substituents represented by R can be attached in any of the 1, 3, 4, 5, 6, 7, or 8 positions:
k) the term "enantiomeric excess" or "ee" refers to the percent by which one enantiomer, E1, is in excess in a mixture of the two enantiomers, E1 plus E2, such that $$\{(E1-E2) \div (E1+E2)\} \times 100\% = ee;$$

l) the term "$C_1$–$C_4$ alkyl" refers to a saturated straight or branched chain alkyl group containing from 1–4 carbon atoms and includes methyl, ethyl, propyl, isopropyl, n-butyl, s-butyl, isobutyl, and t-butyl;
m) the designations —$CO_2R$ and —C(O)OR refer to a group of the formula:

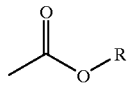

n) the designation —C(O)NRR refer to a group of the formula:

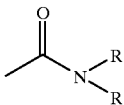

o) the designation

refers to a furan or furyl and it is understood that the radical is attached at either the 2-position or 3-position;
p) the designation "▶━" refers to a bond that protrudes forward out of the plane of the page;
q) the designation "⦀⦀⦀" refers to a bond that protrudes backward out of the plane of the page;
r) the term "pharmaceutically acceptable salts thereof" refers to either an acid addition salt or a basic addition salt.

The expression "pharmaceutically acceptable acid addition salts" is intended to apply to any non-toxic organic or inorganic acid addition salt of the base compounds represented by formula (1) or any of its intermediates. Illustrative inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids which form suitable salts include the mono-, di-, and tricarboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicyclic, 2-phenoxybenzoic, p-toluenesulfonic acid, and sulfonic acids such as methane sulfonic acid and 2-hydroxyethane sulfonic acid. Such salts can exist in either a hydrated or substantially anhydrous form. In general, the acid addition salts of these compounds are soluble in water and various hydrophilic organic solvents, and which in comparison to their free base forms, generally demonstrate higher melting points.

The expression "pharmaceutically acceptable basic addition salts" is intended to apply to any non-toxic organic or inorganic basic addition salts of the compounds represented by formula (1) or any of its intermediates. Illustrative bases which form suitable salts include alkali metal or alkaline-earth metal hydroxides such as sodium, potassium, calcium, magnesium, or barium hydroxides; ammonia, and aliphatic, alicyclic, or aromatic organic amines such as methylamine, dimethylamine, trimethylamine, and picoline.

Preferred embodiments of formula (1) are given below:
1) Compounds wherein q is 1 are preferred;
2) Compounds wherein r is 0 are preferred;
3) Compounds wherein m is 2 are preferred;
4) Compounds wherein $G_1$ is —$CH_2$— are preferred;
5) Compounds wherein $G_2$ is —C(O)— are preferred;
6) Compounds wherein $R_5$ is —$(CH_2)_w$—O—$R_7$ are preferred;
7) Compounds wherein $R_5$ is —$(CH_2)_p Ar_3$ are preferred.

It is understood that further preferred embodiments of formula (1) can be selected by requiring one or more of the preferred embodiments 1 through 7 of formula (1) or by reference to examples given herein.

Examples of compounds encompassed by the present invention include the following. It is understood that the examples encompass the specific stereoisomers and diastereomers, where applicable, of the compound and mixtures thereof. This list is meant to be representative only and is not intended to limit the scope of the invention in any way:

1-(3,4,5-Trimethoxybenzoyl)-3-(2-(4-(1-(2-ethoxyethyl)-1H-benzimidazol-2-yl)[1,4]diazepan-1-yl)ethyl)-3-(3,4-dimethoxyphenyl)pyrrolidine;
1-(3,4,5-Trimethoxybenzoyl)-3-(2-(4-(1-(2-ethoxyethyl)-1H-benzimidazol-2-yl)[1,4]diazepan-1-yl)ethyl)-3-phenylpyrrolidine;
1-(3,4,5-Trimethoxybenzoyl)-3-(2-(4-(1-(2-ethoxyethyl)-1H-benzimidazol-2-yl)[1,4]diazepan-1-yl)ethyl)-3-(3,4-dichlorophenyl)pyrrolidine;
1-(3,4,5-Trimethoxybenzoyl)-3-(2-(4-(1-(2-ethoxyethyl)-1H-benzimidazol-2-yl)[1,4]diazepan-1-yl)ethyl)-3-(3-chlorophenyl)pyrrolidine;
1-(3,4,5-Trimethoxybenzoyl)-3-(2-(4-(1-(2-ethoxyethyl)-1H-benzimidazol-2-yl)[1,4]diazepan-1-yl)ethyl)-3-(4-chlorophenyl)pyrrolidine;
1-(3,4,5-Trimethoxybenzoyl)-3-(2-(4-(1-(2-ethoxyethyl)-1H-benzimidazol-2-yl)[1,4]diazepan-1-yl)ethyl)-3-(3,4-difluorophenyl)pyrrolidine;
1-(3,4,5-Trimethoxybenzoyl)-3-(2-(4-(1-(2-ethoxyethyl)-1H-benzimidazol-2-yl)[1,4]diazepan-1-yl)ethyl)-3-(4-fluorophenyl)pyrrolidine;
1-(3,4,5-Trimethoxybenzoyl)-3-(2-(4-(1-(2-ethoxyethyl)-1H-benzimidazol-2-yl)[1,4]diazepan-1-yl)ethyl)-3-(4-methoxyphenyl)pyrrolidine;
1-(3,4,5-Trimethoxybenzoyl)-3-(2-(4-(1-(2-ethoxyethyl)-1H-benzimidazol-2-yl)[1,4]diazepan-1-yl)ethyl)-3-(pyrid-2-yl)pyrrolidine;
1-(3,4,5-Trimethoxybenzoyl)-3-(2-(4-(1-(2-ethoxyethyl)-1H-benzimidazol-2-yl)[1,4]diazepan-1-yl)ethyl)-3-(pyrid-3-yl)pyrrolidine;
1-(3,4,5-Trimethoxybenzoyl)-3-(2-(4-(1-(2-ethoxyethyl)-1H-benzimidazol-2-yl)[1,4]diazepan-1-yl)ethyl)-3-(pyrid-4-yl)pyrrolidine;
1-(3,4,5-Trimethoxybenzoyl)-3-(2-(4-(1-(2-cyanomethoxyethyl)-1H-benzimidazol-2-yl)[1,4]diazepan-1-yl)ethyl)-3-(3,4-dichlorophenyl)pyrrolidine;
1-(3,4,5-Trimethoxybenzoyl)-3-(2-(4-(1-(4-oxopentyl)-1H-benzimidazol-2-yl)[1,4]diazepan-1-yl)ethyl)-3-(3,4-dichlorophenyl)pyrrolidine;
1-Benzoyl-3-(2-(4-(1-(2-ethoxyethyl)-1H-benzimidazol-2-yl)[1,4]diazepan-1-yl)ethyl)-3-(3,4-dichlorophenyl)pyrrolidine;
1-Benzoyl-3-(2-(4-(1-(2-ethoxyethyl)-1H-benzimidazol-2-yl)[1,4]diazepan-1-yl)ethyl)-3-phenylpyrrolidine;
1-(3,5-Dimethoxy-4-hydroxybenzoyl)-3-(2-(4-(1-(2-ethoxyethyl)-1H-benzimidazol-2-yl)[1,4]diazepan-1-yl)ethyl)-3-(3,4-dichlorophenyl)pyrrolidine;
1-(3,4-Dimethoxy-5-hydroxybenzoyl)-3-(2-(4-(1-(2-ethoxyethyl)-1H-benzimidazol-2-yl)[1,4]diazepan-1-yl)ethyl)-3-(3,4-dichlorophenyl)pyrrolidine;
1-(2-(4-Carboxypropyl)-5-(1H-tetrazol-1-yl)benzoyl)-3-(2-(4-(1-(2-ethoxyethyl)-1H-benzimidazol-2-yl)[1,4]diazepan-1-yl)ethyl)-3-(3,4-dichlorophenyl)pyrrolidine;
1-(2-Methylthio-5-(1H-tetrazol-1-yl)benzoyl)-3-(2-(4-(1-(2-ethoxyethyl)-1H-benzimidazol-2-yl)[1,4]diazepan-1-yl)ethyl)-3-(3,4-dichlorophenyl)pyrrolidine;
1-(2-Methoxy-5-(1H-tetrazol-1-yl)benzoyl)-3-(2-(4-(1-(2-ethoxyethyl)-1H-benzimidazol-2-yl)[1,4]diazepan-1-yl)ethyl)-3-(3,4-dichlorophenyl)pyrrolidine;
1-(2-Methoxy-5-(1H-tetrazol-5-yl)benzoyl)-3-(2-(4-(1-(2-ethoxyethyl)-1H-benzimidazol-2-yl)[1,4]diazepan-1-yl)ethyl)-3-(3,4-dichlorophenyl)pyrrolidine;
1-(2-Methoxy-5-(1H-tetrazol-5-yl)benzoyl)-3-(2-(4-(1-(2-ethoxyethyl)-1H-benzimidazol-2-yl)[1,4]diazeparn-1-yl)ethyl)-3-phenylpyrrolidine;

1-(3-(1H-Tetrazol-1-yl)benzoyl)-3-(2-(4-(1-(2-ethoxyethyl)-1H-benzimidazol-2-yl)[1,4]diazepan-1-yl)ethyl)-3-(3,4-dichlorophenyl)pyrrolidine;

1-(2-Methoxy-5-(5-methylsulfonyltetrazol-1-yl)benzoyl)-3-(2-(4-(1-(2-ethoxyethyl)-1H-benzimidazol-2-yl)[1,4]diazepan-1-yl)ethyl)-3-(3,4-dichlorophenyl)pyrrolidine;

1-(2-Methoxy-5-(5-trifluormethyl-1H-tetrazol-1-yl)benzoyl)-3-(2-(4-(1-(2-ethoxyethyl)-1H-benzimidazol-2-yl)[1,4]diazepan-1-yl)ethyl)-3-(3,4-dichlorophenyl)pyrrolidine 1-(2-Methoxy-5-(5-N,N-dimethylaminomethyl-1H-tetrazol-1-yl)benzoyl)-3-(2-(4-(1-(2-ethoxyethyl)-1H-benzimidazol-2-yl)[1,4]diazepan-1-yl)ethyl)-3-(3,4-dichlorophenyl)pyrrolidine;

1-(2-Methyl-5-(1H-tetrazol-1-yl)benzoyl)-3-(2-(4-(1-(2-ethoxyethyl)-1H-benzimidazol-2-yl)[1,4]diazepan-1-yl)ethyl)-3-(3,4-dichlorophenyl)pyrrolidine;

1-(2-Methoxy-5-(4H-triazol-1-yl)benzoyl)-3-(2-(4-(1-(2-ethoxyethyl)-1H-benzimidazol-2-yl)[1,4]diazepan-1-yl)ethyl)-3-(3,4-dichlorophenyl)pyrrolidine;

1-(2-Methoxy-5-(3,5-dimethyl-4H-triazol-1-yl)benzoyl)-3-(2-(4-(1-(2-ethoxyethyl)-1H-benzimidazol-2-yl)[1,4]diazepan-1-yl)ethyl)-3-(3,4-dichlorophenyl)pyrrolidine;

1-(2-Methoxy-5-methylthiobenzoyl)-3-(2-(4-(1-(2-ethoxyethyl)-1H-benzimidazol-2-yl)[1,4]diazepan-1-yl)ethyl)-3-(3,4-dichlorophenyl)pyrrolidine 1-(3-Methoxy-4,5-methylenedioxybenzoyl)-3-(2-(4-(1-(2-ethoxyethyl)-1H-benzimidazol-2-yl)[1,4]diazepan-1-yl)ethyl)-3-(3,4-dichlorophenyl)pyrrolidine;

1-(3-Methoxy-4,5-ethylenedioxybenzoyl)-3-(2-(4-(1-(2-ethoxyethyl)-1H-benzimidazol-2-yl)[1,4]diazepan-1-yl)ethyl)-3-(3,4-dichlorophenyl)pyrrolidine;

1-(3,4,5-Trimethoxybenzoyl)-3-(2-(4-(1-(4-cyanobutyl)-1H-benzimidazol-2-yl)[1,4]diazepan-1-yl)ethyl)-3-(3,4-dichlorophenyl)pyrrolidine;

1-(3,4,5-Trimethoxybenzoyl)-3-(2-(4-(1-(4-(1H-tetrazol-5-yl)butyl)-1H-benzimidazol-2-yl)[1,4]diazepan-1-yl)ethyl)-3-(3,4-dichlorophenyl)pyrrolidine;

1-(2-Methoxy-5-trifluormethylbenzoyl)-3-(2-(4-(1-(2-ethoxyethyl)-1H-benzimidazol-2-yl)[1,4]diazepan-1-yl)ethyl)-3-(3,4-dichlorophenyl)pyrrolidine;

1-(2-Methoxy-5-methylsulfonamidobenzoyl)-3-(2-(4-(1-(2-ethoxyethyl)-1H-benzimidazol-2-yl)[1,4]diazepan-1-yl)ethyl)-3-(3,4-dichlorophenyl)pyrrolidine;

1-(-Methylbenzyl)-3-(2-(4-(1-(2-ethoxyethyl)-1H-benzimidazol-2-yl)[1,4]diazepan-1-yl)ethyl)-3-(3,4-dichlorophenyl)pyrrolidine;

1-(2-Methoxy-5-(methylthiomethyl)benzoyl)-3-(2-(4-(1-(2-ethoxyethyl)-1H-benzimidazol-2-yl)[1,4]diazepan-1-yl)ethyl)-3-(3,4-dichlorophenyl)pyrrolidine;

1-(2-Methoxy-5-(cyanomethyl)benzoyl)-3-(2-(4-(1-(2-ethoxyethyl)-1H-benzimidazol-2-yl)[1,4]diazepan-1-yl)ethyl)-3-(3,4-dichlorophenyl)pyrrolidine;

1-(2-Methoxy-5-(1H-tetrazol-1-ylmethyl)benzoyl)-3-(2-(4-(1-(2-ethoxyethyl)-1H-benzimidazol-2-yl)[1,4]diazepan-1-yl)ethyl)-3-(3,4-dichlorophenyl)pyrrolidine;

1-(2-Methoxy-5-(1H-triazol-1-ylmethyl)benzoyl)-3-(2-(4-(1-(2-ethoxyethyl)-1H-benzimidazol-2-yl)[1,4]diazepan-1-yl)ethyl)-3-(3,4-dichlorophenyl)pyrrolidine;

1-(2-Methoxy-5-fluorobenzoyl)-3-(2-(4-(1-(2-ethoxyethyl)-1H-benzimidazol-2-yl)[1,4]diazepan-1-yl)ethyl)-3-(3,4-dichlorophenyl)pyrrolidine;

1-(2-Methoxy-5-acetamidobenzoyl)-3-(2-(4-(1-(2-ethoxyethyl)-1H-benzimidazol-2-yl)[1,4]diazepan-1-yl)ethyl)-3-(3,4-dichlorophenyl)pyrrolidine;

1-(3,4,5-Trimethoxybenzyl)-3-(2-(4-(1-(2-ethoxyethyl)-1H-benzimidazol-2-yl)[1l,4]diazepan-1-yl)ethyl)-3-(phenylmethyl)-2-oxopyrrolidine;

1-(3,4,5-Trimethoxybenzyl)-3-(2-(4-(1-(2-ethoxyethyl)-1H-benzimidazol-2-yl)[1,4]diazepan-1-yl)ethyl)-3-(4-fluorophenylmethyl)-2-oxopyrrolidine;

1-(-Methylbenzyl)-3-(2-(4-(1-(2-ethoxyethyl)-1H-benzimidazol-2-yl)[1,4]diazepan-1-yl)ethyl)-3-(4-fluorophenylmethyl)-2-oxopyrrolidine;

1-(3,4,5-Trimethoxybenzoyl)-3-(2-(4-(1-(2-hydroxyethyl)-1H-benzimidazol-2-yl)[1,4]diazepan-1-yl)ethyl)-3-phenylpyrrolidine;

1-(3,4,5-Trimethoxybenzoyl)-3-(2-(4-(1-(2-hydroxyethyl)-1H-benzimidazol-2-yl)[1,4]diazepan-1-yl)ethyl)-3-(3,4-dichlororphenyl)pyrrolidine;

1-(3,4,5-Trimethoxybenzoyl)-3-(2-(4-(1-(2-(2,2,2-trifluoroethoxy)ethyl)-1H-benzimidazol-2-yl)[1,4]diazepan-1-yl)ethyl)-3-(3,4-dichlorophenyl)pyrrolidine;

1-(2-Methoxy-5-(1H-tetrazol-1-yl)benzoyl)-3-(2-(4-(1-(2-(2,2,2-trifluoroethoxy)ethyl)-1H-benzimidazol-2-yl)[1,4]diazepan-1-yl)ethyl)-3-(3,4-dichlorophenyl)pyrrolidine;

1-(2-Methoxy-5-(1H-tetrazol-1-yl)benzoyl)-3-(2-(4-(1-(2-(2,2,2-trifluoroethoxy)ethyl)-1H-benzimidazol-2-yl)[1,4]diazepan-1-yl)ethyl)-3-phenylpyrrolidine;

1-Benzoyl-3-(2-(4-(1-(2-(2,2,2-trifluoroethoxy)ethyl)-1H-benzimidazol-2-yl)[1,4]diazepan-1-yl)ethyl)-3-(3,4-dichlorophenyl)pyrrolidine;

1-Benzoyl-3-(2-(4-(1-(2-(2,2,2-trifluoroethoxy)ethyl)-1H-benzimidazol-2-yl)[1,4]diazepan-1-yl)ethyl)-3-phenylpyrrolidine;

1-(3,4,5-Trimethoxybenzoyl)-3-(2-(4-(1-(2-(2,2,2-trifluoroethoxy)ethyl)-1H-benzimidazol-2-yl)[1,4]diazepan-1-yl)ethyl)-3-(pyrid-3-yl)pyrrolidine;

1-(3,4,5-Trimethoxybenzoyl)-3-(2-(4-(1-(2-(2,2,2-trifluoroethoxy)ethyl)-1H-benzimidazol-2-yl)[1,4]diazepan-1-yl)ethyl)-3-(pyrid-4-yl)pyrrolidine;

1-(3,4,5-Trimethoxybenzoyl)-3-(2-(4-(1-(2-(2-propyloxy)ethyl)-1H-benzimidazol-2-yl)[1,4]diazepan-1-yl)ethyl)-3-phenylpyrrolidine;

1-(3,4,5-Trimethoxybenzoyl)-3-(2-(4-(1-(2-(2-propyloxy)ethyl)-1H-benzimidazol-2-yl)[1,4]diazepan-1-yl)ethyl)-3-(3,4-dichlorophenyl)pyrrolidine;

1-(3,4,5-Trimethoxybenzoyl)-3-(2-(4-(1-(2-oxobutyl)-1H-benzimidazol-2-yl)[1,4]diazepan-1-yl)ethyl)-3-phenylpyrrolidine;

1-(3,4,5-Trimethoxybenzoyl)-3-(2-(4-(1-(2-cyanoethyl)-1H-benzimidazol-2-yl)[1,4]diazepan-1-yl)ethyl)-3-phenylpyrrolidine;

1-(3,4,5-Trimethoxybenzoyl)-3-(2-(4-(1-(2-cyanoethyl)-1H-benzimidazol-2-yl)[1,4]diazepan-1-yl)ethyl)-3-(3,4-dichlorophenyl)pyrrolidine;

1-(2-Methoxy-5-(1H-tetrazol-1-yl)benzoyl)-3-(2-(4-(1-(2-cyanoethyl)-1H-benzimidazol-2-yl)[1,4]diazepan-1-yl)ethyl)-3 -(3,4-dichlorophenyl)pyrrolidine;

1-(2-Methoxy-5-(1H-tetrazol-1-yl)benzoyl)-3-(2-(4-(1-(2-cyanoethyl)-1H-benzimidazol-2-yl)[1,4]diazepan-1-yl)ethyl)-3 -phenylpyrrolidine;

1-Benzoyl-3-(2-(4-(1-(2-cyanoethyl)-1H-benzimidazol-2-yl)[1,4]diazepan-1-yl)ethyl)-3-(3,4-dichlorophenyl)pyrrolidine;

1-Benzoyl-3-(2-(4-(1-(2-cyanoethyl)-1H-benzimidazol-2-yl)[1,4]diazepan-1-yl)ethyl)-3-phenylpyrrolidine;

1-(3,4,5-Trimethoxybenzoyl)-3-(2-(4-(1-(2-cyanoethyl)-1H-benzimidazol-2-yl)[1,4]diazepan-1-yl)ethyl)-3-(pyrid-3-yl)pyrrolidine;

1-(3,4,5-Trimethoxybenzoyl)-3-(2-(4-(1-(2-cyanoethyl)-1H-benzimidazol-2-yl)[1,4]diazepan-1-yl)ethyl)-3-(pyrid-4-yl)pyrrolidine;

1-(3,4,5-Trimethoxybenzoyl)-3-(2-(4-(1-(2-methylsulfonylethyl)-1H-benzimidazol-2-yl)[1,4]diazepan-1-yl)ethyl)-3-(3,4-dichlorophenyl)pyrrolidine;

1-(3,4,5-Trimethoxybenzoyl)-3-(2-(4-(1-(2-ethylsulfonylethyl)-1H-benzimidazol-2-yl)[1,4]diazepan-1-yl)ethyl)-3-(3,4-dichlorophenyl)pyrrolidine;

1-(3,4,5-Trimethoxybenzoyl)-3-(2-(4-(1-(2-phenylsulfonylethyl)-1H-benzimidazol-2-yl)[1,4]diazepan-1-yl)ethyl)-3-(3,4-dichlorophenyl)pyrrolidine;

1-(3,4,5-Trimethoxybenzoyl)-3-(2-(4-(1-(2-methylsulfonylethyl)-1H-benzimidazol-2-yl)[1,4]diazepan-1-yl)ethyl)-3-phenylpyrrolidine;

1-(3,4,5-Trimethoxybenzoyl)-3-(2-(4-(1-(2-ethylsulfonylethyl)-1H-benzimidazol-2-yl)[1,4]diazepan-1-yl)ethyl)-3-phenylpyrrolidine;

1-(3,4,5-Trimethoxybenzoyl)-3-(2-(4-(1-(2-phenylsulfonylethyl)-1H-benzimidazol-2-yl)[1,4]diazepan-1-yl)ethyl)-3-phenylpyrrolidine;

1-(3,4,5-Trimethoxybenzoyl)-3-(2-(4-(1-(2-(1H-triazol-1-yl)ethyl)-1H-benzimidazol-2-yl) [1,4]diazepan-1-yl)ethyl)-3-phenylpyrrolidine;

1-(3,4,5-Trimethoxybenzoyl)-3-(2-(4-(1-(2-(1H-triazol-1-yl)ethyl)-1H-benzimidazol-2-yl)[1,4]diazepan-1-yl)ethyl)-3-(3,4-dichlorophenyl)pyrrolidine;

1-(2-Methoxy-5-(1H-tetrazol-1-yl)benzoyl)-3-(2-(4-(1-(2-(1H-triazol-1-yl)ethyl)-1H-benzimidazol-2-yl)[1,4]diazepan-1-yl)ethyl)-3-(3,4-dichlorophenyl)pyrrolidine;

1-(2-Methoxy-5-(1H-tetrazol-1-yl)benzoyl)-3-(2-(4-(1-(2-(1H-triazol-1-yl)ethyl)-1H-benzimidazol-2-yl)[1,4]diazepan-1-yl)ethyl)-3-phenylpyrrolidine;

1-Benzoyl-3-(2-(4-(1-(2-(1H-triazol-1-yl)ethyl)-1H-benzimidazol-2-yl)[1,4]diazepan-1-yl)ethyl)-3-(3,4-dichlorophenyl)pyrrolidine;

1-Benzoyl-3-(2-(4-(1-(2-(1H-triazol-1-yl)ethyl)-1H-benzimidazol-2-yl)[1,4]diazepan-1-yl)ethyl)-3-phenylpyrrolidine;

1-(3,4,5-Trimethoxybenzoyl)-3-(2-(4-(1-(2-(1H-triazol-1-yl)ethyl)-1H-benzimidazol-2-yl)[1,4]diazepan-1-yl)ethyl)-3-(pyrid-3-yl)pyrrolidine;

1-(3,4,5-Trimethoxybenzoyl)-3-(2-(4-(1-(2-(1H-triazol-1-yl)ethyl)-1H-benzimidazol-2-yl)[1,4]diazepan-1-yl)ethyl)-3-(pyrid-4-yl)pyrrolidine;

1-(3,4,5-Trimethoxybenzoyl)-3-(2-(4-(1-(2-(1H-imidazol-1-yl)ethyl)-1H-benzimidazol-2-yl)[1,4]diazepan-1-yl)ethyl)-3-phenylpyrrolidine;

1-(3,4,5-Trimethoxybenzoyl)-3-(2-(4-(1-(2-(1H-imidazol-1-yl)ethyl)-1H-benzimidazol-2-yl)[1,4]diazepan-1-yl)ethyl)-3-(3,4-dichlorophenyl)pyrrolidine;

1-(2-Methoxy-5-(1H-tetrazol-1-yl)benzoyl)-3-(2-(4-(1-(2-(1H-imidazol-1-yl)ethyl)-1H-benzimidazol-2-yl)[1,4]diazepan-1-yl)ethyl)-3-(3,4-dichlorophenyl)pyrrolidine;

1-(2-Methoxy-5-(1H-tetrazol-1-yl)benzoyl)-3-(2-(4-(1-(2-(1H-imidazol-1-yl)ethyl)-1H-benzimidazol-2-yl)[1,4]diazepan-1-yl)ethyl)-3-phenylpyrrolidine;

1-Benzoyl-3-(2-(4-(1-(2-(1H-imidazol-1-yl)ethyl)-1H-benzimidazol-2-yl)[1,4]diazepan-1-yl)ethyl)-3-(3,4-dichlorophenyl)pyrrolidine;

1-Benzoyl-3-(2-(4-(1-(2-(1H-imidazol-1-yl)ethyl)-1H-benzimidazol-2-yl)[1,4]diazepan-1-yl)ethyl)-3-phenylpyrrolidine;

1-(3,4,5-Trimethoxybenzoyl)-3-(2-(4-(1-(2-(1H-imidazol-1-yl)ethyl)-1H-benzimidazol-2-yl)[1,4]diazepan-1-yl)ethyl)-3-(pyrid-3-yl)pyrrolidine;

1-(3,4,5-Trimethoxybenzoyl)-3-(2-(4-(1-(2-(1H-imidazol-1-yl)ethyl)-1H-benzimidazol-2-yl)[1,4]diazepan-1-yl)ethyl)-3-(pyrid-4-yl)pyrrolidine;

1-(3,4,5-Trimethoxybenzoyl)-3-(2-(4-(1-(2-(1H-tetrazol-1-yl)ethyl)-1H-benzimidazol-2-yl)[1,4]diazepan-1-yl)ethyl)-3-phenylpyrrolidine;

1-(3,4,5-Trimethoxybenzoyl)-3-(2-(4-(1-(2-(1H-tetrazol-1-yl)ethyl)-1H-benzimidazol-2-yl)[1,4]diazepan-1-yl)ethyl)-3-(3,4-dichorophenyl)pyrrolidine;

1-(2-Methoxy-5-(1H-tetrazol-1-yl)benzoyl)-3-(2-(4-(1-(2-(1H-tetrazol-1-yl)ethyl)-1H-benzimidazol-2-yl)[1,4]diazepan-1-yl)ethyl)-3-(3,4-dichlorophenyl)pyrrolidine;

1-(2-Methoxy-5-(1H-tetrazol-1-yl)benzoyl)-3-(2-(4-(1-(2-(1H-tetrazol-1-yl)ethyl)-1H-benzimidazol-2-yl)[1,4]diazepan-1-yl)ethyl)-3-phenylpyrrolidine;

1-Benzoyl-3-(2-(4-(1-(2-(1H-tetrazol-1-yl)ethyl)-1H-benzimidazol-2-yl)[1,4]diazepan-1-yl)ethyl)-3-(3,4-dichlorophenyl)pyrrolidine;

1-Benzoyl-3-(2-(4-(1-(2-(1H-tetrazol-1-yl)ethyl)-1H-benzimidazol-2-yl)[1,4]diazepan-1-yl)ethyl)-3-phenylpyrrolidine;

1-(3,4,5-Trimethoxybenzoyl)-3-(2-(4-(1-(2-(1H-tetrazol-1-yl)ethyl)-1H-benzimidazol-2-yl)[1,4]diazepan-1-yl)ethyl)-3-(pyrid-3-yl)pyrrolidine;

1-(3,4,5-Trimethoxybenzoyl)-3-(2-(4-(1-(2-(1H-tetrazol-1-yl)ethyl)-1H-benzimidazol-2-yl)[1,4]diazepan-1-yl)ethyl)-3-(pyrid-4-yl)pyrrolidine;

1-(3,4,5-Trimethoxybenzoyl)-3-(2-(4-(1-(2-(1H-tetrazol-5-yl)ethyl)-1H-benzimidazol-2-yl)[1,4]diazepan-1-yl)ethyl)-3-phenylpyrrolidine;

1-(3,4,5-Trimethoxybenzoyl)-3-(2-(4-(1-(2-(1H-tetrazol-5-yl)ethyl)-1H-benzimidazol-2-yl)[1,4]diazepan-1-yl)ethyl)-3-(3,4-dichlorophenyl)pyrrolidine;

1-(2-Methoxy-5-(1H-tetrazol-1-yl)benzoyl)-3-(2-(4-(1-(2-(1H-tetrazol-5-yl)ethyl)-1H-benzimidazol-2-yl)[1,4]diazepan-1-yl)ethyl)-3-(3,4-dichlorophenyl)pyrrolidine;

1-(2-Methoxy-5-(1H-tetrazol-1-yl)benzoyl)-3-(2-(4-(1-(2-(1H-tetrazol-5-yl)ethyl)-1H-benzimidazol-2-yl)[1,4]diazepan-1-yl)ethyl)-3-phenylpyrrolidine;

1-Benzoyl-3-(2-(4-(1-(2-(1H-tetrazol-5-yl)ethyl)-1H-benzimidazol-2-yl)[1,4]diazepan-1-yl)ethyl)-3-(3,4-dichlorophenyl)pyrrolidine;

1-Benzoyl-3-(2-(4-(1-(2-(1H-tetrazol-5-yl)ethyl)-1H-benzimidazol-2-yl)[1,4]diazepan-1-yl)ethyl)-3-phenylpyrrolidine;

1-(3,4,5-Trimethoxybenzoyl)-3-(2-(4-(1-(2-(1H-tetrazol-5-yl)ethyl)-1H-benzimidazol-2-yl)[1,4]diazepan-1-yl)ethyl)-3-(pyrid-3-yl)pyrrolidine;

1-(3,4,5-Trimethoxybenzoyl)-3-(2-(4-(1-(2-(1H-tetrazol-5-yl)ethyl)-1H-benzimidazol-2-yl)[1,4]diazepan-1-yl)ethyl)-3-(pyrid-4-yl)pyrrolidine;

1-(3,4,5-Trimethoxybenzoyl)-3-(2-(4-(1-(2-phenoxyethyl)-1H-benzimidazol-2-yl) [1,4]diazepan-1-yl)ethyl)-3-phenylpyrrolidine;

1-(3,4,5-Trimethoxybenzoyl)-3-(2-(4-(1-(2-phenoxyethyl)-1H-benzimidazol-2-yl)[1,4]diazepan-1-yl)ethyl)-3-(3,4-dichlorophenyl)pyrrolidine;

1-(2-Methoxy-5-(1H-tetrazol-1-yl)benzoyl)-3-(2-(4-(1-(2-phenoxyethyl)-1H-benzimidazol-2-yl)[1,4]diazepan-1-yl)ethyl)-3-(3,4-dichlorophenyl)pyrrolidine;

1-(2-Methoxy-5-(1H-tetrazol-1-yl)benzoyl)-3-(2-(4-(1-(2-phenoxyethyl)-1H-benzimidazol-2-yl)[1,4]diazepan-1-yl)ethyl)-3-phenylpyrrolidine;

1-Benzoyl-3-(2-(4-(1-(2-phenoxyethyl)-1H-benzimidazol-2-yl)[1,4]diazepan-1-yl)ethyl)-3-(3,4-dichlorophenyl)pyrrolidine;

1-Benzoyl-3-(2-(4-(1-(2-phenoxyethyl)-1H-benzimidazol-2-yl)[1,4]diazepan-1-yl)ethyl)-3-phenylpyrrolidine;

1-(3,4,5-Trimethoxybenzoyl)-3-(2-(4-(1-(2-phenoxyethyl)-1H-benzimidazol-2-yl)[1,4]diazepan-1-yl)ethyl)-3-(pyrid-3-yl)pyrrolidine;

1-(3,4,5-Trimethoxybenzoyl)-3-(2-(4-(1-(2-phenoxyethyl)-1H-benzimidazol-2-yl)[1,4]diazepan-1-yl)ethyl)-3-(pyrid-4-yl)pyrrolidine;

1-(3,4,5-Trimethoxybenzoyl)-3-(2-(4-(1-(2-(fur-2-ylmethoxy)ethyl)-1H-benzimidazol-2-yl)[1,4]diazepan-1-yl)ethyl)-3-phenylpyrrolidine;

1-(3,4,5-Trimethoxybenzoyl)-3-(2-(4-(1-(2-(fur-2-ylmethoxy)ethyl)-1H-benzimidazol-2-yl)[1,4]diazepan-1-yl)ethyl)-3-(3,4-dichlorophenyl)pyrrolidine;

1-(2-Methoxy-5-(1H-tetrazol-1-yl)benzoyl)-3-(2-(4-(1-(2-(fur-2-ylmethoxy)ethyl)-1H-benzimnidazol-2-yl)[1,4]diazepan-1-yl)ethyl)-3-(3,4-dichlorophenyl)pyrrolidine;

1-(2-Methoxy-5-(1H-tetrazol-1-yl)benzoyl)-3-(2-(4-(1-(2-(fur-2-ylmethoxy)ethyl)-1H-benzimidazol-2-yl)[1,4]diazepan-1-yl)ethyl)-3-phenylpyrrolidine;

1-Benzoyl-3-(2-(4-(1(2-(fur-2-ylmethoxy)ethyl)-1H-benzimidazol-2-yl) [1,4]diazepan-1-yl)ethyl)-3-(3,4-dichlorophenyl)pyrrolidine;

1-Benzoyl-3-(2-(4-(1-(2-(fur-2-ylmethoxy)ethyl)-1H-benzimidazol-2-yl) [1,4]diazepan-1-yl)ethyl)-3-phenylpyrrolidine;

1-(3,4,5-Trimethoxybenzoyl)-3-(2-(4-(1-(2-(fur-2-ylmethoxy)ethyl)-1H-benzimidazol-2-yl)[1,4]diazepan-1-yl)ethyl)-3-(pyrid-3-yl)pyrrolidine;

1-(3,4,5-Trimethoxybenzoyl)-3-(2-(4-(1-(2-(fur-2-ylmethoxy)ethyl)-1H-benzimidazol-2-yl)[1,4]diazepan-1-yl)ethyl)-3-(pyrid-4-yl)pyrrolidine;

1-(3,4,5-Trimethoxybenzoyl)-3-(2-(4-(1-(fur-2-ylmethyl)-1H-benzimidazol-2-yl)[1,4]diazepan-1-yl)ethyl)-3-phenylpyrrolidine;

1-(3,4,5-Trimethoxybenzoyl)-3-(2-(4-(1-(fur-2-ylmethyl)-1H-benzimidazol-2-yl)[1,4]diazepan-1-yl)ethyl)-3-(3,4-dichlorophenyl)pyrrolidine;

1-(2-Methoxy-5-(1H-tetrazol-1-yl)benzoyl)-3-(2-(4-(1-(fur-2-ylmethyl)-1H-benzimidazol-2-yl)[1,4]diazepan-1-yl)ethyl)-3-(3,4-dichlorophenyl)pyrrolidine;

1-(2-Methoxy-5-(1H-tetrazol-1-yl)benzoyl)-3-(2-(4-(1-(fur-2-ylmethyl)-1H-benzimidazol-2-yl)[1,4]diazepan-1-yl)ethyl)-3-phenylpyrrolidine;

1-Benzoyl-3-(2-(4-(1-(fur-2-ylmethyl)-1H-benzimidazol-2-yl) [1,4]diazepan-1-yl)ethyl)-3-(3,4-dichlorophenyl)pyrrolidine;

1-Benzoyl-3-(2-(4-(1-(fur-2-ylmethyl)-1H-benzimidazol-2-yl) [1,4]diazepan-1-yl)ethyl)-3-phenylpyrrolidine;

1-(3,4,5-Trimethoxybenzoyl)-3-(2-(4-(1-(fur-2-ylmethyl)-1H-benzimidazol-2-yl)[1,4]diazepan-1-yl)ethyl)-3-(pyrid-3-yl)pyrrolidine;

1-(3,4,5-Trimethoxybenzoyl)-3-(2-(4-(1-(fur-2-ylmethyl)-1H-benzimidazol-2-yl)[1,4]diazepan-1-yl)ethyl)-3-(pyrid-4-yl)pyrrolidine;

1-(3,4,5-Trimethoxybenzoyl)-3-(2-(4-(1-(5-hydroxymethylfur-2-ylmethyl)-1H-benzimidazol-2-yl)[1,4]diazepan-1-yl)ethyl)-3-phenylpyrrolidine;

1-(3,4,5-Trimethoxybenzoyl)-3-(2-(4-(1-(5-hydroxymethylfur-2-ylmethyl)-1H-benzimidazol-2-yl)[1,4]diazepan-1-yl)ethyl)-3-(3,4-dichlorophenyl)pyrrolidine;

1-(2-Methoxy-5-(1H-tetrazol-1-yl)benzoyl)-3-(2-(4-(1-(5-hydroxymethylfur-2-ylmethyl)-1H-benzimidazol-2-yl)[1,4]diazepan-1-yl)ethyl)-3-(3,4-dichlorophenyl)pyrrolidine;

1-(2-Methoxy-5-(1H-tetrazol-1-yl)benzoyl)-3-(2-(4-(1-(5-hydroxymethylfur-2-ylmethyl)-1H-benzimidazol-2-yl)[1,4]diazepan-1-yl)ethyl)-3-phenylpyrrolidine;

1-Benzoyl-3-(2-(4-(1-(5-hydroxymethylfur-2-ylmethyl)-1H-benzimidazol-2-yl)[1,4]diazepan-1-yl)ethyl)-3-(3,4-dichlorophenyl)pyrrolidine;

1-Benzoyl-3-(2-(4-(1-(5-hydroxymethylfur-2-ylmethyl)-1H-benzimidazol-2-yl)[1,4]diazepan-1-yl)ethyl)-3-phenylpyrrolidine;

1-(3,4,5-Trimethoxybenzoyl)-3-(2-(4-(1-(5-hydroxymethylfur-2-ylmethyl)-1H-benzimidazol-2-yl)[1,4]diazepan-1-yl)ethyl)-3-(pyrid-3-yl)pyrrolidine;

1-(3,4,5-Trimethoxybenzoyl)-3-(2-(4-(1-(5-hydroxymethylfur-2-ylmethyl)-1H-benzimidazol-2-yl)[1,4]diazepan-1-yl)ethyl)-3-(pyrid-4-yl)pyrrolidine;

1-(3,4,5-Trimethoxybenzoyl)-3-(2-(4-(1-(5-methylfur-2-ylmethyl)-1H-benzimidazol-2-yl)[1,4]diazepan-1-yl)ethyl)-3-phenylpyrrolidine;

1-(3,4,5-Trimethoxybenzoyl)-3-(2-(4-(1-(5-methylfur-2-ylmethyl)-1H-benzimidazol-2-yl)[1,4]diazepan-1-yl)ethyl)-3-(3,4-dichlorophenyl)pyrrolidine;

1-(2-Methoxy-5-(1H-tetrazol-1-yl)benzoyl)-3-(2-(4-(1-(5-methylfur-2-ylmethyl)-1H-benzimidazol-2-yl)[1,4]diazepan-1-yl)ethyl)-3-(3,4-dichlorophenyl)pyrrolidine;

1-(2-Methoxy-5-(1H-tetrazol-1-yl)benzoyl)-3-(2-(4-(1-(5-methylfur-2-ylmethyl)-1H-benzimidazol-2-yl)[1,4]diazepan-1-yl)ethyl)-3-phenylpyrrolidine;

1-Benzoyl-3-(2-(4-(1-(5-methylfur-2-ylmethyl)-1H-benzimidazol-2-yl)[1,4]diazepan-1-yl)ethyl)-3-3,4dichlorophenyl)pyrrolidine;

1-Benzoyl-3-(2-(4-(1-(5-methylfur-2-ylmethyl)-1H-benzimidazol-2-yl)[1,4]diazepan-1-yl)ethyl)-3-phenylpyrrolidine;

1-(3,4,5-Trimethoxybenzoyl)-3-(2-(4-(1-(5-methylfur-2-ylmethyl)-1H-benzimidazol-2-yl)[1,4]diazepan-1-yl)ethyl)-3-(pyrid-3-yl)pyrrolidine;

1-(3,4,5-Trimethoxybenzoyl)-3-(2-(4-(1-(5-methylfur-2-ylmethyl)-1H-benzimidazol-2-yl)[1,4]diazepan-1-yl)ethyl)-3-(pyrid-4-yl)pyrrolidine;

1-(3,4,5-Trimethoxybenzoyl)-3-(2-(4-(1-(pyrid-2-ylmethyl)-1H-benzimidazol-2-yl) [1,4]diazepan-1-yl)ethyl)-3-phenylpyrrolidine;

1-(3,4,5-Trimethoxybenzoyl)-3-(2-(4-(1-(pyrid-2-ylmethyl)-1H-benzimidazol-2-yl)[1,4]diazepan-1-yl)ethyl)-3-(3,4-dichlorophenyl)pyrrolidine;

1-(2-Methoxy-5-(1H-tetrazol-1-yl)benzoyl)-3-(2-(4-(1-(pyrid-2-ylmethyl)-1H-benzimidazol-2-yl)[1,4]diazepan-1-yl)ethyl)-3-(3,4-dichlorophenyl)pyrrolidine;

1-(2-Methoxy-5-(1H-tetrazol-1-yl)benzoyl)-3-(2-(4-(1-(pyrid-2-ylmethyl)-1H-benzimidazol-2-yl)[1,4]diazepan-1-yl)ethyl)-3-phenylpyrrolidine;

1-Benzoyl-3-(2-(4-(1-(pyrid-2-ylmethyl)-1H-benzimidazol-2-yl)[1,4]diazepan-1-yl)ethyl)-3-(3,4-dichlorophenyl)pyrrolidine;

1-Benzoyl-3-(2-(4-(1-(pyrid-2-ylmethyl)-1H-benzimidazol-2-yl)[1,4]diazepan-1-yl)ethyl)-3-phenylpyrrolidine;

1-(3,4,5-Trimethoxybenzoyl)-3-(2-(4-(1-(pyrid-2-ylmethyl)-1H-benzimidazol-2-yl)[1,4]diazepan-1-yl)ethyl)-3-(pyrid-3-yl)pyrrolidine;

1-(3,4,5-Trimethoxybenzoyl)-3-(2-(4-(1-(pyrid-2-ylmethyl)-1H-benzimidazol-2-yl)[1,4]diazepan-1-yl)ethyl)-3-(pyrid-4-yl)pyrrolidine;

1-(3,4,5-Trimethoxybenzoyl)-3-(2-(4-(1-(pyrid-3-ylmethyl)-1H-benzimidazol-2-yl)[1,4]diazepan-1-yl)ethyl)-3-(3,4-dichlorophenyl)pyrrolidine;

1-(3,4,5-Trimethoxybenzoyl)-3-(2-(4-(1-(pyrid-3-ylmethyl)-1H-benzimidazol-2-yl)[1,4]diazepan-1-yl)ethyl)-3-phenylpyrrolidine;

1-(3,4,5-Trimethoxybenzoyl)-3-(2-(4-(1-(pyrid-4-ylmethyl)-1H-benzimidazol-2-yl)[1,4]diazepan-1-yl)ethyl)-3-(3,4-dichlorophenyl)pyrrolidine;

1-(3,4,5-Trimethoxybenzoyl)-3-(2-(4-(1-(pyrid-4-ylmethyl)-1H-benzimidazol-2-yl)[1,4]diazepan-1-yl)ethyl)-3-phenylpyrrolidine;

1-(3,4,5-Trimethoxybenzoyl)-3-(2-(4-(1-(5-methylfur-3-ylmethyl)-1H-benzimidazol-2-yl)[1,4]diazepan-1-yl)ethyl)-3-(3,4-dichlorophenyl)pyrrolidine;

1-(3,4,5-Trimethoxybenzoyl)-3-(2-(4-(1-(5-methylfur-3-ylmethyl)-1H-benzimidazol-2-yl)[1,4]diazepan-1-yl)ethyl)-3-phenylpyrrolidine;

1-(3,4,5-Trimethoxybenzoyl)-3-(2-(4-(1-(fur-3-ylmethyl)-1H-benzimidazol-2-yl)[1,4]diazepan-1-yl)ethyl)-3-(3,4-dichlorophenyl)pyrrolidine;
1-(3,4,5-Trimethoxybenzoyl)-3-(2-(4-(1-(fur-3-ylmethyl)-1H-benzimidazol-2-yl)[1,4]diazepan-1-yl)ethyl)-3-phenylpyrrolidine;
1-(3,4,5-Trimethoxybenzoyl)-3-(2-(4-(1-(thien-2-ylmethyl)-1H-benzimidazol-2-yl)[1,4]diazepan-1-yl)ethyl)-3-(3,4-dichlorophenyl)pyrrolidine;
1-(3,4,5-Trimethoxybenzoyl)-3-(2-(4-(1-(thien-2-ylmethyl)-1H-benzimidazol-2-yl)[1,4]diazepan-1-yl)ethyl)-3-phenylpyrrolidine;
1-(3,4,5-Trimethoxybenzoyl)-3-(2-(4-(1-(thien-3-ylmethyl)-1H-benzimidazol-2-yl)[1,4]diazepan-1-yl)ethyl)-3-(3,4-dichlorophenyl)pyrrolidine;
1-(3,4,5-Trimethoxybenzoyl)-3-(2-(4-(1-(thien-3-ylmethyl)-1H-benzimidazol-2-yl)[1,4]diazepan-1-yl)ethyl)-3-phenylpyrrolidine;
1-(3,4,5-Trimethoxybenzoyl)-3-(2-(4-(1-methy-1H-benzimidazol-2-yl)[1,4]diazepan-1-yl)ethyl)-3-(3,4-dichlorophenyl)pyrrolidine;
1-(3,4,5-Trimethoxybenzoyl)-3-(2-(4-(1-methy-1H-benzimidazol-2-yl)[1,4]diazepan-1-yl)ethyl)-3-phenylpyrrolidine;
1-(3,4,5-Trimethoxybenzoyl)-3-(2-(4-(1-ethyl-1H-benzimidazol-2-yl)[1,4]diazepan-1-yl)ethyl)-3-(3,4-dichlorophenyl)pyrrolidine;
1-(3,4,5-Trimethoxybenzoyl)-3-(2-(4-(1-ethyl-1H-benzimidazol-2-yl)[1,4]diazepan-1-yl)ethyl)-3-phenylpyrrolidine;
1-(3,4,5-Trimethoxybenzoyl)-3-(2-(4-(1H-benzimidazol-2-yl)[1,4]diazepan-1-yl)ethyl)-3-phenylpyrrolidine;
1-(3,4,5-Trimethoxybenzoyl)-3-(2-(4-(1H-benzimidazol-2-yl)[1,4]diazepan-1-yl)ethyl)-3-(3,4-dichlorophenyl)pyrrolidine;
1-(2-Methoxy-5-(1H-tetrazol-1-yl)benzoyl)-3-(2-(4-(1H-benzimidazol-2-yl)[1,4]diazepan-1-yl)ethyl)-3-(3,4-dichlorophenyl)pyrrolidine;
1-(2-Methoxy-5-(1H-tetrazol-1-yl)benzoyl)-3-(2-(4-(1H-benzimidazol-2-yl)[1,4]diazepan-1-yl)ethyl)-3-phenylpyrrolidine;
1-(2-Methoxy-5-(1H-tetrazol-5-yl)benzoyl)-3-(2-(4-(1H-benzimidazol-2-yl)[1,4]diazepan-1-yl)ethyl)-3-(3,4-dichlorophenyl)pyrrolidine;
1-(2-Methoxy-5-(1H-tetrazol-5-yl)benzoyl)-3-(2-(4-(1H-benzimidazol-2-yl)[1,4]diazepan-1-yl)ethyl)-3-phenylpyrrolidine;
1-Benzoyl-3-(2-(4-(1H-benzimidazol-2-yl)[1,4]diazepan-1-yl)ethyl)-3-(3,4-dichlorophenyl)pyrrolidine;
1-Benzoyl-3-(2-(4-(1H-benzimidazol-2-yl)[1,4]diazepan-1-yl)ethyl)-3-phenylpyrrolidine;
1-(3,4,5-Trimethoxybenzoyl)-3-(2-(4-(1H-benzimidazol-2-yl)[1,4]diazepan-1-yl)ethyl)-3-(pyrid-2-yl)pyrrolidine;
1-(3,4,5-Trimethoxybenzoyl)-3-(2-(4-(1H-benzimidazol-2-yl)[1,4]diazepan-1-yl)ethyl)-3-(pyrid-3-yl)pyrrolidine;
1-(3,4,5-Trimethoxybenzoyl)-3-(2-(4-(1H-benzimidazol-2-yl)[1,4]diazepan-1-yl)ethyl)-3-(pyrid-4-yl)pyrrolidine;
1-(3,4,5-Trimethoxybenzoyl)-3-(2-(4-(1-(but-2-en-1-yl)-1H-benzimidazol-2-yl)[1,4]diazepan-1-yl)ethyl)-3-(3,4-dimethoxyphenyl)pyrrolidine;
1-(3,4,5-Trimethoxybenzoyl)-3-(2-(4-(1-(but-2-en-1-yl)-1H-benzimidazol-2-yl)[1,4]diazepan-1-yl)ethyl)-3-(3,4-dichlorophenyl)pyrrolidine;
1-Benzoyl-3-(2-(4-(1-(but-2-en-1-yl)-1H-benzimidazol-2-yl)[1,4]diazepan-1-yl)ethyl)-3-(3,4-dichlorophenyl)pyrrolidine;
1-(3,4,5-Trimethoxybenzoyl)-3-(2-(4-(1-(but-2-en-1-yl)-1H-benzimidazol-2-yl)[1,4]diazepan-1-yl)ethyl)-3-phenylpyrrolidine;
1-Benzoyl-3-(2-(4-(1-(but-2-en-1-yl)-1H-benzimidazol-2-yl)[1,4]diazepan-1-yl)ethyl)-3-phenylpyrrolidine;
1-(3,4,5-Trimethoxybenzoyl)-3-(2-(4-(1-(but-2-en-1-yl)-1H-benzimidazol-2-yl)[1,4]diazepan-1-yl)ethyl)-3-(3,4-dimethylphenyl)pyrrolidine;
1-(3,4,5-Trimethoxybenzoyl)-3-(2-(4-(1-(but-2-en-1-yl)-1H-benzimidazol-2-yl)[1,4]diazepan-1-yl)ethyl)-3-(4-chlorophenyl)pyrrolidine;
1-(3,4,5-Trimethoxybenzoyl)-3-(2-(4-(1-(but-2-en-1-yl)-1H-benzimidazol-2-yl)[1,4]diazepan-1-yl)ethyl)-3-(4-fluorophenyl)pyrrolidine;
1-(3,4,5-Trimethoxybenzoyl)-3-(2-(4-(1-(but-2-en-1-yl)-1H-benzimidazol-2-yl)[1,4]diazepan-1-yl)ethyl)-3-(3,4-difluorophenyl)pyrrolidine;
1-(3,4,5-Trimethoxybenzoyl)-3-(2-(4-(1-(but-2-en-1-yl)-1H-benzimidazol-2-yl)[1,4]diazepan-1-yl)ethyl)-3-(pyrid-2-yl)pyrrolidine;
1-(3,4,5-Trimethoxybenzoyl)-3-(2-(4-(1-(but-2-en-1-yl)-1H-benzimidazol-2-yl)[1,4]diazepan-1-yl)ethyl)-3-(pyrid-3-yl)pyrrolidine;
1-(3,4,5-Trimethoxybenzoyl)-3-(2-(4-(1-(but-2-en-1-yl)-1H-benzimidazol-2-yl)[1,4]diazepan-1-yl)ethyl)-3-(pyrid-4-yl)pyrrolidine;
1-(3,4,5-Trimethoxybenzoyl)-3-(2-(4-(1-(3-methylbut-2-en-1-yl)-1H-benzimidazol-2-yl)[1,4]diazepan-1-yl)ethyl)-3-(3,4-dimethoxyphenyl)pyrrolidine;
1-(3,4,5-Trimethoxybenzoyl)-3-(2-(4-(1-(3-methylbut-2-en-1-yl)-1H-benzimidazol-2-yl)[1,4]diazepan-1-yl)ethyl)-3-(3,4-dichlorophenyl)pyrrolidine;
1-Benzoyl-3-(2-(4-(1-(3-methylbut-2-en-1-yl)-1H-benzimidazol-2-yl)[1,4]diazepan-1-yl)ethyl)-3-(3,4-dichlorophenyl)pyrrolidine;
1-(3,4,5-Trimethoxybenzoyl)-3-(2-(4-(1-(3-methylbut-2-en-1-yl)-1H-benzimidazol-2-yl)[1,4]diazepan-1-yl)ethyl)-3-phenylpyrrolidine;
1-Benzoyl-3-(2-(4-(1-(3-methylbut-2-en-1-yl)-1H-benzimidazol-2-yl)[1,4]diazepan-1-yl)ethyl)-3-phenylpyrrolidine;
1-(3,4,5-Trimethoxybenzoyl)-3-(2-(4-(1-(3-methylbut-2-en-1-yl)-1H-benzimidazol-2-yl)[1,4]diazepan-1-yl)ethyl)-3-(3,4-dimethylphenyl)pyrrolidine;
1-(3,4,5-Trimethoxybenzoyl)-3-(2-(4-(1-(3-methylbut-2-en-1-yl)-1H-benzimidazol-2-yl)[1,4]diazepan-1-yl)ethyl)-3-(4-chlorophenyl)pyrrolidine;
1-(3,4,5-Trimethoxybenzoyl)-3-(2-(4-(1-(3-methylbut-2-en-1-yl)-1H-benzimidazol-2-yl)[1,4]diazepan-1-yl)ethyl)-3-(4-fluorophenyl)pyrrolidine;
1-(3,4,5-Trimethoxybenzoyl)-3-(2-(4-(1-(3-methylbut-2-en-1-yl)-1H-benzimidazol-2-yl)[1,4]diazepan-1-yl)ethyl)-3-(3,4-difluorophenyl)pyrrolidine;
1-(3,4,5-Trimethoxybenzoyl)-3-(2-(4-(1-(3-methylbut-2-en-1-yl)-1H-benzimidazol-2-yl)[1,4]diazepan-1-yl)ethyl)-3-(pyrid-2-yl)pyrrolidine;
1-(3,4,5-Trimethoxybenzoyl)-3-(2-(4-(1-(3-methylbut-2-en-1-yl)-1H-benzimidazol-2-yl)[1,4]diazepan-1-yl)ethyl)-3-(pyrid-3-yl)pyrrolidine;
1-(3,4,5-Trimethoxybenzoyl)-3-(2-(4-(1-(3-methylbut-2-en-1-yl)-1H-benzimidazol-2-yl)[1,4]diazepan-1-yl)ethyl)-3-(pyrid-4-yl)pyrrolidine;
1-(3,4,5-Trimethoxybenzoyl)-3-(2-(4-(1-(2-(2,2,2-trifluoroethoxy)ethyl)-1H-benzimidazol-2-yl)[1,4]diazepan-1-yl)ethyl)-3-(3,4-dimethoxyphenyl)pyrrolidine;
1-(3,4,5-Trimethoxybenzoyl)-3-(2-(4-(1-(2-(2,2,2-trifluoroethoxy)ethyl)-1H-benzimidazol-2-yl)[1,4]diazepan-1-yl)ethyl)-3-(3,4-dichlorophenyl)pyrrolidine;
1-Benzoyl-3-(2-(4-(1-(2-(2,2,2-trifluoroethoxy)ethyl)-1H-benzimidazol-2-yl)[1,4]diazepan-1-yl)ethyl)-3-(3,4-dichlorophenyl)pyrrolidine;

1-(3,4,5-Trimethoxybenzoyl)-3-(2-(4-(1-(2-(2,2,2-trifluoroethoxy)ethyl)-1H-benzimidazol-2-yl)[1,4]diazepan-1-yl)ethyl)-3-phenylpyrrolidine;

1-Benzoyl-3-(2-(4-(1-(2-(2,2,2-trifluoroethoxy)ethyl)-1H-benzimidazol-2-yl)[1,4]diazepan-1-yl)ethyl)-3-phenylpyrrolidine;

1-(3,4,5-Trimethoxybenzoyl)-3-(2-(4-(1-(2-(2,2,2-trifluoroethoxy)ethyl)-1H-benzimidazol-2-yl)[1,4]diazepan-1-yl)ethyl)-3-(3,4-dimethylphenyl)pyrrolidine;

1-(3,4,5-Trimethoxybenzoyl)-3-(2-(4-(1-(2-(2,2,2-trifluoroethoxy)ethyl)-1H-benzimidazol-2-yl)[1,4]diazepan-1-yl)ethyl)-3-(4-chlorophenyl)pyrrolidine;

1-(3,4,5-Trimethoxybenzoyl)-3-(2-(4-(1-(2-(2,2,2-trifluoroethoxy)ethyl)-1H-benzimidazol-2-yl)[1,4]diazepan-1-yl)ethyl)-3-(4-fluorophenyl)pyrrolidine;

1-(3,4,5-Trimethoxybenzoyl)-3-(2-(4-(1-(2-(2,2,2-trifluoroethoxy)ethyl)-1H-benzimidazol-2-yl)[1,4]diazepan-1-yl)ethyl)-3-(3,4-difluorophenyl)pyrrolidine;

1-(3,4,5-Trimethoxybenzoyl)-3-(2-(4-(1-(2-(2,2,2-trifluoroethoxy)ethyl)-1H-benzimidazol-2-yl)[1,4]diazepan-1-yl)ethyl)-3-(pyrid-2-yl)pyrrolidine;

1-(3,4,5-Trimethoxybenzoyl)-3-(2-(4-(1-(2-(2,2,2-trifluoroethoxy)ethyl)-1H-benzimidazol-2-yl)[1,4]diazepan-1-yl)ethyl)-3-(pyrid-3-yl)pyrrolidine;

1-(3,4,5-Trimethoxybenzoyl)-3-(2-(4-(1-(2-(2,2,2-trifluoroethoxy)ethyl)-1H-benzimidazol-2-yl)[1,4]diazepan-1-yl)ethyl)-3-(pyrid-4-yl)pyrrolidine;

1-(3,4,5-Trimethoxybenzoyl)-3-(2-(4-(1-(2-(trifluoromethoxy)ethyl)-1H-benzimidazol-2-yl)[1,4]diazepan-1-yl)ethyl)-3-(3,4-dimethoxyphenyl)pyrrolidine;

1-(3,4,5-Trimethoxybenzoyl)-3-(2-(4-(1-(2-(trifluoromethoxy)ethyl)-1H-benzimidazol-2-yl)[1,4]diazepan-1-yl)ethyl)-3-(3,4-dichlorophenyl)pyrrolidine;

1-Benzoyl-3-(2-(4-(1-(2-(trifluoromethoxy)ethyl)-1H-benzimidazol-2-yl)[1,4]diazepan-1-yl)ethyl)-3-(3,4-dichlorophenyl)pyrrolidine;

1-(3,4,5-Trimethoxybenzoyl)-3-(2-(4-(1-(2-(trifluoromethoxy)ethyl)-1H-benzimidazol-2-yl)[1,4]diazepan-1-yl)ethyl)-3-phenylpyrrolidine;

1-Benzoyl-3-(2-(4-(1-(2-(trifluoromethoxy)ethyl)-1H-benzimidazol-2-yl)[1,4]diazepan-1-yl)ethyl)-3-phenylpyrrolidine;

1-(3,4,5-Trimethoxybenzoyl)-3-(2-(4-(1-(2-(trifluoromethoxy)ethyl)-1H-benzimidazol-2-yl)[1,4]diazepan-1-yl)ethyl)-3-(3,4-dimethylphenyl)pyrrolidine;

1-(3,4,5-Trimethoxybenzoyl)-3-(2-(4-(1-(2-(trifluoromethoxy)ethyl)-1H-benzimidazol-2-yl)[1,4]diazepan-1-yl)ethyl)-3-(4-chlorophenyl)pyrrolidine;

1-(3,4,5-Trimethoxybenzoyl)-3-(2-(4-(1-(2-(trifluoromethoxy)ethyl)-1H-benzimidazol-2-yl)[1,4]diazepan-1-yl)ethyl)-3-(4-fluorophenyl)pyrrolidine;

1-(3,4,5-Trimethoxybenzoyl)-3-(2-(4-(1-(2-(trifluoromethoxy)ethyl)-1H-benzimidazol-2-yl)[1,4]diazepan-1-yl)ethyl)-3-(3,4-difluorophenyl)pyrrolidine;

1-(3,4,5-Trimethoxybenzoyl)-3-(2-(4-(1(2-(trifluoromnethoxy)ethyl)-1H-benzimidazol-2-yl)[1,4]diazepan-1-yl)ethyl)-3-(pyrid-2-yl)pyrrolidine;

1-(3,4,5-Trimethoxybenzoyl)-3-(2-(4-(1-(2-(trifluoromethoxy)ethyl)-1H-benzimidazol-2-yl)[1,4]diazepan-1-yl)ethyl)-3-(pyrid-3-yl)pyrrolidine;

1-(3,4,5-Trimethoxybenzoyl)-3-(2-(4-(1-(2-(trifluoromethoxy)ethyl)-1H-benzimidazol-2-yl)[1,4]diazepan-1-yl)ethyl)-3-(pyrid-4-yl)pyrrolidine;

1-(3,4,5-Trimethoxybenzoyl)-3-(2-(4-(1-(2-cyanomethoxyethyl)-1H-benzimidazol-2-yl)[1,4]diazepan-1-yl)ethyl)-3-(3,4-dimethoxyphenyl)pyrrolidine;

1-Benzoyl-3-(2-(4-(1-(2-cyanomethoxyethyl)-1H-benzimidazol-2-yl)[1,4]diazepan-1-yl)ethyl)-3-(3,4-dichlorophenyl)pyrrolidine;

1-(3,4,5-Trimethoxybenzoyl)-3-(2-(4-(1-(2-cyanomethoxyethyl)-1H-benzimidazol-2-yl)[1,4]diazepan-1-yl)ethyl)-3-phenylpyrrolidine;

1-Benzoyl-3-(2-(4-(1-(2-cyanomethoxyethyl)-1H-benzimidazol-2-yl)[1,4]diazepan-1-yl)ethyl)-3-phenylpyrrolidine;

1-(3,4,5-Trimethoxybenzoyl)-3-(2-(4-(1-(2-cyanomethoxyethyl)-1H-benzimidazol-2-yl)[1,4]diazepan-1-yl)ethyl)-3-(3,4-dimethylphenyl)pyrrolidine;

1-(3,4,5-Trimethoxybenzoyl)-3-(2-(4-(1-(2-cyanomethoxyethyl)-1H-benzimidazol-2-yl)[1,4]diazepan-1-yl)ethyl)-3-(4-chlorophenyl)pyrrolidine;

1-(3,4,5-Trimethoxybenzoyl)-3-(2-(4-(1-(2-cyanomethoxyethyl)-1H-benzimidazol-2-yl)[1,4]diazepan-1-yl)ethyl)-3-(4-fluorophenyl)pyrrolidine;

1-(3,4,5-Trimethoxybenzoyl)-3-(2-(4-(1-(2-cyanomethoxyethyl)-1H-benzimidazol-2-yl)[1,4]diazepan-1-yl)ethyl)-3-(3,4-difluorophenyl)pyrrolidine;

1-(3,4,5-Trimethoxybenzoyl)-3-(2-(4-(1-(2-cyanomethoxyethyl)-1H-benzimidazol-2-yl)[1,4]diazepan-1-yl)ethyl)-3-(pyrid-3-yl)pyrrolidine;

1-(3,4,5-Trimethoxybenzoyl)-3-(2-(4-(1-(2-cyanomethoxyethyl)-1H-benzimidazol-2-yl)[1,4]diazepan-1-yl)ethyl)-3-(pyrid-4-yl)pyrrolidine;

1-(3,4,5-Trimethoxybenzoyl)-3-(2-(4-(1-allyl)-1H-benzimidazol-2-yl)[1,4]diazepan-1-yl)ethyl)-3-(3,4-dimethoxyphenyl)pyrrolidine;

1-(3,4,5-Trimethoxybenzoyl)-3-(2-(4-(1-allyl)-1H-benzimidazol-2-yl)[1,4]diazepan-1-yl)ethyl)-3-(3,4-dichlorophenyl)pyrrolidine;

1-Benzoyl-3-(2-(4-(1-allyl)-1H-benzimidazol-2-yl)[1,4]diazepan-1-yl)ethyl)-3-(3,4-dichlorophenyl)pyrrolidine;

1-(3,4,5-Trimethoxybenzoyl)-3-(2-(4-(1-allyl)-1H-benzimidazol-2-yl) [1,4]diazepan-1-yl)ethyl)-3-phenylpyrrolidine;

1-Benzoyl-3-(2-(4-(1-allyl)-1H-benzimidazol-2-yl)[1,4]diazepan-1-yl)ethyl)-3-phenylpyrrolidine;

1-(3,4,5-Trimethoxybenzoyl)-3-(2-(4-(1-allyl)-1H-benzimidazol-2-yl)[1,4]diazepan-1-yl)ethyl)-3-(3,4-dimethylphenyl)pyrrolidine;

1-(3,4,5-Trimethoxybenzoyl)-3-(2-(4-(1-allyl)-1H-benzimidazol-2-yl)[1,4]diazepan-1-yl)ethyl)-3-(4-chlorophenyl)pyrrolidine;

1-(3,4,5-Trimethoxybenzoyl)-3-(2-(4-(1-allyl)-1H-benzimidazol-2-yl)[1,4]diazepan-1-yl)ethyl)-3-(4-fluorophenyl)pyrrolidine;

1-(3,4,5-Trimethoxybenzoyl)-3-(2-(4-(1-allyl)-1H-benzimidazol-2-yl)[1,4]diazepan-1-yl)ethyl)-3-(3,4-difluorophenyl)pyrrolidine;

1-(3,4,5-Trimethoxybenzoyl)-3-(2-(4-(1-allyl)-1H-benzimidazol-2-yl)[1,4]diazepan-1-yl)ethyl)-3-(pyrid-3-yl)pyrrolidine;

1-(3,4,5-Trimethoxybenzoyl)-3-(2-(4-(1-allyl)-1H-benzimidazol-2-yl)[1,4]diazepan-1-yl)ethyl)-3-(pyrid-4-yl)pyrrolidine.

The compounds of formula (1) may be synthesized by use of the following synthetic procedures to produce intermediates or final compounds of the invention:

Reaction Scheme A.1 relates to the synthesis of compounds of formula (1) by alkylation of intermediates derived from alcohols of structure 2.

Reaction Scheme A.2 relates to the synthesis of compounds of formula (1) by reductive amination of aldehydes derived from alcohols of structure 2.

Reaction Scheme A.3 relates to the synthesis of compounds of formula (1) by aroylation or alkylation of intermediates derived from alcohols of structure 40.

Reaction Scheme B relates to the synthesis of alcohols of structure 2 in which $G_3$ is —$CH_2$— used as a starting material in Reaction Schemes A.1 and A.2 and intermediates of structure 11 used to prepare alcohols of structure 40 in Reaction Scheme A.3.

Reaction Scheme C relates to a synthesis of alcohols of structure 2 in which m is 2, q is 1, r is 0, and $G_3$ is —$CH_2$— and relates to the synthesis of intermediates of structure 8 used to prepare alcohols of structure 2 in Reaction Scheme E relates to a synthesis of alcohols of structure 2 in which r is 0 and $G_1$ is —$CH_2$— used as a starting material in Reaction Scheme A.1 and A.2 and intermediates of structure 35 used to prepare alcohols of structure 40 in Reaction Scheme A.3.

A general synthetic procedure for preparing these compounds of formula (1) is set forth in Reaction Scheme A.1. The reagents and starting materials are readily available to one of ordinary skill in the art. In Reaction Scheme A.1, all substituents, unless otherwise indicated, are as previously defined.

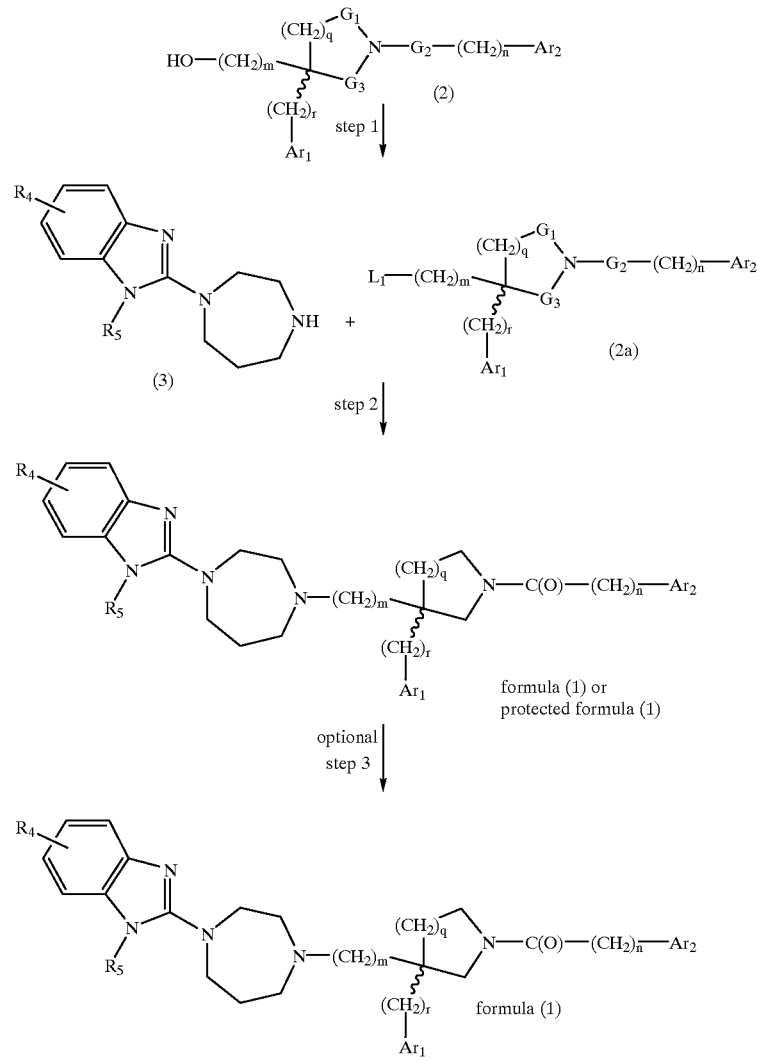

Reaction Scheme A.1

Reaction Scheme B and intermediates of structure 18 used to prepare alcohols of structure 40 in Reaction Scheme A.3.

Reaction Scheme D relates to a synthesis of alcohols of structure 2 in which r is 1 and $G_1$ is —$CH_2$— used as a starting material in Reaction Scheme A.1 and A.2 and intermediates of structure 26 used to prepare alcohols of structure 40 in Reaction Scheme A.3.

In Reaction Scheme A.1, step 1, the hydroxy group of an appropriate alcohol of structure 2 is converted to an appropriate leaving group to give a compound of structure 2a.

An appropriate alcohol of structure 2 is one in which the stereochemistry is as desired in the final product of formula (1) and m, n, q, r, $G_1$, $G_2$, $G_3$, $Ar_1$ and $Ar_2$ are as desired in the final product of formula (1). Alternately, an appropriate alcohol of structure 2 can be one in which the stereochemistry gives rise after resolution to stereochemistry as desired in the final product of formula (1) and m, n, q, r, $G_1$, $G_2$, $G_3$, $Ar_1$ and $Ar_2$ are as desired in the final product of formula (1). An appropriate alcohol of structure 2 can also be one in which the stereochemistry is as desired in the final product of formula (1); and m, n, q, r, $G_1$, $G_2$, and $G_3$ are as desired in the final product of formula (1); and $Ar_1$ and/or $Ar_2$ gives rise upon deprotection to $Ar_1$ and/or $Ar_2$ as desired in the final product of formula (1). Alternately, an appropriate alcohol of structure 2 can also be one in which the stereochemistry gives rise after resolution to stereochemistry as desired in the final product of formula (1); and m, n, q, r, $G_1$, $G_2$, and $G_3$ are as desired in the final product of formula (1); and $Ar_1$ and/or $Ar_2$ gives rise upon deprotection to $Ar_1$ and/or $Ar_2$ as desired in the final product of formula (1). Appropriate alcohols of structure 2 can be prepared as described herein and in International Patent Application (PCT) No. WO 94/26735, published Nov. 24, 1994.

An appropriate leaving group, $L_1$, is one which can be displaced by a 4-(1H-benzimidazol-2-yl)[1,4]diazepane of structure 3 to give rise to a compound of formula (1). Appropriate leaving groups, $L_1$, include but are not limited to chloro, bromo, iodo, mesylate, tosylate, benzenesulfonate, trifluoromethanesulfonate, and the like. The conversion of hydroxy groups to leaving groups such as chloro, bromo, iodo, mesylate, tosylate, benzenesulfonate, and trifluoromethanesulfonate is well known and appreciated in the art.

For example, compounds in which $L_1$ is bromo are formed by contacting an appropriate alcohol of structure 2 with 1.0 to 1.5 molar equivalents of carbon tetrabromide and 1.0 to 1.75 molar equivalents triphenylphosphine. (P. J. Kocienski et al. *J. Org. Chem.* 42, 353–355 (1977)). The reaction is carried out by combining the alcohol of structure 2 with carbon tetrabromide in a suitable solvent, such as dichloromethane or chloroform and then adding a solution of triphenylphosphine in a suitable solvent, such as dichloromethane or chloroform. Generally the reaction is carried out at temperatures of from −10° C. to ambient temperature. Generally, the reactions require from 5 minutes to 24 hours. The product can be isolated and purified by techniques well known in the art, such as extraction, evaporation, trituration, chromatography, and recrystallizationa.

Compounds in which $L_1$ is bromo are also formed by contacting an appropriate alcohol of structure 2 with a slight molar excess of triphenylphosphine dibromide. (R. F Borch et al. *J. Am. Chem. Soc.* 99, 1612–1619 (1977)). The reaction may be carried out by contacting an appropriate alcohol of structure 2 with preformed triphenylphosphine dibromide. The reaction is carried out in a suitable solvent, such as tetrahydrofuran and diethyl ether. The reaction is carried out in the presence of a suitable base, such as pyridine. Generally the reaction is carried out at temperatures of from 0° C. to 50° C. Generally, the reactions require from 5 minutes to 24 hours. The product can be isolated and purified by techniques well known in the art, such as extraction, evaporation, trituration, chromatography, and recrystallization.

Alternately, for example, compounds in which $L_1$ is mesylate are formed by contacting an appropriate alcohol of structure 2 with a molar excess of methanesulfonyl chloride. The reaction is carried out in a suitable solvent, such as acetonitrile, dichloromethane, chloroform, toluene, benzene, or pyridine. The reaction is carried out in the presence of a suitable base, such as triethylamine, diisopropylethylamine, or pyridine. Generally the reaction is carried out at temperatures of from −20° C. to 50° C. Generally, the reactions require from 1 hour to 24 hours. The product can be isolated and purified by techniques well known in the art, such as extraction, evaporation, trituration, chromatography, and recrystallization.

Compounds of structure 2a in which $L_1$ is iodo can be prepared from compounds of structure 2a in which $L_1$ is mesylate, chloro, or bromo by an exchange reaction, such as the Finkelstein reaction.

For example, a compound of structure 2a in which $L_1$ is mesylate, chloro, or bromo is contacted with from 1.0 to 10.0 molar equivalents of an iodide salt, such as sodium iodide or potassium iodide. The reaction is carried out in a suitable solvent, such as acetone, butanone, tetrahydrofuran, tetrahydrofuran/water mixtures, toluene, and acetonitrile. Generally, the reaction is carried out at temperatures of from ambient temperature to the refluxing temperature of the solvent. Generally, the reactions require from 1 hour to 24 hours. The product can be isolated and purified by techniques well known in the art, such as extraction, evaporation, trituration, chromatography, and recrystallization.

In Reaction Scheme A.1, step 2, the compound of structure 2a reacts with an appropriate 4-(1H-benzimidazol-2-yl) [1,4]diazepane compound of structure 3 or a salt thereof to give a protected compound of formula (1) or a compound of formula (1).

An appropriate 4-(1H-benzimidazol-2-yl)[1,4]diazepane of structure 3 or salt thereof is one in which $R_4$ and $R_5$ are as desired in the final product of formula (1) or $R_5$ gives rise after deprotection and/or modification to $R_5$ as desired in the final product of formula (1). Appropriate 4-(1H-benzimidazol-2-yl)[1,4]diazepanes of structure 3 are well known and appreciated in the art. Appropriate 4-(1H-benzimidazol-2-yl)[1,4]diazepanes of structure 3 may be prepared by methods known in the art such as described in *J. Med Chem.* 29, 1178–1183 (1986), *Chem. Pharm. Bull.*, 37 962–966 (1989), and Tet. Lets., 38, 5607–5610 (1997); and by methods analogous to those methods and to those described herein by carrying out suitable deprotections, protections, and alkylations, and modifications, such as the reduction of esters, as are well known in the art, in the order and number required for formation of an appropriate 4-(1H-benzimidazol-2-yl)[1,4]diazepane of structure 3.

For example, the compound of structure 2a is contacted with an appropriate 4-(1H-benzimidazol-2-yl)[1,4] diazepane compound of structure 3 or salt thereof to give a protected compound of formula (1) or a compound of formula (1). The reaction is carried out in a suitable solvent, such as dioxane, tetrahydrofuran, tetrahydrofuran/water mixtures, acetone, acetone/water mixtures, ethyl acetate, ethyl acetate/water mixtures, pyridine, acetonitrile, toluene, toluene/water mixtures, chlorobenzene, or dimethylformamide, with acetonitrile being preferred. The reaction is carried out in the presence of from 1.0 to 6.0 molar equivalents of a suitable base, such as sodium carbonate, sodium bicarbonate, potassium carbonate, potassium bicarbonate, triethylamine, pyridine, or diisopropylethylamine, with diisopropylethylamine being preferred. When a salt of an appropriate 4-(1H-benzimidazol-2-yl)[1,4]diazepane of structure 3 is used, a molar excess of a suitable base may be required to absorb the acid liberated from the salt. The reaction may be facilitated by the addition of a catalytic amount, 0.1 to 0.5 molar equivalents, of an iodide salt, such as sodium iodide, potassium iodide, or tetrabutyl ammonium iodide. The reaction is generally carried out at temperatures of from ambient temperature to the refluxing temperature of the solvent. Generally, the reactions require 1 to 72 hours. The product can be isolated and purified by techniques well known in the art, such as extraction, evaporation, trituration, chromatography, and recrystallization.

In Reaction Scheme A.1, optional step 3, a compound of formula (1) or a protected compound of formula (1) in which $R_5$ is hydrogen is modified to give a compound of formula (1) or a protected compound of formula (1) in which $R_5$ is not hydrogen. Also encompassed by Reaction Scheme A.1, optional step 3, a protected compound of formula (1) is deprotected to give a compound of formula (1).

A modification reaction, encompasses the formation of amides and the alkylation of the benzimidazole nitrogen. The formation of amides from esters and acids is well known and appreciated in the art. The alkylation of a benzimidazole nitrogen using a suitable alkylating agent is well known and appreciated in the art. An alkylation of a benzimidazole nitrogen encompasses the Michael addition using α,β-unsaturated electrophiles. A suitable alkylating agent is one which transfers a group $R_5$ as desired in the final product of formula (1) or a protected group $R_5$ which gives rise after deprotection to $R_5$ as desired in the final product of formula (1).

For example, a compound of formula (1) in which $R_5$ is hydrogen is contacted with a suitable alkylating agent. A suitable alkylating agent is one which transfers a group $R_5$ as is desired in the final product of formula (1). Suitable alkylating agent include but are not limited to 4-fluorobenzyl bromide, 4-fluorobenzyl chloride, 2-(chloromethyl)furan, 3-(chloromethyl)furan, 2-(bromomethyl)thiophene, 3-(chloromethyl)thiophene, 2-(chloromethyl)pyridine, 3-(chloromethyl)pyridine, 4-(chloromethyl)pyridine, 2-chlorethyl ethyl ether, 2-chloroethyl methyl ether, benzyl chloride, 4-methoxybenzyl chloride, 5-(ethoxycarbonyl)-2-(chloromethyl)furan, ethyl chloroacetate, t-butyl bromoacetate, methyl bromoacetate, methyl iodide, ethyl iodide, propyl iodide, isopropyl iodide, butyl bromide, 2-isopropyloxyethyl chloride, 2-phenoxyethyl chloride, 2-(4-fluorophenoxy)ethyl bromide, 3-(4-fluorophenoxy) propyl bromide, methyl 2-(chloromethyl) benzoate, methyl 3-(chloromethyl)benzoate, methyl 4-(chloromethyl) benzoate, ethyl 2-(chloromethyl)benzoate, propyl 2-(chloromethyl)benzoate, N,N-dimethyl-4-(chloromethyl) benzamide, iodoacetamide, allyl chloride, allyl bromide, (E)-1-chlorobut-2-ene, (Z)-1-chlorobut-2-ene, 1-chloro-3-methylbut-2-ene, 2-(2,2,2-trifluoroethoxy)ethyl chloride, 2-trifluoromethoxyethyl chloride, 1-chloro-4,4,4-trifluorobut-2-ene, (E)-1-chloropent-2-ene, (Z)-1-chloropent-2-ene, acrylonitrile, methyl acrylate, t-butyl acrylate, methyl vinyl sulfone, ethyl vinyl sulfone, phenyl vinyl sulfone, and the like. The reaction is carried out in a suitable solvent, such as dioxane, tetrahydrofuran, tetrahydrofuran/water mixtures, acetone, or acetonitrile. The reaction is carried out in the presence of from 1.0 to 6.0 molar equivalents of a suitable base, such as sodium hydride, potassium hydride, sec-butyllithium, sodium carbonate, sodium bicarbonate, potassium carbonate, potassium bicarbonate, triethylamine, 1,8-diazabicyclo[5.4.0] undec-7-ene, 1,5-diazabicyclo[4.3.0]non-5-ene, potassium bis(trimethylsilyl)amide, lithium bis(trimethylsilyl)amide, or diisopropylethylamine; with potassium hydride being preferred when the alkylating agent is an alkyl halide and sec-butyllithium being preferred when the alkylating agent is an Micheal accepter. The reaction is generally carried out at temperatures of from −78° C. to the refluxing temperature of the solvent. Generally, the reactions require 1 to 72 hours. The product can be isolated and purified by techniques well known in the art, such as extraction, evaporation, trituration, chromatography, and recrystallization.

A deprotection reaction, such as the removal of hydroxy protecting groups or hydrolysis of an ester, utilizing suitable protecting groups such as those described in *Protecting Groups in Organic Synthesis* by T. Greene is well known and appreciated in the art.

A general synthetic procedure for preparing the compounds of formula (1) by reductive amination is set forth in Reaction Scheme A.2. The reagents and starting materials are readily available to one of ordinary skill in the art. In Scheme A.2, all substituents, unless otherwise indicated, are as previously defined. For the preparation of compounds of formula (1) in which $Ar_1$ is pyrid-2-yl the reductive amination as set forth in Reaction Scheme A.2 is preferred.

Reaction Scheme A.2

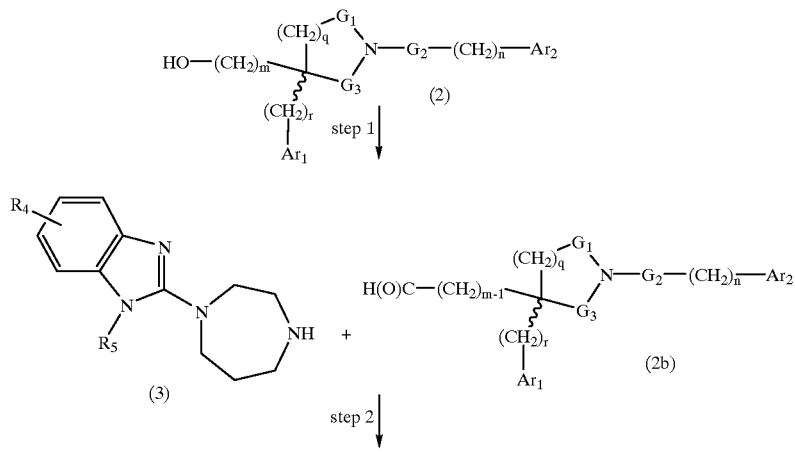

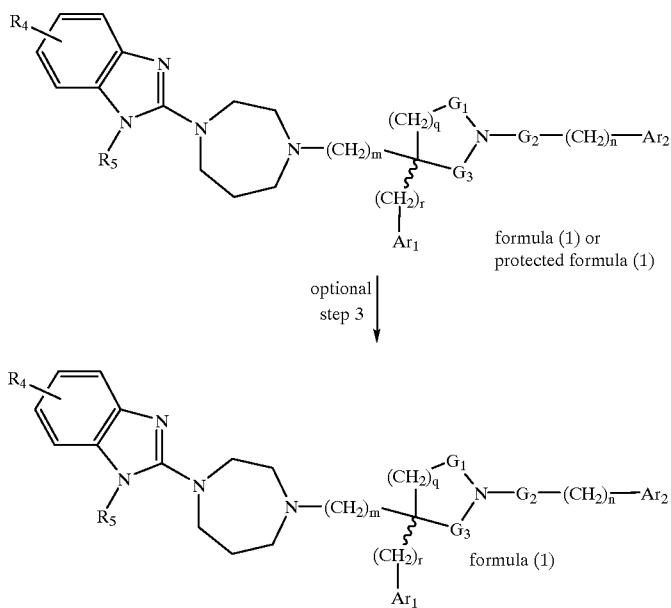

formula (1) or protected formula (1)

optional step 3 formula (1)

In Reaction Scheme A.2, step 1, an appropriate alcohol of structure 2 is oxidized to an aldehyde of structure 2b by the method of Swern. (A. J. Mancuso et al., *J. Org. Chem.*, 43 2480–2482 (1978), C. M. Amon, *J. Org. Chem.*, 52, 4851–4855 (1987), and T. T. Tidwell, *Synthesis*, 857–870 (1990). An appropriate alcohol of structure 2 is as described in Reaction Scheme A.1, step 1.

For example, about two molar equivalents of dimethyl sulfoxide are added dropwise to a solution of oxalyl chloride, pyridine sulfur trioxide complex, or trifluoroacetic anhydride in dichloromethane, at approximately −60° C. After the addition is complete, the reaction is stirred for approximately two minutes. A molar equivalent of the alcohol of structure 2 either neat or as a solution in dichloromethane is added. After the addition is complete the reaction mixture is stirred for 5 to 45 minutes, then about 3 to 5 molar equivalents of triethylamine is added. The reaction mixture is allowed to stir with warming to ambient temperature over 30 minutes to 2 hours. The product can be isolated and purified by techniques well known in the art, such as extraction, evaporation, chromatography, and recrystallization.

In Reaction Scheme A.2, step 2, the compound of structure 2b is contacted with an appropriate 4-(1H-benzimidazol-2-yl)[1,4]diazepane of structure 3 or salt thereof in a reductive amination to give a protected compound of formula (1) or a compound of formula (1). An appropriate 4-(1H-benzimidazol-2-yl)[1,4]diazepane of structure 3 or salt thereof is as defined in Reaction Scheme A-1.

For example, the compound of structure 2b is contacted with an appropriate 4-(1H-benzimidazol-2-yl)[1,4]diazepane compound of structure 3 or salt thereof. The reaction is carried out using a molar excess of a suitable reducing agent such as sodium borohydride or sodium cyanoborohydride with sodium cyanoborohydride being preferred. Reductive aminations using secondary amines and aldehydes are well known and appreciated in the art. The reaction is carried out in a suitable solvent, such as ethanol, methanol, dichloromethane, or dimethylformamide. Generally, the reaction is carried out at temperatures of from 0° C. to 50° C. Generally, the reactions require 1 to 72 hours. The product can be isolated and purified by techniques well known in the art, such as extraction, evaporation, chromatography, and recrystallization.

In Reaction Scheme A.2, optional step 3, a compound of formula (1) or a protected compound of formula (1) in which $R_5$ is hydrogen is modified to give a a compound of formula (1) or a protected compound of formula (1) in which $R_5$ is not hydrogen and/or a protected compound of formula (1) is deprotected to give a compound of formula (1) as described in Reaction Scheme A.1, optional step 3.

A general synthetic procedure for preparing the compounds of formula (1) in which $G_1$ and $G_3$ are $-CH_2-$ is set forth in Reaction Scheme A.3. The reagents and starting materials are readily available to one of ordinary skill in the art. In Scheme A.3, all substituents, unless otherwise indicated, are as previously defined.

Reaction Scheme A.3

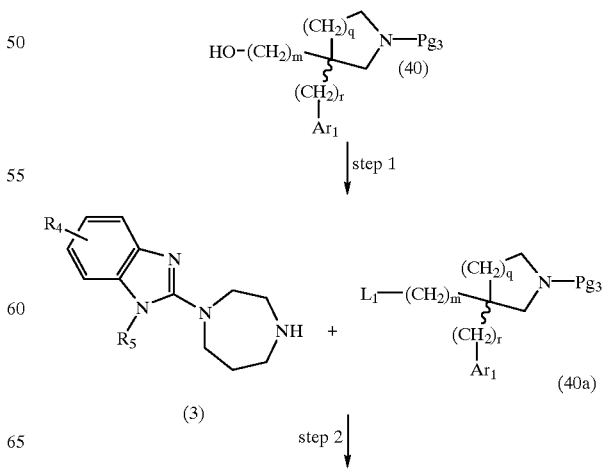

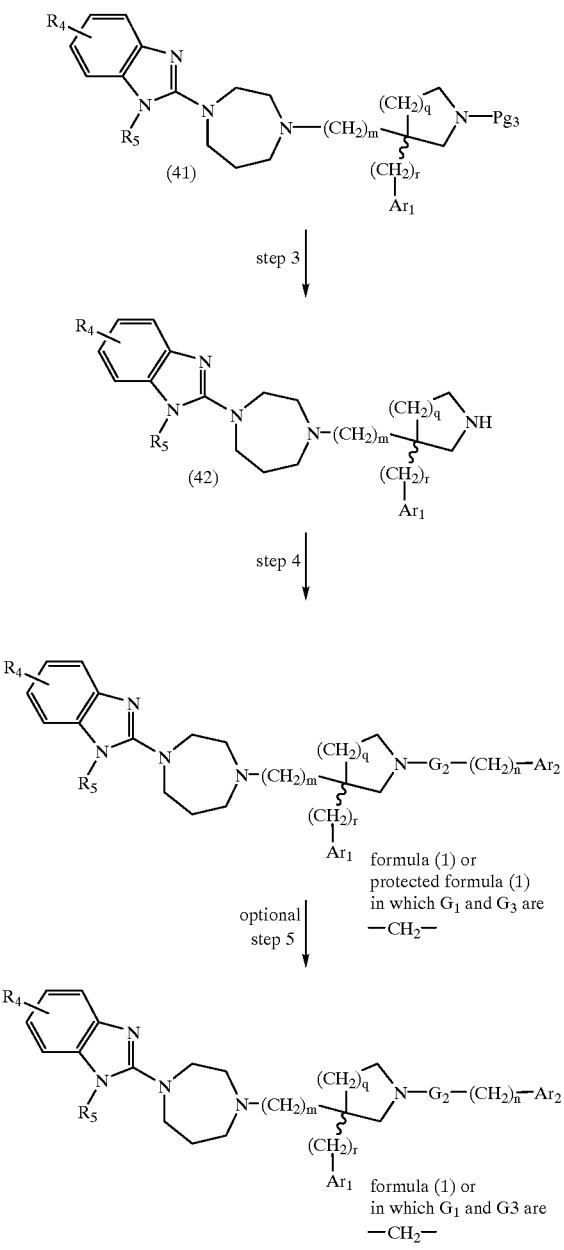

In Reaction Scheme A.3, step 1, the hydroxy group of an appropriate alcohol of structure 40 is converted to an appropriate leaving group, as described in Reaction Scheme A.1, step 1, to give a compound of structure 40a.

In Reaction Scheme A.3, step 1, an appropriate alcohol of structure 40 is one in which the stereochemistry is as desired in the final product of formula (1) and m, q, r, and $Ar_1$ are as desired in the final product of formula (1) and $G_1$ and $G_3$ are —$CH_2$—. Alternately, an appropriate alcohol of structure 40 can be one in which the stereochemistry gives rise after resolution to stereochemistry as desired in the final product of formula (l) and m, q, r, and $Ar_1$ are as desired in the final product of formula (1) and $G_1$ and $G_3$ are —$CH_2$—. An appropriate alcohol of structure 40 can also be one in which the stereochemistry is as desired in the final product of formula (1); and m, q, and r are as desired in the final product of formula (1) and $G_1$ and $G_3$ are —$CH_2$—; and $Ar_1$ gives rise upon deprotection to $Ar_1$ as desired in the final product of formula (1). Alternately, an appropriate alcohol of structure 40 can also be one in which the stereochemistry gives rise after resolution to stereochemistry as desired in the final product of formula (1); and m, q, and r are as desired in the final product of formula (1) and $G_1$ and $G_3$ are —$CH_2$—; and $Ar_1$ gives rise upon deprotection to $Ar_1$ as desired in the final product of formula (1).

An appropriate alcohol of structure 40 can be prepared by protecting the pyrrolidine or piperidine nitrogen of compounds of structure 11 (Reaction Scheme B), compounds of structure 26 (Reaction Scheme D), and compounds of structure 35 (Reaction Scheme E); in which the hydroxy protecting group has been removed; and compounds of structure 18 (Reaction Scheme C). The selection and use of a suitable amine protecting group, $Pg_3$, such as those described in *Protecting Groups in Organic Synthesis* by T. Greene are well known and appreciated in the art. In Reaction Scheme A.3 the use of benzamide and carbamate protecting groups, such as benzoyl, t-butoxycarbonyl and ethoxycarbonyl, is preferred. Reaction Scheme A.3 the use of benzamide protecting groups, such as benzoyl is more preferred.

In Reaction Scheme A.3, step 2, the compound of structure 40a reacts with an appropriate 4-(1H-benzimidazol-2-yl)[1,4]diazepane compound of structure 3 or a salt thereof, as described in Reaction Scheme A.1, step 2, to give a protected compound of structure 41. An appropriate 4-(1H-benzimidazol-2-yl)[1,4]diazepanes of structure 3 is one as described in Reaction Scheme A.1

In Reaction Scheme A.3, step 3, a protected compound of formula 41 is deprotected to give a compound of structure 42. Deprotection reactions, such as the removal of amine protecting groups such as those described in *Protecting Groups in Organic Synthesis* by T. Greene are well known and appreciated in the art.

In Reaction Scheme A.3, step 4, a compound of structure 42 is aroylated or alkylated to give a compound of formula (1) or a protected compound of formula (1) in which $G_1$ and $G_3$ are —$CH_2$—. An aroylation is carried out as described in Reaction Scheme B, optional step 7, above. An alkylation reaction is carried out as described in Reaction Scheme B, optional step 8, above, and can be carried out by reductive amination, such as described n Reaction Scheme A.2, step 2. Aroylations and alkylations of amines are well known and appreciated in the art.

In Reaction Scheme A.3, optional step 5, a compound of formula (1) or a protected compound of formula (1) in which $R_5$ is hydrogen can be modified to give a compound of formula (1) or a protected compound of formula (1) in which $R_5$ is not hydrogen and/or a protected compound of formula (1) is deprotected to give a compound of formula (1), as described in Reaction Scheme A.1, optional step 3.

Reaction Scheme B is a general scheme for preparing alcohols of structure 2 in which $G_3$ is —$CH_2$— used as a starting material in Reaction Schemes A.1 and A.2 and for preparing amine of structure 11 used as starting material in Reaction Scheme A.3. The reagents and starting materials are readily available to one of ordinary skill in the art. In Reaction Scheme B, all substituents, unless otherwise indicated, are as previously defined.

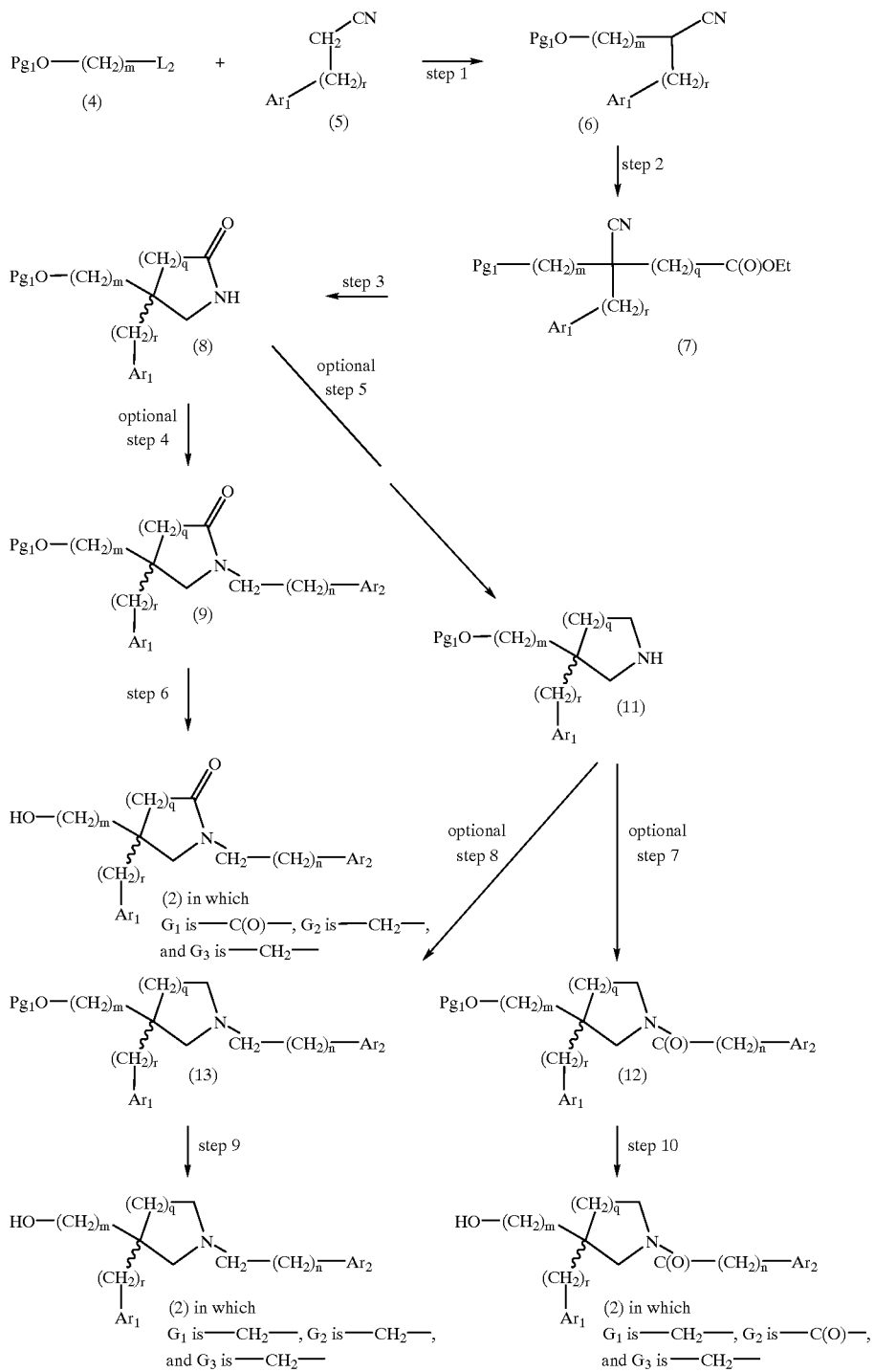

Reaction Scheme B

In Reaction Scheme B, step 1, an appropriate nitrile of structure 5 is alkylated with an appropriate protected alcohol of structure 4 to give an ω-protected-hydroxyalkyl-nitrile of structure 6.

An appropriate nitrile of structure 5 is one in which r and $Ar_1$ are as desired in the final product of formula (1) or $Ar_1$ gives rise after deprotection to an $Ar_1$ as desired in the final product of formula (1). An appropriate protected alcohol of structure 4 is one in which m is as desired in the final product of formula (1) and the leaving group, $L_2$, is one which can be displaced by an anion derived from an appropriate nitrile of structure 5. Suitable leaving groups include but are not limited to chloro, bromo, iodo, and mesylate with iodo and bromo being preferred. The selection and use of a suitable hydroxy protecting group, $Pg_1$, such as those described in *Protecting Groups in Organic Synthesis* by T. Greene are well known and appreciated in the art. The use of tetrahyropyran-2-yl and t-butyldimethylsilyl are generally preferred.

For example, the appropriate nitrile of structure 5 is contacted with 1.0 to 1.2 molar equivalents of the appropriate protected alcohol of structure 4. The reaction is carried out in the presence of an equimolar amount of a suitable base, such as sodium hydride, sodium bis-(trimethylsilyl) amide, potassium t-butoxide, and lithium diisopropylamide with sodium hydride and sodium bis-(trimethylsilyl)amide being preferred. The reaction is carried out in a solvent, such as dimethylformamide or tetrahydrofuran. The reaction is generally carried out at temperatures of from −78° C. to 0° C. Generally, the reactions require 1 to 72 hours. The product can be isolated and purified by techniques well known in the art, such as extraction, evaporation, trituration, chromatography, and recrystallization.

In Reaction Scheme B, step 2, the ω-protected-hydroxyalkyl-nitrile of structure 6 is alkylated with ethyl bromoacetate or ethyl 3-bromopropionate to give a nitrile ester compound of structure 7.

For example, the ω-protected-hydroxyalkyl-nitrile of structure 6 is contacted with approximately a molar equivalent of ethyl bromqacetate or ethyl bromopropionate. The reaction is carried out in the presence of approximately a molar equivalent of a suitable base, such as sodium bis-(trimethylsilyl)amide or lithium diisopropylamide. The reaction is carried out in a suitable solvent, such as tetrahydrofuran. The reaction is generally carried out at temperatures of from −78° C. to 0° C. Generally, the reactions require 1 to 72 hours. The product can be isolated and purified by techniques well known in the art, such as extraction, evaporation, trituration, chromatography, and recrystallization.

In Reaction Scheme B, step 3, the nitrile ester compound of structure 7 is reduced and cyclized to give an oxo-3-(-protected-hydroxyalkyl) compound of structure 8. The cyclization may occur spontaneously after the reduction or may be carried out in a separate step after the isolation of the intermediate amine.

For example, the nitrile ester compound of structure 7 is contacted with an excess of an appropriate reducing agent, such as sodium borohydride in the presence of cobalt (II) chloride hexahydrate or hydrogen in the presence of a suitable catalyst, such as Raney nickel or platinum oxide. For compounds of structure 7 in which $Ar_1$ is thienyl, sodium borohydride in the presence of cobalt (II) chloride hexahydrate is preferred.

When sodium borohydride in the presence of cobalt chloride is used, the reaction is carried out in a suitable solvent, such as methanol, or ethanol. The reaction is generally carried out at temperatures of from 0° C. to 50° C. Generally, the reactions require 1 to 72 hours. Generally, the cyclization occurs spontaneously under these conditions. The product can be isolated and purified by techniques well known in the art, such as extraction with aqueous acid, evaporation, trituration, chromatography, and recrystallization.

When Raney nickel is used, the reaction is carried out in a suitable solvent containing ammonia, such as ethanol/aqueous ammonium hydroxide or methanol/aqueous ammonium hydroxide. The reaction is generally carried out at temperatures of from ambient temperature to 70° C. The reaction is carried out with hydrogen at pressures of from 15 psi to 120 psi in an apparatus designed for carrying out reactions under pressure, such as a Parr hydrogenation apparatus. Generally, the cyclization occurs spontaneously under these conditions. The product can be isolated by carefully removing the catalyst by filtration and evaporation. The product can be purified by extraction, evaporation, trituration, chromatography, and recrystallization.

When platinum oxide is used, the reaction is carried out in a suitable solvent such as ethanol, methanol, chloroform, ethanol/chloroform mixtures, or methanol/chloroform mixtures. The reaction is generally carried out at temperatures of from ambient temperature to 50° C. The reaction is carried out with hydrogen at pressures of from 15 psi to 120 psi in an apparatus designed for carrying out reactions under pressure, such as a Parr hydrogenation apparatus. Generally, an amine intermediate is obtained under these conditions and is isolated by carefully removing the catalyst by filtration and evaporation. The amine intermediate is cyclized by heating in a suitable solvent, such as ethanol, methanol, toluene, or chlorobenzene. The reaction is generally carried out at temperatures of from 50° C. to the refluxing temperature of the solvent. Generally, the reaction requires 8 to 48 hours. The product can be purified by extraction, evaporation, trituration, chromatography, and recrystallization.

In Reaction Scheme B, optional step 4, the oxo-3-(-protected-hydroxyalkyl) compound of structure 8 is alkylated with an appropriate alkylating agent, $X—CH_2—(CH_2)_n—Ar_2$, to an 1-arylaklyl-oxo compound of structure 9. An appropriate alkylating agent, $X—CH_2—(CH_2)_n—Ar_2$, is one in which X is methanesulfonyl, chloro, bromo, or iodo; n is as desired in the final product of formula (1), and $Ar_2$ is as desired in formula (1) or gives rise after deprotection to $Ar_2$ as desired in formula (1).

For example, the oxo-3-(ω-protected-hydroxyalkyl) compound of structure 8 is contacted with from 1 to 5 molar equivalents of an appropriate alkylating agent, $X—CH_2—(CH_2)_n—Ar_2$. The reaction is carried out in a suitable solvent, such as tetrahydrofuran, dimethyl sulfoxide, or dimethylformamide. The reaction is carried out in the presence of a base, such as sodium hydride, potassium t-butoxide, potassium bis(trimethylsilyl)amide, or lithium diisopropylamide with sodium hydride and potassium bis (trimethylsilyl)amide being preferred. The reaction is generally carried out at temperatures of from 0° C. to 50° C. Generally, the reactions require 1 to 72 hours. The product can be isolated and purified by techniques well known in the art, such as extraction, evaporation, trituration, chromatography, and recrystallization.

In Reaction Scheme B, step 6, the 1-aryLalkyl-oxo-3-(ω-protected-hydroxyalkyl) compound of structure 9 is deprotected to give an alcohol of structure 2 in which $G_1$ is —C(O)—. A deprotection reaction, such as the removal of hydroxy protecting groups utilizing suitable protecting groups such as those described in *Protecting Groups in Organic Synthesis* by T. Greene is well known and appreciated in the art.

In Reaction Scheme B, optional step 5, the oxo-3-(ω-protected-hydroxyalkyl) compound of structure 8 is reduced to give a 3-(ω-protected-hydroxyalkyl) compound of structure 11.

For example, the oxo-3-(ω-protected-hydroxyalkyl) compound of structure 8 is contacted with an excess of a suitable reducing agent, such as lithium aluminum hydride, aluminum hydride, or borane dimethyl sulfide complex. The reaction is carried out in a suitable solvent, such as tetrahydrofuran, diethyl ether, tetrahydrofuran/diethyl ether mixtures, or tetrahydrofuran/methyl t-butyl ether mixtures. The reaction is generally carried out at temperatures of from 0° C. to the refluxing temperature of the solvent. Generally, the reactions require 1 to 72 hours. The product can be isolated and purified by techniques well known in the art, such as quenching of borane or aluminum complexes, extraction, evaporation, trituration, chromatography, and recrystallization.

In Reaction Scheme B, optional step 7, the 3-(ω-protected-hydroxyalkyl) compound of structure 11 is aroylated with an appropriate aryl acid, aryl ester, aryl halide, aryl anhydride, or aryl mixed anhydride, A—C(O)—(CH$_2$)$_n$—Ar$_2$, to give an 1-aryl-3-(ω-protected-hydroxyalkyl) compound of structure 12. An appropriate aryl acid, aryl ester, aroyl halide, aryl anhydride, or aryl mixed anhydride, A—C(O)—(CH$_2$)$_n$—Ar$_2$, is one in which A is hydroxyl; an activated ester, such as O-hydroxysuccinimide, O-hydroxybenztriazole; an activated leaving group, such as chloro, bromo; or a group which forms an anhydride; or mixed anhydride, n is as desired in the final product of formula (1), and Ar$_2$ is as desired in formula (1) or give rise after deprotection to Ar$_2$ as desired in formula (1).

For example, the 3-(ω-protected-hydroxyalkyl) compound of structure 11 is contacted with 1 to 1.5 molar equivalents of an appropriate aryl acid, aryl ester, aryl halide, aroyl anhydride, or aryl mixed anhydride, A—C(O)—(CH$_2$)$_n$—Ar$_2$. The reaction is carried out in a suitable solvent, such as dichloromethane, tetrahydrofuran, acetonitrile, dimethylformamide, or pyridine. The reaction is carried out in the presence of a base, such as sodium carbonate, sodium bicarbonate, triethylamine, N-methylmorpholine, diisopropylethylamine, or pyridine. The reaction is generally carried out at temperatures of from −20° C. to 50° C. Generally, the reactions require 1 to 6 hours. The product can be isolated and purified by techniques well known in the art, such as extraction, evaporation, trituration, chromatography, and recrystallization.

In Reaction Scheme B, optional step 8, the 3-(ω-protected-hydroxyalkyl) compound of structure 11 is alkylated with an appropriate alkyl halide, X$_3$—CH$_2$—(CH$_2$)$_n$—Ar$_2$, to give an 1-arylalkyl-3-(ω-protected-hydroxyalkyl) compound of structure 13. An appropriate alkyl halide, X$_3$—CH$_2$—(CH$_2$)$_n$—Ar$_2$, is one in which X$_3$ is chloro or bromo, n is as desired in the final product of formula (1), and Ar$_2$ is as desired in formula (1) or gives rise after deprotection to Ar$_2$ as desired in formula (1).

For example, the 3-(ω-protected-hydroxyalkyl) compound of structure 11 is contacted with from 1.0 to 1.2 molar equivalents of an appropriate alkyl halide, X$_3$—CH$_2$—(CH$_2$)$_n$—Ar$_2$. The reaction is carried out in a suitable solvent, such as tetrahydrofuran, dimethyl sulfoxide, acetonitrile, tetrahydrofuran/water, toluene, toluene/water, or dimethylformamide. The reaction is carried out in the presence of a base, such as sodium carbonate, sodium bicarbonate, potassium carbonate, triethylamine, diisopropylethylamine, or pyridine. The reaction is generally carried out at temperatures of from 0° C. to reflux temperature of the solvent. Generally, the reactions require 1 to 72 hours. The product can be isolated and purified by techniques well known in the art, such as extraction, evaporation, trituration, chromatography, and recrystallization.

In Reaction Scheme B, step 9, the 1-arylaklyl-3-(ω-protected-hydroxyalkyl) compound of structure 13 is deprotected to give an alcohol of structure 2 in which G$_1$, G$_2$, and G$_3$ are —CH$_2$—. A deprotection reaction, such as the removal of hydroxy protecting groups utilizing suitable protecting groups such as those described in *Protecting Groups in Organic Synthesis* by T. Greene is well known and appreciated in the art.

In Reaction Scheme B, step 10, the 1-aryl-3-(ω-protected-hydroxyalkyl) compound of structure 12 is deprotected to give an an alcohol of structure 2 in which G$_1$ is —CH$_2$—, G$_2$ is —C(O)—, and G$_3$ is —CH$_2$—.

Reaction Scheme C is a general scheme for preparing intermediates of structure 8 in which m is 2, r is 0, and q is 1 used in Reaction Scheme B to prepare alcohols of structure 2; and for preparing alcohols of structure 2 in which q is 1, r is 0, m is 2, and G$_3$ is —CH$_2$— used as a starting material in Reaction Schemes A.1 and A.2 and for preparing intermediates of structure 18 used as starting material in Reaction Scheme A.3. The reagents and starting materials are readily available to one of ordinary skill in the art. In Reaction Scheme C, all substituents, unless otherwise indicated, are as previously defined.

Reaction Scheme C

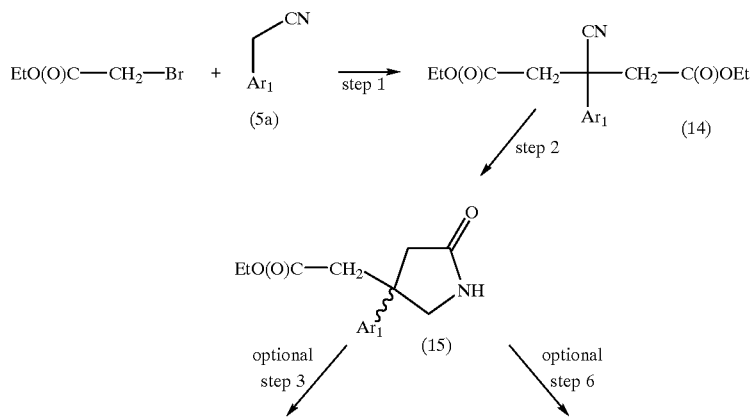

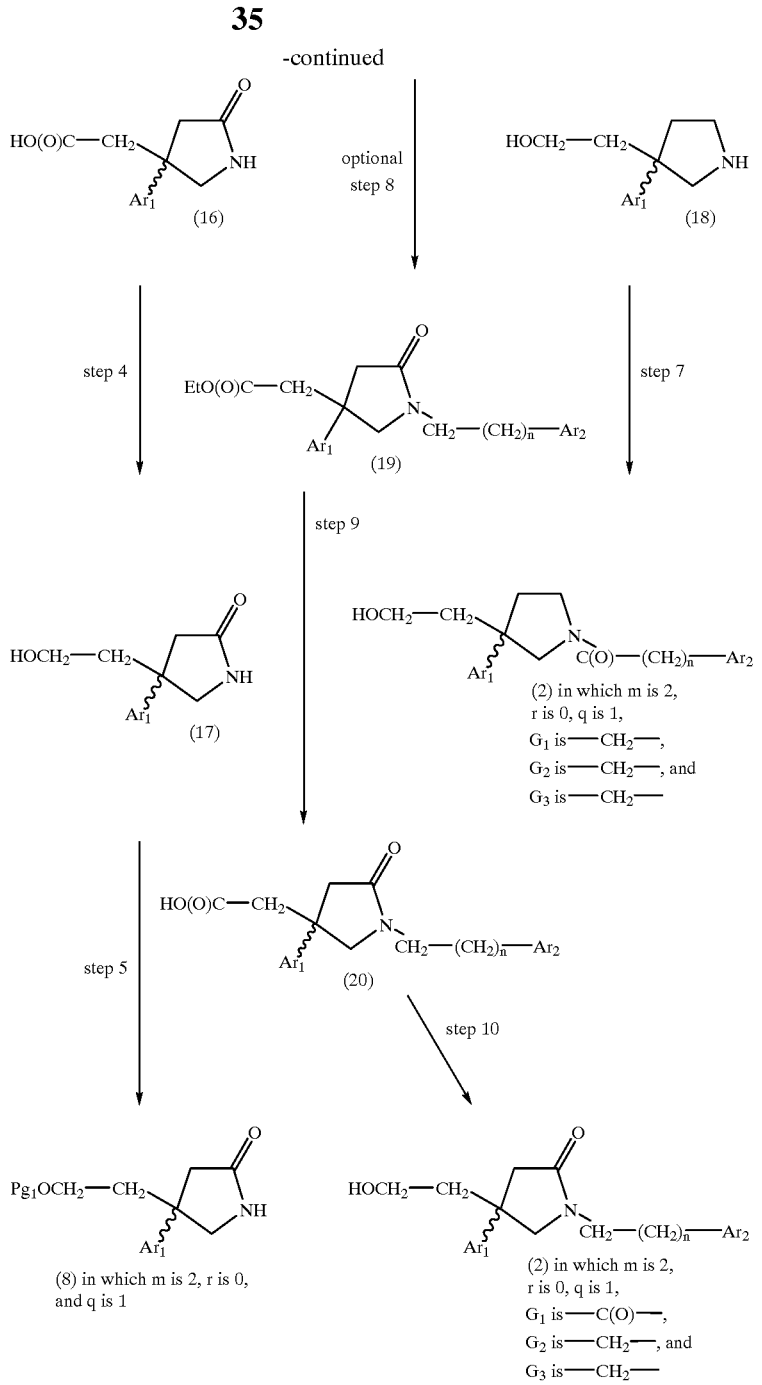

In Reaction Scheme C, step 1, an appropriate aryl-acetonitrile of structure 5a is bis-alkylated with ethyl bromoacetate to give a nitrile bis-ester compound of structure 14. An appropriate aryl-acetonitrile of structure 5a is one in which $Ar_1$ is as desired in the final product of formula (1) or gives rise after deprotection to an $Ar_1$ as desired in the final product of formula (1).

For example, an appropriate aryl-acetonitrile of structure 5a is contacted with 2.0 to 3.0 molar eauivalents of ethyl bromoacetate. The reaction is carried out in the presence of approximately 2.0 to 3.0 molar equivalents of a suitable base, such as sodium bis(trimethylsilyl)amide or lithium diisopropylamide. The reaction is carried out in a suitable solvent, such as tetrahydrofuran. The reaction is generally carried out at temperatures of from −78° C. to 0° C. Generally, the reactions require 1 to 72 hours. The product can be isolated and purified by techniques well known in the art, such as extraction, evaporation, trituration, distillation, chromatography, and recrystallization.

In Reaction Scheme C, step 2, the nitrile bis-ester compound of structure 14 is reduced and cyclized to give a 5-oxo-3-acetic acid ester pyrrolidine of structure 15.

For example, the nitrile bis-ester compound of structure 14 is contacted with a suitable reducing agent, such as sodium borohydride in the presence of cobalt II chloride hexahydrate or hydrogen in the presence of a suitable catalyst, such as Raney nickel or platinum oxide as taught in Reaction Scheme B, step 3. For compounds of structure 14 in which $Ar_1$ is thienyl, sodium borohydride in the presence of cobalt II chloride hexahydrate is preferred.

In Reaction Scheme C, optional step 3, the 5-oxo-3-acetic acid ester pyrrolidine of structure 15 is hydrolyzed to give a 5-oxo-3-acetic acid pyrrolidixie of structure 16.

For example, the 5-oxo-3-acetic acid ester pyrrolidine of structure 15 is contacted with a suitable hydrolyzing agent, such as sodium hydroxide, potassium hydroxide, or lithium hydroxide. The reaction is carried out in a suitable solvent such as water, tetrahydrofuran/water mixtures, methanol, methanol/water mixtures, or ethanol/water mixtures. The reaction is generally carried out at temperatures of from 0° C. to the refluxing temperature of the solvent. Generally, the reactions require 1 to 72 hours. The product can be isolated and purified by techniques well known in the art, such as extraction, evaporation, trituration, chromatography, and recrystallization.

In Reaction Scheme C, step 4, the 5-oxo-3-acetic acid pyrrolidine of structure 16 is reduced to give a 5-oxo-3-(2-hydroxyethyl)pyrrolidine of structure 17.

For example, the 5-oxo-3-acetic acid pyrrolidine of structure 16 is contacted with a suitable borane reagent, such as borane dimethyl sulfide complex. The reaction is carried out in a suitable solvent, such as tetrahydrofuran. The reaction is generally carried out at a temperature of from 0° C. to the refluxing temperature of the solvent. When complete, the reaction is quenched by the careful addition of a suitable aqueous acid solution, such as 1 M hydrochloric acid solution. The product can be isolated and purified by techniques well known in the art, such as extraction, evaporation, trituration, chromatography, and recrystallization.

Alternately, the 5-oxo-3-acetic acid pyrrolidine of structure 16 can be reduced by formation of a mixed anhydride intermediate and contacting the mixed anhydride intermediate with a suitable mild reducing agent, such as sodium borohydride.

For example, the 5-oxo-3-acetic acid pyrrolidine of structure 16 is contacted with 1.2 to 1.7 equivalents of a suitable base, such as N-methylmorpholine, in a suitable solvent, such as tetrahydrofuran or diethyl ether. The reaction mixture is cooled to a temperature of between −50° C. and 0° C. with −25° C. to −20° C. being preferred, before the addition of 1.2 to 1.7 equivalents of isobutyl chloroformate. The reaction is allowed to stir for 30 minutes to 3 hours to allow for the formation of the mixed anhydride. After the formation of the mixed anhydride is complete, sodium borohydride is added. The product can be isolated and purified by techniques well known in the art, such as extraction, evaporation, chromatography, and recrystallization.

In Reaction Scheme C, step 5, the 5-oxo-3-(2-hydroxyethyl)-pyrrolidine of structure 17 is protected to give a 5-oxo-3-(ω-protected-hydroxyethyl)pyrrolidine of structure 8 in which m is 2, r is 0, and q is 1 used in Reaction Scheme B for preparing compounds of structure 2. The selection and use of suitable protecting groups such as those described in *Protecting Groups in Organic Synthesis* by T. Greene is well known and appreciated in the art.

In Reaction Scheme C optional step 6, the 5-oxo-3-acetic acid ester pyrrolidine of structure 15 is reduced to give a 3-(ω-hydroxyethyl)-pyrrolidine of structure 18 as taught in Reaction Scheme B, optional step 5.

In Reaction Scheme C, step 7, the 3-(ωhydroxyethyl) pyrrolidine of structure 18 is aroylated with an appropriate aroyl halide, aryl anhydride, or aryl mixed anhydride, $A_1—C(O)—(CH_2)_n—Ar_2$, to give an alcohol of structure 2. An appropriate aroyl halide, aryl anhydride, or aryl mixed anhydride, $A_1—C(O)—(CH_2)_n—Ar_2$, is one in which $A_1$ is an activated leaving group, such as chloro, bromo, or a group which forms an anhydride or mixed anhydride, n is as desired in the final product of formula (1), and $Ar_2$ is as desired in formula (1) or gives rise after deprotection to $Ar_2$ as desired in formula (1).

For example, the 3-(ω-hydroxyethyl)pyrrolidine of structure 18 is contacted with 1 to 1.1 molar equivalents of an appropriate aroyl halide, aryl anhydride, or aryl mixed anhydride, $A_1—C(O)—(CH_2)_n—Ar_2$. The reaction is carried out in a suitable solvent, such as tetrahydrofuran, dichloromethane, acetone, ethyl acetate, or diethyl ether. The reaction is carried out in the presence of a base, such as N-methylmorpholine, sodium carbonate, triethylamine, diisopropylethylamine, potassium carbonate or sodium bicarbonate. The reaction is generally carried out at temperatures of from −78° C. to ambient temperature. Generally, the reactions require 1 to 24 hours. The product can be isolated and purified by techniques well known in the art, such as extraction, evaporation, trituration, chromatography, and recrystallization.

Alternately, for example, the 3-(ω-hydroxyethyl) pyrrolidine of structure 18 is contacted with 1 to 1.1 molar equivalents of an appropriate aroyl halide, arylanhydride, or aryl mixed anhydride, $A_1—C(O)—(CH_2)_n—Ar_2$ under Schotten-Baumann conditions. The reaction is carried out in a suitable solvent mixture, such as acetone/water, tetrahydrofuran/water, or ethyl acetate/water. The reaction is carried out in the presence of a base, such as potassium carbonate, potassium bicarbonate, sodium bicarbonate, or sodium carbonate. The reaction is generally carried out at temperatures of from −20° C. to 50° C. Generally, the reactions require 15 minutes to 24 hours. The product can be isolated and purified by techniques well known in the art, such as extraction, evaporation, trituration, chromatography, and recrystallization.

In Reaction Scheme C, optional step 8 the 5-oxo-3-acetic acid ester pyrrolidine of structure 15 is alkylated with an appropriate alkyl halide, $X_4—CH_2—(CH_2)_n—Ar_2$, to give an 1-arylalkyl-5-oxo-3-acetic acid ester pyrrolidine of structure 19. An appropriate alkyl halide, $X_4—CH_2—(CH_2)_n—Ar_2$, is one in which $X_4$ is chloro, bromo, or iodo; n is as desired in the final product of formula (1), and $Ar_2$ is as desired in formula (1) or gives rise after deprotection to $Ar_2$ as desired in formula (1).

For example, the 5-oxo-3-acetic acid ester pyrrolidine of structure 15 is contacted with from 1.0 to 1.2 molar equivalents of an appropriate alkyl halide, $X_4—CH_2—(CH_2)_n—Ar_2$. The reaction is carried out in a suitable solvent, such as tetrahydrofuran, dimethyl sulfoxide, acetonitrile, or dimethylformamide. The reaction is carried out in the presence of a base, such as sodium hydride, sodium bis(trimethylsilyl) amide, potassium t-butoxide. The reaction is generally carried out at temperatures of from 0° C. to 50° C. Generally, the reactions require 1 to 72 hours. The product can be isolated and purified by techniques well known in the art, such as extraction, evaporation, trituration, chromatography, and recrystallization.

In Reaction Scheme C, step 9, the 1-arylalkyl-5-oxo-3-acetic acid ester pyrrolidine of structure 19 is hydrolyzed to give an 1-arylalkyl-5-oxo-3-acetic acid pyrrolidine of structure 20.

For example, the 1-arylalkyl-5-oxo-3-acetic acid ester pyrrolidine of structure 19 is contacted with a suitable hydrolyzing agent, such as sodium hydroxide, potassium hydroxide, or lithium hydroxide. The reaction is carried out in a suitable solvent such as water, tetrahydrofuran/water mixtures, methanol, methanol/water mixtures, or ethanol/water mixtures. The reaction is generally carried out at temperatures of from 0°C. to the refluxing temperature of the solvent. Generally, the reactions require 1 to 72 hours. The product can be isolated and purified by techniques well known in the art, such as extraction, evaporation, trituration, chromatography, and recrystallization.

In Reaction Scheme C, step 10, the 1-arylalkyl-5-oxo-3-acetic acid pyrrolidine of structure 20 is reduced as taught in Reaction Scheme C, step 4, above, to give an alcohol of structure 2 in which r is 0, q is 1, m is 2, $G_1$ is —C(O)—, and $G_2$ and $G_3$ are —$CH_2$—.

Reaction Scheme D sets forth a synthetic procedure for preparing alcohols of structure 2 in which $G_1$ is —$CH_2$— used as a starting material in Reaction Scheme A.1 and A.2. The reagents and starting materials used in Reaction Scheme D are readily available to one of ordinary skill in the art. In Reaction Scheme D, all substituents, unless otherwise indicated, are as previously defined.

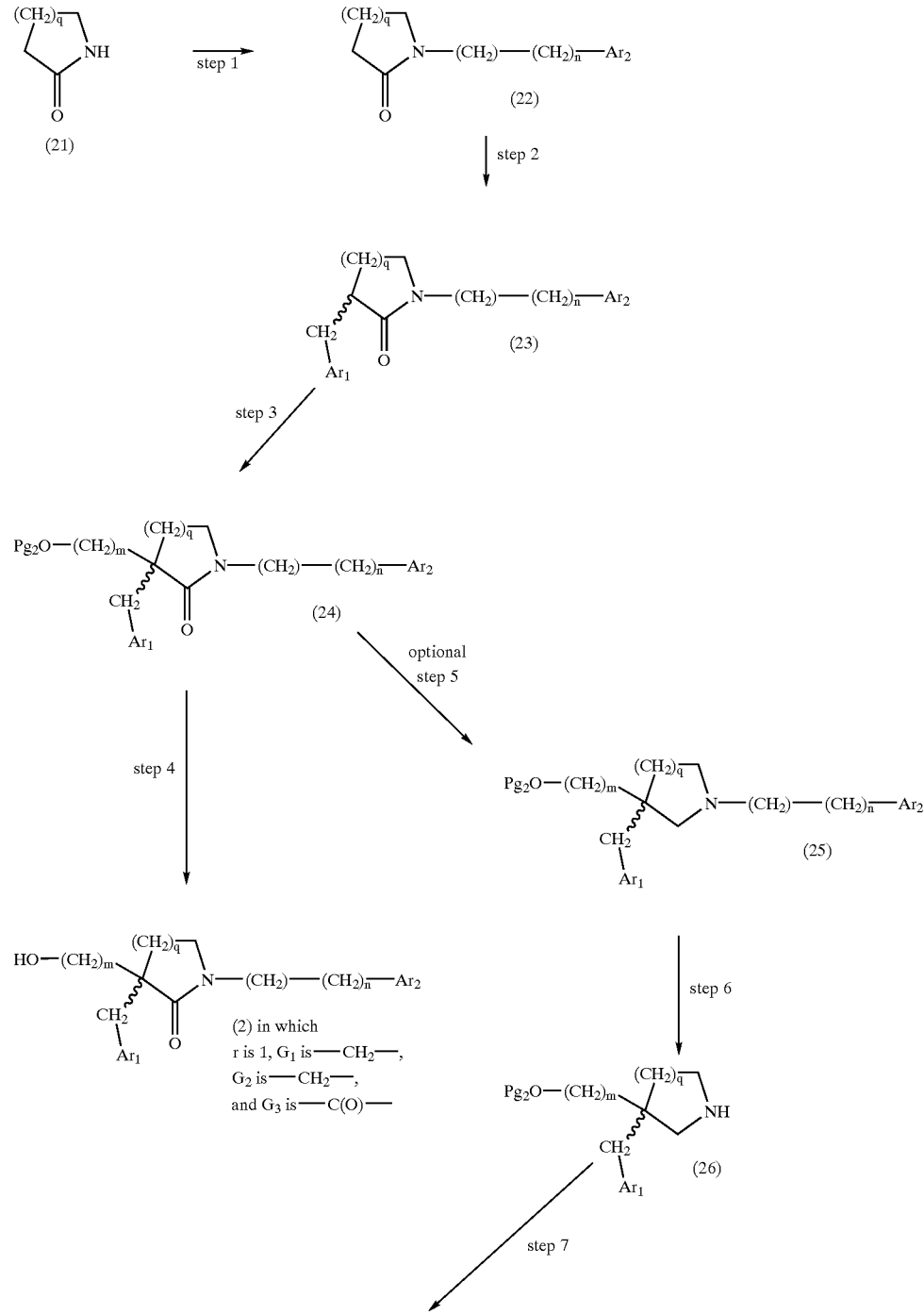

Reaction Scheme D

-continued

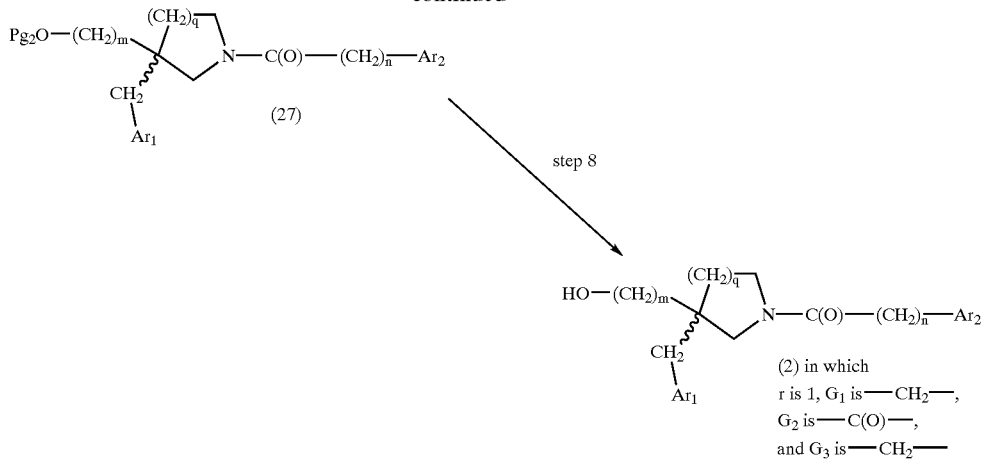

In Reaction Scheme D, step 1, an appropriate compound of structure 21 is alkylated with an appropriate alkylating agent to give an 1-arylalkyl-2-oxo compound of structure 22. An appropriate compound of structure 21 is one in which q is as desired in formula (1). An appropriate alkylating agent, $X—CH_2—(CH_2)_n—Ar_2$, is as defined in Reaction Scheme B, optional step 4.

For example, an appropriate compound of structure 21 is contacted with from 1 to 5 molar equivalents of an appropriate alkylating agent, $X—CH_2—(CH_2)_n Ar_2$. The reaction is carried out in a suitable solvent, such as tetrahydrofuran. The reaction is carried out in the presence of a base, such as sodium hydride, potassium t-butoxide, potassium bis(trimethylsilyl)amide with potassium bis(trimethylsilyl)amide being preferred. The reaction is generally carried out at temperatures of from −78° C. to the refluxing temperature of the solvent. Generally, the reactions require 1 to 72 hours. The product can be isolated and purified by techniques well known in the art, such as extraction, evaporation, trituration, chromatography, and recrystallization.

In Reaction Scheme D, step 2, the 1-arylalkyl-2-oxo compound of structure 22 is arylmethylated with an appropriate arylmethylating agent to give a 1-arylalkyl-2-oxo-3-arylmethyl compound of structure 23. An appropriate arylmethylating agent, $X_5—CH_2—Ar_1$, is one in which $X_5$ is methanesulfonyl, chloro, bromo, or iodo and $Ar_1$ is as desired in formula (1) or gives rise after deprotection to $Ar_1$ as desired in formula (1). Examples of appropriate arylmethylating agents include, but are not limited to benzyl bromide, benzyl chloride, 3,4,5-trimethoxybenzyl methanesulfonate, 4-fluorobenzyl bromide, 4-fluorobenzyl chloride, 3,4-difluorobenzyl bromide, 3,4-difluorobenzyl chloride, 4-methoxybenzyl chloride, 3,4-dimethoxybenzyl bromide, 3,4-dimethoxybenzyl chloride, 3,4-dichlorobenzyl bromide, 3,4-dichlorobenzyl chloride, 3-chlorobenzyl bromide, 4-chlorobenzyl chloride, 2,4-difluorobenzyl bromide, 2,4-difluorobenzyl chloride, 2-(bromomethyl)thiophene, 2-(chloromethyl)pyridine, 3-(chloromethyl)pyridine, 4-(chloromethyl)pyridine, 1-(chloromethyl)naphthlene, 2-(chloromethyl)naphthlene, and the like.

For example, the 1-arylalkyl-2-oxo compound of structure 22 is contacted with from 1 to 5 molar equivalents of an appropriate arylmethylating agent. The reaction is carried out in a suitable solvent, such as tetrahydrofuran. The reaction is carried out in the presence of a base, such as sec-butyl lithium, n-butyl lithium, and lithium bis(trimethylsilyl)amide. The reaction is generally carried out at temperatures of from 0° C. to −78° C. Generally, the reactions require 1 to 72 hours. The product can be isolated and purified by techniques well known in the art, such as extraction, evaporation, trituration, chromatography, and recrystallization.

In Reaction Scheme D, step 3, the 1-arylalkyl-2-oxo-3-arylmethyl compound of structure 23 is alkylated with an appropriate protected alcohol, $Pg_2O—(CH_2)_m—L_3$, to give an 1-arylalkyl-2-oxo-3-arylmethyl-3-(-protected-hydroxyalkyl) compound of structure 24.

An appropriate protected alcohol, $Pg_2O—(CH_2))_m—L_3$, is one in which m is as desired in the final product of formula (1) and the leaving group, $L_3$, is one which can be displaced by an anion derived from an appropriate 1-arylalkyl-2-oxo-3-arylmethyl compound of structure 23. Suitable leaving groups, $L_3$, include but are not limited to methanesulfonyl, chloro, bromo, and iodo. Suitable hydroxy protecting groups such as those described in *Protecting Groups in Organic Synthesis* by T. Greene are well known and appreciated in the art. In Reaction Scheme D, the use of t-butyldimethylsilyl is generally preferred.

For example, the 1-arylalkyl-2-oxo-3-arylmethyl compound of structure 23 is contacted with 1.0 to 1.2 molar equivalents of an appropriate protected alcohol, $Pg_2O\text{-}(CH_2)_m—L_3$. The reaction is carried out in the presence of an equimolar amount of a suitable base, such as sec-butyl lithium, n-butyl lithium, and lithium bis(trimethylsilyl)amide. The reaction is carried out in a solvent, such as tetrahydrofuran. The reaction is generally carried out at temperatures of from −78° C. to 0° C. Generally, the reactions require 1 to 72 hours. The product can be isolated and purified by techniques well known in the art, such as extraction, evaporation, trituration, chromatography, and recrystallization.

In Reaction Scheme D, step 4, the 1-arylalkyl-2-oxo-3-arylmethyl-3-(-protected-hydroxyalkyl) compound of structure 24 is deprotected to give an alcohol of structure 2 in which r is 1 and $G_3$ is —C(O)—. A deprotection reaction, such as the removal of hydroxy protecting groups utilizing suitable protecting groups such as those described in *Protecting Groups in Organic Synthesis* by T. Greene is well known and appreciated in the art.

In Reaction Scheme D, optional step 5, the 1-arylalkyl-2-oxo-3-arylmethyl-3-(-protected-hydroxyalkyl) compound of structure 24 is reduced to give an 1-arylalkyl-3-arylmethyl-3-(-protected-hydroxyalkyl) compound of structure 25.

This reaction is carried out as taught in reaction Scheme B, optional step 5 and may result in the removal of the protecting group Pg$_2$. When the protection group Pg$_2$ is removed the same or another protecting group Pg$_2$ may be introduced or, alternately, the steps that follow may be carried out on the unprotected hydroxy compound.

In Reaction Scheme D, step 6, an appropriate 1-arylalkyl-3-arylmethyl-3-(-protected-hydroxyalkyl) compound of structure 25 is debenzylated to give a 3-arylmethyl-3-(ω-protected-hydroxyalkyl) compound of structure 26. An appropriate 1-arylalkyl-3-arylmethyl-3-(ω-protected-hydiroxyalkyl) compound of structure 25 is one in which n is 0 and Ar$_2$ is phenyl or 4-methoxyphenyl; and m, q, and Ar$_1$ are as desired in the final product of formula (1) or Ar$_1$ gives rise after deprotection to an Ar$_1$ as desired in the final product of formula (1).

For example, and an appropriate 1-arylalkyl-3-arylmethyl-3-(ω-protected-hydroxyalkyl) compound of structure 25 is hydrogenated. The reaction is carried out in a suitable solvent, such as ethanol, methanol, or water. The reaction is carried out in the presence of a suitable catalyst, such as 20% palladium hydroxide-on-carbon. The reaction is carried out at pressures of from atmospheric pressure to about 100 psi. When the reaction is carried out at a pressure greater than atmospheric pressure, the reaction is carried out in a suitable pressure apparatus, such as a Parr apparatus or an autoclave. The reaction is generally carried out at temperatures of from 50° C. to 0° C. Generally, the reactions require 1 to 72 hours. The product can be isolated and purified by techniques well known in the art, such as filtration, evaporation, trituration, chromatography, and recrystallization.

In Reaction Scheme D, step 7, the 3-arylmethyl-3-(ω-protected-hydroxyalkyl) compound of structure 26 is aroylated as taught in Reaction Scheme B, optional step 7 to give an 1-aroyl-3-arylmethyl-3-(ω-protected-hydroxyalkyl) compound of structure 27.

In Reaction Scheme D, step 8, the 1-aroyl-3-arylmethyl-3-(ω-protected-hydroxyalkyl) compound of structure 27 is deprotected, if required, to give an alcohol of structure 2 in which r is 1, G$_3$ is —CH$_2$—, and G$_2$ is —C(O)—. A deprotection reaction, such as the removal of hydroxy protecting groups utilizing suitable protecting groups such as those described in *Protecting Groups in Organic Synthesis* by T. Greene is well known and appreciated in the art.

Reaction Scheme E sets forth the preparation of alcohols of structure 2 in which r is 0 and G$_1$ is —CH$_2$— used as a starting material in Reaction Scheme A.1 and A.2. The reagents and starting materials are readily available to one of ordinary skill in the art. In Reaction Scheme E, all substituents, unless otherwise indicated, are as previously defined.

Reaction Scheme E

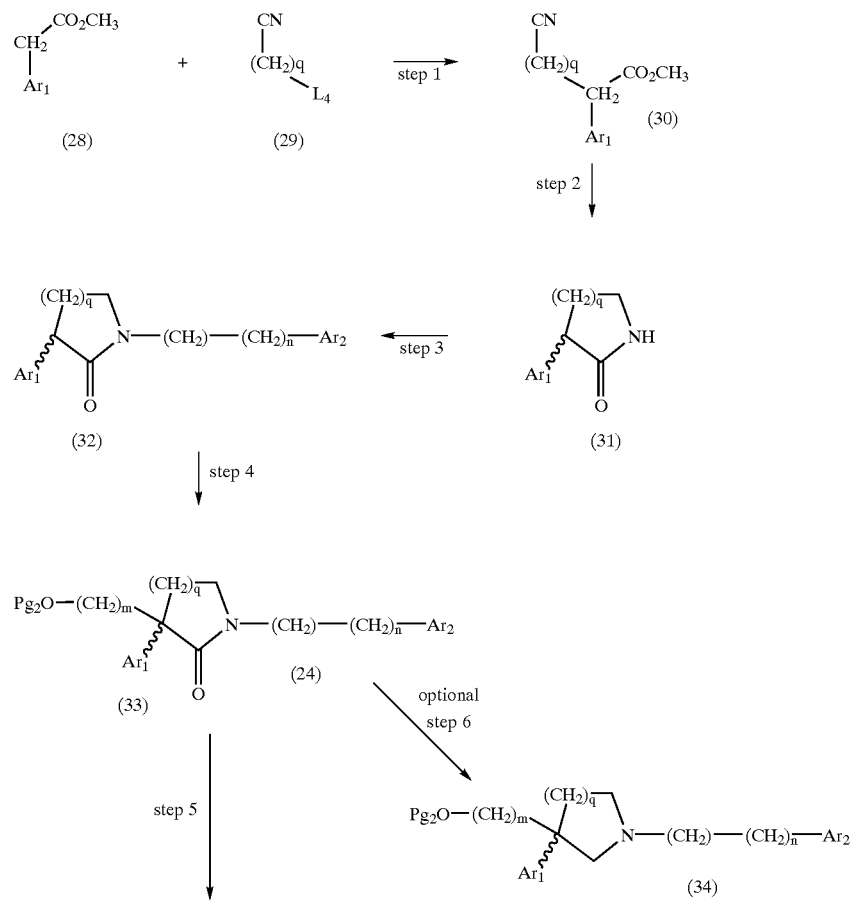

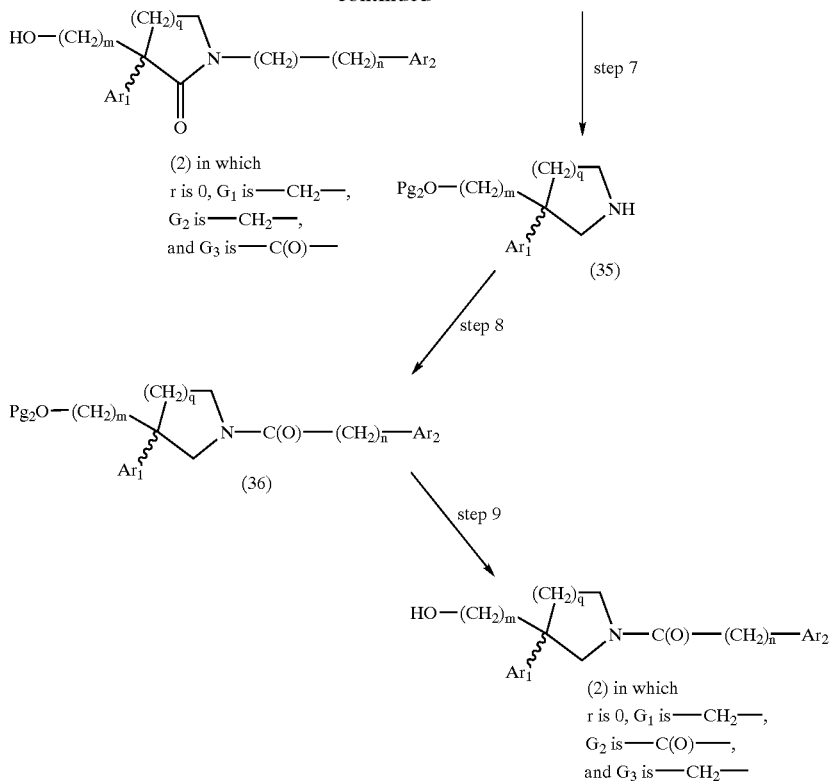

In Reaction Scheme E, step 1, an appropriate methyl arylacetate of structure 28 is alkylated with an appropriate ω-cyano alkylating agent of structure 29 to give a cyano ester of structure 30.

An appropriate methyl arylacetate of structure 28 is one in which $Ar_1$ is as desired in formula (1) or gives rise after deprotection to $Ar_1$ as desired in formula (1). An appropriate ω-cyano alkylating agent of structure 29 is one in which q is as desired in formula (1) and $L_4$ is chloro or bromo. Examples of appropriate ω-cyano alkylating agents of structure 29 include α-chloroacetonitrile, α-bromoacetonitrile, acrylonitrile, β-chloropropionitrile, and β-bromopropionitrile.

For example, an appropriate methyl arylacetate of structure 28 is contacted with from 0.8 to 1.2 molar equivalents of an appropriate ω-cyano alkylating agent of structure 29. The reaction is carried out in a suitable solvent, such as tetrahydrofuran. The reaction is carried out in the presence of a base, such as sodium hydride, lithium bis(trimethylsilyl)amide, or potassium bis(trimethylsilyl)amide. The reaction is generally carried out at temperatures of from 0° C. to −78° C. Generally, the reactions require 1 to 72 hours. The product can be isolated and purified by techniques well known in the art, such as extraction, evaporation, trituration, chromatography, and recrystallization.

In Reaction Scheme E, step 2, the cyano ester of structure 30 is reduced and cyclized to give a 2-oxo-3-aryl compound of structure 31 as taught in Reaction Scheme B, step 3.

In Reaction Scheme E, step 3, the 2-oxo-3-aryl compound of structure 31 is alkylated with an appropriate alkylating agent as taught in Reaction Scheme D, step 1, to give an 1-arylalkyl-2-oxo-3-aryl compound of structure 32.

In Reaction Scheme E, step 4, the 1-arylalkyl-2-oxo-3-aryl compound of structure 32 is alkylated with an appropriate protected alcohol, $Pg_2O$—$(CH_2)_m$—$L_3$, as taught in Reaction Scheme D, step 3, to give a 3-(ω-protected-hydroxyalkyl)-1-arylalkyl-2-oxo-3-aryl compound of structure 33.

In Reaction Scheme E, step 5, the 3-(ω-protected-hydroxyalkyl)-1-arylalkyl-2-oxo-3-aryl compound of structure 33 is deprotected to give an alcohol of structure 2 in which r is 0 and $G_3$ is —C(O)—. A deprotection reaction, such as the removal of hydroxy protecting groups utilizing suitable protecting groups such as those described in Protecting Groups in Organic Synthesis by T. Greene is well known and appreciated in the art.

In Reaction Scheme E, optional step 6, the 3-(ω-protected-hydroxyalkyl)-1-arylalkyl-2-oxo-3-aryl compound of structure 33 is reduced to give a 3-(ω-protected-hydroxyalkyl)-1-arylalkyl-3-aryl compound of structure 34. This reaction is carried out as taught in reaction Scheme 3, optional step 5 and may result in the removal of the protecting group $Pg_2$. When the protection group $Pg_2$ is removed the same or another protecting group $Pg_2$ may be introduced or, alternately, the steps that follow may be carried out on the unprotected hydroxy compound.

In Reaction Scheme E, step 7, an appropriate 3-(ω-protected-hydroxyalkyl)-1-arylalkyl-3-aryl compound of structure 34 is debenzylated as taught in Reaction Scheme D, step 6, to give a 3-(ω-protected-hydroxyalkyl)-3-aryl compound of structure 35. An appropriate 3-(ω-protected-hydroxyalkyl)-1-arylalkyl-3-aryl compound of structure 34 is one in which n is 0 and $Ar_2$ is phenyl or 4-methoxyphenyl; and m, q, and $Ar_1$ are as desired in the final product of formula (1) or $Ar_1$ gives rise after deprotection to an $Ar_1$ as desired in the final product of formula (1).

In Reaction Scheme E, step 8, a 3-(ω-protected-hydroxyalkyl)-3-aryl compound of structure 35 is aroylated as taught in Reaction Scheme B, optional step 7 to give an 1-aroyl-3-(ω-protected-hydroxyalkyl)-3-aryl compound of structure 36.

In Reaction Scheme E, step 9, the 1-aroyl-3-(ω-protected-hydroxyalkyl)-3-aryl compound of structure 36 is deprotected, if required, to give an alcohol of structure 2 in which r is 0, $G_3$ is —$CH_2$—, and $G_2$ is —C(O)—. A deprotection reaction, such as the removal of hydroxy protecting groups utilizing suitable protecting groups such as those described in *Protecting Groups in Organic Synthesis* by T. Greene is well known and appreciated in the art.

The following examples and preparations present typical syntheses of the compounds of formula (1). These examples are understood to be illustrative only and are not intended to limit the scope of the invention in any way.

PREPARATION 1.1
4-(1-(2-Ethoxyethyl)-1H-benzimidazol-2-yl)[1,4]diazepane

According to the method of R. Iemura et al., *J. Med. Chem.*, 29 1178–1183 (1986), combine 1-chloro-2-nitrobenzene (69.0 g, 440 mmol) and 2-aminoethyl ethyl ether (102.5 g, 1.15 mol) and heat to reflux. After 18 hours, cool and dilute the reaction mixture with ethyl acetate (400 mL). Extract with brine. Dry the organic layer over $Na_2SO_4$, filter, and evaporate in vacuo to give a residue. Chromatograph the residue on silica gel eluting with dichloromethane to give N-(2-ethoxyethyl)-2-nitroaniline.

Combine N-(2-ethoxyethyl)-2-nitroaniline (85.4 g, 406 mmol) and ethanol (300 mL). Add a solution of sodium hydroxide (6 g) in water (60 mL). Heat to reflux. Remove the heating and add portionwise zinc metal (106 g, 1.62 mol) at a rate such that the reaction is maintained at reflux. After the addition of zinc metal is complete stir for 30 minutes. Filter the reaction mixture and rinse with water. Extract the filtrate three times with ethyl acetate. Dry the combined organic layers over $Na_2SO_4$, filter, and evaporate in vacuo to give a residue. Chromatograph the residue on silica gel eluting with ethyl acetate to give 1-(2-ethoxyethyl)-1,2-phenylenediamine.

Combine 1-(2-ethoxyethyl)-1,2-phenylenediamine (55.4 g, 307 mmol) and urea (37.5 g, 624 mmol). Heat at 150° C. After 5 hour, cool to ambient temperature and stir. After 18 hours, partition the reaction mixture between ethyl acetate and water. Separate the layers and extract the aqueous layer three times with ethyl acetate. Combine the organic layers and extract with aqueous 1 M hydrochloric acid solution. Dry the organic layer over $Na_2SO_4$, filter, and evaporate in vacuo to give a residue. Chromatograph the residue on silica gel eluting with dichloromethane to give the 2-hydroxy-1-(2-ethoxyethyl)-1H-benzimidazole.

Combine 2-hydroxy-1-(2-ethoxyethyl)-1H-benzimidazole (36.4 g, 177 mmol) and phosphorous oxychloride (72 mL) and reflux. After 30 minutes, cool to ambient temperature and pour the reaction mixture onto crushed ice. Adjust the pH to about 9 using aqueous 50% sodium hydroxide solution. Extract three times with ethyl acetate. Combine the organic layers and extract with brine. Dry the organic layer over $Na_2SO_4$, filter, and evaporate in vacuo to give a residue. Chromatograph the residue on silica gel eluting with ethyl acetate to give the 2-chloro-1-(2-ethoxyethyl)-1H-benzimidazole.

Combine 2-chloro-1-(2-ethoxyethyl)-1H-benzimidazole (12.2 g, 54.2 mmol) and [1,4]diazepane (11.34 g, 113 mmol), 1,8-diazabicyclo[5.4.0]undec-7-ene (9 mL), and pyridine (90 mL). Heat to reflux. After 18 hours, cool to ambient temperature and evaporate in vacuo to give a residue. Partition the residue between aqueous 1 M sodium hydroxide solution and ethyl acetate. Separate the layers and extract the aqueous layer two times with ethyl acetate. Combine the organic layers, dry over $Na_2SO_4$, filter, and evaporate in vacuo to give a residue. Chromatograph the residue on silica gel eluting sequentially with 30% methanol/ethyl acetate and then 2% concentrated aqueous ammonia/methanol to give the title compound: $R_f$=0.26 (silica gel, 2% concentrated aqueous ammonia/methanol).

Alternately, combine 2-chloro-1-(2-ethoxyethyl)-1H-benzimidazole (15.56 g, 69.3 mmol) and [1,4]diazepane (13.89 g, 138.7 mmol), 1,8-diazabicyclo[5.4.0]undec-7-ene (12.34 mL, 83.1 minol), and pyridine (200 mL). Heat to reflux. After 18 hours, cool to ambient temperature and evaporate in vacuo to give a residue. Partition the residue between aqueous 1 M sodium hydroxide solution and dichloromethane. Separate the layers and extract the aqueous layer two times with dichloromethane. Combine the organic layers, extract with aqueous 1 M sodium hydroxide solution, water, and then brine. Dry the organic layer over $Na_2SO_4$, filter, and evaporate in vacuo to give a residue. Chromatograph the residue on silica gel eluting with 2% concentrated aqueous ammonia/methanol to give the title compound: $R_f$=0.26 (silica gel, 2% concentrated aqueous ammonia/methanol).

PREPARATION 1.2
4-(1-(2-Ethoxyethyl)-1H-benzimidazol-2-yl)[1,4]diazepane

Combine 2-chloro-1H-benzimidazole (21.1.4 g, 138.4 mmol) and dimethylformamide (200 mL). Add portionwise, sodium hydride (24.0 g, 60% in oil, 153.3 mmol). After 15 minutes, add 2-chloroethyl ethyl ether (21.9 g, 201,5 mmol). Heat to 60° C. After 18 hours, cool the reaction mixture and dilute with ethyl acetate. Extract with a saturated aqueous sodium bicarbonate solution, water, and then brine. Dry the organic layer over $MgSO_4$, filter, and evaporate in vacuo to give a residue. Chromatograph the residue on silica gel eluting sequentially with 10% ethyl acetate/hexane and then 30% ethyl acetate hexane to give the 2-chloro-1-(2-ethoxyethyl)-1H-benzimidazole: $R_f$=0.74 (silica gel, 7/3 ethyl acetate/hexane).

Combine 2-chloro-1-(2-ethoxyethyl)-1H-benzimidazole (22.3 g, 99.4 mmoL), 1-methyl[1,4]diazepane (19 mL, 152.8 mmol), and triethylamine (75 mL). Heat to 70° C. After 18 hours, add 1-methyl[1,4]diazepane (10 mL) and continue to heat at reflux. After 96 hours, cool to ambient temperature and partition the reaction mixture between water and ethyl acetate. Separate the layers and extract the organic layer with a saturated aqueous sodium bicarbonate solution and then brine. Dry the organic layer over $MgSO_4$, filter, and evaporate in vacuo to give a residue. Chromatograph the residue on silica gel eluting sequentially with 50% ethyl acetate/hexane and then 10% methanol/dichloromethane to give 1-methyl-4-(1-(2-ethoxyethyl)-1H-benzimidazol-2-yl)[1,4]diazepane: $R_f$=0.52 (silica gel, dichloromethane/methanol/concentrated aqueous ammonia, 90/10/0.1).

Combine 1-methyl-4-(1-(2-ethoxyethyl)-1H-benzimidazol-2-yl)[1,4]diazepane (1.79 g, 5.9 mmol) and ethyl chloroformate (0.75 mL, 7.8 mmol) in toluene (20 mL). Heat to 80° C. After 2 hours, cool the reaction mixture and dilute with ethyl acetate. Extract with a saturated aqueous sodium bicarbonate solution, dry the organic layer over $MgSO_4$, filter, and evaporate in vacuo to give 1-ethoxycarbonyl-4-(1-(2-ethoxyethyl)-1H-benzimidazol-2-yl)[1,4]diazepane: $R_f$=0.87 (silica gel, dichloromethane/methanol, 90/10).

Combine 1-ethoxycarbonyl-4-(1-(2-ethoxyethyl)-1H-benzimidazol-2-yl)[1,4]diazepane (17.2 g, 47.6 mmol), hydrazine hydrate (40 mL), and potassium hydroxide (40.7 g, 725 mmol) in ethylene glycol (150 mL). Heat to reflux. After 5 hours, cool the reaction mixture and dilute with water (500 mL). Extract three times with dichloromethane. Combine the dichloromethane layers and extract with a saturated aqueous sodium bicarbonate solution and then brine. Dry the organic layer over MgSO$_4$, filter, and evaporate in vacuo to give the title compound: R$_f$=0.25 (silica gel, dichloromethane/methanol, 90/10).

PREPARATION 2
4-(1-(2-Ethoxyethyl)-1H-benzimidazol-2-yl)[1,4]diazepane Hydriodic Acid Salt Combine 4-(1-(2-ethoxyethyl)-1H-benzimidazol-2-yl)[1,4]diazepane (1.30 g), 48% hydriodic acid (10 mL), ethanol (10 mL), and diethyl ether (80 mL) and stir. After 30 minutes add diethyl ether, (800 mL) and continue to stir to give a solid. Collect the solid by filtration and dry in vacuo to give the title compound: mp; 156–163° C.

Alternately, combine 4-(1-(2-ethoxyethyl)-1H-benzimidazol-2-yl)[1,4]diazepane (18.42 g, 63.9 mmol), 57% hydriodic acid (8.30 mL), ethanol (80 mL) and stir. After 2.5 hours, cool to give a solid. Collect the solid by filtration, rinse with diethyl ether, and dry in vacuo to give the title compound.

EXAMPLE 1
1-(3,4,5-Trimethoxybenzoyl)-3-(2-(4-(1-(2-ethoxyethyl)-1H-benzimidazol-2-yl)[1,4]diazepan-1-yl)ethyl)-3-(3,4-dimethoxyphenyl)pyrrolidine

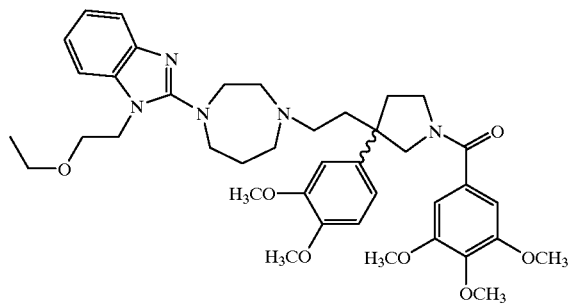

1.1 Synthesis of 3-cyano-3-(3,4-dimethoxyphenyl)pentanedioic diethyl ester

Combine 3,4-dimethoxyphenylacetonitrile (20 g, 113 mmol) and anhydrous tetrahydrofuran (100 mL). Cool in a dry-ice/acetone bath. Add dropwise a solution of sodium bis(trimethylsilyl)amide (226 mL, 1 M in THF, 226 mmol). When the addition is complete warm the reaction mixture to 10° C. and allow to stir for 15 minutes. Cool in a dry-ice/acetone bath, add dropwise ethyl bromoacetate (37.7 g, 226 mmol). When the addition of ethyl bromoacetate is complete, warm the reaction mixture to ambient temperature. After 18 hours, partition the reaction mixture between diethyl ether and water. Extract the organic layer with water and saturated aqueous solution of ammonium chloride. Separate the organic layer, dry over MgSO$_4$, filter, and concentrate inuacuo to obtain a residue. Chromatograph the residue on silica gel eluting with 33% ethyl acetate/hexane. Remove residual solvent in vacuo at 82° C. to give the title compound: R$_f$=0.37 (silica gel, 33% ethyl acetate/hexane). Elemental Analysis calculated for C$_{18}$H$_{23}$NO$_6$: C$_{61.88}$; H 6.64; N 4.01; Found: C$_{61.79}$; H 6.62; N 3.91.

1.2 Synthesis of 3-(3,4-dimethoxyphenyl)-5-oxopyrrolidin-3-yl)acetic acid ethyl ester Combine 3-cyano-3-(3,4-dimethoxyphenyl)pentanedioic diethyl ester (1.3 g, 3.24 mmol) and cobalt(II)chloride hexahydrate (1.54 g, 6.48 mmol) in methanol (50 mL). While maintaining the temperature at or below 20° C. with an ice-bath, add portionwise sodium borohydride (2.17 g, 57 mmol). After the addition is complete, allow the reaction mixture to stand at ambient temperature for 18 hours. Evaporate the reaction mixture in vacuo to obtain a residue. Partition the residue between dichloromethane and 1M hydrochloric acid solution. Extract the aqueous layer several times with dichloromethane, combine the organic layers, dry over Na$_2$SO$_4$, filter, and concentrate in vacuo to obtain a residue. Chromatograph the residue on silica gel eluting with 20/1 ethyl acetate/methanol. Remove residual solvent: in vacuo at 82° C. to give the title compound: R$_f$=0.74 (silica gel, 5/1 ethyl acetate/methanol); mp; 116–118° C. Elemental Analysis calculated for C$_{16}$H$_{21}$NO$_5$: C, 62.53; H, 6.89; N, 4.56; Found: C, 62.52; H, 6.85; N, 4.50.

1.3 Synthesis of 3-(3,4-dimethoxyphenyl)-3-(2-hydroxyethyl)pyrrolidine

Combine lithium aluminum hydride (0.99 g, 26.0 mmol) and anhydrous tetrahydrofuran (20 mL). Slowly, add (3-(3,4-dimethoxyphenyl)-5-oxopyrrolidin-3-yl)acetic acid ethyl ester (2.0 g, 6.5 mmol) as a solution in anhydrous tetrahydrofuran (40 mL). After the addition is complete, heat to reflux. After 18 hours, cool in an ice-bath. Add water (1 mL) dropwise at such a rate that the temperature of the reaction mixture does not rise above 20° C. Cool to 10° C., add 15% sodium hydroxide solution (1.0 mL). Add water (3 mL). After 15 minutes, filter the reaction mixture and concentrate the filtrate in vacuo to give the title compound: R$_f$=0.68 (silica gel, 5/1 ethyl acetate/methanol).

Prepare an analytical sample as follows: Combine 3-(3,4-dimethoxyphenyl)-3-(2-hydroxyethyl)pyrrolidine (0.51 g, 2.02 mmol) and oxallic acid (0.18 g, 2.00 mmol) in tetrahydrofuran (70 mL). After 18 hours, filter and dry. Triturate with diethyl ether (100 mL), filter and dry in vacuo at 81° C. to give the title compound as its oxalate salt: mp; 140–142° C. Elemental Analysis calculated for C$_{14}$H$_{21}$NO$_3$•C$_2$H$_2$O$_4$: C, 56.30; H, 6.79; N, 4.10; Found: C, 56.15; H, 6.76; N, 4.13.

1.4.1 Synthesis of 1-(3,4,5-trimethoxybenzoyl)-3-(3,4-dimethoxyphenyl)-3-(2-hydroxyethyl)pyrrolidine Combine 3-(3,4-dimethoxyphenyl)-3-(2-hydroxyethyl)pyrrolidine (2.27 g, 9.03 mmol) and N-methylmorpholine (2.48 mL, 22.6 mmol) in anhydrous dichloromethane (100 mL). Cool the reaction mixture to −5° C. with an salt-ice bath. Slowly, add 3,4,5-trimethoxybenzoyl chloride (2.2 g, 9.5 mmol) as a solution in dichloromethane (30 mL). Warm to ambient temperature. After 18 hours, extract the reaction mixture with a saturated solution of potassium carbonate. Dry the organic layer over Na$_2$SO$_4$, filter, and concentrate in vacuo to obtain a residue. Chromatograph the residue on silica gel eluting with 95% dichloromethane/methanol to obtain a residue. Combine the residue and dichloromethane (100 mL), and extract 3 times with 1M hydrochloric acid solution and saturated solution of potassium carbonate. Dry the organic layer over Na$_2$SO$_4$, filter, and concentrate in vacuo to obtain a residue. Chromatograph the residue on silica gel eluting with 20/1 ethyl acetate/methanol to obtain an oil: R$_f$=0.14 (silica gel, 20/1 ethyl acetate/methanol). Dry in vacuo at 110° C. to obtain the title compound as a glass: mp; 60–62° C. Elemental Analysis calculated for C$_{24}$H$_{31}$NO$_7$: C, 64.70; H, 7.01; N, 3.14; Found C, 64.40; H, 7.21; N, 2.85.

1.4.2 Synthesis of 1-(3,4,5-trimethoxybenzoyl)-3-(3,4-dimethoxyphenyl)-3-(2-hydroxyethyl)pyrrolidine Combine 3-(3,4-dimethoxyphenyl)-3-(2-hydroxyethyl)pyrrolidine (5.34 g, 21.2 mmol) and sodium carbonate (1.24 g, 11.7 mmol) in ethyl acetate/water (4/1) (120 mL). Cool the reaction mixture to −5° C. with an salt-ice bath. Slowly, add 3,4,5-trimethoxybenzoyl chloride (5.14 g, 22.3 mmol)

as a solution in ethyl acetate (60 mL) at a rate such that the temperature of the reaction mixture does not rise above 0° C. Maintain the reaction temperature at about 0° C. After 18 hours, separate the organic layer. Extract the organic layer twice with 1 M aqueous hydrochloric acid solution, saturated solution of sodium bicarbonate, water and a saturated solution of sodium chloride. Dry the organic layer over $Na_2SO_4$, filter, and concentrate in vacuo to obtain a residue. Combine the aqueous layers and neutralize with a saturated solution of sodium bicarbonate. Extract the neutralized aqueous layers with dichloromethane. Dry the organic layer over $Na_2SO_4$, filter, and concentrate in vacuo to obtain another residue. Combine the residues and chromatograph on silica gel eluting with 10/1 dichloromethane/methanol to obtain a residue. Combine the residue and dichloromethane (100 mL), and extract 3 times with 1M hydrochloric acid solution and saturated solution of potassium carbonate. Dry the organic layer over $Na_2SO_4$, filter, and concentrate in vacuo to obtain the title compound: $R_f$=0.23 (silica gel, 10/1 ethyl acetate/methanol).

1.5 Synthesis of 1-(3,4,5-trimethoxybenzoyl)-3-(3,4-dimethoxyphenyl)-3-(2-methanesulfonyloxyethyl) pyrrolidine Combine 1-(3,4,5-trimethoxybenzoyl)-3-(3,4-dimethoxyphenyl)-3-(2-hydroxyethyl)pyrrolidine (0.43 g, 0.97 mmol), triethylamine (3.3 mL, 2.4 mmol), and anhydrous dichloromethane (30 mL). Cool the reaction mixture to −5° C. with an salt-ice bath. Slowly, add methanesulfonyl chloride (0.082 mL, 1.06 mmol) at such a rate that the temperature of the reaction mixture does not rise above 2° C. Warm to ambient temperature. After 18 hours, quench the reaction by the addition of ice. Separate the organic layer and extract 3 times with 1M hydrochloric acid solution and 2 times with a saturated solution of sodium bicarbonate. Dry the organic layer over $Na_2SO_4$, filter, and concentrate in vacuo to obtain the title compound: $R_f$=0.48 (silica gel, 20/1 ethyl acetate/methanol).

1.6 Synthesis of 1-(3,4,5-trimethoxybenzoyl)-3-(2-(4-(1-(2-ethoxyethyl)-1H-benzimidazol-2-yl)[1,4]diazepan-1-yl)ethyl)-3-(3,4-dimethoxyphenyl)pyrrolidine Combine 1-(3,4,5-trimethoxybenzoyl)-3-(3,4-dimethoxyphenyl)-3-(2-methanesulfonyloxyethyl) pyrrolidine (0.86 g, 1.64 mmol), 4-(1-(2-ethoxyethyl)-1H-benzimidazol-2-yl)[1,4]diazepane (0.57 g, 1.97 mmol), sodium iodide (0.25 g, 1.64 mmol), and N,N-diisopropylethylamine (0.42 g, 3.3 mmol) in acetonitrile (9 mL). Heat to reflux. After 3 days, cool and dilute the reaction mixture ethyl acetate. Extract three times with a saturated aqueous ammonium chloride solution, twice with a saturated aqueous sodium bicarbonate solution, and then brine. Dry the organic layer over $Na_2SO_4$, filter, and concentrate in vacuo to obtain a residue. Chromatograph the residue on silica gel eluting with 1/1 ethyl acetate/methanol to give, after drying in vacuo at 70° C., the title compound: mp; 45–50° C. Elemental Analysis calculated for $C_{40}H_{53}N_5O_7 \cdot 0.9\ H_2O$: C, 65.56; H, 7.55; N, 9.56; Found: C, 65.57; H, 7.38; N, 9.63.

1.7 Synthesis of 1-(3,4,5-trimethoxybenzoyl)-3-(2-(4-(1-(2-ethoxyethyl)-1H-benzimidazol-2-yl)[1,4]diazepan-1-yl)ethyl)-3-(3,4-dimethoxyphenyl)pyrrolidine fumaric acid salt Combine 1-(3,4,5-trimethoxybenzoyl)-3-(2-(4-(1-(2-ethoxyethyl)-1H-benzimidazol-2-yl)[1,4]diazepan-1-yl)ethyl)-3-(3,4-dimethoxyphenyl)pyrrolidine (0.29 g, 0.40 mmol), fumaric acid (0.14 g, 1.21 mmol), and ethyl acetate (100 mL). Heat to reflux. After 18 hours, cool to ambient temperature and evaporate in vacuo to give a residue. Triturate the residue with diethyl ether (100 mL) with stirring to give a solid. Collect the solid by filtration and dry in vacuo at 65° C. to give the title compound; mp; 90–100° C. Elemental Analysis calculated for $C_{40}H_{53}N_5O_7 \cdot 2C_4H_4O_4 \cdot 1.6\ H_2O$: C, 59.03; H, 6.62; N, 7.17; Found: C, 59.18; H, 6.43; N, 7.18.

EXAMPLE 2

1-(3,4,5-Trimethoxybenzoyl)-3-(2-(4-(1-(2-ethyoxyethyl)-1H-benzimidazol-2-yl)[1,4]diazepan-1-yl)ethyl)-3-(3,4-dichlorophenyl)pyrrolidine

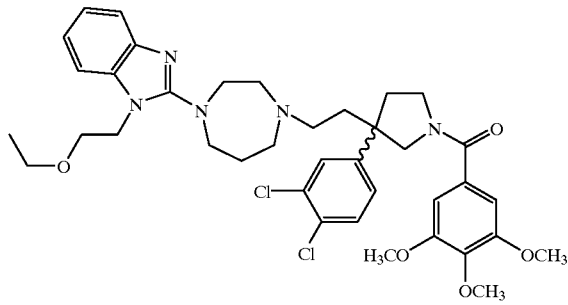

2.1.1 Synthesis of 3-cyano-3-(3,4-dichlorophenyl) pentanedioic acid diethyl ester Prepare by the method of Example 1.1 using 3,4-dichlorophenylacetonitrile (30.0 g, 0.161 mol). Purify by recrystallization from diethyl ether to give the title compound: $R_f$=0.28 (silica gel, 20% ethyl acetate/hexane), mp; 68–69° C. Elemental Analysis calculated for $C_{16}H_{17}C_{12}NO_4$: C, 53.65; H, 4.78; N, 3.91; Found: C, 53.69; H, 4.79; N, 3.93.

2.1.2 Synthesis of 3-cyano-3-(3,4-dichlorophenyl) pentanedioic acid diethyl ester Cool a solution of sodium bis(trimethylsilyl)amide (480 lb, 1 M in THF) to about −10° C. and stir. Add a solution of 3,4-dichlorophenylacetonitrile in methyl t-butyl ether (34.5% by weight, 125 lb of solution) at such a rate that the temperature of the reaction mixture does not rise above about 10° C. Combine ethyl bromoacetate (94 lb) and methyl t-butyl ether (about 125 lb) and cool to about −18° C. and then add the solution prepared above over 60–90 minutes. After the reaction is complete, as determined by chromatography, add water (18 gal). Add a 12 M aqueous hydrochloric acid solution until the pH is about 4. If the pH falls below 3, use 20% aqueous sodium hydroxide solution to raise the pH to about 4. Separate the layers and extract the organic layer with brine. Evaporate in vacuo at about 40° C. to give a residue. Combine the residue and isopropanol (about 45 lb) and evaporate in vacuo at about 40° C. to give a residue. Add isopropanol (190 lb), warm to about 35° C., and then cool to about −10° C. to give a solid. Collect the solid by filtration, rinse with cold isopropanol, and centrifuge to give the title compound as a wet cake containing isopropanol.

2.2.1 Synthesis of (3-(3,4-dichlorophenyl)-5-oxopyrrolidin-3-yl)acetic acid ethyl ester Prepare by the method of Example 1.2 using 3-cyano-3-(3,4-dichlorophenyl)pentanedioic acid diethyl ester (10 g, 28 mmol). Purify by chromatography on silica gel eluting sequentially with 3% methanol/dichloromethane and then 6% methanol/dichloroinethane to give the title compound.

2.2.2 Synthesis of (3-(3,4-dichlorophenyl)-5-oxopyrrolidin-3-yl)acetic acid ethyl ester Combine 3-cyano-3-(3,4-dichlorophenyl)pentanedioic acid diethyl ester (32 g, 89 mmol) and ethanol (150 mL) in a Parr bottle. Add Raney nickel (100 g) and an aqueous concentrated ammonia solution (40 mL). Hydrogenate at 50 psi for 24 h. Filter through a celite pad and rinse the solids with ethanol. Evaporate the filtrate in vacuo to obtain a residue. Chromatograph the residue on silica gel eluting with 6% methanol/dichloromethane to give the title compound: $R_f$=0.34 (silica gel, 6% methanol/dichloromethane); mp; 87–90° C. Elemental Analysis calculated for $C_{14}H_{15}C_{12}NO_3$: C, 53.18; H, 4.78; N, 4.43; Found: C, 53.34; H, 4.71; N, 4.51.

2.2.3 Synthesis of (3-(3,4-dichlorophenyl)-5-oxopyrrolidin-3-yl)acetic acid ethyl ester Combine Raney nickel (24 lb) and an aqueous concentrated ammonia solution (19 lb). Add a solution of 3-cyano-3-(3,4-dichlorophenyl)pentanedioic acid diethyl ester (15 lb) and ethanol (117 lb) in a pressure reactor. Hydrogenate at 200 psi and 35° C. After 20 hours, cool, vent the vessel, purge with nitrogen, and filter. Rinse the solids with ethanol. Evaporate the filtrate in vacuo to give a residue. Crystallize the residue by dissolving in ethyl acetate and triturate the solution with heptane to give a solid. Collect the solid to give the title compound. Elemental Analysis calculated for $C_{14}H_{15}C_{12}NO_3$: C 53.18; H 4.78; N 4.43; Found: C, 53.18; H, 4.72; N, 4.46.

2.2.4 Synthesis of (3-(3,4-dichlorophenyl)-5-oxopyrrolidin-3-yl)acetic acid ethyl ester Combine 3-cyano-3-(3,4-dichlorophenyl)pentanedioic acid diethyl ester (6.7 kg, wet cake containing isopropanol, about 3% L.O.D.) and 3C ethanol (52 kg) in a pressure reactor. Add Raney nickel in water (17.5 kg, about 11 kg of active catalyst) and an aqueous concentrated ammonia solution (8.7 kg). Hydrogenate at 200 psi and 35° C. When the reaction is complete, cool, vent the reactor, and purge with nitrogen. Filter through a filter bag, rinse with ethanol, and then filter through a 0.2 micron cartridge filter, and rinse the solids with ethanol. Evaporate the filtrate in vacuo to give the title compound.

2.2.5 Synthesis of (3-(3,4-dichlorophenyl)-5-oxopyrrolidin-3-yl)acetic acid ethyl ester Combine Raney nickel (twice washed with water and twice washed with ethanol, 3.6 kg), 3-cyano-3-(3,4-dichlorophenyl)pentanedioic acid diethyl ester (1260 g, 3.51 mol), ethanol (9 L), and an aqueous concentrated ammonia solution (1.6 L) in a 5 gallon autoclave. Hydrogenate at 55 psi. After 20 hours, vent the vessel, purge with nitrogen, and filter. Rinse the solids with ethanol (about 1 L,). Evaporate the filtrate in vacuo to give a residue. Combine the residue and ethyl acetate (10 L) and extract twice with water (1 L) and then with brine. Dry the organic layer over $MgSO_4$, filter, and concentrate in vacuo to give a residue. Crystallize the residue from ethyl acetate (about 1.8 L) and heptane (about 7.2 L) to give a solid. Collect the solid to give the title compound: mp; 98–99° C.

2.3 Synthesis of 3-(3,4-dichlorophenyl)-3-(2-hydroxyethyl)pyrrolidine

Cool a solution of lithium aluminum hydride (450 mL, 1M in THF, 450 mmol) to −10° C. in a ice/acetone bath. Add dropwise, a solution of sulfuric acid (12 mL, 99.999%, 225.3 mmol) in THF (35 mL). (Use caution when adding the sulfuric acid to the THF and also when adding the sulfuric acid/THF solution to the lithium aluminum hydride solution). After the addition is complete, stir for 1 hour. Warm to ambient temperature and stir for 2 hours. Add dropwise, a solution of (3-(3,4-dichlorophenyl)-5-oxopyrrolidin-3-yl)acetic acid ethyl ester (23.2 g, 73.4 mmol) in THF (70 mL). Heat to 45–50° C. for 36 hours. Cool in an ice bath. Add dropwise, a solution of THF/water (1/1, 70 mL). Filter and rinse the filter cake with THF and dichloromethane, retain the filtrate. Combine the filter cake with THF/water/15% sodium hydroxide solution (1 L/70 mL/20 mL) and vigorously stir for 2 hours. Filter and combine the filtrate with the filtrate obtained above. Concentrate the combined filtrates in vacuo to obtain a residue. Dissolve the residue in dichloromethane and dry over $MgSO_4$, filter, and concentrate in vacuo to obtain a residue. Recrystallize the residue from diethyl ether to give the title compound: $R_f$=0.27 (silica gel, 9:1:0.2; dichloromethane/methanol/ammonium hydroxide); mp; 91–94° C. Elemental Analysis calculated for $C_{12}H_{15}Cl_2NO$: C,55.40; H, 5.81; N, 5.38; Found: C, 55.64; H, 5.88; N, 5.20.

2.4 Synthesis of 1-(3,4,5-trimethoxybenzoyl)-(3-(3,4-dichlorophenyl)-3-(2-hydroxyethyl)pyrrolidine Combine 3-(3,4-dichlorophenyl)-3-(2-hydroxyethyl) pyrrolidine (288 mg, 1.1 mmol) and 4-methylmorpholine (0.25 mL, 2.27 mmol) in dichloromethane (10 mL). Cool to −78° C. in a dry-ice/acetone bath. Add a solution of 3,4,5-trimethoxybenzoyl chloride (250 mg, 1.1 mmol) in dichloromethane (3 mL). Warm the reaction mixture to 0° C. After 1 hour, extract the reaction mixture with 1M hydrochloric acid solution and 5% sodium bicarbonate solution. Dry the organic layer over $MgSO_4$, filter, and concentrate in vacuo to give a residue. Chromatograph the residue on silica gel eluting sequentially with 50% ethyl acetate/hexane and 6% methanol/dichloromethane to give the title compound: $R_f$=0.38 (silica gel, 6% methanol/dichloromethane).

2.5.1 Synthesis of 1-(3,4,5-trimethoxybenzoyl)-3-(3,4-dichlorophenyl)-3-(2-methanesulfonyloxyethyl)pyrrolidine Prepare by the method of Example 1.5 using 1-(3,4,5-trimethoxybenzoyl)-3-(3,4-dichlorophenyl)-3-(2-hydroxyethyl)pyrrolidine to give the title compound: $R_f$=0.65 (silica gel, 6% methanol/dichloromethane).

2.5.2 Synthesis of 1-(3,4,5-trimethoxybenzoyl)-3-(3,4-dichlorophenyl)-3-(2-methanesulfonyloxyethyl)pyrrolidine Combine 1-(3,4,5-trimethoxybenzoyl)-3-(3,4-dichlorophenyl)-3-(2-hydroxyethyl)pyrrolidine (200 mg, 0.44 mmol) and N,N-diisopropylethylamine (0.17 mL, 0.97 mmol) in dichloromethane (25 mL). Cool in a ice-bath. Add dropwise, methanesulfonyl chloride (0.066 g, 0.57 mmol). After 2 hours, extract with 1 M hydrochloric acid solution and 5% sodium bicarbonate solution. Dry the organic layer over $MgSO_4$, filter, and concentrate in vacuo to give the title compound: $R_f$=0.42 (silica gel, 6% methanol/dichloromethane); mp; 64.0–66.0° C.

2.6 Synthesis of 1-(3,4,5-trimethoxybenzoyl)-3-(2-(4-(1-(2-ethoxyethyl)-1H-benzimidazol-2-yl)[1,4]diazepan-1-yl)ethyl)-3-(3,4-dichlorophenyl)pyrrolidine Prepare by the method of Example 1.6 using 1-(3,4,5-trimethoxybenzoyl)-3-(3,4-dichlorophenyl)-3-(2-methanesulfonyloxyethyl)pyrrolidine and 4-(1-(2-ethoxyethyl)-1H-benzimidazol-2-yl)[1,4]diazepane to give the title compound.

EXAMPLE 3
1-(3,4,5-Trimethoxybenzoyl)-3-(2-(4-(1-(2-ethoxyethyl)-1H-benzimidazol-2-yl)[1,4]diazepan-1-yl)ethyl)-3-phenylpyrrolidine

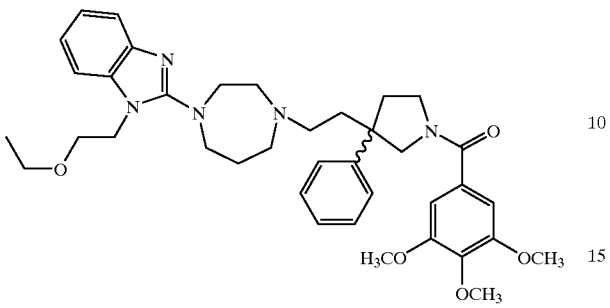

3.1.1 Synthesis of 3-cyano-3-phenylpentanedioic acid diethyl ester

Prepare by the method of Example 1.1 using phenylacetonitrile (5.85 g, 50.0 mmol). Purify by chromatography on silica gel eluting with 20% ethyl acetate in hexane to obtain the title compound: $R_f$=0.23 (silica gel, 20% ethyl acetate in hexane).

3.1.2 Synthesis of 3-cyano-3-phenylpentanedioic acid diethyl ester

Combine phenylacetonitrile (5.85 g, 50.0 mmol) and tetrahydrofuran (140 mL). Cool to about 5° C. Add dropwise, a solution of sodium bis(trimethylsilyl)amide (800 mL, 1 M in tetrahydrofuran, 800 mmol). When the addition is complete, warm the reaction mixture to ambient temperature and allow to stir for 1 hour. Transfer the above solution via cannula into a cooled (−8° C.) solution of ethyl bromoacetate (84.5 mL, 762 mmol) in tetrahydrofuran (500 mL) at such a rate that the temperature of the reaction mixture does not rise above about 20° C. Allow to stir at ambient temperature. After 18 hours, dilute with diethyl ether (1.5 L) and extract with saturated aqueous solution of ammonium chloride, then water, and then saturated aqueous solution of sodium chloride. Dry the organic layer over MgSO$_4$, filter, and concentrate in vacuo to obtain a residue. Distill the residue by bulb-to-bulb distillation to give the title compound: bp; 140–150° C. at 0.2 mm Hg.

3.1.3 Synthesis of 3-cyano-3-phenylpentanedioic acid diethyl ester

Combine phenylacetonitrile (175.5 g, 1.5 mol) and tetrahydrofuran (1.95 L). Cool to about 0° C. Add dropwise over about 15 minutes, a solution of sodium bis (trimethylsilyl)amide (3.2 L, 1 M in tetrahydrofuran, 3.2 mol). When the addition is complete, warm the reaction mixture to ambient temperature and allow to stir for 1 hour. Transfer the above solution over about 45 minutes into a cooled (about −20° C.) solution of ethyl bromoacetate (510 g, 3.05 mol) in tetrahydrofuran (1.95 L). Warm to ambient temperature and allow to stir. After 18 hours, dilute with diethyl ether (3 L) and water (1.5 L). Extract twice with saturated aqueous solution of ammonium chloride (2.25 L) and then brine. Dry the organic layer over MgSO$_4$, filter, and concentrate in vacuo to obtain a residue. Distill the residue by bulb-to-bulb distillation to give the title compound: bp; 180–190° C. at 30 mm of Hg. Elemental Analysis calculated for $C_{16}H_{19}NO_4$: C, 66.43; H, 6.62; N, 4.84. Found: C, 66.34; H, 6.57; N, 4.82.

3.2.1 Synthesis of (3-phenyl-5-oxopyrrolidin-3-yl)acetic acid ethyl ester

Prepared by the method of Example 2.2.2 using 3-cyano-3-phenylpentanedioic acid diethyl ester to give the title compound: $R_f$=0.60 (silica gel, 6% methanol/dichloromethane).

3.2.2 Synthesis of (3-phenyl-5-oxopyrrolidin-3-yl)acetic acid ethyl ester

Combine 3-cyano-3-phenylpentanedioic acid diethyl ester (93 g, 321 mmol) and ethanol (400 mL) in a 2 gallon pressure reactor. Add Raney nickel (280 g). Heat to 50° C. and charge with 200 psi of hydrogen. After 15 minutes, vent the reactor and add aqueous concentrated ammonia solution (120 mL) Charge the reactor with 200 psi of hydrogen. After 7 hours, vent the reactor and allow to stand for 18 hours. Filter through a celite pad and rinse the solids with ethanol. Evaporate the filtrate in vacuo to obtain a residue. Combine the residue and 1/5 diethyl ether/hexane (500 mL) and cool to −20° C. After 18 hours, decant and add 1/5 diethyl ether/hexane (500 mL) and cool to −20° C. to give a solid. Collect the solid by filtration and triturate with 1/5 diethyl ether/hexane (500 mL). Filter and dissolve in diethyl ether (300 mL) and add hexane (700 mL) to give a solid. Collect the solid by filtration and dry to give the title compound. Elemental Analysis calculated for $C_{14}H_{17}NO_3$: C, 68.00; H, 6.93; N, 5.66; Found: C, 67.63; H, 6.99; N, 5.81.

3.2.3 Synthesis of (3-phenyl-5-oxopyrrolidin-3-yl)acetic acid ethyl ester

Combine 3-cyano-3-phenylpentanedioic acid diethyl ester (396.6 g, 1.37 mol) and ethanol (4 L), and concentrated aqueous ammonia (530 mL), in a two gallon autoclave. Add Raney nickel (410 g). Heat to 24° C. and charge with 205 psi of hydrogen. After 26 hours, vent the reactor and purge with nitrogen. Filter the reaction mixture through a celite pad and rinse the solids with ethanol (1.5 L). Evaporate the filtrate in vacuo to give the title compound.

3.2.4 Synthesis of (3-phenyl-5-oxopyrrolidin-3-yl)acetic acid ethyl ester

Combine 3-cyano-3-phenylpentanedioic acid diethyl ester (243 g, 0.84 mol) and ethanol (2.5 L), concentrated aqueous ammonia (325 mL), and Raney nickel (250 g, prewashed three times with water) in a two gallon autoclave. Charge with 200 psi of hydrogen. Heat to 50° C. After 24 hours, vent the reactor and purge with nitrogen. Filter the reaction mixture through a celite pad and rinse the solids with ethanol (1 L). Evaporate the filtrate in vacuo to give the title compound.

3.3.1 Synthesis of 3-phenyl-3-(2-hydroxyethyl)pyrrolidine

Prepare by the method of Example 1.3 using (3-phenyl-5-oxopyrrolidin-3-yl)acetic acid ethyl ester (8.7 g, 35 mmol) to give, after recrystallization from dichloromethane/diethyl ether, the title compound: mp; 115.0–117.0° C.; $R_f$=0.03 (silica gel, 6% methanol/dichloromethane). Elemental Analysis calculated for $C_{12}H_{17}NO$: C, 75.36; H, 8.96; N, 7.32; Found: C, 75.78; H, 8.96; N, 7.45.

3.3.2 Synthesis of 3-phenyl-3-(2-hydroxyethyl)pyrrolidine

Combine (3-phenyl-5-oxopyrrolidin-3-yl)acetic acid ethyl ester (301 g, 1.25 mol) and tetrahydrofuran (3.5 L). Cool to about 5° C. Slowly, add portionwise over about 45 minutes a solution of lithium aluminum hydride in tetrahydrofuran (3.9 L, 1 M, 3.9 mol). After the addition is complete heat to 60° C. After 18 hours, cool in an ice-bath. Add water/tetrahydrofuran 1/1 (1.95 L) dropwise at such a rate that the temperature of the reaction mixture does not rise above 20° C. Dilute the reaction mixture with tetrahydrofuran (2.25 L) and stir. After 1.5 hours, filter the reaction mixture. Suspend the solids in diethyl ether (3 L) and filter. Combine the filtrates and concentrate the in vacuo to give a residue. Combine the residue and dichloromethane (4 L) and extract three times with water (1 L). Dry the organic layer over MgSO$_4$, filter, and concentrate in vacuo to obtain a solid. Triturate the solid with diethyl ether (0.3 L), collect by filtration, rinse with diethyl ether, and dry to give the title compound: $R_f$=0.12 (silica gel dichloromethane/methanol/concentrated aqueous ammonia, 9/1/0.1).

3.3.3 Synthesis of 3-phenyl-3-(2-hydroxyethyl)pyrrolidine

Combine (3-phenyl-5-oxopyrrolidin-3-yl)acetic acid ethyl ester (171 g, 0.69 mol) and tetrahydrofuran (2 L). Cool to about 5° C. Slowly, add over about 15 minutes a solution of lithium aluminum hydride in tetrahydrofuran (2.24 L, 1 M, 2.24 mol). After the addition is complete heat to about 60° C. After 18 hours, cool in an ice-bath. Slowly quench by adding a saturated aqueous solution of sodium potassium tartrate (208 mL). After the quench is complete, add $Na_2SO_4$ (100 g) and celite (150 g) and stir. After 3 hours, dilute the reaction mixture with tetrahydrofuran (2 L) and filter. Suspend the solids in diethyl ether (2 L) and and filter. Combine the filtrates and concentrate the in vacuo to give the title compound: mp; 106–110° C. $R_f$=0.2 (silica gel dichloromethane/methanol/concentrated aqueous ammonia, 9/1/0.1).

3.4.1 Synthesis of 1-(3,4,5-trimethoxybenzoyl)-3-phenyl-3-(2-hydroxyethyl)-pyrrolidine Prepared by the method of Example 1.4.1 using 3-phenyl-3-(2-hydroxyethyl)pyrrolidine to give the title compound: $R_f$=0.38 (silica gel, 6% methanol/dichloromethane).

3.4.2 Synthesis of 1-(3,4,5-trimethoxybenzoyl)-3-phenyl-3-(2-hydroxyethyl)pyrrolidine Prepared by the method of Example 1.4.2 using 3-phenyl-3-(2-hydroxyethyl)pyrrolidine to give the title compound: $R_f$=0.05 (silica gel, ethyl acetate).

3.5 Synthesis of 1-(3,4,5-trimethoxybenzoyl)-3-phenyl-3-(2-methanesulfonyloxyethyl)pyrrolidine Combine 1-(3,4,5-trimethoxybenzoyl)-3-phenyl-3-(2-hydroxyethyl)pyrrolidine (0.5 g, 1.3 mmol), N,N-diisopropylethylamine (0.5 mL, 2.9 mmol), and anhydrous dichloromethane (17 mL). Cool to 0° C. using an ice bath. Add methanesulfonyl chloride (201 mg, 1.36 mmol). After 2 hours, dilute the reaction mixture with dichloromethane and extract with a saturated solution of sodium bicarbonate. Dry the organic layer over $Na_2SO_4$, filter, and concentrate in vacuo to give the title compound: $R_f$=0.26 (silica gel, ethyl acetate).

3.6 Synthesis of 1-(3,4,5-trimethoxybenzoyl)-3-(2-(4-(1-(2-ethoxyethyl)-1H-benzimidazol-2-yl)[1,4]diazepan-1-yl)ethyl)-3-phenylpyrrolidine Combine 1-(3,4,5-trimethoxybenzoyl)-3-phenyl-3-(2-methanesulfonyloxyethyl)pyrrolidine (1.0 g, 2.2 mmol) and 4-(1-(2-ethoxyethyl)-1H-benzimidazol-2-yl)[1,4]diazepane (0.72 g, 2.2 mmol), and N,N-diisopropylethylamine (0.75 mL, 4.4 mmol) in acetonitrile (70 mL). Heat to reflux. After 72 hours, cool and pour the reaction mixture into dichloromethane (700 mL). Extract twice with water and then brine. Dry the organic layer over $Na_2SO_4$, filter, and concentrate in vacuo to obtain a residue. Chromatograph the residue on a short column of silica gel eluting with 25% methanol/0.6% concentrated aqueous ammonia/ethyl acetate to give the title compound: $R_f$=0.38 (silica gel; 25% methanol/0.6% concentrated aqueous ammonia/ethyl acetate).

3.7 Synthesis of 1-(3,4,5-trimethoxybenzoyl)-3-(2-(4-(1-(2-ethoxyethyl)-1H-benzimidazol-2-yl)[1,4]diazepan-1-yl)ethyl)-3-phenylpyrrolidine methanesulfonic acid salt Combine 1-(3,4,5-trimethoxybenzoyl)-3-(2-(4-(1-(2-ethoxyethyl)-1H-benzimidazol-2-yl)[1,4 )diazepan-1-yl)ethyl)-3-phenylpyrrolidine (1.45 g) and ethyl acetate (40 mL). Add dropwise a solution of methanesulfonic acid (0.42 g, 8.7 mmol) in ethyl acetate (5 mL). After 18 hours, add diethyl ether (100 mL). Decant solvent and add diethyl ether. Again, decant solvent, add diethyl ether, and evaporate in vacuo to give a solid. Dry the solid in vacuo at 56° C. to give the title compound: mp; 68–85° C.

EXAMPLE 4

1-(3,4,5-Trimethoxybenzoyl)-3-(2-(4-(1-(2-ethyoxyethyl)-1H-benzimidazol-2-yl)[1,4]diazepan-1-yl)ethyl)-3-(3,4-dichlorophenyl)pyrrolidine

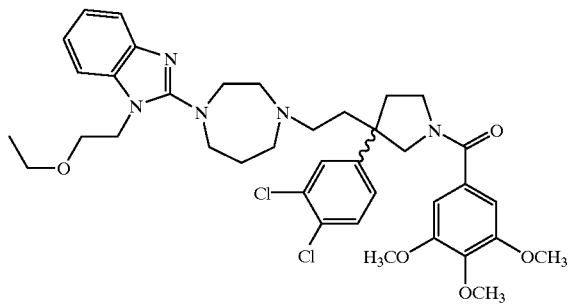

4.1 Synthesis of 1-(3,4,5-trimethoxybenzoyl)-3-(3,4-dichlorophenyl)-3-(2-oxoethyl)pyrrolidine Combine oxalyl chloride (0.32 g, 2.5 mmol) with dichloromethane (6 mL) and cool to −60° C. Add dropwise a solution of dimejthyl sulfoxide (0.39 g, 5.0 mmol) in dichloromethane (1 mL) while maintaining the temperature below −50° C. After addition is complete, stir for 5 minutes. Add a solution of 1-(3,4,5-trimethoxybenzoyl)-3-(3,4-dichlorophenyl)-3-(2-hydroxyethyl)pyrrolidine (1.03 g, 2.3 mmol) in dichloromethane (2 mL) and stir. After 15 minutes, cool the reaction to 78° C. and add dropwise triethylamine (15.6 mL, 11.3 mmol). Allow the reaction to warm to ambient temperature and stir for 30 minutes. Pour the reaction mixture into water. Extract three times with dichloromethane. Combine the organic layers and dry over $Na_2SO_4$, filter, and evaporate in vacuo to give a residue. Chromatograph the residue on silica gel eluting with ethyl acetate to give, after drying in vacuo at 90° C., the title compound: mp; 45–48° C. $R_f$=0.28 (silica gel, ethyl acetate).

4.2 Synthesis of 1-(3,4,5-trimethoxybenzoyl)-3-(2-(4-(1-(2-ethoxyethyl)-1H-benzimidazol-2-yl)[1,4]diazepan-1-yl)ethyl)-3-(3,4-dichlorophenyl)pyrrolidine Combine 1-(3,4,5-trimethoxybenzoyl)-3-(3,4-dichlorophenyl)-3-(2-oxoethyl)pyrrolidine (0.51 g, 1.13 mmol), 4-(1-(2-ethoxyethyl)-1H-benzimidazol-2-yl)[1,4] diazepane (0.40 g, 1.36 mmol), and silica gel (about 2 g) in methanol (24 mL) and stir. After 3 days, add sodium cyanoborohydride (0.71 g, 11.3 mmol) and 3 Å molecular sieves (about 12 g) and stir under an inert atmosphere. After 18 hours, add a solution of 2 M sodium hydroxide and dichloromethane and stir. After 18 hours, filter, separate the layers in the filtrate, and extract the organic layer with brine. Dry the organic layer over $Na_2SO_4$, filter, and evaporate in vacuo to give a residue. Chromatograph the residue on silica gel eluting with 1/1 ethyl acetate/methanol to give, after drying in vacuo at 82° C., the title compound: mp; 55–65° C. $R_f$=0.36 (silica gel, 1/1 ethyl acetate/methanol). Elemental Analysis calculated for $C_{38}H_{47}C_{12}N_5O_5$: C, 62.98; H, 6.54; N, 9.66; Found: C, 62.65; H, 6.65; N,9.51.

EXAMPLE 5
(R)-1-(3,4,5-Trimethoxybenzoyl)-3-(2-(4-(1-(2-ethoxyethyl)-1H-benzimidazol-2-yl)[1,4]diazepan-1-yl)ethyl)-3-(3,4-dichlorophenyl)pyrrolidine

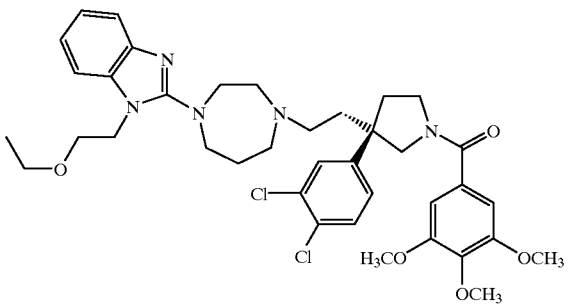

5.1.1 Resolution of (S)-3-(3,4-dichlorophenyl)-3-(2-hydroxyethyl)pyrrolidine (R,R)-di-p-anisoyltartaric acid salt and (R)-3-(3,4-dichlorophenyl)-3-(2-hydroxyethyl)pyrirolidine (R,R)-di-p-anisoyltartaric acid salt Combine 3-(3,4-dichlorophenyl)-3-(2-hydroxyethyl)pyrrolidine (1.0 g, 38.5 mmol) and butanone. Add a solution of (R,R)-di-p-anisoyltartaric acid (1.6 g, 38.0 mmol) in butanone (80 mL). Heat to reflux. After 15 minutes, cool to ambient temperature and then cool further in an salt-ice bath. Filter the solid that forms and rinse with butanone. Recrystallize the solid from water/methanol to give (S)-(−)-3-(3,4-dichlorophenyl)-3-(2-hydroxyethyl)pyrrolidine (R,R)-di-p-anisoyltartaric acid salt: mp; 201–204° C. (dec). $[\alpha]_D^{20}$= 18.9° (c=0.60, dimethylsulfoxide). X-ray diffraction analysis of a single crystal confirms the (S)-configuration. Analysis on HPLC, on an analytical sample of the free amine obtained by extraction, using a CHIRALPAK AD 25 cm×0.46 cm column eluting with pentane/methanol/triethylamine (80/10/0.1) with a flow rate of 1.0 mL/minute indicates an enantiomeric excess of 96%, (96% ee), retention time of the (S)-isomer 11.2 minutes, retention time of the (R)-isomer 14.5 minutes.

5.1.2 Resolution of (S)-3-(3,4-dichlorophenyl)-3-(2-hydroxyethyl)pyrrolidine (R,R)-di-p-anisoyltartaric acid salt and (R)-3-(3,4-dichlorophenyl)-3-(2-hydroxyethyl)pyrrolidine hydrochloric acid salt Combine (R,R)-di-p-anisoyltartaric acid (0.8 g, 19 mmol) and aqueous 12 M hydrochloric acid solution (0.16 mL, 19 mmol) in water/methanol (10 mL)/(10 mL). Heat to reflux. Add dropwise, a solution of 3-(3,4-dichlorophenyl)-3-(2-hydroxyethyl)pyrrolidine (1.0 g, 38.5 mmol) in methanol (10 mL). After 15 minutes, slowly cool to ambient temperature. Filter the solid that forms and rinse with water to give (S)-3-(3,4-dichlorophenyl)-3-(2-hydroxyethyl)pyrrolidine (R,R)-di-p-anisoyltartaric acid: mp; 201–204° C. (dec). Analysis by HPLC, as described in Example 5.1.1 indicates an enantiomeric excess of 97%, (97% ee).

5.1.3 Synthesis and resolution of (S)-3-(3,4-dichlorophenyl)-3-(2-hydroxyethyl)pyrrolidine (R,R)-di-p-anisoyltartaric acid salt Combine (3-(3,4-dichlorophenyl)-5-oxopyrrolidin-3-yl)-acetic acid ethyl ester (40 lb) and tetrahydrofuran (260 lb). Purge the vessel with nitrogen. Add a solution of borane dimethylsulfide complex (38 lb, 2 M solution in tetrahydrofuran). Heat to reflux. After 60 hours, distill until the internal temperature rises to about 70° C. and then slowly quench the reaction with methanol (650 lb). Add water (650 lb). Add methanesulfonic acid (16 lb). Heat to reflux and remove the distillate to remove most of the residual tetrahydrofuran. Combine methanol (about 18 gal) and (R,R)-di-p-anisoyltartaric acid (32 lb). Heat to reflux and transfer to the vessel containing the above residue. Add seed crystals and slowly cool to 10° C. to give a solid. Collect the solid and combine methanol (145 gal) and water (145 gal). Heat to reflux. After 1 hour, slowly cool to 10° C. to give a solid. Collect the solid to give, after drying, the title compound.

5.1.4 Resolution to give (S)-1-(3,4,5-trimethoxybenzoyl)-3-(3,4-dichlorophenyl)-3-(2-hydroxyethyl)pyrrolidine Combine 1-(3,4,5-trimethoxybenzoyl)-3-(3,4-dichlorophenyl)-3-(2-hydroxyethyl)pyrrolidine (4.5 g, 9.9 mmol) and dichloromethane/pyridine (70 mL, 6/1). Add acetic anhydride (1.04 mL, 11.0 mmol) and 4-dimethylaminopyridine (50 mg, 0.41 mmol). After 2 hours, concentrate the reaction mixture in vacuo to obtain a residue. Dissolve the residue in ethyl acetate and extract with 1M hydrochloric acid solution (2×200 mL), saturated sodium bicarbonate solution, and saturated sodium chloride solution. Dry the organic layer over $MgSO_4$, filter, and concentrate in vacuo to obtain a residue. Chromatograph the residue on silica gel eluting with ethyl acetate to give 1-(3,4,5-trimethoxybenzoyl)-3-(3,4-dichlorophenyl)-3-(2-acetoxyethyl)pyrrolidine: $R_f$=0.38 (silica gel, ethyl acetate). Elemental Analysis calculated for $C_{24}H_{27}Cl_2NO_6$: C 58.07; H 5.48; N 2.82; Found: C, 57.67; H, 5.46; N, 2.84.

Combine 1-(3,4,5-trimethoxybenzoyl)-3-(3,4-dichlorophenyl)-3-(2-acetoxyethyl)pyrrolidine (6.6 g, 13.3 mmol) and dichloromethane (100 mL). Add silica gel (32 g). Concentrate the slurry in vacuo to give a residue. Suspend the residue in phosphate buffer (800 mL, 0.1 M, pH=7.5, the buffer was prepared with 11.5 g $H_3PO_4$ (85%) diluted to 1 L with deionized water and then adjusting the pH with solid potassium hydroxide pellets to 7.5) to obtain a slurry. Treat the slurry with Lipase (13 g, $EC_{3.1.1.3}$, Type VII, from *Candida cylindracea*). Monitor the reaction by HPLC on a CHIRALPAK AD 25 cm×0.46 cm column eluting with pentane/ethanol/methanol (80/15/5) with a flow rate of 1.0 mL/minute. Prepare an aliquot for analysis as follows: centrifuge the solution for 10 minutes at 14000 $cm^{-1}$, remove the supernatant and concentrate under a nitrogen stream to obtain a residue, dissolve the residue in dichloromethane (ca. 1 mL) and inject on the column for analysis. When the enantiomeric excess (ee) is satisfactory (>95% ee) for the (+)-acetate, filter the reaction. Rinse the solids with dichloromethane (8×500 mL). Extract the filtrate with dichloromethane (8×500 mL). Chromatograph the solids on silica gel eluting with 6% methanol/dichloromethane. Concentrate the combined eluant and extracts in vacuo to obtain a residue. Dissolve the residue in dichloromethane, dry over $MgSO_4$, filter, and concentrate in vacuo to give a residue. Chromatograph the residue on silica gel eluting with ethyl acetate to give (+)-1-(3,4,5-trimethoxybenzoyl)-3-(3,4-dichlorophenyl)-3-(2-acetoxyethyl)pyrrolidine: $R_f$=0.38 (silica gel, ethyl acetate). Elemental Analysis calculated for $C_{24}H_{27}Cl_2NO_6 \cdot 0.5\ H_2O$: C, 57.14; H, 5.59; N, 2.78; Found: C, 57.37; H, 5.45; N, 2.87. $[\ ]_D^{20}$=+36.4° (c=0.894, chloroform).

Combine (+)-1-(3,4,5-trimethoxybenzoyl)-3-(3,4-dichlorophenyl)-3-(2-acetoxyethyl)pyrrolidine (670 mg, 1.35 mmol) and aqueous lithium hydroxide solution (4.2 mL, 1M) in methanol (15 mL). After 3.5 hours, concentrate in vacuo to give a residue. Dissolve the residue in dichloromethane and extract with 1M hydrochloric acid solution and saturated sodium bicarbonate solution. Dry the organic layer over $MgSO_4$, filter, and concentrate in vacuo to obtain a residue. The residue was dried under high vacuum for 18 hours to give (S)-1-(3,4,5-trimethoxybenzoyl)-3-(3,4-dichlorophenyl)-3-(2-hydroxyethyl)pyrrolidine: R$_f$=0.11 (silica gel, ethyl acetate).

5.2.1 Synthesis of (S)-(+)-1-(3,4,5-trimethoxybenzoyl)-3-(3,4-dichlorophenyl)-3-(2-hydroxyethyl)pyrrolidine Combine (S)-3-(3,4-dichlorophenyl)-3-(2-hydroxyethyl) pyrrolidine (R,R)-di-p-anisoyltartaric acid salt (0.14 g, 0.21 mmol) ethyl acetate (15 mL), acetonitrile (6 mL), water (6 mL), and sodium bicarbonate (0.09 g, 1.03 mmol). Cool to 0° C. in an salt-ice bath. Add 3,4,5-trimethoxybenzoyl chloride (0.048 g, 0.21 mmol). After 30 minutes, warm to ambient temperature. After 30 minutes at ambient temperature, partition the reaction mixture between ethyl acetate and brine. Extract the organic layer with 1 M hydrochloric acid solution, then saturated aqueous sodium bicarbonate solution. Dry the organic layer over MgSO$_4$, filter, and evaporate in vacuo to give the title compound: R$_f$=0.11 (silica gel, ethyl acetate). $[\alpha]^{20}_D$=+61.7°(c=1.01, methanol).

5.2.2 Synthesis of (S)-(+)-1-(3,4,5-trimethoxybenzoyl)-3-(3,4-dichlorophenyl)-3-(2-hydroxyethyl)pyrrolidine Combine (S)-3-(3,4-dichlorophenyl)-3-(2-hydroxyethyl) pyrrolidine (R,R)-di-p-anisoyltartaric acid salt (6.0 g, 8.84 mmol) acetone (40 mL), water (40 mL), sodium hydroxide (0.335 g, 8.87 mmol), and sodium bicarbonate (3.73 g, 8.87 mmol). Cool to about 0° C. Add a solution of 3,4,5-trimethoxybenzoyl chloride (2,2 g, 9.7 mmol) in acetone (12 mL) over about 15 minutes. After 3 hours, partition the reaction mixture between ethyl acetate and brine. Extract the organic layer with 1 M sodium hydroxide solution, saturated sodium bicarbonate solution, 1 M hydrochloric acid solution, then brine. Dry the organic layer over MgSO$_4$, filter, and evaporate in vacuo to give the title compound: R$_f$=0.11 (silica gel, ethyl acetate).

5.3 Synthesis of (S)-1-(3,4,5-trimethoxybenzoyl)-3-(3,4-dichlorophenyl)-3-(2-methanesulfonyloxyethyl)pyrrolidine Prepare by the method of Example 2.5.2 using (S)-(+)-1-(3,4,5-trimethoxybenzoyl)-3-(3,4-dichlorophenyl)-3-(2-hydroxyethyl)pyrrolidine (1.351 mmol) and methanesulfonyl chloride (0.14 ml,, 1.81 mmol) to give the title compound: R$_f$=0.27 (silica gel, ethyl acetate).

5.4.1 Synthesis of (R)-1-(3,4,5-trimethoxybenzoyl)-3-(2-(4-(1-(2-ethoxyethyl)-1H-benzimidazol-2-yl)[1,4]diazepan-1-yl)ethyl)-3-(3,4-dichlorophenyl)pyrrolidine Prepare by the method of Example 1.6 using (S)-1-(3,4,5-trimethoxybenzoyl)-3-(3,4-dichlorophenyl)-3-(2-methanesulfonyloxyethyl)pyrrolidine and 4-(1-(2-ethoxyethyl)-1H-benzimidazol-2-yl)[1,4]diazepane to give the title compound.

5.4.2 Synthesis of (R)-1-(3,4,5-trimethoxybenzoyl)-3-(2-(4-(1-(2-ethoxyethyl)-1H-benzimidazol-2-yl)[1,4]diazepan-1-yl)ethyl)-3-(3,4-dichlorophenyl)pyrrolidine Combine 3,4,5-trimethoxybenzoic acid (3.5 kg, 16.5 mol) and 1,2-dimethoxyethane (14.2 kg) and dimethyl formamide (4 g). Cool in an ice bath. Add oxalyl chloride (2.99 kg, 23.5 mmol) over about 50 minutes not allowing the temperature of the reaction to raise above about 19° C. After 20 hours, concentrate in vacuo at 25° C. to remove about 3.7 kg of distillate to give a solution of 3,4,5-trimethoxybenzoyl chloride.

Combine (S)-3-(3,4-dichlorophenyl)-3-(2-hydroxyethyl) pyrrolidine (R,R)-di-p-anisoyltartaric acid salt (9.05 kg, 13.3 mol), potassium carbonate (6.42 kg) in acetone (27.2 kg). Cool to about 5° C. and add water (8.3 gal). Cool to about 3° C. and slowly add a solution of 3,4,5-trimethoxybenzoyl chloride (14.0 kg, 26.9% in 1,2-dimethoxethane, 16.3 mol) over about 25 minutes. When the reaction is complete, warm to 25° C. Dilute the reaction mixture with toluene (36.35 kg). Separate the layers and extract the organic layer with a solution of water (2 gal) and 3 M aqueous hydrochloric acid solution (2 kg) and then brine. Concentrate the organic layer in vacuo until about 5 gallons remains. Add toluene (18.2 kg) and again concentrate in vacuo until about 5 gallons remain. Add toluene (36.15 kg) and cool to about −3° C. Add N-methylmorpholine (6.85 kg, 67.7 mol) and then methanesulfonyl chloride (3.40 kg, 29.7 mol). When the reaction is complete, add water (4.8 gal) and warm to about 25° C. Separate the layers and extract the organic layer with a 3 M aqueous hydrochloric acid solution (18.1 kg). Separate the layers to give a solution of (S)-1-(3,4,5-trimethoxybenzoyl)-3-(3,4-dichlorophenyl)-3-(2-methanesulfonyloxyethyl) pyrrolidine.

Combine the above solution of (S)-1-(3,4,5-trimethoxybenzoyl)-3-(3,4-dichlorophenyl)-3-(2-methanesulfonyloxyethyl)pyrrolidine, potassium carbonate (4.07 kg, 29.5 mol), 4-(1-(2-ethoxyethyl)-1H-benzimidazol-2-yl)[1,4]diazepane (12.0 mol), and water (3.3 gal). Heat to about 70° C. When the reaction is complete, dilute the reaction mixture with methyl ethyl ketone (18.1 kg) and after 15 minutes of stirring, separate the layers. Extract the organic layer with water (3.4 gal) and then concentrate in vacuo to give the title compound.

EXAMPLE 6

1-(3,4,5-Trimethoxybenzoyl)-3-(2-(4-(1-(2-ethoxethyl)-1H-benzimidazol-2-yl)diazepan-1-yl)ethyl-3-(3,4-dimethylphenyl)pyrrolidine

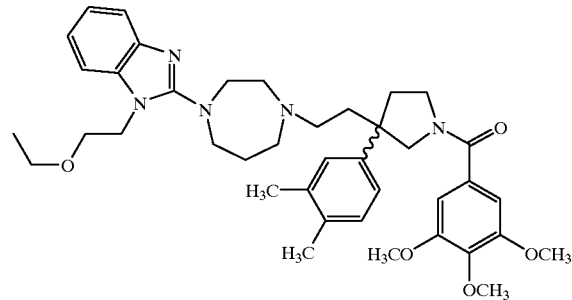

6.1.1 Synthesis of 3-cyano-3-(3,4-dimethylphenyl) pentanedioic acid diethyl ester Combine 3,4-dimethylphenylacetonitrile (50.0 mmol) and tetrahydrofuran (140 mL). Cool to about 5° C. Add dropwise a solution of sodium bis(trimethylsilyl)amide (800 mL, 1 M in tetrahydrofuran, 800 mmol). When the addition is complete, warm the reaction mixture to ambient temperature and allow to stir for 1 hour. Transfer the above solution via cannula into a cooled (−8° C.) solution of ethyl bromoacetate (84.5 mL, 762 mmol) in tetrahydrofuran (500 mL) at such a rate that the temperature of the reaction mixture does not rise above 20° C. Allow to stir at ambient temperature. After 18 hours, dilute with diethyl ether (1.5 L) and extract with saturated aqueous solution of ammonium chloride, then water, and then saturated aqueous solution of sodium chloride. Dry the organic layer over MgSO$_4$, filter, and concentrate in vacuo to give the title compound.

6.1.2 Synthesis of 3-cyano-3-(3,4-dimethylphenyl) pentanedioic acid diethyl ester Cool a solution of sodium bis(trimethylsilyl)amide (723 mL, 1 M in tetrahydrofuran, 723 mmol) to 0° C. in an ice bath. Add a solution of 3,4-dimethylphenylacetonitrile (50.0 mmol) in tetrahydrofuran (130 mL) over about 1.5 hours. When the addition is complete, warm the reaction mixture to ambient. temperature and allow to stir. After 2 hours, transfer the above solution via cannula into a cooled (−50° C.) solution of ethyl bromoacetate (126 g, 757 mmol) in tetrahydrofuran (250 mL). After the transfer is complete, allow the reaction mixture to warm to ambient temperature. After 18 hours, dilute with diethyl ether (500 mL) and extract with water, 1 M hydrochloric acid solution, saturated aqueous solution of sodium bicarbonate, and then brine. Dry the organic layer over $MgSO_4$, filter, and concentrate in vacuo to give a residue. Recrystallize the residue from diethyl ether to give the title compound as a solid.

6.2.1 Synthesis of (3-(3,4-dimethylphenyl)-5-oxopyrrolidin-3-yl)acetic acid ethyl ester Prepare by the method of Example 2.2.2 using 3-cyano-3-(3,4-dimethylphenyl)pentanedioic acid diethyl ester to give the title compound.

6.2.2 Synthesis of (3-(3,4-dimethylphenyl)-5-oxopyrrolidin-3-yl)acetic acid ethyl ester Combine 3-cyano-3-(3,4-dimethylphenyl)pentanedioic acid diethyl ester (56 g, 177 mmol) and ethanol (500 mL) in a Parr bottle. Add Raney nickel (50 g) and an aqueous concentrated ammonia solution (85 mL). Hydrogenate at 50° C. and 100 psi for 48 h. Filter through a celite pad and rinse the solids with ethanol. Evaporate the filtrate in vacuo to obtain a residue. Chromatograph the residue on silica gel eluting with 6% methanol/dichloromethane to give the title compound.

6.3 Synthesis of 3-(3,4-dimethylphenyl)-3-(2-hydroxyethyl) pyrrolidine

Prepare by the method of Example 2.3 using (3-(3,4-dimethylphenyl)-5-oxopyrrolidin-3-yl)acetic acid ethyl ester to give, after recrystallization from dichloromethane/diethyl ether, the title compound: $R_f$=0.35 (silica gel, 85/10/5 dichloromethane/methanol/acetic acid).

6.4 Synthesis of 1-(3,4,5-trimethoxybenzoyl)-(3-(3,4-dimethylphenyl)-3-(2-hydroxyethyl)pyrrolidine Combine 3-(3,4-dimethylphenyl)-3-(2-hydroxyethyl) pyrrolidine (20 mmol) and sodium bicarbonate (8.4 g) in acetone (50 mL)/water (50 mL). Add a solution of 3,4,5-trimethoxybenzoyl chloride (4.6 g, 19.9 mmol) in acetone (50 mL). After 3 hours, extract the reaction mixture three times with ethyl acetate. Dry the organic layer over $MgSO_4$, filter, and concentrate in vacuo to give the title compound: $R_f$=0.25 (silica gel, 6% methanol/dichloromethane).

6.5 Synthesis of 1-(3,4,5-trimethoxybenzoyl)-3-(3,4-dimethylphenyl)-3-(2-methanesulfonyloxyethyl)pyrrolidine Prepare by the method of Example 2.5.2 using 1-(3,4,5-trimethoxybenzoyl)-3-(3,4-dimethylphenyl)-3-(2-hydroxyethyl)pyrrolidine to give the title compound: $R_f$=0.44 (silica gel, ethyl acetate).

6.6 Synthesis of 1-(3,4,5-trimethoxybenzoyl)-3-(2-(4-(1-(2-ethoxyethyl)-1H-benzimidazol-2-yl)[1,4]diazepan-1-yl) ethyl)-3-(3,4-dimethylphenyl)pyrrolidine Prepare by the method of Example 1.6 using 1-(3,4,5-trimethoxybenzoyl)-3-(3,4-dimethylphenyl)-3-(2-methanesulfonyloxyethyl)pyrrolidine and 4-(1-(2-ethoxyethyl)-1H-benzimidazol-2-yl)[1,4]diazepane to give the title compound.

EXAMPLE 7

1-(3,4,5-Trimethoxybenzoyl)-3-(2-(4-(1-(2-ethoxyethyl)-1H-benzimidazol-2-yl)[1,4]diazepan-1-yl)ethyl)-3-(3-chlorophenyl)pyrrolidine

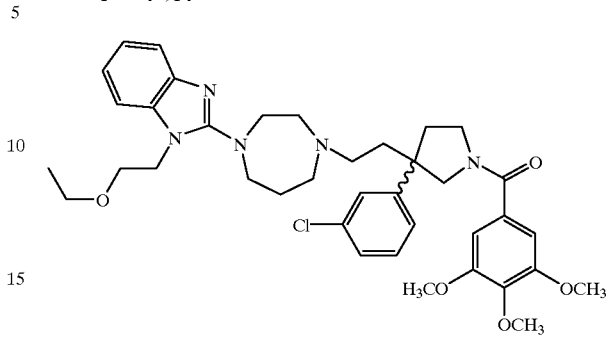

7.1 Synthesis of 3-cyano-3-(3-chlorophenyl)pentanedioic acid diethyl ester

Prepare by the method of Example 6.1.1 using 3-chlorophenylacetonitrile to give the title compound. Elemental Analysis calculated for $C_{16}H_{18}ClNO_4$: C, 59.35; H 5.55: N 4.33: Found: $C_{59.47:}$ H 5.54; N 4.51.

7.2 Synthesis of (3-(3-chlorophenyl)-5-oxolpyrrolidin-3-yl)-acetic acid ethyl ester Prepare by the method of Example 2.2.2 using 3-cyano-3-(3-chlorophenyl)pentanedioic acid diethyl ester to give the title compound.

7.3 Synthesis of 3-(3-chlorophenyl)-3-(2-hydroxyethyl) pyrrolidine

Prepare by the method of Example 1.3 using (3-(3-chlorophenyl)-5-oxopyrrolidin-3-yl)acetic acid ethyl ester to give the title compound: $R_f$=0.30 (silica gel, 85/10/5 dichloromethane/methanol/acetic acid).

7.4 Synthesis of 1-(3,4,5-trimethoxybenzoyl)-(3-(3-chlorophenyl)-3-(2-hydroxyethyl)pyrrolidine Combine 3-(3-chlorophenyl)-3-(2-hydroxyethyl) pyrrolidine (4.5 g, 20 mmol) and sodium bicarbonate (8.4 g) in acetone (50 mL)/water (50 mL). Add a solution of 3,4,5-trimethoxybenzoyl chloride (4.6 g, 19.9 mmol) in acetone (50 mL). After 3 hours, extract the reaction mixture three times with ethyl acetate. Dry the organic layer over $MgSO_4$, filter, and concentrate in vacuo to give the title conmpound: $R_f$=0.46 (silica gel, 6% methanol/dichloromethane).

7.5 Synthesis of 1-(3,4,5-trimethoxybenzoyl)-3-(3-chlorophenyl)-3-(2-methanesulfonyloxyethyl)pyrrolidine Prepare by the method of Example 2.5.2 using 1-(3,4,5-trimethoxybenzoyl)-3-(3-chlorophenyl)-3-(2-hydroxyethyl) pyrrolidine to give the title compound: $R_f$=0.47 (silica gel, ethyl acetate).

7.6 Synthesis of 1-(3,4,5-trimethoxybenzoyl)-3-(2-(4-(1-(2-ethoxyethyl)-1H-benzimidazol-2-yl)[1,4]diazepan-1-yl) ethyl)-3-(3-chlorophenyl)pyrrolidine Combine 1-(3,4,5-trimethoxybenzoyl)-3-(3-chlorophenyl)-3-(2-methanesulfonyloxyethyl)pyrrolidine (0.82 g, 1.65 mmol), 4-(1-(2-ethoxyethyl)-1H-benzimidazol-2-yl)[1,4]diazepane hydriodic acid salt (1.04 g, 1.91 mmol), and N,N-diisopropylethylamine (1.3 mL, 7.43 mmol) in acetonitrile (50 mL). Heat to reflux. After 2 days, cool and dilute the reaction mixture with ethyl acetate (300 mL). Extract with a saturated aqueous sodium bicarbonate solution and then brine. Dry over $Na_2SO_4$, filter, and evaporate in vacuo to give a residue. Chromatograph the residue on silica gel eluting with 24% methanol/ethyl acetate containing concentrated aqueous ammonia (20 mL/3L) to give the title compound.

7.7 Synthesis of 1-(3,4,5-trimethoxybenzoyl)-3-(2-(4-(1-(2-ethoxyethyl)-1H-benzimidazol-2-yl)[1,4]diazepan-1-yl) ethyl)-3-(3-chlorophenyl)pyrrolidine fumaric acid salt Combine 1-(3,4,5-trimethoxybenzoyl)-3-(2-(4-(1-(2-ethoxyethyl)-1H-benzimidazol-2-yl)[1,4]diazepan-1-yl) ethyl)-3-(3-chlorophenyl)pyrrolidine (0.76 g) and fumaric acid (0.31 g, 2.68 mmol) in methanol (30 mL). Add ethyl acetate (100 mL) and stir. After 3 days, evaporate in vacuo to give a residue. Combine the residue with diethyl ether (200 mL) and stir. After 18 hours, decant and add diethyl ether and stir. After 6 days, decant, collect the solid which forms, and dry in vacuo to give the title compound: mp; 66–78° C.

PREPARATION 3

4-(1H-Benzimidazol-2-yl)[1,4]diazepane hydriodic acid salt

Combine [1,4]diazepane (33.9 g, 340 mmol) and water (250 mL). Add methyl orange and adjust the pH using 3 M aqueous hydrochloric acid solution until the indicator turns red. Add dropwise, ethyl chloroformate (38 mL, 400 mmol) over about 2.5 hours while maintaining the pH using first aqueous sodium acetate and then aqueous sodium hydroxide solution. After the addition is complete adjust the pH to 8 using aqueous sodium hydroxide solution and extract three times with diethyl ether. Discard the organic extracts and saturate the aqueous layer with potassium carbonate. Extract three times with diethyl ether. Combined organic layers from the second extraction, dry the over $Na_2SO_4$, filter, and evaporate in vacuo to give a 1-ethoxycarbonyl[1,4] diazepane.

Combine 1-ethoxycarbonyl[1,4]diazepane (36.6 g, 212 mmol) and 2-chlorobenzimidazole (18.0 g, 106 mmol). Heat to 130° C. After 4 hours, cool to ambient temperature and add hot methanol to dissolve the reaction mixture. Partition the methanol solution between dichloromethane (700 mL) and a solution of sodium hydroxide (20 g) in water (500 mL). Separate the layers and extract the aqueous layer three times with dichloromethane. Combine the organic layers, extract with brine, dry over $Na_2SO_4$, filter, and evaporate in vacuo to give a solid. Triturate the solid with ethyl acetate (100 mL) and cool to 0° C. Collect solid by filtration and dry in vacuo to give 1-ethoxycarbonyl-4-(1H-benzimidazol-2-yl)[1,4]diazepane.

Combine 1-ethoxycarbonyl-4-(1H-benzimidazol-2-yl)[1,4]diazepane (16.7 g, 58 mmol) and aqueous 48% hydrobromic acid solution (80 mL). Heat to reflux. After 3 hours, cool to ambient temperature, add to ethanol (700 mL), and cool to 0° C. to give a solid. Combine the solid with aqueous 48% hydriodic acid (80 mL) and water (150 mL). Heat on a steam bath. After about 1 hour, cool to ambient temperature, dilute with ethanol (500 mL), and add to diethyl ether (8 L) to give a solid. Collect solid by filtration and dry in vacuo to give the title compound: mp; >290° C.

EXAMPLE 8

1-(3,4,5-Trimethoxybenzoyl)-3-(2-(4-(1H-benzimidazol-2-yl)[1,4]diazepan-1-yl)ethyl)-3-phenylpyrrolidine

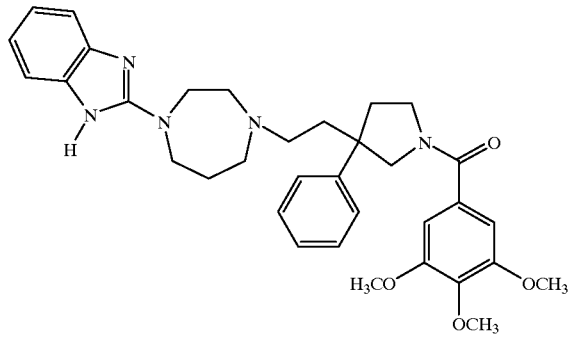

8.1.1 Resolution of (+)-3-phenyl-3-(2-hydroxyethyl) pyrrolidine (R,R)-di-p-anisoyltartaric acid salt and (−)-3-phenyl-3-(2-hydroxyethyl)pyrrolidine hydrochloride salt Combine (R,R)-di-p-anisoyltartaric acid (1.10 g, 2.62 mmol) in water/methanol (13.6 mL/13.6 mL). Add 12 M hydrochloric acid solution (0.217 mL, 2.63 mmol). Add a hot solution of 3-phenyl-3-(2-hydroxyethyl)pyrrolidine (1.0 g, 5.23 mmol) in methanol (13.6 mL). Heat to reflux. After 30 minutes, slowly cool to ambient temperature to give a solid. Collect the solid by filtration and recrystallize the solid twice from methanol/water, once from methanol/2-butanone, and once from ethanol to give (−)-3-phenyl-3-(2-hydroxyethyl)pyrrolidine (R,R)-di-p-anisoyltartaric acid. After conversion of a sample to the 3,4,5-trimethoxybenzamide using sodium carbonate and 3,4,5-trimethoxybenzoyl chloride in acetone/water, analysis on HPLC using a CHIRALPAK AD (10 µm×4.6 cm×250 cm) column eluting with pentane/ethanol/methanol/triethylamine (80/15/5/0.1) with a flow rate of 1.5 mL/minute indicates an enantiomeric excess of 98%, (98% ee), retention time 22.30 minutes for the 3,4,5-trimethoxybenzamide of the isomer prepared from the (−)-isomer of (R,R)-di-p-anisoyltartaric acid salt.

8.1.2 Resolution of (+)-3-phenyl-3-(2-hydroxyethyl) pyrrolidine (R,R)-di-p-anisoyltartaric acid salt and (−)-3-phenyl-3-(2-hydroxyethyl)pyrrolidine (R,R)-di-p-anisoyltartaric acid salt Add a hot solution of 3-phenyl-3-(2-hydroxyethyl) pyrrolidine (5.0 g, 20.2 mmol) in ethanol (100 mL) to a refluxing solution of (R,R)-di-p-anisoyltartaric acid (8.46 g, 20.2 mmol, containing a small amount of acetone) in ethanol (200 mL). After the addition is complete, slowly cool to ambient temperature to give a solid. Collect the solid by filtration and recrystallize the solid three times from ethanol to give (−)-3-phenyl-3-(2-hydroxyethyl)pyrrolidine (R,R)-di-p-anisoyltartaric acid salt: mp; 178.0–179.0° C. Elemental Analysis calculated for $C_{12}H_{17}NO \cdot C_{20}H_{18}O_{10}$: C, 63.05; H 5.79; N 2.30; Found: C 62.72; H 5.80; N 2.33. After conversion of a sample to the 3,4,5-trimethoxybenzamide using sodium carbonate and 3,4,5-trimethoxybenzoyl chloride in acetone/water, analysis on HPLC using a CHIRALPAK AD (10 µm×4.6 cm×250 cm) column eluting with pentane/ethanol/methanol/triethylamine (80/15/5/0.1) with a flow rate of 1.5 mL/minute indicates an enantiomeric excess of 99.9%, (99.9% ee), retention time 22.30 minutes for the 3,4,5-trimethoxybenzamide prepared from the (−)-isomer of (R,R)-di-p-anisoyltartaric acid salt.

Upon standing, the mother liquors from above give a solid. Collect the solid by filtration and recrystallize twice from ethanol to give (+)-3-phenyl-3-(2-hydroxyethyl) pyrrolidine (R,R)-di-p-anisoyltartaric acid salt: mp; 175.0–176.0° C. Elemental Analysis calculated for $C_{12}H_{17}NO \cdot C_{20}H_{18}O_{10} \cdot 0.8\ C_3H_6O$: C, 62.98; H, 6.11; N, 2.13; Found: C, 62.86; H, 5.94; N, 2.33. After conversion of a sample to the 3,4,5-trimethoxybenzamide using sodium carbonate and 3,4,5-trimethoxybenzoyl chloride in acetone/water, analysis on HPLC using a CHIRALPAK AD (10 μm×4.6 cm×250 cm) column eluting with pentane/ethanol/methanol/triethylamine (80/15/5/0.1) with a flow rate of 1.5 mL/minute indicates an enantiomeric excess of 99.9%, (99.9% ee), retention time 10.26 minutes for the 3,4,5-trimethoxybenzamide prepared from the (+)-isomer of (R,R)-di-p-anisoyltartaric acid salt.

8.1.3 Resolution of (+)-3-phenyl-3-(2-hydroxyethyl)pyrrolidine (R,R)-di-p-anisoyltartaric acid salt and (−)-3-phenyl-3-(2-hydroxyethyl)pyrrolidine (R,R)-di-p-anisoyltartaric acid salt Combine 3-phenyl-3-(2-hydroxyethyl)pyrrolidine (99.2 g, 659 mmol) and ethanol (2.5 L). Heat to reflux. Add a refluxing solution of (R,R)-di-p-anisoyltartaric acid (212 g, 507 mmol) in ethanol (5.07 L). After the addition is complete, slowly cool to ambient temperature with stirring to give an oil. Dissolve the oil in ethanol at reflux (595 mL) and add a refluxing solution of (R,R)-di-p-anisoyltartaric acid (49.2 g) in ethanol (1.1 L). Cool to ambient temperature with stirring to give a solid. Collect the solid by filtration and recrystallize from ethanol (3.2 L) to give a second solid. Collect the second solid by filtration and recrystallize from ethanol (2.6 L), seed with (−)-3-phenyl-3-(2-hydroxyethyl)pyrrolidine (R,R)-di-p-anisoyltartaric acid salt to give (−)-3-phenyl-3-(2-hydroxyethyl)pyrrolidine (R,R)-di-p-anisoyltartaric acid salt (121 g).

8.1.4 Resolution of (+)-3-phenyl-3-(2-hydroxyethyl)pyrrolidine (R,R)-di-p-anisoyltartaric acid salt and (−)-3-phenyl-3-(2-hydroxyethyl)pyrrolidine (R,R)-di-p-anisoyltartaric acid salt Combine 3-phenyl-3-(2-hydroxyethyl)pyrrolidine (101 g, 530 mmol) and ethanol (1.92 L). Heat to reflux. Add a refluxing solution of (R,R)-di-p-anisoyltartaric acid (107 g, 410 mmol) in ethanol (3.9 L). Continue to reflux. After 10 minutes, slowly cool to ambient temperature and add seed crystals. After 18 hours, collect the solid that forms by filtration, rinse with ethanol (200 mL). Recrystallize twice from ethanol to give (−)-3-phenyl-3-(2-hydroxyethyl)pyrrolidine (R,R)-di-p-anisoyltartaric acid salt: mp; 179–180° C. $[\alpha]^2_D{}^0 = -108.8$ (c=1.02, methanol).

8.1.5 Resolution of (+)-3-phenyl-3-(2-hydroxyethyl)pyrrolidine (R,R)-di-p-anisoyltartaric acid salt and (−)-3-phenyl-3-(2-hydroxyethyl)pyrrolidine (R,R)-di-p-anisoyltartaric acid salt Evaporate the filtrate obtained from collecting the first formed solid in Example 8.14 to give a residue. Dissolve the residue in the minimum amount of hot ethanol (about 450 mL). Reduce the volume to about 300 mL by heating under a stream of nitrogen gas to obtain a solid. Recrystallize the three times from ethanol to give (+)-3-phenyl-3-(2-hydroxyethyl)pyrrolidine (R,R)-di-p-anisoyltartaric acid salt.

8.2.1 Synthesis of 1-(3,4,5-trimethoxybenzoyl)-3-phenyl-3-(2-hydroxyethyl)pyrrolidine Combine (−)-3-phenyl-3-(2-hydroxyethyl)pyrrolidine (R,R)-di-p-anisoyltartaric acid salt (3.95 g, 6.48 mmol) and acetone (20 mL), water (6 mL), and potassium carbonate (2.70 g, 19.5 mmol). Cool to 0° C. in an ice bath. After 30 minutes, add dropwise a solution of 3,4,5-trimethoxybenzoyl chloride (1.71 g, 7.4 mmol) in acetone (20 mL). Warm to ambient temperature. After 18 hours, partition the reaction mixture between ethyl acetate and saturated aqueous sodium bicarbonate solution. Separate the organic layer and extract with brine. Dry the organic layer over $Na_2SO_4$, filter, and evaporate in vacuo to give the title compound: $R_f=0.23$ (silica gel, ethyl acetate). Analysis on HPLC using a CHIRALPAK AD (10 μm×4.6 cm×250 cm) column eluting with pentane/ethanol/methanol/triethylamine (80/15/5/0.1) with a flow rate of 1.5 mL/minute indicates an enantiomeric excess of 98%, (98% ee), retention time of 22.30 minutes.

8.2.2 Synthesis of 1-(3,4,5-trimethoxybenzoyl)-3-phenyl-3-(2-hydroxyethyl)pyrrolidine Combine (−)-3-phenyl-3-(2-hydroxyethyl)pyrrolidine (R,R)-di-p-anisoyltartaric acid salt (56.0 g, 92.1 mmol), sodium carbonate (19.5 g, 184 mmol) in ethyl acetate (2 L) and water (2 L). Cool to about 0° C. in an ice bath. After 30 minutes, slowly add dropwise portionwise 3,4,5-trimethoxybenzoyl chloride (21.2 g, 92.1 mmol). After the addition is complete, warm to ambient temperature. After 1 hour, dilute the reaction mixture ethyl acetate and extract with water, 1 M aqueous hydrochloric acid solution, and then brine. Dry the organic layer over $Na_2SO_4$, filter, and evaporate in vacuo to give the title compound.

8.3 Synthesis of 1-(3,4,5-trimethoxybenzoyl)-3-phenyl-3-(2-methanesulfonyloxyethyl)pyrrolidine Prepare by the method of Example 2.5.2 using 1-(3,4,5-trimethoxybenzoyl)-3-phenyl-3-(2-hydroxyethyl)pyrrolidine (prepared from (−)-3-phenyl-3-(2-hydroxyethyl)pyrrolidine (R,R)-di-p-anisoyltartaric acid salt) (2.21 g, 5.51 mmol) and methanesulfonyl chloride (0.7 mL, 9.0 mmol) to give the title compound: $R_f=0.47$ (silica gel, ethyl acetate).

8.4 Synthesis of 1-(3,4,5-trimethoxybenzoyl)-3-(2-(4-(1H-benzimidazol-2-yl)[1,4]diazepan-1-yl)ethyl)-3-phenylpyrrolidine Combine 1-(3,4,5-trimethoxybenzoyl)-3-phenyl-3-(2-methanesulfonyloxyethyl)pyrrolidine (5.0 g, 10.7 mmol), 4-(1H-benzimidazol-2-yl)[1,4]diazepane hydriodic acid salt (5.76 g, 12.2 mmol), and N,N-diisopropylethylamine (16 mmol) in acetonitrile (100 mL). Heat to reflux. After 20 hours, cool to ambient temperature, dilute with ethyl acetate, and extract with a combination of water (500 mL) and saturated aqueous sodium bicarbonate (100 mL). Extract the organic layer with brine, dry over $Na_2SO_4$, filter, and evaporate in vacuo to give a residue. Chromatograph the residue on silica gel eluting with 25% methanol/ethyl acetate containing aqueous concentrated ammonia (20 mL/3L) to give, after drying in vacuo at 56° C., the title compound: mp; 99–107° C. $R_f=0.27$ (silica gel, 30% methanol/ethyl acetate).

EXAMPLE 9

1-(3,4,5-Trimethoxybenzoyl)-3-(2-(4-(1-(2-ethoxyethyl)-1H-benzimidazol-2-yl)[1,4]diazepan-1-yl)ethyl)-3-phenylpyrrolidine

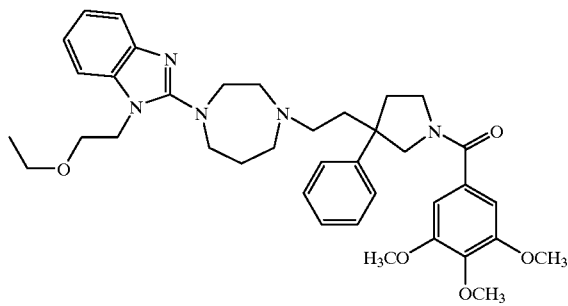

9.1.1 Synthesis of 1-(3,4,5-trimethoxybenzoyl)-3-2-(4-(1-(2-ethoxyethyl)-1H-benzimidazol-2-yl)[1,4]diazepan-1-yl)ethyl)-3-phenylpyrrolidine Combine 1-(3,4,5-trimethoxybenzoyl)-3-phenyl-3-(2-methanesulfonyloxyethyl)pyrrolidine (prepared from (−)-3-phenyl-3-(2-hydroxyethyl)pyrrolidine (R,R)-di-p-anisoyltartaric acid salt)(5.5 g, 11.9 mmol), 4-(1-(2-ethoxyethyl)-1H-benzimidazol-2-yl) [1,4]diazepane hydriodic acid salt (7.0 g, 12.9 mmol), and N,N-diisopropylethylamine (9.0 mL, 51.4 mmol) in acetonitrile (100 mL). Heat to reflux. After 18 hours, cool to ambient temperature and dilute the reaction mixture with ethyl acetate (400 mL). Extract with a saturated aqueous sodium bicarbonate solution and then with brine. Dry the organic layer over $Na_2SO_4$, filter,, and evaporate in vacuo to give a residue. Chromatograph the residue on silica gel eluting with 25% methanol/dichloromethane containing aqueous concentrated ammonia (20 mL/3 L). Combine the product containing fractions to give a residue. Dissolve the residue in dichloromethane and filter. Evaporate the filtrate in vacuo to give the title compound: mp; 43–48° C.

9.1.2 Synthesis of 1-(3,4,5-trimethoxybenzoyl)-3-(2-(4-(1-(2-ethoxyethyl)-1H-benzimidazol-2-yl)[1,4]diazepan-1-yl)ethyl)-3-phenylpyrrolidine Combine 1-(3,4,5-trimethoxybenzoyl)-3-phenyl-3-(2-methanesulfonyloxyethyl)pyrrolidine (prepared from (−)-3-phenyl-3-(2-hydroxyethyl)pyrrolidine (R,R)-di-p-anisoyltartaric acid salt)(1.83 g, 3.94 mmol), 4-(1-(2-ethoxyethyl)-1H-benzimidazol-2-yl)[1,4]diazepane hydriodic acid salt (2.04 g, 3.75 mmol), potassium iodide ((0.62 g, 3.75 mmol), and triethylamine (1.15 mL, 8.25 mmol) in acetonitrile (54 mL). Heat to reflux. After 43 hours, evaporate in vacuo, dilute the evaporated reaction mixture with dichloromethane, extract with a saturated aqueous sodium bicarbonate solution, water, and then with brine. Dry the organic layer over $MgSO_4$, filter, and evaporate in vacuo to give a residue. Chromatograph the residue on silica gel eluting sequentially with dichloromaethane, then 10% methanol/dichloromethane to give the title compound.

9.2 Synthesis of 1-(3,4,5-trimethoxybenzoyl)-3-(2-(4-(1-(2-ethoxyethyl)-1H-benzimidazol-2-yl)[1,4]diazepan-1-yl)ethyl)-3-phenylpyrrolidine fumaric acid salt Combine 1-(3,4,5-trimethoxybenzoyl)-3-(2-(4-(1-(2-ethoxyethyl)-1H-benzimidazol-2-yl)[1,4]diazepan-1-yl)ethyl)-3-phenylpyrrolidine (0.47 g) and fumaric acid (0.17 g) in methanol (about 20 mL). Add ethyl acetate (100 mL) and stir. After 18 hours, evaporate in vacuo to give a residue. Triturate the residue with diethyl ether to give the title compound: mp; 82–94° C.

9.3 Synthesis of 1-(3,4,5-trimethoxybenzoyl)-3-(2-(4-(1-(2-ethoxyethyl)-1H-benzimidazol-2-yl)[1,4]diazepan-1-yl)ethyl)-3-phenylpyrrolidine maleic acid salt Combine 1-(3,4,5-trimethoxybenzoyl)-3-(2-(4-(1-(2-ethoxyethyl)-1H-benzimidazol-2-yl)[1,4]diazepan-1-yl)ethyl)-3-phenylpyrrolidine (0.47 g) and maleic acid (0.17 g) in methanol (15 mL). Add ethyl acetate (100 mL) and stir. After 18 hours, evaporate in vacuo to give a residue. Triturate the residue with diethyl ether to give the title compound: mp; 69–79° C.

9.4 Synthesis of 1-(3,4,5-trimethoxybenzoyl-(2)3-(4-(1-(2-ethoxyethyl)-1H-benzimidazol-2-yl)[1,4]diazepan-1-yl)ethyl)-3-phenylpyrrolidine hydrochloric acid salt Combine 1-(3,4,5-trimethoxybenzoyl)-3-(2-(4-(1-(2-ethoxyethyl)-1H-benzimidazol-2-yl)[1,4]diazepan-1-yl)ethyl)-3-phenylpyrrolidine (0.61 g) and methanol (20 mL). Add a solution of hydrochloric acid in methanol (0.035 mL, 4 M, 1.4 mmol) and stir. After 10 minutes, evaporate invacuo to give a residue. Dissolve the residue in methanol (about 5 mL) and dilute with diethyl ether (200 mL) to give a solid. Stir for 3 hours, allow he solid to settle and decant the solvent. Add diethyl ether and collect the solid by filtration to give, after drying, the title compound: mp; 137–142° C. (shrinks), 145–149° C.

EXAMPLE 10

1-(3,4,5-Trimethoxybenzoyl)-3-(2-(4-(1-(2-ethoxyethyl)-1H-benzimidazol-2-yl)[1,4]diazepan-1-yl)ethyl)-3-phenylpyrrolidine

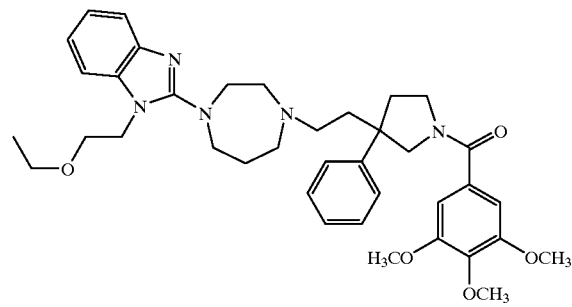

10.1.1 Synthesis of 1-(3,4,5-trimethoxybenzoyl)-3-phenyl-3-(2-hydroxyethyl)pyrrolidine Prepare by the method of Example 8.2.1 using (+)-3-phenyl-3-(2-hydroxyethyl)pyrrolidine (R,R)-di-p-anisoyltartaric acid salt to give the title compound: $R_f$=0.23 (silica gel, ethyl acetate).

10.1.2 Synthesis of 1-(3,4,5-trimethoxybenzoyl)-3-phenyl-3-(2-hydroxyethyl)pyrrolidine Combine (+)-3-phenyl-3-(2-hydroxyethyl)pyrrolidine (R,R)-di-p-anisoyltartaric acid salt (2.0 g, 3.28 mmol) and sodium bicarbonate (1.11 g, 13.2 mmol) in ethyl acetate (45 mL) and water (45 mL). Add 3,4,5-trimethoxybenzoyl chloride (0.76 g, 3.28 mmol). After 2 hours, partition the reaction mixture between ethyl acetate (150 mL) and water (100 mL). Separate the layers and extract the aqueous layer twice with ethyl acetate. Extract the combined organic layers with a saturated aqueous sodium bicarbonate solution. Dry the organic layer over $MgSO_4$, filter, and evaporate in vacuo to give a residue. Chromatograph the residue on silica gel eluting sequentially with dichloromethane and then 5% methanol/dichloromethane to give the title compound.

10.2 Synthesis of 1-(3,4,5-trimethoxybenzoyl)-3-phenyl-3-(2-methanesulfonyloxyethyl)pyrrolidine Prepare by the method of Example 2.5.2 using 1-(3,4,5-trimethoxybenzoyl)-3-phenyl-3-(2-hydroxyethyl)pyrrolidine (prepared from (+)-3-phenyl-3-(2-hydroxyethyl)pyrrolidine (R,R)-di-p-anisoyLtartaric acid salt) to give the title compound: $R_f$=0.47 (silica gel, ethyl acetate).

10.3.1 Synthesis of 1-(3,4,5-trimethoxybenzoyl)-3-(2-(4-(1-(2-ethoxyethyl)-1H-benzimidazol-2-yl)[1,4]diazepan-1-yl)ethyl)-3-phenylpyrrolidine Prepare by the method of Example 9.1 using 1-(3,4,5-trimethoxybenzoyl-3-phenyl-3-(2-methanesulfonyloxyethyl)pyrrolidine (prepared from (+)-3-phenyl-3-(2-hydroxyethyl)pyrrolidine (R,R)-di-p-anisoyltartaric acid salt) and 4-(1-(2-ethoxyethyl)-1H-benzimidazol-2-yl)[1,4]diazepane hydriodic acid salt to give the title compound.

10.3.2 Synthesis of 1-(3,4,5-trimethoxybenzoyl)-3-(2-(4-(1-(2-ethoxyethyl)-1H-benzimidazol-2-yl)[1,4]diazepan-1-yl)ethyl)-3-phenylpyrrolidine Combine 1-(3,4,5-trimethoxybenzoyl)-3-phenyl-3-(2-methanesulfonyloxyethyl)pyrrolidine (prepared from (+)-3-phenyl-3-(2-hydroxyethyl)pyrrolidine (R,R)-di-p-anisoyltartaric acid salt) (1.43 g, 3.1 mmol), triethylamine (2.05 mL, 14.75 mmol), sodium iodide (0.46 g, 3.1 mmol), and 4-(1-(2-ethoxyethyl)-1H-benzimidazol-2-yl)[1,4]diazepane hydriodic acid salt (1.6 g, 2.95 mmol) in acetonitrile (40 ml). Heat to reflux. After 40 hours, evaporate in vacuo to give a residue. Partition the residue between dichloromethane and water. Separate the layers and extract the organic layer with a saturated aqueous sodium bicarbonate solution, water, and then brine. Dry the organic layer over $MgSO_4$, filter, and evaporate in vacuo to give a residue. Chromatograph the residue on silica gel eluting sequentially with dichloromethane, 5% methanol/dichloromethane, and then 10% methanol/dichloromethane to give the title compound.

10.4 Synthesis of 1-(3,4,5-trimethoxybenzoyl)-3-(2-(4-(1-(2-ethoxyethyl)-1H-benzimidazol-2-yl)[1,4]diazepan-1-yl)ethyl)-3-phenylpyrrolidine hydrochloric acid salt Combine 1-(3,4,5-trimethoxybenzoyl)-3-(2-(4-(1-(2-ethoxyethyl)-1H-benzimidazol-2-yl)[1,4]diazepan-1-yl)ethyl)-3-phenylpyrrolidine Prepare by the method of Example 9.1 using 1-(3,4,5-trimethoxybenzoyl)-3-phenyl-3-(2-methanesulfonyloxyethyl)pyrrolidine (prepared from (+)-3-phenyl-3-(2-hydroxyethyl)pyrrolidine (R,R)-di-p-anisoyltartaric acid salt)(0.66 g, 2.3 mmol) and methanol (35 mL). Add a solution of hydrochloric acid in dioxane (1.15 mL, 4 M, 4.6 mmol). After 1.5 hours, evaporate in vacuo to give a residue. Repeatedly add dichloromethane and evaporate in vacuo to give a residue. Triturate the residue with diethyl ether to give a solid. Collect the solid by filtration and dry to give the title compound: mp; 147–167° C.

EXAMPLE 11

1-(3,4,5-Trimethoxybenzoyl)-3-(2-(4-(1-(2-ethoxyethyl)-1H-benzimidazol-2-yl)[1,4]diazean-1-yethyl-3-(4-chlorophenyl)pyrrolidine

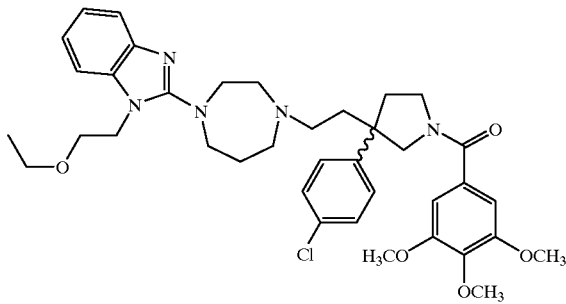

11.1.1 Synthesis of 3-cyano-3-(4-chlorophenyl)pentanedioic acid diethyl ester

Combine 4-chlorophenylacetonitrile (50.0 mmol) and tetrahydrofuran (140 mL). Cool to about 5° C. Add dropwise a solution of sodium bis(trimethylsilyl)amide (800 mL, 1 M in tetrahydrofuran, 800 mmol). When the addition is complete, warm the reaction mixture to ambient temperature and allow to stir for 1 hour. Transfer the above solution via cannula into a cooled (−8° C.) solution of ethyl bromoacetate (84.5 mL, 762 mmol) in tetrahydrofuran (500 mL) at such a rate that the temperature of the reaction mixture does not rise above about 20° C. Allow to stir at ambient temperature. After 18 hours, dilute with diethyl ether (1.5 L) and extract with saturated aqueous solution of ammonium chloride, then water, and then saturated aqueous solution of sodium chloride. Dry the organic layer over $MgSO_4$, filter, and concentrate in vacuo to give the title compound. Elemental Analysis calculated for $C_{16}H_{18}ClNO_4$: C, 59.35; H, 5.60; N, 4.33; Found: C, 59.27; H, 5.54; N, 4.33.

11.1.2 Synthesis of 3-cyano-3-(4-chlorophenyl)pentanedioic acid diethyl ester

Prepare by the method of Example 6.1.2 using 4-chlorophenylacetonitrile (60.65 g, 400 mmol) to give the title compound.

11.2.1 Synthesis of (3-(4-chlorophenyl)-5-oxopyrrolidin-3-yl)acetic acid ethyl ester Prepare by the method of Example 2.2.2 using 3-cyano-3-(4-chlorophenyl)pentanedioic acid diethyl ester to give the title compound.

11.2.2 Synthesis of (3-(4-chlorophenyl)-5-oxopyrrolidin-3-yl)acetic acid ethyl ester Prepare by the method of Example 6.2.2 using 3-cyano-3-(4-chlorophenyl)pentanedioic acid diethyl ester to give the title compound.

11.3 Synthesis of 3-(4-chlorophenyl)-3-(2-hydroxyethyl)pyrrolidine

Prepare by the method of Example 2.3 using (3-(4-chlorophenyl)-5-oxopyrrolidin-3-yl)acetic acid ethyl ester to give the title compound: $R_f$=0.30 (silica gel, 85/10/5 dichloromethane/methanol/acetic acid).

11.4 Synthesis of 1-(3,4,5-trimethoxybenzoyl)-(3-(4-chlorophenyl)-3-(2-hydroxyethyl)pyrrolidine Combine 3-(4-chlorophenyl)-3-(2-hydroxyethyl) pyrrolidine (20 mmol) and sodium bicarbonate (8.4 g) in acetone (50 mL)/water (50 mL). Add a solution of 3,4,5-trimethoxybenzoyl chloride (4.6 g, 19.9 mmol) in acetone (50 mL). After 3 hours, extract the reaction mixture three times with ethyl acetate. Dry the organic layer over $MgSO_4$, filter, and concentrate in vacuo to give the title compound: $R_f$=0.42 (silica gel, 6% methanol/dichloromethane).

11.5 Synthesis of 1-(3,4,5-trimethoxybenzoyl)-3-(4-chlorophenyl)-3-(2-methanesulfonyloxyethyl)pyrrolidine Prepare by the method of Example 2.5.2 using 1-(3,4,5-trimethoxybenzoyl)-3-(4-chlorophenyl)-3-(2-hydroxyethyl)pyrrolidine to give the title compound: $R_f$=0.44 (silica gel, ethyl acetate).

11.6 Synthesis of 1-(3,4,5-trimethoxybenzoyl)-3-(2-(4-(1-(2-ethoxyethyl)-1H-benzimidazol-2-yl)[1,4]diazepan-1-yl)ethyl)-3-(4-chlorophenyl)pyrrolidine Combine 1-(3,4,5-trimethoxybenzoyl)-3-(4-chlorophenyl)-3-(2-methanesulfonyloxyethyl)pyrrolidine (1.0 g, 2.0 mmol), 4-(1-(2-ethoxyethyl)-1H-benzimidazol-2-yl)[1,4]diazepane hydriodic acid salt (1.2 g, 2.2 mmol), and N,N-diisopropylethylamine (1.4 mL, 8.1 mmol) in acetonitrile (60 mL). Heat to reflux. After 20 hours, cool and dilute the reaction mixture with ethyl acetate. Extract three times with a saturated aqueous sodium bicarbonate solution, and then brine. Dry the organic layer over $Na_2SO_4$, filter, and concentrate in vacuo to obtain a residue. Chromatograph the residue on silica gel eluting with 25% methanol/ethyl acetate containing concentrated aqueous ammonia 20 mL/3 L to give the title compound: $R_f$=0.49 (silica gel, 30% methanol/ethyl acetate).

11.7 Synthesis of 1-(3,4,5-trimethoxybenzoyl)-3-(2-(4-(1-(2-ethoxyethyl)-1H-benzimidazol-2-yl)[1,4]diazepan-1-yl)ethyl)-3-(4-chlorophenyl)pyrrolidine fumaric acid salt Combine 1-(3,4,5-trimethoxybenzoyl)-3-(2-(4-(1-(2-ethoxyethyl)-1H-benzimidazol-2-yl)[1,4]diazepan-1-yl)

ethyl)-3-(4-chlorophenyl)pyrrolidine (0.79 g) and fumaric acid (0.31 g, 2.7 mmol) in methanol (145 mL). Add ethyl acetate (150 mL) and stir. After 18 hours, evaporate in vacuo to give a residue. Triturate the residue with diethyl ether to give a solid. Decant the solvent and collect the solid after evaporation in vacuo to give the title compound; mp; 74–81° C.

EXAMPLE 12

1-(3,4,5-Trimethoxybenzoyl)-3-(2-(4-(1-(2-ethoxyethyl)-1H-benzimidazol-2-yl)[1,4]diazepan-1-yl)ethyl)-3-(3,4-dichlorophenyl)piperidine

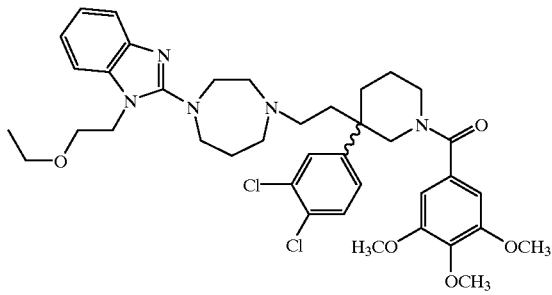

12.1 Synthesis of 2-(3,4-dichlorophenyl)-4-(t-butyldimethylsilyloxy)butyronitrile Combine 3,4-,dichlorophenylacetonitrile (10 g, 53.8 mmol) and anhydrous tetrahydrofuran (50 mL). Cool in a dry-ice/acetone bath. Add dropwise a solution of lithium bis(trimethylsilyl)amide (64.5 mL, 1 M in THF, 64.5 mmol). Add dropwise, 2-(t-butyldimethylsilyloxy)-1-bromoethane (15.43 g, 64.5 mmol). When the addition of 2-(t-butyldimethylsilyloxy)-1-bromoethane is complete, warm the reaction mixture to ambient temperature. After 12 hours, partition the reaction mixture between ethyl acetate and water. Extract the aqueous layer twice with ethyl acetate. Combine the organic layers and extract with 1 M hydrochloric acid solution, dry over $Na_2SO_4$, filter, and concentrate in vacuo to obtain a residue. Chromatograph the residue on silica gel eluting with 10% ethyl acetate/hexane to give the title compound: $R_f$=0.42 (silica gel, 10% ethyl acetate/hexane).

12.2 Synthesis of ethyl 4-cyano-4-(3,4-dichlorophenyl)-6-(t-butyldimethylsilyloxy)hexanoate Combine 2-(3,4-dichlorophenyl)-4-(t-butyldimethylsilyloxy)butyronitrile (13.35 g, 38.8 mmol) and anhydrous tetrahydrofuran (50 mL). Cool in a dry-ice/acetone bath. Add dropwise a solution of lithium bis (trimethylsilyl)amide (42.6 mL, 1 M in THF, 42.6 mmol). Add dropwise, ethyl 3-bromopropionate (7.71 g, 42.6 mmol). Warm the reaction mixture to ambient temperature. After 18 hours, add water. Separate the aqueous layer and extract three times with ethyl acetate. Combine the organic layers, dry over $Na_2SO_4$, filter, and concentrate in vacuo to obtain a residue. Chromatograph the residue on silica gel eluting with 90% ethyl acetate/hexane to give the title compound: $R_f$=0.35 (silica gel, 10% ethyl acetate/hexane).

12.3 Synthesis of 3-(3,4-dichlorophenyl)-3-(2-(t-butyldimethylsilyloxy)ethyl)-6-oxopiperidine Combine ethyl 4-cyano-4-(3,4-dichlorophenyl)-6-(t-butyldimethylsilyloxy)hexanoate (9.58 g, 21.55 mmol) and cobalt(II)chloride hexahydrate (10.25 g, 43.1 mmol) in methanol (200 mL). Cool in an ice-bath, add portionwise sodium borohydride (8.15 g, 215.5 mmol). After 18 hours, concentrate the reaction mixture in vacuo to obtain a residue. Dissolve the residue in dichloromethane and extract with 1M hydrochloric acid solution. Dry the organic layer over $Na_2SO_4$, filter, and concentrate in vacuo to obtain a residue. Chromatograph the residue on silica gel eluting with 1/1 ethyl acetate/hexane to give the title compound: $R_f$=0.46 (silica gel, 1/1 ethyl acetate/hexane).

12.4 Synthesis of 3-(3,4-dichlorophenyl)-3-(2-hydroxyethyl)piperidine

Combine a solution of lithium aluminum hydride (42 mL, 1 M in THF, 42.0 mmol). Cool to about −10° C. using an isopropyl alcohol/ice bath. Slowly add a solution of sulfuric acid (1.15 mL, 21.6 mmol) in tetrahydrofuran (4 mL) at such a rate that the reaction temperature does not rise above −10° C. Stir vigorously and warm to ambient temperature. After 2 hours, add a solution of 3-(3,4-dichlorophenyl)-3-(2-(t-butyldimethylsilyloxy)-ethyl)-6-oxopiperidine (5.56 g, 13.85 mmol) in tetrahydrofuran (12 mL). Heat to reflux. After 18 hours, add 1/1 tetrahydrofuran/water. After 1 hour, filter and rinse with dichloromethane. Suspend the solids removed by filtration in tetrahydrofuran (400 mL). To the tetrahydrofuran suspension add water (20 mL) and 15% aqueous sodium hydroxide solution (8 mL) and stir vigorously. After 2 hours, filter. Combine the filtrates and concentrate in vacuo to give an aqueous suspension. Extract twice with dichloromethane. Dry the organic layers over $Na_2SO_4$, filter, and concentrate in vacuo to give the title compound.

12.5 Synthesis of 1-(3,4,5-trimethoxybenzoyl)-3-(3,4-dichlorophenyl)-3-(2-hydroxyethyl)piperidine Combine 3-(3,4-dichlorophenyl)-3-(2-hydroxyethyl) piperidine (1.08 g, 3.94 mmol) and sodium carbonate (0.21 g, 2.00 mmol) in 1/1 ethyl acetate/water (50 mL). Cool the reaction mixture to 0° C. with an ice bath. Add 3,4,5-trimethoxybenzoyl chloride (0.83 g, 3.58 mmol). Warm to ambient temperature. After 18 hours, separate the layers and extract the aqueous layer three times with ethyl acetate. Dry the combined organic layers over $Na_2SO_4$, filter, and concentrate in vacuo to obtain a residue. Chromatograph the residue on silica gel to give the title compound: $R_f$=0.5 (silica gel, 1/1 ethyl acetate/hexane). Elemental Analysis calculated for $C_{23}H_{27}Cl_2NO_5$: C, 58.97; H, 5.81; N, 2.99; Found C, 58.85; H, 5.90; N, 2.96.

12.6 Synthesis of 1-(3,4,5-trimethoxybenzoyl)-3-(3,4-dichlorophenyl)-3-(2-methanesulfonyloxyethyl)piperidine Combine 1-(3,4,5-trimethoxybenzoyl)-3-(3,4-dichlorophenyl)-3-(2-hydroxyethyl)piperidine (0.61 g, 1.3 mmol) and N,N-diisopropylethylamine (0.37 g, 2.86 mmol) in anhydrous dichloromethane (12 mL). Cool the reaction mixture to 0° C. with an ice bath. Slowly add methanesulfonyl chloride (0.19 g, 1.7 mmol). After 3.5 hours, dilute the reaction mixture with dichloromethane and extract with 1M hydrochloric acid and with a saturated solution of sodium bicarbonate. Dry the organic layer over $Na_2SO_4$, filter, and concentrate in vacuo to obtain the title compound: $R_f$=0.60 (silica gel, 1/1 ethyl acetate/hexane).

12.7 Synthesis of 1-(3,4,5-trimethoxybenzoyl)-3-(2-(4-(1-(2-ethoxyethyl)-1H-benzimidazol-2-yl)[1,4]diazepan-1-yl) ethyl)-3-(3,4-dichlorophenyl)piperidine Combine 1-(3,4,5-trimethoxybenzoyl)-3-(3,4-dichlorophenyl)-3-(2-methanesulfonyloxyethyl)piperidine (0.71 g, 1.32 mmol) and 4-(1-(2-ethoxyethyl)-1H-benzimidazol-2-yl)[1,4]diazepane (0.38 g, 1.32 mmol), and N,N-diisopropylethylamine (0.37 g, 2.9 mmol) in acetonitrile (15 mL). Heat to reflux. After 36 hours, partition the residue between ethyl acetate and saturated aqueous sodium bicarbonate solution. Dry the organic layer over $Na_2SO_4$, filter, and concentrate in vacuo to obtain a residue. Chromatograph the residue on silica gel eluting with 15% methanol/2% triethylamine/ethyl acetate to give the title compound. Elemental Analysis calculated for $C_{39}H_{49}Cl_2N_5O_5$: C, 63.40; H, 6.68; N, 9.48; Found: C, 63.68; H, 6.69; N, 9.57.

PREPARATION 4
Synthesis of 3,4,5-Trimethoxybenzyl mesylate

Combine 3,4,5-trimethoxybenzyl alcohol (9.0 g, 45.4 mmol), N,N-diisopropylethylamine (12.9 g, 100 mmol), and acetonitrile (60 mL). Cool in an ice bath. Add methanesulfonyl chloride (6.76 g, 49.0 mmol). After 2 hours, partition the reaction mixture between water and ethyl acetate. Separate the layers and extract the organic layer with 1 M hydrochloric acid solution and them a saturated solution of sodium bicarbonate. Dry the organic layer over $Na_2SO_4$, filter, and evaporate in vacuo to give the title compound.

EXAMPLE 13
1-(3,4,5-Trimethoxybenzyl)-3-(2-(4-(1-(2-ethoxyethyl)-1H-benzimidazol-2-yl)[1,4]diazepan-1-yl)ethyl)-3-(phenylmethyl)-2-oxopyrrolidine

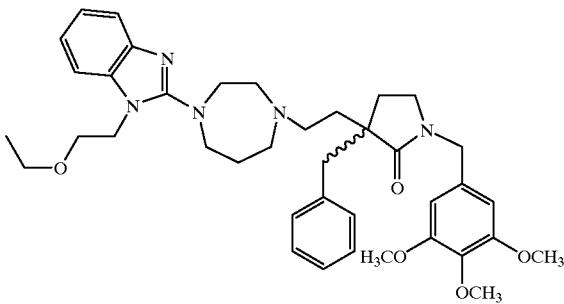

13.1 Synthesis of 1-(3,4,5-trimethoxybenzyl)-2-oxopyrrolidine

Combine 2-pyrrolidinone (2.85 g, 33.5 mmol) and tetrahydrofuran (70 mL). Cool to −78° C. using a dry-ice/acetone bath. Add a solution of potassium bis(trimethylsilyl)amide (67 mL, 0.5 M in toluene, 33.5 mmol). After 45 minutes, add a solution of 3,4,5-trimethoxybenzyl mesylate (8.8 g, 32 mmol) in tetrahydrofuran (60 mL). After the addition of 3,4,5-trimethoxybenzyl mesylate is complete, heat to reflux. After 18 hours, cool the reaction mixture and partition between water and ethyl acetate. Separate the aqueous layer and extract 4 times with ethyl acetate. Dry the combined organic layers over $Na_2SO_4$, filter, and concentrate in vacuo to obtain a residue. Chromatograph the residue on silica gel eluting with ethyl acetate to give the title compound: $R_f$=0.35 (silica gel, ethyl acetate).

13.2 Synthesis of 1-(3,4,5-trimethoxybenzyl)-3-(phenylmethyl)-2-oxopyrrolidine Combine 1-(3,4,5-trimethoxybenzyl)-2-oxopyrrolidine (1.0 g, 3.77 mmol) and tetrahydrofuran (5 mL). Cool to −78° C. using a dry-ice/acetone bath. Add a solution of lithium bis(trimet-hylsilyl)amide (4.25 mL, 1 M in THF, 4.52 mmol). After 30 minutes, add a solution of benzyl bromide (0.77 g, 4.52 mmol) in tetrahydrofuran (1 mL). After the addition of benzyl bromide is complete, warm slowly to ambient temperature. After 15 minutes, add water and extract three times with dichloromethane. Dry the combined organic layers over $Na_2SO_4$, filter, and concentrate in vacuo to obtain a residue. Chromatograph the residue on silica gel eluting with 1/1 ethyl acetate/hexane to give the title compound: $R_f$=0.69 (silica gel, 1/1 ethyl acetate/hexane).

13.3 Synthesis of 1-(3,4,5-trimethoxybenzyl)-3-(phenylmethyl)-3-(2-(t-butyldimethylsilyloxy)ethyl)-2-oxopyrrolidine Combine 1-(3,4,5-trimethoxybenzyl)-3-(phenylmethyl)-2-oxopyrrolidine (1.0 g, 2.81 mmol) and tetrahydrofuran (10 mL). Cool to −78° C. using a dry-ice/acetone bath. Add a solution of lithium bis(trimethylsilyl)amide (3.09 mL, 1 M in THF, 3.09 mmol). After 30 minutes, add a solution of 2-(t-butyldimethylsilyloxy)ethyl bromide (0.74 g, 3.09 mmol) in tetrahydrofuran (1 mL). After the addition of 2-(t-butyldimethylsilyloxy)ethyl bromide is complete, warm slowly to ambient temperature. After 2 hours, add water and extract three times with ethyl acetate. Dry the combined organic layers over $Na_2SO_4$, filter, and concentrate in vacuo to obtain a residue. Chromatograph the residue on silica gel eluting with 1/3 ethyl acetate/hexane to give the title compound: $R_f$=0.58 (silica gel, 1/3 ethyl acetate/hexane).

13.4 Synthesis of 1-(3,4,5-trimethoxybenzyl)-3-(phenylmethyl)-3-(2-hydroxyethyl)-2-oxopyrrolidine Combine 1-(3,4,5-trimethoxybenzyl)-3-(phenylmethyl)-3-(2-(t-butyldimethylsilyloxy)ethyl)-2-oxopyrrolidine (1.0 g, 1.95 mmol) and tetrahydrofuran (5 mL). Cool to 0° C. using a ice bath. Add a solution of tetrabutylammonium fluoride (3.90 mL, 1 M in THF, 3.90 mmol). After the addition is complete, warm to ambient temperature. After 1.5 hours, add aqueous 1 M hydrochloric acid solution (20 mL). Extract three times with ethyl acetate. Dry the combined organic layers over $Na_2SO_4$, filter, and concentrate in vacuo to obtain a residue. Chromatograph the residue on silica gel eluting with 1/1 ethyl acetate/hexane to give the title compound: $R_f$=0.27 (silica gel, 1/1 ethyl acetate/hexane).

13.5 Synthesis of 1-(3,4,5-trimethoxybenzyl)-3-(phenylmethyl)-3-(2-methanesulfonyloxyethyl)-2-oxopyrrolidine Prepare by the method of Example 2.5.2 using 1-(3,4,5-trimethoxybenzyl)-3-(phenylmethyl)-3-(2-hydroxyethyl)-2-oxopyrrolidine to give the title compound.

13.6 Synthesis of 1-(3,4,5-trimethoxybenzyl)-3-(4-(1-(2-ethoxyethyl)-1H-benzimidazol-2-yl)[1,4]diazepan-1-yl)ethyl)-3-(phenylmethyl)-2-oxopyrrolidine Prepare by the method of Example 1.6 using 1-(3,4,5-trimethoxybenzyl)-3-(phenylmethyl)-3-(2-methanesulfonyloxyethyl)-2-oxopyrrolidine and 4-(1-(2-ethoxyethyl)-1H-benzimidazol-2-yl)[1,4]diazepane to give the title compound.

EXAMPLE 14
1-(3,4,5-Trimethoxybenzyl)-3-(2-(4-(1-(2-ethoxyethyl)-1H-benzimidazol-2-yl)[1,4]diazepan-1-yl)ethyl)-3-(4-fluorophenylmethyl)-2-oxopyrrolidine

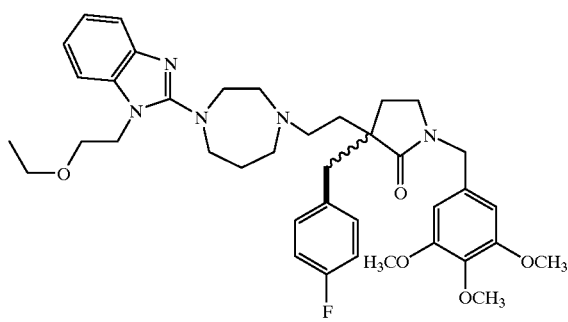

14.1 Synthesis of 1-(3,4,5-trimethoxybenyl)-3-(4-fluorophenylmethyl)-2-oxopyrrolidine Prepare by the method of Example 13.2 using 4-fluorobenzyl bromide to give the title compound: $R_f$=0.58 (silica gel, 1/1 ethyl acetate/hexane).

14.2 Synthesis of 1-(3,4,5-trimethoxybenzyl)-3-(4-fluorophenylmethyl)-3-(2-(t-butyldimethylsilyloxy)ethyl)-2-oxopyrrolidine Prepare by the method of Example 13.3 using 1-(3,4,5-trimethoxybenzyl)-3-(4-fluorophenylmethyl)-2-oxopyrrolidine to give the title compound: $R_f$=0.89 (silica gel, 1/1 ethyl acetate/hexane).

14.3 Synthesis of 1-(3,4,5-trimethoxybenzyl)-3-(4-fluorophenylmethyl)-3-(2-hydroxyethyl)-2-oxopyrrolidine Prepare by the method of Example 13.4 using 1-(3,4,5-trimethoxybenzyl)-3-(4-fluorophenylmethyl)-3-(2-(t-butyldimethylsilyloxy)ethyl)-2-oxopyrrolidine to give the title compound: $R_f$=0.22 (silica gel, ethyl acetate).

14.4 Synthesis of 1-(3,4,5-trimethoxybenzyl)-3-(4-fluorophenylmethyl)-3-(2-methanesulfonyloxyethyl)-2-oxopyrrolidine Prepare by the method of Example 2.5.2 using 1-(3,4,5-trimethoxybenzyl)-3-(4-fluorophenylmethyl)-3-(2-hydroxyethyl)-2-oxopyrrolidine to give the title compound: $R_f$=0.92 (silica gel, ethyl acetate).

14.5 Synthesis of 1-(3,4,5-trimethoxybenzyl)-3-(2-(4-(1-(2-ethoxyethyl)-1H-benzimidazol-2-yl)[1,4]diazepan-1-yl)ethyl)-3-(4-fluorophenylmethyl)-2-oxopyrrolidine Combine 1-(3,4,5-trimethoxybenzyl)-3-(4-fluorophenylmethyl)-3-(2-methanesulfonyloxyethyl)-2-oxopyrrolidine (0.34 g, 0.63 mmol) and 4-(1-(2-ethoxyethyl)-1H-benzimidazol-2-yl)[1,4]diazepane hydriodic acid salt (0.35 g, 0.63 mmol), and N,N-diisopropylethylamine (0.33 g, 2.5 mmol) in acetonitrile (10 mL). Heat to reflux. After 12 hours, cool and partition the reaction mixture between dichloromethane and a saturated aqueous ammonium chloride solution. Separate the layers and extract the organic layer with a saturated aqueous sodium bicarbonate solution. Dry the organic layer over $Na_2SO_4$, filter, and concentrate in vacuo to obtain a residue. Chromatograph the residue on a short column of silica gel eluting with 2% triethylamine/5% methanol/ethyl acetate to give the title compound: $R_f$=0.39 (silica gel, 2% triethylamine/10% methanol/ethyl acetate).

14.6 Synthesis of 1-(3,4,5-trimethoxybenzyl)-3-(2-(4-(2-ethoxyethyl)-1H-benzimidazol-2-yl)[1,4]diazepan-1-yl)ethyl)-3-(4-fluorophenylmethyl)-2-oxopyrrolidie hydrochloric acid salt Combine 1-(3,4,5-trimethoxybenzyl)-3-(2-(4-(1-(2-ethoxyethyl)-1H-benzimidazol-2-yl)[1,4]diazepan-1 -yl) ethyl)-3-(4-fluorophenylmethyl)-2-oxopyrrolidine (0.35 g, 0.51 mmol) and methanol (20 mL). Add a solution of hydrochloric acid (0.26 g, 4 M, 1.02 mmoL) in dioxane. After 18 hours, evaporate the reaction mixture invacuo to give a residue. Triturate the residue with diethyl ether (100 mL) and stir to give a solid. After 3 hours, decant the supernatant and add diethyl ether and stir. Repeatedly, decant the supernatant and add diethyl ether. Decant the supernatant and evaporate in vacuoto give the title compound: mp; 191–194° C.

EXAMPLE 15

1-Benzyl-3-(2-(4-(1-(2-ethoxyethyl)-1H-benzimidazol-2-yl)[1,4]diazepan-1-yl)ethyl)-3-(phenylmethyl)-2-oxopyrrolidine

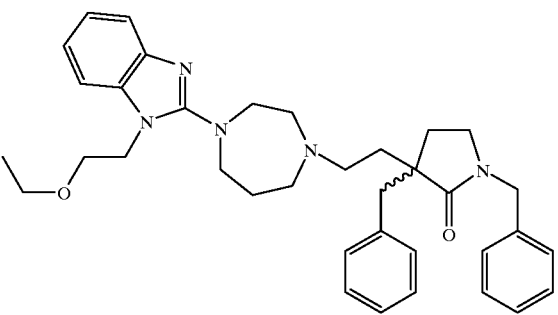

15.1 Synthesis of 1-benzyl-3-(phenylmethyl)-2-oxopyrrolidine

Prepare by the method of Example 13.2 using 1-benzyl-2-oxopyrrolidine and benzyl bromide to give the title compound: $R_f$=0.46 (silica gel, 1/1 ethyl acetate/hexane)

15.2 Synthesis of 1-benzyl-3-(phenylmethyl)-3-(2-(t-butyldimethylsilyloxy)ethyl)-2-oxopyrrolidine Prepare by the method of Example 13.3 using 1-benzyl-3-(phenylmethyl)-2-oxopyrrolidine to give the title compound: $R_f$=0.35 (silica gel, 1/4 ethyl acetate/hexane).

15.3 Synthesis of 1-benzyl-3-(phenylmethyl)-3-(2-hydroxyethyl)-2-oxopyrrolidine

Prepare by the method of Example 13.4 using 1-benzyl-3-(phenylmethyl)-3-(2-(t-butyldimethylsilyloxy)ethyl)-2-oxopyrrolidine to give the title compound: $R_f$=0.40 (silica gel, ethyl acetate).

15.4 Synthesis of 1-benzyl-3-(phenylmethyl)-3-(2-methanesulfonyloxyethyl)-2-oxopyrrolidine Prepare by the method of Example 2.5.2 using 1-benzyl-3-(phenylmethyl)-3-(2-hydroxyethyl)-2-oxopyrrolidine to give the title compound: $R_f$=0.68 (silica gel, ethyl acetate).

15.5 Synthesis of 1-benzyl-3-(2-(4-(1-(2-ethoxyethyl)-1H-benzimidazol-2-yl)[1,4]diazepan-1-yl)ethyl)-3-(phenylmethyl)-2-oxopyrrolidine Prepare by the method of Example 1.6 using 1-benzyl-3-(phenylmethyl)-3-(2-methanesulfonyloxyethyl)-2-oxopyrrolidine and 4-(1-(2-ethoxyethyl)-1H-benzimnidazol-2-yl)[1,4]diazepane to give the title compound.

EXAMPLE 16

1-(3,4,5-Trimethoxybenzoyl)-3-(2-(4-(1-(2-ethoxyethyl)-1H-benzimidazol-2-yl)[1,4]diazepan-1-yl)ethyl)-3-(phenylmethyl)pyrrolidine

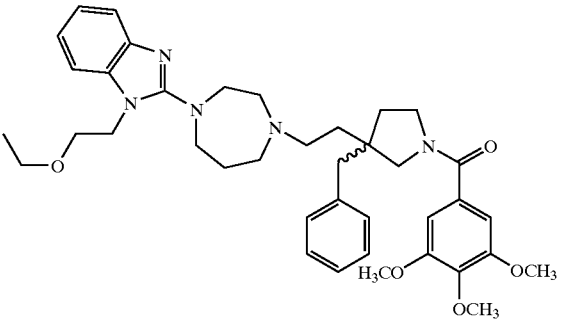

16.1 Synthesis of 1-benzyl-3-(phenylmethyl)-3-(2-hydroxyethyl)pyrrolidine

Combine 1-benzyl-3-(phenylmethyl)-3-(2-(t-butyldimethylsilyloxy)ethyl)-2-oxopyrrolidine (1.19 g, 2.81 mmol) and tetrahydrofuran (20 mL). Cool in an ice bath. Add dropwise a solution of lithium aluminum hydride (2.81 mL, 1 M in THF, 2.81 mmol). After the addition is complete, warm to ambient temperature. After 2 hours, heat to reflux. After 1 hour, cool to ambient temperature and cautiously add water (0.11 mL), a solution of 1 M sodium hydroxide (2.67 mL), and water (0.32 mL). Stir vigorously. After 2 hours, filter through celite and rinse with dichloromethane. Dry the filtrate over $Na_2SO_4$, filter, and concentrate invacuo to give a residue. Chromatograph the residue on silica gel eluting with ethyl acetate to give the title compound: $R_f$=0.34 (silica gel, 2% triethylamine/30% methanol/ethyl acetate)

16.2 Synthesis of 3-(phenylmethyl)-3-(2-hydroxyethyl)pyrrolidine

Combine 1-benzyl-3-(phenylmethyl)-3-(2-hydroxyethyl)pyrrolidine (0.72 g, 2.45 mmol) and methanol (20 mL). Add 20% palladium hydroxide-on-carbon (0.231 g). Hydrogenate in a Parr apparatus at an initial pressure of 50 psi. After 24 hours, filter through celite, rinse with methanol. Evaporate the filtrate in vacuo to give the title compound: $R_f$=0.01 (silica gel, 2% triethylamine/methanol).

16.3 Synthesis of 1-(3,4,5-trimethoxybenzoyl)-3-(phenylmethyl)-3-(2-hydroxyethyl)pyrrolidine Combine 3-(phenylmethyl)-3-(2-hydroxyethyl)pyrrolidine (3.94 mmol) and sodium carbonate (0.21 g, 2.00 mmol) in 1/1 ethyl acetate/water (50 mL). Cool the reaction mixture to 0° C. with an ice bath. Add 3,4,5-trimethoxybenzoyl chloride (0.83 g, 3.58 mmol). Warm to ambient temperature. After 18 hours, separate the layers and extract the aqueous layer three times with ethyl acetate. Dry the combined organic layers over $Na_2SO_4$, filter, and concentrate in vacuo to obtain a residue. Chromatograph the residue on silica gel eluting with ethyl acetate to give the title compound: $R_f$=0.0⁹ (silica gel, ethyl acetate).

16.4 Synthesis of 1-(3,4,5-trimethoxybenzoyl)-3-(phenylmethyl)-3-(2-methanesulfonyloxyethyl)pyrrolidine Prepare by the method of Example 2.5.2 using 1-(3,4,5-trimethoxybenzoyl)-3-(phenylmethyl)-3-(2-hydroxyethyl)pyrrolidine to give the title compound: $R_f$=0.54 (silica gel, 1/4 ethyl acetate/hexane).

16.5 Synthesis of 1-(3,4,5-trimethoxybenzoyl)-3-(2-(4-(1H-benzimidazol-2-yl)[1,4]diazepan-1-yl)ethyl)-3-(phenylmethyl)pyrrolidine Prepare by the method of Example 1.6 using 1-(3,4,5-trimethoxybenzoyl)-3-(phenylmethyl)-3-(2-methanesulfonyloxyethyl)pyrrolidine and 4-(1-(2-ethoxyethyl)-1H-benzimidazol-2-yl)[1,4]diazepane.

EXAMPLE 17

1-(3,4,5-Trimethoxybenzoyl)-3-(2-(4-(1-(2-ethoxyethyl)-1H-benzimidazol-2-yl)[1,4]diazepan-1-yl)ethyl)-3-(4-methoxyphenyl)pyrrolidine

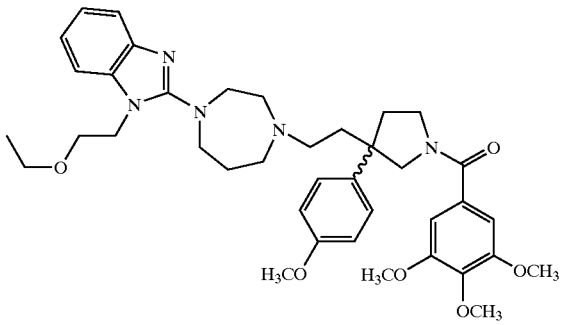

17.1 Synthesis of 3-cyano-3-(4-methoxyphenyl)pentanedioic acid diethyl ester Combine 4-methoxyphenylacetonitrile (200 g, 1.36 mol) and tetrahydrofuran (500 mL). Cool to about −5° C. Add dropwise a solution of sodium bis(trimethylsi.yl)amide (2900 mL, 1 M in tetrahydrofuran, 2.90 mol). When the addition is complete warm the reaction mixture to ambient temperature and allow to stir for 1 hour. Transfer the above solution via cannula into a cooled (−12° C.) solution of ethyl bromoacetate (459.9 g) in tetrahydrofuran (1800 mL) at such a rate that the temperature of the reaction mixture does not rise above about 15° C. Allow to stir at ambient temperature. After 18 hours, dilute with diethyl ether and extract with water, 10% hydrochloric acid solution, and saturated aqueous solution of sodium bicarbonate. Dry the organic layer over $MgSO_4$, filter, and concentrate in vacuo to obtain a residue. Distill the residue by bulb-to-bulb distillation to give the title compound: bp; 175–185° C. at 1.0 mm Hg.

17.2 Synthesis of (3-(4-methoxyphenyl)-5-oxopyrrolidin-3-yl)acetic acid ethyl ester Prepare by the method of Example 2.2.2 using 3-cyano-3-(4-methoxyphenyl)pentanedioic acid diethyl ester to give the title compound.

17.3 Synthesis of 3-(4-methoxyphenyl)-3-(2-hydroxyethyl)pyrrolidine

Prepare by the method of Example 2.3 using (3-(4-methoxyphenyl)-5-oxopyrrolidin-3-yl)acetic acid ethyl ester to give the title compound: $R_f$=0.35 (silica gel, 85/10/5 dichloromethane/methanol/acetic acid).

17.4 Synthesis of 1-(3,4,5-trimethoxybenzoyl)-(3-(4-methoxyphenyl)-3-(2-hydroxyethyl)pyrrolidine Combine 3-(4-inethoxyphenyl)-3-(2-hydroxyethyl)pyrrolidine (20 mmol) and sodium bicarbonate (8.4 g) in acetone (50 mL)/water (50 mL). Add a solution of 3,4,5-trimethoxybenzoyl chloride (4.6 g, 19.9 mmol) in acetone (50 mL). After 3 hours, extract the reaction mixture three times with ethyl acetate. Dry the organic layer over $MgSO_4$, filter, and concentrate in vacuo to give the title compound: $R_f$=0.²⁵ (silica gel, 6% methanol/dichloromethane).

17.5 Synthesis of 1-(3,4,5-trimethoxybenzoyl)-3-(4-methoxyphenyl)-3-(2-methanesulfonyloxyethyl)pyrrolidine Prepare by the method of Example 2.5.2 using 1-(3,4,5-trimethoxybenzoyl)-3-(4-methoxyphenyl)-3-(2-hydroxyethyl)pyrrolidine to give the title compound: $R_f$=0.44 (silica gel, ethyl acetate).

17.6 Synthesis of 1-(3,4,5-trimethoxybenzoyl)-3-(2-(4-(1-(2-ethoxyethyl)-1H-benzimidazol-2-yl)[1,4]diazepan-1-yl)ethyl)-3-(4-methoxyphenyl)pyrrolidine Combine 1-(3,4,5-trimethoxybenzoyl)-3-(4-methoxyphenyl)-3-(2-methanesulfonyloxyethyl)pyrrolidine (0.94 g, 1.90 mmol), 4-(1-(2-ethoxyethyl)-1H-benzimidazol-2-yl)[1,4]diazepane (0.52 g, 1.80 mmol), and N,N-diisopropylethylamine (0.7 mL, 4.0 mmol) in acetonitrile (30 mL). Heat to reflux. After 18 hours, cool and dilute the reaction mixture ethyl acetate (300 mL). Extract three times with an aqueous 1% sodium bicarbonate solution, and then brine. Dry the organic layer over $Na_2SO_4$, filter, and concentrate in vacuo to obtain a residue. Chromatograph the residue on silica gel eluting with 25% methanol/ethyl acetate containing concentrated ammonium hydroxide (20 mL/3L). Evaporate the product containing fractions in vacuo to give a residue. Dissolve the residue in dichloromethane, filter, and evaporate in vacuo to give a the title compound: $R_f=0.20$ (silica gel, 20% methanol/ethyl acetate).

17.7 Synthesis of 1-(3,4,5-trimethoxybenzoyl)-3-(2-(4-(1-(2-ethoxyethyl)-1H-benzimidazol-2-yl)[1,4]diazepan-1-yl)ethyl)-3-(4-methoxyphenyl)pyrrolidine fumaric acid salt Combine 1-(3,4,5-trimethoxybenzoyl)-3-(2-(4-(1-(2-ethoxyethyl)-1H-benzimidazol-2-yl)[1,4]diazepan-1-yl)ethyl)-3-(4-methoxyphenyl)pyrrolidine (0.53 g) and ethyl acetate (50 mL). Add a solution of fumaric acid (0.17 g) in methanol (5 mL). Add diethyl ether (200 mL) and stir. After 18 hours, evaporate in vacuo to give a residue. Triturate the residue with diethyl ether and stir to give a solid. Decant the solvent, add diethyl ether, and stir. After 18 hours, decant the solvent and evaporate in vacuo to give the title compound.

EXAMPLE 18

1-(3,4,5-Trimethoxybenzyl)-3-(3-(4-(1-(2-ethoxyethyl)-1H-benzimidazol-2-yl)[1,4]diazepan-1-yl)propyl)-3-(4-fluorophenylmethyl)-2-oxopyrrolidine

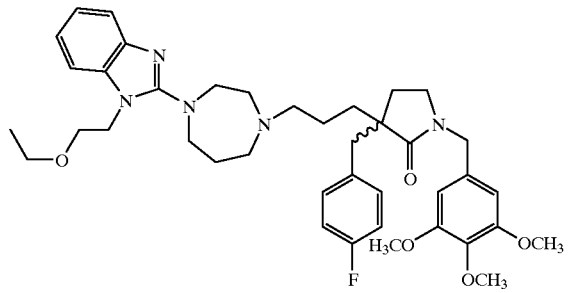

18.1 Synthesis of 1-(3,4,5-trimethoxybenzyl)-3-(4-fluorophenylmethyl)-3-(3-t-butyldimethylsilyloxypropyl)-2-oxopyrrolidine Prepare by the method of Example 13.3 using 1-(3,4,5-trimethoxybenzyl)-3-(4-fluorophenylmethyl)-2-oxopyrrolidine and 3-t-butyldimethylsilyloxypropyl iodide to give the title compound: $R_f=0.52$ (silica gel, 1/4 ethyl acetate/hexane).

18.2 Synthesis of 1-(3,4,5-trimethoxybenzyl)-3-(4-fluorophenylmethyl)-3-(3-hydroxypropyl)-2-oxopyrrolidine Combine 1-(3,4,5-trimethoxybenzyl)-3-(4-fluorophenylmethyl)-3-(3-(t-butyldimethylsilyloxy)propyl)-2-oxopyrrolidine (1.08 mmol) and ammonium fluoride (0.24 g, 6.48 mmol) in methanol (10 mL). Heat to reflux. After 2 hours, cool to ambient temperature and pour the reaction mixture into a brine (30 mL). Extract five times with dichloromethane. Dry the combined organic layers over $Na_2SO_4$, filter, and concentrate in vacuo to give a residue. Chromatograph the residue on silica gel eluting with ethyl acetate to give the title compound: $R_f=0.30$ (silica gel, ethyl acetate).

18.3 Synthesis of 1-(3,4,5-trimethoxybenzyl)-3-(4-fluorophenylmethyl)-3-(3-methanesulfonyloxypropyl)-2-oxopyrrolidine Combine 1-(3,4,5-trimethoxybenzyl)-3-(4-fluorophenylmethyl)-3-(3-hydroxypropyl)-2-oxopyrrolidine (2.6 mmol), and dichloromethane (15 mL). Cool to −5° C. using a salt-ice bath. Add dropwise, methanesulfonyl chloride (0.19 g, 1.62 mmol) at such a rate as to maintain the reaction temperature below 0° C. After 1 hour, the reaction mixture is extracted with 1 M hydrochloric acid solution and then a 5% sodium bicarbonate solution. Dry the organic layer over $Na_2SO_4$, filter, and evaporate in vacuo to give the title compound: $R_f=0.71$ (silica gel, ethyl acetate).

18.4 Synthesis of 1-(3,4,5-trimethoxybenzyl)-3-(3-(4-(1-(2-ethoxyethyl)-1H-benzimidazol-2-yl)[1,4]diazepan-1-yl)propyl)-3-(4-fluorophenylmethyl)-2-oxopyrrolidine Prepare by the method of Example 1.6 using 1-(3,4,5-trimethoxybenzyl)-3-(4-fluorophenylmethyl)-3-(3-methanesulfonyloxypropyl)-2-oxopyrrolidine and 4-(1-(2-ethoxyethyl)-1H-benzimidazol-2-yl)[1,4]diazepane to give the title compound: $R_f=0.39$ (silica gel, 2%triethylamine/20% methanol/ethyl acetate).

EXAMPLE 19

1-(3,4,5-Trimethoxybenzoyl)-3-(2-(4-(1-(2-ethoxyethyl)-1H-benzimidazol-2-yl)[1,4]diazepan-1-yl)ethyl)-3-(4-fluorophenyl)pyrrolidine

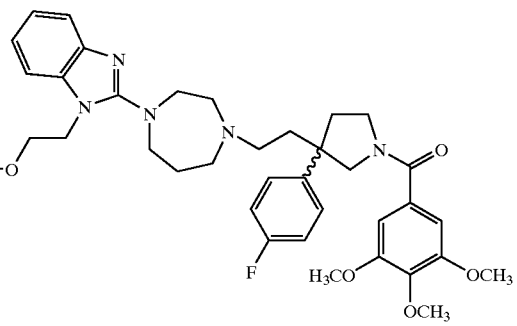

19.1.1 Synthesis of 3-cyano-3-(4-fluorophenyl)pentanedioic acid diethyl ester

Prepare by the method of Example 17.1 using 4-fluorophenylacetonitrile to give the title compound.

19.1.2 Synthesis of 3-cyano-3-(4-fluorophenyl)pentanedioic acid diethyl ester

Prepare by the method of Example 6.1.2 using 4-fluorophenylacetonitrile to give, after recrystallization prom diethyl ether, the title compound.

19.2 Synthesis of (3-(4-fluorophenyl)-5-oxopyrrolidin-3-yl)acetic acid ethyl ester Prepare by the method of Example 2.2.2 using 3-cyano-3-(4-fluorophenyl)pentanedioic acid diethyl ester to give the title compound.

19.3 Synthesis of 3-(4-fluorophenyl)-3-(2-hydroxyethyl)pyrrolidine

Prepare by the method of Example 2.3 using (3-(4-fluorophenyl)-5-oxopyrrolidin-3-yl)acetic acid ethyl ester to give the title compound: $R_f=0.10$ (silica gel, 90/10/10 dichloromethane/methanol/acetic acid).

19.4 Synthesis of 1-(3,4,5-trimethoxybenzoyl)-(3-(4-fluorophenyl)-3-(2-hydroxyethyl)pyrrolidine Combine 3-(4-fluorophenyl)-3-(2-hydroxyethyl)pyrrolidine (4.0 g, 19 mmol) and sodium bicarbonate (8.0 g, 95 mmol) in acetone (50 mL) and water (50 mL). Add a solution of 3,4,5-trimethoxybenzoyl chloride (4.4 g, 19.0 mmol) in acetone (50 mL). After 3 hours, extract the reaction mixture three times with ethyl acetate. Dry the organic layer over MgSO$_4$, filter, and concentrate in vacuo to give the title compound: R$_f$=0.41 (silica gel, 6% methanol/dichloromethane).

19.5 Synthesis of 1-(3,4,5-trimethoxybenzoyl)-3-(4-fluorophenyl)-3-(2-methanesulfonyloxyethyl)pyrrolidine Prepare by the method of Example 2.5.2 using 1-(3,4,5-trimethoxybenzoyl)-3-(4-fluorophenyl)-3-(2-hydroxyethyl)pyrrolidine to give the title compound: R$_f$=0.31 (silica gel, ethyl acetate).

19.6 Synthesis of 1-(3,4,5-trimethoxybenzoyl)-3-(2-(4-(1-(2-ethoxyethyl)-1H-benzimidazol-2-yl)[1,4]diazepan-1-yl)ethyl)-3-(4-fluorophenyl)pyrrolidine Combine 1-(3,4,5-trimethoxybenzoyl)-3-(4-fluorophenyl)-3-(2-methanesulfonyloxyethyl)pyrrolidine (0.62 g, 1.4 mmol) and 4-(1-(2-ethoxyethyl)-1H-benzimidazol-2-yl)[1,4]diazepane (0.5 g, 1.7 mmol), and N,N-diisopropylethylamine (0.39 g, 3.0 mmol) in acetonitrile (10 mL). Heat to reflux. After 2 days, cool evaporate in vacuo to obtain a residue. Chromatograph the residue on silica gel eluting with 2% triethylamine/20% methanol/ethyl acetate to give a residue. Dissolve the residue in dichloromethane, extract with brine, dry the organic layer over Na$_2$SO$_4$, filter, and evaporate in vacuo to give the title compound: R$_f$=0.36 (silica gel, 2% triethylamine/30% methanol/ethyl acetate).

19.7 Synthesis of 1-(3,4,5-trimethoxybenzoyl)-3-(2-(4-(1-(2-ethoxyethyl)-1H-benzimidazol-2-yl)[1,4]diazepan-1-yl)ethyl)-3-(4-fluorophenyl)pyrrolidine maleic acid salt Combine 1-(3,4,5-trimethoxybenzoyl)-3-(2-(4-(1-(2-ethoxyethyl)-1H-benzimidazol-2-yl)[1,4]diazepan-1-yl)ethyl)-3-(4-fluorophenyl)pyrrolidine (0.41 g) and maleic acid (0.12 g, 1.03 mmol) in ethyl acetate (5 mL) and heat to reflux. After 1 hour, cool to ambient temperature. After 18 hours, evaporate in vacuo to give a residue. Triturate the residue with diethyl ether (15 mL) and stir to give a solid. Collect the solid by filtration, rinse with diethyl ether, and dry in vacuo to give the title compound.

EXAMPLE 20

1-(2-Methoxybenzyl)-3-(2-(4-(1-(2-ethoxyethyl)-1H-benzimidazol-2-yl)[1,4]diazepan-1-yl)ethyl)-3-(4-fluorophenylmethyl)-2-oxopyrrolidine

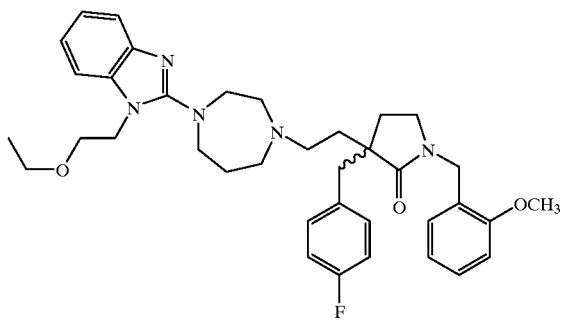

20.1 Synthesis of 1-(2-methoxybenzyl)-2-oxopyrrolidine

Prepare by the method of Example 13.1 using 2-methoxybenzyl chloride to give the title compound: R$_f$=0.55 (silica gel, 1/1 ethyl acetate/hexane).

20.2 Synthesis of 1-(2-methoxybenzyl)-3-(4-fluorophenylmethyl)-2-oxopyrrolidine

Prepare by the method of Example 13.2 using 4-fluorobenzyl bromide to give the title compound: R$_f$=0.54 (silica gel, 1/1 ethyl acetate/hexane).

20.3 Synthesis of 1-(2-methoxybenzyl)-3-(4-fluorophenylmethyl)-3-(2-(t-butyldimethylsilyloxy)ethyl)-2-oxopyrrolidine Prepare by the method of Example 13.3 using 1-(2-methoxybenzyl)-3-(4-fluorophenylmethyl)-2-oxopyrrolidine to give the title compound: R$_f$=0.89 (silica gel, 1/1 ethyl acetate/hexane).

20.4 Synthesis of 1-(2-methoxybenzyl)-3-(4-fluorophenylmethyl)-3-(2-hydroxyethyl)-2-oxopyrrolidine Prepare by the method of Example 18.2 using 1-(2-methoxybenzyl)-3-(4-fluorophenylmethyl)-3-(2-(t-butyldimethylsilyloxy)ethyl)-2-oxopyrrolidine to give the title compound: R$_f$=0.28 (silica gel, ethyl acetate).

20.5 Synthesis of 1-(2-methoxybenzyl)-3-(4-fluorophenylmethyl)-3-(2-methanesulfonyloxyethyl)-2-oxopyrrolidine Prepare by the method of Example 2.5.2 using 1-(2-methoxybenzyl)-3-(4-fluorophenylmethyl)-3-(2-hydroxyethyl)-2-oxopyrrolidine to give the title compound: R$_f$=0.45 (silica gel, 1/4 ethyl acetate/hexane).

20.6 Synthesis of 1-(2-methoxybenzyl)-3-(2-(4-(1-(2-ethoxyethyl)-1H-benzimidazol-2-yl)[1,4]diazepan-1-yl)ethyl)-3-(4-flluorophenylmethyl)-2-oxopyrrolidine Prepare by the method of Example 1.6 using 1-(2-methoxybenzyl)-3-(4-fluorophenylmethyl)-3-(2-methanesulfonyloxyethyl)-2-oxopyrrolidine and 4-(1-(2-ethoxyethyl)-1H-benzimidazol-2-yl)[1,4]diazepane to give the title compound.

EXAMPLE 21

1-(3,4,5-Trimethoxybenzyl)-3-(2-(4-(1-(2-ethoxyethyl)-1H-benzimidazol-2-yl)[1,4]diazepan-1-yl)ethyl)-3-phenyl-2-oxopyrrolidine

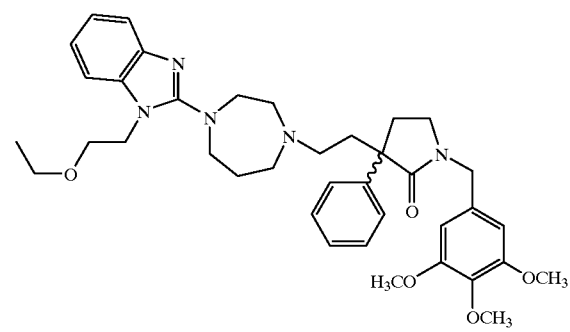

21.1 Synthesis of methyl 3-cyano-2-phenylpropionate

Combine methyl phenylacetate (2.0 g, 13.3 mmol) and tetrahydrofuran (15 mL). Cool in a dry-ice/acetone bath. Add dropwise a solution of lithium diisopropylamide (6.66 mL, 2 M in THF, 13.32 mmol). After 1 hour, add α-bromoacetonitrile (1.6 g, 13.3 mmol). After 2 hours, warm the reaction mixture to ambient temperature and partition the reaction mixture between ethyl acetate and water. Separate the aqueous layer and extract three times with ethyl acetate. Dry the combined organic layers over Na$_2$SO$_4$, filter, and concentrate in vacuo to obtain a residue. Distill the residue bulb-to-bulb to give the title compound: bp; 150° C. at 0.5 mm Hg; R$_f$=0.72 (silica gel, 25% ethyl acetate/hexane).

21.2 Synthesis of 3-phenyl-2-oxopyrrolidine

Prepare by the method of Example 2.2.2 using methyl 3-cyano-2-phenylpropionate to give the title compound R$_f$=0.20 (silica gel, ethyl acetate).

21.3 Synthesis of 1-(3,4,5-trimethoxybenzyl)-3-phenyl-2-oxopyrrolidine

Prepare by the method of Example 13.1 using 3-phenyl-2-oxopyrrolidine to give the title compound R$_f$=0.24 (silica gel, 1/1 ethyl acetate/hexane).

21.4 Synthesis of 1-(3,4,5-trimethoxybenzyl)-3-(2-(t-butyldimethylsilyloxy)ethyl)-3-phenyl-2-oxopyrrolidine Prepare by the method of Example 13.3 using 1-(3,4,5-trimethoxybenzyl)-3-phenyl-2-oxopyrrolidine to give the title compound: $R_f$=0.66 (silica gel, 1/1 ethyl acetate/hexane).

21.5 Synthesis of 1-(3,4,5-trimethoxybenzyl)-3-(2-hydroxyethyl)-3-phenyl-2-oxopyrrolidine Prepare by the method of Example 18.2 using 1-(3,4,5-trimethoxybenzyl)-3-(2-(t-butyldimethylsilyloxy)ethyl)-3-phenyl-2-oxopyrrolidine to give the title compound: $R_f$=0.55 (silica gel, ethyl acetate).

21.6 Synthesis of 1-(3,4,5-trimethoxybenzyl)-3-(2-methanesulfonylox ethyl)-3-phenyl-2-oxopyrrolidine Prepare by the method of Example 2.5.2 using 1-(3,4,5-trimethoxybenzyl)-3-(2-hydroxyethyl)-3-phenyl-2-oxopyrrolidine to give the title compound: $R_f$=0.74 (silica gel, ethyl acetate).

21.7 Synthesis of 1-(3,4,5-trimethoxybenzyl)-3-(2-(4-(1-(2-ethoxyethyl)-1H-benzimidazol-2-yl)[1,4]diazepan-1-yl)ethyl)-3-phenyl-2-oxopyrrolidine Prepare by the method of Example 1.6 using 1-(3,4,5-trimethoxybenzyl)-3-(2-methanesulfonyloxyethyl)-3-phenyl-2-oxopyrrolidine and 4-(1-(2-ethoxyethyl)-1H-benzimidazol-2-yl)[1,4]diazepane to give the title compound.

EXAMPLE 22

1-(3,4,5-Trimethoxybenzoyl)-3-(2-(4-(1-(2-ethoxyethyl)-1H-benzimidazol-2-yl)[1,4]diazepan-1-yl)ethyl)-3-(3,4-difluorophenyl)pyrrolidine

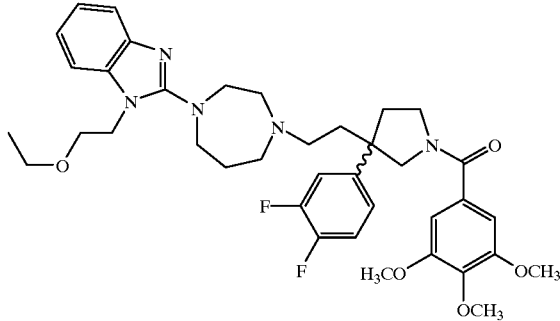

22.1.1 Synthesis of 3-cyano-3-(3,4-difluorophenyl)pentanedioic acid diethyl ester Prepare by the method of Example 3.1.2 using 3,4-difluorophenylacetonitrile to give the title compound.

22.1.2 Synthesis of 3-cyano-3-(3,4-difluorophenyl)pentanedioic acid diethyl ester Prepare by the method of Example 6.1.2 using 3,4-difluorophenylacetonitrile to give the title compound.

22.2.1 Synthesis of (3-(3,4-difluorophenyl)-5-oxopyrrolidin-3-yl)acetic acid ethyl ester Prepare by the method of Example 2.2.2 using 3-cyano-3-(3,4-difluorophenyl)pentanedioic acid diethyl ester to give the title compound.

22.2.2 Synthesis of (3-(3,4-difluorophenyl)-5-oxopyrrolidin-3-yl)acetic acid ethyl ester Combine 3-cyano-3-(3,4-difluorophenyl)pentanedioic acid diethyl ester (106 g, 326 mmol), ethanol (3 L), concentrated aqueous ammonia (160 mL), and Raney nickel (100 g). Hydrogenate at about 50° C. and 200 psi in an autoclave. After 22 hours, filter through celite and rinse the solids with ethanol. Evaporate the filtrate in vacuo to give a residue. Triturate the residue with ethyl acetate/hexane to give the title compound.

22.3 Synthesis of 3-(3,4-difluorophenyl)-3-(2-hydroxyethyl)pyrrolidine

Prepare by the method of Example 2.3 using (3-(3,4-difluorophenyl)-5-oxopyrrolidin-3-yl)acetic acid ethyl ester to give the title compound: $R_f$=0.26 (silica gel, 85/10/5 dichloromethane/methanol/acetic acid).

22.4 Synthesis of 1-(3,4,5-trimethoxybenzoyl)-(3-(3,4-difluorophenyl)-3-(2-hydroxyethyl)pyrrolidine Prepare by the method of Example 7.4 using 3-(3,4-difluorophenyl)-3-(2-hydroxyethyl)pyrrolidine to give the title compound: $R_f$=0.25 (silica gel, ethyl acetate).

22.5 Synthesis of 1-(3,4,5-trimethoxybenzoyl)-3-(3,4-difluorophenyl)-3-(2-methanesulfonyloxyethyl)pyrrolidine Prepare by the method of Example 2.5.2 using 1-(3,4,5-trimethoxybenzoyl)-3-(3,4-difluorophenyl)-3-(2-hydroxyethyl)pyrrolidine to give the title compound: $R_f$=0.44 (silica gel, ethyl acetate).

22.6 Synthesis of 1-(3,4,5-trimethoxybenzoyl)-3-(2-(4-(1-(2-ethoxyethyl)-1H-benzimidazol-2-yl)[1,4]diazepan-1-yl)ethyl)-3-(3,4-difluorophenyl)pyrrolidine Combine 1-(3,4,5-trimethoxybenzoyl)-3-(3,4-difluorophenyl)-3-(2-methanesulfonyloxyethyl)pyrrolidine (0.37 g, 1.6 mmol), 4-(1-(2-ethoxyethyl)-1H-benzimidazol-2-yl)[1,4]diazepane hydriodic acid salt (0.43 g, 0.8 mmol), and N,N-diisopropylethylamine (0.41 g, 3.2 mmol) in acetonitrile (10 mL). Heat to reflux. After 12 hours, cool and concentrate in vacuo to obtain a residue. Chromatograph the residue on silica gel eluting with 2% triethylamine/10% methanol/ethyl acetate to give the title compound: $R_f$=0.36 (silica gel, 2% triethylamine/10% methanol/ethyl acetate).

22.7 Synthesis of 1-(3,4,5-trimethoxybenzoyl)-3-(2-(4-(1-(2-ethoxyethyl)-1H-benzimidazol-2-yl)[1,4]diazepan-1-yl)ethyl)-3-(3,4-difluorophenyl)pyrrolidine fumaric acid salt Combine 1-(3,4,5-trimethoxybenzoyl)-3-(2-(4-(1-(2-ethoxyethyl)-1H-benzimidazol-2-yl)[1,4]diazepan-1-yl)ethyl)-3-(3,4-difluorophenyl)pyrrolidine (0.57 g) and fumaric acid (0.19 g, 1.64 mmol) in ethyl acetate (20 mL) and heat to reflux. After 2 hours, cool to ambient temperature and stir to give a solid. After 18 hours, decant the solvent and repeatedly add diethyl ether, stir, and decant. Collect the solid by filtration to give, after drying in vacuo, the title compound.

PREPARATION 4

Synthesis of 4-Methoxybenzyl mesylate

Combine 4-methoxybenzyl alcohol (45.4 mmol), N,N-diisopropylethylamine (12.9 g, 100 mmol), and acetonitrile (60 mL). Cool in an ice bath. Add methanesulfonyl chloride (6.76 , 49.0 mmol). After 2 hours, partition the reaction mixture between water and ethyl acetate. Separate the layers and extract the organic layer with 1 M hydrochloric acid solution and then a saturated solution of sodium bicarbonate. Dry the organic layer over Na₂SO₄, filter, and evaporate in vacuo to give the title compound.

EXAMPLE 23

1-(3,4,5-Trimethoxybenzyl)-3-(2-(4-(1-(2-ethoxyethyl)-1H-benzimidazol-2-yl)[1,4]diazepan-1-yl)ethyl)-3-(4-methoxyphenylmethyl)-2-oxopyrrolidine

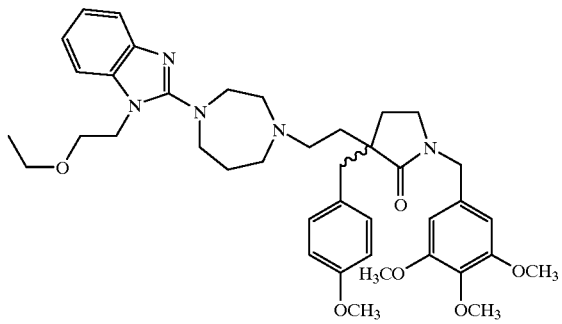

23.1 Synthesis of 1-(3,4,5-trimethoxybenzyl)-3-(2-(t-butyldimethylsilyloxy)ethyl)-2-oxopyrrolidine Prepare by the method of Example 13.:3 using 1-iodo-2-t-butyldimethylsilyloxyethane to give the title compound.

23.2 Synthesis of 1-(3,4,5-trimethoxybenyl)-3-(4-methoxyphenylmethyl)-3-(2-(t-butyldimethylsilyloxy)ethyl)-2-oxopyrrolidine Prepare by the method of Example 13.3 using 4-methoxybenzyl mesylate and 1-(3,4,5-trimethoxybenzyl)-3-(2-(t-butyldimethylsilyloxy)ethyl)-2-oxopyrrolidine to give the title compound: $R_f$=0.15 (silica gel, 1/4 ethyl acetate/hexane).

23.3 Synthesis of 1-(3,4,5-trimethoxybenzyl-3-4-methoxyphenylmethyl)-3-(2-hydroxyethyl)-2-oxopyrrolidine Prepare by the method of Example 18.2 using 1-(3,4,5-trimethoxybenzyl)-3-(4-methoxyphenylmethyl)-3-(2-(t-butyldimethylsilyloxy)ethyl)-2-oxopyrrolidine to give the title compound: $R_f$=0.33 (silica gel, ethyl acetate).

23.4 Synthesis of 1-(3,4,5-trimethoxybenzyl)-3-(4-methoxyphenylmethyl)-3-(2-methanesulfonyloxyethyl)-2-oxopyrrolidine Prepare by the method of Example 2.5.2 using 1-(3,4,5-trimethoxybenzyl)-3-(4-methoxyphenylmethyl)-3-(2-hydroxyethyl)-2-oxopyrrolidine to give the title compound: $R_f$=0.53 (silica gel, ethyl acetate).

23.5 Synthesis of 1-(3,4,5-trimethoxybenzyl)-3-(2-(4-(1-(2-ethoxyethyl)-1H-benzimidazol-2-yl)[1,4]diazepan-1-yl)ethyl)-3-(4-methoxyphenylmethyl)-2-oxopyrrolidine Prepare by the method of Example 1.6 using 1-(3,4,5-trimethoxybenzyl)-3-(4-methoxyphenylmethyl)-3-(2-methanesulfonyloxyethyl)-2-oxopyrrolidine and 4-(1-(2-ethoxyethyl)-1H-benzimidazol-2-yl)[1,4]diazepane to give the title compound.

EXAMPLE 24

1-(3,4,5-Trimethoxybenzyl)-3-(2-(4-(1-(2-ethoxyethyl)-1H-benzimidazol-2-yl)[1,4]diazepan-1-yl)ethyl)-3-(phenylmethyl)-5-oxopyrrolidine

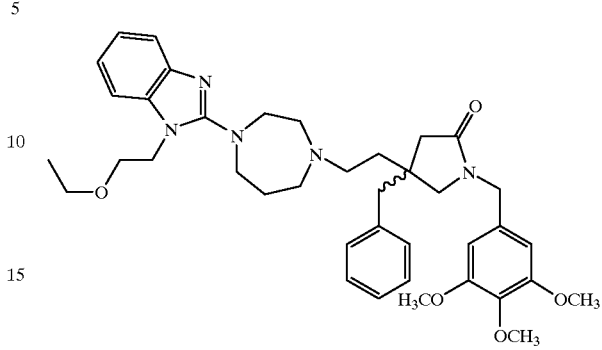

24.1 Synthesis of 2-(2-(t-butyldimethylsilyloxy)ethyl)-3-3-phenylpropionitrile Combine 3-phenylpropionitrile (2.0 g, 15.25 mmol) and tetrahydrofuran (15 mL). Cool to −78° C. using a dry-ice/acetone bath. Add a solution of lithium bis(trimethylsilyl) amide (16.0 mL, 1 M in THF, 16.0 mmol). After 1 hour, add 2-(t-butyldimethylsilyloxy)ethyl iodide (4.58 g, 16.0 mmol). After the addition of 2-(t-butyldimethylsilyloxy)ethyl iodide is complete, warm slowly to ambient temperature over about 7 hours. Add water and extract twice with ethyl acetate. Dry the combined organic layers over Na₂SO₄, filter, and concentrate in vacuo to obtain a residue. Chromatograph the residue on silica gel eluting with 5% ethyl acetate/hexane to give the title compound: $R_f$=0.50 (silica gel, 10% ethyl acetate/hexane).

24.2 Synthesis of 2-(2-(t-butyldimethylsilyloxy)ethyl)-2-allyl-3-phenylpropionitrile Combine 2-(2-(t-butyldimethylsilyloxy)ethyl)-3-phenylpropionitrile (1.32 g, 4.55 mmol) and tetrahydrofuran (8 mL). Cool to −78° C. using a dry-ice/acetone bath. Add a solution of lithium bis(trimethylsilyl)amide (9.1 mL, 1 M in THF, 9.1 mmol). After 30 minutes, add hexamethylphosphoramide (0.25 mL) and allyl bromide (1.10 g, 9.1 mmol). Warm slowly to ambient temperature. After 12 hours, add water and separate the layers. Extract the aqueous layer three times with ethyl acetate. Combine the organic layers and extract with aqueous 1 M hydrochloric acid solution. Dry the combined organic layers over Na₂SO₄, filter, and concentrate in vacuo to obtain a residue. Chromatograph the residue on silica gel eluting with 5% -ethyl acetate/hexane to give the title compound: $R_f$=0.83 -(silica gel, 1,/4 ethyl acetate/hexane).

24.3 Synthesis of 2-(2-hydroxyethyl)-2-carbomethyloxymethyl-3-phenylpropionitrile Combine 2-(2-(t-butyldimethylsilyloxy)ethyl)-2-allyl-3-phenylpropionitrile (1.19 g) and dichloromethane (25 mL) and water (25 mL). Add tetrabutyl ammonium bromide (0.01 g) and acetic acid (8.0 mL). Add potassium permanganate (2.24 g) portionwise over 2 hours. After 18 hours, add sodium sulfite to dissolve the precipitated manganese dioxide. Separate the layers and adjust the pH of the aqueous layer to about 2 using aqueous 1 M hydrochloric acid solution. Extract the aqueous layer three times with dichloromethane. Dry the combined organic layers over Na₂SO₄, filter, and concentrate in vacuo to obtain a residue. Chromatograph the residue on silica gel eluting with 1/1 ethyl acetate/hexane to give 4-cyano-4-phenylmethyl-δ-valerolactone.

Combine 4-cyano-4-phenylmethyl-δ-valerolactone (0.52 g), methanol (20 mL), and sulfuric acid (2 drops). Heat to reflux. After 2 days, add sodium bicarbonate (about 1 g) and stir, filter and evaporate in vacuo to give the title compound. $R_f$=0.28 (silica gel, ethyl acetate).

24.4 Synthesis of 2-(2-(t-butyldimethylsilyloxy)ethyl)-2-carbomethyloxymethyl-3-phenylpropionitrile Combine t-butyldimethylsilyl chloride (2.5 mmol), imidazole (5 mmol), and dimethylformamide (5 mL). Cool to 0° C. in an ice bath. Add a solution of 2-(2-hydroxyethyl)-2-carbomethyloxymethyl-3-phenylpropionitrile (0.54 g, 2.28 mmol) in dimethylformamide (5 mL). Warm to ambient temperature. After 12 hours, dilute the reaction mixture with hexane (100 mL) and ethyl acetate (10 mL). Extract with aqueous 1 M hydrochloric acid solution and aqueous 5% sodium bicarbonate solution. Dry the organic layer over $Na_2SO_4$, filter, and concentrate in vacuo to obtain a residue. Chromatograph the residue on silica gel eluting with 1/4 ethyl acetate/hexane to give the title compound: $R_f$=0.65 (silica gel, 1/1 ethyl acetate/hexane).

24.5 Synthesis of 3-(2-(t-butyldimethylsilyloxy)ethyl)-3-(phenylmethyl)-5-oxopyrrolidine Combine 2-(2-(t-butyldimethylsilyloxy)ethyl)-2-carbomethyloxymethyl-3-phenylpropionitrile (0.26 g, 0.72 mmol) and 10% aqueous concentrated ammonia solution/ethanol (20 mL) in a Parr bottle. After rinsing with water and ethanol, add Raney nickel (2.21 g). Hydrogenate at 50 psi for 24 h. Filter through a celite pad and rinse the solids with ethanol. Evaporate the filtrate in vacuo to obtain a residue. Partition the residue between dichloromethane and water. Extract the aqueous layer with dichloromethane. Dry the combined organic layers over $Na_2SO_4$, filter, and concentrate in vacuo to obtain a residue. Chromatograph the residue on silica gel eluting with 1/1 ethyl acetate/hexane to give the title compound: $R_f$=0.11 (silica gel, 1/1 ethyl acetate/hexane).

24.6 Synthesis of 1-(3,4,5-trimethoxybenzyl)-3-(2-(t-butyldimethylsilyloxy)ethyl)-3-(phenylmethyl)-5-oxopyrrolidine Combine 3-(2-(t-butyldimethylsilyloxy)ethyl)-3-(phenylmethyl)-5-oxopyrrolidine (0.13 g, 0.38 mmol) and tetrahydrofuran (2 mL). Cool to −78° C. using a dry-ice/acetone bath. Add a solution of potassium bis(trimethylsilyl)amide (0.76 mL, 0.5 M in toluene, 0.38 mmol). After 30 minutes, add a solution of 3,4,5-trimethoxybenzyl chloride (0.08 g, 0.38 mmol) in tetrahydrofuran (1 mL). Warm to ambient temperature and add tetrabutylammonium bromide (0.01 g). Heat to reflux. After 12 hours, cool the reaction mixture and partition between water and ethyl acetate. Separate the aqueous layer and extract twice with ethyl acetate. Dry the combined organic layers over $Na_2SO_4$, filter, and concentrate in vacuo to obtain a residue. Chromatograph the residue on silica gel eluting with 1/4 ethyl acetate/hexane to give the title compound: $R_f$=0.43 (silica gel, 1/1 ethyl acetate/hexane).

24.7 Synthesis of 1-(3,4,5-trimethoxybenzyl)-3-(2-hydroxyethyl)-3-(phenylmethyl)-5-oxopyrrolidine Prepare by the method of Example 18.2 using 1-(3,4,5-trimethoxybenzyl)-3-(2-(t-butyldimethylsilyloxy)ethyl)-3-(phenylmethyl)-5-oxopyrrolidine to give the title compound.

24.8 Synthesis of 1-(3,4,5-trimethoxybenzyl)-3-(2-methanesulfonyloxyethyl)-3-(phenylmethyl)-5-oxopyrrolidine Prepare by the method of Example 2.5.2 using 1-(3,4,5-trimethoxybenzyl)-3-(2-hydroxyethyl)-3-(phenylmethyl)-5-oxopyrrolidine to give the title compound: $R_f$=0.42 (silica gel, ethyl acetate).

24.9 Synthesis of 1-(3,4,5-trimethoxybenzyl)-3-(2-(4-(1-(2-ethoxyethyl)-1H-benzimidazol-2-yl)[1,4]diazepan-1-yl)ethyl)-3-(phenylmethyl)-5-oxopyrrolidine Prepare by the method of Example 1.6 using 1-(3,4,5-trimethoxybenzyl)-3-(2-methanesulfonyloxyethyl)-3-(phenylmethyl)-5-oxopyrrolidine and 4-(1-(2-ethoxyethyl)-1H-benzimidazol-2-yl)[1,4]diazepane to give the title compound.

EXAMPLE 25

1-(3,4,5-Trimethoxybenzyl)-3-(2-(4-(1-(2-ethoxyethyl)-1H-benzimidazol-2-yl)[1,4]diazepan-1-yl)ethyl)-3-(4-(trifluoromethyl)phenylmethyl)-2-oxypyrrolidine

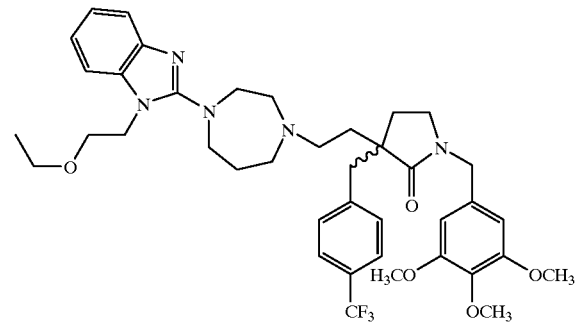

25.1 Synthesis of 1-(3,4,5-trimethoxybenzyl)-3-(4-(trifluoromethyl)phenylmethyl)-2-oxopyrrolidine Combine 1-(3,4,5-trimethoxybenzyl)-2-oxopyrrolidine (1.76 g, 6.63 mmol) and tetrahydrofuran (10 mL). Cool to −78° C. using a dry-ice/acetone bath. Add dropwise a solution of set-butyllithium (5.10 mL, 1.3 M in hexane, 6.63 mmol). After 45 minutes, slowly add a solution of 4-(trifluoromethyl)benzyl bromide (1.58 g, 6.63 mmol) in tetrahydrofuran (5 mL). After 5 hours, add water (10 mL) and warm to ambient temperature. Separate the layers and extract the aqueous layer three times with ethyl acetate. Dry the combined organic layers over $Na_2SO_4$, filter, and evaporate in vacuo to give a residue. Chromatograph the residue on silica gel eluting with 1/1 ethyl acetate/hexane to give the title compound: $R_f$=0.35 (silica gel, 1/1 ethyl acetate/hexanes).

25.2 Synthesis of 1-(3,4,5-trimethoxybenzyl)-3-(4-(trifluoromethyl)phenylmethyl)-3-(2-(t-butyldimethylsilyloxy)ethyl)-2-oxopyrrolidine Combine 1-(3,4,5-trimethoxybenzyl)-3-(4-(trifluoromethyl)phenylmethyl)-2-oxopyrrolidine (1.55 g, 3.66 mmol) and tetrahydrofuran (10 mL). Cool to −78° C. using a dry-ice/acetone bath. Add a solution of sec-butyllithium (3.1 mL, 1.3 M in hexane, 4.0 mmol). After 30 minutes, add a solution of 1-iodo-2-(t-butyldimethylsilyloxy)ethane (1.15 g, 4.0 mmol) in tetrahydrofuran (1 mL). After 2 hours, warm to ambient temperature. After 12 hours, add water (5 mL). Separate the layers and extract the aqueous layer three times with ethyl acetate. Dry the combined organic layers over $Na_2SO_4$, filter, and evaporate in vacuo to give a residue. Chromatograph the residue on silica gel eluting with 1/4 ethyl acetate/hexane to give the title compound: $R_f$=0.79 (silica gel, 1/1 ethyl acetate/hexane).

25.3 Synthesis of 1-(3,4,5-trimethoxybenzyl)-3-(4-(trifluoromethyl)phenylmethyl)-3-(2-hydroxyethyl)-2-oxopyrrolidine Prepare by the method of Example 18.2 using 1-(3,4,5-trimethoxybenzyl)-3-(4-(trifluoromethyl)phenylmethyl)-3-(2-(t-butyldimethylsilyloxy)ethyl)-2-oxopyrrolidine (0.6 g, 1.0 mmol) and ammonium fluoride (0.23 g, 6.2 mmol) to give the title compound: $R_f$=0.35 (silica gel, ethyl acetate).

25.4 Synthesis of 1-(3,4,5-trimethoxybenzyl)-3-(4-(trifluoromethyl)phenylmethyl)-3-(2-methanesulfonyloxyethyl)-2-oxopyrrolidine Prepare by the method of Example 2.5.2 using 1-(3,4,5-trimethoxybenzyl)-3-(4-(trifluoromethyl)phenylmethyl)-3-(2-hydroxyethyl)-2-oxopyrrolidine (0.46 g, 0.99 mmol) to give the title compound: $R_f$=0.67 (silica gel, ethyl acetate).

25.5 Synthesis of 1-(3,4,5-trimethoxybenzyl)-3-(2-(4-(1-(2-ethoxyethyl)-1H-benzimidazol-2-yl)[1,4]diazepan-1-yl)ethyl)-3-((4-(trifluoromethyl)phenylmethyl)-2-oxopyrrolidine Combine 1-(3,4,5-trimethoxybenzyly-3-(4-(trifluoromethyl)phenylmethyl)-3-(2-methanesulfonyloxyethyl)-2-oxopyrrolidine (0.54 g, 0.99 mmol), 4-(1-(2-ethoxyethyl)-1H-benzimidazol-2-yl)[1,4]diazepane hydriodic acid salt (0.54 g, 0.99 mmol), and N,N-diisopropylethylamine (0.5 g, 3.94 mmol) and acetonitrile (10 mL). Heat to reflux. After 12 hours, cool to ambient temperature, dilute with dichloromethane and extract twice with water. Dry the organic layer over $Na_2SO_4$, filter, and evaporate in vacuo to give a residue. Chromatograph the residue on silica gel elu.ting with 0.5% concentrated aqueous ammonia solution/5% methanol/ethyl acetate to give the title compound: $R_f$=0.34 (silica gel, 0.5% concentrated aqueous ammonia solution/5% methanol/ethyl acetate).

EXAMPLE 26

1-(3,4,5-Trimethoxybenzoyl)-3-(2-(4-(1-(2-ethoxyethyl)-1H-benzimidazol-2-yl)[1,4]diazepan-1-yl)ethyl)-3-(3,4-difluorophenyl)pyrrolidine

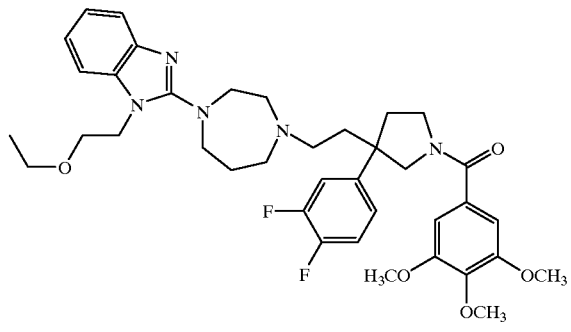

26.1.1 Resolution of (+)-3-(3,4-difluorophenyl)-3-(2-hydroxyethyl)pyrrolidine (R,R)-di-p-anisoyltartaric acid salt and (−)-3-(3,4-difluorophenyl)-3-(2-hydroxyethyl)pyrrolidine hydrochloric acid salt Combine (R,R)-di-p-anisoyltartaric acid (0.93 g, 2.2 mmol) and aqueous 12 M hydrochloric acid solution (0.19 mL, 2.28 mmol) in water/methanol (10 mL)/(10 mL). Heat to reflux. Add dropwise, a solution of 3-(3,4-difluorophenyl)-3-(2-hydroxyethyl)pyrrolidine (1.0 g, 4.4 mmol) in methanol (10 mL). After 15 minutes, slowly cool to ambient temperature. Filter the solid that forms and rinse with water to give (−)-3-(3,4-difluorophenyl)-3-(2-hydroxyethyl)pyrrolidine (R,R)-di-p-anisoyltartaric acid salt. $[\alpha]_D^{20}$=−25.1 (c=1.02, dimethylsulfoxide). Analysis on HPLC, on an analytical sample of the free amine obtained by extraction, using a CHIRALPAK AD 25 cm×0.46 cm column eluting with pentane/methanol/triethylamine (80/10/0.1) with a flow rate of 1.0 mL/minute indicates an ienantiomeric excess of 97.8%, (97.8% ee), retention time 19.0 minutes for the 3,4,5-trimethoxybenzamide prepared from the (−)-isomer of the (R,R)-di-p-anisoyltartaric acid salt, retention time 12.5 minutes for the 3,4,5-trimethoxybenzamide prepared from the (+)-isomer of the (R,R)-di-p-anisoyltartaric acid salt.

26.1.2 Resolution of (+)-3-(3,4-difluorophenyl)-3-(2-hydroxyethyl)pyrrolidine (R,R)-di-p-anisoyltartaric acid salt and (−)-3-(3,4-difluorophenyl)-3-(2-hydroxyethyl)pyrrolidine hydrochloric acid salt Combine (R,R)-di-p-anisoyltartaric acid (6.6 g, 15.8 mmol) and water/methanol (70 mL)/(70 mL). Heat to reflux. Add aqueous 12 M hydrochloric acid solution (1.31 mL, 15.7 mmol). Add dropwise, a solution of 3-(3,4-difluorophenyl)-3-(2-hydroxyethyl)pyrrolidine (7.15 g, 31.5 mmol) in methanol (70 mL). After 15 minutes, allow to cool slightly and add seed crystals of (−)-3-(3,4-difluorophenyl)-3-(2-hydroxyethyl)pyrrolidine (R,R)-di-p-anisoyltartaric acid salt and then slowly cool to ambient temperature. Filter the solid that forms. Retain the filtrate which is enriched in the slower eluting isomer. Combine the solid with hot ethanol (800 mL), filter, reduce the volume of the solution to about 600 mL and slowly cool to ambient temperature to give a solid. Collect the solid by filtration and dry in vacuo at 82° C. to give (−)-3-(3,4-difluorophenyl)-3-(2-hydroxyethyl)pyrrolidine (R,R)-di-p-anisoyltartaric acid salt. Analysis on HPLC, on an analytical sample of the 3,4,5-trimethoxybenzamide derivative using a CHIRALPAK AD 25 cm×0.46 cm column eluting with pentane/ethanol/methanol/triethylamine (80/15/5/0.1) with a flow rate of 1.0 mL/minute indicates an enantiomeric excess of greater than 99%, (>99% ee).

26.2 Synthesis of 1-(3,4,5-trimethoxybenzoyl)-3-(3,4-difluorophenyl)-3-(2-hydroxyethyl)pyrrolidine Prepare by the method of Example 5.2.2 using (−)-3-(3,4-difluorophenyl)-3-(2-hydroxyethyl)pyrrolidine (R,R)-di-p-anisoyltartaric acid salt.

26.3 Synthesis of 1-(3,4,5-trimethoxybenzoyl)-3-(3,4-difluorophenyl)-3-(2-methanesulfonyloxyethyl)pyrrolidine Prepare by the method of Example 2.5.2 using 1-(3,4,5-trimethoxybenzoyl)-3-(3,4-difluorophenyl)-3-(2-hydroxyethyl)pyrrolidine (prepared from (−)-3-(3,4-difluorophenyl)-3-(2-hydroxyethyl)pyrrolidine (R,R)-di-p-anisoyltartaric acid salt) to give the title compound.

26.4 Synthesis of 1-(3,4,5-trimethoxybenzoyl)-3-(2-(4-(1-(2-ethoxyethyl)-1H-benzimidazol-2-yl)[1,4]diazepan-1-yl)ethyl)-3-(3,4-difluorophenyl)pyrrolidine Prepare by the method of Example 1.6 using 1-(3,4,5-trimethoxybenzoyl)-3-(3,4-difluorophenyl)-3-(2-methanesulfonyloxyethyl)pyrrolidine(prepared from (−)-3-(3,4-difluorophenyl)-3-(2-hydroxyethyl)pyrrolidine (R,R)-di-p-anisoyltartaric acid salt) to give the title compound.

EXAMPLE 27
1-(3,4,5-Trimethoxybenzyl)-3-(2-(4-(1-(2-ethoxyethyl)-1H-benzimidazol-2-yl)[1,4]diazepan-1-yl)ethyl)-3-(3,4-difluorophenylmethyl)-2-oxopyrrolidine

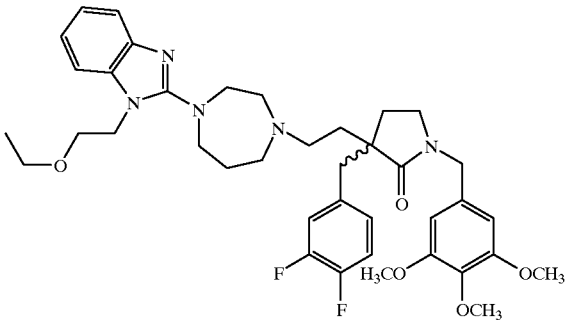

27.1 Synthesis of 1-(3,4,5-trimethoxybenzyl)-3-(2-(t-butyldimethylsilyloxy)ethyl)-2-oxopyrrolidine Combine 1-(3,4,5-trimethoxybenzyl)-2-oxopyrrolidine and (1.0 g, 3.77 mmol) and tetrahydrofuran (5 mL). Cool to −78° C. using a dry-ice/acetone bath. Add a solution of lithium bis(trimethylsilyl)amide (4.25 mL, 1 M in THF, 4.52 mmol). After 30) minutes, add a solution of 1-iodo-2-t-butyldimethylsilyloxyethane (4.52 mmol) in tetrahydrofuran (1 mL). After the addition of 1-iodo-2-t-butyldimethylsilyloxyethane is complete, warm slowly to ambient temperature. After 15 minutes, add water and extract three times with dichloromethane. Dry the combined organic layers over Na$_2$SO$_4$, filter, and concentrate in vacuo to obtain a residue. Chromatograph the residue on silica gel eluting with 1/1 ethyl acetate/hexane to give the title compound: R$_f$=0.48 (silica gel, 1/1 ethyl acetate/hexane).

27.2 Synthesis of 1-(3,4,5-trimethoxybenzyl)-3-(3,4-diflurorphenylmethyl)-3-(2-(t-butyldimethylsilyloxy)ethyl)-2-oxopyrrolidine Combine 1-(3,4,5-trimethoxybenzyl)-3-(2-(t-butyldimethylsilyloxy)ethyl)-2-oxopyrrolidine (0.7 g, 1.66 mmol) and tetrahydrofuran (10 mL). Cool to −78° C. using a dry-ice/acetone bath. Add a solution of lithium bis (trimethylsilyl)amide (1.66 mL, 1 M in THF, 1.66 mmol). After 30 minutes, add a solution of 3,4-difluorobenzyl bromide (0.34 g, 1.66 mmol) in tetrahydrofuran (1 mL). After the addition of 3,4-difluorobenzyl bromide is complete, warm slowly to ambient temperature. After 12 hours, add water and extract three times with ethyl acetate. Dry the combined organic layers over Na$_2$SO$_4$, filter, and concentrate in vacuo to obtain a residue. Chromatograph the residue on silica gel eluting with 1/1 ethyl acetate/hexane to give the title compound: R$_f$=0.48 (silica gel, 1/1 ethyl acetate/hexane).

27.3 Synthesis of 1-(3,4,5-trimethoxybenzyl)-3-(3,4-diflurorphenylmethyl)-3-(2-hydroxyethyl)-2-oxopyrrolidine Prepare by the method of Example 18.2 using 1-(3,4,5-trimethoxybenzyl)-3-(3,4-diflurorphenylmethyl)-3-(2-(t-butyldimethylsilyloxy)ethyl)-2-oxopyrrolidine (0.55 g, 1.05 mmol) and ammonium fluoride (0.23 g, 6.33 mmol) to give the title compound: R$_f$=0.41 (silica gel, 1/1 ethyl acetate/hexane).

27.4 Synthesis of 1-(3,4,5-trimethoxybenzyl)-3-(3,4-diflurorphenylmethyl)-3-(2-methanesulfonyloxyethyl)-2-oxopyrrolidine Prepare by the method of Example 2.5.2 using 1-(3,4,5-trimethoxybenzyl)-3-(3,4-diflurorphenylmethyl)-3-(2-hydroxyethyl)-2-oxopyrrolidine to give the title compound.

27.5 Synthesis of 1-(3,4,5-trimethoxybenzyl)-3-(2-(4-(1-(2-ethoxyethyl)-1H-benzimidazol-2-yl)[1,4]diazepan-1-yl)ethyl)-3-(3,4-diflurorphenylmethyl)-2-oxopyrrolidine Combine 1-(3,4,5-trimethoxybenzyl)-3-(3,4-diflurorphenylmethyl)-3-(2-methanesulfonyloxyethyl)-2-oxopyrrolidine (0.47 g, 0.91), 4-(1-(2-ethoxyethyl)-1H-benzimidazol-2-yl)[1,4]diazepane hydriodic acid salt (0.49 g, 0.91 mmol), and diisopropylamine (0.47 g, 3.62 mmol) in acetonitrile (10 mL). Heat to reflux. After 12 hours, cool to ambient temperature, dilute with dichloromethane, and extract with a saturated aqueous ammonium chloride solution, a saturated aqueous sodium bicarbonate solution. Dry the organic layer over Na$_2$SO$_4$, filter, and evaporate in vacuo to give a residue. Chromatograph the residue on silica gel eluting with 2% triethylamine/5% methanol/ethyl acetate to give the title compound: R$_f$=0.39 (silica gel, 2% triethylamine/5% methanol/ethyl acetate).

27.6 Synthesis of 1-(3,4,5-trimethoxybenzyl)-3-(2-(4-(1-(2-ethoxyethyl)-1H-benzimidazol-2-yl)[1,4]diazepan-1-yl)ethyl)-3-(3,4-diflurorphenylmethyl)-2-oxopyrrolidine hydrochloric acid salt Combine 1-(3,4,5-trimethoxybenzyl)-3-(2-(4-(1-(2-ethoxyethyl)-1H-benzimidazol-2-yl)[1,4]diazepan-1-yl)ethyl)-3-(3,4-diflurorphenylmethyl)-2-oxopyrrolidine (0.52 g, 0.74) and methanol (25 mL). Add a solution of hydrochloric acid (0.37 mL, 4 M, 1.47 mmol) in dioxane. After 18 hours, evaporate in vacuo to give a residue. Triturate the residue with diethyl ether and stir to give a solid. decant the solvent and add diethyl ether. Decant, collect the solid by evaporation, and dry to give the title compound: mp; 184–188° C.

EXAMPLE 28
1-(3,4,5-Trimethoxybenzoyl)-3-(2-(4-(1-(2-cyanoethyl)-1H-benzimidazol-2-yl)[1,4]diazepan-1-yl)ethyl)-3-phenylpyrrolidine

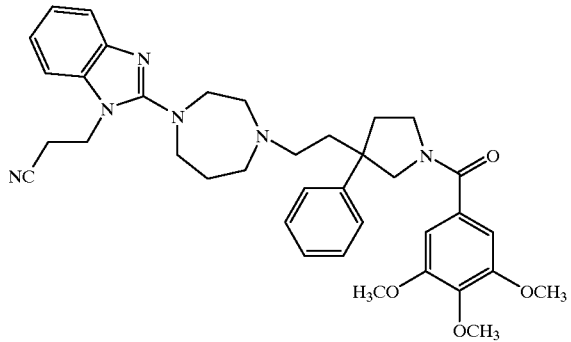

28.1 Synthesis of 1-(3,4,5-trimethoxybenzoyl)-3-(2-(4-(1-(2-cyanoethyl)-1H-benzimidazol-2-yl)[1,4]diazepan-1-yl)ethyl)-3-phenylpyrrolidine Combine 1-(3,4,5-trimethoxybenzoyl)-3-(2-(4-(1H-benzimidazol-2-yl)[1,4]diazepan-1-yl)ethyl)-3-phenylpyrrolidine (prepared from (−)-3-phenyl-3-(2-hydroxyethyl)pyrrolidine (R,R)-di-p-anisoyltartaric acid salt)(0.05 g, 0.09 mmol) and tetrahydrofuran (4 mL). Cool to −78° C. using a dry-ice /acetone bath. Add dropwise a solution of sec-butyllithium (0.08 mL, 1.3 M, 0.10 mmol). When the addition of sec-butyllithium is complete, warm the reaction mixture to ambient temperature. Add acrylonitrile (0.005 g, 0.10 mmol) and heat the reaction mixture to reflux. After 12 hours, cool, add acrylonitrile (0.01 g, 0.20 mmol), and heat the reaction mixture to reflux. After 12 hours, cool, add water, separate the layers and extract the aqueous layer twice with ethyl acetate. Combine the organic layers, dry over Na$_2$SO$_4$, filter, and evaporate in vacuo to give a residue. Chromatograph the residue on silica gel eluting with 0.5% concentrated aqueous ammonia solution/3% methanol/dichloromethane to give the title compound: R$_f$=0.47 (silica gel, 0.5% concentrated aqueous ammonia solution/3% methanol/dichloromethane).

PREPARATION 5

Synthesis of 2-Methylsulfonylethyl mesylate

Combine 2-methylsulfonylethanol (7.7 g, 62 mmol) and dichloromethane (50 mL). Cool in an ice bath. Add methanesulfonyl chloride (7.81 g, 68.2 mmol). Add N,N-diisopropylethylamine (8.0 g, 62 mmol). After the addition of N,N-diisopropylethylamine, warm to ambient temperature. After 12 hours, add water and separate the layers. Extract the organic, layer and extract with a saturated aqueous sodium bicarbonate solution. Dry the organic layer over Na$_2$SO$_4$, filter and evaporate in vacuo to give the title compound: mp; 55–57° C.

EXAMPLE 29

1-(3,4,5-Trimethoxybenzoyl)-3-(2-(4-(1-1,2-methylsulfonylethyl)-1H-benzimidazol-2-yl)[1,4]diazepan-1-yl)ethyl)-3-phenylpyrrolidine

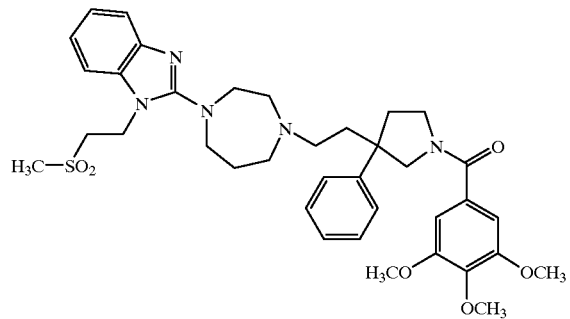

29.1 Synthesis of 1-(3,4,5-trimethoxybenzoyl)-3-(2-[4-(1-(2-methylsulfonylethyl)-1H-benzimidazol-2-yl)[1,4]diazepan-1-yl)ethyl)-3-phenylpyrrolidine Combine 1-(3,4,5-trimethoxybenzoyl)-3-(2-(4-(1H-benzimidazol-2-yl)[1,4]diazepan-1-yl)ethyl)-3-phenylpyrrolidine (prepared from (−)-3-phenyl-3-(2-hydroxyethyl)pyrrolidine (R,R)-di-p-anisoyltartaric acid salt)(0.05 g, 0.09 mmol) and tetrahydrofuran (5 mL). Cool to −78° C. using a dry-ice/acetone bath. Add dropwise a solution of sec-butyllithium (0.15 mL, 1.3 M, 0.19 mmol). When the addition of sec-butyllithium is complete, add a solution 2-methylsulfonylethyl mesylate (0.02 g, 0.10 mmol) in tetrahydrofuran (2 mL). Heat the reaction mixture to reflux. After 12 hours, cool, add sec-butyllithium (0.10 mL) and 2-methylsulfonylethyl mesylate (0.02 g, 0.10 mmol) and again heat the reaction mixture to reflux. After 12 hours, cool, add water, separate the layers and extract the aqueous layer twice with ethyl acetate. Combine the organic layers, dry over Na$_2$SO$_4$, filter, and evaporate in vacuo to give a residue. Chromatograph the residue on silica gel eluting with 0.5% concentrated aqueous ammonia solution/ 5% methanol/dichloromethane to give the title compound: R$_f$=0.38 (silica gel, 0.5% concentrated aqueous ammonia solution/5% methanol/dichloromethane).

EXAMPLE 30

1-(3,4,5-Trimethoxybenzoyl)-3-(2-(4-(1-(2-ethylsulfonylethyl)-1H-benzimidazol-2-yl)[1,4]diazepan-1-yl)ethyl)-3-phenylpyrrolidine

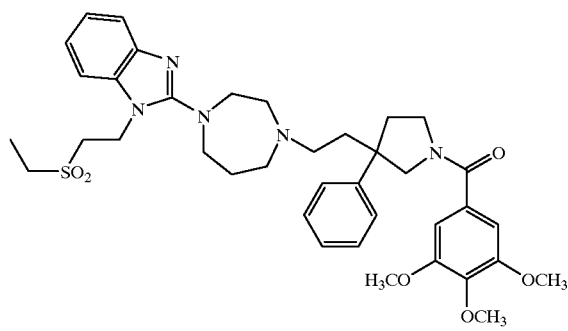

30.1 Synthesis of 1-(3,4,5-trimethoxybenzoyl)-3-(2-(4-(1-(2-ethylsulfonylethyl)-1H-benzimidazol-2-yl)[1,4]diazepan-1-yl)ethyl)-3-phenylpyrrolidine Combine 1-(3,4,5-trimethoxybenzoyl)-3-(2-(4-(1H-benzimidazol-2-yl)[1,4]diazepan-1-yl)ethyl)-3-phenylpyrrolidine (prepared from (−)-3-phenyl-3-(2-hydroxyethyl)pyrrolidine (R,R)-di-p-anisoyltartaric acid salt)(0.6 g, 1.0 mmol) and tetrahydrofuran (10 mL). Cool to −78° C. using a dry-ice/acetone bath. Add dropwise a solution of sec-butyllithium (1.26 mL, 1.3 M, 1.64 mmol). When the addition of sec-butyllithium is complete, add a solution ethyl vinyl sulfone (0.37 g, 3.08 mmol) in tetrahydrofuran (2 mL). Heat the reaction mixture to reflux and seal with a rubber septum. After 18 hours, cool, add ethyl vinyl sulfone (0.37 g, 3.08 mmol) and again heat the reaction mixture to reflux. After 6 hours, cool, add water, separate the layers and extract the aqueous layer twice with ethyl acetate. Combine the organic layers, dry over Na$_2$SO$_4$, filter, and evaporate in vacuo to give a residue. Chromatograph the residue on silica gel eluting with 0.2% concentrated aqueous ammonia solution/5% methanol/dichloromethane to give the title compound.

30.2 Synthesis of 1-(3,4,5-trimethoxybenzoyl)-3-(2-(4-(1-(2-ethylsulfonylethyl)-1H-benzimidazol-2-yl)[1,4]diazepan-1-yl)ethyl)-3-phenylpyrrolidine hydrochloric acid salt Combine 1-(3,4,5-trimethoxybenzoyl)-3-(2-(4-(1-(2-ethylsulfonylethyl)-1H-benzimidazol-2-yl)[1,4]diazepan-1-yl)ethyl)-3-phenylpyrrolidine (0.49 g, 0.70 mmol) and methanol (10 mL). Add a solution of hydrochloric acid (0.52 mL, 4 M, 2.09 mmol) in dioxane. After 2.5 hours, evaporate in vacuo to give a residue. Triturate the residue with diethyl ether and stir to give a solid. Repeatedly, decant and add diethyl ether, collect the solid by filtration and dry to give the title compound.

EXAMPLE 31

1-(3,4,5-Trimethoxybenzoyl)-3-(2-(4-(1-(2-phenylsulfonylethyl)-1H-benzimidazol-2-yl)[1,4]diazepan-1-yl)ethyl)-3-phenylpyrrolidine

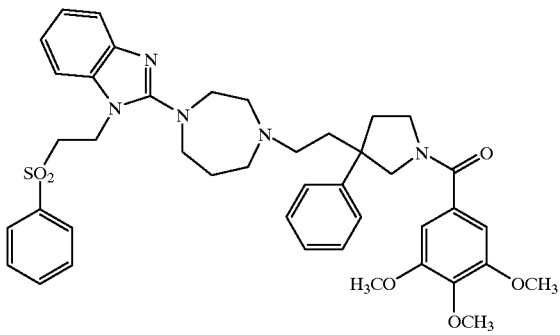

31.1 Synthesis of 1-(3,4,5-trimethoxybenzoyl)-3-(2-(4-(1-(2-phenylsulfonylethyl)-1H-benzimidazol-2-yl) [1,4]diazepan-1-yl)ethyl)-3-phenylpyrrolidine Combine 1-(3,4,5-trimethoxybenzoyl)-3-(2-(4-(1H-benzimidazol-2-yl)[1,4]diazepan-1-yl)ethyl)-3-phenylpyrrolidine (prepared from (−)-3-phenyl-3-(2-hydroxyethyl)pyrrolidine (R,R)-di-p-anisoyltartaric acid salt)(0.63 g, 1.07 mmol) and tetrahydrofuran (10 mL). Cool to −78° C. using a dry-ice /acetone bath. Add dropwise a solution of sec-butyllithium (1.23 mL, 1.3 M, 1.61 mmol). When the addition of sec-butyllithium is complete, add a solution phenyl vinyl sulfone (0.36 g, 2.14 mmol). Heat the reaction mixture to reflux. After 12 hours, cool, add phenyl vinyl sulfone (0.36 g, 2.14 mmol) and again heat the reaction mixture to reflux. After 3 hours, cool, add phenyl vinyl sulfone (0.36 g, 2.14 mmol) and again heat the reaction mixture to reflux. After 2.5 hours, cool, add water, separate the layers and extract the aqueous layer twice with ethyl acetate. Combine the organic layers, dry over $Na_2SO_4$, filter, and evaporate in vacuo to give a residue. Chromatograph the residue on silica gel eluting with 0.5% concentrated aqueous ammonia solution/5% methanol/dichloromethane to give the title compound.

31.2 Synthesis of 1-(3,4,5-trimethoxybenzoyl)-3-(2-(4-(1-(2-phenylsulfonylethyl)-1H-benzimidazol-2-yl)[1,4]diazepan-1-yl)ethyl)-3-phenylpyrrolidine hydrochloric acid salt Combine 1-(3,4,5-trimethoxybenzoyl)-3-(2-(4-(1-(2-phenylsulfonylethyl)-1H-benzimidazol-2-yl)[1,4]diazepan-1-yl)ethyl)-3-phenylpyrrolidine (0.40 g, 0.53 mmol) and methanol (10 mL). Add a solution of hydrochloric acid (0.4 mL, 4 M, 1.6 mmol) in dioxane. After 2.5 hours, evaporate in vacuo to give a residue. Triturate the residue with diethyl ether and stir to give a solid. Repeatedly, decant and add diethyl ether, collect the solid by filtration and dry to give the title compound.

EXAMPLE 32

1-(3,4,5-Trimethoxybenzoyl)-3-(2-(4-(1-(2-ethoxyethyl)-1H-benzimidazol-2-yl)[1,4]diazepan-1-yl)ethyl)-3-(pyrid-2-yl)pyrrolidine

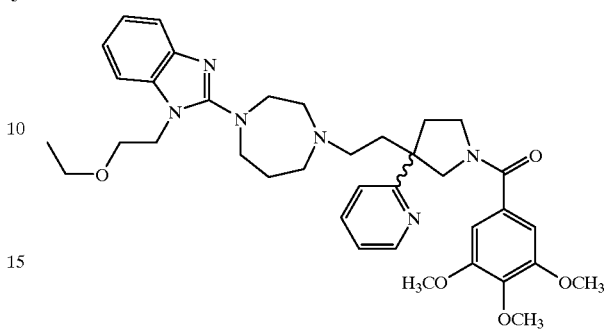

32.1 Synthesis of 3-cyano-3-(pyrid-2-yl)-pentanedioic acid diethyl ester

Prepare by the method of Example 1.1 using 2-pyridineacetonitrile to give the title compound: mp; 86.5–88.0° C.; $R_f$=0.46 (silica gel, 1/2 ethyl acetate/hexane). Elemental Analysis calculated for $C_{15}H_{18}N_2O_4$: C, 62.06; H, 6.25; N, 9.65; Found: C, 62.23; H, 6.27; N, 9.66.

32.2 Synthesis of (3-(pyrid-2-yl)-5-oxopyrrolidin-3-yl)acetic acid ethyl ester Prepare by the method of Example 1.2 using 3-cyano-3-(pyrid-2-yl)pentanedioic acid diethyl ester to give the title compound: $R_f$=0.31 (silica gel, 20/1 ethyl acetate/methanol). Elemental Analysis calculated for $C_{27}H_{16}N_2O_3$: C, 62.89; H, 6.50; N, 11.28; Found: C, 62.54; H 6.50; N, 11.18.

32.3 Synthesis of 3-(pyrid-2-yl)-3-(2-hydroxyethyl) pyrrolidine

Prepare by the method of Example 1.3 using (3-(pyrid-2-yl)-5-oxo-pyrrolidin-3-yl)acetic acid ethyl ester to give the title compound: mp; 50–55° C.

32.4 Synthesis of 1-(3,4,5-trimethoxybenzoyl)-3-(pyrid-2-yl)-3-(2-hydroxyethyl)pyrrolidine Prepare by the method of Example 1.4.1 using 3-(pyrid-2-yl)-3-(2-hydroxyethyl)pyrrolidine to give the title compound: mp; 52.0–55.0; $R_f$=0.23 (silica gel, 3% methanol/dichloromethane). Elemental Analysis calculated for $C_{21}H_{26}N_2O_5 \cdot 0.30\ H_2O$: C, 64.37; H, 6.84; N, 7.15; Found: C 64.71; H, 6.87; N, 7.05.

32.5 Synthesis of 1-(3,4,5-trimethoxybenzoyl)-3-(3-(pyrid-2-yl)-3-(2-oxoethyl)pyrrolidine Combine oxalyl chloride (0.11 g, 0.83 mmol) with dichloromethane (2 mL) and cool to −60° C. Add dropwise a solution of dimethyl sulfoxide (0.13 g, 1.65 mmol) in dichloromethane (0.12 mL) while maintaining the temperature below −50° C. After addition is complete, stir for 10 minutes. Add a solution of 1-(3,4,5-trimethoxybenzoyl)-(3-(pyrid-2-yl)-3-(2-hydroxyethyl)pyrrolidine (0.92 g, 0.75 mmol) in dichloromethane (1.5 mL) and stir for 1 hour. Cool the reaction to −78° C. and add dropwise triethylamine (3.75 mmol). Allow the reaction to warm to ambient temperature and stir for 2 hours. Pour the reaction mixture into water. Extract this mixture with dichloromethane. Separate the organic layer and dry over $Na_2SO_4$, filter, and evaporate in vacuo to give a residue. Chromatograph the residue on silica gel to give the title compound.

32.6 Synthesis of 1-(3,4,5-trimethoxybenzoyl)-3-(2-(4-(1-(2-ethoxyethyl)-1H-benzimidazol-2-yl)[1,4]diazepan-1-yl)ethyl)-3-(pyrid-2-yl)pyrrolidine Combine 1-(3,4,5-trimethoxybenzoyl)-3-(pyrid-2-yl)-3-(2-oxoethyl)pyrrolidine (0.29 g, 0.75 mmol) and 4-(1-(2- ethoxyethyl)-1H-benzimidazol-2-yl)[1,4]diazepane (0.26 g, 0.91 mmol) silica gel (about 2 g) and 3 Å molecular sieves (about 2 g) in methanol (16 mL). After 18 hours, add sodium cyanoborohydride (0.47 g, 7.5 mmol) and stir. After 7 days, add a solution of 2 M sodium hydroxide and dichloromethane. After 1 hour, filter, separate the layers in the filtrate, dry the organic layer over $Na_2SO_4$, filter, and evaporate in vacuo to give a residue. Chromatograph the residue on silica gel eluting with 1/1 methanol/ethyl acetate to give the title compound: mp; 40–42° C. Elemental Analysis calculated for $C_{37}H_{48}N_6O_5 \cdot 0.75\ H_2O$: C, 66.30; H 7.44; N, 12.54; Found: C, 66.33; H, 7.50; N, 12.49.

EXAMPLE 33

(+)-1-(3,4,5-Trimethoxybenzoyl )-3-(2-(4-(1-(2-ethoxyethyl)-1H-benzimidazol-2-yl)[1,4]diazepan-1-yl) ethyl)-3-(4-fluorophenyl)pyrrolidine

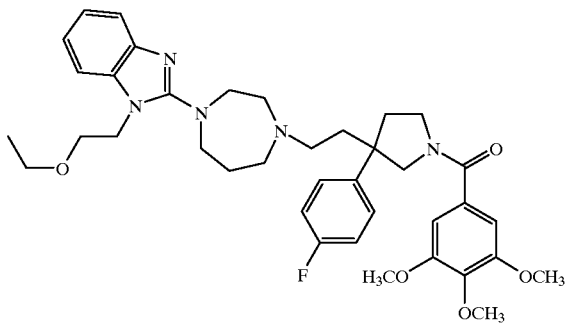

33.1 Resolution of (+)-3-(4-fluorophenyl)-3-(2-hydroxethyl)pyrrolidine (R,R)-di-p-anisoyltartaric acid salt and (−)-3-(4-fluorophenyl-3-(2-hydroxyethyl)pyrrolidine (R,R)-di-p-anisoyltartaric acid salt Combine 3-(4-fluorophenyl)-3-(2-hydroxyethyl) pyrrolidine (32 mmol) and butanone (400 mL). Add a solution of (R,R)-di-p-anisoyltartaric acid (32 mmol) in butanone (80 mL). Heat to reflux. After 15 minutes, cool to ambient temperature and evaporate in vacuo to give a residue. Combine the residue and butanone (1000 mL) and methanol (430 mL) and heat. Add methanol (about 100 mL). Slowly cool to ambient temperature to give a solid. After 18 hours, filter the solid. Recrystallize the solid from butanone/methanol (80 mL/80 mL) to give (−)-3-(4-fluorophenyl)-3-(2-hydroxyethyl)pyrrolidine (R,R)-di-p-anisoyltartaric acid salt. $[\alpha]^{20}_D = -98.9$ (c=0.70, methanol). Analysis on HPLC, on an analytical sample of the 3,4,5-trimethoxybenzamide derivative, using a CHIRALPAK AD 25 cm×0.46 cm column eluting with pentane/ethanol/methanol/triethylamine (80/15/10/0.1) with a flow rate of 1.0 ml/minute indicates an enantiomeric excess of 99.6%, (99.6% ee), the 3,4,5-trimethoxybenzamide prepared from (−)-3-(4-fluorophenyl)-3-(2-hydroxyethyl)pyrrolidine (R,R)-di-p-anisoyltartaric acid salt gave a retention time of 23.0 minutes, the 3,4,5-trimethoxybenzamide prepared from (+)-3-(4-fluorophenyl)-3-(2-hydroxyethyl)pyrrolidine (R,R)-di-p-anisoyltartaric acid salt gave a retention time of 15.4 minutes.

33.2.1 Synthesis of (+)-1-(3,4,5-trimethoxybenzoyl)-(3-(4-fluorophenyl)-3-(2-hydroxyethyl)pyrrolidine Prepare by the method of Example 8.2.1 using (−)-3-(4-fluorophenyl)-3-(2-hydroxyethyl)pyrrolidine (R,R)-di-p-anisoyltartaric acid to give the title compound.

33.2.2 Synthesis of (+)-1-(3,4,5-trimethoxybenzoyl)-(3-(4-fluorophenyl)-3-(2-hydroxyethyl)pyrrolidine Combine (−)-3-(4-fluorophenyl)-3-(2-hydroxyethyl) pyrrolidine (R,R)-di-p-anisoyltartaric acid salt (5.0 g, 8.0 mmol) and sodium carbonate (3.39 g, 32 mmol) in ethyl acetate/water (41/, 125 mL). Cool in an ice bath and add a solution of 3,4,5-trimethoxybenzoyl chloride (1.94 g, 8.4 mmol) in ethyl acetate (60 mL). After 2 hours, warm to ambient temperature. After 18 hours, separate the layers, and extract the organic layer twice with a 1 M aqueous hydrochloric acid solution, twice with a saturated aqueous sodium bicarbonate solution, water and then brine. Dry the organic over $Na_2SO_4$, filter, and concentrate in vacuo to give a residue. Chromatograph the residue on silica gel eluting with 1/20 methanol/ethyl acetate to give, after drying, the title compound: mp; 55–60° C. $R_f=0.28$ (silica gel, 1/20 methanol/ethyl acetate). $[\alpha]^{20}_D = +36.70$ (1.04, chloroform).

33.3 Synthesis of 1-(3,4,5-trimethoxybenzoyl)-3-(4-fluorophenyl)-3-(2-methanesulfonyloxyethyl)pyrrolidine Prepare by the method of Example 2.5.2 using (+)-1-(3,4,5-trimethoxybenzoyl)-3-(4-fluorophenyl)-3-(2-hydroxyethyl)pyrrolidine to give the title compound: $R_f=0.47$ (silica gel, 1/20 methanol/ethyl acetate).

33.4 Synthesis of (+)-1-(3,4,5-trimethoxybenzoyl)-3-(2-(4-(1-(2-ethoxyethyl)-1H-benzimidazol-2-yl)[1,4]diazepan-1-yl)ethyl)-3-(4-fluorophenyl)pyrrolidine Combine 1-(3,4,5-trimethoxybenzoyl)-3-(4-fluorophenyl)-3-(2-methanesulfonyloxyethyl)pyrrolidine (prepared from (+)-1-(3,4,5-trimethoxybenzoyl)-3-(4-fluorophenyl)-3-(2-hydroxyethyl)pyrrolidine) (0.86 g, 1.8 mmol), N,N-diisopropylethylamine (1.5 mL), and 4-(1-(2-ethoxyethyl)-1H-benzimidazol-2-yl)[1,4]diazepane hydriodic acid salt (1.0 g, 1.86 mmol) in acetonitrile (50 mL). Heat to reflux. After 2 days, dilute the reaction mixture with ethyl acetate (250 mL) and extract with a saturated aqueous sodium bicarbonate solution. Dry the organic layer over $Na_2SO_4$, filter, and evaporate in vacuo to give a residue. Chromatograph the residue on silica gel eluting with 25% methanol/ethyl acetate containing concentrated aqueous -ammonia (20 mL/:3L) to give the title compound: $R_f=0.30$ (silica gel, 40% methanol/ethyl acetate).

33.5 Synthesis of (+)-1-(3,4,5-trimethoxybenz[]oyl)-3-(2-(4-(1-(2-ethoxyethyl)-1H-benzimidazol-2-yl)[1,4] diazepan-1-yl)ethyl)-3-(4-fluorophenyl)pyrrolidine hydrochloric acid salt Combine (+)-1-(3,4,5-trimethoxybenzoyl)-3-(2-(4-(1-(2-ethoxyethyl)-1H-benzimidazol-2-yl)[1,4]diazepan-1-yl) ethyl)-3-(4-fluorophenyl)pyrrolidine (0.75 g) and methanol (20 mL). Add a solution of hydrochloric acid (1.5 mL, 4 M, 6 mmol) in dioxane. After 24 hours, evaporate in vacuo to give a residue. Dissolve the residue in methanol (about 5 mL) and add diethyl ether (200 mL) and stir to give a solid. Decant the solvent add diethyl ether and stir. Decant the solvent and collect the solid to give, after drying in vacuo, the title compound. $[\alpha]^{20}_D = +5.8°$ (c=0.86, chloroform).

EXAMPLE 34
1-(3,4,5-Trimethoxybenzoyl)-3-(2-(4-(1-(2-ethoxyethyl)-1H-benzimidazol-2-yl)[1,4]diazepan-1-yl)ethyl)-3-(pyrid-3-yl)pyrrolidine

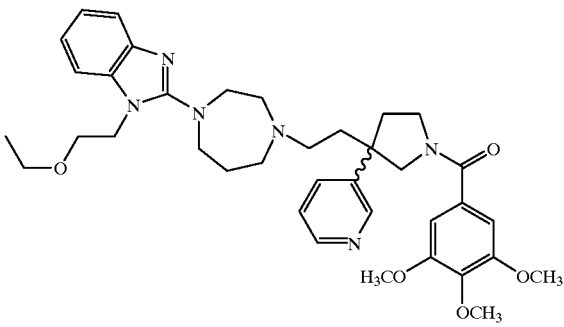

34.1.1 Synthesis of 3-cyano-3-(pyrid-3-yl)pentanedioic acid diethyl ester
Prepare by the method of Example 3.1.2 using 3-pyridineacetonitrile to give the title compound.

34.1.2 Synthesis of 3-cyano-3-(pyrid-3-yl)pentanedioic acid diethyl ester
Combine 3-pyridineacetonitrile (25 g, 212 mmol) and tetrahydrofuran (200 mL). Cool to about −70° C. using a dry-ice/acetone bath. Add dropwise, a solution of sodium bis(trimethylsilyl)amide (435 mL, 1 M in tetrahydrofuran, 435 mmol) while maintaining the reaction temperature below about −68° C. When the addition is complete, warm the reaction mixture to ambient temperature and allow to stir for 1 hour. Transfer the above solution via cannula into a cooled (−5° C.) solution of ethyl bromoacetate (84.5 mL, 762 mmol) in tetrahydrofuran (500 mL) at such a rate that the temperature of the reaction mixture does not rise above about 15° C. Allow to stir at ambient temperature. After 18 hours, quench with saturated aqueous solution of ammonium chloride and evaporate in vacuo to remove most of the tetrahydrofuran. Extract the evaporated reaction mixture twice with diethyl ether. Dry the organic layer over MgSO$_4$, filter, and concentrate in vacuo to obtain a residue. Chromatograph the residue on silica gel eluting with 1/1 ethyl acetate/hexane to give the title compound.

34.2.1 Synthesis of (3-(pyrid-3-yl)-5-oxopyrrolidin-3-yl)acetic acid ethyl ester
Prepare by the method of Example 1.2 using 3-cyano-3-(pyrid-3-yl)pentanedioic acid diethyl ester to give the title compound.

34.2.2 Synthesis of (3-(pyrid-3-yl)-5-oxopyrrolidin-3-yl)acetic acid ethyl ester
Combine 3-cyano-3-(pyrid-3-yl)pentanedioic acid diethyl ester (50 g, 172 mmol) and cobalt(II)chloride hexahydrate (81.8 g, 344 mmol) in methanol (500 mL). While maintaining the temperature at or below 20° C. with an ice-bath, add portionwise sodium borohydride (65.1 g, 1.72 mol). After the addition is complete, allow the reaction mixture to stand at ambient temperature. After 18 hours, evaporate the reaction mixture in vacuo to obtain a residue. Quench the reaction mixture by adding ammonium chloride and 0.5 M aqueous sodium hydroxide solution. Adjust the pH of the quenched reaction mixture to about 8 using 1 M aqueous hydrochloric acid solution. Filter through celite and extract the aqueous filtrate twice with dichloromethane. Combine the organic layers, dry over Na$_2$SO$_4$, filter, and concentrate in vacuo to give a residue. Chromatograph the residue on silica gel eluting with dichloromethane/methanol 10/1 to give the title compound.

34.3.1 Synthesis of 3-(pyrid-3-yl)-3-(2-hydroxyethyl)pyrrolidine
Prepare by the method of Example 1.3 using 3-(pyrid-3-yl)-5-oxo-pyrrolidin-3-yl)acetic acid ethyl ester to give the title compound.

34.3.2 Synthesis of 3-(pyrid-3-yl)-3-(2-hydroxyethyl)pyrrolidine
Combine lithium aluminum hydride (4.0 g, 105 mmol) and anhydrous tetrahydrofuran (200 mL). Slowly, add a solution of 3-(pyrid-3-yl)-5-oxo-pyrrolidin-3-yl)acetic acid ethyl ester (13.0 g, 52.4 mmol) in anhydrous tetrahydrofuran (100 mL). After the addition is complete, heat to reflux. After 4 hours, cool in an ice-bath. Add water (4 mL) dropwise at such a rate that the temperature of the reaction mixture does not rise above 20° C. Cool to 10° C., add 2 M aqueous sodium hydroxide solution (4.0 mL). Add water (16 mL) and stir. After 16 hours, filter the reaction mixture and concentrate the filtrate in vacuo to give an aqueous layer. Extract with dichloromethane and lyophilize the aqueous layer to give a residue. Combine the residue and dichloromethane and methanol. Filter and evaporate the filtrate in vacuo to give the title compound.

34.3.3 Synthesis of 3-(pyrid-3-yl)-3-(2-hydroxyethyl)pyrrolidine
Combine lithium aluminum hydride (2.65 g, 70 mmol) and 3-(pyrid-3-yl)-5-oxo-pyrrolidin-3-yl)acetic acid ethyl ester (7.2 g, 35 mmol) in anhydrous tetrahydrofuran (100 mL). Heat to reflux. After 12 hours, cool the reaction mixture and add lithium aluminum hydride (2.65 g, 70 mmol). After 20 hours, cool in an ice-bath. Add water (8 mL) dropwise at such a rate that the temperature of the reaction mixture does not rise above 20° C. Cool to 10° C., add 2M aqueous sodium hydroxide solution (8.0 mL). Add water (16 mL) and stir. After 1 hour, filter the reaction mixture and extract with dichloromethane. Evaporate the aqueous layer to give a residue. Combine the residue and dichloromethane, filter thorough celite, and evaporate the filtrate in vacuo to give the title compound.

34.4 Synthesis of 1-(3,4,5-trimethoxybenzoyl)-3-(pyrid-3-yl)-3-(2-hydroxyethyl)pyrrolidine
Prepare by the method of Example 7.4 using 3-(pyrid-3-yl)-3-(2-hydroxyethyl)pyrrolidine to give, after chromatography on silica gel eluting with dichloromethane/methanol 5/1, the title compound.

34.5 Synthesis of 1-(3,4,5-trimethoxybenzoyl)-3-(pyrid-3-yl)-3-(2-methanesulfonyloxyethyl)pyrrolidine
Combine 1-(3,4,5-trimethoxybenzoyl)-3-(pyrid-3-yl)-3-(2-hydroxyethyl)pyrrolidine (0.45 g, 1.16 mmol) in dichloromethane (6 mL). Cool in an ice bath. Add methanesulfonyl chloride (0.015 mL, 1.15 mmol) and triethylamine (0.032 mL, 1.6 mmol). After 1 hour, dilute the reaction mixture with dichloromethane and extract with brine. Separate the layers and extract the aqueous layers twice with dichloromethane. Combine the organic layers. Dry over MgSO$_4$, filter, and evaporate in vacuo to give the title compound.

34.6 Synthesis of 1-(3,4,5-trimethoxybenzoyl)-3-(2-(4-(1-(2-ethoxyethyl)-1H-benzimidazol-2-yl)[1,4]diazepan-1-yl)ethyl)-3-(pyrid-3-yl)pyrrolidine
Combine 1-(3,4,5-trimethoxybenzoyl)-3-(pyrid-3-yl-3-(2-methanesulfonyloxyethyl)pyrrolidine (0.54 g, 1.16 mmol), 4-(1-(2-ethoxyethyl)-1H-benzimidazol-2-yl)[1,4]diazepane (0.95 g, 1.74 mmol), and N,N-diisopropylethylamine (0.81 mL, 4.64 mmol) in acetonitrile (16 mL). Heat to reflux. After 24 hour, evaporate in vacuo, dilute with dichloromethane, and extract with brine. Dry the organic layer over Na$_2$SO$_4$, filter, and evaporate in vacuo to give a residue. Chromatograph the residue on silica gel eluting with 6/1/0.5 methanol/ethyl acetate/concentrated aqueous ammonia to give the title compound: $R_f$=0.27 (silica gel, 6/1/0.5 methanol/ethyl acetate/concentrated aqueous ammonia).

EXAMPLE 35

1-(3,4,5-Trimethoxybenzoyl)-3-(2-(4-(1-(pyrid-2-ylmethyl)-1H-benzimidazol-2-yl)[1,4]diazepan-1-yl)ethyl)-3-phenylpyrrolidine

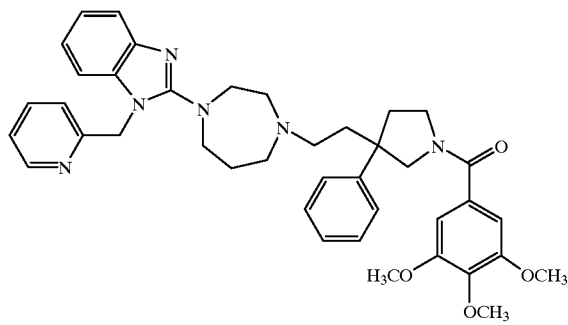

35.1 Synthesis of 1-(3,4,5-trimethoxybenzoyl)-3-(2-(4-(1-(pyrid-2-ylmethyl)-1H-benzimidazol-2-yl) [1,4]diazepan-1-yl)ethyl)-3-phenylpyrrolidine Combine 1-(3,4,5-trimethoxybenzoyl)-3-(2-(4-(1H-benzimidazol-2-yl)[1,4]diazepan-1-yl)ethyl)-3-phenylpyrrolidine (prepared from (−)-3-phenyl-3-(2-hydroxyethyl)pyrrolidine (R,R)-di-p-anisoyltartaric acid salt) (0.89, 1.37 mmol) and tetrahydrofuran (50 mL). Cool to 0° C. using ice-bath. Add potassium hydride (82.5 mg, 2.06 mmol). After 1 hour, add 2-picolyl chloride (175 mg, 1.37 mmol). The 2-picolyl chloride is obtained from 2-picolyl chloride hydrochloride by treatment with excess sodium bicarbonate in dichloromethane, filtration, and evaporation in vacuo. Allow to warm to ambient temperature. After 18 hours, add potassium hydride (82.5 mg, 2.06 mmol), 2-picolyl chloride (87 mg, 0.68 mmol), and morpholine (0.1 mL). After 18 hours, cool to −78° C. and quench with methanol (5 mL) followed by water (15 mL). Warm to ambient temperature and evaporate invacuo to remove most of the methanol. Extract twice with dichloromethane. Combine the organic layers, dry over $Na_2SO_4$, filter, and evaporate in vacuo to give a residue. Chromatograph the residue on silica gel eluting with 0.1% concentrated aqueous ammonia solution/10% methanol/dichloromethane to give the title compound: $R_f$=0.30 (silica gel, 0.1% concentrated aqueous ammonia solution/10% methanol/dichloromethane).

35.2 Synthesis of 1-(3,4,5-trimethoxybenzoyl)-3-(2-(4-(1-(pyrid-2-methyl)-1H-benzimidazol-2-yl)[1,4]diazepan-1-yl)ethyl)-3-phenylpyrrolidine hydrochloric acid salt Combine 1-(3,4,5-trimethoxybenzoyl)-3-(2-(4-(1-(pyrid-2-ylmethyl)-1H-benzimidazol-2-yl)[1,4]diazepan-1-yl)ethyl)-3-phenylpyrrolidine (0.3 g, 0.43 mmol) and dichloromethane (15 mL). Add a solution of hydrochloric acid (0.22 mL, 4 M, 0.86 mmol) in dioxane. After 3 hours, evaporate in vacuo to give a residue. Triturate the residue with diethyl ether to give a solid, collect the solid by filtration and dry to give the title compound.

EXAMPLE 36

1-(3,4,5-Trimethoxybenzoyl)-3-(2-(4-(1-(thien-2-ylmethyl)-1H-benzimidazol-2-yl) [1,4]diazepan-1-yl) ethyl)-3-phenylpyrrolidine

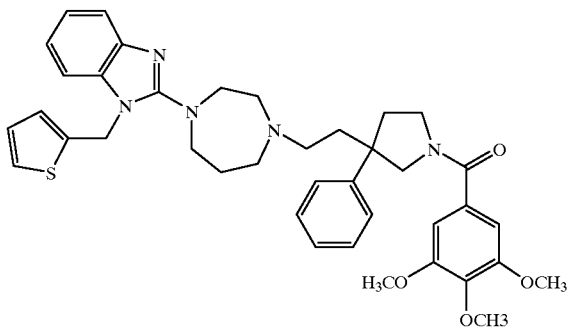

36.1 Synthesis of 1-(3,4,5-trimethoxybenzoyl)-3-(2-(4-(thien-2-ylmethyl)-1H-benzimidazol-2-yl)[1,4]diazepan-1-yl)ethyl)-3-phenylpyrrolidine Prepare by the method of Example 35.1 using 1-(3,4,5-trimethoxybenzoyl)-3-(2-(4-(1H-benzimidazol-2-yl)[1,4]diazepan-1-yl)ethyl)-3-phenylpyrrolidine (prepared from (−)-3-phenyl-3-(2-hydroxyethyl)pyrrolidine (RrR)-di-p-anisoyltartaric acid salt) and 2-(bromomethyl)thiophene (*J. Am. Chem. Soc.*, 71 1201–1204 (1949)) to give the title compound.

EXAMPLE 37

1-(3,4,5-Trimethoxybenzoyl)-3-(2-(4-(1-(fur-3-ylmethyl)-1H-benzimidazol-2-yl)[1,4]diazepan-1-yl)ethyl)-3-phenylpyrrolidine

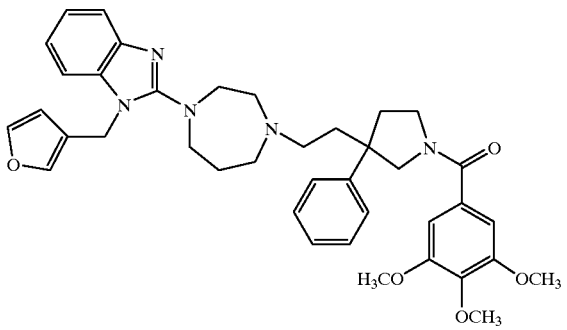

37.1 Synthesis of 1-(3,4,5-trimethoxybenzoyl)-3-(2-(4-(1-(fur-3-ylmethyl)-1H-benzimidazol-2-yl)[1,4]diazepan-1-yl) ethyl)-3-phenylpyrrolidine Prepare by the method of Example 35.1 using 1-(3,4,5-trimethoxybenzoyl)-3-(2-(4-(1H-benzimidazol-2-yl)[1,4]diazepan-1-yl)ethyl)-3-phenylpyrrolidine (prepared from (−)-3-phenyl-3-(2-hydroxyethyl)pyrrolidine (R,R)-di-p-anisoyltartaric acid salt) and 3-(chloromethyl)furan (*J. Am. Chem. Soc.* 72, 2195–2199 (1950)) to give the title compound.

EXAMPLE 38

1-(3,4,5-Trimethoxybenzoyl)-3-(2-(4-(1-(fur-2-ylmethyl)-1H-benzimidazol-2-yl)[1,4]diazepan-1-yl)ethyl)-3-phenylpyrrolidine

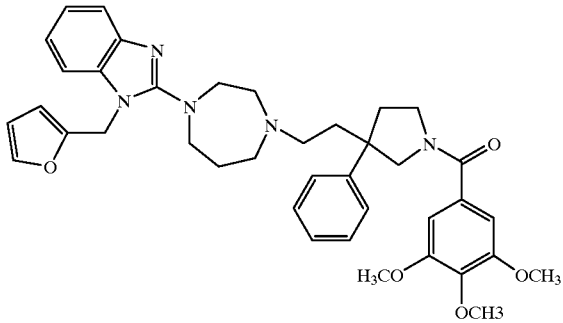

38.1 Synthesis of 1-(3,4,5-trimethoxybenzoyl)-3-(2-(4-(1-(fur-2-ylmethyl)-1H-benzimidazol-2-yl)[1,4]diazepan-1-yl)ethyl)-3-phenylpyrrolidine Prepare by the method of Example 35.1 using 1-(3,4,5-trimethoxybenzoyl)-3-(2-(4-(1H-benzimidazol-2-yl)[1,4]diazepan-1-yl)ethyl)-3-phenylpyrrolidine (prepared from (−)-3-phenyl-3-(2-hydroxyethyl)pyrrolidine (R,R)-di-p-anisoyltartaric acid salt) and 2-(chloromethyl)furan (T. Reichstein et al., *Ber.*, 63 749–754 (1930)) to give the title compound.

EXAMPLE 39

1-(3,4,5-Trimethoxybenzoyl)-3-(2-(4-(1-(2-oxobutyl)-1H-benzimidazol-2-yl)[1,4]diazepan-1-yl)ethyl)-3-phenylpyrrolidine

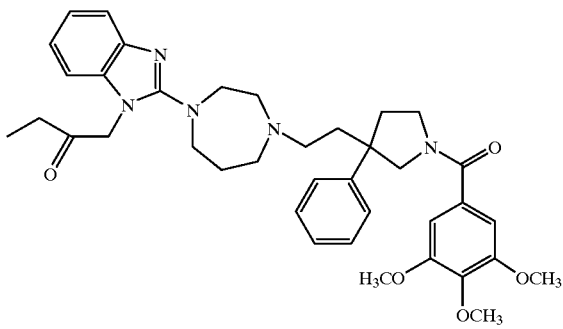

39.1 Synthesis of 1-(3,4,5-trimethoxybenzoyl)-3-(2-(4-(1-(2-oxobutyl)-1H-benzimidazol-2-yl)[1,4]diazepan-1-yl)ethyl)-3-phenylpyrrolidine Prepare by the method of Example 35.1 using 1-(3,4,5-trimethoxybenzoyl)-3-(2-(4-(1H-benzimidazol-2-yl)[1,4]diazepan-1-yl)ethyl)-3-phenylpyrrolidine (prepared from (−)-3-phenyl-3-(2-hydroxyethyl)pyrrolidine (R,R)-di-p-anisoyltartaric acid salt) and 1-bromo-butan-2-one to give the title compound.

EXAMPLE 40

(+)-1-(2,3,4-Trimethoxybenzoyl)-3-(2-(4-(1(2-ethoxyethyl)-1H-benzimidazol-2-yl)[1,4]diazepan-1-yl)ethyl)-3-phenylpyrrolidine

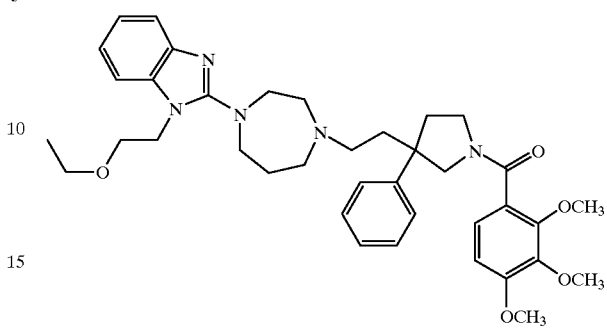

40.1 Synthesis of 1-(2,3,4-trimethoxybenzoyl)-3-phenyl-3-(2-hydroxyethyl)pyrrolidine Combine 2,3,4-trimethoxybenzoyl chloride (10 mmol) and 3-phenyl-3-(2-hydroxyethyl)pyrrolidine (prepared by extraction from (−)-3-phenyl-3-(2-hydroxyethyl)pyrrolidine R,R-di-p-anisoyltartaric acid salt) (2.1 g, 9.2 mmol) in acetone (70 mL). Add water (25 mL) and potassium carbonate (1.93 g, 14 mmol). Dilute the reaction mixture with ethyl acetate and extract with aqueous sodium bicarbonate solution and brine. Dry the organic layer over $Na_2SO_4$, filter, and evaporate invacuo to give the title compound.

40.2 Synthesis of 1-(2,3,4-trimethoxybenzoyl)-3-phenyl-3-(2-methanesulfonyloxyethyl)pyrrolidine Prepare by the method of Example 2.5.2 using 1-(2,3,4-trimethoxybenzoyl)-3-phenyl-3-(2-hydroxyethyl)pyrrolidine (prepared from (−)-3-phenyl-3-(2-hydroxyethyl)pyrrolidine R,R-di-p-anisoyltartaric acid salt)(1.01 g, 2.6 mmol) to give the title compound.

40.3 Synthesis of 1-(2,3,4-trimethoxybenzoyl)-3-(2-(4-(1-(2-ethoxyethyl)-1H-benzimidazol-2-yl)[1,4]diazepan-1-yl)ethyl)-3-phenylpyrrolidine Prepare by the method of Example 7.6 using 1-(2,3,4-trimethoxybenzoyl)-3-phenyl-3-(2-methanesulfonyloxyethyl)pyrrolidine and 4-(1-(2-ethoxyethyl)-1H-benzimidazol-2-yl)[1,4]diazepane hydriodic acid salt to give the title compound. $[\alpha]_D^{20}=+15.1$ (c=0.83, chloroform).

PREPARATION 6

4-(1-(5-Hydroxymethylfur-2-ylmethyl)-1H-benzimidazol-2-yl)[1,4]diazepane

Combine 1-ethoxycarbonyl-4-(1H-benzimidazol-2-yl)[1,4]diazepane (10 mmol) and sodium hydride (10 mmol) in dimethylformamide (20 mL). After gas evolution ceases, add ethyl 5-chloromethyl-2-furoate (10 mmol) and stir. After 3 days, evaporate in vacuo to give a residue. Combine the residue and ethyl acetate. Extract with water and brine. Dry the the organic layer over $Na_2SO_4$, filter, and evaporate in vacuo to give 1-ethoxycarbonyl-4-(1-(5-(ethoxycarbonyl)fur-2-ylmethyl)-1H-benzimidazol-2-yl)[1,4]diazepane.

Combine 1-ethoxycarbonyl-4-(1-(5-(ethoxycarbonyl)fur-2-ylmethyl)-1H-benzimidazol-2-yl)[1,4]diazepane (5 mmol) and lithium aluminum hydride (5 mmol) in tetrahydrofuran. Heat to reflux. After 12 hour, cool and carefully quench the reaction mixture with 10% aqueous ammonium chloride solution. Extract the reaction mixture with ethyl acetate. Dry the the organic layer over $Na_2SO_4$, filter, and evaporate in vacuo to give 1-ethoxycarbonyl-4-(1-(5-hydroxymethylfur-2-ylmethyl)-1H-benzimidazol-2-yl)[1,4]diazepane.

Combine 1-ethoxycarbonyl-4-(1-(5-hydroxymethylfur-2-ylmethyl)-1H-benzimidazol-2-yl)[1,4]diazepane (4 mmol) and sodium hydroxide (8 mmol) in isopropanol (20 mL). Heat to reflux. After 2 days, evaporate the reaction mixture in vacuo to give a residue. Combine the residue and ethyl acetate. Extract with water and brine. Dry the organic layer over $Na_2SO_4$, filter, and evaporate in vacuo to give the title compound.

Alternately, combine 2-chlorobenzimidazole (20 mmol) and sodium hydride (20 mmol) in dimethylformamidle (30 mL). After gas evolution ceases, add ethyl 5-chloromethyl-2-furoate (20 mmol) and stir. After 1 day, evaporate in vacuo to give a residue. Combine the residue and ethyl acetate. Extract with water and brine. Dry the the organic layer over $Na_2SO_4$, filter, and evaporate in vacuo to give 1-(5-(ethoxycarbonyl)fur-2-ylmethyl)-2-chloro-1H-benzimidazole.

Combine 1-(5-(ethoxycarbonyl)fur-2-ylmethyl)-2-chloro-1H-benzimidazole (10 mmol), [1,4]diazepane (10 mmol), and 1,8-diazabicyclo[5.4.0]undec-7-ene (1.8 mL) in pyridine (20 mL). Heat to reflux. After 2 days, evaporate in vacuo to give a residue. Combine the residue and ethyl acetate. Extract with water and brine. Dry the the organic layer over $Na_2SO_4$, filter, and evaporate in vacuo to give 4-(1-(5-(ethoxycarbonyl)fur-2-ylmethyl)-1H-benzimidazol-2-yl)[1,4]diazepane.

Combine 4-(1-(5-(ethoxycarbonyl)fur-2-ylmethyl)-1H-benzimidazol-2-yl)[1,4]diazepane (10 mmol) and lithium aluminum hydride (10 mmol) in tetrahydrofuran. Heat to reflux. After 12 hour, cool and carefully quench the reaction mixture with water (0.4 mL), 15% aqueous sodium hydroxide solution (0.4 mL) and water (1.2 mL). Filter and extract the filtrate with ethyl acetate. Dry the the organic layer over $Na_2SO_4$, filter, and evaporate in vacuo to give the title compound.

Alternatively, combine 4-(1-(5-(ethoxycarbonyl)fur-2-ylmethyl)-1H-benzimidazol-2-yl)[1,4]diazepane (1.0 g, 2.7 mmol) and tetrahydrofuran (10 mL). Add a solution of lithium aluminum hydride in tetrahydrofuran (2.7 mL, 1 M, 2.7 mmol). After 18 hour, quench by slow portionwise addition of Glauber's salt ($Na_2SO_4$•10 $H_2O$) until gas evolution ceases. Add dichloromethane (20 mL) and celite and stir. Filter and evaporate in vacuo to give the title compound.

EXAMPLE 41
1-(3,4,5-Trimethoxybenzoyl)-3-(2-(4-1-(5-hydroxymethylfur-2-ylmethyl)-1H-benzimidazol-2-yl)[1,4]diazepan-1-yl)ethyl)-3-phenylpyrrolidine

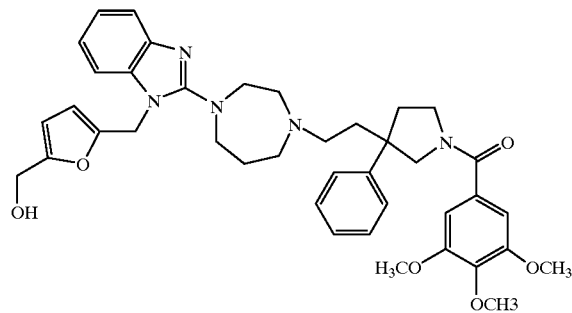

41.1 Synthesis of 1-(3,4,5-trimethoxybenzoyl)-3-(2-(4-(1-(5-hydroxymethylfur-2-ylmethyl)-1H-benzimidazol-2-yl)[1,4]diazepan-1-yl)ethyl)-3-phenylpyrrolidine Prepare by the method of Example 1.6 using 1-(3,4,5-trimethoxybenzoyl)-3-(2-methanesulfonyloxyethyl)-3-phenylpyrrolidine (prepared from (−)-3-phenyl-3-(2-hydroxyethyl)pyrrolidine (R,R)-di-p-anisoyltartaric acid salt) and 4-(1-(5-hydroxymethylfur-2-ylmethyl)-1H-benzimidazol-2-yl)[1,4]diazepane to give, after chromatography on silica gel eluting with methanol, the title compound: $R_f$=0.41 (silica gel, methanol).

41.2 Synthesis of 1-(3,4,5-trimethoxybenzoyl)-3-(2-(4-(1-(5-hydroxymethylfur-2-ylmethyl)-1H-benzimidiazol-2-yl)[1,4]diazepan-1-yl)ethyl)-3-phenylpyrrolidine Hydrochloride salt Combine 1-(3,4,5-trimethoxybenzoyl)-3-(2-(4-(1-(5-hydroxymethylfur-2-ylmethyl)-1H-benzimidazol-2-yl)[1,4]diazepan-1-yl)ethyl)-3-phenylpyrrolidine (0.47 g, 0.68 mmol) and methanol (10 ml). Add a solution of hydrochloric acid in dioxane (0.17 mL, 4M, 0.68 mmol). After 18 hours, evaporate in vacuo to give a residue. Triturate the residue with diethyl ether to give a solid. Repeatedly, decant solvent and add diethyl ether. Collect the solid by filtration to give the title compound.

EXAMPLE 42
1-(2,4,5-trimethoxybenzoyl)-3-(2-(4-(1-(2-ethoxyethyl)-1H-benzimidazol-2-yl)[1,4]diazepan-1-yl)ethyl)-3-phenylpyrrolidine

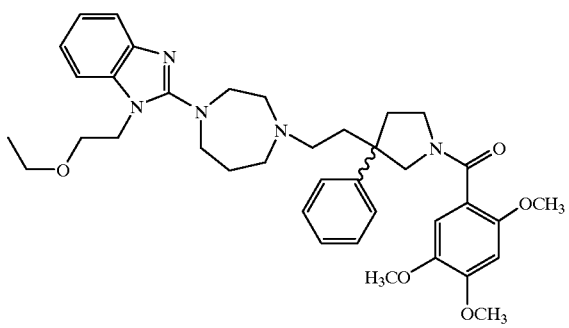

42.1 Synthesis of 1-(2,4,5-trimethoxybenzoyl)-3-phenyl-3-2-hydroxyethyl)pyrrolidine Combine 3-phenyl-3-(2-hydroxyethyl)pyrrolidine (1.8 mmol) and sodium carbonate (0.76 g, 7.2 mmol) in ethyl acetate/water (10 mL/10 mL). With stirring, add a solution of 2,4,5-trimethoxybenzoyl chloride (1.1 g, 1.8 mmol) in ethyl acetate (1 mL). After 18 hours, separate the layers and extract the aqueous layer twice with ethyl acetate. Combine the organic layers, dry over $Na_2SO_4$, filter, and evaporate in vacuo to give a residue. Chromatograph the residue on silica gel eluting with 9/1 ethyl acetate/ethanol to give the title compound.

42.2 Synthesis of 1-(2,4,5-trimethoxybenzoyl)-3-phenyl-3-(2-methanesulfonyloxyethyl)pyrrolidine Prepare by the method of Example 2.5.2 using 1-(2,4,5-trimethoxybenzoyl)-3-phenyl-3-(2-hydroxyethyl) pyrrolidine (0.33 g, 0.81 mmol) to give the title compound.

42.3 Synthesis of 1-(2,4,5-trimethoxybenzoyl)-3-(2-(4-(1-(2-ethoxyethyl)-1H-benzimidazol-2-yl)[1,4]diazepan-1-yl) ethyl)-3-phenylpyrrolidine Prepare by the method of Example 7.6 using 1-(2,4,5-trimethoxybenzoyl)-3-phenyl-3-(2-methanesulfonyloxyethyl) pyrrolidine and 4-(1-(2-ethoxyethyl)-1H-benzimidazol-2-yl)[1,4]diazepane hydriodic acid salt to give the title compound: $R_f$=0.42 (silica gel, 9/1/0/1 dichloromethane/methanol/concentrated aqueous ammonia).

PREPARATION 7
4-(1-(2-Hydroxyethyl)-1H-benzimidazol-2-yl)[1,4]diazepane hydrochloric acid salt Combine 4-(1-(2-ethoxyethyl)-1H-benzimidazol-2-yl)[1,4]diazepane (5.10 g, 1.8 mmol) and 48% hydrobromic acid (25 mL). Heat to reflux. After 18 hours, dilute with water and adjust the pH to 12 using aqueous 5 M sodium hydroxide solution. Extract three times with dichloromethane. Dry the combined organic layers over $Na_2SO_4$, filter, and evaporate in vacuo to give a residue. Combine the residue and methanol (50 mL). Add a solution of hydrochloric acid (5.0 mL, 4 M, 20 mmol) in dioxane. Evaporate in vacuo to give a residue. Triturate the residue with diethyl ether to give a solid. Collect the solid by filtration and dry to give the title compound.

EXAMPLE 43
(+)-1-3,4,5-Trimethoxybenzoyl )-3-(2-(4-(1-2-hydroxyethyl)-1H-benzimidazol-2-yl)[1,4]diazepan-1-yl)ethyl)-3-phenylpyrrolidine

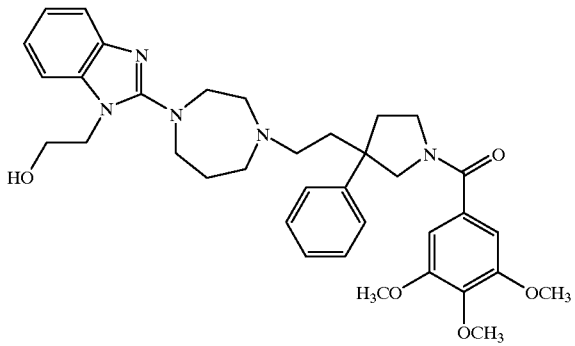

43.1 Synthesis of (+)-1-(3,4,5-trimethoxybenzoyl)-3-(2-(4-(1-(2-hydroxyethyl)-1H-benzimidazol-2-yl)[1,4]diazepan-1-yl)ethyl)-3-phenylpyrrolidine Combine 1-(3,4,5-trimethoxybenzoyl)-3-phenyl-3-(2-methanesulfonyloxyethyl)pyrrolidine (prepared from (−)-3-phenyl-3-(2-hydroxyethyl)pyrrolidine (R,R)-di-p-anisoyltartaric acid salt) (0.3 g, 1.2 mmol), 4-(1-(2-hydroxyethyl)-1H-benzimidazol-2-yl)[1,4]diazepane hydrochloric acid salt (0.52 g, 1.12 mmol), potassium iodide (0.2 g), and N,N-diisopropylethylamine (0.4 g, 4 mmol) in acetonitrile (20 mL). Heat to reflux. After 18 hours, cool and dilute the reaction mixture ethyl acetate. Extract three times with a half saturated aqueous sodium bicarbonate solution, and then brine. Dry the organic layer over $Na_2SO_4$, filter, and concentrate invacuo to obtain a residue. Chromatograph the residue on silica gel eluting with 40% methanol/ethyl acetate/1% concentrated aqueous ammonia solution to give, after drying invacuo at 70° C., the title compound: mp; 73–78° C. $[\alpha]_D^{20}=+7.7°$ (c=1.04, methanol). $R_f=0.23$ (silica gel, 40% methanol/ethyl acteate).

PREPARATION 8
4-(1-(2-Cyanomethyloxyethyl)-1H-benzimidazol-2-yl)[1,4]diazepane Hydriodic acid salt Combine 4-(1-(2-ethoxyethyl)-1H-benzimidazol-2-yl)[1,4]diazepane (5.95 g, 20.6 mmol) and 48% hydrobromic acid (50 mL). Heat to reflux. After 3.5 hours, cool the reaction mixture and dilute with a solution of sodium hydroxide (23 g, 0.57 mmol) in water (250 mL). Extract three times with dichloromethane. Combine the aqueous layer, dichloromethane (200 mL), and sodium chloride (50 g) and stir. After 18 hours, separate the layers and combine all the organic layers, dry over $Na_2SO_4$, filter, and evaporate in vacuo to give 4-(1-(2-hydroxyethyl)-1H-benzimidazol-2-yl)[1,4]diazepane.

Combine 4-(1-(2-hydroxyethyl)-1H-benzimidazol-2-yl)[1,4]diazepane (1.30 g, 5.0 mmol), tetrahydrofuran (40 mL), and water (10 mL). Add dropwise a solution of di-t-butyl dicarbonate (1.09 g, 5.0 mmol) in tetrahydrofuran (15 mL). After 18 hours, concentrate the reaction mixture in vacuo to remove most of the tetrahydrofuran and combine the concentrated reaction mixture with dichloromethane. Separate the layers, dry over $Na_2SO_4$, filter, and evaporate in vacuo to give a residue. Chromatograph the residue on silica gel eluting with ethyl acetate to give 1-(t-butoxycarbonyl)-4-(1-(2-hydroxyethyl)-1H-benzimidazol-2-yl)[1,4]diazepane: $R_f=0.25$ (silica gel, ethyl acetate).

Alternately, combine 4-(1-(2-hydroxyethyl)-1H-benzimidazol-2-yl)[1,4]diazepane (4.9 g, 18.8 mmol) and dichloromethane (120 mL). Add dropwise a solution of di-t-butyl dicarbonate (4.31 g, 19.7 mmol) in dichloromethane (20 mL). After 72 hours, concentrate the reaction mixture in vacuo to give a residue. Chromatograph the residue on silica gel eluting with ethyl acetate to give upon standing 1-(t-butoxycarbonyl)-4-(1-(2-hydroxyethyl)-1H-benzimidazol-2-yl)[1,4]diazepane: mp: 108–112° C. $R_f=0.25$ (silica gel, ethyl acetate).

Combine 1-(t-butoxycarbonyl)-4-(1-(2-hydroxyethyl)-1H-benzimidazol-2-yl)[1,4]diazepane (1.7 g, 4.7 mmol), tetrahydrofuran (70 mL), and dimethylformamide (8 mL). Cool in an ice bath. Add with stirring, sodium hydride (0.28 g, 60% in oil, 7.0 mmol). After 3 hours, warm to ambient temperature. After 30 minutes, again cool in an ice bath and add bromoacetonitrile (1.12 g, 9.36 mmol). Warm to ambient temperature. After 18 hours, again cool in an ice bath and add a saturated aqueous solution of ammonium chloride (5 mL) and then water (5 mL). Concentrate the reaction mixture in vacuo to remove most to the tetrahydrofuran and dilute with dichloromethane (150 mL). Extract three times with water, dry the organic layer over $Na_2SO_4$, filter, and evaporate in vacuo to give a residue. Chromatograph the residue on silica gel eluting with ethyl acetate to give 1-(t-butoxycarbonyl)-4-(1-(2-cyanomethyloxyethyl)-1H-benzimidazol-2-yl)[1,4]diazepane: $R_f=0.38$ (silica gel, ethyl acetate).

Combine 1-(t-butoxycarbonyl)-4-(1-(2-cyanomethyloxyethyl)-1H-benzimidazol-2-yl)[1,4]diazepane (0.36 g, 0.91 mmol), dichloromethane (15 mL), and methanol (5 mL). Cool in an ice bath and add hydriodic acid (0.25 mL, 57%, 1.86 mmol). Warm to ambient temperature. After 5 hours, concentrate the reaction mixture in vacuo to give a residue. Combine the residue and diethyl ether (40 mL) and stir. After 18 hours, decant the solvent, add diethyl ether, and stir to give a solid. Collect the solid by filtration and dry to give the title compound.

EXAMPLE 44
1-(3,4,5-Trimethoxybenzoyl-3-(2-(4-(1-(2-cyanomethoxyethyl)-1H-benzimidazol-2-y)[1,4]diazepan-1-yl)ethyl)-3-phenylpyrrolidine

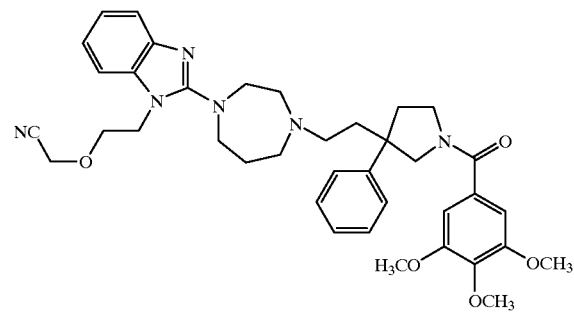

44.1 Synthesis of 1-(3,4,5-trimethoxybenzoyl)-3-(2-(4-(1-(2-cyanomethyloxyethyl)-1H-benzimidazol-2-yl)[1,4]diazepan-1-yl)ethyl)-3-phenylpyrrolidine Combine 1-(3,4,5-trimethoxybenzoyl)-3-phenyl-3-(2-methanesulfonyloxyethyl)pyrrolidine (prepared from (−)-3-phenyl-3-(2-hydroxyethyl)pyrrolidine (R,R)-di-p-anisoyltartaric acid salt) (0.62 g, 1.34 mmol), 4-(1-(2-cyanomethyloxyethyl)-1H-benzimidazol-2-yl)[1,4]diazepane hydriodic acid salt (0.67 g, 1.22 mmol), and N,N-diisopropylethylamine (0.8 mL, 4.6 mmol) in acetonitrile (15 mL). Heat to reflux. After 40 hours, cool and dilute the reaction mixture with ethyl acetate, Extract with a saturated aqueous sodium bicarbonate solution, and then brine. Dry the organic layer over $Na_2SO_4$, filter, and concentrate inveacuo to obtain a residue. Chromatograph the residue on silica gel eluting with 5% methanol/dichloromethane/1% concentrated aqueous ammonia solution to give, after drying, the title compound: $R_f$=0.20 (silica gel, 5% methanol/dichloromethane/1% concentrated aqueous ammonia solution)

44.2 Synthesis of 1-(3,4,5-trimethoxybenzoyl)-3-(2-(4-(1-(2-cyanomethyloxyethyl)-1H-benzimidazol-2-yl)[1,4]diazepan-1-yl)ethyl)-3-phenylpyrrolidine hydrochloric acid salt Combine 1-(3,4,5-trimethoxybenzoyl)-3-(2-(4-(1-(2-cyanomethyloxyethyl)-1H-benzimidazol-2-yl)[1,4]diazepan-1-yl)ethyl)-3-phenylpyrrolidine (0.31 g, 0.46 mmol) and dichloromethane (15 mL). Cool in an ice bath and add a solution of hydrochloric acid in dioxane (0.23 ml, 4 M, 0.94 mmol). Warm to ambient temperature. After 18 hours, concentrate the reaction mixture in vacuo to give a residue. Combine the residue and diethyl ether (150 mL) and stir. After 18 hours, decant the solvent, add diethyl ether, and stir to give a solid. Collect the solid by filtration and dry to give the title compound; mp: 134–148° C.

PREPARATION 9
4-(1-(4-Oxopentyl)-1H-benzimidazol-2-yl)[1,4]diazepane Hydriodic acid salt Combine 4-(1H-benzimidazol-2-yl)[1,4]diazepane hydriodic acid salt (6.5 g, 25.4 mmol), tetrahydrofuran (130 mL), and water (40 mL). Add sodium bicarbonate (4.26 g, 50.7 mmol) and cool in an ice bath. Add dropwise a solution of di-t-butyl dicarbonate (5.54 g, 25.4 mmol) in tetrahydrofuran (20 mL). Warm to ambient temperature. After 18 hours, concentrate the reaction mixture in vacuo to remove most of the tetrahydrofuran and combine the concentrated reaction mixture with dichloromethane. Extract with water and then brine. Dry the organic layer over $Na_2SO_4$, filter, and evaporate in vacuo to give 1-(t-butoxycarbonyl)-4-(1H-benzimidazol-2-yl)[1,4]diazepane: mp: 225–226° C. $R_f$=0.28 (silica gel, 5% methanol/dichloromethane/1% saturated aqueous ammonia solution).

Combine 1-(t-butoxycarbonyl)-4-(1H-benzimidazol-2-yl)[1,4]diazepane (1.10 g, 3.5 mmol) and tetrahydrofuran (45 mL) and dimethylformamide (5 mL). Cool in an ice bath and add sodium hydride (0.21 g, 60% in oil, 5.22 mmol). After 1 hour, add 5-chloropentan-2-one, ethylene ketal (0.79 mL, 5.22 mmol) and tetra-n-butylammonium bromide (112 mg, 0.35 mmol). Heat to reflux. After 18 hours, cool, add sodium hydride (0.1 g) and 5-chloropentan-2-one, ethylene ketal (0.50 mL) and again heat to reflux. After 24 hours, cool in a dry-ice/acetone bath and add a saturated aqueous solution of ammonium chloride. Warm to ambient temperature and dilute the reaction mixture with a saturated aqueous solution of sodium bicarbonate. Concentrate in vacuo to remove most to the tetrahydrofuran and extract three times with ethyl acetate. Extract the combined organic layers with water and then brine, dry the organic layer over $Na_2SO_4$, filter, and evaporate in vacuo to give a residue. Chromatograph the residue on silica gel eluting with 5% methanol/dichloromethane/0.1% saturated aqueous ammonia solution to give 1-(t-butoxycarbonyl)-4-(1-(4-oxopentyl)-1H-benzimidazol-2-yl)[1,4]diazepane, ethylene ketal: $R_f$=0.47 (silica gel, 5% methanol/dichloromethane/0.1% saturated aqueous ammonia solution).

Combine 1-(t-butoxycarbonyl)-4-(1-(4-oxopentyl)-1H-benzimidazol-2-yl)[1,4]diazepane, ethylene ketal (0.9 g, 2.0 mmol) and dichloromethane (20 mL). Cool in an ice bath and add hydriodic acid (0.53 mL, 57%, 4.05 mmol). Warm to ambient temperature. After 0.5 hours, add water (0.5 mL) and heat to reflux. After 18 hours, cool to ambient temperature and evaporate in vacuo to give a residue. Combine the residue and methanol (45 mL) and add diethyl ether (250 mL) with stirring to give a solid. After 30 minutes, collect the solid by filtration to give, after drying the title compound. Elemental Analysis calculated for $C_{17}H_{24}N_4O \cdot 2HI$: C, 36.71; H, 4.71; N, 10.07; Found: C 36.94; H, 4.47; N, 9.84.

EXAMPLE 45

1-(3,4,5-Trimethoxybenzoyl)-3-(2-(4-(1-(4-oxopentyl)-1H-benzimidazol-2-yl)-[1,4diazepanyl)ethyl)-3-phenylpyrrolidine

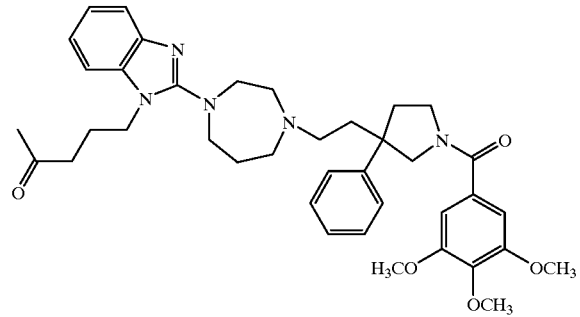

45.1 Synthesis of 1-3,4,5-trimethoxybenzoyl)-3-(2-(4-(1-(4-oxopentyl)-1H-benzimidazol-2-yl)[1,4]diazepan-1-yl)ethyl)-3-phenylpyrrolidine Combine 1-(3,4,5-trimethoxybenzoyl)-3-phenyl-3-(2-methanesulfonyloxyethyl)pyrrolidine (prepared from (−)-3-phenyl-3-(2-hydroxyethyl)pyrrolidine (R,R)-di-p-anisoyltartaric acid salt) (0.40 g, 0.72 mmol), 4-(1-(4-oxopentyl)-1H-benzimidazol-2-yl)[1,4]diazepane hydriodic acid salt (0.30 g, 0.65 mmol), and N,N-diisopropylethylamine (0.52 mL, 3.02 mmol) in acetonitrile (10 mL). Heat to reflux. After 24 hours, cool and partition the reaction mixture between ethyl acetate and a half saturated aqueous sodium bicarbonate solution. Separate the organic layer extract with a saturated aqueous sodium bicarbonate solution and then brine. Dry the organic layer over $Na_2SO_4$, filter, and concentrate in vacuo to obtain a residue. Chromatograph the residue on silica gel eluting with 10% methanol/dichloromethane/0.1% concentrated aqueous ammonia solution to give the title compound: $R_f$=0.45 (silica gel, 10% methanol/dichloromethane/0.1% concentrated aqueous ammonia solution).

45.2 Synthesis of 1-(3,4,5-trimethoxybenzoyl)-3-(2-(4-(1-(4-oxopentyl)-1H-benzimidazol-2-yl)[1,4]diazepan-1-yl)ethyl)-3-phenylpyrrolidine hydrochloric acid salt Combine 1-(3,4,5-trimethoxybenzoyl)-3-(2-(4-(1-(4-oxopentyl)-1H-benzimidazol-2-yl)[1,4]diazepan-1-yl)ethyl)-3-phenylpyrrolidine (0.34 g, 0.5 mmol) and dichloromethane (5 mL). Cool in an ice bath and add a solution of hydrochloric acid in dioxane (0.15 ml, 4 M, 0.6 mmol). Warm to ambient temperature. After 20 minutes, add diethyl ether (80 mL) and stir to give a solid. Collect the solid by filtration and dry to give the title compound: mp; 95–112° C.

PREPARATION 10

1-(t-Butoxycarbonyl)-4-(1H-benzimidazol-2-yl)[1,4]diazepane

Combine 1-ethoxycarbonyl[1,4]diazepane (18.0 g, 104 mmol) and 2-chlorobenzimidazole (7.93 g, 52 mmol). Heat to 130° C. After 4 hours, cool to ambient temperature and add hot methanol to dissolve the reaction mixture. Add a saturated aqueous solution of sodium bicarbonate (150 mL) and concentrate in vacuo to remove most of the methanol. Combine the aqueous reaction mixture and 95/5 diethyl ether/ethyl acetate. Separate the aqueous layer and extract three times with dichloromethane. Combine the dichloromethane layers, dry over $Na_2SO_4$, filter, and evaporate in vacuo to give a residue. Triturate the residue with ethyl acetate (100 mL) to give a solid. Chromatograph on silica gel eluting with 10% methanol/dichloromethane/0.1% concentrated aqueous ammonia to give a residue. Triturate that residue with 9/1 diethyl ether/ethyl acetate to give a solid. Collect solid by filtration and dry in vacuo to give 1-ethoxycarbonyl-4-(1H-benzimidazol-2-yl)[1,4]diazepane: mp; 161–162° C.

Combine 1-ethoxycarbonyl-4-(1H-benzimidazol-2-yl)[1,4]diazepane (5.22 g, 18.1 mmol) and aqueous 48% hydrobromic acid solution (25 mL). Heat to reflux. After 4 hours, cool to ambient temperature and concentrate in vacuo to give a residue. Combine the residue and ethanol (150 mL). Evaporate in vacuo to a volume of about 75 mL and cool to give a solid. Collect solid by filtration, rinse with ethanol and then diethyl ether, and dry in vacuo to give 4-(1H-benzimidazol-2-yl)[1,4]diazepane hydrobromic acid salt. Elemental Analysis calculated for $C_{12}H_{16}N_4 \cdot 2HBr$: C, 38.12; H, 4.80; N, 14.82. Found: C, 38.17; H, 4.84; N, 14.60.

Combine 4-(1H-benzimidazol-2-yl)[1,4]diazepane hydrobromic acid salt (5.2 g, 13.8 mmol), 4/1 tetrahydrofuran/water (100 mL), and sodium bicarbonate (3.47 g, 41.3 mmol). Add di-t-butyl dicarbonate (3.3 g, 15.1 mmol). After 18 hours, concentrate the reaction mixture invacuo to remove most of the tetrahydrofuran and combine the concentrated reaction mixture with 5% methanol/dichloromethane. Extract with water, dry over $Na_2SO_4$, filter, and evaporate in vacuo to give a residue. Chromatograph the residue on silica gel eluting with ethyl acetate to give the title compound: mp; 225–226° C. $R_f$=0.28 (silica gel, 5% methanol/dichloromethane/0.1% concentrated aqueous ammonia).

EXAMPLE 46

1-(3,4,5-Trimethoxybenzoyl)-3-(2-(4-(1-(2-ethoxyethyl)-1H-benzimidazol-2-yl)[1,4]diazepan-1-yl)ethyl)-3-(pyrid-4-yl)pyrrolidine

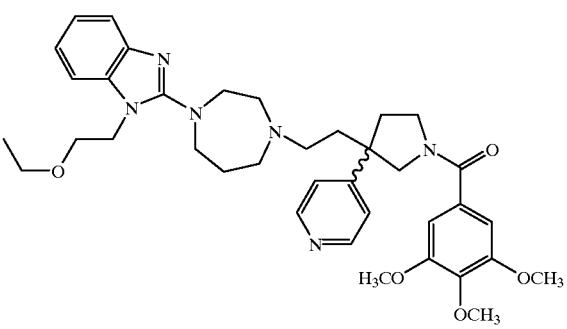

46.1.1 Synthesis of 3-cyano-3-(pyrid-4-yl)-pentanedioic acid diethyl ester

Prepare by the method of Example 34.1.2 using 4-pyridineacetonitrile to give, after chromatography on silica gel eluting with ethyl acetate/hexane 1/1, the title compound.

46.2 Synthesis of (3-(pyrid-4-yl)-5-oxopyrrolidin-3-yl) acetic acid ethyl ester Prepare by the method of Example 34.2.2 using 3-cyano-3-(pyrid-4-yl)pentanedioic acid diethyl ester to give the title compound: $R_f$=0.46 (silica gel, 8% methanol/dichloromethane).

46.3 Synthesis of 3-(pyrid-4-yl)-3-(2-hydroxyethyl)pyrrolidine

Prepare by the method of Example 34.3.3 using 3-(pyrid-4-yl)-5-oxo-pyrrolidin-3-yl)acetic acid ethyl ester to give the title compound: $R_f$=0.23 (silica gel, 15% methanol/dichloromethane).

46.4 Synthesis of 1-(3,4,5-trimethoxybenzoyl)-3-(pyrid-4-yl)-3-(2-hydroxyethyl)pyrrolidine Prepare by the method of Example 7.4 using 3-(pyrid-4-yl)-3-(2-hydroxyethyl)pyrrolidine to give the title compound: $R_f$=0.42 (silica gel, 8% methanol/dichloromethane).

46.5 Synthesis of 1-(3,4,5-trimethoxybenzoyl)-3-(pyrid-4-yl)-3-(2-methanesulfonyloxyethyl)pyrrolidine Combine 1-(3,4,5-trimethoxybenzoyl)-3-(pyrid-4-yl)-3-(2-hydroxyethyl)pyrrolidine (0.32 g, 0.83 mmol) and N,N-diisopropylethylamine (0.46 mL, 2.64 mmol) in dichloromethane (50 mL). Cool in an ice bath. Add dropwise methanesulfonyl chloride (0.096 mL, 1.24 mmol). After 1 hour, warm to ambient temperature. Again cool in an ice bath and add N,N-diisopropylethylamine (0.23 mL, 1.32 mmol) followed by methanesulfonyl chloride (0.096 ml, 1.24 mmol). After 1 hour, dilute the reaction mixture with dichloromethane and extract with a saturated aqueous solution of sodium bicarbonate. Dry the organic layer over $MgSO_4$, filter, and evaporate in vacuo to give the title compound: $R_f$=0.24 (silica gel, 5% methanol/dichloromethane/0.1% concentrated aqueous ammonia).

46.6 Synthesis of 1-(3,4,5-trimethoxybenzoyl)-3-(2-(4-(1-(2-ethoxyethyl)-1H-benzimidazol-2-yl)[1,4]diazepan-1-yl)ethyl)-3-(pyrid-4-yl)pyrrolidine Combine 1-(3,4,5-trimethoxybenzoyl)-3-(pyrid-4-yl)-3-(2-methanesulfonyloxyethyl)pyrrolidine (0.90 g, 1.65 mmol), 4-(1-(2-ethoxyethyl)-1H-benzimidazol-2-yl)[1,4]diazepane (0.49 g, 0.83 mmol), and N,N-diisopropylethylamine (2.1 mL, 11.6 mmol) in acetonitrile (14 mL). Heat to reflux. After 48 hour, add sodium carbonate and stir. After 1 hour, dilute the reaction mixture with dichloromethane, filter and evaporate in vacuo to give a residue. Chromatograph the residue on silica gel eluting sequentially with 10% methanol/dichloromethane/0.1% concentrated aqueous ammonia and then 50% methanol/dichloromethane/0.1% concentrated aqueous ammonia to give a residue. Dissolve the residue in dichloromethane, extract with a saturated aqueous sodium bicarbonate solution, dry over $Na_2SO_4$, filter, and evaporate in vacuo to give the title compound: $R_f$=0.39 (silica gel, 10% methanol/dichloromethane/0.1% concentrated aqueous ammonia).

46.7 Synthesis of 1-(3,4,5-trimethoxybenzoyl)-3-(2-(4-(1-(2-ethoxyethyl)-1H-benzimidazol-2-yl)[1,4]diazepan-1-yl)ethyl)-3-(pyrid-4-yl)pyrrolidine hydrochloric acid salt Combine 1-(3,4,5-trimethoxybenzoyl)-3-(2-(4-(1-(2-ethoxyethyl)-1H-benzimidazol-2-yl)[1,4]diazepan-1-yl)ethyl)-3-(pyrid-4-yl)pyrrolidine (0.36 g, 0.51 mmol) and dichloromethane 50 mL. Add a solution of hydrochloric acid in dioxane (0.128 mL, 4 M, 0.51 mmol). After 2 hours, evaporate in vacuo to give a residue. Combine the residue and dichloromethane (5 mL) and add diethyl ether (200 mL) to give a solid. collect the solid by filtration, rinse with diethyl ether, and dry to give the title compound: mp; 85–95° C.

PREPARATION 11
2-Methoxy-5-(1H-tetrazol-1-yl)benzoyl chloride

Combine 2-hydroxy-5-nitrobenzoic acid (21.5 g, 117 mmol), potassium carbonate (162.3 g, 1.174 mol), and methyl iodide (136.8 g, 96.4 mmol) in acetone (500 mL). Heat to reflux. After 18 hours, cool the reaction mixture to ambient temperature and add methyl iodide (136.8 g, 96.4 mmol). Again, heat to reflux. After 56 hours, cool the reaction mixture to ambient temperature and filter, rinse with acetone, and evaporate the filtrate in vacuo to give a residue. Recrystallize the residue form ethanol to give a second residue. Combine the second residue and chloroform (about 100 mL), filter and evaporate the filtrate in vacuo to give methyl 2-methoxy-5-nitrobenzoate. $R_f$=0.38 (silica gel, ethyl acetate/hexane 1/1).

Combine methyl 2-methoxy-5-nitrobenzoate (13.3 g, 63 mmol) and methanol. Add 5% palladium-on-carbon (0.66 g). Hydrogenate on a pressure apparatus at 50 psi. After 17 hours, filter through celite to remove the catalyst and evaporate the filtrate in vacuo to give a residue. Combine the residue and dichloromethane and extract with water. Dry the organic layer over $Na_2SO_4$, filter, and evaporate in vacuo to give methyl 2-methoxy-5-aminobenzoate. $R_f$=0.18 (silica gel, ethyl acetate/methanol 1/1). Elemental Analysis calculated for $C_9H_{11}NO_3$: C, 59.66; H, 6.12; N, 7.73. Found: C, 59.44; H, 6.04; N, 7.62.

Combine methyl 2-methoxy-5-aminobenzoate (3.94 g, 21.7 mmol) and triethyl orthoformate (12.8 g, 86.7 mmol) in glacial acetic acid (20 mL). After 20 hours, concentrate the reaction mixture in vacuo to remove ethanol. Add glacial acetic acid (20 mL) and sodium azide (5.64 g, 86.7 mmol). Heat to 70° C. After 1 hour, add glacial acetic acid (10 mL) and continue to heat to 70° C. After an additional hour, cool the reaction mixture to ambient temperature, dilute with water (500 mL). Collect the solid by filtration, rinse with water, and dry to give methyl 2-methoxy-5-(1H-tetrazol-1-yl)benzoate.

Combine methyl 2-methoxy-5-(1H-tetrazol-1-yl)benzoate (2.86 g, 12.2 mmol) and a 1 M aqueous solution of sodium hydroxide (13.43 mL, 13.43 mmol) in methanol/water (100 mL, 5:1 vol./vol.). Heat to reflux. After 4 hours, concentrate in vacuo to remove most of the methanol, add water (50 mL), and adjust the pH to about 4 using a 1 M aqueous hydrochloric acid solution. Evaporate in vacuo to give a solid, slurry the solid with water, filter, and dry to give 2-methoxy-5-(1H-tetrazol-1-yl)benzoic acid.

Alternately, combine methyl 2-methoxy-5-(1H-tetrazol-1-yl)benzoate (13.3 g, 56.8 mmol) and methanol (150 mL). Add 1 M aqueous solution of sodium hydroxide (62.5 mL, 62.5 mmol). Heat to reflux. After 30 minutes, add methanol (50 mL) and water (50 mL) and continue the heat at reflux. After 1 hour, concentrate in vacuo to remove most of the solvent. Adjust the pH to about 1 to 2 using a 1 M aqueous hydrochloric acid solution to give a solid. Collect the solid by filtration, rinse with water, and dry to give 2-methoxy-5-(1H-tetrazol-1-yl)benzoic acid.

Combine 2-methoxy-5-(1H-tetrazol-1-yl)benzoic acid (1.2 g, 5.5 mmol) and dichloromethane (40 mL). Add dropwise oxalyl chloride (0.72 mL, 8.25 mmol) followed by dimethylformamide (3 drops). After 4 hours, evaporate in vacuo and dry to give the title compound.

EXAMPLE 47
1-2-Methoxy-5-(1H-tetrazol-1-yl)benzoyl)-3(2-4-(1-(2-ethoxyethyl)-1H-benzimidazol-2-yl)[1,4]diazepan-1-yl)ethyl)-3-phenylpyrrolidine

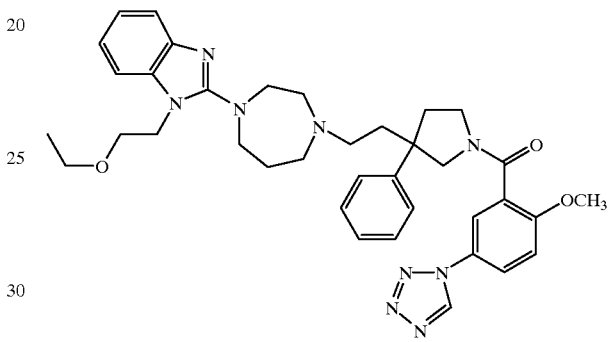

47.1 Synthesis of 1-(2-methoxy-5-(1H-tetrazol-1-yl)benzoyl)-3-phenyl-3-(2-hydroxyethyl)pyrrolidine Add (-)-3-phenyl-3-(2-hydroxyethyl)pyrrolidine (R,R)-di-p-anisoyltartaric acid salt (6.72 g, 11.0 mmol) and sodium bicarbonate (4.87 g, 58 mmol) in acetone/water (50 mL/50 mL). Cool in an ice bath. Add a solution of 2-methoxy-5-(1H-tetrazol-1-yl)benzoyl chloride (1.66 g, 9.9 mmol) in acetone (100 mL). After 30 minutes, warm to ambient temperature. After 60 hours, filter the reaction mixture and dilute the filtrate with ethyl acetate. Extract the filtrate with a saturated aqueous sodium bicarbonate solution and then brine. Dry the organic layer over $MgSO_4$, filter, and evaporate in vacuo to give residue. Chromatograph the residue on silica gel eluting sequentially with ethyl acetate, 3% methanol/ethyl acetate, and then 5% methanol/ethyl acetate to give the title compound: $R_f$=0.48 (5% methanol/dichloromethane).

47.2 Synthesis of 1-(2-methoxy-5-(1H-tetrazol-1-yl)benzoyl)-3-phenyl-3-(2-methanesulfonyloxyethyl)pyrrolidine Prepare by the method of Example 2.5.2 using 1-(2-methoxy-5-(1H-tetrazol-1-yl)benzoyl)-3-phenyl-3-(2-hydroxyethyl)pyrrolidine (2.6 g, 6.50 mmol) and methanesulfonyl chloride (0.8 mL, 10.4 mmol) to give the title compound: $R_f$=0.20 (silica gel, ethyl acetate).

47.3 Synthesis of 1-(2-methoxy-5-(1H-tetrazol-1-yl)benzoyl)-3-(2-(4-(1-(2-ethoxyethyl)-1H-benzimidazol-2-yl)[1,4]diazepan-1-yl)ethyl)-3-phenylpyrrolidine Combine 1-(2-methoxy-5-(1H-tetrazol-1-yl)benzoyl)-3-phenyl-3-(2-methanesulfonyloxyethyl)pyrrolidine (0.92 g, 1.95 mmol), 4-(1-(2-ethoxyethyl)-1H-benzimidazol-2-yl)[1,4]diazepane hydriodic acid salt (1.6 g, 2.9 mmol), and N,N-diisopropylethylamine (2.2 mL, 12.6 mmol) in acetonitrile (36 mL). Heat to reflux. After 22 hours, cool and partition the residue between a saturated aqueous sodium bicarbonate solution and ethyl acetate. Separate the organic layer and extract with a saturated aqueous sodium bicarbonate solution and then brine. Dry the organic layer over $Na_2SO_4$, filter, and evaporate in vacuo to give residue. Chromatograph the residue on silica gel eluting with dichloromethane/methanol/concentrated aqueous ammonia 90/10/0.1 to give the title compound.

47.4 Synthesis of 1-(2-methoxy-5-(1H-tetrazol-1-yl)benzoyl)-3-(2-(4-(1-(2-ethoxyethyl)-1H-benzimidazol-2-yl)[1,4]diazepan-1-yl)ethyl)-3-phenylpyrrolidine hydrochloric acid salt Combine 1-(2-methoxy-5-(1H-tetrazol-1-yl)benzoyl)-3-(2-(4-(1-(2-ethoxyethyl)-1H-benzimidazol-2-yl)[1,4]diazepan-1-yl)ethyl)-3-phenylpyrrolidine (1.11 g, 1.67 mmol) and dichloromethane. (10 mL). Cool in an ice bath. Add a solution of hydrochloric acid in dioxane (1 mL, 4 M, 40. mmol). Warm to ambient temperature. Add diethyl ether (200 mL) and stir to give a solid. After 1 hour, collect the solid by filtration and dry to give the title compound.

EXAMPLE 48

1-(3,5-Dimethoxy-4-hydroxybenzoyl)-3-(2-(4-(1-(2-ethoxyethyl)-1H-benzimidazol-2-yl)[1,4]diazepan-1-yl)ethyl)-3-phenylpyrrolidine

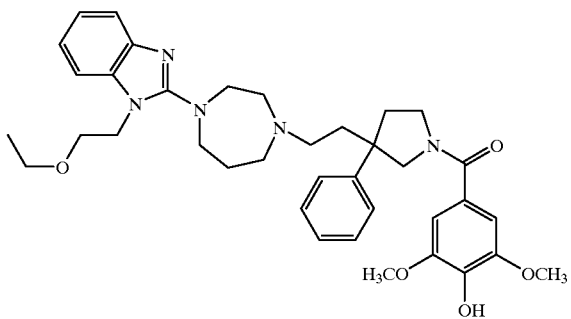

48.1 Synthesis of 1-(3,5-dimethoxy-4-hydroxybenzoyl)-3-phenyl-3-(2-hydroxyethyl)pyrrolidine Combine 3-phenyl-3-(2-hydroxyethyl)pyrrolidine (0.50 g, 2.7 mmol) (prepared by extraction from (−)-3-phenyl-3-(2-hydroxyethyl)pyrrolidine (R,R)-di-p-anisoyltartaric acid salt) and dichloromethane (25 mL). Add 3,5-dimethoxy-4-hydroxybenzoic acid (0.55 g, 2.78 mmol), 1-hydroxybenzotriazole hydrate (0.4 g, 2.9 mmol) and 1-ethyl-3-(3-dimethylaminopropyl)carbodiimide hydrochloride (0.56 g, 2.9 mmol). After 18 hours, dilute the reaction mixture with dichloromethane and extract with saturated aqueous sodium bicarbonate solution and then brine. Dry the organic layer over $MgSO_4$, filter, and evaporate in vacuo to give residue. Chromatograph the residue on silica gel eluting with methanol/dichloromethane/concentrated aqueous ammonia 1/10/0.1 to give the title compound: $R_f$=0.74 (silica gel, methanol/dichloromethane/concentrated aqueous ammonia 1/10/0.1)

48.2 Synthesis of 1-(3,5-dimethoxy-4-methanesulfonyloxybenzoyl)-3-phenyl-3-2-methanesulfonyloxyethyl)pyrrolidine Combine 1-(3,5-dimethoxy-4-hydroxybenzoyl)-3-phenyl-3-(2-hydroxyethyl)pyrrolidine (0.95 g, 2.6 mmol) and triethylamine (1.0 mL, 7.7 mmol) in dichloromethane (15 mL). Cool the reaction mixture to −5° C. with an salt-ice bath. Slowly, add methanesulfonyl chloride (0.45 mL, 5.8 mmol). Warm to ambient temperature. After 18 hours, quench the reaction by the addition of ice. Separate the organic layer and extract with aqueous 1M hydrochloric acid solution. Dry the organic layer over $Na_2SO_4$, filter, and concentrate in vacuo to obtain the title compound.

48.3 Synthesis of 1-(3,5-dimethoxy-4-methanesulfonyloxybenzoyl)-3-(2-(4-(1-(2-ethoxyethyl)-1H-benzimidazol-2-yl)[1,4]diazepan-1-yl)ethyl)-3-phenylpyrrolidine Combine 1-(3,5-dimethoxy-4-methanesulfonyloxybenzoyl)-3-phenyl-3-(2-methanesulfonyloxyethyl)pyrrolidine (0.77 g, 1.46 mmol), 4-(1-(2-ethoxyethyl)-1H-benzimidazol-2-yl)[1,4]diazepane hydriodic acid salt (1.0 g, 1.8 mmol), and N,N-diisopropylethylamine (0.76 g, 4.4 mmol) in acetonitrile (36 mL). Heat to reflux. After 16 hours, cool and evaporate in vacuo to give residue. Chromatograph the residue on silica gel eluting with dichloromethane/methanol/concentrated aqueous ammonia 6/1/0.1 to give the title compound.

48.4 Synthesis of 1-(3,5-dimethoxy-4-hydroxybenzoyl)-3-(2-(4-(1-(2-ethoxyethyl)-1H-benzimidazol-2-yl)[1,4]diazepan-1-yl)ethyl)-3-phenylpyrrolidine hydrochloric acid salt Combine 1-(3,5-dimethoxy-4-methanesulfonyloxybenzoyl)-3-(2-(4-(1-(2-ethoxyethyl)-1H-benzimidazol-2-yl)[1,4]diazepan-1-yl)ethyl)-3-phenylpyrrolidine (0.5 g, 0.5 mmol) and methanol (4 mL). Add potassium carbonate (0.5 g). After 18 hours, add a 1 M aqueous sodium hydroxide solution (1 mL) and extract with dichloromethane. Dry the organic layer over $Na_2SO_4$, filter, and concentrate in vacuo to give a residue. Chromatograph the residue on silica gel eluting with dichloromethane/methanol/concentrated aqueous ammonia 6/1/0.1 to give a residue. Combine the residue and dichloromethane (4 mL). Add a solution of hydrochloric acid in dioxane (0.12 mL, 4 M, 0.48 mmol). Warm to ambient temperature. After 1 hour, evaporate in vacuo to give a residue. Triturate with diethyl ether to give a solid. After 1 hour, collect the solid by filtration and dry to give the title compound.

EXAMPLE 49

1-(3,4-Dimethoxy-5-hydroxybenzoyl)-3-(2-(4-(1-(2-ethoxyethyl)-1H-benzimidazol-2-yl)[1,4]diazepan-1-yl)ethyl)-3-phenylpyrrolidine

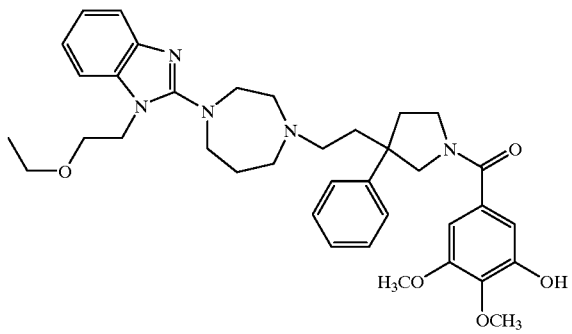

49.1 Synthesis of 1-(3,4-dimethoxy-5-hydroxybenzoyl)-3-phenyl-3-(2-hydroxyethyl)pyrrolidine Combine 3-phenyl-3-(2-hydroxyethyl)pyrrolidine (0.50 g, 2.7 mmol) (prepared by extraction from (−)-3-phenyl-3-(2-hydroxyethyl)pyrrolidine (R,R)-di-p-anisoyltartaric acid salt) and dichloromethane (25 mL). Add 3,4-dimethoxy-5-hydroxybenzoic acid (0.55 g, 2.78 mmol), 1-hydroxybenzotriazole hydrate (0.4 g, 2.9 mmol) and 1-ethyl-3-(3-dimethylaminopropyl)carbodiimide hydrochloride (0.56 g, 2.9 mmol). After 18 hours, dilute the reaction mixture with dichloromethane and extract with saturated aqueous sodium bicarbonate solution and then brine. Dry the organic layer over MgSO$_4$, filter, and evaporate in vacuo to give residue. Chromatograph the residue on silica gel eluting with methanol/dichloromethane/concentrated aqueous ammonia 1/10/0.1 to give the title compound.

49.2 Synthesis of 1-(3,4-dimethoxy-5-methanesulfonyloxybenzoyl)-3-phenyl-3-(2-methanesulfonyloxyethyl)pyrrolidine Combine 1-(3,4-dimethoxy-5-hydroxybenzoyl)-3-phenyl-3-(2-hydroxyethyl)pyrrolidine (0.95 g, 2.6 mmol) and triethylamine (1.0 mL, 7.7 mmol) in dichloromethane (15 mL). Cool the reaction mixture to −5° C. with an salt-ice bath. Slowly, add methanesulfonyl chloride (0.45 mL, 5.8 mmol). Warm to ambient temperature. After 18 hours, quench the reaction by the addition of ice. Separate the organic layer and extract with aqueous 1M hydrochloric acid solution. Dry the organic layer over Na$_2$SO$_4$, filter, and concentrate in vacuo to obtain the title compound.

49.3 Synthesis of 1-(3,4-dimethoxy-5-methanesulfonyloxybenzoyl)-3-(2-(4-(1-(2-ethoxyethyl)-1H-benzimidazol-2-yl)[1,4]diazepan-1-yl)ethyl)-3-phenylpyrrolidine Combine 1-(3,4-dimethoxy-5-methanesulfonyloxybenzoyl)-3-phenyl-3-(2-methanesulfonyloxyethyl)pyrrolidine (0.77 g, 1.46 mmol), 4-(1-(2-ethoxyethyl)-1H-benzimidazol-2-yl)[1,4]diazepane hydriodic acid salt (1.0 g, 1.8 mmol), and N,N-diisopropylethylamine (0.76 g, 4.4 mmol) in acetonitrile (36 mL). Heat to reflux. After 16 hours, cool and evaporate in vacuo to give residue. Chromatograph the residue on silica gel eluting with dichloromethane/methanol/concentrated aqueous ammonia 6/1/0.1 to give the title compound.

49.4 Synthesis of 1-(3,4-dimethoxy-5-hydroxybenzoyl)-3-(2-(4-(1-(2-ethoxyethyl)-1H-benzimidazol-2-yl)[1,4]diazepan-1-yl)ethyl)-3-phenylpyrrolidine hydrochloric acid salt Combine 1-(3,4-dimethoxy-5-methanesulfonyloxybenzoyl)-3-(2-(4-(1-(2-ethoxyethyl)-1H-benzimidazol-2-yl)[1,4]diazepan-1-yl)ethyl)-3-phenylpyrrolidine (0.5 g, 0.5 mmol) and methanol (4 mL). Add potassium carbonate (0.5 g). After 18 hours, add a 1 M aqueous sodium hydroxide solution (1 mL) and extract with dichloromethane. Dry the organic layer over Na$_2$SO$_4$, filter, and concentrate in vacuo to give a residue. Chromatograph the residue on silica gel eluting with dichloromethane/methanol/concentrated aqueous ammonia 6/1/0.1 to give a residue. Combine the residue and dichloromethane (4 mL). Add a solution of hydrochloric acid in dioxane (0.12 mL, 4 M, 0.48 mmol). Warm to ambient temperature. After 1 hour, evaporate in vacuo to give a residue. Triturate with diethyl ether to give a solid. After 1 hour, collect the solid by filtration and dry to give the title compound.

EXAMPLE 50

1-(2-(4-Carboxypropyloxy)-5-(1H-tetrazol-1-yl)benzoyl)-3-(2-(4-(1-(2-ethoxyethyl)-1H-benzimidazol-2-yl)[1,4]diazepan-1-yl)ethyl)-3-phenylpyrrolidine

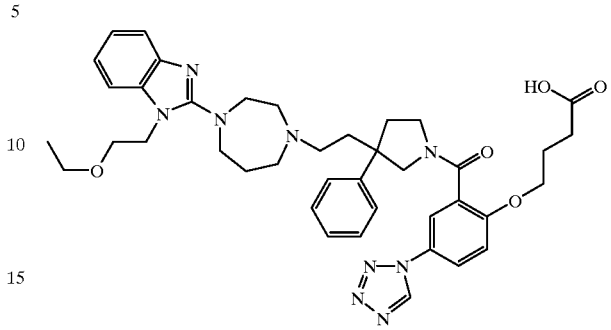

50.1 Synthesis of 1-(2-hydroxy-5-(1H-tetrazol-1-yl)benzoyl)-3-phenyl-3-(2-hydroxyethyl)pyrrolidine Combine 1-(2-methoxy-5-(1H-tetrazol-1-yl)benzoyl)-3-phenyl-3-(2-hydroxyethyl)pyrrolidine (prepared from (−)-3-phenyl-3-(2-hydroxyethyl)pyrrolidine (R,R)-di-p-anisoyltartaric acid salt) (2.0 g, 5.1 mmol) and anhydrous dichloromethane (100 mL). Cool in an ice bath. Add a solution of boron tribromide (17.8 mL, 1 M, 17.8 mmol) and stir. After 2 hours, pour the reaction mixture into ice-water and stir vigorously. After 18 hours, separate the layers and extract the organic layer with water. Saturate the aqueous layer with sodium chloride and extract with dichloromethane. Combine the organic layers, dry over Na$_2$SO$_4$, filter, and evaporate in vacuo to give a residue. Chromatograph the residue on silica gel eluting with 5% methanol/dichloromethane/0.5% concentrated aqueous ammonia to give a residue. combine the residue and toluene/methanol. Evaporate in vacuo to give a residue, dissolve in dichloromethane, filter, evaporate, combine with dichloromethane, again evaporate to remove residual toluene to give the title compound: mp; 86–96° C., R$_f$=0.37 (silica gel, 5% methanol/dichloromethane/0.5% concentrated aqueous ammonia).

50.2 Synthesis of 1-(2-(3-carboethoxypropyloxy)-5-(1H-tetrazol-1-yl)benzoyl)-3-phenyl-3-(2-hydroxyethyl)pyrrolidine Combine 1-(2-hydroxy-5-(1H-tetrazol-1-yl)benzoyl)-3-phenyl-3-(2-hydroxyethyl)pyrrolidine (0.19 g, 0.5 mmol) and dimethylformamide (5 mL). Add potassium carbonate (82 mg, 0.6 mmol) and 1-bromo-3-carboethoxypropane (0.21 mL, 0.29 g, 1.5 mmol). Heat at 100° C. After 2.5 hours, cool to ambient temperature. After 18 hours, dilute the reaction mixture with ethyl acetate, extract with water, aqueous 1 M hydrochloric acid solution, and then brine. Dry the organic layer over Na$_2$SO$_4$, filter, and evaporate in vacuo to give a residue. Chromatograph the residue on silica gel eluting with 5% methanol/dichloromethane/0.5% concentrated aqueous ammonia to give the title compound: R$_f$=0.28 (silica gel, 5% methanol/dichloromethane/0.5% concentrated aqueous ammonia).

50.3 Synthesis of 1-(2-(3-carboethoxypropyloxy)-5-(1H-tetrazol-1-yl)benzoyl)-3-phenyl-3-(2-methanesulfonyloxyethyl)pyrrolidine Combine 1-(2-(3-carboethoxypropyloxy)-5-(1H-tetrazol-1-yl)benzoyl)-3-phenyl-3-(2-hydroxyethyl)pyrrolidine (0.15 g, 0.3 mmol) and dichloromethane (5 mL). Cool in an ice bath. Add N,N,-diisopropylethylamine (0.12 mL, 86.5 mg, 0.67 mmol), and methanesulfonyl chloride (0.035 mL, 52 mg, 0.46 mmol). After 2 hours, dilute the reaction mixture with dichloromethane and extract with aqueous 1 M hydrochloric acid solution, water, and then a saturated aqueous solution of sodium bicarbonate. Dry the organic layer over Na$_2$SO$_4$, filter, and evaporate in vacuo to give the title compound: R$_f$=0.23 (silica gel, ethyl acetate).

50.4 Synthesis of 1-(2-(3-carboethoxypropyloxy)-5-(1H-tetrazol-1-yl)benzoyl)-3-(2-(4-(1-(2-ethoxyethyl)-1H-benzimidazol-2-yl)[1,4]diazepan-1-yl)ethyl)-3-phenylpyrrolidine Combine 1-(2-(3-carboethoxypropyloxy)-5-(1H-tetrazol-1-yl)benzoyl)-3-phenyl-3-(2-methanesulfonyloxyethyl)pyrrolidine (0.17 g, 0.3 mmol), N,N,-diisopropylethylamine (0.24 mL, 175 mg, 1.35 mmol), and 4-(1-(2-ethoxyethyl)-1H-benzimidazol-2-yl)[1,4]diazepane hydriodic acid salt (0.33 g, 0.6 mmol) in acetonitrile (5 mL). Heat to reflux. After 22 hours, cool the reaction mixture, dilute with ethyl acetate, extract with a saturated aqueous solution of sodium bicarbonate and then brine. Dry the organic layer over Na$_2$SO$_4$, filter, and evaporate in vacuo to give a residue. Chromatograph the residue on silica gel eluting sequentially with 10% methanol/dichloromethane/0.5% concentrated aqueous ammonia and then methanol to give, after drying, the title compound: R$_f$=0.10 (silica gel, 5% methanol/dichloromethane/0.5% concentrated aqueous ammonia/ethyl acetate).

50.5 Synthesis of 1-(2-(3-carboxypropyloxy)-5-(1H-tetrazol-1-yl)benzoyl)-3-(2-(4-(1-(2-ethoxyethyl)-1H-benzimidazol-2-yl)[1,4]diazepan-1-yl)ethyl)-3-phenylpyrrolidine lithium salt Combine 1-(2-1(3-carboethoxypropyloxy)-5-(1H-tetrazol-1-yl)benzoyl)-3-(2-(4-(1-(2-ethoxyethyl)-1H-benzimidazol-2-yl)[1,4]diazepan-1-yl)ethyl)-3-phenylpyrrolidine (0.185 g, 0.24 mmol) and lithium hydroxide hydrate (23 mg, 0.97 mmol) in tetrahydrofuran/water 3/1 (5 mL). After 2 hours, evaporate in vacuo to give a residue. Triturate the residue with dichloromethane. Evaporate the dichloromethane to give, after drying, the title compound.

50.6 Synthesis of 1-(2-(3-carboxypropyloxy)-5-(1H-tetrazol-1-yl)benzoyl)-3-(2-(4-(1-(2-ethoxyethyl)-1H-benzimidazol-2 -yl)[1,4]diazepan-1-yl)ethyl)-3-phenylpyrrolidine hydrochloric acid salt Combine 1-(2-(3-carboxypropyloxy)-5-(1H-tetrazol-1-yl)benzoyl)-3-(2-(4-(1-(2-ethoxyethyl)-1H-benzimidazol-2-yl)[1,4]diazepan-1-yl)ethyl)-3-phenylpyrrolidine lithium salt (0.18 g, 0.24 mmol) and dichloromethane (5 mL). Add a solution of hydrochloric acid in dioxane (0.18 mL, 4 M, 0.72 mmol). Add methanol (5 mL) and evaporate in vacuo to give a residue. Dissolve the residue in methanol (about 5 mL) and add 10% methanol/diethyl ether (90 mL) to form a solid. Decant the solvent and add diethyl ether (90 mL) and stir. After 30 minutes collect the solid by filtration and dry in vacuo at 110° C., to give the title compound: mp; 155–175° C.

PREPARATION 12.1
3-(2-(4-(1-(2-Ethoxyethyl)-1H-benzimidazol-2-yl)[1,4]diazepan-1-yl)ethyl)-3-phenylpyrrolidine Combine 3-phenyl-3-(2-hydroxyethyl)pyrrolidine (prepared by extraction from (−)-3-phenyl-3-(2-hydroxyethyl)pyrrolidine (R,R)-di-p-anisoyltartaric acid salt) (20 g, 32.8 mmol) and sodium bicarbonate (16.5 g, 197 mmol) in acetone/water (160 mL/80 mL). Add dropwise benzyl chloroformate (4.7 mL, 32.8 mmol). After 16 hours, evaporate the reaction mixture in vacuo to give a residue. Combine the residue and dichloromethane, extract with water and then brine, to give a residue. Dry the organic layer over MgSO$_4$, filter, and evaporate in vacuo to give residue. Chromatograph the residue on silica gel eluting with methanol/dichloromethane 1/7 containing 1% concentrated aqueous ammonia to give 1-carbobenzyloxy-3-phenyl-3-(2-hydroxyethyl)pyrrolidine.

Combine 1-carbobenzyloxy-3-phenyl-3-(2-hydroxyethyl) pyrrolidine (9.6 g, 29.6 mmol) and triethylamine (8.2 mL, 59.2 mmol) in dichloromethane (150 mL). Cool in an ice-bath. Add methanesulfonyl chloride (2.5 mL, 32.6 mmol). After 16 hours, dilute the reaction mixture with dichloromethane and extract with brine. Dry the organic layer over MgSO$_4$, filter, and evaporate in vacuo to give residue. Chromatograph the residue on silica gel eluting with methanol/dichloromethane 1/10 containing 1% concentrated aqueous ammonia to give 1-carbobenzyloxy-3-phenyl-3-(2-methanesulfonyloxyethyl)pyrrolidine.

Combine 1-carbobenzyloxy-3-phenyl-3-(2-methanesulfonyloxyethyl)pyrrolidine (10.2 g, 25.3 mmol), (1.34 g, 2.5 mmol), 4-(1-(2-ethoxyethyl)-1H-benzimidazol-2-yl)[1,4]diazepane hydriodic acid salt (16.5 g, 30.4 mmol), and N,N-diisopropylethylamine (18 mL, 101 mmol) in acetonitrile (300 mL). Heat to reflux. After 18 hours, evaporate in vacuo to give a residue. Chromatograph the residue on silica gel eluting with 1/6 containing 1% concentrated aqueous ammonia to give 1-carbobenzyloxy-3-(2-(4-(1-(2-ethoxyethyl)-1H-benzimidazol-2-yl)[1,4]diazepan-1-yl) ethyl)-3-phenylpyrrolidine.

Alternately, combine 1-carbobenzyloxy-3-phenyl-3-(2-methanesulfonyloxyethyl)pyrrolidine (5.7 g, 14.1 mmol), 4-(1-(2-ethoxyethyl)-1H-benzimidazol-2-yl)[1,4]diazepane hydriodic acid salt (7.52 g, 213.8 mmol), and N,N-diisopropylethylamine (9.6 mL, 55 mmol) in acetonitrile (200 mL). Heat to reflux. After 18 hours, evaporate in vacuo to give a residue. Combine the residue and dichloromethane. Extract twice with saturated aqueous sodium bicarbonate solution and then brine. Dry the organic layer over Na$_2$SO$_4$, filter, and evaporate in vacuo to give residue. Chromatograph the residue on silica gel eluting sequentially with ethyl acetate and then 5% methanol/dichloromethane to give 1-carbobenzyloxy-3-(2-(4-(1-(2-ethoxyethyl-1H-benzimidazol-2-yl) [1,4]diazepan-1-yl)ethyl)-3-phenylpyrrolidine: R$_f$=0.38 (silica gel, 5% methanol/dichloromethane).

Combine 1-carbobenzyloxy-3-(2-(4-(1-(2-ethoxyethyl)-1H-benzimidazol-2-yl)[1,4]diazepan-1-yl)ethyl)-3-phenylpyrrolidine 3.78 g, 6.35 mmol) and potassium hydroxide (1.07 g, 19.0 mmol) in isopropanol (150 mL). Heat to reflux. After 66 hours, cool the reaction mixture and evaporate in vacuo to give a residue. dilute the residue with dichloromethane (300 mL) and extract with brine. Dry the organic layer over Na$_2$SO$_4$, filter, and evaporate in vacuo to give residue. Chromatograph the residue on silica gel eluting sequentially with 10% methanol/dichloromethane/0.1% concentrated aqueous ammonia/methanol, and then 5% concentrated aqueous ammonia/methanol to give a residue. Combine the residue and dichloromethane, filter, extract with a saturated aqueous sodium bicarbonate solution, dry over Na$_2$SO$_4$, filter, and evaporate in vacuo to give 3-(2-(4-(1-(2-ethoxyethyl)-1H-benzimidazol-2-yl)[1,4]diazepan-1-yl)ethyl)-3-phenylpyrrolidine.

Alternately, combine 1-carbobenzyloxy-3-(2-(4-(1-(2-ethoxyethyl)-1H-benzimidazol-2-yl)[1,4]diazepan-1-yl) ethyl)-3-phenylpyrrolidine (1.23 g, 2.06 mmol) in ethanol (20 mL). Add 10% palladium-on-carbon (0.2 g) and palladium hydroxide (0.2 g). Hydrogenate on a pressure apparatus at 50 psi. After 72 hours, remove the catalyst by filtration, and evaporate in vacuo to give a residue. Combine the residue and dichloromethane (50 mL). Add a solution of hydrochloric acid an dioxane (1.01 mL, 4 M, 4.0 mmol) and stir. After 3 hours, add dither ether (180 mL) to give a solid. Collect the solid by filtration and dry to give 3-(2-(4-(1-(2-ethoxyethyl)-1H-benzimidazol-2-yl)[1,4]diazepan-1-yl)ethyl)-3-phenylpyrrolidine hydrochloric acid salt: mp; 117–126° C.

PREPARATION 12.2

3-(2-(4-(1-(2-Ethoxyethyl)-1H-benzimidazol-2-yl)[1,4]diazepan-1-yl)ethyl)-3-phenylpyrrolidine Combine (–)-3-phenyl-3-(2-hydroxyethyl)pyrrolidine (R,R)-di-p-anisoyltartaric acid salt (11.1 g, 18.3 mmol) and acetone/water (1/1, 200 mL). Cool to about 0° C. in an ice bath and add sodium bicarbonate (10.6 g, 217.6 mmol). Warm to ambient temperature and slowly add a solution of benzoyl chloride (4.2 g, 365 mmol) in acetone (10 mL). After 18 hours, filter and dilute the filtrate with ethyl acetate. Extract the diluted filtrate with a saturated aqueous sodium bicarbonate solution and then brine. Dry the organic layer over $Na_2SO_4$, filter, and evaporate in vacuo to give a residue. Chromatograph the residue on silica gel eluting with dichloromethane/methanol 95/5 to give 1-benzoyl-3-phenyl-3-(2-hydroxyethyl)pyrrolidine: $R_f$=0.81 (silica gel, dichloromethane/methanol 95/5).

Prepare 1-benzoyl-3-phenyl-3-(2-methanesulfonyloxyethyl)pyrrolidine by the method of Example 2.5.2 using 1-benzoyl-3-phenyl-3-(2-hydroxyethyl)pyrrolidine.

Prepare 1-benzoyl-3-(2-(4-(1-(2-ethoxyethyl)-1H-benzimidazol-2-yl)[1,4]diazepan-1-yl)ethyl)-3-phenylpyrrolidine by the method of Example 8.4 using 1-benzoyl-3-phenyl-3-(2-methanesulfonyloxyethyl) pyrrolidine.

Combine 1-benzoyl-3-phenyl-3-(2-methanesulfonyloxyethyl)pyrrolidine (7.22 g, 12.76 mmol) and ethylene glycol (200 mL). Add potassium hydroxide (5.13 g, 91.4 mmoL) and hydrazine hydrate (4.4 mL, 90.7 mmol). Heat to reflux. After 18 hours, dilute the reaction mixture with water and extract three times with dichloromethane. Combine the organic layers and extract with brine. Dry over $MgSO_4$, filter, and evaporate in vacuo to give a residue. Chromatograph the residue on silica gel eluting sequentially with methanol/dichloromethane/concentrated aqueous ammonia 50/50/0.5, methanol/dichloromethane/concentrated aqueous ammonia 75/25/0.75 and then methanol/concentrated aqueous ammonia 100/1.0. Combine the product containing fractions, evaporate in vacuo, combine with dichloromethane, and extract twice with water, dry over $MgSO_4$, filter, and evaporate in vacuo to give the title compound: $R_f$=0.38 (silica gel, methanol/dichloromethane/concentrated aqueous ammonia 10/90/0.1).

PREPARATION 12.3

3-(2-(4-(1-(2-Ethoxyethyl)-1H-benzimidazol-2-yl)[1,4]diazepan-1-yl)ethyl)-3-phenylpyrrolidine Combine 3-phenyl-3-(2-hydroxyethyl)pyrrolidine (prepared by extraction from (–)-3-phenyl-3-(2-hydroxyethyl)pyrrolidine (R,R)-di-p-anisoyltartaric acid salt) (20 g, 32.8 mmol) and sodium hydroxide (2.8 g, 70 mmol) in tetrahydrofuran/water (120 mL/120 mL). Add dropwise a solution of di-t-butyl dicarbonate (32.8 mmol) in tetrahydrofuran (60 mL). After 16 hours, evaporate the reaction mixture in vacuo to give a residue. Combine the residue and dichloromethane, extract with aqueous 1 M sodium hydroxide solution, water, and then brine. Dry the organic layer over $MgSO_4$, filter, and evaporate in vacuo to give 1-t-butoxycarbonyl-3-phenyl-3-(2-hydroxyethyl) pyrrolidine. $[\alpha]^{20}_D$=+55.4° (c=0.932, chloroform).

Prepare 1-t-butoxycarbonyl-3-phenyl-3-(2-methanesulfonyloxyethyl)pyrrolidine by the method of Preparation 12.1 using 1-t-butoxycarbonyl-3-phenyl-3-(2-hydroxyethyl)pyrrolidine.

Prepare 1-t—butoxycarbonyl-3-(2-(4-(1-(2-ethoxyethyl)-1H-benzimidazol-2-yl)[1,4]diazepan-1-yl)ethyl)-3-phenylpyrrolidine by the method of Preparation 12.1 using 1-t-butoxycarbonyl-3-phenyl-3-(2-methanesulfonyloxyethyl)pyrrolidine and 4-(1-(2-ethoxyethyl)-1H-benzimidazol-2-yl)[1,4]diazepane hydriodic acid salt to give 1-t-butoxycarbonyl-3-(2-(4-(1-(2-ethoxyethyl)-1H-benzimidazol-2-yl)[1,4]diazepan-1-yl)ethyl)-3-phenylpyrrolidine. $[\alpha]^{20}_D$=+14.2° (c=1.07, chloroform).

Combine 1-t-butoxycarbonyl-3-(2-(4-(1-(2ethoxyethyl)-1H-benzimidazol-2-yl)[1,4]diazepan-1-yl)ethyl)-3-phenylpyrrolidine (5.0 g) and dichloromethane (50 mL). Add a solution of hydrochloric acid in dioxane (10 mL, 4 M, 40 mmol). After 8 hours, evaporate in vacuo to give 3-(2-(4-(1-(2-ethoxyethyl)-1H-benzimidazol-2-yl)[1,4]diazepan-1-yl)ethyl)-3-phenylpyrrolidine hydrochloric acid salt.

PREPARATION 13

2-Methylthio-5-(1H-tetrazol-1-yl)benzoic acid

Combine 2-fluoro-5-nitrobenzoic acid (prepared by the method of Tetrahedron, 23, 4041–4045 (1967)) (3.7 g, 20 mmol) and sodium thiomethoxide (2.8 g, 40 mmol) in methanol (60 mL). Heat to reflux. After 24 hours, cool the reaction mixture, adjust the pH to about 2 using aqueous 1 M hydrochloric acid solution. Extract the reaction mixture with ethyl acetate. Dry the organic layer over $MgSO_4$, filter, and evaporate in vacuo to give 2-methylthio-5-nitrobenzoic acid: $R_f$=0.5 (silica gel, 10% methanol/dichloromethane).

Combine 2-methylthio-5-nitrobenzoic acid, (3.2 g, 15 mmol), N,N-diisopropylethylamine (17.0 mL, 100 mmol), and methyl iodide (12.45 mL, 200 mmol) in acetonitrile (50 mL). After 18 hours, dilute the reaction mixture with ethyl acetate, extract with brine, dry the organic layer over $MgSO_4$, filter, and evaporate in vacuo to give a residue. Chromatograph the residue on silica gel eluting with 20% ethyl acetate/hexane to give methyl 2-methylthio-5-nitrobenzoate. $R_f$==0.58 (silica gel, 30% ethyl acetate/hexane).

Combine methyl 2-methylthio-5-nitrobenzoate (2.9 g, 12.7 mmol) and glacial acetic acid (100 mL). Heat to 90° C. Add iron powder (5 g) and water (20 mL) over about 10 minutes. After 30 minutes, the reaction mixture was filtered while still hot and diluted with water (500 mL). Extract the reaction mixture with ethyl acetate. Dry the organic layer over $MgSO_4$, filter, and evaporate in vacuo to give a residue. Chromatograph the residue on silica gel eluting with 20% ethyl acetate/hexane to give methyl 2-methylthio-5-aminobenzoate. $R_f$=0.51 (silica gel, 30% ethyl acetate/hexane).

Combine methyl 2-methylthio-5-aminobenzoate (2.18 g, 11.1 mmol) and triethyl orthoformate (7.4 mL, 44.3 mmol) in glacial acetic acid (20 mL). After the formation of a yellow solid, add glacial acetic acid (40 mL). After 50 minutes, add sodium azide (2.9 g, 44.3 mmol). Heat to 70° C. After 2 hours, cool the reaction mixture to ambient temperature and stir. After 56 hours, cool in an ice bath and dilute with water (400 mL) to give a solid. After 1 hour, collect the solid by filtration, rinse with water, and dry to give methyl 2-methylthio-5-(1H-tetrazol-1-yl)benzoate: $R_f$=0.90 (silica gel, 10% methanol/ethyl acetate).

Combine methyl 2-methylthio-5-(1H-tetrazol-1-yl) benzoate (0.5 g, 2.0 mmol) and a 1 M aqueous solution of

EXAMPLE 51
1-(2-Methylthio-5-(1H-tetrazol-1-yl)benzoyl)-3-(2-(4-(1-(2-ethoxyethyl)-1H-benzimidazol-2-yl)[1,4]diazepan-1-yl)ethyl)-3-phenylpyrrolidine

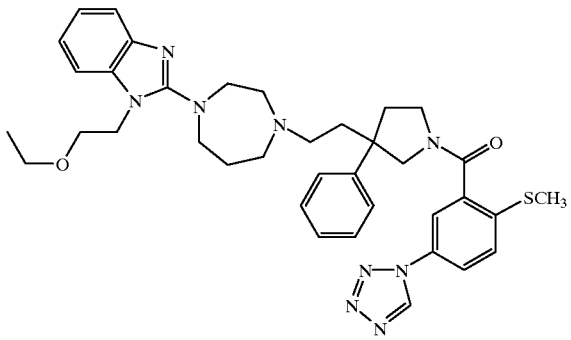

51.1 Synthesis of 1-(2-methylthio-5-(1H-tetrazol-1-yl)benzoyl)-3-(2-(4-(1-(2-ethoxyethyl)-1H-benzimidazol-2-yl)[1,4]diazepan-1-yl)ethyl)-3-phenylpyrrolidine Combine 3-(2-(4-(1-(2-ethoxyethyl)-1H-benzimidazol-2-yl)[1,4]diazepan-1-yl)ethyl)-3-phenylpyrrolidine hydrochloric acid salt (prepared from (−)-3-phenyl-3-(2-hydroxyethyl)pyrrolidine (R,R)-di-p-anisoyltartaric acid salt) (0.53 g, 1.0 mmol) and dichloromethane (10 mL). Add 2-methylthio-5-(1H-tetrazol-1-yl)benzoic acid (0.24 g, 1.0 mmol), 1-hydroxybenzotriazole hydrate (0.16 f, 1.2 mmol), N,N-diisopropylethylamine (0.34 mL, 2.0 mmol), and 1-ethyl-3-(3-dimethylaminopropyl)carbodiimide hydrochloride (0.23 g, 1.2 mmol). After 18 hours, dilute the reaction mixture with ethyl acetate and extract with brine. Dry the organic layer over Na$_2$SO$_4$, filter, and evaporate in vacuo to give a residue. Chromatograph the residue on silica gel eluting sequentially with ethyl acetate, 2% methanol/ethyl acetate, and the 8% methanol/ethyl acetate to give a residue. Combine the residue and dichloromethane, extract with brine, twice with a saturated aqueous solution of ammonium chloride, and then a saturated aqueous solution of sodium bicarbonate. Dry the organic layer over MgSO$_4$, filter, and evaporate in vacuo to give the title compound: R$_f$=0.34 (silica gel, 10% methanol/ethyl acetate).

51.2 Synthesis of 1-(2-methylthio-5-(1H-tetrazol-1-yl)benzoyl)-3-(2-(4-(1-(2-ethoxyethyl)-1H-benzimidazol-2-yl)[1,4]diazepan-1-yl)ethyl)-3-phenylpyrrolidine hydrochloric acid salt Combine 1-(2-methylthio-5-(1H-tetrazol-1-yl)benzoyl)-3-(2-(4-(1-(2-ethoxyethyl)-1H-benzimidazol-2-yl)[1,4] diazepan-1-yl)ethyl)-3-phenylpyrrolidine (0.35 g, 0.52 mmol) and dichloromethane (20 mL). Add a solution of hydrochloric acid in dioxane (0.26 mL, 4 M, 1.04 mmol). After 1 hour, evaporate in vacuo to give a residue. Combine the residue and diethyl ether (50 mL) and stir to give a solid. After 18 hours, collect the solid by filtration to give, after drying, the title compound.

PREPARATION 14
2-Methylsulfonyl-5-(1H-tetrazol-1-yl)benzoic acid

Combine 2-methylthio-5-(1H-tetrazol-1-yl)benzoic acid (0.68 g, 0.29 mmol), 30% hydrogen peroxide (3 ml.) and sodium hydroxide (20 mL, 20 mmol) in methanol (20 mL). After 2 hours, adjust the pH to about 2 using a 1 M aqueous hydrochloric acid solution and extract with ethyl acetate. Dry the organic layer over MgSO$_4$, filter, and concentrate in vacuo to give the title compound: R$_f$=0.70 (silica gel, 10% methanol/85% chloroform/5% acetic acid).

EXAMPLE 52
1-(2-Methylsulfonyl-5-(1H-tetrazol-1-yl)benzoyl)-3-(2-(4-(1-(2-ethoxyethyl)-1H-benzimidazol-2-yl)[1,4]diazepan-1-yl)ethyl)-3-phenylpyrrolidine

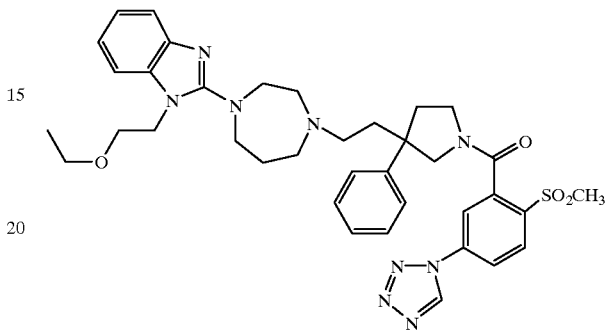

52.1 Synthesis of 1-(2-methylsulfonyl-5-(1H-tetrazol-1-yl)benzoyl)-3-(2-(4-(1-(2-ethoxyethyl)-1H-benzimidazol-2-yl)[1,4]diazepan-1-yl)ethyl)-3-phenylpyrrolidine Combine 3-(2-(4-(1-(2-ethoxyethyl)-1H-benzimidazol-2-yl)[1,4]diazepan-1-yl)ethyl)-3-phenylpyrrolidine hydrochloric acid salt(prepared from (−)-3-phenyl-3-(2-hydroxyethyl)pyrrolidine (R,R)-di-p-anisoyltartaric acid salt) (0.53 g, 1.0 mmol) and dichloromethane (10 mL). Add 2-methylsulfonyl-5-(1H-tetrazol-1-yl)benzoic acid (0.27 g, 1.0 mmol), 1-hydroxybenzotriazole hydrate (0.16 g, 1.2 mmol), N,N-diisopropylethylamine (0.34 mL, 2.0 mmol), and 1-ethyl-3-(3-dimethylaminopropyl)carbodiimide hydrochloride (0.23 g, 1.2mmol). After 18 hours, dilute the reaction mixture with ethyl acetate and extract with brine. Dry the organic layer over Na$_2$SO$_4$, filter, and evaporate in vacuo to give a residue. Chromatograph the residue on silica gel eluting sequentially with 2% methanol/ethyl acetate and then 5% methanol/ethyl acetate give the title compound: R$_f$=0.41 (silica gel, 10% methanol/ethyl acetate)

52.2 Synthesis of 1-(2-methylsulfonyl-5-(1H-tetrazol-1-yl)benzoyl)-3-(2-(4-(1-(2-ethoxyethyl)-1H-benzimidazol-2-yl)[1,4]diazepan-1-yl)ethyl)-3-phenylpyrrolidine hydrochloric acid salt Combine 1-(2-methylsulfonyl-5-(1H-tetrazol-1-yl)benzoyl)-3-(2-(4-(1-(2-ethoxyethyl)-1H-benzimidazol-2-yl)[1,4]diazepan-1-yl)ethyl)-3-phenylpyrrolidine (0.59 g, 0.83 mmol) and dichloromethane (20 mL). Add a solution of hydrochloric acid in dioxane (0.415 mL, 4 M, 1.66 mmol) and stir. After 1 hour, evaporate in vacuo to give a residue. Triturate the residue with diethyl ether and stir to give a solid. After 18 hours, collect the solid by filtration and dry to give the title compound.

PREPARATION 17
2-Methoxy-5-(5-trifluoromethyl-1H-tetrazol-1-yl)benzoic acid

Combine methyl 2-methoxy-5-aminobenzoate (1.8 g, 10 mmol) and pyridine (0.88 mL, 11 mmol) in tetrahydrofuran (10 mL). Cool in an ice bath. Add trifluoroacetic anhydride (1.56 mL, 11 mmol). Warm to ambient temperature. After 2 hours, add water and dilute the reaction mixture with ethyl acetate. Separate the organic layer, extract with brine, dry over MgSO₄, filter, and evaporate in vacuo to give methyl 2-methoxy-5-trifluoroacetylamidobenzoate.

Combine methyl 2-methoxy-5-trifluoroacetylamidobenzoate (3.1 g, 15 mmol), triphenylphosphine (5.2 g, 20 mmol) and carbon tetrachloride (30 mL) in tetrahydrofuran (30 mL). Heat to reflux. After 18 hours, add carbon tetrachloride (100 mL) and continue to heat at reflux. After 18 hours, evaporate in vacuo to give a residue. Chromatograph the residue on a short column of silica gel eluting with 30% ethyl acetate/hexane to give methyl 2-methoxy-5-(2-trifluoromethyl-2-chloroiminobenzoate.

Combine methyl 2-methoxy-5-(2-trifluoromethyl-N2chloroiminobenzoate (3.4 g, 12 mmol) and sodium azide (3.12 g, 48 mmol) in glacial acetic acid (60 mL). Heat to 70° C. After 3 hours, cool the reaction mixture in an ice bath, add water (800 mL), and stir to give a solid. After 1 hour, collect the solid by filtration and dry to give methyl 2-methoxy-5-(5-trifluormethyl-1H-tetrazol-1-yl)benzoate: $R_f$=0.58 (silica gel, 30% ethyl acetate/toluene).

Combine methyl 2-methoxy-5-(5-trifluormethyl-1H-tetrazol-1-yl)benzoate (1.46 g, 5.27 mmol) and an aqueous solution of sodium hydroxide (20 mL, 2 M, 40 mmol) in methanol/tetrahydrofuran (20 mL/10 mL). After 2 hours, adjust the pH of the reaction mixture to about 2 using a 1 M aqueous hydrochloric acid solution. Extract the reaction mixture with ethyl acetate and then dichloromethane. Dry the combined organic layers over MgSO₄, filter, and evaporate invacuo to give a the title compound: $R_f$=0.55 (silica gel, 85% chloroform/10% methanol/5% acetic acid)

EXAMPLE 54

1(2-Methoxy-5-(5-trifluoromethyl-1H-tetrazol-1-yl)benzoyl)-3-(2-(4-(1-(2-ethoxyethyl)-1H-benzimidazol-2-yl)[1,4]diazepan-1-yl)ethyl)-3-phenylpyrrolidine

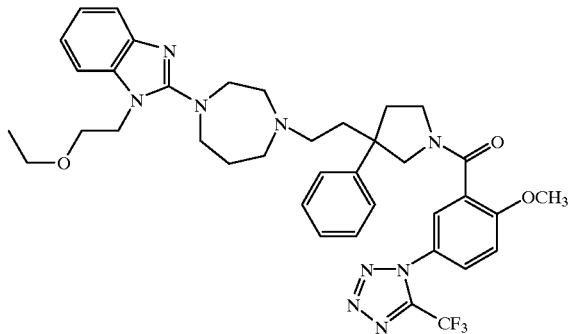

54.1 Synthesis of 1-(2-methoxy-5-(5-trifluoromethyl-1H-tetrazol-1-yl)benzoyl)-3-phenyl-3-(2-hydroxyethyl) pyrrolidine Prepare by the method of Example 51.1 using 3-(2-(4-(1-(2-ethoxyethyl)-1H-benzimidazol-2-yl)[1,4]diazepan-1-yl)ethyl)-3-phenylpyrrolidine hydrochloric acid salt (prepared from (−)-3-phenyl-3-(2-hydroxyethyl)pyrrolidine (R,R)-di-p-anisoyltartaric acid salt) and 2-methoxy-5-(5-trifluoromethyl-1H-tetrazol-1-yl)benzoic acid to give the title compound.

PREPARATION 18

2-Methoxy-5-(5-N,N-dimethylaminomethyl-1H-tetrazol-1-yl)benzoic acid

Combine methyl 2-methoxy-5-(1H-tetrazol-1-yl)benzoate (0.12 g, 0.5 mmol) and Eschenmoser's salt (N,N-dimethylmethyleneammonium iodide) (0.28 g, 1.5 mmol) in acetic acid (5 mL). Heat to reflux. After 8 hours, evaporate invacuo to give methyl 2-methoxy-5-(5-N,N-dimethylaminomethyl-1H-tetrazol-1-yl)benzoate: $R_f$=0.30 (silica gel, ethyl acetate)

EXAMPLE 55

1-(2-Methoxy-5-(5-N,N-dimethylaminomethyl-1H-tetrazol-1-yl)benzoyl)-3-(2-(4-(1-(2-ethoxyethyl)-1H-benzimidazol-2-yl)[1,4]diazepan-1-yl)ethyl)-3-phenylpyrrolidine

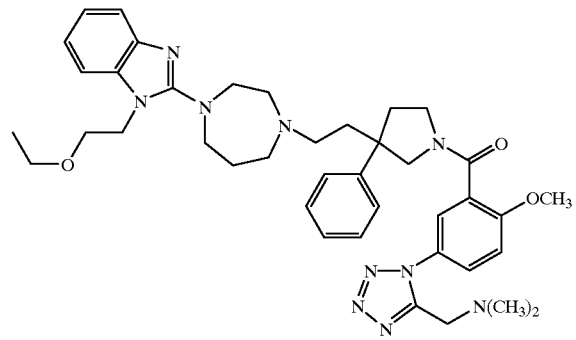

55.1 Synthesis of 1-(2-methoxy-5-(5-N,N-dimethylaminomethyl-1H-tetrazol)benzoyl)-3-(2-(4-(1-(2-ethoxyethyl)-1H-benzimidazol-2-yl)[1,4]diazepan-1-yl)ethyl)-3-phenylpyrrolidine Prepare by the method of Example 51.1 using 2-methoxy-5-(5-N,N-dimethylaminomethyl-1H-tetrazol-1-yl)benzoic acid and 3-(2-(4-(1-(2-ethoxyethyl)-1H-benzimidazol-2-yl)[1,4]diazepan-1-yl)ethyl)-3-phenylpyrrolidine hydrochloric acid salt (prepared from (−)-3-phenyl-3-(2 -hydroxyethyl)pyrrolidine (R,R)-di-p-anisoyltartaric acid salt) to give the title compound.

55.2 Synthesis of 1-(2-methoxy-5-(5-N,N-dimethylaminomethyl-1H-tetrazol)benzoyl)-3-(2-(4-(1-(2-ethoxyethyl)-1H-benzimidazol-2-yl)[1,4]diazepan-1-yl)ethyl)-3-phenylpyrrolidine hydrochloric acid salt Prepare by the method of Example 52.2 using 1-(2-methoxy-5-(5-N,N-dimethylaminomethyl-1H-tetrazol)benzoyl)-3-(2-(4-(1-(2-ethoxyethyl)-1H-benzimidazol-2-yl)[1,4]diazepan-1-yl)ethyl)-3-phenylpyrrolidine to give the title compound: $R_f$=0.40 (silica gel, 10% methanol/dichloromethane).

PREPARATION 19

2-Methylsulfinyl-5-(1H-tetrazol-1-yl)benzoic acid

Combine 2-methylthio-5-(1H-tetrazol-1-yl)benzoic acid (0.50 g, 2.0 mmol), pyridine (20 mL) and water (20 mL). Cool in an ice bath. Add phenyltrimethylammonium tribromide (0.75 g, 2 mmol) and tetrahydrofuran (20 mL). Warm to ambient temperature. After 1 hour, add a solution a of sodium bisulfite (1 g) in water (1 mL). Extract the reaction mixture with ethyl acetate and then dichloromethane. Combine the organic layers, dry over MgSO₄, filter, and evaporate in vacuo to give a residue. the title compound. Chromatograph the residue on silica gel eluting sequentially with ethyl acetate and then 10% methanol/ethyl acetate to give methyl 2-methylsulfinyl-5-(1H-tetrazol-1-yl)benzoate.

Combine methyl 2-methylsulfinyl-5-(1H-tetrazol-1-yl)benzoate (0.46 g, 1.73 mmol) and a 1 M aqueous solution of sodium hydroxide (30 mL, 30 mmol) in methanol (10 mL) and tetrahydrofuran (10 mL). After 1 hour, adjust the pH to about 2 using a 1 M aqueous hydrochloric acid solution and extract with ethyl acetate and then dichloromethane. Dry the combined organic layers over MgSO$_4$, filter, and concentrate in vacuo to give the title compound: R$_f$=0.15 (silica gel, 10% methanol/85% dichloromethane/5% acetic acid).

EXAMPLE 56

1-(2-Methylsulfinyl-5-(1H-tetrazol-1-yl)benzoyl)-3-(2-(4-(1-(2-ethoxyethyl)-1H-benzimidazol-2-yl)[1,4]diazepan-1-yl)ethyl)-3-phenylpyrrolidine

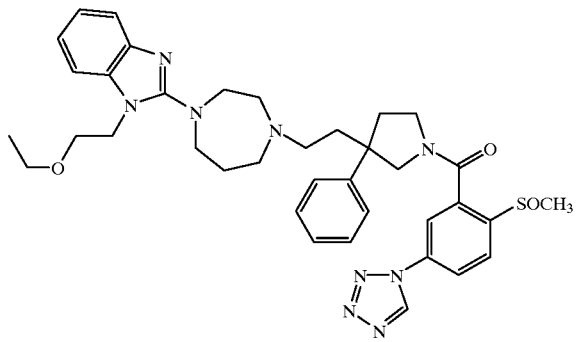

56.1 Synthesis of 1-(2-methylsulfinyl-5-(1H-tetrazol-1-yl)benzoyl)-3-(2-(4-(1-(2-ethoxyethyl)-1H-benzimidazol-2-yl)[1,4]diazepan-1-yl)ethyl)-3-phenylpyrrolidine Combine 3-(2-(4-(1-(2-ethoxyethyl)-1H-benzimidazol-2-yl)[1,4]diazepan-1-yl)ethyl)-3-phenylpyrrolidine hydrochloric acid salt (prepared from (−)-3-phenyl-3-(2-hydroxyethyl)pyrrolidine (R,R)-di-p-anisoyltartaric acid salt) (0.46 g, 1.0 mmol) and dichloromethane (20 mL). Add 2-methylsulfinyl-5-(1H-tetrazol-1-yl)benzoic acid (0.32 g, 1.3 mmol), 1-hydroxybenzotriazole hydrate (0.2 g, 1.5 mmol), 1-ethyl-3-(3-dimethylaminopropyl)carbodiimide hydrochloride (0.29 g, 1.5 mmol), and N,N-diisopropylethylamine (0.34 mL, 2 mmol). After 18 hours, dilute the reaction mixture with ethyl acetate and extract with brine, dry the organic layer over MgSO$_4$, filter, and concentrate invacuo to give a residue. Chromatograph the residue on silica gel eluting sequentially with ethyl acetate and then 10% methanol/ethyl acetate give the title compound.

56.2 Synthesis of 1-(2-methylsulfinyl-5-(1H-tetrazol-1-yl)benzoyl)-3-(2-(4-(1-(2-ethoxyethyl)-1H-benzimidazol-2-yl)[1,4]diazepan-1-yl)ethyl)-3-phenylpyrrolidine hydrochloric acid salt Prepare by the method of Example 52.2 using 1-(2-methylsulfinyl-5-(1H-tetrazol-1-yl)benzoyl)-3-(2-(4-(1-(2-ethoxyethyl)-1H-benzimidazol-2-yl)[1,4]diazepan-1-yl)ethyl)-3-phenylpyrrolidine (0.34 g, 0.49 mmol) to give the title compound.

PREPARATION 20

2-chloro-3,4,5-trimethoxybenzoic acid

Combine methyl 2-amino-3,4,5-trimethoxybenzoate (4.8 g, 20 mmol) and dichloromethane (20 mL). Cool in an ice bath. Add a solution of hydrochloric acid in dioxane (10 mL, 4 M, 40 mmol). Add polyethylene glycol 200 (20 mL) followed by sodium nitrite (2.76 g, 40 mmol). After 10 minutes add copper (I) chloride (3.96 g, 40 mmol). Warm to ambient temperature. After 18 hours, dilute the reaction mixture with ethyl acetate and extract with a 1 M aqueous solution of sodium hydroxide an then brine. Dry the organic layer over MgSO$_4$, filter, and evaporate in vacuo to give a residue. the title compound. Chromatograph the residue on silica gel eluting sequentially with hexane and then 5% ethyl acetate/hexane to give methyl 2-chloro-3,4,5-trimethoxybenzoate: R$_f$=0.7 (silica gel, 20% ethyl acetate/toluene).

Combine methyl 2-chloro-3,4,5-trimethoxybenzoate (2.0 g, 7.8 mmol) and a 1 M aqueous solution of sodium hydroxide (100 mL, 100 mmol) in methanol (50 mL). After 6 hours, adjust the pH to about 2 using a 1 M aqueous hydrochloric acid solution and extract with dichloromethane. Dry the combined organic layers over MgSO$_4$, filter, and concentrate in vacuo to give the title compound: R$_f$=0.81 (silica gel, 10% methanol/85% c.hloroform/5% acetic acid).

EXAMPLE 57

1-(2-chloro-3,4,5-trimethoxybenzoyl)-3-(2-(4-(1-(2-ethoxyethyl)-1H-benzimidazol-2-yl)[1,4]diazepan-1-yl)ethyl)-3-phenylpyrrolidine

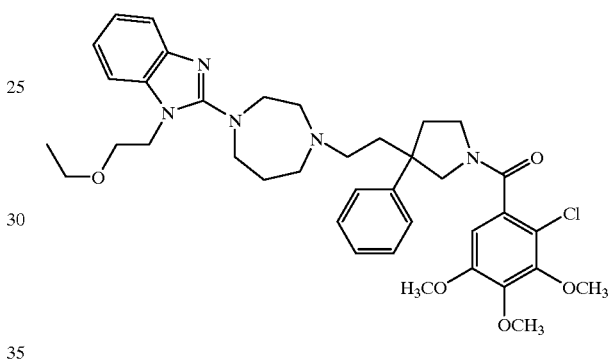

57.1 Synthesis of 1-(2-chloro-3,4,5-trimethoxybenzoyl)-3-(2-(4-(1-(2-ethoxyethyl)-1H-benzimidazol-2-yl)[1,4]diazepan-1-yl)ethyl)-3-phenylpyrrolidine Prepare by the method of Example 56.1 using 2-chloro-3,4,5-trimethoxybenzoic acid and 3-(2-(4-(1-(2-ethoxyethyl)-1H-benzimidazol-2-yl)[1,4]diazepan-1-yl)ethyl)-3-phenylpyrrolidine hydrochloric acid salt(prepared from (−)-3-phenyl-3-(2-hydroxyethyl)pyrrolidine (R,R)-di-p-anisoyltartaric acid salt) to give the title compound.

PREPARATION 21

2-Methoxy-5-methylthiobenzoic acid

According to the method of *J. Organometallic Chem.*, 132, 321 (1977), combine 4-methoxythioanisole (6.3 mL, 45.3 mmol) and tetrahydrofuran (90 mL). Cool in an ice bath. Add dropwise a solution of n-butyllithium (20 mL, 2.5 M, 50 mmol). After 2.5 hours, pour the reaction mixture onto freshly crushed dry-ice. Add diethyl ether and allow the dry-ice to dissipate. Dilute the reaction mixture with diethyl ether and water and 0.5 M aqueous sodium hydroxide solution (50 mL). Separate the layers and extract the aqueous layer with diethyl ether. Acidify the aqueous layer with a 12 M aqueous hydrochloric acid solution (about 9.0 mL). Extract the acidified aqueous layer three times with ethyl acetate. Combine the ethyl acetate extracts, extract with brine, dry over Na$_2$SO$_4$, filter, and evaporate in vacuo to give the title compound.

EXAMPLE 58
1-(2-Methoxy-5-methylthiobenzoyl)-3-(2-(4-(1-(2-ethoxyethyl)-1H-benzimidazol-2-yl)[1,4]diazepan-1-yl)ethyl)-3-phenylpyrrolidine

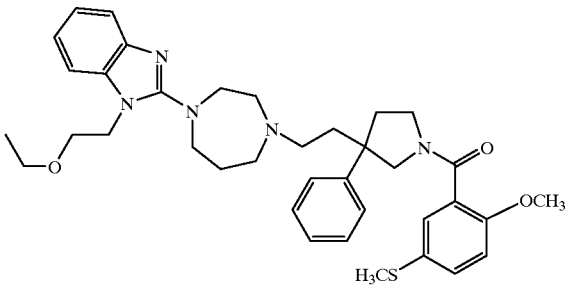

58.1 Synthesis of 1-(2-methoxy-5-methylthiobenzoyl)-3-(2-(4-(1-(2-ethoxyethyl)-1H-benzimidazol-2-yl)[1,4]diazepan-1-yl)ethyl)-3-phenylpyrrolidine Prepare by the method of Example 56.1 using 2-methoxy-5-methylthiobenzoic acid and 3-(2-(4-(1-(2-ethoxyethyl)-1H-benzimidazol-2-yl)[1,4]diazepan-1-yl)ethyl)-3-phenylpyrrolidine hydrochloric acid salt (prepared from (−)-3-phenyl-3-(2-hydroxyethyl)pyrrolidine (R,R)-di-p-anisoyltartaric acid salt) to give the title compound.

PREPARATION 22
2-Methoxy-5-methylsulfinylbenzoic acid

Combine 2-methoxy-5-methylthiobenzoic acid (6.82 g, 34.4 mmol) and methanol (65 mL). Cool in an ice bath. Add slowly dropwise thionyl chloride (2.8 mL, 38 mmol). Warm to ambient temperature. After 18 hours, evaporate in vacuo to give a residue. Chromatograph the residue on silica gel eluting with 25% hexane/dichloromethane to give methyl 2-methoxy-5-methylthiobenzoate: $R_f$=0.06 (silica gel, 65% hexane/dichloromethane).

Alternately, combine methyl 2-methoxy-5-aminobenzoate (1.0 g, 5.6 mmol) and 12 M aqueous hydrochloric acid solution (1.2 g and cool in an ice bath. Add a solution of sodium nitrite (0.37 g, 5.3 mmol) in water (3 mL). After 1.5 hours, add ethyl xanthic acid, sodium salt (0.76 g, 6.3 mmol) and sodium carbonate (0.67 g, 6.3 mmol). After 2 hours, evaporate in vacuo and add sodium sulfide (0.69 g, 2.7 mmol) and a 1 M aqueous sodium hydroxide solution (10 mL). After 4 hours, add dimethylsulfate and heat to reflux. After 24 hours, cool to ambient temperature, acidify with 12 M hydrochloric acid solution and extract with ethyl acetate. Separate the organic layer, extract with brine, dry over $Na_2SO_4$, filter, and evaporate in vacuo to give a residue. Chromatograph the residue on silica gel eluting with ethyl acetate/hexane 2/1 to give methyl 2-methoxy-5-methylthiobenzoate. Elemental Analysis calculated for $C_9H_{12}O_3S$: C, 54.53; H, 5.08. Found: C, 54.64; H, 4.95.

Combine methyl 2-methoxy-5-methylthiobenzoate (3.0 g, 14.1 mmol), pyridine (10 mL) and water (10 mL). Cool in an ice bath. Add portionwise phenyltrimethylammonium tribromide (5.84 g, 15.5 mmol). After 30 minutes, warm to ambient temperature. After 3 hour, add a solution of sodium bisulfite (1.6 g) in water (4 mL). After 10 minutes, add a 12 M aqueous hydrochloric acid solution (11 mL) and water. Extract the reaction mixture four times with dichloromethane. Combine the organic layers, extract with brine, dry over $Na_2SO_4$, filter, and evaporate in vacuo to give a residue. Chromatograph the residue on silica gel eluting with ethyl acetate to give methyl 2-methoxy-5-methylsulfinylbenzoate: mp; 64–66° C. Elemental Analysis calculated for $C_9H_{12}O_4S$: C, 52.62; H, 5.30. Found: C, 52.51; H, 5.:37.

Combine methyl 2-methoxy-5-methylsulfinylbenzoate (2.37 g, 12.0 mmol) and a 1 M aqueous solution of potassium hydroxide (13 mL, 13 mmol). Heat to reflux. After 2 hours, cool to ambient temperature and adjust the pH to about 2 using a 1 M aqueous hydrochloric acid (14.5 mL, 14.5 mmol). Evaporate in vacuo to give a solid. Combine the solid and dichloromethane and stir. Decant the solvent and add more dicliloromethane. Again decant and combine with the first decantate, dry over $Na_2SO_4$, filter, and evaporate in vacuo to to give the title compound: mp; 114–116° C.

EXAMPLE 59
1-(2-Methoxy-5-methylsulfinylbenzoyl)-3-(2-(4-(1-2-ethoxyethyl)-1H-benzimidazol-2-yl)[1,4]diazepan-1-yl)ethyl)-3-phenylpyrrolidine

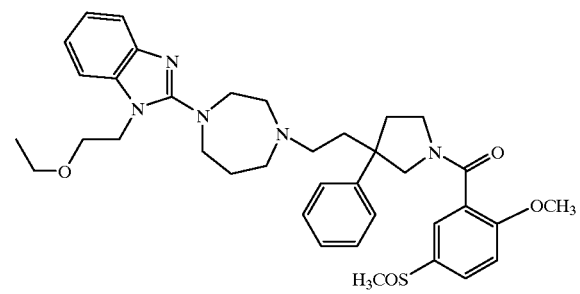

59.1 Synthesis of 1-(2-methoxy-5-methylsulfinylbenzoyl)-3-(2-(4-(1-(2-ethoxyethyl)-1H-benzimidazol-2-yl)([1,4]diazepan-1-yl)ethyl)-3-phenylpyrrolidine.

Prepare by the method of Example 56.1 using 2-methoxy-5-methylsulfinylbenzoic acid and 3-(2-(4-(1-(2-ethoxyethyl)-1H-benzimidazol-2-yl)[1,4]diazepan-1-yl)ethyl)-3-phenylpyrrolidine hydrochloric acid salt(prepared from (−)-3-phenyl-3-(2-hydroxyethyl)pyrrolidine (R,R)-di-p-anisoyltartaric acid salt) to give, after chromatography on silica gel eluting with 10% methanol/dichloromethane, the title compound.

59.2 Synthesis of 1-(2-methoxy-5-methylsulfinylbenzoyl)-3-(2-(4-(1-(2-ethoxyethyl)-1H-benzimidazol-2-yl)[1,4]diazepan-1-yl)ethyl)-3-phenylpyrrolidine hydrochloric acid salt Combine 1-(2-methoxy-5-methylsulfinylbenzoyl)-3-(2-(4-(1-(2-ethoxyethyl)-1H-benzimidazol-2-yl)[1,4]diazepan-1-yl)ethyl)-3-phenylpyrrolidine (0.57 g, 0.87 mmol) and methanol (13 mL). Add a solution of hydrochloric acid in dioxane (0.44 mL, 4 M, 1.76 mmol). After 18 hours, evaporate in vacuo to give a residue. Add methanol (2 mL) and then with vigorous stirring add diethyl ether to give a solid. Repeatedly, decant, add diethyl ether, and stir. Collect the solid and dry to give the title compound.

PREPARATION 23
2-Methoxy-5-methylsulfonylbenzoic acid

Combine methyl 2-methoxy-5-methylthiobenzoate (1.30 g, 6.1 mmol) and dichloromethane (50 mL). Cool in an ice bath. Add m-chloroperbenzoic acid (5.28 g, 50%, 1.53 mmol). After 10 minutes, warm to ambient temperature. After 18 hour, dilute the reaction mixture with dichloromethane. Extract with a saturated aqueous solution of sodium bicarbonate and then brine. Dry the combined organic layers over $MgSO_4$, filter, and concentrate in vacuo to give a residue. Chromatograph the residue on silica gel eluting with 5% ethyl acetate/dichloromethane to give a residue. Combine the residue and dichloromethane, extract with a saturated aqueous solution of sodium bicarbonate and then brine, dry over MgSO$_4$, filter, and concentrate in vacuo to give a residue. Crystallize the residue from ethyl acetate/hexane to give methyl 2-methoxy-5-methylsulfonylbenzoate: mp; 113–115° C.

Combine methyl 2-methoxy-5-methylsulfonylbenzoate (2.24 g, 9.2 mmol) and a 1 M aqueous potassium hydroxide solution (10 mL, 10 mmol). Heat to reflux. After 2 hours, filter while still hot, cool in an ice bath, and acidify by dropwise addition of a 1 M aqueous hydrochloric acid solution (11 mL) to give a solid. Collect the solid by filtration, rinse with water, and dry to give the title compound: mp; 189–191° C. Elemental Analysis Calculated for $C_9H_{10}SO_5$: C, 46.95; H, 4.38. Found: C, 46.76; H, 4.40.

EXAMPLE 60

1-(2-Methoxy-5-methylsulfonylbenzoyl)-3-(2-(4-(1-(2-ethoxyethyl)-1H-benzimidazol-2-yl)[1,4]diazepan-1-yl) ethyl)-3-phenylpyrrolidine

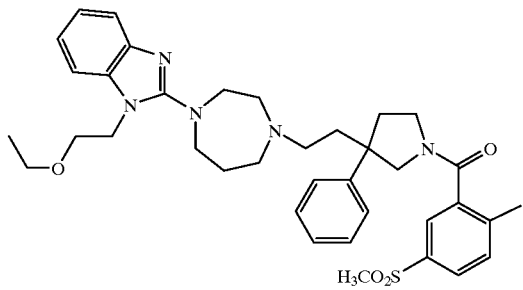

60.1 Synthesis of 1-(2-methoxy-5-methylsulfonylbenzoyl)-3-(2-(4-(1-(2-ethoxyethyl)-1H-benzimidazol-2-yl)[1,4] diazepan-1-yl)ethyl)-3-phenylpyrrolidine Prepare by the method of Example 56.1 using 2-methoxy-5-methylsulfonylbenzoic acid and 3-(2-(4-(1-(2-ethoxyethyl)-1H-benzimidazol-2-yl)[1,4]diazepan-1-yl) ethyl)-3-phenylpyrrolidine hydrochloric acid salt (prepared from (−)-3-phenyl-3-(2-hydroxyethyl)pyrrolidine (R,R)-di-p-anisoyltartaric acid salt) to give the title compound: $R_f$=0.31L (silica gel, 5% methanol/dichloromethane).

60.2 Synthesis of 1-(2-methoxy-5-methylsulfonylbenzoyl)-3-(2-(4-(1-(2-ethoxyethyl)-1H-benzimidazol-2-yl)[1,4] diazepan-1-yl)ethyl)-3-phenylpyrrolidine hydrochloric acid salt Combine 1-(2-methoxy-5-methylsulfonylbenzoyl)-3-(2-(4-(1-(2-ethoxyethyl)-1H-benzimidazol-2-yl)[1,4]diazepan-1-yl)ethyl)-3-phenylpyrrolidine (0.45 g, 0.66 mmol) and methanol (10 mL). Add a solution of hydrochloric acid in dioxane (0.34 mL, 4 M, 1.36 mmol). After 18 hours, evaporate in vacuo to give a residue. Add methanol (2 mL) and then with vigorous stirring add diethyl ether to give a solid. Decant, collect the solid, and dry to give the title compound.

PREPAPATION 24

3-Methoxy-4,5-methylenedioxybenzoic acid

Combine methyl 3-methoxy-4,5-dihydroxybenzoate (0.93 g, 4.6 mmol) and potassium carbonate (3.2 g, 23.4 mmol) in acetone (25 mL) and dimethylformamide (25 mL). Add diiodomethane (6.3 g, 23.3 mmol). Heat to reflux. After 24 hours, cool in an ice bath, acidify with a 1 M aqueous hydrochloric acid solution (35 mL), and extract twice with ethyl acetate. Combine the organic layers and extract with brine. Dry over MgSO$_4$, filter, and concentrate in vacuo to give methyl 3-methoxy-4,5-methylenedioxybenzoate.

Combine methyl 3-methoxy-4,5-methylenedioxybenzoate (0.84 g, 4.0 mmol) and tetrahydrofuran (25 mL). Add a 1 M aqueous solution of lithium hydroxide (8.0 mL, 8.0 mmol). Heat to reflux. After 4 hours, cool the reaction, concentrate in vacuo to remove most of the tetrahydrofuran. Extract with ethyl acetate. Cool in a ice bath and acidify the aqueous layer with a 6 M aqueous hydrochloric acid solution to give a solid. collect the solid by filtration and dry to give the title compound.

EXAMPLE 61

1-(3-Methoxy-4,5-methylenedioxybenzoyl-3(2-(4-(1-(2-ethoxyethyl)-1H-benzimidazol-2-yl)[1,4]diazepan-1-yl) ethyl)-3-phenylpyrrolidine

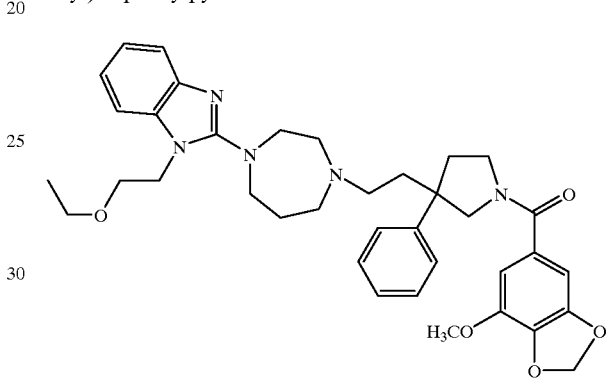

61.1 Synthesis of 1-(3-methoxy-4,5-methylenedioxybenzoyl)-3-(2-(4-(1-(2-ethoxyethyl)-1H-benzimidazol-2-yl)[1,4]diazepan-1-yl)ethyl)-3-phenylpyrrolidine Prepare by the method of Example 56.1 using 3-methoxy-4,5-methylenedioxybenzoic acid and 3-(2-(4-(1-(2-ethoxyethyl)-1H-benzimidazol-2-yl)[1,4]diazepan-1-yl) ethyl)-3-phenylpyrrolidine hydrochloric acid salt(prepared from (−)-3-phenyl-3-(2-hydroxyethyl)pyrrolidine (R,R)-di-p-anisoyltartaric acid salt) to give the title compound.

PREPARATION 25

3-Methoxy-4,5-ethylenedioxybenzoic acid

Combine methyl 3-methoxy-4,5-dihydroxybenzoate (0.5 g, 2.5 mmol) and potassium carbonate (1.74 g, 12.65mmol) in acetone (25 mL). Add dibromoethane (2.37 g, 12.65mmol). Heat to reflux. After 24 hours, cool in an ice bath, acidify with a 1 M aqueous hydrochloric acid solution (35 mL), add water (25 mL), and extract three times with ethyl acetate. Combine the organic layers and extract with brine. Dry over MgSO$_4$, filter, and concentrate in vacuo to give methyl 3-methoxy-4,5-ethylenedioxybenzoate.

Combine methyl 3-methoxy-4,5-ethylenedioxybenzoate (0.46 g, 2.0 mmol) and tetrahydrofuran (15 mL). Add a 1 M aqueous solution of lithium hydroxide (2.5 mL, 2.5 mmol). Heat to reflux. After 15 hours, cool the reaction, concentrate in vacuo to remove most of the tetrahydrofuran. Cool in a ice bath and acidify with a 1 M aqueous hydrochloric acid solution to give a solid. Collect the solid by filtration and dry to give the title compound.

EXAMPLE 62
1-(3-Methoxy-4,5-ethylenedioxybenzoyl)-3-(2-(4-(1(2-ethoxyethyl)-1H-benzimidazol-2-yl)[1,4]diazepan-1-yl)ethyl)-3-phenylpyrrolidine

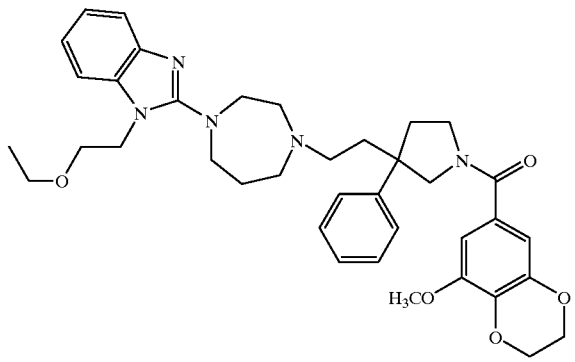

62.1 Synthesis of 1-(3-methoxy-4,5-ethylenedioxybenzoyl)-3-(2-(4-(1-(2-ethoxyethyl)-1H-benzimidazol-2-yl)[1,4]diazepan-1-yl)ethyl)-3-phenylpyrrolidine Prepare by the method of Example 56.1 using 3-methoxy-4,5-ethylenedioxybenzoic acid and 3-(2-(4-(1-(2-ethoxyethyl)-1H-benzimidazol-2-yl)[1,4]diazepan-1-yl)ethyl)-3-phenylpyrrolidine hydrochloric acid salt(prepared from (−)-3-phenyl-3-(2-hydroxyethyl)pyrrolidine (R,R)-di-p-anisoyltartaric acid salt) to give the title compound.

EXAMPLE 63
1-Benzoyl-3-2-(4-(1-(2-ethoxyethyl)-1H-benzimidazol-2-yl)[1,4]diazepan-1-yl)ethyl)-3-phenylpyrrolidine

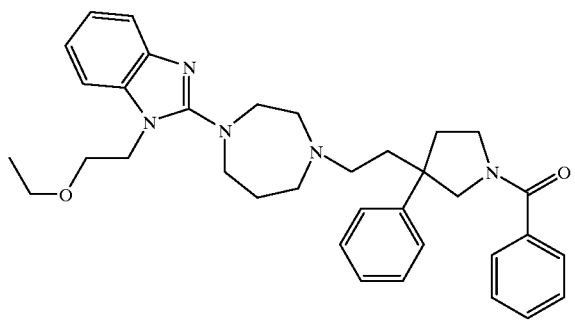

63.1.1 Synthesis of 1-benzoyl-3-phenyl-3-(2-hydroxyethyl)pyrrolidine

Combine (−)-3-phenyl-3-(2-hydroxyethyl)pyrrolidine (R,R)-di-p-anisoyltartaric acid salt (11.1 g, 18.3 mmol) and acetone/water (1/1, 200 mL). Cool to about 0° C. in an ice bath and acid sodium bicarbonate (10.6 g, 217.6 mmol). Warm to ambient temperature and slowly add a solution of benzoyl chloride (4.2 g, 365 mmol) in acetone (10 mL). After 18 hours, filter and dilute the filtrate with ethyl acetate. Extract the diluted filtrate with a saturated aqueous sodium bicarbonate solution and then brine. Dry the organic layer over $Na_2SO_4$, filter, and evaporate in vacuo to give a residue. Chromatograph the residue on silica gel eluting with dichloromethane/methanol 95/5 to give the title compound: $R_f$=0.81 (silica gel, dichloromethane/methanol 95/5).

63.1.2 Synthesis of 1-benzoyl-3-phenyl-3-(2-hydroxyethyl)pyrrolidine

Combine (−)-3-phenyl-3-(2-hydroxyethyl)pyrrolidine (R,R)-di-p-anisoyltartaric acid salt (40 g, 65.6 mmol) and sodium bicarbonate (33 g, 394 mmol) in tetrahydrofuran/water (200 mL/200 mL). With vigorous stirring, add benzoyl chloride (8.4 g, 72.7 mmol). After 3 hours, partition between ethyl acetate and water. Separate the layers and extract the aqueous layer with ethyl acetate. Combine the organic layers and extract with water and then brine. Dry the organic layer over $Na_2SO_4$, filter, and evaporate in vacuo to give a residue. Chromatograph the residue on silica gel eluting sequentially with dichloromethane and then dichloromethane/methanol 95/5 to give the title compound.

63.2 Synthesis of 1-benzoyl-3-phenyl-3-(2-methanesulfonyloxy ethyl)pyrrolidine Prepare by the method of Example 2.5.2 using 1-benzoyl-3-phenyl-3-(2-hydroxyethyl)pyrrolidine to give the title compound: $R_f$=0.34 (silica gel, ethyl acetate).

63.3 Synthesis of 1-benzoyl-3-(2-(4-(1-(2-ethoxyethyl)-1H-benzimidazol-2-yl)[1,4]diazepan-1-yl)ethyl)-3-phenylpyrrolidine Prepare by the method of Example 8.4 using 1-benzoyl-3-phenyl-3-(2-methanesulfonyloxyethyl)pyrrolidine to give the title compound.

PREPARATION 26
2-Methoxy-5-(1H-tetrazol-1-ylmethyl)benzoyl chloride

Combine 5-formylsalicylic acid (5.0 g, 30.1 mmol), potassium carbonate (16.6 g, 120.4 mmol), and methyl iodide (34.06 g, 240 mmol) in acetone (20 mL). Heat to reflux. After 12 hours, cool and extract five times with ethyl acetate. Combine the organic layers and extract with brine. Dry over $MgSO_4$, filter, and concentrate in vacuo to give a residue. Chromatograph the residue on silica gel eluting with ethyl acetate/hexane 1/1 to give methyl 2-methoxy-5-formylbenzoate: $R_f$=0.44 (silica gel, 1/1 ethyl acetate/hexane).

Combine methyl 2-methoxy-5-formylbenzoate (0.1 g, 0.5 mmol) and tetrahydrofuran (2 mL). Cool in an ice bath. Add a solution of borane tetrahydrofuran complex (0.17 mL, 1 M in tetrahydrofuran, 0.17 mmol). After 1.5 hours, again add a solution of borane tetrahydrofuran complex (0.17 mL, 1 M in tetrahydrofuran, 0.17 mmol). After 2 hours, add a 1 M aqueous solution of hydrochloric acid (2 mL) and stir. After 15 minutes, dilute the reaction mixture with ethyl acetate. Separates the layers, extract the aqueous layer three times with ethyl acetate and combine the organic layers. Dry the organic layer over $Na_2SO_4$, filter, and evaporate in vacuo to give methyl 2-methoxy-5-hydroxymethylbenzoate: $R_f$=0.32 (silica gel, ethyl acetate).

Combine methyl 2-methoxy-5-hydroxymethylbenzoate (1.34 g, 6.8 mmol) and N,N-diisopropylethylamine (1.4 mL) in dichloromethane (25 mL). Cool in a ice-bath. Add dropwise, methanesulfonyl chloride (0.56 mL). After 30 minutes, warm to ambient temperature. After 2 hours, dilute with dichloromethane and extract with 1 M hydrochloric acid solution and 5% sodium bicarbonate solution. Dry the organic layer over $Na_2SO_4$, filter, and concentrate in vacuo to give methyl 2-methoxy-5-chloromethylbenzoate: $R_f$=0.64 (silica gel, 1/1 ethyl acetate/hexane).

Combine tetrazole (0.45 g, 6.42 mmol) and dimethylformamide (6 mL). Cool in an ice bath and add sodium hydride (0.26 g, 60% i oil, 6.5 mmol). After 30 minutes, warm to ambient temperature. Add a solution of methyl 2-methoxy-5-chloromethylbenzoate (1.13 g, 4.12 mmol) in dimethylformamide (10 mL). Heat to 75° C. After 5.5 hours, partition the reaction mixture between water and ethyl acetate. Extract the organic layer with water, dry over $Na_2SO_4$, filter, and concentrate in vacuo to give a residue. Chromatograph the residue on silica gel eluting with 7/3 hexane/ethyl acetate to give methyl 2-methoxy-5-(1H-tetrazol-1-ylmethyl)benzoate: $R_f$=0.67 (silica gel, ethyl acetate).

Combine methyl 2-methoxy-5-(1H-tetrazol-1-ylmethyl) benzoate (0.45 g, 1.73 mmol) and methanol/tetrahydrofuran (1/1, 10 mL). Add a 1 M aqueous solution of lithium hydroxide (5.8 mL, 5.8 mmol). After 4 hours, partition the reaction mixture between water and ethyl acetate. Acidify the aqueous with a 10% aqueous citric acid solution, extract four times with ethyl acetate, combine the ethyl acetate layers, dry the organic layer over $Na_2SO_4$, filter, and evaporate in vacuo to give 2-methoxy-5-(1H-tetrazol-1-ylmethyl) benzoic acid: $R_f$=0.60 (silica gel, 1/1 methanol/dichloromethane).

Combine 2-methoxy-5-(1H-tetrazol-1-ylmethyl)benzoic acid (0.35 g, 1.5 mmol) and dichloromethane (25 mL). Add dropwise oxalyl chloride (0.21 mL, 2.35 mmol) followed by dimethylformamide (5 drops). After 4 hours, evaporate in vacuo and dry to give the title compound.

EXAMPLE 64
1-(2-Methoxy-5-(1H-tetrazol-1-ylmethyl)benzoyl)-3-(2-(4-(1-(2-ethoxthetyl)-1H-benzimidazol-2-yl)[1,4]diazepan-1-yl)ethyl)-3-phenylpyrrolidine

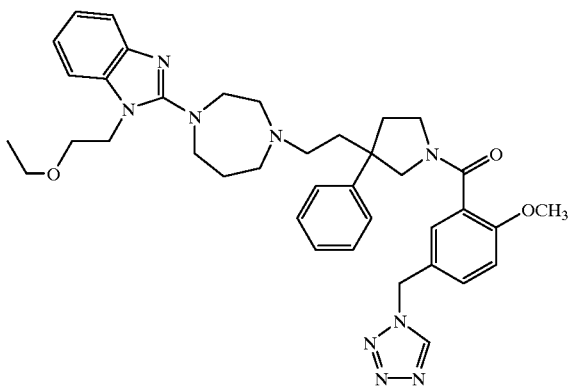

64.1 Synthesis of 1-(2-methoxy-5-(1H-tetrazol-1-ylmethyl) benzoyl)-3-(2-(4-(1-(2-ethoxyethyl-1H-benzimidazol-2-yl) [1,4]diazepan-1-yl)ethyl)-3-phenylpyrrolidine Combine 3-(2-(4-(1-(2-ethoxyethyl)-1H-benzimidazol-2-yl)[1,4]diazepan-1-yl)ethyl)-3-phenylpyrrolidine (prepared from (−)-3-phenyl-3-(2-hydroxyethyl)pyrrolidine (R,R)-di-p-anisoyltartaric acid salt) (0.69 g, 1.49 mmol) and sodium bicarbonate (0.93 g, 11.07 mmol) in acetone/water (1/1, 40 mL). Cool in an ice bath. Add a solution of 2-methoxy-5-(1H-tetrazol-1-ylmethyl)benzoyl chloride (0.38 g, 1.49 mmol) in acetone (25 mL). After 18 hours, dilute the reaction mixture with ethyl acetate and extract twice with a saturated aqueous sodium bicarbonate solution and then brine. Dry the organic layer over $Na_2SO_4$, filter, and concentrate invacuo to give a residue. Chromatograph the residue on silica gel eluting with ethyl acetate and then methanol/dichloromethane/concentrated aqueous ammonia 10/90/0.1 give the title compound: $R_f$=0.82 (silica gel, methanol/dichloromethane/concentrated aqueous ammonia 10/90/0.1).

64.2 Synthesis of 1-(2-methoxy-5-(1H-tetrazol-1-ylmethyl) benzoyl)-3-(2-(4-(1-(2-ethoxyethyl)-1H-benzimidazol-2-yl) [1,4]diazepan-1-yl)ethyl)-3-phenylpyrrolidine hydrochloric acid salt Combine 1-(2-methoxy-5-(1H-tetrazol-1Hylmethyl) benzoyl)-3-(2-(4-(1-(2-ethoxyethyl)-1H-benzimidazol-2-yl) [1,4]diazepan-1-yl)ethyl)-3-phenylpyrrolidine (0.35 g, 0.52 mmol) and dichloromethane (10 mL). Cool in an ice bath and add a solution of hydrochloric acid in dioxane (0.26 mL, 4 M, 1.04 mmol). After 15 minutes, evaporate in vacuo to give the title compound.

PREPARATION 27
2-Methoxy-5-(1H-triazol-1-ylmethyl)benzoyl chloride

Combine triazole (0.72 g, 10.4 mmol) and dimethylformamide (6 mL). Cool in an ice bath and add sodium hydride (0.42 g, 60% i oil, 10.4 mmol). After 30 minutes, warm to ambient temperature. Add a solution of methyl 2-methoxy-5-chloromethylbenzoate (1.85 g, 6.74 mmol) in dimethylformamide (6 mL). Heat to 75° C. After 3 hours, partition the reaction mixture between water and ethyl acetate. Extract the organic layer with water, dry over $Na_2SO_4$, filter, and concentrate in vacuo to give a residue. Chromatograph the residue on silica gel eluting with 95/5 dichloromethane/methanol containing 0.5% concentrated aqueous ammonia to give methyl 2-methoxy-5-(1H-triazol-1-ylmethyl) benzoate: $R_f$=0.1 (silica gel, 1/1 hexane/ethyl acetate).

Combine methyl 2-methoxy-5-(1H-triazol-1-ylmethyl) benzoate (1.14 g, 4.61 mmol) and methanol/tetrahydrofuran (1/1, 30 mL). Add a 1 M aqueous solution of lithium hydroxide (15 mL, 15 mmol). After 4 hours, acidify the reaction mixture with a 10% aqueous citric acid solution, add water, and extract twice with ethyl acetate. Combine the organic layers, dry over $Na_2SO_4$, filter, and evaporate in vacuo to give 2-methoxy-5-(1H-triazol-1-ylmethyl)benzoic acid: $R_f$=0.09 (silica gel, ethyl acetate).

Combine 2-methoxy-5-(1H-triazol-1-ylmethyl)benzoic acid (0.22 g, 0.94 mmol) and dichloromethane (50 mL). Add dropwise oxalyl chloride (0.14 mL, 1.6 mmol) followed by dimethylformamide (5 drops). After 4 hours, evaporate in vacuo and dry to give the title compound.

EXAMPLE 65
1-(2-Methoxy-5-(1H-triazol-1-ylmethyl)benzoyl)-3-(2-(4-(1-(2-ethoxyethyl)-1H-benzimidazol-2-yl)[1,4]diazepan-1-yl)ethyl)-3-phenylpyrrolidine

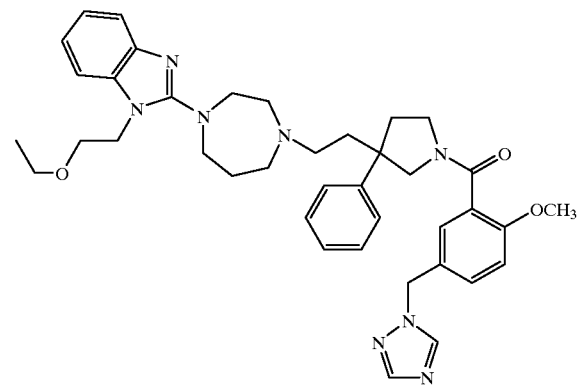

65.1 Synthesis of 1-(2-methoxy-5-(1H-triazol-1-ylmethyl) benzoyl)-3--(2-(4-(1-(2-ethoxyethyl)-1H-benzimidazol-2-yl)[1,4]diazepan-1-yl)ethyl)-3-phenylpyrrolidine Combine 3-(2-(4-(1-(2-ethoxyethyl)-1H-benzimidazol-2-yl)[1,4]diazepan-1-yl)ethyl)-3-phenylpyrrolidine (0.48 g, 1.04 mmol), N,N-diisopropylethylamine (0.35 mL), and 2-methoxy-5-(1H-triazol-1-ylmethyl)benzoyl chloride (0.22 g, 0.94 mmol) in tetrahydrofuran (50 mL). After 18 hours, dilute the reaction mixture with ethyl acetate and extract with a saturated aqueous sodium bicarbonate solution and then brine. Dry the organic layer over Na$_2$SO$_4$, filter, and concentrate in vacuo to give a residue. Chromatograph the residue on silica gel eluting with methanol/dichloromethane/concentrated aqueous ammonia 10/90/0.5 give the title compound: R$_f$=0.68 (silica gel, methanol/dichloromethane/concentrated aqueous ammonia 10/90/0.1).

65.2 Synthesis of 1-(2-methoxy-5-(1H-triazol-1-ylmethyl) benzoyl)-3-(2-(4-(1-(2-ethoxyethyl)-1H-benzimidazol-2-yl) [1,4]diazepan-1-yl)ethyl)-3-phenylpyrrolidine hydrochloric acid salt Prepare by the method of Example 64.2 using 1-(2-methoxy-5-(1H-triazol-1-ylmethyl)benzoyl)-3-(2-(4-(1-(2-ethoxyethyl)-1H-benzimidazol-2-yl)[1,4]diazepan-1-yl) ethyl)-3-phenylpyrrolidine (0.28 g, 0.49 mmol) to give the title compound.

PREPARATION 28

4-(1-(2-(1H-Imidazol-1-yl)ethyl)-1H-benzimidazol-2-yl)[1,4]diazepane Hydriodic acid salt Combine 1-(t-butoxycarbonyl)-4-(1-(2-hydroxyethyl)-1H-benzimidazol-2-yl)[1,4]diazepane (1.0 g, 2.77 mmol), N,N-diisopropylethylamine (0.79 g, 6.1 mmol), and dichloromethane (10 mL). Cool in an ice bath. Add dropwise methanesulfonyl chloride (0.41 g, 3.6 mmol). After 1 hour, warm to ambient temperature and dilute the reaction mixture with dichloromethane. Extract with a 1 M aqueous hydrochloric acid solution and three times with saturated aqueous sodium bicarbonate solution. Dry the organic layer over Na$_2$SO$_4$, filter, and concentrate in vacuo to give 1-(t-butoxycarbonyl)-4-(1-(2-methanesulfonyloxyethyl)-1H-benzimidazol-2-yl)[1,4]diazepane: R$_f$=0.58 (silica gel, ethyl acetate).

Combine imidazole (0.08 g, 1.2 mmol) and dimethylformamide (2 mL). Cool in an ice bath and add sodium hydride (0.04 g, 60% i oil, 1.2 mmol). After 30 minutes, warm to ambient temperature. Add a solution of 1-(t-butoxycarbonyl)-4-(1-(2-methanesulfonyloxyethyl)-1H-benzimidazol-2-yl)[1,4]diazepane (0.35 g, 0.80 mmol) in dimethylformamide (2 mL). Heat to 75° C. After 12 hours, partition the reaction mixture between water and dichloromethane. Extract the organic layer twice with water, dry over Na$_2$SO$_4$, filter, and concentrate in vacuo to give a residue. Chromatograph the residue on silica gel eluting with 5% methanol/dichloromethane/0.5% concentrated aqueous ammonia to give 1-(t-butoxycarbonyl)-4-(1-(2-(1H-imidazol-1-yl)ethyl)-1H-benzimidazol-2-yl)[1,4] diazepane: R$_f$=0.44 (silica gel, 5% methanol/dichloromethane/0.5% concentrated aqueous ammonia).

Combine 1-(t-butoxycarbonyl)-4-(1-(2-(1H-imidazol-1-yl)ethyl)-1H-benzimidazol-2-yl)[1,4]diazepane (0.22 g, 0.54 mmol), 57% hydriodic acid (0.25 mL, 1.13 mmol), methanol (10 mL) and heat to reflux. After 20 hours, cool the reaction mixture and evaporate in vacuo to give a residue. Triturate the residue with diethyl ether to give a solid. Repeatedly, decant and add diethyl ether before collecting the solid by filtration, rinse with diethyl ether, and dry in vacuo to give the title compound.

EXAMPLE 66

1-(3,4,5-Trimethoxybenzoyl)-3-2-(4-(1-(2-1H-imidazol-1-yl)ethyl)-1H-benzimidazol-2-yl)[1,4]diazepan-1-yl)ethyl)-3-phenylpyrrolidine

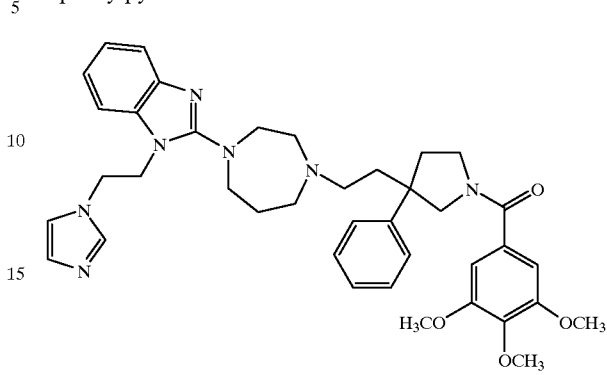

66.1 Synthesis of 1-(3,4,5-trimethoxybenzoyl-3-(2-(4-(1-(2-(1H-imidazol-1-yl)ethyl)-1H-benzimidazol-2-yl)[1,4] diazepan-1-yl)ethyl)-3-phenylpyrrolidine Combine 1-(3,4,5-trimethoxybenzoyl)-3-phenyl-3-(2-methanesulfonyloxyethyl)pyrrolidine (0.34 g, 0.60 mmol), 4-(1-(2-(1H-imidazol-1-yl)ethyl)-1H-benzimidazol-2-yl)[1,4]diazepane hydriodic acid salt (0.27 g, 0.60 mmol), and N,N-diisopropylethylamine (0.31 g, 2.39 mmol) in acetonitrile (10 mL). Heat to reflux. After 12 hours, cool to ambient temperature and dilute the reaction mixture with dichloromethane and extract with twice water. Dry the organic layer over Na$_2$SO$_4$, filter, and evaporate in vacuo to give a residue. Chromatograph the residue on silica gel eluting with 10% methanol/dichloromethane/0.5% concentrated aqueous ammonia) to give the title compound: R$_f$=0.32 (silica gel, 10% methanol/dichloromethane/0.5% concentrated aqueous ammonia).

66.2 Synthesis of 1-(3,4,5-trimethoxybenzoyl)-3-(2-(4-(1-(2-1H-imidazol-1-yl)ethyl)-1H-benzimidazol-2 -yl)[1,4] diazepan-1-yl)ethyl)-3-phenylpyrrolidine hydrochloric acid salt Combine 1-(3,4,5-trimethoxybenzoyl)-3-(2-(4-(1-(2-(1H-imidazol-1-yl)ethyl)-1H-benzimidazol-2-yl)[1,4]diazepan-1-yl)ethyl)-3-phenylpyrrolidine (0.26 g, 0.39 mmol) and methanol (10 mL). Add a solution of hydrochloric acid in dioxane (0.195 mL, 4 M, 0.78 mmol). heat to reflux. After 1 hour, evaporate in vacuo to give a residue. Triturate the residue with diethyl ether (50 mL) and stir to give a solid. After 12 hours, decant the solvent and collect the solid to give the title compound.

PREPARATION 29

4-(1-(2-(1H-triazol-1-yl)ethyl)-1H-benzimidazol-2-yl)[1,4] diazepane Hydriodic acid salt Prepare by the method of Preparation 28 using triazole (0.045 g, 1.13 mmol) and 1-(t-butoxycarbonyl)-4-(1-(2-methanesulfonyloxyethyl)-1H-benzimidazol-2-yl)[1,4] diazepane (0.33 g, 0.75 mmol) to give 1-(t-butoxycarbonyl)-4-(1-(2-(1H-triazol-1-yl)ethyl)-1H-benzimidazol-2-yl)[1,4] diazepane: R$_f$=0.32 (silica gel, 5% methanol/dichloromethane/0.5% concentrated aqueous ammonia).

Prepare the method of Preparation 28 using 1-(t-butoxycarbonyl)-4-(1-(2-(1H-triazol-1-yl)ethyl)-1H-benzimidazol-2-yl)[1,4]diazepane (0.22 g, 0.54 mmol) the title compound.

EXAMPLE 67

1-(3,4,5-Trimethoxybenzoyl)-3-(2-(4-(1-(2-(1H-triazol-1-yl)ethyl)-1H-benzimidazol-2-yl)[1,4]diazepan-1-yl)ethyl)-3-phenylpyrrolidine

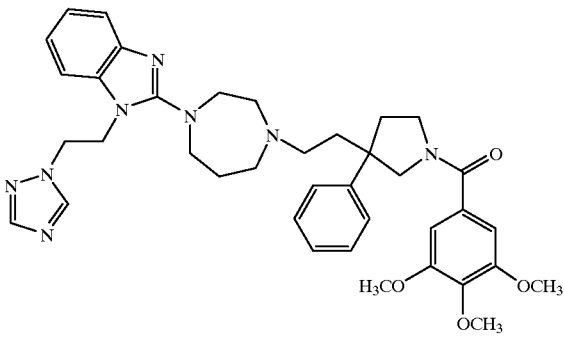

67.1 Synthesis of 1-(3,4,5-trimethoxybenzoyl)-3-(2-(4-(1-(2-(1H-triazol-1-yl)ethyl)-1H-benzimidazol-2-yl)[1,4]diazepan-1-yl)ethyl)-3-phenylpyrrolidine Prepare by the method of Example 66.1 using 1-(3,4,5-trimethoxybenzoyl)-3-phenyl-3-(2-methanesulfonyloxyethyl)pyrrolidine (0.25 g, 0.54 mmol), 4-(1-(2-(1H-triazol-1-yl)ethyl)-1H-benzimidazol-2-yl)[1,4]diazepane hydriodic acid salt (0.31 g, 0.54 mmol) to give the title compound: $R_f$=0.41 (silica gel, 10% methanol/dichloromethane/0.5% concentrated aqueous ammonia).

67.2 Synthesis of 1-(3,4,5-trimethoxybenzoyl)-3-(2-(4-(1-(2-(1H-triazol-1-yl)ethyl)-1H-benzimidazol-2-yl)[1,4]diazepan-1-yl)ethyl)-3-phenylpyrrolidine hydrochloric acid salt Prepare by the method of Example 66.2 using 1-(3,4,5-trimethoxybenzoyl)-3-(2-(4-(1-(2-(1H-triazol-1-yl)ethyl)-1H-benzimidazol-2-yl)[1,4]diazepan-1-yl)ethyl)-3-phenylpyrrolidine (0.31 g, 0.46 mmol) to give the title compound.

PREPARATION 30

4-(1-(2-(1H-tetrazol-1-yl)ethyl)-1H-benzimidazol-2-yl)[1,4]diazepane Hydriodic acid salt Combine 1-(t-butoxycarbonyl)-4-(1-(2-hydroxyethyl)-1H-benzimidazol-2-yl)[1,4]diazepane (1.0 g, 2.77 mmol), triphenylphosphine (0.73 g, 2.78 mmol), and tetrazole (0.24 g, 3.38 mmol) in tetrahydrofuran (25 mL). Add a solution of diethylazodicarboxylate (0.59 g, 3.38 mmol) in tetrahydrofuran (1 mL). After 12 hours, concentrate in vacuo to give a residue. Chromatograph the residue on silica gel eluting with 1/1 ethyl acetate/hexane to give 1-(t-butoxycarbonyl)-4-(1-(2-(1H-tetrazol-1-yl)ethyl)-1H-benzimidazol-2-yl)[1,4]diazepane: $R_f$=0.57 (silica gel, 1/1 hexane/ethyl acetate).

Combine 1-(t-butoxycarbonyl)-4-(1-(2-(1H-tetrazol-1-yl)ethyl)-1H-benzimidazol-2-yl)[1,4]diazepane (2.06 g) and methanol (15 mL). Add a solution of hydrochloric acid in dioxane (4 mL, 4 M, 16 mmol) and stir. After 4 hours, add a 1 M aqueous solution of sodium hydroxide until the pH is about 14. Concentrate in vacuo to remove most of the methanol and then extract 5 times with dichloromethane. Dry the combined organic layers over $Na_2SO_4$, filter, and concentrate in vacuo to give a residue. Chromatograph the residue on silica gel eluting with 10% methanol/dichloromethane/0.5% concentrated aqueous ammonia to give 4-(1-(2-(1H-tetrazol-1-yl)ethyl)-1H-benzimidazol-2-yl)[1,4]diazepane: $R_f$=0.30 (silica gel, 10% methanol/dichloromethane/0.5% concentrated aqueous ammonia).

Combine 4-(1-(2-(1H-tetrazol-1-yl)ethyl)-1H-benzimidazol-2-yl)[1,4]diazepane (0.30 g, 0.96 mmol) and methanol (10 mL). Add hydriodic acid (0.27 mL, 57%, 2.02 mmol). After 2 hour, evaporate in vacuo to give a residue. Triturate the residue with diethyl ether (about 20 mL) to give a solid. Collect the solid and dry to give the titlecompound.

EXAMPLE 68

1-(3,4,5-Trimethoxybenzoyl)-3-(2-(4-(1-(2-(1H-tetrazol-1-yl)ethyl)-1H-benzimidazol-2-yl)[1,4]diazepan-1-yl)ethyl)-3-phenylpyrrolidine

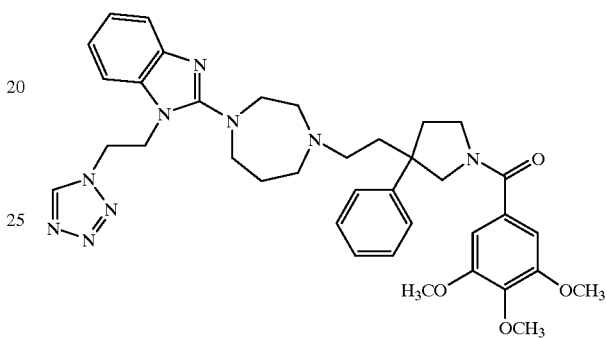

68.1 Synthesis of 1-(3,4,5-trimethoxybenzoyl)-3-(2-(4-(1-(2-(1H-tetrazol-1-yl)ethyl)-1H-benzimidazol-2-yl) 1,4]diazepan-1-yl)ethyl)-3-phenylpyrrolidine Combine 1-(3,4,5-trimethoxybenzoyl)-3-phenyl-3-(2-methanesulfonyloxyethyl)pyrrolidine (0.34 g, 0.72 mmol), 4-(1-(2-(1H-tetrazol-1-yl)ethyl)-1H-benzimidazol-2-yl)[1,4]diazepane hydriodic acid salt (0.41 g, 0.72 mmol), and N,N-diisopropylethylamine (0.33 g, 2.53 mmol) in acetonitrile (10 mL). Heat to reflux. After 12 hours, cool to ambient temperature and dilute the reaction mixture with dichloromethane and extract with twice water. Dry the organic layer over $Na_2SO_4$, filter, and evaporate in vacuo to give a residue. Chromatograph the residue on silica gel eluting with 5% methanol/dichloromethane/0.5% concentrated aqueous ammonia). Combine the product containing fractions, evaporate in vacuo, dissolve in dichloromethane, and extract with water, dry over $Na_2SO_4$, filter, and evaporate invacuo to to give the title compound: $R_f$=0.30 (silica gel, 5% methanol/dichloromethane/0.5% concentrated aqueous ammonia).

68.2 Synthesis of 1-(3,4,5-trimethoxybenzoyl)-3-(2-(4-(1-(2-(1H-tetrazol-1-yl)ethyl)-1H-benzimidazol-2-yl)[1,4]diazepan-1-yl)ethyl)-3-phenylpyrrolidine Hydriodic acid salt Combine 1-(3,4,5-trimethoxybenzoyl)-3-(2-(4-(1-(2-(1H-tetrazol-1-yl)ethyl)-1H-benzimidazol-2-yl)[1,4]diazepan-1-yl)ethyl)-3-phenylpyrrolidine (0.33 g, 0.48 mmol) and methanol (10 ml). Add hydriodic acid (0.13 mL, 57%, 1.0 mmol). After 4 hour, evaporate in vacuo to give a residue. Triturate the residue with diethyl ether (about 20 mL) and stir to give a solid. Collect the solid and dry to give the title compound.

EXAMPLE 69

1-(3,4,5-Trimethoxybenzoyl)-3-(2-(4-(1-(4-cyanobutyl)-1H-benzimidazol-2-yl)[1,4]diazepan-1-yl)ethyl)-3-phenylpyrrolidine

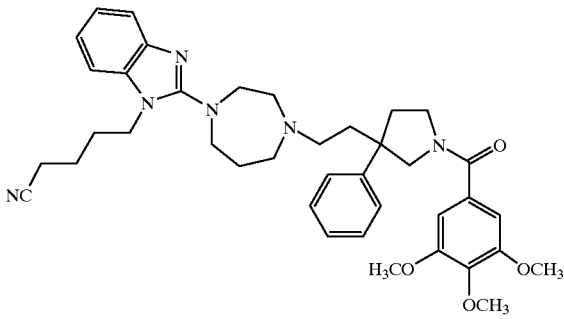

69.1 Synthesis of 1-(3,4,5-trimethoxybenzoyl)-3-(2-(4-(1-(4-cyanobutyl)-1H-benzimidazol-2-yl)[1,4]diazepan-1-yl)ethyl)-3-phenylpyrrolidine Combine 1-(3,4,5-trimethoxybenzoyl)-3-(2-(4-(1H-benzimidazol-2-yl)[1,4]diazepan-1-yl)ethyl)-3-phenylpyrrolidine (0.1 g, 0.17 mmol) and dimethylformamide (2 mL). Add sodium hydride (8 mg, 60% in oil, 0.34 mmol). After 12 hours, add 1-bromo-4-cyanobutane (27 mg, 0.17 mmol). After 1.5 hours, add water (5 mL) and dichloromethane (20 mL). Separate the layers and extract the aqueous layer twice with dichloromethane. Combine the organic layers, dry over $Na_2SO_4$, filter, and evaporate in vacuo to give a residue. Chromatograph the residue on silica gel eluting with 5% methanol/dichloromethane/0.5% concentrated aqueous ammonia to give the title compound: $R_f$=0.26 (silica gel, 5% methanol/dichloromethane/0.5% concentrated aqueous ammonia).

69.2 Synthesis of 1-(3,4,5-trimethoxybenzoyl)-3-(2-(4-(1-(4-cyanobutyl)-1H-benzimidazol-2-yl)[1,4]diazepan-1-yl)ethyl)-3-phenylpyrrolidine hydrochloric acid salt Combine 1-(3,4,5-trimethoxybenzoyl)-3-(2-(4-(1-(4-cyanobutyl)-1H-benzimidazol-2-yl)[1,4]diazepan-1-yl)ethyl)-3-phenylpyrrolidine (0.12 g, 0.19 mmol) and methanol (10 mL). Add a solution of hydrochloric acid in dioxane (0.093 mL, 4 M, 0.37 mmol) and stir. After 12 hours, evaporate in vacuo to give a residue. Triturate the residue with diethyl ether (about 20 mL) to give a solid. Three times, decant the solvent and add diethyl ether. Collect the solid and dry to give the title compound.

EXAMPLE 70

1-(3,4,5-Trimethoxybenzoyl)-3-(2-(4-(1-(4-(1H-tetrazol-5-yl)butyl)-1H-benzimidazol-2-yl)[1,4]diazepan-1-yl)ethyl)-3-phenylpyrrolidine

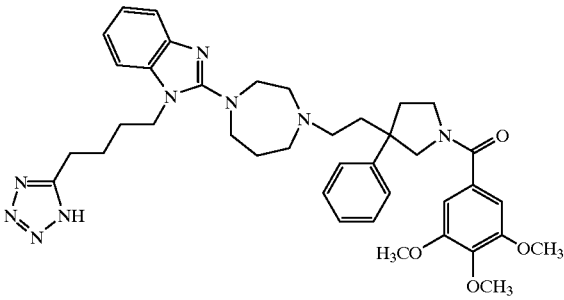

70.1 Synthesis of 1-(3,4,5-trimethoxybenzoyl)-3-(2-(4-(1-(4-(1H-tetrazol-5-yl)butyl)-1H-benzimidazol-2-yl)[1,4]diazepan-1-yl)ethyl)-3-phenylpyrrolidine Combine 1-(3,4,5-trimethoxybenzoyl)-3-(2-(4-(1-(4-cyanobutyl)-1H-benzimidazol-2-yl)[1,4]diazepan-1-yl)ethyl)-3-phenylpyrrolidine (0.45 g, 0.67 mmol), sodium azide (0.13 g, 2.04 mmol), and triethylammonium hydrochloride (0.14 g, 1.03 mmol) in N-methylpyrrolidinone (6 mL). Heat to 150° C. After 4 hours, cool to ambient temperature and partition the reaction mixture between water and ethyl acetate. Separate the layers and extract the aqueous layer three times with ethyl acetate. Adjust the pH of the aqueous layer to about 1 using a 1 M aqueous hydrochloric acid solution. The aqueous layer is again extracted three times with ethyl acetate, and twice with dichloromethane. The aqueous layer is saturated with sodium chloride and again extracted four times with dichloromethane. Combine the organic layers, dry over $MgSO_4$, filter, and evaporate in vacuo to give residue. Chromatograph the residue on silica gel eluting with 20% methanol/dichloromethane to give the title compound: $R_f$=0.33 (silica gel, 20% methanol/dichloromethane/0.5% concentrated aqueous ammonia).

PREPARATION 31

3-(1H-Tetrazol-1-yl)benzoic acid

Prepare by the method of Preparation 11 using ethyl 3-aminobenzoate to give ethyl 3-(1H-tetrazol-1-yl)benzoate: $R_f$=0.51 (silica gel, 1/1 ethyl acetate/hexane).

Combine ethyl 3-(1H-tetrazol-1-yl)benzoate (4.93 g, 22.6 mmol) and tetrahydrofuran/water (100 mL/25 mL). Add lithium hydroxide (1.9 g, 45.2 mmol) and heat to reflux. After 2 hours, cool to ambient temperature and extract the reaction mixture five times with a 1 M aqueous sodium hydroxide solution. Combine the aqueous layers and extract with ethyl acetate. Acidify the aqueous layers with a 1 M aqueous hydrochloric acid solution (pH about 1) to give a solid. Collect the solid by filtration to give the title compound.

EXAMPLE 71

1-(3-(1H-Tetrazol-1-yl)benzoyl-3-(2-(4-(1-(2-ethoxyethyl)-1H-benzimidazol-2-yl)[1,4]diazepan-1-yl)ethyl-3-phenylpyrrolidine

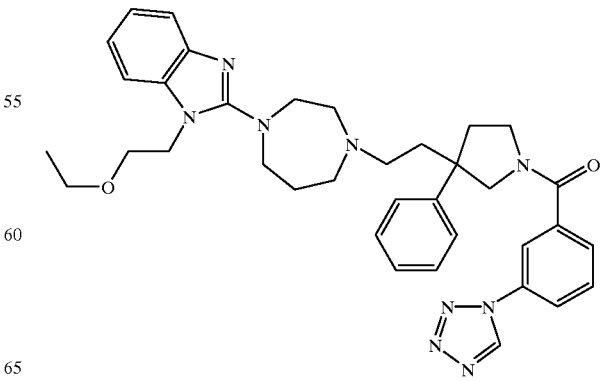

71.1 Synthesis of 1-3-(1H-tetrazol-1-yl)benzoyl)-3-(2-(4-(1-(2-ethoxyethyl)-1H-benzimidazol-2-yl)[1,4]diazepan-1-yl)ethyl)-3-phenylpyrrolidine Prepare by the method of Example 56.1 using 3-(1H-tetrazol-1-yl)benzoic acid and 3-(2-(4-(1-(2-ethoxyethyl)-1H-benzimidazol-2-yl)[1,4]diazepan-1-yl)ethyl)-3-phenylpyrrolidine hydrochloric acid salt(prepared from (−)-3-phenyl-3-(2-hydroxyethyl)pyrrolidine (R,R)-di-p-anisoyltartaric acid salt) to give the title compound.

PREPARATION 32.1
2-Methoxy-5-(5-methylsulfonyl-1H-tetrazol-1-yl)benzoic acid

According to the method of Tet. Let., 26, 1661 (1985), combine methyl 2-methoxy-5-aminobenzoate (0.5 g, 2.76 mmol) and di-2-pyridyl thionocarbonate (0.64 g, 2.76 mmol) in dichloromethane (10 mL). After 30 minutes, dilute the reaction mixture with dichloromethane and extract five times with water. Dry the organic layer over $Na_2SO_4$, filter, and concentrate in vacuo to give methyl 2-methoxy-5-isothiocyanatobenzoate: $R_f$=0.51 (silica gel, dichloromethane).

Combine methyl 2-methoxy-5-isothiocyanatobenzoate (0.61 g, 2.71 mmol), sodium azide (0.25 g, 3.87 mmol), ammonium chloride (0.23 g, 4.35 mmol) in water (10 mL). Heat to 70° C. After 2 hours, cool to ambient temperature and acidify to pH about 1 using a 1 M aqueous hydrochloric acid solution to give a solid. Collect the solid by filtration to give methyl 2-methoxy-5-(5-thio-1H-tetrazol-1-yl)benzoate: $R_f$=0.45 (silica gel, 1/1 ethyl acetate/hexane).

Combine methyl 2-methoxy-5-(5-thio-1H-tetrazol-1-yl)benzoate, methyl iodide (1.2 g, 8.45 mmol), N,N-diisopropylethylamine (1.09 g, 8.45 mmol) and dichloromethane (75 mL). After 20 hours, extract the reaction mixture twice with a saturated aqueous ammonium chloride solution. Dry the organic layer over $Na_2SO_4$, filter, and evaporate in vacuo to give a residue. Chromatograph the residue on silica gel eluting with 1% acetone/dichloromethane to give methyl 2-methoxy-5-(5-methylthio-1H-tetrazol-1-yl)benzoate: $R_f$=0.43 (silica gel, 1% acetone/dichloromethane).

Combine methyl 2-methoxy-5-(5-methylthio-1H-tetrazol-1-yl)benzoate (0.35 g, 1.23 mmol) and dichloromethane (20 mL). Add m-chloroperbenzoic acid (1.06 g, 50%, 3.1 mmol). After 2 hour, filter and dilute the reaction mixture with dichloromethane. Extract with a 1 M aqueous solution of sodium hydroxide. Dry the organic layer over $Na_2SO_4$, filter, and concentrate in vacuo to give a residue. Chromatograph the residue on silica gel eluting with 0.1% acetone/dichloromethane to give a methyl 2-methoxy-5-(5-methylsulfonyl-1H-tetrazol-1-yl)benzoate.

Combine methyl 2-methoxy-5-(5-methylsulfonyl-1H-tetrazol-1-yl)benzoate (5 mmol), methanol (10 mL), and a 1 M aqueous sodium hydroxide solution (6 mL, 6.0 mmol). After 18 hours, evaporate in vacuo to give a residue. Combine the residue, water (5 mL) and acidify by dropwise addition of a 1 M aqueous hydrochloric acid solution (6.5 mL). Evaporate in vacuo to give a residue. Combine the residue and dichloromethane and stir. Decant and add dichloromethane and stir. Decant and combine with the first decantate. Dry over $Na_2SO_4$, filter, and concentrate in vacuo to give the title compound.

PREPARATION 32.2
2-Methoxy-5-(5-methylthio-1H-tetrazol-1-yl)benzoic acid

Combine methyl 2-methoxy-5-isothiocyanatobenzoate (4.0 g, 17.9 mmol), sodium azide (1.4 g, 21.5 mmol), ammonium chloride (1.4 g, 26.2 mmol) in water (70 mL). Heat to 70° C. After 4 hours, cool to ambient temperature and acidify to pH about 1 using a 1 M aqueous hydrochloric acid solution to give a solid. Collect the solid by filtration to give methyl 2-methoxy-5-(5-thio-1H-tetrazol-1-yl)benzoate.

Combine methyl 2-methoxy-5-(5-thio-1H-tetrazol-1-yl)benzoate obtained above, methyl iodide (1 mL), N,N-diisopropylethylamine (3 mL) and dichloromethane (100 mL). After 12 hours, extract the reaction mixture twice with a saturated aqueous ammonium chloride solution. Dry the organic layer over $Na_2SO_4$, filter, and evaporate invacuo to give a residue. Chromatograph the residue on silica gel eluting with 2% acetone/dichloromethane to give methyl 2-methoxy-5-(5-methylthio-1H-tetrazol-1-yl)benzoate.

Combine methyl 2-methoxy-5-(5-methylthio-1H-tetrazol-1-yl)benzoate (0.51 g, 1.81 mmol) and lithium hydroxide (0.065 g, 2.71 mmol) and tetrahydrofuran/water (5 mL/5 mL). Heat to reflux. After 1 hour, cool to ambient temperature, separate the layers, and extract the organic layer 2 times with 1 M aqueous sodium hydroxide solution. Combine the aqueous layers and extract with diethyl ether. Acidify the aqueous layer using aqueous 1 M hydrochloric acid solution to give the title compound.

EXAMPLE 72.1
1-(2-Methoxy-5-(5-methylsulfonyl-1H-tetrazol-1-yl)benzoyl)-3-(2-(4-(1-(2-ethoxyethyl)-1H-benzimidazol-2-yl)[1,4]diazepan-1-yl)ethyl)-3-phenylpyrrolidine

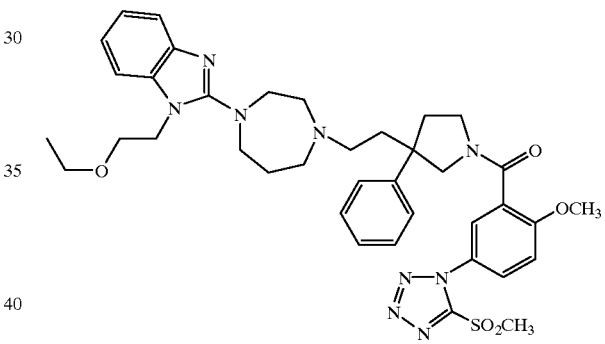

72.1.1 Synthesis of 1-(2-methoxy-5-(5-methylsulfonyl-1H-tetrazol-1-yl-benzoyl)-3-(2-(4-(1-(2-ethoxyethyl)-1H-benzimidazol-2-yl)[1,4]diazepan-1-yl )-3-phenylpyrrolidine Prepare by the method of Example 56.1 using 2-methoxy-5-(5-methylsulfonyl-1H-tetrazol-1-yl)benzoic acid and 3-(2-(4-(1-(2-ethoxyethyl)-1H-benzimidazol-2-yl)[1,4] diazepan-1-yl)ethyl)-3-phenylpyrrolidine hydrochloric acid salt (prepared from (−)-3-phenyl-3-(2-hydroxyethyl) pyrrolidine (R,R)-di-p-anisoyltartaric acid salt) to give the title compound.

EXAMPLE 72.2
1-(2-Methoxy-5-(5-methylsulfonyl-1H-tetrazol-1-yl)benzoyl)-3-(2-(4-(1-(2-ethoxyethyl)-1H-benzimidazol-2-yl)[1,4]diazepan-1-yl)ethyl)-3-phenylpyrrolidine
72.2.1 Synthesis of 1-(2-methoxy-5-(5-methylthio-1H-tetrazol-1-yl)benzoyl)-3-(2-hydroxyethyl)-3-phenylpyrrolidine Prepare by the method of Example 56.1 using 2-methoxy-5-(5-methylthio-1H-tetrazol-1-yl)benzoic acid and 3-(2-(4-(1-(2-ethoxyethyl)-1H-benzimidazol-2-yl)[1,4]diazepan-1-yl)ethyl)-3-phenylpyrrolidine hydrochloric acid salt (prepared from (−)-3-phenyl-3-(2-hydroxyethyl)pyrrolidine (R,R)-di-p-anisoyltartaric acid salt) to give the title compound.

72.2.2 Synthesis of 1-(2-methoxy-5-(5-methylsulfonyl-1H-tetrazol-1-yl)benzoyl)-3-(2-hydroxyethyl)-3-phenylpyrrolidine Combine 1-(2-methoxy-5-(5-methylthio-1H-tetrazol-1-yl)benzoyl)-3-(2-hydroxyethyl)-3-phenylpyrrolidine (0.55 g, 1.25 mmol) and dichloromethane (20 mL). Add m-chloroperbenzoic acid (1.04 g, 50%, 3.0 mmol) and potassium carbonate (0.41 g). After 2 hour, filter and dilute the reaction mixture with dichloromethane. Extract three times with a 1 M aqueous solution of sodium hydroxide. Dry the organic layer over $Na_2SO_4$, filter, and concentrate in vacuo to give a residue. Chromatograph the residue on silica gel eluting with 5% methanol/dichloromethane to give the title compound: $R_f$=0.36 (silica gel, 5% methanol/dichloromethane).

72.2.3 Synthesis of 1-(2-methoxy-5-(5-methylsulfonyl-1H-tetrazol-1-yl)benzoyl)-3-(2-methanesulfonyloxyethyl)-3-phenylpyrrolidine Prepare by the method of Example 2.5.2 using 1-(2-methoxy-5-(5-methylsulfonyl-1H-tetrazol-1-yl)benzoyl)-3-(2-hydroxyethyl)-3-phenylpyrrolidine (0.41 g, 0.87 mmol) to give the title compound: $R_f$=0.69 (silica gel, 5% methanol/dichloromethane).

72.2.4 Synthesis of 1-(2-methoxy-5-(5-methylsulfonyl-1H-tetrazol-1-yl)benzoyl)-3-(2-(4-(1-(2-ethoxyethyl)-1H-benzimidazol-2-yl)[1,4]diazepan-1-yl)ethyl)-3-phenylpyrrolidine Combine 1-(2-methoxy-5-(5-methylsulfonyl-1H-tetrazol-1-yl)benzoyl)-3-(2-methanesulfonyloxyethyl)-3-phenylpyrrolidine (0.44 g, 0.81 mmol), triethylamine (0.33 g, 3.23 mmol), and 4-(1-(2-ethoxyethyl)-1H-benzimidazol-2-yl)[1,4]diazepane hydriodic acid salt (0.44 g, 8.1 mmol) in acetonitrile (10 mL). Heat to reflux. After 12 hours, cool the reaction mixture, dilute with dichloromethane, and extract with water. Dry the organic layer over $MgSO_4$, filter, and evaporate in vacuo to give a residue. Chromatograph the residue on silica gel eluting with 5% methanol/dichloromethane to give the title compound.

72.2.4 Synthesis of 1-(2-methoxy-5-(5-methylsulfonyl-1H-tetrazol-1-yl)benzoyl)-3-(2-(4-(1-(2-ethoxyethyl)-1H-benzimidazol-2-yl)[1,4]diazepan-1-yl)ethyl)-3-phenylpyrrolidine hydrochloric acid salt Combine 1-(2-methoxy-5-(5-methylsulfonyl-1H-tetrazol-1-yl)benzoyl)-3-(2-(4-(1-(2-ethoxyethyl)-1H-benzimidazol-2-yl)[1,4]diazepan-1-yl)ethyl)-3-phenylpyrrolidine (0.31 g, 0.41 mmol) and ethyl acetate (10 mL). Add a solution of hydrochloric acid in dioxane (0.216 mL, 4 M, 0.87 mmol). Heat to reflux. After 30 minutes, cool to ambient temperature and add diethyl ether (80 mL) to give a solid. Collect the solid by filtration and dry to give the title compound.

PREPARATION 33

2-Methyl-5-(1H-tetrazol-1-yl)benzoic acid

Combine 2-methyl-5-nitrobenzoic acid (4.98 g, 27.5 mmol), potassium carbonate (1.93 g, 14.0 mol), and methyl iodide (7.80 g, 55.0 mmol) in acetone (100 mL). Heat to reflux. After 4 hours, cool the reaction mixture, dilute with water, and extract five times with ethyl acetate. Combine the organic layers, extract with a saturated aqueous sodium bicarbonate solution and then brine. Dry the organic layer over $Na_2SO_4$, filter, and evaporate in vacuo to give methyl 2-methyl-5-nitrobenzoate: $R_f$=0.61 (silica gel, ethyl acetate/hexane 1/1).

Combine methyl 2-methyl-5-nitrobenzoate (5.32 g, 27.2 mmol) and methanol (100 mL). Add 5% palladium-on-carbon (0.27 g). Hydrogenate on a pressure apparatus at 50 psi. After 18 hours, filter through celite to remove the catalyst and evaporate the filtrate in vacuo to give methyl 2-methyl-5-aminobenzoic acid: $R_f$=0.34 (silica gel, ethyl acetate/hexane 1/4).

Combine methyl 2-methyl-5-aminobenzoate (4.5 g, 27.2 mmol) and triethyl orthoformate (16.2 g, 109 mmol) in glacial acetic acid (25 mL). After 12 hours, add portionwise sodium azide (7.08 g, 109 mmol). Heat to 70° C. After 2 hours, cool the reaction mixture to ambient temperature, dilute with water (250 mL). Collect the solid by filtration, rinse with water, and dry to give methyl 2-methyl-5-(1H-tetrazol-1-yl)benzoate: $R_f$=0.13 (silica gel, ethyl acetate/hexane 1/4).

Combine methyl 2-methyl-5-(1H-tetrazol-1-yl)benzoate (5.2 g, 23.9 mmol) and lithium hydroxide hydrate (2.0 g, 47.7 mmol) in tetrahydrofuran/water (50 mL/50 mL). Heat to reflux. After 2 hours, dilute with diethyl ether and separate the Layers. Extract the aqueous layer three times with diethyl ether. Extract the combined diethyl ether layers three times with a 1 M sodium hydroxide solution (20 mL). Combine the aqueous layers, acidify with a 1 M aqueous hydrochloric acid solution (pH about 1) to give a solid. Collect the solid by filtration and recrystallize form water to give the title compound.

EXAMPLE 73

1-(2-Methyl-5-(1H-tetrazol-1-yl)benzoyl)-3-(2-(4-(1-(2-ethoxyethyl)-1H-benzimidazol-2-yl)[1,4]diazepan-1-yl)ethyl)-3-phenylpyrrolidine

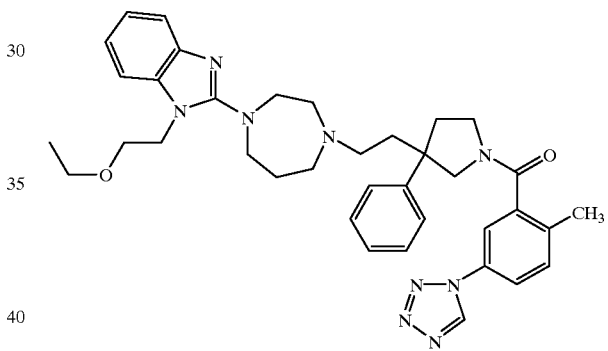

73.1 Synthesis of 1-(2-methyl-5-(1H-tetrazol-1-yl)benzoyl)-3-(2-(4-(1-(2-ethoxyethyl)-1H-benzimidazol-2-yl)[1,4]diazepan-1-yl)ethyl)-3-phenylpyrrolidine Prepare by the method of Example 56.1 using 2-methyl-5-(1H-tetrazol-1-yl)benzoic acid and 3-(2-(4-(1-(2-ethoxyethyl)-1H-benzimidazol-2-yl)[1,4]diazepan-1-yl)ethyl)-3-phenylpyrrolidine hydrochloric acid salt (prepared from (−)-3-phenyl-3-(2-hydroxyethyl)pyrrolidine (R,R)-di-p-anisoyltartaric acid salt) to give the title compound.

PREPARATION 34

2-Methoxy-5-trifluoromethoxybenzoyl chloride

Combine 2-methoxy-5-trifluoromethoxybenzene (1.0 g, 5.2 mmol) and trifluoroacetic acid (200 mL). Add slowly portionwise hexamethylenetetraamine (26 g, 185.7 mmol). Heat at 60° C. After 24 hours, cool to ambient temperature and pour the reaction mixture into a 2 M aqueous solution of sulfuric acid (500 mL). Cool and extract ten times with diethyl ether. Dry the combined organic layers over $Na_2SO_4$, filter, and evaporate in vacuo to give a residue. Chromatograph the residue on silica gel eluting with 1/4 ethyl acetate/hexane to give 2-methoxy-5-trifluoromethoxybenzaldehyde.

According to the method of Heterocycles, 16, 2091 (1981), combine 2-methoxy-5-trifluoromethoxybenzaldehyde (0.58 g, 2.65 mmol) and 2-methylbut-2-ene (37 mL) in t-butanol (16 mL). Add dropwise a solution of sodium dihydrogen phosphate hydrate (0.92 g) and sodium chlorite (0.42 g, 4.7 mmol) in water (10 mL). After 4 hours, adjust the pH of the reaction mixture to about 8 to 9 using a 1 M aqueous sodium hydroxide solution. Evaporate the reaction mixture in vacuo at about ambient temperature to remove most of the t-butanol. Add water (40 mL) and extract three times with hexane (10 mL). Adjust the pH of the aqueous layer to about 1 using a 1 M aqueous hydrochloric acid solution and extract five times with diethyl ether. Combine the organic layers, dry over $Na_2SO_4$, filter, and evaporate in vacuo to give a residue. Chromatograph the residue on silica gel eluting with 1/1 ethyl acetate/hexane containing 0.5% acetic acid to give 2-methoxy-5-trifluoromethoxybenzoic acid: $R_f$=0.34 (silica gel, 1/1 ethyl acetate/hexane containing 0.5% acetic acid).

Combine 2-methoxy-5-trifluoromethoxybenzoic acid (0.6 g, 2.53 mmol) and dichloromethane (10 mL). Cool in an ice bath. Add dropwise oxalyl chloride (0.64 mL, 5.0 mmol) followed by dimethylformamide (1 drop). Warm to ambient temperature. After 3 hours, evaporate in vacuo and dry to give the title compound.

EXAMPLE 74

1-(2-Methoxy-5-trifluoromethylbenzoyl)-3-(2-(4-(1-(2-ethoxyethyl)-1H-benzimidazol-2-yl)[1,4]diazepan-1-yl) ethyl)-3-phenylpyrrolidine

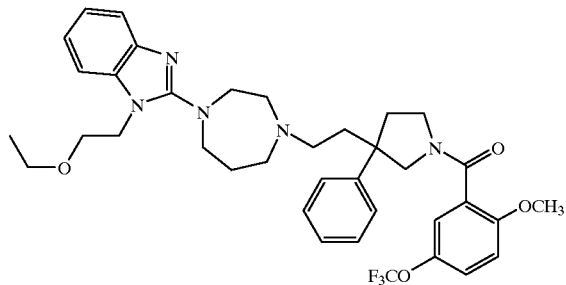

74.1 Synthesis of 1-(2-methoxy-5-trifluoromethylbenzoyl)-3-phenyl-3-(2-hydroxyethyl)pyrrolidine Combine (−)-3-phenyl-3-(2-hydroxyethyl)pyrrolidine (R,R)-di-p-anisoyltartaric acid salt (1.7 g, 2.5 mmol) and sodium carbonate (1.32 g, 12.5 mmol) in ethyl acetate/water (1/1) (20 mL). Add a solution of 2-methoxy-5-trifluoromethoxybenzoyl chloride (0.64 g, 2.5 mmol) in ethyl acetate (10 mL). After 14 hours, separate the organic layer. Extract the aqueous layer four times with dichloromethane. Dry the combined organic layers over $Na_2SO_4$, filter, and concentrate in vacuo to obtain a residue. Chromatograph the residue on silica gel eluting with ethyl acetate to give the title compound: $R_f$=0.32 (silica gel, ethyl acetate).

74.2 Synthesis of 1-(2-methoxy-5-trifluoromethylbenzoyl)-3-phenyl-3-(2-methanesulfonyloxyethyl)pyrrolidine Prepare by the method of Example 2.5.2 using 1-(2-ethoxy-5-trifluoromethylbenzoyl)-3-phenyl-3-(2-hydroxyethyl)pyrrolidine to give the title compound.

74.3 Synthesis of 1-(2-methoxy-5-trifluoromethylbenzoyl)-3-(2-(4-(1-(2-ethoxyethyl)-1H-benzimidazol-2-yl)[1,4] diazepan-1-yl)ethyl)-3-phenylpyrrolidine Prepare by the method of Example 1.6 using 1-(2-methoxy-5-trifluoromethylbenzoyl)-3-phenyl-3-(2-methanesulfonyloxyethyl)pyrrolidine and 4-(1-(2-ethoxyethyl)-1H-benzimidazol-2-yl)[1,4]diazepane to give the title compound.

EXAMPLE 75

1-((R)-α-Methylbenzyl)-3-(2-(4-(1-(2-ethoxyethyl)-1H-benzimidazol-2-yl)[1,4]diazepan-1-yl)ethyl)-3-1-(4-fluorophenylmethyl)-2-oxopyrrolidine

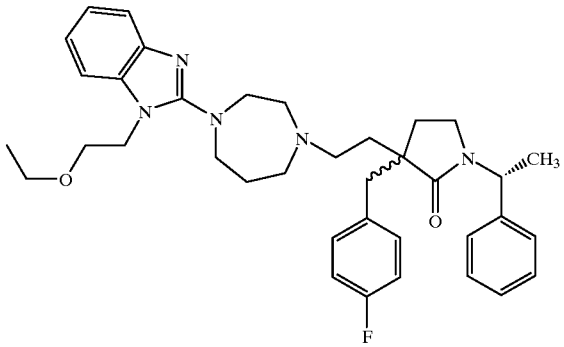

75.1 Synthesis of 1-((R)-α-methylbenzyl)-2-oxopyrrolidine

According the the procedure of *J. Am. Chem. Soc.*, 74, 1952 (1959), combine butyrolactone (8.6 g, 100 mmol) and (R)-α-methylbenzylamine (15.0 g, 123 mmol) and heat to 180° C. After 48 hours, heat to 210° C. After 6 hours, cool the reaction mixture and evaporate in vacuo using a short path distillation apparatus to obtain a residue: bp 110° C. at 0.5 mm Hg. Chromatograph the residue on silica gel eluting with ethyl acetate to give the title compound: $R_f$=0.45 (silica gel, ethyl acetate).

75.2 Synthesis of 1-((R)-α-methylbenzyl)-3-(4-fluorophenylmethyl)-2-oxopyrrolidine Combine 1-((R)-α-methylbenzyl)-2-oxopyrrolidine (1.0 g, 5.29 mmol) and tetrahydrofuran (10 mL). Cool to −78° C. using a dry-ice/acetone bath. Add dropwise a solution of sec-butyllithium (4.5 mL, 1.3 M in hexane, 5.8 mmol). After 30 minutes, slowly add a solution of 4-fluorobenzyl bromide (1.1 g, 5.8 mmol). After 15 minutes, warm to ambient temperature. After 3 hours, add water (10 mL). Separate the layers and extract the aqueous layer three times with ethyl acetate. Dry the combined organic layers over $Na_2SiO_4$, filter, and evaporate in vacuo to give a residue. Chromatograph the residue on silica gel eluting with 1/4 ethyl acetate/hexane to give diastereomers of the title compound: $R_f$=0.44 and 0.75 (silica gel, 1/1 ethyl acetate/hexane).

75.3 Synthesis of 1-((R)-α-methylbenzyl)-3-(4-fluorophenylmethyl)-3-(2-(t-butyldimethylsilyloxy)ethyl)-2-oxopyrrolidine Prepare by the method of Example 25.2 using 1-((R)-α-methylbenzyl)-3-(4-fluorophenylmethyl)-2-oxopyrrolidine to give the title compound: $R_f$=0.55 (silica gel, 1/4 ethyl acetate/hexane).

75.4 Synthesis of 1-((R)-α-methylbenzyl)-3-(4-fluorophenylmethyl)-3-(2-hydroxyethyl)-2-oxopyrrolidine Prepare by the method of Example 18.2 using 1-((R)-α-methylbenzyl)-3-(4-fluorophenylmethyl)-3-(2-(t-butyldimethylsilyloxy)ethyl)-2-oxopyrrolidine (1.7 g, 3.73 mmol) and ammonium fluoride (0.83 g, 22.4 mmol) to give, after chromatography on silica gel eluted with 1/1 ethyl acetate/hexane, the title compound as diastereomers: $R_f$=0.51 and 0.25 (silica gel, 1/1 ethyl acetate/hexane).

75.5 Synthesis of 1-((R)-α-methylbenzyl)-3-(4-fluorophenylmethyl)-3-(2-methanesulfonyloxyethyl)-2-oxopyrrolidine Prepare by the method of Example 2.5.2 using 1-((R)-α-methylbenzyl)-3-(4-fluorophenylmethyl)-3-(2- hydroxyethyl)-2-oxopyrrolidine (R$_f$=0.51 silica gel, 1/1 ethyl acetate/hexane) to give a diastereomer of the title compound: R$_f$=0.75 (silica gel, ethyl acetate).

Prepare by the method of Example 2.5.2 using 1-((R)-α-methylbenzyl)-3-(4-fluorophenylmethyl)-3-(2-hydroxyethyl)-2-oxopyrrolidine (R$_f$=0.25 silica gel, 1/1 ethyl acetate/hexane) to give a diastereomer of the title compound: R$_f$=0.55 (silica gel, ethyl acetate).

75.6 Synthesis of 1-((R)-α-methylbenzyl)-3-(2-(4-(1-(2-ethoxyethyl)-1H-benzimidazol-2-yl)[1,4]diazepan-1-yl)ethyl)-3-(4-fluorophenylmethyl)-2-oxopyrrolidine Combine 1-((R)-α-methylbenzyl)-3-(4-fluorophenylmethyl)-3-(2-methanesulfonyloxyethyl)-2-oxopyrrolidine (R$_f$=0.75 silica gel, ethyl acetate) (0.44 g, 1.04 mmol) and 4-(1-(2-ethoxyethyl)-1H-benzimidazol-2-yl)[1,4]diazepane hydriodic acid salt (0.49 g, 1.04 mmol), and N,N-diisopropylethylamine (0.54 g, 4.2 mmol) in acetonitrile (10 mL). Heat to reflux. After 16 hours, cool and partition the reaction mixture between dichloromethane and water. Separate the layers and extract the organic layer twice with water. Dry the organic layer over Na$_2$SO$_4$, filter, and concentrate in vacuo to obtain a residue. Chromatograph the residue on a short column of silica gel eluting with 2.5% methanol/dichloromethane/0.5% concentrated aqueous ammonia to give a diastereomer of the title compound: R$_f$=0.60 (silica gel, 5% methanol/dichloromethane/0.5% concentrated aqueous ammonia).

Combine 1-((R)-α-methylbenzyl)-3-(4-fluorophenylmethyl)-3-(2-methanesulfonyloxyethyl)-2-oxopyrrolidine (R$_f$=0.55 silica gel, ethyl acetate) (0.77 g, 1.84 mmol) and 4-(1-(2-ethoxyethyl)-1H-benzimidazol-2-yl)[1,4]diazepane hydriodic acid salt (0.87 g, 1.84 mmol), and N,N-diisopropylethylamine (0.95 g, 4957.4 mmol) in acetonitrile (10 mL). Heat to reflux. After 16 hours, cool and dilute the reaction mixture with dichloromethane. Extract twice with water, dry over Na$_2$SO$_4$, filter, and concentrate in vacuo to obtain a residue. Chromatograph the residue on a short column of silica gel eluting with 2.5% methanol/dichloromethane/0.5% concentrated aqueous ammonia to give a diastereomer of the title compound: R$_f$=0.46 (silica gel, 5% methanol/dichloromethane/0.5%6 concentrated aqueous ammonia).

75.7 Synthesis of 1-((R)-α-methylbenzyl)-3-(2-(4-(2-ethoxyethyl)-1H-benzimidazol-2-yl)[1,4]diazepan-1-yl)ethyl)-3-(4-fluorophenylmethyl)-2-oxopyrrolidine hydrochloric acid salt Combine 1-((R)-α-methylbenzyl)-3-(2-(4-(1-(2-ethoxyethyl)-1H-benzimidazol-2-yl)[1,4]diazepan-1-yl)ethyl)-3-(4-fluorophenylmethyl)-2-oxopyrrolidine (R$_f$=0.46 silica gel, 5% methanol/dichloromethane/0.5% concentrated aqueous ammonia) (0.71 g, 1.16 mmol) and methanol (10 mL). Add a solution of hydrochloric acid in dioxane (0.60 mL, 4 M, 2.4 mmol). After 12 hours, evaporate the reaction mixture in vacuo to give a residue. Triturate the residue with diethyl ether (100 mL) and stir to give a solid. After 6 hours, collect the solid and dry to give the title compound.

EXAMPLE 76

1-((S)-α-Methylbenzyl)-3-(2-(4-(1-(2-ethoxyethyl)-1H-benzimidazol-2-yl)[1,4]diazepan-1-yl)ethyl)-3-(4-fluorophenylmethyl)-2-oxopyrrolidine

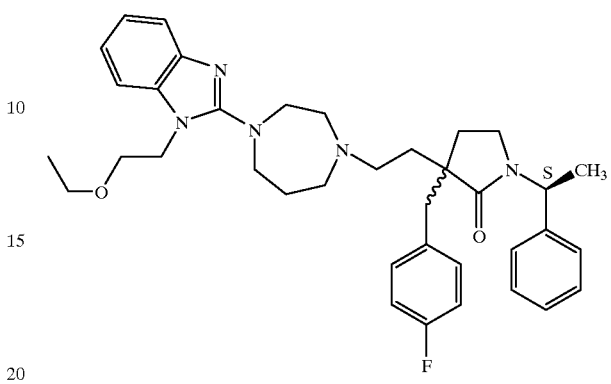

76.1 Synthesis of 1-((S)-α-methylbenzyl)-2-oxopyrrolidine

Prepare by the method of Example 75.1 using (S)-α-methylbenzylamine to give the title compound: R$_f$=0.46 (silica gel, ethyl acetate).

76.2 Synthesis of 1-((S)-α-methylbenzyl)-3-(4-fluorophenylmethyl)-2-oxopyrrolidine Prepare by the method of Example 75.2 using 1-((S)-α-methylbenzyl)-2-oxopyrrolidine (1.0 g, 5.29 mmol) to give, after chromatograph on silica gel eluting with 1/4 ethyl acetate/hexane, diastereomers of the title compound: R$_f$=0.46 and 0.70 (silica gel, 1/1 ethyl acetate/hexane).

76.3 Synthesis of 1-((S)-α-methylbenzyl)-3-(4-fluorophenylmethyl)-3-(2-(t-butyldimethylsilyloxy)ethyl)-2-oxopyrrolidine Prepare by the method of Example 75.3 using 1-((S)-α-methylbenzyl)-3-(4-fluorophenylmethyl)-2-oxopyrrolidine to give the title compound: R$_f$=0.51 (silica gel, 1/4 ethyl acetate/hexane).

76.4 Synthesis of 1-((S)-α-methylbenzyl)-3-(4-fluorophenylmethyl)-3-(2-hydroxyethyl)-2-oxopyrrolidine Prepare by the method of Example 18.2 using 1-((S)-α-methylbenzyl)-3-(4-fluorophenylmethyl)-3-(2-(t-butyldimethylsilyloxy)ethyl)-2-oxopyrrolidine (1.7 g, 3.73 mmol) and ammonium fluoride (0.83 g, 22.4 mmol) to give, after chromatography on silica gel eluting with 1/1 ethyl acetate/hexane to give the title compound as diastereomers: R$_f$=0.49 and 0.27 (silica gel, 1/1 ethyl acetate/hexane).

76.5 Synthesis of 1-((S)-α-methylbenzyl)-3-(4-fluorophenylmethyl)-3-(2-methanesulfonyloxyethyl)-2-oxopyrrolidine Prepare by the method of Example 2.5.2 using 1-((S)-α-methylbenzyl)-3-(4-fluorophenylmethyl)-3-(2-hydroxyethyl)-2-oxopyrrolidine (R$_f$=0.49 silica gel, 1/1 ethyl acetate/hexane) to give a diastereomer of the title compound: R$_f$=0.71 (silica gel, ethyl acetate).

Prepare by the method of Example 2.5.2 using 1-((S)-α-methylbenzyl)-3-(4-fluorophenylmethyl)-3-(2-hydroxyethyl)-2-oxopyrrolidine (R$_f$=0.27 silica gel, 1/1 ethyl acetate/hexane) to give a diasterebmer of the title compound: R$_f$=0.59 (silica gel, ethyl acetate).

76.6 Synthesis of 1-((S)-α-methylbenzyl)-3-(2-(4-(1-(2-ethoxyethyl)-1H-benzimidazol-2-yl)[1,4]diazepan-1-yl)ethyl)-3-(4-fluorophenylmethyl)-2-oxopyrrolidine Combine 1-((S)-α-methylbenzyl)-3-(4-fluorophenylmethyl)-3-(2-methanesulfonyloxyethyol)-2-oxopyrrolidine (R$_f$=0.71 silica gel, ethyl acetate) (0.45 g, 1.06 mmol) and 4-(1-(2-ethoxyethyl)-1H-benzimidazol-2-yl)[1,4]diazepane hydriodic acid salt (0.58 g, 1.06 mmol), and N,N-diisopropylethylamine (0.85 mL, 4.8 mmol) in acetonitrile (10 mL). Heat to reflux. After 16 hours, cool and evaporate in vacuo to give a residue. Combine the residue and ethyl acetate, extract twice with a saturated aqueous sodium bicarbonate solution and then brine. Dry the organic layer over Na$_2$SO$_4$, filter, and concentrate in vacuo to obtain a residue. Chromatograph the residue on silica gel eluting sequentially with with 15% methanol/dichloromethane and then 15% methanol/dichloromethane/1.0% concentrated aqueous ammonia to give a diastereomer of the title compound.

Combine 1-((S)-α-methylbenzyl)-3-(4-fluorophenylmethyl)-3-(2-methanesulfonyloxyethyl)-2-oxopyrrolidine (R$_f$=0.59 silica gel, ethyl acetate) (0.67 g, 1.59 mmol) and 4-(1-(2-ethoxyethyl)-1H-benzimidazol-2-yl)[1,4]diazepane hydriodic acid salt (0.86 g, 1.59 mmol), and N,N-diisopropylethylamine (1.24 mL, 7.13 mmol) in acetonitrile (20 mL). Heat to reflux. After 16 hours, cool and evaporate in vacuo to give a residue. Combine the residue and ethyl acetate, extract twice with a saturated aqueous sodium bicarbonate solution and then brine. Dry the organic layer over Na$_2$SO$_4$, filter, and concentrate in vacuo to obtain a residue. Chromatograph the residue on silica gel eluting sequentially with with 15% methanol/dichloromethane and then 15% methanol/dichloromethane/1.0% concentrated aqueous ammonia to give a diastereomer of the title compound.

76.7 Synthesis of 1-((S)-α-methylbenzyl)-3-(2-(4-(2-ethoxyethyl)-1H-benzimidazol-2-yl)[1,4]diazepan-1-yl)ethyl)-3-(4-fluorophenylmethyl)-2-oxopyrrolidine hydrochloric acid salt Combine 1-((S)-α-methylbenzyl)-3-(2-(4-(1-(2-ethoxyethyl)-1H-benzimidazol-2-yl)[1,4]diazepan-1-yl)ethyl)-3-(4-fluorophenylmethyl)-2-oxopyrrolidine (higher R$_f$ diastereomer) (0.50 g, 0.80 mmol) and methanol (20 mL). Add a solution of hydrochloric acid in dioxane (0.50 mL, 4 M, 2.0 mmol). After 18 hours, evaporate the reaction mixture in vacuo to give a residue. Triturate the residue with diethyl ether and stir to give a solid. Repeatedly, decant and add diethyl ether. Collect the solid and dry to give the title compound.

Combine 1-((S)-α-methylbenzyl)-3-(2-(4-(1-(2-ethoxyethyl)-1H-benzimidazol-2-yl)[1,4]diazepan-1-yl)ethyl)-3-(4-fluorophenylmethyl)-2-oxopyrrolidine (lower R$_f$ diastereomer) (0.74 g, 1.18 mmol) and methanol (25 mL). Add a solution of hydrochloric acid in dioxane (0.74 mL, 4 M, 2.94 mmol). After 18 hours, evaporate the reaction mixture invacuo to give a residue. Triturate the residue with diethyl ether and stir to give a solid. Repeatedly, decant and add diethyl ether. Collect the solid and dry to give the title compound.

EXAMPLE 77
1-(α-Methylbenzyl)-3-(2-(4-(1-(2ethoxyethyl)-1H-benzimidazol-2-yl)[1,4]diazepan-1-1-yl)ethyl)-3-phenylpyrrolidine

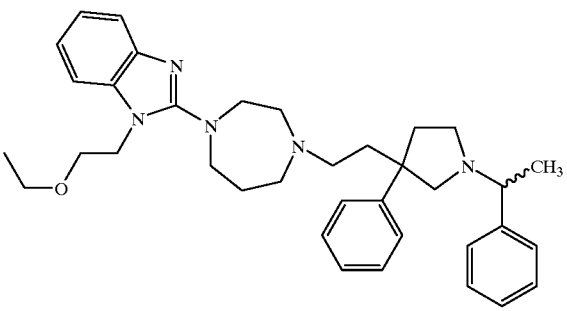

77.1 Synthesis 1-(α-methylbenzy-3-(2-(4-(1-(2-ethoxyethyl)-1H-benzimidazol-2-yl)[1,4]diazepan-1-yl)ethyl)-3-phenylpyrrolidine According to the method of *J. Am. Chem. Soc.*, 93, 2897 (1971), combine acetophenone (10 mmol) and 3-(2-(4-(1-(2-ethoxyethyl)-1H-benzimidazol-2-yl)([1,4]diazepan-1-yl)ethyl)-3-phenylpyrrolidine hydrochloric acid salt (prepared from (−)-3-phenyl-3-(2-hydroxyethyl)pyrrolidine (R,R)-di-p-anisoyltartaric acid salt) (10 mmol) in methanol (100 mL). Add bromocreosol green (0.5% by weight in methanol, 1 drop). Add dropwise, a solution of sodium cyanoborohydride (10 mL, 1M in tetrahydrofuran, 10 mmol) and at the same time maintain the pH of the reaction mixture, as indicated by a yellow color for the indicator, by the addition of a 5 M solution of hydrochloric acid in methanol. When the reaction is complete, concentrate the reaction mixture in vacuo to obtain a residue. Dilute the residue with ethyl acetate and extract with water. Separate the layers, dry the organic layer over MgSO$_4$, filter, and evaporate in vacuo to give the title compound.

EXAMPLE 78
(R)-1-(2-Methoxy-5-(1H-tetrazol-1-yl)benzoyl-3-(2-(4-(1-(2-ethoxyethyl)-1H-benzimidazol-2-yl)[1,4]diazepan-1-yl)ethyl)-3-(3,4-dichlorophenyl)pyrrolidine

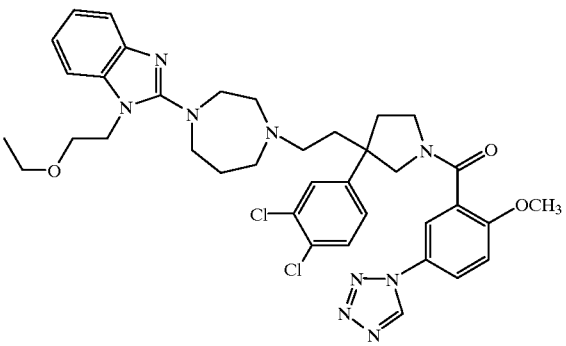

78.1 Synthesis of (S)-1-(2-methoxy-5-(1H-tetrazol-1-yl)benzoyl)-3-(3,4-dichlorphenyl)-3-(2-hydroxyethyl)pyrrolidine Combine (S)-3-(3,4-dichlorophenyl)-3-(2-hydroxyethyl)pyrrolidine (R,R)-di-p-anisoyltartaric acid salt (1.20 g, 1.77 mmol) and sodium bicarbonate (0.75 g, 9 mmol) in acetone/water (5 mL/5 mL). Cool in an ice bath. Add 2-methoxy-5-(1H-tetrazol-1-yl)benzoyl chloride (0.37 g, 1.6 mmol) in acetone (20 mL). After 30 minutes, warm to ambient temperature. After 5 hours, filter the reaction mixture and extract the filtrate with ethyl acetate. Extract the organic layer with a saturated aqueous sodium. bicarbonate solution and then brine. Dry the organic layer over $MgSO_4$, filter, and evaporate in vacuo to give residue. Chromatograph the residue on silica gel eluting sequentially with ethyl acetate, 3% methanol/dichloromethane, and then 6% methanol/dichloromethane to give the title compound: $R_f$=0.38 (silica gel, 6% methanol/dichloromethane).

78.2 Synthesis of (S)-1-(2-methoxy-5-(1H-tetrazol-1-yl) benzoyl)-3-(3,4-dichlorophenyl)-3-(2-methanesulfonyloxyethyl)pyrrolidine Prepare by the method of Example 2.5.2 using (S)-1-(2-methoxy-5-(1H-tetrazol-1-yl)benzoyl)-3-(3,4-dichlorophenyl)-3-(2-hydroxyethyl)pyrrolidine (0.6 g, 1.3 mmol) and methanesulfonyl chloride (0.12 mL, 1.2 mmol) to give the title compound: $R_f$=0.15 (silica gel, ethyl acetate).

78.3 Synthesis of (R)-1-(2-methoxy-5-(1H-tetrazol-1-yl) benzoyl)-3-(2-(4-(1-(2-ethoxyethyl)-1H-benzimidazol-2-yl) [1,4]diazepan-1-yl)ethyl)-3-(3,4-dichlorophenyl)pyrrolidine Prepare by the method of Example 47.3 using (S)-1-(2-methoxy-5-(1H-tetrazol-1-yl)benzoyl)-3-(3,4-dichlorophenyl)-3-(2-methanesulfonyloxyethyl)pyrrolidine and 4-(1-(2-ethoxyethyl)-1H-benzimidazol-2-yl)[1,4] diazepane hydriodic acid salt to give the title compound.

PREPARATION 35
2-Methoxy-5-(methylthiomethyl)benzoic acid

Combine methyl 2-methoxy-5-chloromethylbenzoate (5 mmol) and dimethylformamide (10 mL). Cool in an ice bath and add sodium thiomethoxide (15 mmol). Heat to 75° C. After 5.5 hours, partition the reaction mixture between water and ethyl acetate. Extract the organic layer with water, dry over $Na_2SO_4$, filter, and concentrate in vacuo to give methyl 2-methoxy-5-(methylthiomethyl)benzoate.

Hydrolyze by the method of Preparation 22 to give the title compound.

EXAMPLE 79
1-(2-Methoxy-5-(methylthiomethylbenzoyl)-3-(2-(4-(1-(2-ethoxyethyl)-1H-benzimidazol-2-yl)[1,4]diazepan-1-yl) ethyl)-3-phenylpyrrolidine

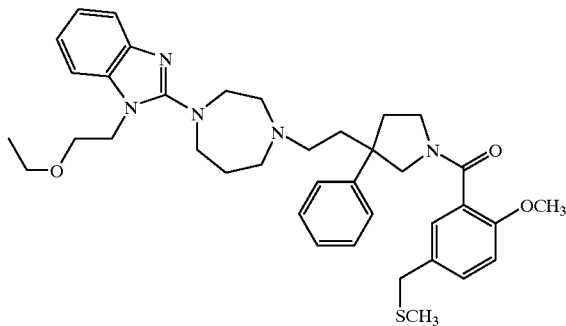

79.1 Synthesis of 1-(2-methoxy-5-(methylthiomethyl) benzoyl)-3-(2-(4-(1-(2-ethoxyethyl)-1H-benzimidazol-2-yl) [1,4]diazepan-1-yl)ethyl)-3-phenylpyrrolidine Prepare by the method of Example 56.1 using 2-methoxy-5-(methylthiomethyl)benzoic acid and 3-(2-(4-(1-(2-ethoxyethyl)-1H-benzimidazol-2-yl)[1,4]diazepan-1-yl) ethyl)-3-phenylpyrrolidine hydrochloric acid salt (prepared from (–)-3-phenyl-3-(2-hydroxyethyl)pyrrolidine (R,R)-di-p-anisoyltartaric acid salt) to give the title compound.

PREPARATION 36
2-Methoxy-5-(methylsulfinylmethyl)benzoic acid

Prepare by the method of Preparation 22 using methyl 2-methoxy-5-(methylthiomethyl)benzoate to give the title compound.

EXAMPLE 80
1-(2-Methoxy-5-(methylsulfinylmethyl)benzoyl)-3-(2-(4-(1-(2-ethoxyethyl)-1H-benzimidazol-2-yl)[1,4]diazepan-1-yl)ethyl)-3-phenylpyrrolidine

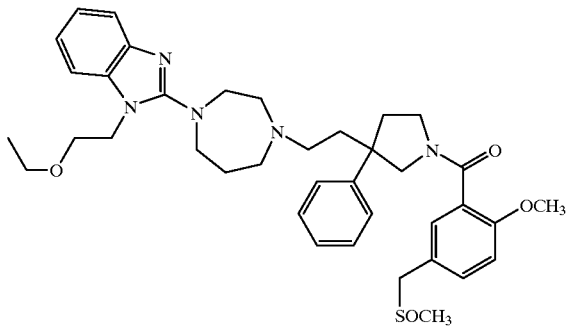

80.1 Synthesis of 1-(2-methoxy-5-(methylsulfinylmethyl) benzoyl)-3-(2-(4-(1-(2-ethoxyethyl)-1H-benzimidazol-2-yl) [1,4]diazepan-1-yl)ethyl)-3-phenylpyrrolidine Prepare by the method of Example 56.1 using 2-methoxy-5-(methylsulfinylmethyl)benzoic acid and 3-(2-(4-(1-(2-ethoxyethyl)-1H-benzimidazol-2-yl)[1,4]diazepan-1-yl) ethyl)-3-phenylpyrrolidine hydrochloric acid salt (prepared from (–)-3-phenyl-3-(2-hydroxyethyl)pyrrolidine (R,R)-di-p-anisoyltartaric acid salt) to give the title compound.

PREPARATION 37
2-Methoxy-5-(methylsulfonylmethyl)benzoic acid

Prepare by the method of Preparation 23 using methyl 2-methoxy-5-(methylthiomethyl)benzoate to give the title compound.

EXAMPLE 81
1-(2-Methoxy-5-(methylsulfonylmethyl)benzoyl)-3-(2-(4-(1-(2-ethoxyethyl)-1H-benzimidazol-2-yl)[1,4]diazepan-1-yl)ethyl)-3-phenylpyrrolidine

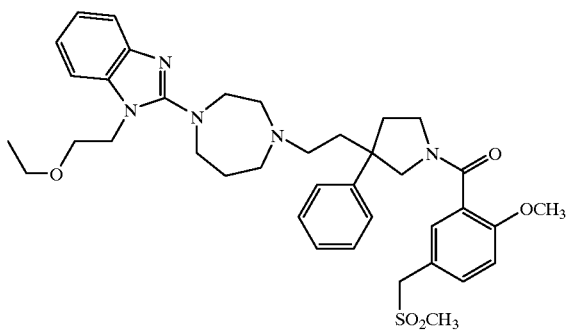

81.1 Synthesis of 1-(2-methoxy-5-(methylsulfonylmethyl) benzoyl)-3-(2-(4-(1-(2-ethoxyethyl)-1H-benzimidazol-2-yl) [1,4]diazepan-1-yl)ethyl)-3-phenylpyrrolidine Prepare by the method of Example 56.1 using 2-methoxy-5-(methylsulfonylmethyl)benzoic acid and 3-(2-(4-(1-(2-ethoxyethyl)-1H-benzimidazol-2-yl)[1,4]diazepan-1-yl) ethyl)-3-phenylpyrrolidine hydrochloric acid salt (prepared from (–)-3-phenyl-3-(2-hydroxyethyl)pyrrolidine (R,R)-di-p-anisoyltartaric acid salt) to give the title compound.

PREPARATION 38
2-Methoxy-5-(4H-triazol-4-yl)benzoic acid

According to the method of *J. Chem. Soc.* (C), 1664 (1967), combine methyl 2-methoxy-5-aminobenzoate (2.0 g, 11 mmol), N,N-dimethylformamide azine (1.56 g, 11 mmol), p-toluenesulfonic acid (190 mg) in toluene (25 mL). Fit the reaction vessel with a gas inlet such that the head space of the vessel is swept with argon and scrub the effluent through dilute aqueous hydrochloric acid solution. Heat to reflux. After 20 hours, concentrate the reaction mixture in vacuo to give a residue. Partition the residue between dichloromethane and a saturated aqueous sodium bicarbonate solution. Extract the aqueous layer twice with dichloromethane. Combine the organic layers, dry over $MgSO_4$, filter, and evaporate in vacuo to give a residue. Chromatograph the residue on silica gel eluting sequentially with 70% ethyl acetate/dichloromethane and then 5% methanol/dichloromethane to give a residue. Recrystallize the residue form ethyl acetate/hexane to give methyl 2-methoxy-5-(4H-triazol-4-yl)benzoate: mp; 191–195.5° C.

Hydrolyze methyl 2-methoxy-5-(4H-triazol-4-yl) benzoate by the method of Preparation 11 to give the title compound.

Alternately, according to the method of *J. Med. Chem.*, 21, 1100 (1978), combine methyl 2-methoxy-5-aminobenzoate (1.8 g, 10 mmol), diformyl hydrazine (0.97 g, 11 mmol), and phosphorous pentoxide (1.84 g, 13 mmol). Heat to 160° C. After 1.5 hours, cool the reaction mixture and add a saturated aqueous solution of sodium bicarbonate. Extract three times with dichloromethane. Dry the combined organic layers over $MgSO_4$, filter, and evaporate in vacuo to give a residue. Chromatograph the residue on silica gel eluting sequentially with 40% ethyl acetate/dichloromethane and then 5% methanol/dichloromethane to give methyl 2-methoxy-5-(4H-triazol-4-yl)benzoate: mp; 179–182° C.

Hydrolyze 2-methoxy-5-(4H-triazol-4-yl)benzoate by the method of Preparation 11 to give the title compound.

EXAMPLE 82
1-(2-Methoxy-5-(4H-triazol-4-yl)benzoyl)-3-(2-(4-(1-(2-ethoxyethyl)-1H-benzimidazol-2-yl)[1,4]diazepan-1-yl)ethyl)-3-phenylpyrrolidine

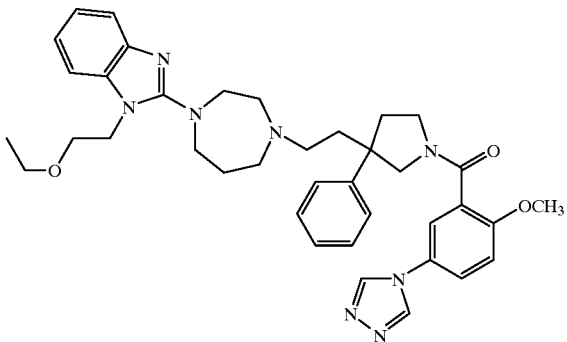

82.1 Synthesis of 1-(2-methoxy-5-(4H-triazol-4-yl)benzoyl)-3-(2-(4-(1-(2-ethoxyethyl)-1H-benzimidazol-2-yl)[1,4]diazepan-1-yl)ethyl)-3-phenylpyrrolidine Prepare by the method of Example 56.1 using 2-methoxy-5-(4H-triazol-4-yl)benzoic acid and 3-(2-(4-(1-(2-ethoxyethyl)-1H-benzimidazol-2-yl)[1,4]diazepan-1-yl)ethyl)-3-phenylpyrrolidine hydrochloric acid salt (prepared from (−)-3-phenyl-3-(2-hydroxyethyl)pyrrolidine (R,R)-di-p-anisoyltartaric acid salt) to give, after chromatography on silica gel eluting sequentially with 10% methanol/ethyl acetate and then 50% methanol/ethyl acetate, the title compound.

82.2 Synthesis of 1-(2-methoxy-5-4H-triazol-4-yl)benzoy)-3-(2-(4-(1-(2-ethoxyethyl)-1H-benzimidazol-2-yl)[1,4]diazepan-1-yl)ethyl)-3-phenylpyrrolidine hydrochloric acid salt Combine 1-(2-methoxy-5-(4H-triazol-4-yl)benzoyl)-3-(2-(4-(1-(2-ethoxyethyl)-1H-benzimidazol-2-yl)[1,4]diazepan-1-yl)ethyl)-3-phenylpyrrolidine (0.26 g, 0.38 mmol) and methanol (8 mL). Add a solution of hydrochloric acid in dioxane (0. 19 mL, 4 M, 0.77 mmol). After 18 hours, evaporate in vacuo and then repeatedly add dichloromethane (about 15 mL), and evaporate in vacuo to give a solid. Combine the solid dichloromethane (40 mL) and evaporate until a solid begins to form and then add diethyl ether to give a solid. Collect the solid by filtration and dry to give the title compound: mp; 176–190° C. (dec).

PREPARATION 39
2-Methoxy-5-acetamidobenzoic acid

Combine methyl 2-methoxy-5-aminobenzoate (2.0 g, 11 mmol), pyridine, 2.8 mL, 35 mmol), and acetic anhydride (3.2 mL, 34 mmol) in tetrahydrofuran (50 mL). After 20 hours, concentrate the reaction mixture in vacuo to remove most of the tetrahydrofuran, partition between ethyl acetate and water. Separate the layers and extract the aqueous layer twice with ethyl acetate. Combine the organic layers, extract with brine, dry over $MgSO_4$, filter, and evaporate in vacuo to give a residue. Crystallize the residue from ethyl acetate/cyclohexane to give methyl 2-methoxy-5-acetamidobenzoate.

Alternately, combine methyl 2-methoxy-5-aminobenzoate (1.5 g, 8.3 mmol) and dichloromethane (25 mL). Cool in an ice bath. Add N,N-diisopropylethylamine (3.2 mL, 18.2 mmol), and acetyl chloride (0.62 mL, 9.7 mmol). Warm to ambient temperature. After 4 hours, dilute the reaction mixture with dichloromethane and extract three times with half saturated aqueous ammonium chloride solution. Dry the organic layer over $Na_2SO_4$, filter, and evaporate in vacuo to give a residue. Chromatograph the residue on silica gel eluting with 3% methanol/dichloromethane/ 0.1% concentrated aqueous ammonia to give methyl 2-methoxy-5-acetamidobenzoate: mp; 132–134° C. Elemental Analysis calculated for $C_{11}H_{13}NO_4$: C, 59.19; H, 5.87. Found C, 59.04; H, 5.86.

Hydrolyze methyl 2-methoxy-5-acetamidobenzoate by the method of Preparation 24 to give the title compound: mp; 208–210° C.

EXAMPLE 83
1-(2-Methoxy-5-acetamidobenzoyl)-3-(2-(4-(1-(2-ethoxyethyl)-1H-benzimidazol-2-yl)[1,4]diazepan-1-yl)ethyl)-3-phenylpyrrolidine

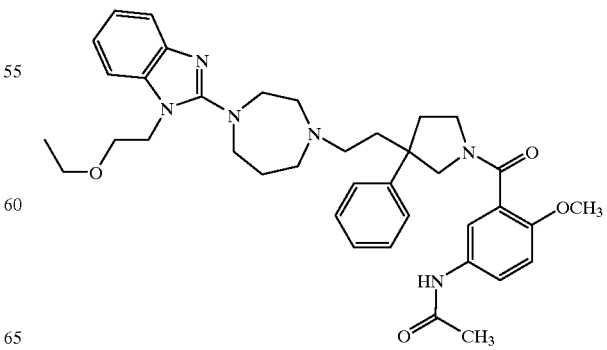

83.1 Synthesis of 1-(2-methoxy-5-acetamidobenzoyl)-3-(2-(4-(1-(2-ethoxyethyl)-1H-benzimidazol-2-yl)[1,4]diazepan-1-yl)ethyl)-3-phenylpyrrolidine Prepare by the method of Example 56.1 using 2-methoxy-5-acetamidobenzoic acid and 3-(2-(4-(1-(2-ethoxyethyl)-1H-benzimidazol-2-yl)[1,4]diazepan-1-yl)ethyl)-3-phenylpyrrolidine hydrochloric acid salt(prepared from (−)-3-phenyl-3-(2-hydroxyethyl)pyrrolidine (R,R)-di-p-anisoyltartaric acid salt) to give the title compound:$R_f$=0.18 (silica gel, 1/1 ethyl acetate/methanol).

83.2 Synthesis of 1-(2-methoxy-5-acetamidobenzoyl)-3-(2-(4-(1-(2-ethoxyethyl)-1H-benzimidazol-2-yl)[1,4]diazepan-1-yl)ethyl)-3-phenylpyrrolidine hydrochloric acid salt Combine 1-(2-methoxy-5-acetamidobenzoyl)-3-(2-(4-(1-(2-ethoxyethyl)-1H-benzimidazol-2-yl)[1,4]diazepan-1-yl)ethyl)-3-phenylpyrrolidine (0.17 g, 0.26 mmol) and dichloromethane/methanol (3/1, 10 mL). Add a solution of hydrochloric acid in dioxane (0.065 mL, 4 M, 0.26 mmol) After 18 hours, evaporate in vacuo to give a residue. Triturate the residue with diethyl ether and stir to give a solid. collect the solid by filtration to give the title compound: mp; 145–150° C.

PREPARATION 40

2-Methoxy-5-(3,5-dimethyl-4H-triazol-4-yl)benzoic acid

Combine methyl 2-methoxy-5-acetamidobenzoate (2.23 g, 10 mmol) and tetrahydrofuran (1000 mL). Add Lawesson's reagent (2.02 g, 5 mmol). After 18 hours, evaporate in vacuo to give a residue. Chromatograph the residue on silica gel eluting with 12% ethyl acetate/dichloromethane to give methyl 2-methoxy-5-thioacetamidobenzoate.

According to the method of *Heterocycles*, 34, 771 (1992), combine methyl 2-methoxy-5-thioacetamidobenzoate (1.00 g, 4.2 mmol) and acetylhydrazine (0.35 g, 4.8 mmol) in n-butanol (8 mL). Heat to reflux. After 18 hours, cool and evaporate in vacuo to give a residue. Chromatograph the residue on silica gel eluting sequentially with 30% ethyl acetate/dichloromethane and then 5% methanol/dichloromethane to give a residue. Recrystallize the residue from ethyl acetate/hexame to give methyl 2-methoxy-5-(3,5-dimethyl-4H-triazol-4-yl)benzoate: mp; 180–182° C.

Hydrolyze the methyl 2-methoxy-5-(3,5-dimethyl-4H-triazol-4-yl)benzoate by the method of Preparation 11 to give the title compound: mp; 206–207° C.

EXAMPLE 84

1-(2-Methoxy-5-(3,5-dimethyl-4H-triazol-4-yl)benzoyl)-3-(2-(4-(1-(2-ethoxyethyl)-1H-benzimidazol-2-yl)[1,4]diazepan-1-yl)ethyl)-3-phenylpyrrolidine

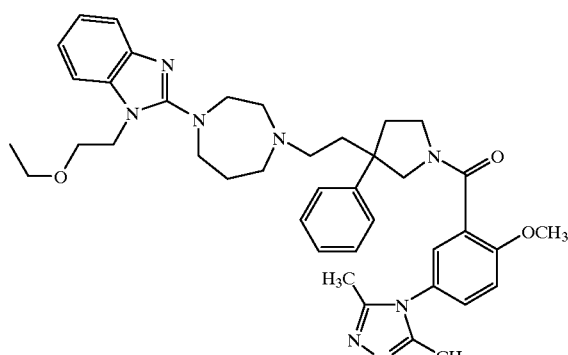

84.1.1 Synthesis of 1-(2-methoxy-5-(3,5-dimethyl-4H-triazol-4-yl)benzoyl)-3-(2-(4-(1-(2-ethoxyethyl)-1H-benzimidazol-2-yl)[1,4]diazepan-1-yl)ethyl)-3-phenylpyrrolidine Prepare by the method of Example 56.1 using 2-methoxy-5-(3,5-dimethyl-4H-triazol-4-yl)benzoic acid and 3-(2-(4-(1-(2-ethoxyethyl)-1H-benzimidazol-2-yl)[1,4]diazepan-1-yl)ethyl)-3-phenylpyrrolidine hydrochloric acid salt (prepared from (−)-3-phenyl-3-(2-hydroxyethyl)pyrrolidine (R,R)-di-p-anisoyltartaric acid salt) to give the title compound.

84.1.2 Synthesis of 1-(2-methoxy-5-(3,5-dimethyl-4H-triazol-4-yl)benzoyl)-3-(2-(4-(1-(2-ethoxyethyl)-1H-benzimidazol-2-yl)[1,4]diazepan-1-yl)ethyl)-3-phenylpyrrolidine Combine 3-(2-(4-(1-(2-ethoxyethyl)-1H-benzimidazol-2-yl)[1,4]diazepan-1-yl)ethyl)-3-phenylpyrrolidine hydrochloric acid salt (prepared from (−)-3-phenyl-3-(2-hydroxyethyl)pyrrolidine (R,R)-di-p-anisoyltartaric acid salt) (0.64 g, 1.2 mmol) and dichloromethane (12 mL). Add 2-methoxy-5-(3,5-dimethyl-4H-triazol-4-yl)benzoic acid (0.3 g, 1.2 mmol), 1-hydroxybenzotriazole hydrate (0.17 g, 1.23 mmol), 1-ethyl-3-(3-dimethylaminopropyl) carbodiimide hydrochloride (0.29 g, 1.5 mmol), and triethylamine (0.34 mL, 2.4 mmol). After 6 days, dilute the reaction mixture with dichloromethane and extract with a saturated aqueous sodium bicarbonate solution and then brine, dry the organic layer over $MgSO_4$, filter, and concentrate in vacuo to give a residue. Chromatograph the residue on silica gel eluting sequentially with 10% methanol/dichloromethane and then 20% methanol/dichloromethane to give a residue. Combine the residue and dichloromethane, extract with water and then brine, dry over $Na_2SO_4$, and evaporate in vacuo to give the title compound.

84.2 Synthesis of 1-(2-methoxy-5-(3,5-dimethyl-4H-triazol-4-yl)benzoyl)-3-(2-(4-(1-(2-ethoxyethyl)-1H-benzimidazol-2-yl)[1,4]diazepan-1-yl)ethyl)-3-phenylpyrrolidine hydrochloric acid salt Prepare by the method of Example 82.2 using 1-(2-methoxy-5-(3,5-dimethyl-4H-triazol-4-yl)benzoyl)-3-(2-(4-(1-(2-ethoxyethyl)-1H-benzimidazol-2-yl)[1,4]diazepan-1-yl)ethyl)-3-phenylpyrrolidine to give the title compound.

PREPARATION 41

2-Methoxy-5-methylsulfonamidobenzoic acid

Combine methyl 2-methoxy-5-aminobenzoate (1.5 g, 8.3 mmol) and dichloromethane (25 mL). Cool in an ice bath. Add N,N-diisopropylethylamine (3.17 mL, 18.2 mmol) and methanesulfonyl chloride (0.71 mL, 9.1 mmol). After 30 minutes, warm to ambient temperature. After 4 hours, dilute the reaction mixture with dichloromethane and extract three times with a 1 M aqueous hydrochloric acid solution and then brine. Dry the organic layer over $Na_2SO_4$, filter, and evaporate in vacuo to give a residue.

Chromatograph the residue on silica gel eluting with 3% methanol/dichloromethane/0.1% concentrated aqueous ammonia to give methyl 2-methoxy-5-methylsulfonamidobenzoate: mp; 82–83° C. Elemental Analysis calculated for $C_{10}H_{13}NO_5S$: C, 46.32; H. 5.05; N, 5.40. Found C, 46.44; H, 4.96; N, 5.19.

Combine methyl 2-methoxy-5-methylsulfonamidobenzoate (1.0 g, 3.86 mmol) and lithium hydroxide (93 mg, 3.86 mmol) in tetrahydrofuran/water (50 mL/10 mL). After 18 hours, add lithium hydroxide (100 mg) and heat to reflux. After 1 hour, cool to ambient temperature and evaporate to remove most of the tetrahydrofuran. Dilute the evaporated reaction mixture with water (about 70 mL) and acidify to pH of about 1 using a 1 M aqueous hydrochloric acid solution. Evaporate to dryness and triturate with dichloromethane (200 mL). Filter and evaporate the filtrate to give the title compound: mp; 160–163° C.

EXAMPLE 85
1-(2-Methoxy-5-methylsulfonamidobenzoyl)-3-(2-(4-(1-(2-ethoxyethyl)-1H-benzimidazol-2-yl)[1,4]diazepan-1-yl)ethyl)-3-phenylpyrrolidine

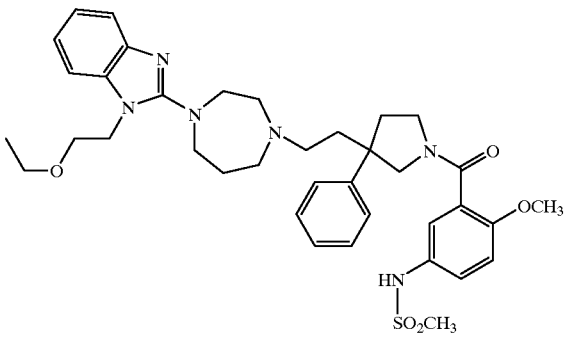

85.1 Synthesis of 1-(2-methoxy-5-methylsulfonamidobenzoyl)-3-(2-(4-(1-(2-ethoxyethyl)-1H-benzimidazol-2-yl)[1,4]diazepan-1-yl)ethyl)-3-phenylpyrrolidine Prepare by the method of Example 56.1 using 2-methoxy-5-methylsulfonamidobenzoic acid and 3-(2-(4-(1-(2-ethoxyethyl)-1H-benzimidazol-2-yl)[1,4]diazepan-1-yl)ethyl)-3-phenylpyrrolidine hydrochloric acid salt (prepared from (−)-3-phenyl-3-(2-hydroxyethyl)pyrrolidine (R,R)-di-p-anisoyltartaric acid salt) to give the title compound.

PREPARATION 42
2-Methoxy-5-fluorobenzoic acid

Combine 5-fluorosalicylic acid (5.00 g, 32 mmol), finely ground potassium carbonate (15.0 g, 108 mmol), and methyl iodide (34.2 g, 240 mmol) in acetone (100 mL). Heat to reflux. After 18 hours, cool, filter, and evaporate in vacuo to give a residue. Combine the residue and dichloromethane and extract twice with water, dry over $Na_2SO_4$, filter, and concentrate in vacuo to give methyl 2-methoxy-5-fluorobenzoate. Elemental Analysis calculated for $C_9H_9FO_3$: C, 58.70; H, 4.93. Found C, 58.72; H, 5.12.

Hydrolyze methyl 2-methoxy-5-fluorobenzoate by the method of Preparation 11 to give the title compound.

EXAMPLE 86
1-(2-Methoxy-5-fluorobenzoyl)-3-(2-(4-(1-(2-ethoxyethyl)-1H-benzimidazol-2-yl)[1,4]diazepan-1-yl)ethyl)-3-phenylpyrrolidine

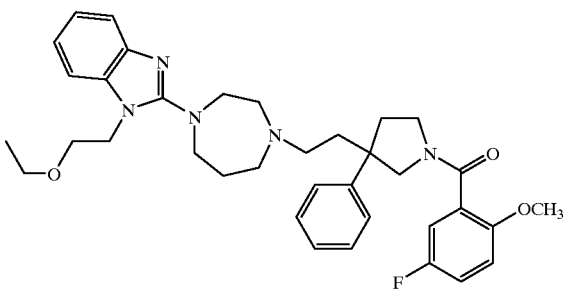

86.1 Synthesis of 1-(2-methoxy-5-fluorobenzoyl)-3-(2-(4-(1-(2-ethoxyethyl)-1H-benzimidazol-2-yl)[1,4]diazepan-1-yl)ethyl)-3-phenylpyrrolidine Prepare by the method of Example 56.1 using 2-methoxy-5-fluorobenzoic acid and 3-(2-(4-(1-(2-ethoxyethyl)-1H-benzimidazol-2-yl)[1,4]diazepan-1-yl)ethyl)-3-phenylpyrrolidine hydrochloric acid salt (prepared from (−)-3-phenyl-3-(2-hydroxyethyl)pyrrolidine (R,R)-di-p-anisoyltartaric acid salt) to give the title compound.

PREPARATION 43
3,4-Dimethoxy-5-ethoxybenzoic acid

Combine 3,4-dimethoxy-5-hydroxybenzoic acid (1.0 g, 5.0 mmol), potassium carbonate (4.2 g, 30.2 mmol), and ethyl iodide (3.9 g, 25.2 mmol) in acetone (50 mL). Heat to reflux. After 24 hours, cool, add methanol (25 mL) and water (5 mL) After 18 hours, concentrate in vacuo to give a residue. Combine the residue and ethanol (50 mL) and potassium hydroxide (0.56 g, 10 mmol). After 18 hours, concentrate in vacuo to give a residue. Partition the residue between ethyl acetate and a 1 M aqueous solution of hydrochloric acid. Extract the aqueous layer three times with ethyl acetate. Combine the organic layers, dry over $Na_2SO_4$, filter, and concentrate in vacuo to give a residue. Triturate the residue to give a solid. Collect the solid to give the title compound.

EXAMPLE 87
1-(3,4-Dimethoxy-5-ethoxybenzoyl)-3-(2-(4-(1-(2-ethoxyethyl)-1H-benzimidazol-2-yl)[1,4]diazepan-1-yl)ethyl)-3-phenylpyrrolidine

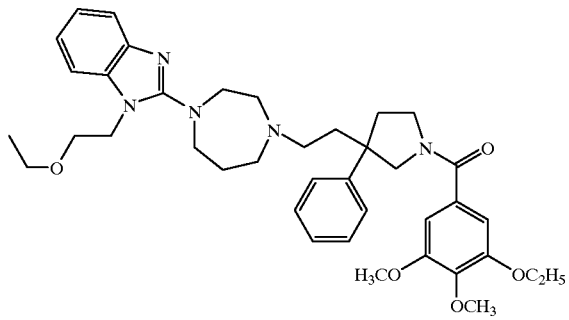

Prepare by the method of Example 56.1 using 3,4-dimethoxy-5-ethoxybenzoic acid and 3-(2-(4-(1-(2-ethoxyethyl)-1H-benzimidazol-2-yl)[1,4]diazepan-1-yl)ethyl)-3-phenylpyrrolidine hydrochloric acid salt (prepared from (−)-3-phenyl-3-(2-hydroxyethyl)pyrrolidine (R,R)-di-p-anisoyltartaric acid salt) to give the title compound.

EXAMPLE 88
(S)-1-(3 4,5-Trimethoxybenzoyl)-3-(2-(4-(1-2-ethoxyethyl)-1H-benzimidazol-2-yl)[1,4]diazepan-1-yl)ethyl-3-(3,4-dichlorophenyl)pyrrolidine

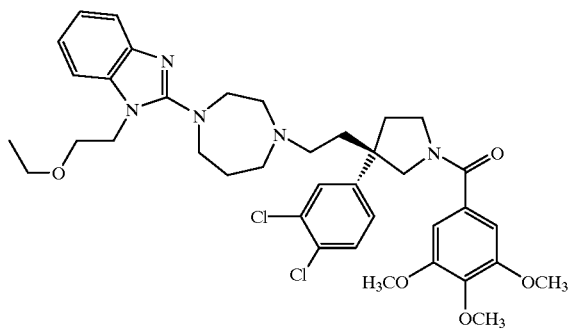

88.1 Resolution of (R)-(+)-3-(3,4-dichlorophenyl)-3-(2-hydoxyethyl)pyrrolidine (S,S)-di-p-anisoyltartaric acid salt Combine (S,S)-di-p-anisoyltartaric acid (14.77 g, 35 mmol), water (200 mL) and methanol (200 mL). Heat to reflux. Add dropwise, a solution of 3-(3,4-dichlorophenyl)-3-(2-hydroxyethyl)pyrrolidine (18.36 g, 70 mmol) in methanol (135 mL). After 1.5 hours, add water (135 mL) and slowly cool to ambient temperature to give a solid. Filter the solid that forms and rinse with water to give the title compound: mp; 201–202° C. (dec). Analysis by HPLC, as described in Example 5.1.1 indicates an enantiomeric excess of 99.9%, (99.9% ee). $[\alpha]^2{}_D{}^0 = +17.9°$ (c=1.00, dimethylsulfoxide)

88.2 Synthesis of (R)-1-(3,4,5-trimethoxybenzoyl)-3-(3,4-dichlorophenyl)-3-(2-hydroxyethyl)pyrrolidine Prepare by the method of Example 5.2.2 using (R)-(+)-3-(3,4-dichlorophenyl)-3-(2-hydroxyethyl)pyrrolidine (S,S)-di-p-anisoyltartaric acid salt to give the title compound: $R_f$=0.29 (silica gel, 6% methanol/dichloromethane).

88.3 Synthesis of (R)-1-(3,4,5-trimethoxybenzoyl)-3-(3,4-dichlorophenyl)-3-(2-methanesulfonyloxyethyl)pyrrolidine Prepare by the method of Example 2.5.2 using (R)-1-(3,4,5-trimethoxybenzoyl)-3-(3,4-dichlorophenyl)-3-(2-hydroxyethyl)pyrrolidine to give the title compound: $R_f$=0.33 (silica gel, ethyl acetate) and $R_f$=0.44 (silica gel, 6% methanol/dichloromethane).

88.4 Synthesis of (S)-1-(3,4,5-trimethoxybenzoyl)-3-(2-(4-(1-(2-ethoxyethyl)-1H-benzimidazol-2-yl)[1,4]diazepan-1-yl)ethyl)-3-(3,4-dichlorophenyl)pyrrolidine Prepare by the method of Example 1.6 using (R)-1-(3,4,5-trimethoxybenzoyl)-3-(3,4-dichlorophenyl)-3-(2-methanesulfonyloxyethyl)pyrrolidine and 4-(1-(2-ethoxyethyl)-1H-benzimidazol-2-yl)[1,4]diazepane to give the title compound.

PREPARATION 44.1
1-(2-(2,2,2-Trifluoroethoxy)ethyl)-1H-benzimidazol-2-yl)[1,4]diazepane Hydriodic acid salt According to the procedure of *Tet. Let.*, 35, 5997–6000 (1994), combine 1-hydroxy-2-tetrahydropyran-2-yloxyethane (*J. Chem. Soc. Chem. Commun.*, 1766 (1990)) (5.0 mmol), 1,1-diethylazodicarboxylate (10 mmol), 2,2,2-trifluoroethanol (100 mmol), and tributylphosphine (10 mmol) in benzene (100 mL). After 6 hours, concentrate in vacuo to give a residue. Chromatograph on silica gel to give 2-tetrahydropyran-2-yloxyethyl 2,2,2-trifluorethyl ether.

Combine 2-tetrahydropyran-2-yloxyethyl 2,2,2-trifluoroethyl ether (2 mmol) and magnesium bromide (6 mmol) in diethyl ether (10 mL). After 24 hours, extract with water and then brine. Dry the organic layer over $Na_2SO_4$, filter, and concentrate in vacuo to give 2-hydroxyethyl 2,2,2-trifluoroethyl ether.

Combine 2-hydroxyethyl 2,2,2-trifluoroethyl ether (0.5 mmol) and N,N-diisopropylethylamine (1 mmol) in dichloromethane (20 mL). Cool in a ice-bath. Add dropwise, methanesulfonyl chloride (0.6 mmol). After 2 hours, extract with 1 M hydrochloric acid solution and 5% sodium bicarbonate solution. Dry the organic layer over $MgSO_4$, filter, and concentrate in vacuo to give 2-methanesulfonyloxyethyl 2,2,2-trifluoroethyl ether.

Combine 1-(t-butoxycarbonyl)-4-(1H-benzimidazol-2-yl)[1,4]diazepane (0.5 g, 1.6 mmol), tetrahydrofuran (10 mL), and dimethylformamide (10 mL). Add sodium hydride (0.13 g, 3.2 mmol). After 2 hours, add 2-methanesulfonyloxyethyl 2,2,2-trifluoroethyl ether (6.0 mmol). After 18 hours, heat to 70° C. After 4 hours, cool to ambient temperature and partition the reaction mixture between water and dichloromethane. Separate the layers, dry the organic layer over $Na_2SO_4$, filter, and evaporate in vacuo to give 1-(t-butoxycarbonyl)-4-(1-(2-(2,2,2-triflurorethoxy)ethyl)-1H-benzimidazol-2-yl)[1,4]diazepane.

Combine 1-(t-butoxycarbonyl)-4-(1-(2-(2,2,2-triflurorethoxy)ethyl)-1H-benzimidazol-2-yl)[1,4]diazepane (0.5 mmol) and dichloromethane (10 mL). Add hydriodic acid (0.18 mL, 57%, 1.0 mmol) and warm to 40° C. After 8 hours, cool to ambient temperature and evaporate in vacuo to give the title compound.

PREPARATION 44.2
1-(2,2,2-Trifluoroethoxy)ethyl)-1H-benzimidazol-2-yl)[1,4]diazepane Hydriodic acid salt According to the procedure of *Tet. Let.*, 35, 5997–6000 (1994), combine 1-(t-butoxycarbonyl)-4-(1-(2-hydroxyethyl)-1H-benzimidazol-2-yl)[1,4]diazepane (0.0.66 g, 1.81 mmol) and 1,1-diazodicarbonyl dipiperidine (0.5 g, 2 mmol) in toluene (20 mL). Add tributylphosphine (0.5 mL, 2 mmol). After 10 minutes add 2,2,2-trifluoroethanol (0.7 mL, 10 mmol). Heat to 55° C. After 6 hours, cool to ambient temperature. After 18 hours, evaporate in vacuo to give a residue. Chromatograph the residue on silica gel eluting sequentially with hexane, 5% ethyl acetate/hexane, 10% ethyl acetate/hexane, 12% ethyl acetate/hexane, and then 30% ethyl acetate/hexane to give 1-(t-butoxycarbonyl)-4-(1-(2-(2,2,2-triflurorethoxy)ethyl)-1H-benzimidazol-2-yl)[1,4]diazepane.

Combine 1-(t-butoxycarbonyl)-4-(1-(2-(2,2,2-triflurorethoxy)ethyl)-1H-benzimidazol-2-yl)[1,4]diazepane (0.47 g, 1.07 mmol) and methanol (10 mL). Add hydriodic acid (0.7 mL, 57%, 9.4 mmol). After 4 hours, evaporate in vacuo to give a residue. Combine the residue and diethyl ether and stir to give a solid. After 18 hours, collect the solid by filtration, rinse with diethyl ether, and dry to give the title compound: $R_f$=0.39 (silica gel, dichloromethane/methanol/acetic acid 85/10/5).

EXAMPLE 89
1-(3,4,5-Trimethoxybenzoyl)-3-(2-(4-(1-(2-(2,2,2-triflurorethoxy)ethyl)-1H-benzimidazol-2-yl)[1,4]diazepan-1-yl)ethyl)-3-phenylpyrrolidine

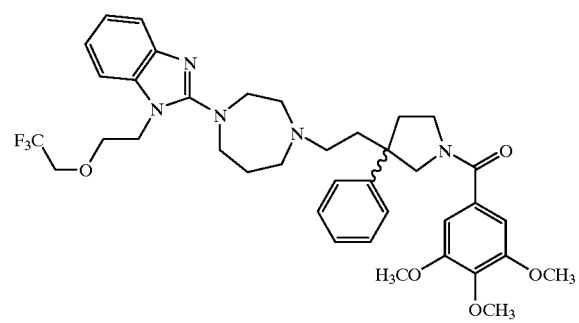

89.1 Synthesis of 1-(3,4,5-trimethoxybenzoyl)-3-(2-(4-(1-(2-(2,2,2-triflurorethoxy)ethyl)-1H-benzimidazol-2-yl)[1,4]diazepan-1-yl)ethyl)-3-phenylpyrrolidine Prepare by the method of Example 45.1 using 1-(3,4,5-trimethoxybenzoyl)-3-phenyl-3-(2-methanesulfonyloxyethyl)pyrrolidine and 4-(1-(2-(2,2,2-triflurorethoxy)ethyl)-1H-benzimidazol-2-yl)[1,4]diazepane hydriodic acid salt to give the title compound.

EXAMPLE 90
1-(3,4,5-Trimethoxybenzoyl)-3-(2-(4-(1-3-methylbut-2-en-1-yl)-1-benzimidazol-2-yl)[1,4]diazepan-1-yl)ethyl)-3-phenylpyrrolidine

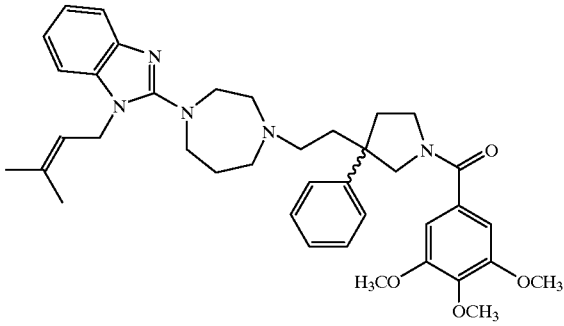

90.1 Synthesis of 1-(3,4,5-trimethoxybenzoyl-3-(2-(4-(1-(3-methylbut-2-en-1-yl)-1H-benzimidazol-2-yl)[1,4]diazepan-1-yl)ethyl)-3-phenylpyrrolidine Prepare by the method of Example 35.1 using 1-(3,4,5-trimethoxybenzoyl)-3-(2-(4-(1H-benzimidazol-2-yl)[1,4]diazepan-1-yl)ethyl)-3-phenylpyrrolidine and 1-chloro-3-methylbut-2-ene to give the title compound.

EXAMPLE 91
1-(3,4,5-Trimethoxybenzoyl)-3-(2-(4-(1-allyl-1H-benzimidazol-2-y)[1,4]diazepan-1-yl)ethyl)-3-phenylpyrrolidine

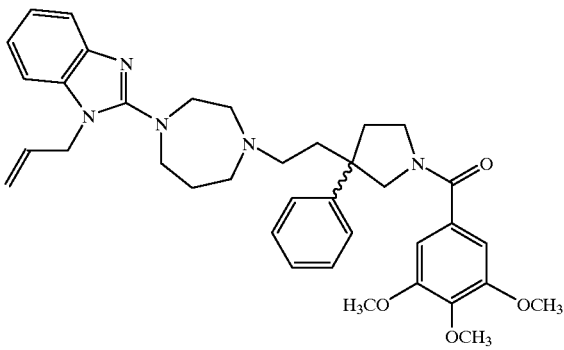

91.1 Synthesis of 1-(3,4,5-trimethoxybenzoyl-3-(2-(4-(1-allyl-1H-benzimidazol-2-yl)[1,4]diazepan-1-yl)ethyl)-3-phenylpyrrolidine Prepare by the method of Example 35.1 using 1-(3,4,5-trimethoxybenzoyl)-3-(2-(4-(1H-benzimidazol-2-yl)[1,4]diazepan-1-yl)ethyl)-3-phenylpyrrolidine and allyl chloride to give the title compound.

PREPARATION 45
2-Methoxy-5-cyanobenzoic acid

Combine methyl $^2$-methoxy-5-formylbenzoate (5.0 g, 25.9 mmol), hydroxylamine hydrochloride (8.55 g, 133 mmol), and sodium acetate (10.25 g, 125 mmol) in ethanol/water (200 mL, 1/1). Heat: to 50° C. After 1 hour, pour the reaction mixture onto ice to give a solid. Collect the solid byfiltration to give methyl $^2$-methoxy-5-formylbenzoate oxime: $R_f$=0.76 (silica gel, 9/1 dichloromethane/methanol).

Combine methyl 2-methoxy-5-formylbenzoate oxime (3.5 g, 16.7 mmol) in dichloromethane (75 mL) and cool in an ice-bath. Add dropwise thionyl chloride (2.0 mL, 27.2 mmol). After 20 minutes, dilute the reaction mixture with dichloromethane and extract with a saturated aqueous solution of sodium bicarbonate and then brine. Dry the organic layer over MgSO$_4$, filter, and concentrate in vacuo to give a residue. Chromatograph the residue on silica gel eluting with 1/1 ethyl acetate/hexane to give methyl 2-methoxy-5-cyanobenzoate Hydrolyze methyl 2-methoxy-5-cyanobenzoate by the method of Preparation 24 using 1.1 equivalents of lithium hydroxide to give the title compound.

EXAMPLE 92
1-(2-Methoxy-5-cyanobenzoyl)-3-(2-(4-(1-(2-ethoxyethyl)-1H-benzimidazol-2-yl)[1,4]diazepan-1-yl)ethyl)-3-phenylpyrrolidine

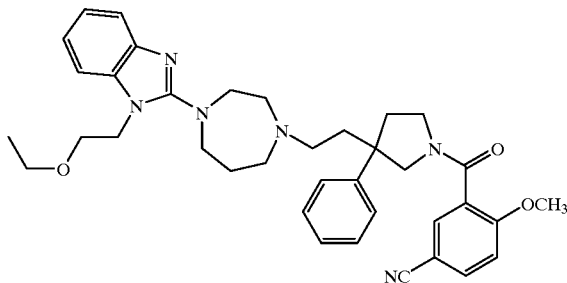

92.1 Synthesis of 1-(2-methoxy-5-cyanobenzoyl)-3-(2-(4-(1-(2-ethoxyethyl)-1H-benzimidazol-2-yl)[1,4]diazepan-1-yl)ethyl-3-phenylpyrrolidine Prepare by the method of Example 56.1 using 2-methoxy-5-cyanobenzoic acid and 3-(2-(4-(1-(2-ethoxyethyl)-1H-benzimidazol-2-yl)[1,4]diazepan-1-yl)ethyl)-3-phenylpyrrolidine hydrochloric acid salt (prepared from (−)-3-(2-hydroxyethyl)-3-phenylpyrrolidine (R,R)-di-p-anisoyltartaric acid salt) to give the title compound.

PREPARATION 46
2-Methoxy-5-(1H-tetrazol-5-yl)benzoic acid

Prepare by the method of Example 70.1 using methyl 2-methoxy-5-cyanobenzoate to give methyl 2-methoxy-5-(1H-tetrazol-5-yl)benzoate: $R_f$=0.21 (silica gel, dichloromethane/methanol 80/20).

Hydrolyze methyl 2-methoxy-5-(1H-tetrazol-5-yl) benzoate by the method of Preparation 11 to give the title compound.

Alternately, combine 2-methoxy-5-(1H-tetrazol-5-yl) benzoate (1.71 g, 7.3 mmol) and an aqueous solution of lithium hydroxide (25 mL, 1 M) in methanol (40 mL). After 18 hours, heat to reflux. After 1 hour, add an aqueous solution of lithium hydroxide (15 mL, 1 M) and continue the reflux. After 15 hours, cool to ambient temperature, acidify with a 1 M aqueous hydrochloric acid solution and extract four times with ethyl acetate and then with dichloromethane. Combine the organic layers, dry over MgSO$_4$, filter and evaporate in vacuo to give a residue. Chromatograph the residue on silica gel eluting sequentially with dichloromethane/methanol 70/30, dichloromethane/methanol 50/50, dichloromethane/methanol 30/70, and then methanol to give the title compound.

EXAMPLE 93
1-(2-Methoxy-5-(1H-tetrazol-5-yl)benzoyl)-3-(2-(4-(1-(2-ethoxyethyl)-1H-benzimidazol-2-yl)[1,4]diazepan-1-yl)ethyl)-3-phenylpyrrolidine

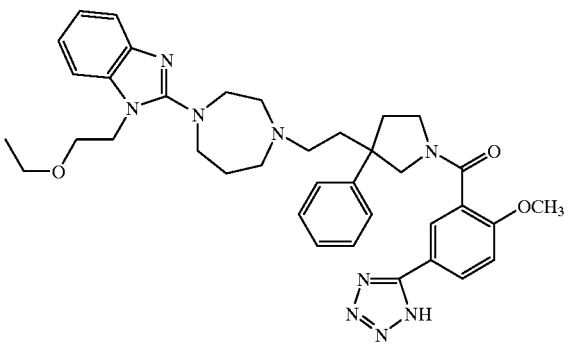

93.1 Synthesis of 1-(2-methoxy-5-(1H-tetrazol-5-yl)benzoyl)-3-(2-(4-(1-(2-ethoxyethyl)-1H-benzimidazol-2-yl)[1,4]diazepan-1-yl)ethyl)-3-phenylpyrrolidine Prepare by the method of Example 56.1 using 2-methoxy-5-(1H-tetrazol-5-yl)benzoic acid and 3-(2-(4-(1-(2-ethoxyethyl)-1H-benzimidazol-2-yl)[1,4]diazepan-1-yl)ethyl)-3-phenylpyrrolidine hydrochloric acid salt (prepared from (−)-3-(2-hydroxyethyl)-3-phenylpyrrolidine (R,R)-di-p-anisoyltartaric acid salt) to give, after chromatography on silica gel eluting sequentially with dichloromethane/methanol/concentrated ammonium hydroxide) 95/5/0.1 dichloromethane/methanol/concentrated ammonium hydroxide) 80/20/0.2, the title compound: $R_f$=0.81 (silica gel, dichloromethane/methanol/concentrated ammonium hydroxide) 90/10/0.1).

93.2 Synthesis of 1-(2-methoxy-5-(1H-tetrazol-5-yl)benzoyl)-3-(2-(4-(1-(2-ethoxyethyl)-1H-benzimidazol-2-yl)[1,4]diazepan-1-yl)ethyl)-3-phenylpyrrolidine hydrochloric acid salt Prepare by the method of Example 69.2 using 1-(2-methoxy-5-(1H-tetrazol-5-yl)benzoyl)-3-(2-(4-(1-(2-ethoxyethyl)-1H-benzimidazol-2-yl)[1,4]diazepan-1-yl)ethyl)-3-phenylpyrrolidine to give the title compound.

EXAMPLE 94
1-(2-Methoxybenzyl)-3-(2-(4-(1-(2-ethoxyethyl)-1H-benzimidazol-2-yl)(1,4)diazepan-1-yl)ethyl)-3-(3,5-di(trifluoromethylphenylmethyl)-2-oxopyrrolidine

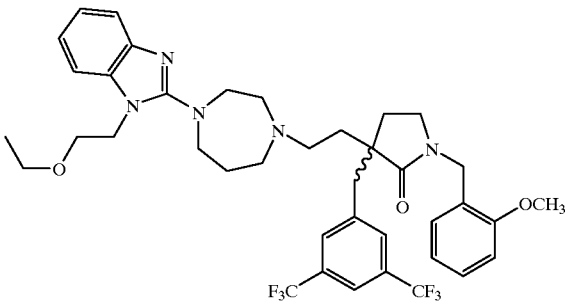

94.1 Synthesis of 1-(2-methoxybenzyl)-3-(3,5-di(trifluoromethyl)phenylmethyl)-2-oxopyrrolidine Combine 1-(2-methoxybenzyl)-2-oxopyrrolidine (2.4 g, 11.7 mmol) and tetrahydrofuran (20 mL). Cool to −78° C. using a dry-ice /acetone bath. Add a solution of sec-butyllithium (9.0 mL, 1.3 M in hexane, 11.7 mmol). After 30 minutes, add a solution of 3,5-di(trifluoromethyl)benzyl bromide (3.6 g, 11.7 mmol) in tetrahydrofuran (1 mL). After 2 hours, add water (10 mL). Separate the layers and extract the aqueous layer three times with ethyl acetate. Dry the combined organic layers over $Na_2SO_4$, filter, and evaporate in vacuo to give a residue. Chromatograph the residue on silica gel eluting with 1/1 ethyl acetate/hexane to give the title compound: $R_f$=0.53 (silica gel, 1/1 ethyl acetate/hexane).

94.2 Synthesis of 1-(2-methoxybenzyl)-3-(3,5-di(trifluoromethyl)phenylmethyl)-3-(2-(t-butyldimethylsilyloxy)ethyl)-2-oxopyrrolidine Combine 1-(2-methoxybenzyl)-3-(3,5-di(trifluoromethyl)phenylmethyl)-2-oxopyrrolidine (4.1 g, 9.5 mmol) and tetrahydrofuran (20 mL). Cool to −78° C. using a dry-ice /acetone bath. Add a solution of sec-butyllithium (7.7 mL, 1.3 M in hexane, 9.9 mmol). After 30 minutes, add 1-iodo-2-(t-butyldimethylsilyloxy)ethane (2.9 g, 10 mmol) in tetrahydrofuran (1 mL). After 2 hours, add water (10 mL). Separate the layers and extract the aqueous layer three times with ethyl acetate. Dry the combined organic layers over $Na_2SO_4$, filter, and evaporate in vacuo to give a residue. Chromatograph the residue on silica gel eluting with 1/4 ethyl acetate/hexane to give the title compound: $R_f$=0.63 (silica gel, 1/4 ethyl acetate/hexane).

94.3 Synthesis of 1-(2-methoxybenzyl)-3-(3,5-di(trifluoromethyl)phenylmethyl)-3-(2-hydroxyethyl)-2-oxopyrrolidine Prepare by the method of Example 18.2 using 1-(2-methoxybenzyl)-3-(3,5-di(trifluoromethyl)phenylmethyl)-3-(2-(t-butyldimethylsilyloxy)ethyl)-2-oxopyrrolidine to give the title compound: $R_f$=0.60 (silica gel, ethyl acetate).

94.4 Synthesis of 1-(2-methoxybenzyl)-3-(3,5-di(trifluoromethyl)phenylmethyl)-3-(2-methanesulfonyloxyethyl)-2-oxopyrrolidine Prepare by the method of Example 2.5.2 using 1-(2-methoxybenzyl)-3-(3,5-di(trifluoromethyl)phenylmethyl)-3-(2-hydroxyethyl)-2-oxopyrrolidine to give the title compound.

94.5 Synthesis of 1-(2-methoxybenzyl)-3-(2-(4-(1-(2-ethoxyethyl)-1H-benzimidazol-2-yl)[1,4]diazepan-1-yl)ethyl)-3-(3,5-di(trifluoromethyl)phenylmethyl)-2-oxopyrrolidine Prepare by the method of Example 7.6 using 1-(2-methoxybenzyl)-3-(3,5-di(trifluoromethyl)phenylmethyl)-3-(2-methanesulfonyloxyethyl)-2-oxopyrrolidine and 4-(1-(2-ethoxyethyl)-1H-benzimidazol-2-yl)[1,4]diazepane hydriodic acid salt to give the title compound: $R_f$=0.54 (silica gel, 5% methanol/dichloromethane/0.5% concentrated aqeous ammonia).

94.6 Synthesis of 1-(2-methoxybenzyl)-3-(2-(4-(1-(2-ethoxyethyl)-1H-benzimidazol-2-yl)[1,4]diazepan-1-yl)ethyl)-3-(3,5-di(trifluoromethyl)phenylmethyl)-2-oxopyrrolidine hydrochloric acid salt Combine 1-(2-methoxybenzyl)-3-(2-(4-(1-(2-ethoxyethyl)-1H-benzimidazol-2-yl)[1,4]diazepan-1-yl)ethyl)-3-(3,5-di(trifluoromethyl)phenylmethyl)-2-oxopyrrolidine (0.94 g, 1.25 mmol) and methanol (10 mL). Add a solution of hydrochloric acid in dioxane (0.63 mL, 4 M, 2.5 mmol). After 12 hours, evaporate in vacuo to give a residue. Triturate the residue with diethyl ether to give a solid. Repeatedly, decant and add diethyl ether before collecting the solid by filtration to give the title compound.

PREPARATION 47
4-(1-(N-Methylacetamido)-1H-benzimidazol-2-yl)[1,4]diazepane Hydriodic acid salt Combine 1-(t-butoxycarbonyl)-4-(1H-benzimidazol-2-yl)[1,4]diazepane (0.5 g, 1.6 mmol) and dimethylformamide (20 mL). Add sodium hydride (0.08 g, 3.2 mmol). After 12 hours, add N-methyl-1-chloroacetamide (0.34 g, 3.14 mmol). After 12 hours, add N-methyl-1-chloroacetamide (0.17 g, 1.6 mmol). After 12 hours, heat to 70° C. After 4 hours, cool to ambient temperature and partition the reaction mixture between water (10 mL) and dichloromethane (100 mL). Separate the layers, dry the organic layer over $Na_2SO_4$, filter, and evaporate in vacuo to give a residue. Chromatograph the residue on silica gel eluting with 1.2% methanol/dichloromethane/0.5% saturated aqueous ammonia solution to give 1-(t-butoxycarbonyl)-4-(1-(N-methylacetamido)-1H-benzimidazol-2-yl)[1,4]diazepane: $R_f$=0.24 (silica gel, 1.8% methanol/dichloromethane/0.5% saturated aqueous ammonia solution).

Combine 1-(t-butoxycarbonyl)-4-(1-(N-methylacetamido)-1H-benzimidazol-2-yl)[1,4]diazepane (0.18 g, 0.48 mmol) and dichloromethane (10 mL). Add hydriodic acid (0.17 mL, 57%, 0.95 mmol) and warm to 40° C. After 3 hours, cool to ambient temperature and evaporate in vacuo to give a residue. Combine the residue and diethyl ether with stirring to give a solid. Collect the solid by filtration to give, after drying, the title compound.

EXAMPLE 95
1-(3,4,5-Trimethoxybenzoyl)-3-(2-(4-(1-(N-methylacetamido)-1H-benzimidazol-2-yl)[1,4]diazepan-1-yl)ethyl)-3-phenylpyrrolidine

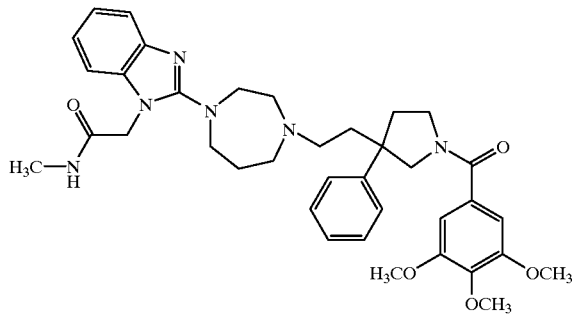

95.1 Synthesis of 1-(3,4,5-trimethoxybenzoyl)-3-(2-(4-(1-(N-methylacetamido)-1H-benzimidazol-2-yl)[1,4]diazepan-1-yl)ethyl)-3-phenylpyrrolidine Prepare by the method of Example 45.1 using 1-(3,4,5-trimethoxybenzoyl)-3-phenyl-3-(2-methanesulfonyloxyethyl)pyrrolidine (prepared from (−)-3-phenyl-3-(2-hydroxyethyl)pyrrolidine (R,R)-di-p-anisoyltartaric acid salt) and 4-(1-(N-methylacetamido)-1H-benzimidazol-2-yl)[1,4]diazepane hydriodic acid salt to give, after chromatography on silica gel eluting with 5% methanol/dichloromethane/0.5% concentrated aqueous ammonia solution, the title compound: $R_f$=0.32 (silica gel, 5% methanol/dichloromethane/0.5% concentrated aqueous ammonia solution).

95.2 Synthesis of 1-(3,4,5-trimethoxybenzoyl)-3-(2-(4-(1-(N-methylacetamido)-1H-benzimidazol-2-yl)[1,4]diazepan-1-yl)ethyl)-3-phenylpyrrolidine hydrochloric acid salt Prepare by the method of Example 94.6 using -1-(3,4,5-trimethoxybenzoyl)-3-(2-(4-(1-(N-methylacetamido)-1H-benzimidazol-2-yl)[1,4]diazepan-1-yl)ethyl)-3-phenylpyrrolidine to give the title compound.

PREPARATION 48
4-(1-Allyl-1H-benzimidazol-2-yl)[1,4]diazepane Hydriodic acid salt Combine 1-(t-butoxycarbonyl)-4-(1H-benzimidazol-2-yl) [1,4]diazepane (0.79 g, 2.50 mmol) and sodium hydride (0.13 g, 60%n in oil, 3.254 mmol) in dimethylformlamide (10 mL). After 30 minutes add allyl bromide (0.35 mL, 3.25 mmol). Heat to 75° C. After 4 hours, cool the reaction mixture, dilute with dichloromethane, and extract with a saturated aqueous sodium bicarbonate solution and then brine. Dry the organic layer over $MgSO_4$, filter, and evaporate in vacuo to give 1-(t-butoxycarbonyl)-4-(1-allyl-1H-benzimidazol-2-yl)[1,4]diazepane: $R_f$=0.83 (silica gel, dichloromethane/methanol/concentrated ammonium hydroxide 90/10/0.1).

Combine 1-(t-butoxycarbonyl)-4-(1-allyl-1H-benzimidazol-2-yl)[1,4]diazepane (0.89 g, 2.5 mmol), aqueous hydriodic acid (10 mL, 57%), and ethanol (10 mL). Heat to reflux. After 1 hour, cool to ambient temperature, pour the reaction mixture into diethyl ether (250 mL), and stir to give a solid. After 1 hour, collect the solid by filtration, rinse with diethyl ether, and dry in vacuo to give the title compound.

EXAMPLE 96
1-(2-Methoxy-5-(1H-tetrazol-1-yl)benzoyl)-3-(2-(4-(1-allyl-1H-benzimidazol-2-yl)[1,4]diazepan-1-yl)ethyl)-3-phenylpyrrolidine

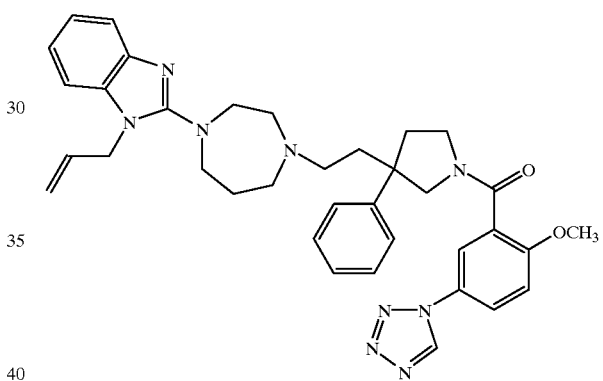

96.1 Synthesis of 1-(2-methoxy-5-(1H-tetrazol-1-yl) benzoyl)-3-(2-(4-(1-allyl-1H-benzimidazol-2-yl) [1,4] diazepan-1-yl)ethyl)-3-phenylpyrrolidine Prepare by the method of Example 47.3 1-(2-methoxy-5-(1H-tetrazol-1-yl)benzoyl)-3-phenyl-3-(2-methanesulfonyloxyethyl)pyrrolidine (prepared from (−)-3-phenyl-3-(2-hydroxyethyl)pyrrolidine (R,R)-di-p-anisoyltartaric acid salt) and 4-(1-allyl-1H-benzimidazol-2-yl)[1,4]diazepane hydriodic acid salt to give, after purification by chromatography on silica gel eluting sequentially with dichloromethane/methanol/concentrated ammonium hydroxide 95/5/0.1 and then dichloromethane/methanol/concentrated ammonium hydroxide 90/10/0.1, the title compound: $R_f$=0.71 (silica gel, dichloromethane/methanol/concentrated ammonium hydroxide 90/10/0.1).

96.2 Synthesis of 1-(2-methoxy-5-(1H-tetrazol-1-yl) benzoyl)-3-(2-(4-(1-allyl-1H-benzimidazcol-2 -yl)[1,4] diazepan-1-yl)ethyl)-3-phenylpyrrolidine hydrochloric acid salt Prepare by the method of Example 52.2 using 1-(2-methoxy-5-(1H-tetrazol-1-yl)benzoyl)-3-(2-(4-(1-allyl-1H-benzimidazol-2-yl)[1,4]diazepan-1-yl)ethyl)-3-phenylpyrrolidine, to give the title compound.

EXAMPLE 97

1-(2-Methoxy-5-(1H-tetrazol-1-yl)benzoyl)-3-(2-(4-(1-(2-(2,2,2-triflurorethoxy)ethyl)-1H-benzimidazol-2-yl)[1,4]diazepan-1-yl)ethyl)-3-phenylpyrrolidine

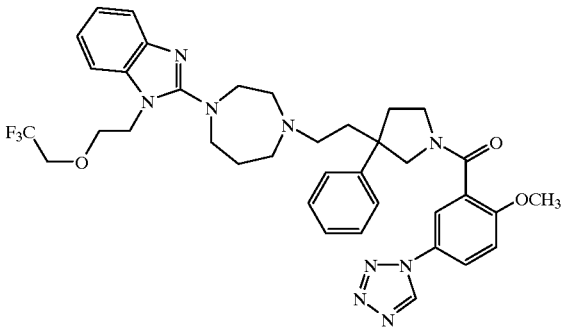

97.1 Synthesis of 1-(2-methoxy-5-(1H-tetrazol-1-yl)benzoyl)-3-(2-(4-(1-(2-(2,2,2-triflurorethoxy)ethyl)-1H-benzimidazol-2-yl)[1,4]diazepan-1-yl)ethyl)-3-phenylpyrrolidine Prepare by the method of Example 47.3 1-(2-methoxy-5-(1H-tetrazol-1-yl)benzoyl)-3-phenyl-3-(2-methanesulfonyloxyethyl)pyrrolidine (prepared from (−)-3-phenyl-3-(2-hydroxyethyl)pyrrolidine (R,R)-di-p-anisoyltartaric acid salt) and 4-(1-(2-(2,2,2-trifluoroethoxy)ethyl)-1H-benzimidazol-2-yl)[1,4]diazepane hydriodic acid salt to give, after purification by chromatography on silica gel eluting sequentially with 2% methanol/dichloromethane, 3% methanol/dichloromethane, 4% methanol/dichloromethane, and then 5% methanol/dichloromethane, the title compound: $R_f$=0.44 (silica gel, 10% methanol/dichloromethane).

97.2 Synthesis of 1-(2-methoxy-5-(1H-tetrazol-1-yl)benzoyl)-3-(2-(4-(1-(2-(2,2,2-triflurorethoxy)ethyl)-1H-benzimidazol-2-yl)[1,4]diazepan-1-yl)ethyl)-3-phenylpyrrolidine hydrochloric acid salt Prepare by the method of Example 52.2 using 1-(2-methoxy-5-(1H-tetrazol-1-yl)benzoyl)-3-(2-(4-(1-(2-(2,2,2-triflurorethoxy)ethyl)-1H-benzimidazol-2-yl)[1,4]diazepan-1-yl)ethyl)-3-phenylpyrrolidine to give the title compound.

PREPARATION 50

1-(Fur-2-ylmethyl)-1H-benzimidazol-2-yl)[1,4]diazepane Hydriodic acid salt

Combine furfuryl alcohol (3.52 mL, 40.8 mmol) and triethylamine (11.4 mL, 81.5 mmol) in dichloromethane (70 mL). Cool in an ice-bath. Add dropwise, methanesulfonyl chloride (4.73 mL, 61.2 mmol). After 3 hours dilute the reaction mixture with dichloromethane, extract with water, and then a saturated aqueous sodium bicarbonate solution. Dry over $Na_2SO_4$, filter, and evaporate at reduced pressure and a bath temperature of about 20° C. to give a residue. Distill the residue at about 25° C. and 0.2 mm Hg into a dry-ice trap to obtain 2-(chloromethyl)furan which is used immediately without further manipulation.

Combine 1-(t-butoxycarbonyl)-4-(1H-benzimidazol-2-yl)[1,4]diazepane (1.7 g, 5.37 mmol), tetrahydrofuran (45 mL), and dimethylformamide (5 mL). Cool in an ice-bath. Add sodium hydride (0.32 g, 60%n in oil, 8.06 mmol). After 15 minutes, warm to ambient temperature. When gas evolution ceases add 2-(chloromethyl)furan (0.94 g, 8.06 mmol). After 18 hours, cool the reaction mixture, quench by the addition of a saturated aqueous ammonium chloride solution. Evaporate to remove most of the tetrahydrofuran, dilute with ethyl acetate, and extract with water, a saturated aqueous sodium bicarbonate solution, and then brine. Dry the organic layer over $MgSO_4$, filter, and evaporate in vacuo to give a residue. Chromatograph the residue on silica gel eluting with 50% ethyl acetate/hexane to give 1-(t-butoxycarbonyl)-4-(fur-2-ylmethyl-1H-benzimidazol-2-yl)[1,4]diazepane: $R_f$=0.47 (silica gel, ethyl acetate) Elemental Analysis Calculated for $C_{22}H_{28}N_4O_3$: C, 66.66; H, 7.17; N, 14.04. Found C, 66.65; H, 7.12; N, 14.13.

Combine 1-(t-butoxycarbonyl)-4-(fur-2-ylmethyl-1H-benzimidazol-2-yl)[1,4]diazepane (0.6 g, 1.5 mmol) and dioxane (10 mL). Add a solution of hydrochloric acid in dioxane (6 mL, 4 M). After 1 hour, add diethyl ether (50 mL) to give a solid. Collect the solid by filtration and dry to give 4-(fur-2-ylmethyl-1H-benzimidazol-2-yl)[1,4]diazepane hydrochloric acid salt: 219–221° C.

Combine 4-(fur-2-ylmethyl-1H-benzimidazol-2-yl)[1,4]diazepane hydrochloric acid salt (0.56 g, 1.53 mmol) and dichloromethane (150 mL). Extract with a saturated aqueous sodium bicarbonate solution. Dry the organic layer over $MgSO_4$, filter, and evaporate in vacuo to give a residue (about 0.45 g). Combine the residue and methanol (50 mL). Cool in an ice-bath. Add aqueous hydriodic acid (0.11 mL, 57%). After 10 minutes, evaporate in vacuo to obtain a residue. Triturate the residue with diethyl ether to obtain a solid. Collect the solid by filtration, rinse with diethyl ether, and dry to give the title compound.

EXAMPLE 98

1-(2-Methoxy-5-(1H-tetrazol-1-yl)benzoyl)-3-(2-(4-(1-(fur-2-ylmethyl)-1H-benzimidazol-2-yl)[1,4]diazepan-1-yl)ethyl)-3-phenylpyrrolidine

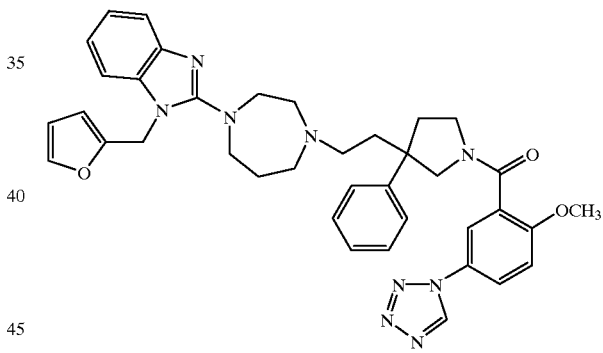

98.1 Synthesis of 1-(2-methoxy-5-(1H-tetrazol-1-yl)benzoyl)-3-(2-(4-(1-(fur-2-ylmethyl)-1H-benzimidazol-2-yl)[1,4]diazepan-1-yl)ethyl)-3-phenylpyrrolidine Prepare by the method of Example 47.3 1-(2-methoxy-5-(1H-tetrazol-1-yl)benzoyl)-3-phenyl-3-(2-methanesulfonyloxyethyl)pyrrolidine (prepared from (−)-3-phenyl-3-(2-hydroxyethyl)pyrrolidine (R,R)-di-p-anisoyltartaric acid salt) and 1-(fur-2-ylmethyl)-1H-benzimidazol-2-yl)[1,4]diazepane hydriodic acid salt to give, after purification by chromatography on silica gel eluting with 10% methanol/dichloromethane/0.1% concentrated ammonium hydroxide: $R_f$=0.40 (silica gel, 10% methanol/dichloromethane/0.1% concentrated ammonium hydroxide).

98.2 Synthesis of 1-(2-methoxy-5-(1H-tetrazol-1-yl)benzoyl)-3-(2-(4-(1-(fur-2-ylmethyl)-1H-benzimidazol-2-yl)[1,4]diazepan-1-yl)ethyl)-3-phenylpyrrolidine hydrochloric acid salt Combine 1-(2-methoxy-5-(1H-tetrazol-1-yl)benzoyl)-3-(2-(4-(1-(fur-2-ylmethyl)-1H-benzimidazol-2-yl)[1,4]

diazepan-1-yl)ethyl)-3-phenylpyrrolidine (0.73 g, 1.08 mmol) in dichloromethane (15 mL) and methanol (5 mL). Cool in an ice-bath. Add a solution of hydrochloric acid in dioxane (0.54 mL, 4 M). Warm to ambient temperature. After 12 hours, add diethyl ether (200 mL) to form a solid. Collect the solid by filtration to give the title compound.

PREPARATION 51
2-Methoxy-5-hydroxybenzoic acid

Combine methyl 2,5-dihydroxybenzoate (8.45 g, 50.2 mmol), imidazole (4.1 g, 60.3 mmol), and t-butyldimethylsilyl chloride (9.09 g, 60.3 mmol) in dichloromethane (100 mL). After 30 minutes, dilute the reaction mixture with dichloromethane (100 mL) and extract with water. Dry the organic layer over MgSO$_4$, filter and evaporate in vacuo to give methyl 2-hydroxy-5-(t-butyldimethylsilyloxy)benzoate.

Combine methyl 2-hydroxy-5-(t-butyldimethylsilyloxy) benzoate (14.2 g, 50.2 mmol), potassium carbonate (13.88 g, 100.4 mmol), and methyl iodide (20 mL, 321 mmol) in acetone (125 mL). Heat to reflux. After 17 hours, add methyl iodide (10 mL). After 23 hours, cool the reaction mixture to ambient temperature and add diethyl ether (600 mL), filter, and evaporate the filtrate in vacuo to give a residue. Chromatograph the residue on silica gel eluting with 10% ethyl acetate/hexane to give methyl 2-methoxy-5-(t-butyldimethylsilyloxy)benzoate. $R_f$=0.39 (silica gel, 5% ethyl acetate/hexane).

Combine methyl 2-methoxy-5-(t-butyldimethylsilyloxy) benzoate (11.1 g, 37.4 mmol) and ammonium fluoride (6.94 g, 0.187 mmol) in methanol (150 mL). Heat to reflux. After 1 hour, evaporate in vacuo to give a residue. Partition the residue between ethyl acetate and water, separate the layers, extract the organic layer with water and then brine. Dry the organic layer over MgSO$_4$, filter, and evaporate in vacuo to give methyl 2-methoxy-5-hydroxybenzoate: mp; 110–112° C. $R_f$=0.27 (silica gel, 5% ethyl acetate/hexane).

Combine methyl 2-methoxy-5-hydroxybenzoate (0.37 g, 2.0 mmol) and a 1 M aqueous sodium hydroxide solution (20 mL, 20 mmol) in methanol (20 mL). After 2 hours, adjust the pH to about 2 using a 1 M aqueous hydrochloric acid solution and extract with dichloromethane. Dry the organic layer over MgSO$_4$, filter, and evaporate in vacuo to give the title compound.

EXAMPLE 99
1-(2-Methoxy-5-hydroxybenzoyl)-3-(2-(4-(1-(2-ethoxyethyl)-1H-benzimidazol-2-yl)[1,4diazepan-1-yl)ethyl)-3-phenylpyrrolidine

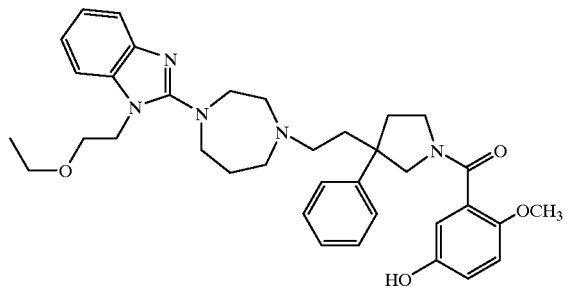

99.1 Synthesis of 1-(2-methoxy-5-hydroxybenzoyl)-3-(2-(4-(1-(2-ethoxyethyl)-1H-benzimidazol-2-yl)[1,4]diazepan-1-yl)ethyl)-3-phenylpyrrolidine Combine 3-(2-(4-(1-(2-ethoxyethyl)-1H-benzimidazol-2-yl)[1,4]diazepan-1-yl)ethyl)-3-phenylpyrrolidine hydrochloric acid salt (prepared from (−)-3-phenyl-3-(2-hydroxyethyl)pyrrolidine (R,R)-di-p-anisoyltartaric acid salt) (0.53 g, 1.0 mmol), 2-methoxy-5-hydroxybenzoic acid (0.17 g, 1.0 mmol), 1-hydroxybenzotriazole hydrate (0.13 g, 1.0 mmol), 1-ethyl-3-(3-dimethylaminopropyl) carbodiimide hydrochloride (0.19 g, 1.0 mmol), and N,N-diisopropylethylamine (0.34 mL, 2.0 mmol) in dichloromethane (10 mL). After 18 hours, dilute the reaction mixture with dichloromethane and extract with brine. Dry the organic layer over MgSO$_4$, filter, and evaporate in vacuo to give a residue. Chromatograph the residue on silica gel eluting sequentially with 3% methanol/dichloromethane, 5% methanol/dichloromethane, 7% methanol/dichloromethane, and then 10% methanol/dichloromethane to give the title compound.

99.2 Synthesis of 1-(2-methoxy-5-hydroxybenzoyl)-3-(2-(4-(1-(2-ethoxyethyl)-1H-benzimidazol-2-yl)[1,4]diazepan-1-yl)ethyl)-3-phenylpyrrolidine hydrochloric acid salt Prepare by the method of Example 52.2 using 1-(2-methoxy-5-hydroxybenzoyl)-3-(2-(4-(1-(2-ethoxyethyl)-1H-benzimidazol-2-yl)[1,4]diazepan-1-yl)ethyl)-3-phenylpyrrolidine to give the title compound.

PREPARATION 52
1-(2-Methoxyethyl)-1H-benzimidazol-2-yl)[1,4]diazepane Hydriodic acid salt Combine 1-(t-butoxycarbonyl)-4-(1H-benzimidazol-2-yl) [1,4]diazepane (2.03 g, 6.41 mmol) and dimethylformamide (50 mL). Cool in an ice-bath. Add sodium hydride (0.28 g, 60%n in oil, 7.0 mmol). After 20 minutes, add 2-chloroethyl methyl ether (0.7 mL, 7.66 mmol). Heat to 85° C. After 18 hours, cool to ambient temperature and dilute with dichloromethane, and extract with water, a saturated aqueous sodium bicarbonate solution, and then brine. Dry the organic layer over MgSO$_4$, filter, and evaporate in vacuo to give a residue. Chromatograph the residue on silica gel eluting with dichloromethane/methanol/concentrated ammonium hydroxide 95/5/0.05 to give 1-(t-butoxycarbonyl)-4-(1-(2-methoxyethyl)-1H-benzimidazol-2-yl)[1,4]diazepane.

Combine 1-(t-butoxycarbonyl)-4-(1-(2-methoxyethyl)-1H-benzimidazol-2-yl)[1,4]diazepane (1.69 g, 5.23 mmol), aqueous hydriodic acid (10 mL, 57%), and ethanol (20 mL). Heat to reflux. After 1 hour, cool to ambient temperature and pour the reaction mixture into diethyl ether (350 mL) and stir to give a solid. After 1 hour, collect the solid S by filtration, rinse with diethyl ether, and dry in vacuo to give the title compound.

EXAMPLE 100
1-(2-Methoxy-5-(1H-tetrazol-1-yl)benzoyl)-3-(2-(4-(1-(2-methoxyethyl)-1H-benzimidazol-2-yl)[1,4]diazepan-1-yl) ethyl)-3-phenylpyrrolidine

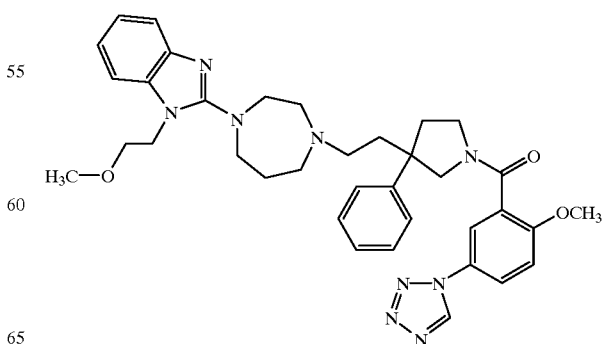

100.1 Synthesis of 1-(2-methoxy-5-(1H-tetrazol-1-yl)benzoyl)-3-(2-(4-(1-(2-methoxyethyl)-1H-benzimidazol-2-yl)[1,4]diazepan-1-yl)ethyl)-3-phenylpyrrolidine Combine 1-(2-methoxy-5-(1H-tetrazol-1-yl)benzoyl)-3-phenyl-3-(2-methanesulfonyloxyethyl)pyrrolidine (prepared from (−)-3-phenyl-3-(2-hydroxyethyl)pyrrolidine (R,R)-di-p-anisoyltartaric acid salt)(0.93 g, 1.97 mmol), 4-(1-(2-methoxyethyl)-1H-benzimidazol-2-yl)[1,4]diazepane hydriodic acid salt (1.04 g, 1.97 mmol), and triethylamine (1.5 mL, 10.76 mmol) in acetonitrile (20 mL). Heat to reflux. After 18 hours, cool and partition the reaction mixture between brine and dichloromethane. Dry the organic layer over MgSO$_4$, filter, and evaporate in vacuo to give residue. Chromatograph the residue on silica gel eluting with dichloromethane/methanol/concentrated aqueous ammonia 95/5/0.05 to give the title compound: $R_f$=0.49 (silica gel, dichloromethane/methanol/concentrated aqueous ammonia 95/5/0.1).

100.2 Synthesis of 1-(2-methoxy-5-(1H-tetrazol-1-yl)benzoyl)-3-(2-(4-(1-(2-methoxyethyl)-1H-benzimidazol-2-yl)[1,4]diazepan-1-yl)ethyl)-3-phenylpyrrolidine hydrochloric acid salt Prepare by the method of Example 52.2 using 1-(2-methoxy-5-(1H-tetrazol-1-yl)benzoyl)-3-(2-(4-(1-(2-methoxyethyl)-1H-benzimidazol-2-yl)[1,4]diazepan-1-yl)ethyl)-3-phenylpyrrolidine to give the title compound.

PREPARATION 53

1-(But-2-en-1-yl)-1H-benzimidazol-2-yl)[1,4]diazepane Hydriodic acid salt

Prepare by the method of Preparation 52 using 1-(t-butoxycarbonyl)-4-(1H-benzimidazol-2-yl)[1,4]diazepane (0.85 g, 2.69 mmol) and crotyl bromide (technical, 0.38 mL, 3.69 mmol) to give the title compound.

EXAMPLE 101

1-(2-Methoxy-5-(1H-tetrazol-1-yl)benzoyl)-3-(2-(4-(1-(but-2-en-1-yl)-1H-benzimidazol-2-yl)[1,4]diazepan-1-yl)ethyl)-3-phenylpyrrolidine

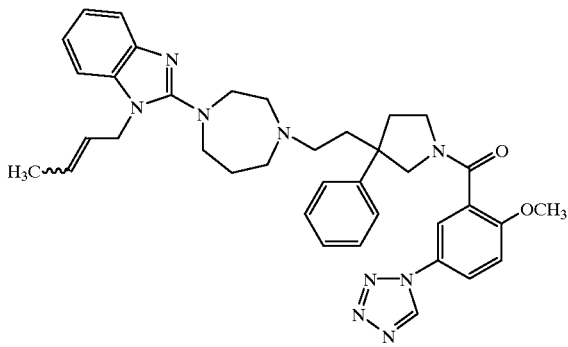

101.1 Synthesis of 1-(2-methoxy-5-(1H-tetrazol-1-yl)benzoyl)-3-(2-(4-(1-(but-2-en-1-yl)-1H-benzimidazol-2-yl)[1,4]diazepan-1-yl)ethyl)-3-phenylpyrrolidine Prepare by the method of Example 47.3 using 1-(2-methoxy-5-(1H-tetrazol-1-yl)benzoyl)-3-phenyl-3-(2-methanesulfonyloxyethyl)pyrrolidine (prepared from (−)-3-phenyl-3-(2-hydroxyethyl)pyrrolidine (R,R)-di-p-anisoyltartaric acid salt)(0.74 g, 1.41 mmol) and 4-(1-(but-2-en-1-yl)-1H-benzimidazol-2-yl)[1,4]diazepane hydriodic acid salt (0.66 g, 1.40 mmol) to give the title compound: $R_f$=0.37 (silica gel, dichloromethane/methanol/concentrated aqueous ammonia 95/5/0.1).

101.2 Synthesis of 1-(2-methoxy-5-(1H-tetrazol-1-yl)benzoyl)-3-(2-(4-(1-(but-2-en-1-yl)-1H-benzimidazol-2-yl)[1,4]diazepan-1-yl)ethyl)-3-phenylpyrrolidine hydrochloric acid salt Prepare by the method of Example 52.2 using 1-(2-methoxy-5-(1H-tetrazol-1-yl)benzoyl)-3-(2-(4-(1-(but-2-en-1-yl)-1H-benzimidazol-2-yl)[1,4]diazepan-1-yl)ethyl)-3-phenylpyrrolidine to give the title compound.

PREPARATION 54

4-(1-(4-Fluorobenzyl)-1H-benzimidazol-2-yl)[1,4]diazepane Hydriodic acid salt

Combine 1-(t-butoxycarbonyl)-4-(1H-benzimidazol-2-yl)[1,4]diazepane (1.5 g, 5.03 mmol) and dimethylformamide (30 mL). Add sodium hydride (0.27 g, 60%n in oil, 6.5 mmol). After 30 minutes, add 4-fluorobenzyl bromide (1.0 mL, 8.03 mmol). Heat to 80° C. After 2 hours, cool to ambient temperature and partition the reaction mixture between dichloromethane and a saturated aqueous sodium bicarbonate solution. Separate the layers and extract the organic layer with brine. Dry the organic layer over MgSO$_4$, filter, and evaporate in vacuo to give 1-(t-butoxycarbonyl)-4-(1-(4-fluorobenzyl-1H-benzimidazol-2-yl)[1,4]diazepane.

Alternately, combine 1-(t-butoxycarbonyl)-4-(1H-benzimidazol-2-yl)[1,4]diazepane (1.7 g, 5.37 mmol) and dimethylformamide (40 mL). Add sodium hydride (0.23 g, 60%n in oil, 5.75 mmol). After 15 minutes, add 4-fluorobenzyl bromide (0.73 mL, 5.86 mmol). After 18 hours, partition the reaction mixture between dichloromethane and a saturated aqueous sodium bicarbonate solution, Separate the layers and extract the organic layer five times with water and then brine. Dry the organic layer over Na$_2$SO$_4$, filter, and evaporate in vacuo to give 1-(t-butoxycarbonyl)-4-(1-(4-fluorobenzyl-1H-benzimidazol-2-yl)[1,4]diazepane: $R_f$=0.42 (silica gel, 50% ethyl acetate/hexane).

Combine 1-(t-butoxycarbonyl)-4-(1-(4-fluorobenzyl-1H-benzimidazol-2-yl)[1,4]diazepane (2.50 g, 5.89 mmol), aqueous hydriodic acid (5 mL, 57%), and ethanol (10 mL). Heat to reflux. After 1 hour, cool to ambient temperature and pour the reaction mixture into diethyl ether (450 mL) and stir to give a solid. After 1 hour, collect the solid by filtration, rinse with diethyl ether, and dry in vacuo to give the title compound: $R_f$=0.16 (silica gel, dichloromethane/methanol/concentrated aqueous ammonia 90/10/0.1).

EXAMPLE 102

1-(2-Methoxy-5-(1H-tetrazol-1-yl)benzoyl)-3-(2-(4-(1-(4-fluorobenzyl)-1H-benzimidazol-2-yl)[1,4]diazepan-1-yl)ethyl)-3-phenylpyrrolidine

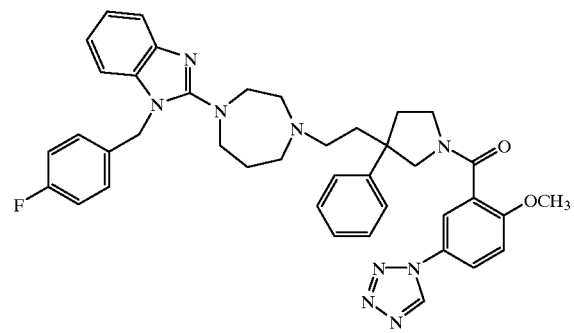

102.1.1 Synthesis of 1-(2-methoxy-5-(1H-tetrazol-1-yl)benzoyl)-3-(2-(4-(1-(4-fluorobenzyl)-1H-benzimidazol-2-yl)[1,4]diazepan-1-yl)ethyl)-3-phenylpyrrolidine Prepare by the method of Example 47.3 using 1-(2-methoxy-5-(1H-tetrazol-1-yl)benzoyl)-3-phenyl-3-(2-methanesulfonyloxyethyl)pyrrolidine (prepared from (−)-3-phenyl-3-(2-hydroxyethyl)pyrrolidine (R,R)-di-p-anisoyltartaric acid salt)(2.2 g, 4.67 mmol) and 4-(1-(4-fluorobenzyl)-1H-benzimidazol-2-yl)[1,4]diazepane hydriodic acid salt (2.82 g, 4.86 mmol) to give the title compound: $R_f$=0.37 (silica gel, dichloromethane/methanol/concentrated aqueous ammonia 90/10/0.1).

102.1.2 Synthesis of 1-(2-methoxy-5-(1H-tetrazol-1-yl)benzoyl)-3-(2-(4-1-(4-fluorobenzyl)-1H-benzimidazol-2-yl)[1,4]diazepan-1-yl)ethyl)-3-phenylpyrrolidine Combine 1-(2-methoxy-S-(1H-tetrazol-1-yl)benzoyl)-3-phenyl-3-(2-methanesulfonyloxyethyl)pyrrolidine (prepared from (−)-3-phenyl-3-(2-hydroxyethyl)pyrrolidine (R,R)-di-p-anisoyltartaric acid salt) (1.51 g, 3.2 mmol), 4-(1-(4 -fluorobenzyl)-1H-benzimidazol-2-yl)[1,4]diazepane hydriodic acid salt (1.78 g, 3.07 mmol), and triethylamine (2 mL, 14.35 mmol) in acetonitrile (40 mL). Heat to reflux. After 22 hours, cool to ambient temperature and dilute with dichloromethane, and extract with a saturated aqeous sodium bicarbonate solution and then brine. Dry the organic layer over MgSO$_4$, filter, and evaporate in vacuo to give a residue. Chromatograph the residue on silica gel eluting with dichloromethane/methanol/concentrated ammonium hydroxide 95/5/0.05 to give the title compound.

102.2 Synthesis of 1-(2-methoxy-5-(1H-tetrazol-1-yl)benzoyl)-3-(2-(4-(1-(4-fluorobenzyl)-1H-benzimidazol-2-yl)[1,4]diazepan-1-yl)ethyl)-3-phenylpyrrolidine hydrochloric acid salt Prepare by the method of Example 52.2 using 1-(2-methoxy-5-(1H-tetrazol-1-yl)benzoyl)-3-(2-(4-(1-(4-fluorobenzyl)-1H-benzimidazol-2-yl)[1,4]diazepan-1-yl)ethyl)-3-phenylpyrrolidine to give the title compound.

EXAMPLE 103

1-(3,4,5-Trimethoxybenzoyl)-3-(2-(4-(1-(4-fluorobenzyl)-1H-benzimidazol-2-yl)[1,4]diazepan-1-yl)ethyl)-3-phenylpyrrolidine

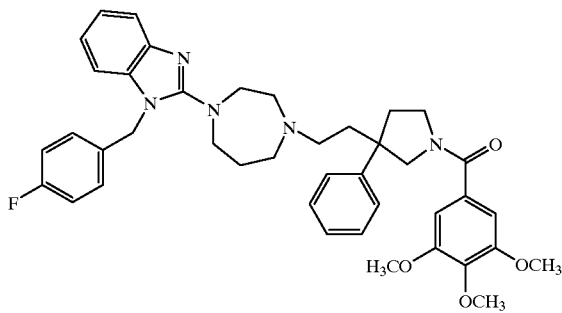

103.1 Synthesis of 1-(3,4,5-trimethoxybenzoyl)-3-(2-(4-(1-(4-fluorobenzyl)-1H-benzimidazol-2-yl)[1,4]diazepan-1-yl)ethyl)-3-phenylpyrrolidine Prepare by the method of Example 47.3 using 1-(3,4,5-trimethoxybenzoyl)-3-phenyl-3-(2-methanesulfonyloxyethyl)pyrrolidine (prepared from (−)-3-phenyl-3-(2-hydroxyethyl)pyrrolidine (R,R)-di-p-anisoyltartaric acid salt)(0.72 g, 1.55 mmol.) and 4-(1-(4-fluorobenzyl)-1H-benzimidazol-2-yl)[1,4]diazepane hydriodic acid salt (0.88 g, 1.52 mmol) to give the title compound: $R_f$=0.26 (silica gel, dichloromethane/methanol/concentrated aqueous ammonia 90/10/0.1).

103.2 Synthesis of 1-(3,4,5-trimethoxybenzoyl)-3-(2-(4-(1-(4-fluorobenzyl)-1H-benzimidazol-2-yl)[1,4]diazepan-1-yl)ethyl)-3-phenylpyrrolidine hydrochloric acid salt Prepare by the method of Example 52.2 using 1-(3,4,5-trimethoxybenzoyl)-3-(2-(4-(1-(4-fluorobenzyl)-1H-benzimidazol-2-yl)[1,4]diazepan-1-yl)ethyl)-3-phenylpyrrolidine to give the title compound,

PREPARATION 55

4-(1-(2-(Isopropoxy)ethyl)-1H-benzimidazol-2-yl)[1,4]diazepane Hydriodic acid salt Combine 2-isopropoxyethanol (1.0 g, 9.6 mmol), N,N-diisopropylethylamine (2.73 g, 21.12 mmol), and dichloromethane (20 mL). Cool in an ice bath. Add dropwise methanesulfonyl chloride (1.43 g, 9.6 mmol). After 2 hours, dilute the reaction mixture with dichloromethane and extract with 1 M hydrochloric acid solution, a saturated solution of sodium bicarbonate, and then brine. Dry the organic layer over Na$_2$SO$_4$, filter, and evaporate in vacuo to give a residue. Distill the residue to give 2-(isopropoxy)ethyl mesylate: bp; 84° C. at 0.1 mm Hg.

Alternately, combine 2-isopropoxyethanol (5.0 g, 48 mmol) and dichloromethane (50 mL). Cool in an ice bath. Add triethylamine (10.7 g, 105 mmol). Add dropwise methanesulfonyl chloride (1.43 g, 9.6 mmol). After 2 hours, dilute the reaction mixture with dichloromethane and extract with 1 M hydrochloric acid solution, a saturated aqueous solution of sodium bicarbonate, and then brine. Dry the organic layer over Na$_2$SO$_4$, filter, and evaporate in vacuo to give a residue. Distill the residue at reduced pressure to give 2-(isopropoxy)ethyl mesylate.

Combine 1-(t-butoxycarbonyl)-4-(1H-benzimidazol-2-yl)[1,4]diazepane (0.54 g, 1.71 mmol), and sodium hydride (0.87 g, 3.48 mmol in dimethylformamide (10 mL). After 30 minutes, add 2-(isopropoxy)ethyl mesylate (0.51 g, 5.5 mmol). Heat to 80° C. After 2 hours, cool the reaction mixture to ambient temperature and partition between dichloromethane and a saturated aqueous sodium bicarbonate solution. Separate the layers and extract the organic layer with brine. Dry the organic layer over MgSO$_4$, filter, and evaporate in vacuo to give 1-(t-butoxycarbonyl)-4-(1-(2-(isopropoxy)ethyl)-1H-benzimidazol-2-yl)[1,4]diazepane.

Combine 1-(t-butoxycarbonyl)-4-(1-(2-(isopropoxy)ethyl)-1H-benzimidazol-2-yl)[1,4]diazepane (0.63 g, 1.57 mmol), aqueous hydriodic acid (5 mL, 57%), and ethanol (10 mL). Heat to reflux. After 1 hour, cool to ambient temperature and pour the reaction mixture into diethyl ether (350 mL) and stir to give a solid. After 1 hour, collect the solid by filtration, rinse with diethyl ether, and dry in vacuo to give the title compound.

EXAMPLE 104

1-(2-Methoxy-5-(1H-tetrazol-1-yl)benzoyl)-3-(2-(4-(1-(2-(isopropoxy)ethyl)-1H-benzimidazol-2-yl)[1,4]diazepan-1-yl)ethyl)-3-phenylpyrrolidine

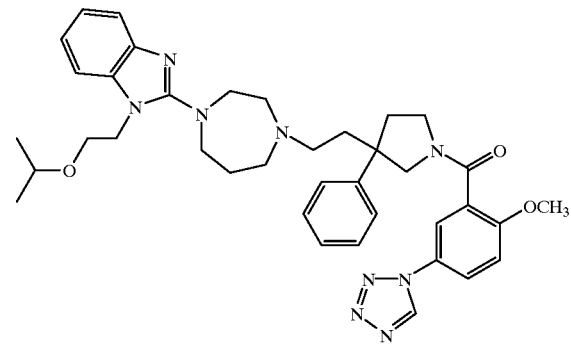

104.1 Synthesis of 1-(2-methoxy-5-(1H-tetrazol-1-yl)benzoyl)-3-(2-4-(1-(2-(isopropoxy)ethyl)-1H-benzimidazol-2-yl)[1,4]diazepan-1-yl)ethyl)-3-phenylpyrrolidine Prepare by the method of Example 102.1.2 using 1-(2-methoxy-5-(1H-tetrazol-1-yl)benzoyl)-3-phenyl-3-(2-methanesulfonyloxyethyl)pyrrolidine (prepared from (−)-3-phenyl-3-(2-hydroxyethyl)pyrrolidine (R,R)-di-p-anisoyltartaric acid salt)(0.52 g, 1.10 mmol) and 4-(1-(2-(isopropoxy)ethyl)-1H-benzimidazol-2-yl)[1,4]diazepane hydriodic acid salt (0.60 g, 1.08 mmol) to give the title compound: R$_f$=0.28 (silica gel, dichloromethane/methanol/concentrated aqueous ammonia 90/10/0.1).

104.2 Synthesis of 1-(2-methoxy-5-(1H-tetrazol-1-yl)benzoyl)-3-(2-(4-(1-(2-(isopropoxy)ethyl)-1H-benzimidazol-2-yl)[1,4]diazepan-1-yl)ethyl)-3-phenylpyrrolidine hydrochloric acid salt Prepare by the method of Example 52.2 using 1-(2-methoxy-5-(1H-tetrazol-1-yl)benzoyl)-3-(2-(4-(1-(2-(isopropoxy)ethyl)-1H-benzimidazol-2-yl)[1,4]diazepan-1-yl)ethyl)-3-phenylpyrrolidine to give the title compound.

PREPARATION 56

4-(1-(2-(t-Butoxy)ethyl)-1H-benzimidazol-2-yl)[1,4]diazepane

Combine 2-t-butoxyethanol (3.37 g, 28.5 mmol), triethylamine (6 mL, 43 mmol), and dichloromethane (150 mL). Cool in an ice bath. Add dropwise methanesulfonyl chloride (2.9 mL, 37.5 mmol). After 3 days, dilute the reaction mixture with dichloromethane and extract with a saturated solution of sodium bicarbonate and then brine. Dry the organic layer over Na$_2$SO$_4$, filter, and evaporate in vacuo to give 2-(t-butoxy)ethyl mesylate: R$_f$=0.75 (silica gel, 50% ethyl acetate/hexane).

Combine 1-(t-butoxycarbonyl)-4-(1H-benzimidazol-2-yl)[1,4]diazepane (0.56 g, 1.77 mmol), and sodium hydride (0.088 g, 60% in oil, 2.20 mmol) in dimethylformamide (10 mL). Add 2-(t-butoxy)ethyl mesylate (0.40 g, 2.04 mmol). Heat to 80° C. After 2 hours, cool to ambient temperature and partition the reaction mixture between dichloromethane and a saturated aqueous sodium bicarbonate solution. Separate the layers and extract the organic layer with brine. Dry the organic layer over MgSO$_4$, filter, and evaporate in vacuo to give 1-(t-butoxycarbonyl)-4-1-(2-t-butoxy)ethyl)-1H-benzimidazol-2-yl)[1,4]diazepane.

Combine 1-(t-butoxycarbonyl)-4-(1-(2-t-butoxy)ethyl)-1H-benzimidazol-2-yl)[1,4]diazepane (0.89 g, 2.14 mmol), potassium hydroxide (2.46 g, 43.84 mmol), and hydrazine hydrate (2.2. mL, 45.35 mmol) in ethylene glycol (25 mL). Heat to 140° C. After 16 hours, heat to 170° C. After 4 hour, cool to ambient temperature and partition the reaction mixture between dichloromethane and a saturated aqueous sodium bicarbonate solution. Separate the layers and extract the organic layer with brine. Dry the organic layer over MgSO$_4$, filter, and evaporate in vacuo to give the title compound.

EXAMPLE 104

1-(2-Methoxy-5-(1H-tetrazol-1-yl)benzoyl)-3-(2-(4-(1-(2-(t-butoxy)ethyl)-1H-benzimidazol-2-yl)[1,4]diazepan-1-yl)ethyl)-3-phenylpyrrolidine

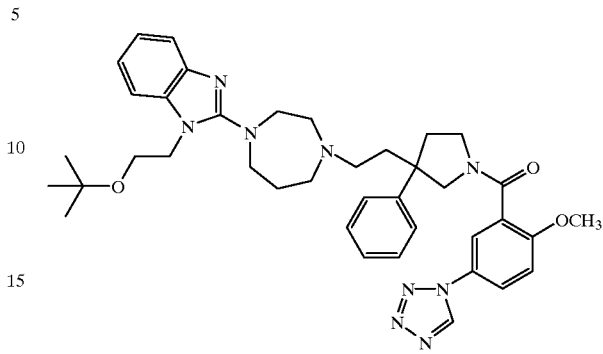

104.1 Synthesis of 1-(2-methoxy-5-(1H-tetrazol-1-yl)benzoyl)-3-(2-(4-(1-(2-(t-butoxy)ethyl)-1H-benzimidazol-2-yl) [1,4]diazepan-1-yl)ethyl)-3-phenylpyrrolidine Combine 1-(2-methoxy-5-(1H-tetrazol-1-yl)benzoyl)-3-phenyl-3-(2-methanesulfonyloxyethyl)pyrrolidine (prepared from (−)-3-phenyl-3-(2-hydroxyethyl)pyrrolidine (R,R)-di-p-anisoyltartaric acid salt)(0.62 g, 1.31 mmol), 4-(1-(2-t-butoxy)ethyl)-1H-benzimidazol-2-yl)[1,4]diazepane (0.41 g, 1.3 mmol), sodium iodide (0.42 g, 2.80 mmol), and triethylamine (0.55 mL, 3.95 mmol) in acetonitrile (13 mL). Heat to 80° C. After 16 hours, cool to ambient temperature and partition the reaction mixture between dichloromethane and a saturated aqueous sodium bicarbonate solution. Separate the layers and extract the organic layer with brine. Dry the organic layer over MgSO$_4$, filter, and evaporate in vacuo to give a residue. Chromatograph the residue on silica gel eluting sequentially with dichloromethane/methanol/concentrated aqueous ammonia 95/5/0.05 and then dichloromethane/methanol/concentrated aqueous ammonia 90/10/0.1 to give the title compound: R$_f$=0.86 (silica gel, dichloromethane/methanol/concentrated aqueous ammonia 90/10/0.1).

104.2 Synthesis of 1-(2-methoxy-5-(1H-tetrazol-1-yl)benzoyl)-3-(2-(4-(1-(2-(t-butoxy)ethyl)-1H-benzimidazol-2-yl)[1,4]diazepan-1-yl)ethyl)-3-phenylpyrrolidine hydrochloric acid salt Combine 1-(2-methoxy-5-(1H-tetrazol-1-yl)benzoyl)-3-(2-(4-(1-((2-t-butoxy)ethyl))-1H-benzimidazol-2-yl)[1,4]diazepan-1-yl)ethyl)-3-phenylpyrrolidine (0.63 g, 0.91 mmol) and dichloromethane (15 mL). Cool in an ice-bath. Add a solution of hydrochloric acid in dioxane (0.5 mL, 4 M, 2.0 mmol). After 10 minutes, pour the reaction mixture into diethyl ether (400 mL) to obtain a solid. Collect the solid by filtration and dry to give the title compound.

PREPARATION 57

4-(1-(2-Hydroxyethyl)-1H-benzimidazol-2-yl)[1,4]diazepane Hydriodic acid salt

Combine 2-(t-butyldimethylsilyloxy)ethyl bromide (116.2 g, 486 mmol), and sodium iodide (100 g, 663 mol) in acetone (350 mL) and dimethylformamide (25 mL). Heat to reflux. After 4 hours, cool, filter and evaporate in vacuo to give a residue. Distill the residue to give 2-(t-butyldimethylsilyloxy)ethyl iodide: bp; 60° C. at 0.5 mm Hg.

Combine 1-(t-butoxycarbonyl)-4-(1H-benzimidazol-2-yl)[1,4]diazepane (3.06 g, 9.67 mmol) and sodium hydride (0.43 g, 60% in oil, 10.64 mmol) in tetrahydrofuran (60 mL) and dimethylformamide (6 mL). After 2 hours, add 2-(t- butyldimethylsilyloxy)ethyl iodide (2.78 g, 9.67 mmol). After 20 hours, heat to reflux. After 4 hours, cool to ambient temperature and add ice to quench. Evaporate in vacuo to remove most of the tetrahydrofuran. Partition the evaporated reaction mixture between ethyl acetate (250 mL) and water (200 mL). Separate the layers and extract the organic layer with water. Dry the organic layer over MgSO$_4$, filter, and evaporate in vacuo to give a residue. Chromatograph the residue on silica gel eluting with ethyl acetate to give 1-(t-butoxycarbonyl)-4-(1-(2-(t-butyldimethylsilyloxy)ethyl)-1H-benzimidazol-2-yl)[1,4]diazepane: R$_f$=0.58 (silica gel, ethyl acetate).

Alternately, combine 1-(t-butoxycarbonyl)-4-(1H-benzimidazol-2-yl)[1,4]diazepane (1.72 g, 5.43 mmol) and sodium hydride (0.36 g, 60% in oil, 8.15 mmol) in dimethylformamide (40 mL). After 4 hours, add 2-(t-butyldimethylsilyloxy)ethyl iodide (1.56 g, 5.43 mmol). After 72 hours, heat to 80° C. After 3 hours, cool to ambient temperature and add ice to quench. Partition the reaction mixture between ethyl acetate (250 mL) and a saturated aqueous solution of sodium bicarbonate (200 mL). Separate the layers and extract the organic layer with water. Dry the organic layer over MgSO$_4$, filter, and evaporate in vacuo to give a residue. Chromatograph the residue on silica gel eluting with 40% ethyl acetate/dichloromethane to give 1-(t-butoxycarbonyl)-4-(1-(2-(t-butyldimethylsilyloxy)ethyl)-1H-benzimidazol-2-yl)[1,4]diazepane.

Combine 1-(t-butoxycarbonyl)-4-(1-(2-(t-butyldimethylsilyloxy)ethyl)-1H-benzimidazol-2-yl)[1,4]diazepane (4.22 g, 8.88 mmol), and methanol (60 mL). Add ammonium fluoride (1.97 g, 53.3 mmol). Heat to reflux. After 2 hours, cool the reaction mixture and partition between dichloromethane (300 mL) and a saturated aqueous solution of sodium bicarbonate (200 mL). Separate the layers and extract the organic layer three times with water and then brine. Dry the organic layer over MgSO$_4$, filter, and evaporate in vacuo to give a residue.

Chromatograph the residue on silica gel eluting with ethyl acetate to give 1-(t-butoxycarbonyl)-4-(1-(2-hydroethyl)-1H-benzimidazol-2-yl)[1,4]diazepane: R$_f$=0.32 (silica gel, ethyl acetate).

Combine 1-(t-butoxycarbonyl)-4-(1-(2-hydroethyl)-1H-benzimidazol-2-yl)[1,4]diazepane (0.4 g, 1.11 mmol) and methanol (10 mL). Add hydriodic acid (5 mL, 57 %) and heat to reflux. After 2 hours, cool to ambient temperature. Add diethyl ether (250 mL) to give a solid. Collect the solid by filtration to give the title compound.

EXAMPLE 106
1-(2-Methoxy-5-(1H-tetrazol-1-yl)benzoyl)-3-(2-(4-(1-(2-hydroxyethyl)-1H-benzimidazol-2-yl)[1,4]diazepan-1-yl)ethyl)-3-phenylpyrrolidine

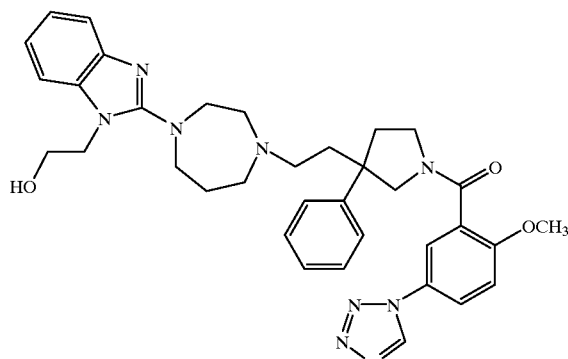

106.1 Synthesis of 1-(2-methoxy-5-(1H-tetrazol-1-yl)benzoyl)-3-(2-(4-(1-(2-hydroxyethyl)-1H-benzimidazol-2-yl)[1,4]diazepan-1-yl)ethyl)-3-phenylpyrrolidine Combine 1-(2-methoxy-5-(1H-tetrazol-1-yl)benzoyl)-3-phenyl-3-(2-methanesulfonyloxyethyl)pyrrolidine (prepared from (−)-3-phenyl-3-(2-hydroxyethyl)pyrrolidine (R,R)-di-p-anisoyltartaric acid salt)(0.40 g, 0.85 mmol), 4-(1-(2-hydroxyethyl)-1H-benzimidazol-2-yl)[1,4]diazepane hydriodic acid salt (0.44 g, 0.85 mmol) (1.51 g, 3.2 mmol), sodium iodide (0.127 g, 0.84 mmol), and triethylamine (0.59 mL, 4.23 mmol) in acetonitrile (20 mL). Heat to reflux. After 30 hours, cool to ambient temperature and evaporate in vacuo, and partition the evaporated reaction mixture between dichloromethane and a saturated aqueous sodium bicarbonate solution. Separate the organic layer and extract three times with water. Dry the organic layer over MgSO$_4$, filter, and evaporate in vacuo to give a residue. Chromatograph the residue on silica gel eluting sequentially with dichloromethane, 5% methanol/dichloromethane, 10% methanol/dichloromethane, and then 25% methanol/dichloromethane to give the title compound.

106.2 Synthesis of 1-(2-methoxy-5-(1H-tetrazol-1-yl)benzoyl)-3-(2-(4-(1-(2-hydroxyethyl)-1H-benzimidazol-2-yl)[1,4]diazepan-1-yl)ethyl)-3-phenylpyrrolidine hydrochloric acid salt Prepare by the method of Example 98.2 using 1-(2-methoxy-5-(1H-tetrazol-1-yl)benzoyl)-3-(2-(4-(1-(2-hydroxyethyl)-1H-benzimidazol-2-yl)[1,4]diazepan-1-yl)ethyl)-3-phenylpyrrolidine to give the title compound: mp; 172–190° C. (dec).

EXAMPLE 107
1-(2,5-Dimethoxybenzoyl)-3-(2-(4-(1-(2-ethoxyethyl)-1H-benzimidazol-2-yl)[1,4]diazepan-1-yl)ethyl)-3-phenylpyrrolidine

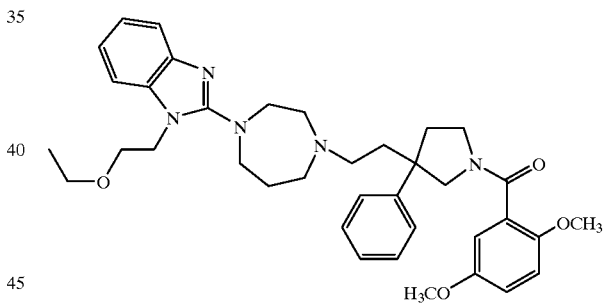

107.1 Synthesis of 1-(2,5-dimethoxybenzoyl)-3-phenyl-3-(2-hydroxyethyl)-pyrrolidine Combine 2,5-dimethoxybenzoic acid (0.71 g, 3.9 mmol) and dichloromethane (30 mL) containing dimethylformamide (0.5 mL). Add oxalyl chloride (0.70 mL, 8.55 mmol). After 2 hours, evaporate in vacuo to give a residue, combine the residue and tetrahydrofuran, and add to (−)-3-phenyl-3-(2-hydroxyethyl)pyrrolidine (R,R)-di-p-anisoyltartaric acid salt) (2.33 g, 3.82 mmol) and sodium bicarbonate (2.27 g, 27.02 mmol) in tetrahydrofuran/water (20 mL/20 mL). After 2 hours, partition the reaction mixture between ethyl acetate and an saturated aqueous solution of sodium bicarbonate. Separate the layers and and extract the organic layer with brine, dry over MgSO$_4$, filter, and evaporate in vacuo to the title compound.

107.2 Synthesis of 1-(2,5-dimethoxybenzoyl)-3-phenyl-3-(2-methanesulfonyloxyethyl)pyrrolidine Prepare by the method of Example 1.5 using 1-(2,5-dimethoxybenzoyl)-3-phenyl-3-(2-hydroxyethyl)pyrrolidine to give the title compound.

107.3 Synthesis of 1-(2,5-dimethoxybenzoyl)-3-(2-(4-(1-(2-ethoxyethyl)-1H-benzimidazol-2-yl)[1,4]diazepan-1-yl)ethyl)-3-phenylpyrrolidine Prepare by the method of Example 102.1.2 using 1-(2,5-dimethoxybenzoyl)-3-phenyl-3-(2-methanesulfonyloxyethyl)pyrrolidine (prepared from (−)-3-phenyl-3-(2-hydroxyethyl)pyrrolidine (R,R)-di-p-anisoyltartaric acid salt) (0.55 g, 1.27 mmol) and 4-(1-(2-ethoxyethyl)-1H-benzimidazol-2-yl)[1,4]diazepane hydriodic acid salt (0.71 g, 1.3 mmol) to give, after chromatography on silica gel eluting with dichloromethane/methanol/concentrated aqueous ammonia 95/5/0.05, the title compound: $R_f$=0.85 (silica gel, dichloromethane/methanol/concentrated aqueous ammonia 90/10/0.1).

107.4 Synthesis of 1-(2,5-dimethoxybenzoyl)-3-(2-(4-(1-(2-ethoxyethyl)-1H-benzimidazol-2-yl)[1,4]diazepan-1-yl)ethyl)-3-phenylpyrrolidine hydrochloric acid salt Prepare by the method of Example 52.2 using 1-(2,5-dimethoxybenzoyl)-3-(2-(4-(1-(2-ethoxyethyl)-1H-benzimidazol-2-yl)[1,4]diazepan-1-yl)ethyl)-3-phenylpyrrolidine to give the title compound.

PREPARATION 58
1-(2-(Trifluoromethoxy)ethyl)-1H-benzimidazol-2-yl)[1,4]diazepane Hydriodic acid salt According to the procedure of *Syn. Comm.* 22(17), 2459–2477 (1992), combine 2-benzyloxyethanol (15.21 g, 100 mmol) and tetrahydrofuran. Cool in an ice bath. Add sodium hydride (3.6 g, 150 mmol) and imidazole (0.68 g, 10 mmol) After 45 minutes, warm to ambient temperature and add carbon disulfide (15.64 mL, 260 mmol) After 10 minutes add methyl iodide (12.45 mL,. 200 mmol) After 20 minutes concentrate in vacuo to give a residue. Chromatograph the residue on silica del eluting with hexane to give O-(2-benxyloxyethyl)-S-methyl dithiocarbonate.

According to the procedure of *Tet Lets.* 33(29), 4173–4176 (1992), combine 1,3-dibromo-5,5-hydantoin (17.16 g, 60 mmol) and dichloromethane (100 mL). Cool in a dry-ice/acetone bath. Add a solution of O-(2-benxyloxyethyl)-S-methyl dithiocarbonate (4.8 g, 20 mmol) in dichloromethane (20 mL). Add pyridinium poly(hydrogen fluoride) (40 mL). After 3 hours, warm to about 0° C. After 0.5 hours, slowly pour the reaction mixture into an ice-cooled buffered solution saturated aqueous sodium bicarbonate and aqueous saturated sodium bisulfate and 1 M aqueous sodium hydroxide (pH about 10). Extract three times with ethyl acetate. Combine the organic layers, dry over $MgSO_4$, filter and evaporate in vacuo to give 2-(4-bromobenzyloxy)ethyl trifluoromethyl ether.

Combine 2-(4-bromobenzyloxy)ethyl trifluoromethyl ether (2.4 g, 8.1 mmol), thioanisole (28.5 mL, 243 mmol), and trifluoroacetic acid (30 mL). After 24 hours, add potassium bicarbonate to neutralize. Add $MgSO_4$ and chloroform (30 mL). Filter and distill through a short path distillation apparatus to give 2-(trifluoroacetoxy) ethyl trifluoromethyl ether containing chloroform which can be used without further purification.

Combine 2-(trifluoroacetoxy)ethyl trifluoromethyl ether as obtained above (containing chloroform), an aqueous solution of sodium hydroxide (405 by weight, 1 mL), and tetrahydrofuran (1 mL). After 30 minutes, filter to give a solution of 2-hydroxyethy trifluoromethyl ether. Add add molecular sieves to the filtrate. After 30 minutes, filter the above solution of 2-hydroxyethy trifluoromethyl ether to remove the molecular sieves. Cool the filtered solution in an ice-bath. Add N,N-diisopropylethylamine (1.4 mL) and methanesulfonyl chloride (0.63 mL, 8.1 mmol). After 4 hours, filter the reaction mixture and concentrate in vacuo to give a residue. Chromatograph the residue on silica gel eluting sequentially with hexane and then 20% ethyl acetate/hexane to give 2-(methanesulfonyloxy)ethyl trifluoromethoxy ether: $R_f$=0.21 (silica gel, 20% ethyl acetate/hexane).

Combine 1-(t-butoxycarbonyl)-4-(1H-benzimidazol-2-yl)[1,4]diazepane (0.31 g, 1 mmol) and dimethylformamide (8 mL). Cool in an ice-bath. Add sodium hydride (0.024 g, 1 mmol). After 2 hours, add 2-(methanesulfonyloxy)ethyl trifluoromethoxy ether (0.31 g, 1.5 mmol) and sodium iodide (0.14 g, 1 mmol). Heat to 80° C. After 6 hours, cool to ambient temperature. After 56 hours dilute the reaction mixture with ethyl acetate and extract brine. Dry the organic layer over $MgSO_4$, filter, and evaporate in vacuo to give a residue. Chromatograph the residue on silica gel eluting sequentially with hexane, 30% ethyl acetate/hexane and then 50% ethyl acetate/hexane to give 1-(t-butoxycarbonyl)-4-(1-(2-(trifluoromethoxy)ethyl)-1H-benzimidazol-2-yl)[1,4]diazepane; $R_f$=0.24 (silica gel, 50% ethyl acetate/hexane).

Combine 1-(t-butoxycarbonyl)-4-(1-(2-(trifluoromethoxy)ethyl)-1H-benzimidazol-2-yl)[1,4]diazepane (0.18 g, 0.42 mmol) and methanol (5 mL). Add hydriodic acid (2 mL, 57%). After 4 hours, evaporate in vacuo to give the title compound.

EXAMPLE 108
1-(2-Methoxy-5-(1H-tetrazol-1-yl)benzoyl)-3-(2-(4-(1-(2-(trifluoromethoxy)ethyl)-1H-benzimidazol-2-yl)[1,4]diazepan-1-yl)ethyl)-3-phenylpyrrolidine

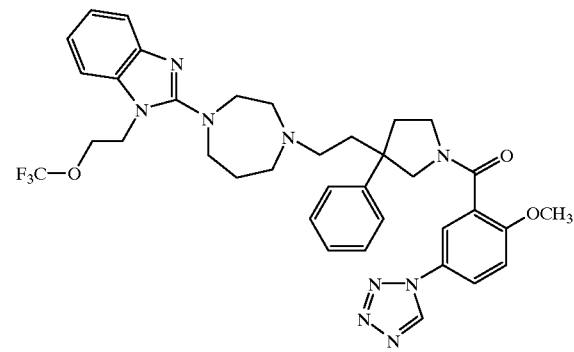

108.1 Synthesis of 1-(2-methoxy-5-(1H-tetrazol-1-yl)benzoyl)-3-(2-(4-(1-(2-(trifluoromethoxy)ethyl)-1H-benzimidazol-2-yl)[1,4]diazepan-1-yl)ethyl)-3-phenylpyrrolidine Prepare by the method of Example 1.6 1-(2-methoxy-5-(1H-tetrazol-1-yl)benzoyl)-3-phenyl-3-(2-methanesulfonyloxyethyl)pyrrolidine (prepared from (−)-3-phenyl-3-(2-hydroxyethyl)pyrrolidine (R,R)-di-p-anisoyltartaric acid salt) (0.20 g, 0.42 mmol) and 1-(2-trifluoromethoxy)ethyl)-1H-benzimidazol-2-yl)[1,4]diazepane hydriodic acid salt (0.25 g, 0.53 mmol) to give, after purification by chromatography on silica gel eluting sequentially with ethyl acetate, 15% methanol/ethyl acetate, and then 10% methanol/dichloromethane, the title compound: $R_f$=0.44 (silica gel, 10% methanol/dichloromethane).

108.2 Synthesis of 1-(2-methoxy-5-(1H-tetrazol-1-yl)benzoyl)-3-(2-(4-(1-(2-(trifluoromethoxy)ethyl)-1H-benzimidazol-2-yl)[1,4]diazepan-1-yl)ethyl)-3-phenylpyrrolidine hydrochloric acid salt Prepare by the method of Example 52.2 using 1-(2-methoxy-5-(1H-tetrazol-1-yl)benzoyl)-3-(2-(4-(1-(2-trifluoromethoxy)ethyl)-1H-benzimidazol-2-yl)[1,4]diazepan-1-yl)ethyl)-3-phenylpyrrolidine to give the title compound.

EXAMPLE 109

(−)-1-(3,4,5-Trimethoxybenzoyl)-3-(2-(4-(1-(2-ethoxyethyl)-1H-benzimidazol-2-yl)[1,4]diazepan-1-yl)ethyl)-3-(4-fluorophenyl)pyrrolidine

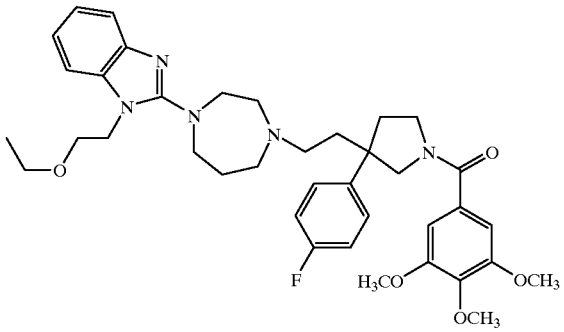

109.1 Resolution of (+)-3-(4-fluorophenyl)-3-(2-hydroxyethyl)pyrrolidine (R,R)-di-p-anisoyltartaric acid salt Concentrate the mother liquors from the first filtration of Example 33.1 to give a residue. Recrystallize three times from methanol/butanone to give the title compound.

109.2 Synthesis of (−)-1-(3,4,5-trimethoxybenzoyl)-(3-(4-fluorophenyl)-3-(2-hydroxyethyl)pyrrolidine Prepare by the method of Example 33.2.2 using (+)-3-(4-fluorophenyl)-3-(2-hydroxyethyl)pyrrolidine (R,R)-di-p-anisoyltartaric acid to give the title compound.

109.3 Synthesis of 1-(3,4,5-trimethoxybenzoyl)-3-(4-fluorophenyl)-3-(2-methanesulfonyloxyethyl)pyrrolidine Prepare by the method of Example 2.5.2 using (−)-1-(3,4,5-trimethoxybenzoyl)-3-(4-fluorophenyl)-3-(2-hydroxyethyl)pyrrolidine to give the title compound: $R_f$=0.30 (silica gel, ethyl acetate).

109.4 Synthesis of (−)-1-(3,4,5-trimethoxybenzoyl)-3-(2-(4-(1-(2-ethoxyethyl)-1H-benzimidazol-2-yl)[1,4]diazepan-1-yl)ethyl)-3-(4-fluorophenyl)pyrrolidine Combine 1-(3,4,5-trimethoxybenzoyl)-3-(4-fluorophenyl)-3-(2-methanesulfonyloxyethyl)pyrrolidine (prepared from (−)-1-(3,4,5-trimethoxybenzoyl)-3-(4-fluorophenyl)-3-(2-hydroxyethyl)pyrrolidine) (0.60 g, 1.24 mmol), sodium iodide (0.195 g, 1.30 mmol), triethylamine (0.864 mL, 6.2 mmol), and 4-(1-(2-ethoxyethyl)-1H-benzimidazol-2-yl)[1,4]diazepane hydriodic acid salt (0.67 g, 1.24 mmol) in acetonitrile (18 mL). Heat to reflux. After 24 hours, cool to ambient temperature. After 56 hours, evaporate in vacuo to obtain a residue. Partition the residue between dichloromethane and a saturated aqueous sodium bicarbonate solution. Separate the organic layer, extract with water and then brine, dry over $Na_2SO_4$, filter, and evaporate in vacuo to give a residue. Chromatograph the residue on silica gel eluting with 10% methanol/dichloromethane to give the title compound.

109.5 Synthesis of (−)-1-(3,4,5-trimethoxybenzoyl)-3-(2-(4-(1-(2-ethoxyethyl)-1H-benzimidazol-2-yl)[1,4]diazepan-1-yl)ethyl)-3-(4-fluorophenyl)pyrrolidine hydrochloric acid salt Prepare by the method of Example 33.5 using (−)-1-(3,4,5-trimethoxybenzoyl)-3-(2-(4-(1-(2-ethoxyethyl)-1H-benzimidazol-2-yl)[1,4]diazepan-1-yl)ethyl)-3-(4-fluorophenyl)pyrrolidine to give the title compound.

EXAMPLE 110

1-(2-Methoxy-5-(1H-tetrazol-1-yl)benzoyl)-3-(2-(4-1-(2-(1H-imidaol-1-yl)ethyl)-1H-benzimidazol-2-yl)[1,4]diazepan-1-yl)ethyl)-3-phenylpyrrolidine

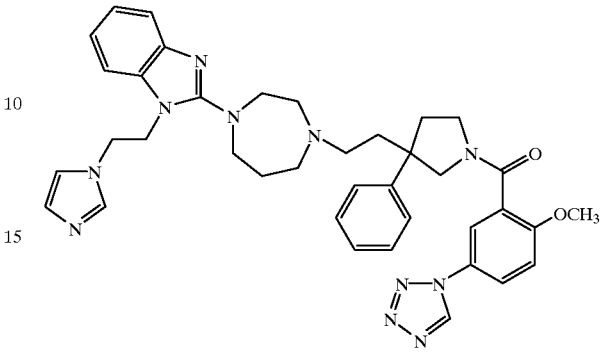

110.1 Synthesis of 1-(2-methoxy-5-(1H-tetrazol-1-yl)benzoyl)-3-(2-(4-(1-(2-(1H-imidazol-1-yl)ethyl)-1H-benzimidazol-2-yl)[1,4]diazepan-1-yl)ethyl)-3-phenylpyrrolidine Prepare by the method of Example 66.1 using 1-(2-methoxy-5-(1h-tetrazol-1-yl)benzoyl)-3-phenyl-3-(2-methanesulfonyloxyethyl)pyrrolidine (0.40 g, 0.84 mmol) and 4-(1-(2-(1H-imidazol-1-yl)ethyl)-1H-benzimidazol-2-yl)(1,4]diazepane hydriodic acid salt (0.48 g, 0.84 mmol) to give the title compound: $R_f$=0.18 (silica gel, 5% methanol/dichloromethane/0.5% concentrated aqueous ammonia).

In another aspect of the present invention, there are disclosed other novel substituted 4-(1H-benzimidazol-2-yl)[1,4]diazepane derivatives of the formula:

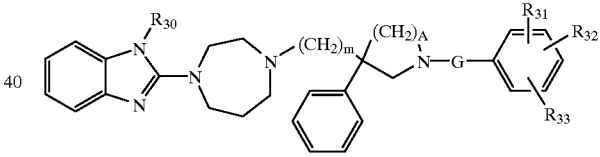

wherein m is 2 or 3;

A is 1 or 2;

G is —C(O)—, —C(O)—$CH_2$—, or —$SO_2$—;

$R_{30}$ is selected from the group consisting of:

—$C_5$–$C_8$ alkyl, —$(CH_2)_pCF_3$, vinyl,

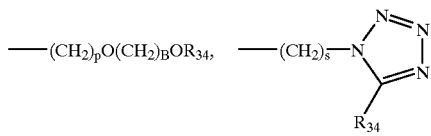

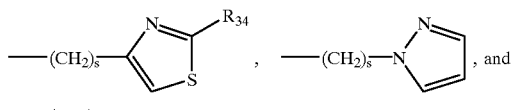

—$(CH_2)_sOR_{34}$, wherein
p is an integer from 1 to 4;
B is an integer from 1 to 4;
D is an integer from 1 to 4;
s is an integer from 1 to 4; and
$R_{34}$ is $C_1$–$C_4$ alkyl;
$R_{31}$ and $R_{32}$ are the same or different and are independently selected from hydrogen or $C_1$–$C_4$ alkoxy; and
$R_{33}$ is selected from the group consisting of:
hydrogen, $C_1$–$C_4$ alkoxy,

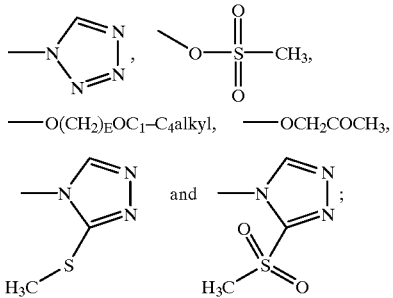

wherein
E is an integer from 2 to 4.

Examples of compounds encompassed by this aspect of the present invention include the following. It is understood that the examples encompass the specific stereoisomers and diastereomers, where applicable, of the compounds and mixtures thereof. This list is meant to be representative only and is not intended to limit the scope of the invention in any way:

1-[(R)-3-(2-{4-[1-(2-Cyclopropylmethoxy-ethyl)-1H-benzoimidazol-2-yl]-[1,4]diazepan-1-yl}-ethyl)-3-phenyl-pyrrolidin-1-yl]-1-(2-methoxy-5-tetrazol-1-yl-phenyl)-methanone 1-((R)-3-{2-[4-(1-Cyclopropylmethyl-1H-benzoimidazol-2-yl)-[1,4]diazepan-1-yl]-ethyl}-3-phenyl-pyrrolidin-1-yl)-1-(2-methoxy-5-tetrazol-1-yl-phenyl)-methanone 1-(2-Methoxy-5-tetrazol-1-yl-phenyl)-1-{(R)-3-[2-(4-{1-[2-(5-methyl-tetrazol-1-yl)-ethyl]-1H-benzoimidazol-2-yl}-[1,4]diazepan-1-yl)-ethyl]-3-phenyl-pyrrolidin-1-yl}-methanone 1-{(R)-3-[2-(4-{1-[2-(2-Methoxy-ethoxy)-ethyl]-1H-benzoimidazol-2-yl}-[1,4]diazepan-1-yl)-ethyl]-3-phenyl-pyrrolidin-1-yl}-1-(2-methoxy-5-tetrazol-1-yl-phenyl)-methanone 1-(2-Methoxy-5-tetrazol-1-yl-phenyl)-1-[(R)-3-(2-{4-[1-(2-methyl-thiazol-4-ylmethyl)-1H-benzoimidazol-2-yl]-[1,4]diazepan-1-yl}-ethyl)-3-phenyl-pyrrolidin-1-yl]-methanone 1-(2-Methoxy-5-tetrazol-1-yl-phenyl)-1-[(R)-3-phenyl-3-(2-{4-[1-(2-pyrazol-1-yl-ethyl)-1H-benzoimidazol-2-yl]-[1,4]diazepan-1-yl}-ethyl)-pyrrolidin-1-yl]-methanone Methanesulfonic acid 3-{1-[(R)-3-(2-{4-[1-(2-ethoxy-ethyl)-1H-benzoimidazol-2-yl]-[1,4]diazepan-1-yl}-ethyl)-3-phenyl-pyrrolidin-1-yl]-methanoyl}-4-methoxy-phenyl ester 1-[(R)-3-(2-{4-[1-(2-Ethoxy-ethyl)-1H-benzoimidazol-2-yl]-[1,4]diazepan-1-yl}-ethyl)-3-phenyl-pyrrolidin-1-yl]-1-[2-methoxy-5-(2-methoxy-ethoxy)-phenyl]-methanone 1-(2-Methoxy-5-tetrazol-1-yl-phenyl)-1-((R)-3-{2-[4-(1-pentyl-1H-benzoimidazol-2-yl)-[1,4]diazepan-1-yl]-ethyl}-3-phenyl-pyrrolidin-1-yl)-methanone 1-(3-{1-[(R)-3-(2-{4-1-(2-Ethoxy-ethyl)-1H-benzoimidazol-2-yl]-[1,4]diazepan-1-yl}-ethyl)-3-phenyl-pyrrolidin-1-yl]-methanoyl}-4-methoxy-phenoxy)-propan-2-one 1-(2-Methoxy-5-tetrazol-1-yl-phenyl)-1-[(R)-3-phenyl-3-(2-{4-[1-(2,2,2-trifluoro-ethyl)-1H-benzoimidazol-2-yl]-[1,4]diazepan-1-yl}-ethyl)-pyrrolidin-1-yl]-methanone 1-(2-Methoxy-5-tetrazol-1-yl-phenyl)-1-[(R)-3-phenyl-3-(2-{4-[1-(4,4,4-trifluoro-butyl)-1H-benzoimidazol-2-yl]-[1,4]diazepan-1-yl}-ethyl)-pyrrolidin-1-yl]-methanone 1-(2-Methoxy-5-tetrazol-1-yl-phenyl)-1-((R)-3-phenyl-3-{2-[4-(1-vinyl-1H-benzoimidazol-2-yl)-[1,4]diazepan-1-yl]-ethyl}-pyrrolidin-1-yl)-methanone Methanesulfonic acid 4-{1-[(R)-3-(2-{4-[1-2(ethoxy-ethyl)-1H-benzoimidazol-2-yl]-[1,4]diazepan-1-yl}-ethyl)-3-phenyl-pyrrolidin-1-yl]-methanoyl}-2,6-dimethoxy-phenyl ester hydrochloride 1-[(R)-3-(2-{4-[1-(2-Ethoxy-ethyl)-1H-benzoimidazol-2-yl]-[1,4]diazepan-1-yl}-ethyl)-3-phenyl-pyrrolidin-1-yl]-1-[2-methoxy-5-(3-methylsulfanyl-[1,2,4]triazol-4-yl)-phenyl]-methanone 1-[(R)-3-(2-{4-[1-(2-Ethoxy-ethyl)-1H-benzoimidazol-2-yl]-[1,4]diazepan-1-yl}-ethyl)-3-phenyl-pyrrolidin-1-yl]-1-[5-(3-methanesulfonyl-[1,2,4]triazol-4-yl)-2-methoxy-phenyl]-methanone 2-(4-{2-[(R)-1-(2,5-Dimethoxy-benzenesulfonyl)-3-phenyl-pyrrolidin-3-yl]-ethyl}-[1,4]diazepan-1-yl)-1-(2-ethoxy-ethyl)-1H-benzoimidazole hydrochloride 1-[3-(2-{4-[1-(2-Ethoxy-ethyl)-1H-benzoimidazol-2-yl]-[1,4]diazepan-1-yl}-ethyl)-3-phenyl-azetidin-1-yl]-2-(3,4,5-trimethoxy-phenyl)-ethanone hydrochloride

EXAMPLE 111

1-(2-Methoxy-5-tetrazol-1-yl-phenyl)-1-[(R)-3-(2-{4-[1-(2-methyl-thiazol-4-ylmethyl)-1H-benzoimidazol-2-yl]-[1,4]diazepan-1-yl}-ethyl)-3-phenyl-pyrrolidin-1-yl-methanone

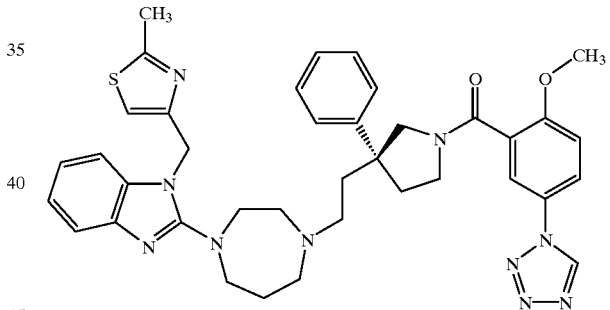

Treat a solution of 1-(t-butoxycarbonyl)-4-(1H-benzimidazol-2-yl)[1,4]diazepan (0.89 g, 2.77 mmol, Preparation 9) and dimethylformamide (10 mL) with sodium hydride (0.15 g, 3.05 mmol, 49% dispersion in oil) at room temperature. After 15 minutes, add slowly a solution of 4-chloromethyl-2-methylthiazole hydrochloride (0.56 g, 3.05 mmol, Lancaster Synthesis) and dimethylformamide (10 mL). After stirring 12 hours at room temperature, add water (10 mL) slowly and extract with dichloromethane. (150 mL). Wash the organic phase with water (3×10 mL), dry ($Na_2SO_4$) the organic layer, filter, concentrate the filtrate to remove the solvent and purify the residue by chromatography on silica gel eluting with 5% methanol in dichloromethane. Concentrate the desired fractions to afford 1.02 g of 4-[1-(2-methyl-thiazol-4-ylmethyl)-1H-benzoimidazol-2-yl]-[1,4]diazepane-1-carboxylic acid tert-butyl ester.

Hydrolyze 4-[1-(2-methyl-thiazol-4-ylmethyl)-1H-benzoimidazol-2-yl]-[1,4]diazepane-1-carboxylic acid tert-butyl ester (0.59 g, 1.38 mmol) by refluxing with hydriodic acid (57%, 3.04 mmol) in methanol (10 mL) for 10 hours. Concentrate to remove the methanol, add ether (70 mL) and allow the resultant slurry to stand for 1 hour. Decant the supernatant and dry the solid residue in vacuo at 60° C. to provide 0.78 g of 2-[1,4]diazepan-1-yl-1-(2-methyl-thiazol-4-ylmethyl)-1H-benzoimidazole dihydroiodide.

Add diisopropylethylamine (0.69 g, 5.32 mmol) to a mixture of 2-[1,4]diazepan-1-yl-1-(2-methyl-thiazol-4-ylmethyl)-1H-benzoimidazole dihydroiodide (0.78 g, 1.33 mmol), methanesulfonic acid 2-{(S)-1-[-(2-methoxy-5-tetrazol-1-yl-phenyl)-methanoyl]-3-phenyl-pyrrolidin-3-yl}-ethyl ester (0.63 g, 1.33 mmol, Example 47.2) and acetonitrile (20 mL). Reflux for 12 hours. Cool and pour the mixture into a separatory funnel, dilute with dichloromethane (100 mL), wash twice with water (10 mL portions), dry (Na$_2$SO$_4$) the organic phase, filter and evaporate. Purify the residue by silica gel chromatography eluting with 5% methanol in dichloromethane to afford 0.45 g of the title compound, Rf =0.41 (silica gel, 10% methanol in dichloromethane). The material may be converted to the dihydrochloride salt by methods well known in the art.

EXAMPLE 112

1-(2-Methoxy-5-tetrazol-1-yl-phenyl)-1-((R)-3-{2-[4-(1-pentyl-1H-benzoimidazol-2-yl)-[1,4]diazepan-1-yl]-ethyl}-3-phenyl-pyrrolidin-1-yl)-methanone

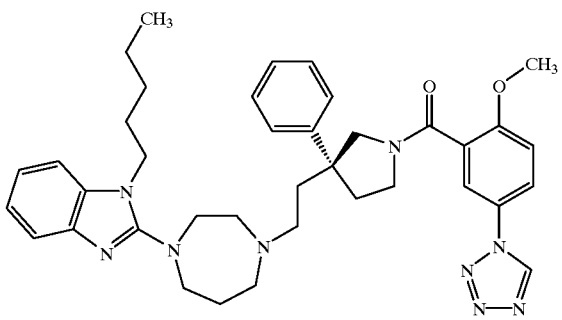

Treat a solution of 1-(t-butoxycarbonyl)-4-(1H-benzimidazol-2-yl)[1,4]diazepan (0.59 g, 1.86 mmol, Preparation 9) and dimethylformamide (10 mL) with sodium hydride (0.11 g, 2.75 mmol, 60% dispersion in oil) at room temperature. After 15 minutes, add pentyl bromide (0.34 mL, 2.74 mmol, Aldrich Chemical Company) and heat overnight at 80° C. Cool the reaction and dilute with dichloromethane (150 mL). Extract the organic phase with brine, dry (Na$_2$SO$_4$), filter and concentrate the filtrate to afford 4-(1-pentyl-1H-benzoimidazol-2-yl)-[1,4]diazepane-1-carboxylic acid tert-butyl ester (0.71 g, R$_f$=0.87, silica gel, 95:5:0.5 dichloromethane:methanol:ammonium hydroxide).

Hydrolyze 4-(1-pentyl-1H-benzoimidazol-2-yl)-[1,4]diazepane-1-carboxylic acid tert-butyl ester (0.70 g, 1.81 mmol) by refluxing an ethanol solution of the compound with hydroiodic acid (57%, 5 mL) as described in Example 111 to provide 2-[1,4]diazepan-1-yl-1-pentyl-1H-benzoimidazole dihydroiodide (0.85 g).

Heat a mixture of 2-[1,4]diazepan-1-yl-1-pentyl-1H-benzoimidazole dihydroiodide (0.83 g, 1.53 mmol), methanesulfonic acid 2-{(S)-1-[1-(2-methoxy-5-tetrazol-1-yl-phenyl)-methanoyl]-3-phenyl-pyrrolidin-3-yl}-ethyl ester (0.713 g, 1.51 mmol, example 47.2), diisopropylethylamine (1 mL, 5.74 mmol) and acetonitrile (15 mL) at 90° C. for 72 hours. Concentrate to dryness and dissolve the residue in dichloromethane. Wash the dichloromethane phase with NaHCO$_3$ (10%, 10 mL) and brine (four 10 mL portions), dry (Na$_2$SO$_4$) the organic phase, filter and evaporate. Purify the residue by silica gel chromatography (3.5×35 cm) eluting with 95:5:0.05 dichloromethane:methanol:30% ammonium hydroxide solution. Concentrate the desired fractions to afford 0.19 g of the title compound, R$_f$=0.80 (silica gel, 90:10:0.1 dichloromethane:methanol:30% ammonium hydroxide solution). The product may be converted to the dihydrochloride by methods as are well known in the art.

EXAMPLE 113

1-((R)-3-{2-[4-(1-Cyclopropylmethyl-1H-benzoimidazol-2-yl)-[1,4]diazepan-1-yl]-ethyl}-3-phenyl-pyrrolidin-1-yl)-1-(2-methoxy-5-tetrazol-1-yl-phenyl)-methanone

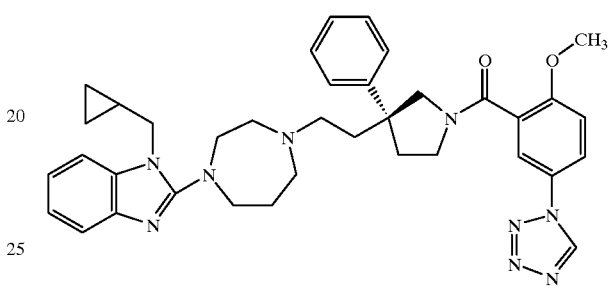

Treat a solution of 1-(t-butoxycarbonyl)-4-(1H-benzimidazol-2-yl)[1,4]diazepan (0.50 g, 1.58 mmol, Preparation 9) and dimethylformamide (10 mL) with sodium hydride (0.083 g, 2.08 mmol, 60% dispersion in oil) at room temperature. After 15 minutes, add (bromomethyl)cyclopropane (0.21 mL, 2.17 mmol, Aldrich Chemical Company) and heat two hours at 80° C. Cool the reaction and partition between dichloromethane (150 mL) and NaHCO$_3$ solution (40 mL). Wash the organic phase with brine (40 mL), dry (MgSO$_4$), filter and concentrate the filtrate to afford 4-(1-cyclopropylmethyl-1H-benzoimidazol-2-yl)-[1,4]diazepane-1-carboxylic acid tert-butyl ester (0.71 g, R$_f$=0.87, silica gel, 95:5:0.5 dichloromethane:methanol:ammonium hydroxide).

Hydrolyze 4-(1-cyclopropylmethyl-1H-benzoimidazol-2-yl)-[1,4]diazepane-1-carboxylic acid tert-butyl ester (0.70 g, 1.81 mmol) by refluxing an ethanol (10 mL) solution of the compound with hydroiodic acid (57%, 5 mL) for 1 hour as described in Example 111 to provide 1-cyclopropylmethyl-2-[1,4]diazepan-1-yl-1H-benzoimidazole dihydroiodide (0.85 g)

Reflux a mixture of 1-cyclopropylmethyl-2-[1,4]diazepan-1-yl-1H-benzoimidazole dihydroiodide (0.60 g, 1.14 mmol), methanesulfonic acid 2-{(S)-1-[1-(2-methoxy-5-tetrazol-1-yl-phenyl)-methanoyl]-3-phenyl-pyrrolidin-3-yl}-ethyl ester (0.53 g, 1.12 mmol, example 47.2), triethylamine (0.65 mL, 4.66 mmol) and acetonitrile (10 mL) for 8 hours. Cool and dilute with dichloromethane (150 mL), wash the organic phase with NaHCO$_3$ (30 mL) and saturated brine solution (30 mL), dry (MgSO$_4$) the organic phase, filter and evaporate. Purify the residue by silica gel chromatography (4×41 cm) eluting with dichloromethane:methanol:30% ammonium hydroxide (95:5:0.05} to afford 0.47 g of the title compound, R$_f$=0.32

EXAMPLE 114

1-{(R)-3-[2-(4-{1-[2-(2-Methoxy-ethoxy)-ethyl]-1H-benzoimidazol-2-yl}-[1,4]diazepan-1-yl)-ethyl]-3-phenyl-pyrrolidin-1-yl}-1-(2-methoxy-5-tetrazol-1-yl-phenyl)-methanone

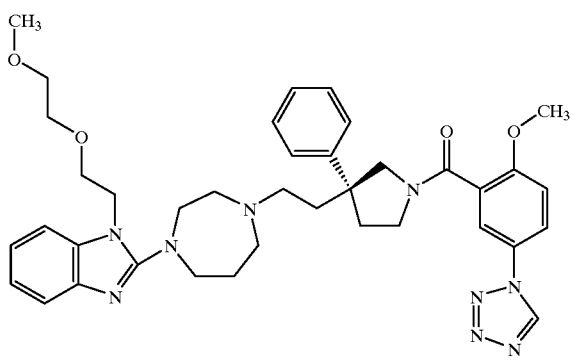

Treat a solution of 1-(t-butoxycarbonyl)-4-(1H-benzimidazol-2-yl)[1,4]diazepan (preparation 9, 0.50 g, 1.58 mmol) and dimethylformamide (10 mL) with sodium hydride (0.083 g, 2.08 mmol, 60% dispersion in oil) at room temperature. After 30 minutes, add 1-bromo-2-(2-methoxyethoxy)ethane (0.34 g, 1.88 mmol, Aldrich Chemical Company) and heat two hours at 70° C. Cool the reaction, add water (10 mL) and extract with dichloromethane (100 mL). Wash the organic phase with water, dry (Na$_2$SO$_4$), filter and concentrate the filtrate to afford 4-{1-[2-(2-methoxy-ethoxy)-ethyl]-1H-benzoimidazol-2-yl}-[1,4]diazepane-1-carboxylic acid tert-butyl ester (0.62 g).

Hydrolyze 4-{1-[2-(2-methoxy-ethoxy)-ethyl]-1H-benzoimidazol-2-yl}-[1,4]diazepane-1-carboxylic acid tert-butyl ester (0.73 g, 1.73 mmol) with hydroiodic acid (57%, 5 mL) for 1 hour as described in Example 113 to provide 2-[1,4]diazepan-1-yl-1-[2-(2-methoxy-ethoxy)-ethyl]-1H-benzoimidazole dihydroiodide (0.73 g).

Heat a mixture of 2-[1,4]diazepan-1-yl-1-[2-(2-methoxy-ethoxy)-ethyl]-1H-benzoimidazole dihydroiodide (0.71 g, 1.24 mmol), methanesulfonic acid 2-{(S)-1-[1-(2-methoxy-5-tetrazol-1-yl-phenyl)-methanoyl]-3-phenyl-pyrrolidin-3-yl}-ethyl ester (0.60 g, 1.27 mmol, example 47.2) and acetonitrile (10 mL), triethylamine (1.2 mL, 8.61 mmol) and acetonitrile (15 mL) at 85° C. for 18 hours. Quench the reaction and purify the crude product as described in Example 113 to afford 0.51 g of the title compound, R$_f$=0.40 (silica gel, dichloromethane:methanol:30% ammonium hydroxide, 90:10:0.1). The compound may be converted to the dihydrochloride salt by methods well known in the art.

(silica gel, dichloromethane:methanol:30% ammonium hydroxide solution. The compound may be converted to the dihydrochloride salt by methods well known in the art.

EXAMPLE 115

1-[(R)-3-(2-{4-[1-(2-Cyclopropylmethoxy-ethyl)-1H-benzoimidazol-2-yl]-[1,4]diazepan-1-yl}-ethyl)-3-phenyl-pyrrolidin-1-yl]-1-(2-methoxy-5-tetrazol-1-yl-phenyl)-methanone

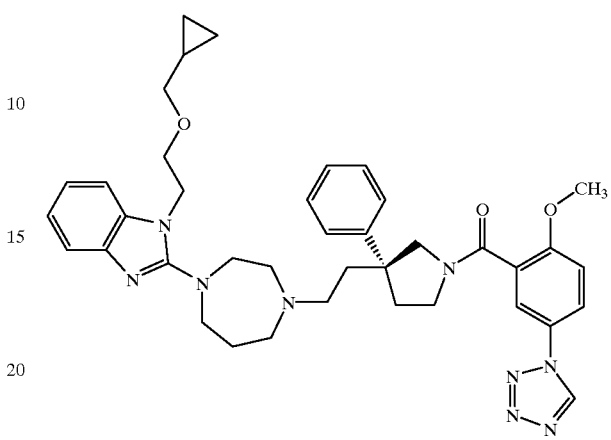

Treat a dry ice/acetone chilled mixture of 1-(t-butoxycarbonyl)-4-(1-2-hydroxyethyl)1H-benzimidazol-2-yl)-[1,4]diazepane (0.50 g, 1.39 mmol, Preparation 8) and sodium hydride (0.058 g, 1.46 mmol, 60% in oil dispersion) under argon via syringe with anhydrous tetrahydrofuran (9 mL). Allow the mixture to stir at 0° C. for 1.5 hours, then add (bromomethyl)cyclopropane (1.1 equivalents, Aldrich Chemical Company) dropwise. Stir the reaction mixture at room temperature for 20 hours and then reflux under argon for 1.5 hours. Thin layer chromatographic analysis (silica gel, ethyl acetate) indicates the presence of starting material. Treat the reaction mixture with sodium hydride (0.03 g). Stir 18 hours, quench the reaction with ice, stir 30 minutes and concentrate in vacuo. Dissolve the residue in dichloromethane, wash with NaHCO$_3$ solution (100 mL) and water (3×150 mL), wash with saturated brine (100 mL), dry the organic phase (MgSO$_4$) and concentrate. Purify the residue by column chromatography on silica gel (6×45 mm) eluting the column with 60% ethyl acetate in dichloromethane to give 4-[1-(2-cyclopropylmethoxyethyl)-1H-benzoimidazol-2-yl]-[1,4]diazepane-1-carboxylic acid tert-butyl ester (0.32 g; R$_f$=0.55, silica gel, ethyl acetate).

Treat a solution of 4-[1-(2-cyclopropylmethoxy-ethyl)-1H-benzoimidazol-2-yl]-[1,4]diazepane-1-carboxylic acid tert-butyl ester (0.32 g, 0.76 mmol) and dioxane (4 mL) with 4N HCl in dioxane (2.3 mL, 12 equivalents) with stirring. After 90 minutes concentrate to remove the solvent, add 2.5 mL, of dichloromethane and then add ether dropwise with stirring. Repeat the process of concentration, dissolving in dichloromethane (2 mL) and treating the solution with ether and allowing the mixture to stir overnight until a suspension of yellow crystalline material is obtained. Collect the prpeipitate by filtration under argon, wash with ether and dry in vacuo overnight to give 1-(2-cyclopropylmethoxy-ethyl)-2-[1,4]diazepan-1-yl-1H-benzoimidazole dihydrochloride (0.22 g). Treat a slurry of 1-(2-cyclopropylmethoxy-ethyl)-2-[1,4]diazepan-1-yl-1H-benzoimidazole dihydrochloride (0.16 g, 0.42 mmol) and dichloromethane (150 mL) with saturated NaHCO$_3$ solution. Extract the aqueous phase once with dichloromethane (100 mL). Wash the combined dichloromethane phases with water (3×200 mL) and saturated brine (100 mL), dry (MgSO$_4$) the organic phase, filter and concentrate to afford a 1-(2-cyclopropylmethoxy-ethyl)-2-[1,4]diazepan-1-yl-1H-benzoimidazole as a yellow oil (0.10 g).

Heat at 81° C. a mixture of 1-(2-cyclopropylmethoxy-ethyl)-2-[1,4]diazepan-1-yl-1H-benzoimidazole (0.10 g, 0.33 mmol) and methanesulfonic acid 2-{(S)-1-[1-(2-methoxy-5-tetrazol-1-yl-phenyl)-methanoyl]-3-phenyl-pyrrolidin-3-yl}-ethyl ester (0.60 g, 1.27 mmol, example 47.2), triethylamine (0.136 mL, 3 equivalents), sodium iodide (0.097 g, 2 equivalents) and acetonitrile (8.1 mL) under argon for 30 hours. Quench the reaction as described in Example 113. Purify the crude material by column chromatography (silica gel, 4.5 cm×15 cm, using step gradient elution with 0%, 5% and 10% methanol in dichloromethane. Concentrate the appropriate fractions to afford 0.16 g of the title compound, $R_f$=0.33 (silica gel, 10% methanol in dichloromethane). The compound may be converted to the dihydrochloride salt, m.p. 135–155° C. (dec.), by methods well known in the art.

EXAMPLE 116

1-(2-Methoxy-5-tetrazol-1-yl-phenyl)-1-[(R)-3-phenyl-3-(2-{4-[1-(2-pyrazol-1-yl-ethyl)-1H-benzoimidazol-2-yl]-[1,4]diazepan-1-yl}-ethyl)-pyrrolidin-1-yl]-methanone

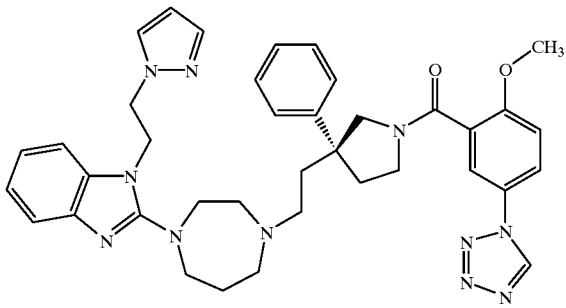

Treat a stirred solution of pyrazole (0.22 g, 3.18 mmol, Aldrich Chemical Company) and dimethylformamide (5 mL) at room temperature portionwise with sodium hydride (0.15 g, 3.18 mmol). After 30 minutes, slowly add a solution of 1-(t-butoxycarbonyl)-4-(1-(2-methanesulfonyloxyethyl)-1H-benzimidazol-2-yl)-[1,4]diazepane (0.93 g, 2.12 mmol, Preparation 28) and dimethylformamide, and then heat at 75° C. for 12 hours. Cool, add dichloromethane (100 mL) and wash with water (2×20 mL). Dry (Na$_2$SO$_4$) the organic phase, filter and concentrate. Dry the residue under high vacuum at 100° C. to remove residual dimethylformamide. Purify the residue by radial chromatography (silica gel, ethyl acetate:hexane, 1:1) to afford 4-[1-(2-pyrazol-1-yl-ethyl)-1H-benzoimidazol-2-yl]-[1,4]diazepane-1-carboxylic acid tert-butyl ester (0.71 g, $R_f$=0.44 (silica gel, ethyl acetate).

Reflux 4-[1-(2-pyrazol-1-yl-ethyl)-1H-benzoimidazol-2-yl]-[1,4]diazepane-1-carboxylic acid tert-butyl ester (0.71 g, 1.73 mmol) in methanol (15 mL) with hydroiodic acid (57%, 0.5 mL) for 12 hours. Cool, add ether (80 mL) to afford a suspension and stir the suspension for one hour. Collect the solid by filtration and dry to provide 2-[1,4]diazepan-1-yl-1-(2-pyrazol-1-yl-ethyl)-1H-benzoimidazole dihydroiodide (0.81 g).

Reflux a mixture of 2-[1,4]diazepan-1-yl-1-(2-pyrazol-1-yl-ethyl)-1H-benzoimidazole dihydroiodide (0.48 g, 0.84 mmol), methanesulfonic acid 2-{(S)-1-[1-(2-methoxy-5-tetrazol-1-yl-phenyl)-methanoyl]-3-phenyl-pyrrolidin-3-yl}-ethyl ester (0.40 g, 0.84 mmol, example 47.2), diisopropylethylamine (0.44 g, 3.37 mmol) and acetonitrile (20 mL) for 12 hours. Cool and dilute with dichloromethane (150 mL), wash the organic phase with water (2×10 mL), dry (MgSO$_4$) the organic phase, filter and evaporate. Purify the residue by silica gel chromatography eluting with 0.5% methanol in dichloromethane to afford 0.29 g of the title compound, $R_f$=0.18 (silica gel, 0.5% methanol in dichloromethane). The compound may be converted to the dihydrochloride salt by methods well known in the art.

EXAMPLE 117

1-(2-Methoxy-5-tetrazol-1-yl-phenyl)-1-{(R)-3-[2-(4-{1-[2-(5-methyl-tetrazol-1-yl)-ethyl]-1H-benzoimidazol-2-yl-[1,4]diazepan-1-yl)-ethyl]-3-phenyl-pyrrolidin-1-yl}-methanone

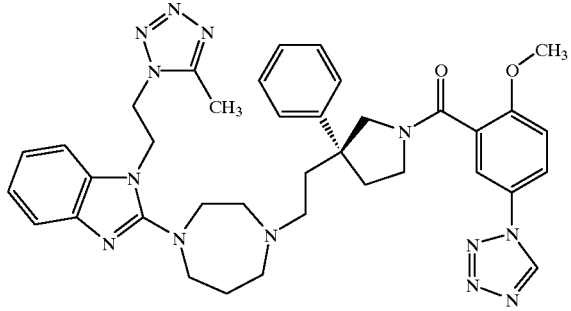

Treat a stirred solution of 5-methyltetrazole (0.38 g, 4.52 mmol, obtained from TCI US) and dimethylformamide (7 mL) at 0° C. portionwise with sodium hydride (0.19 g, 4.75 mmol, 60% dispersion in oil). Allow to warm to room temperature over one hour and add a solution of 1-(t-butoxycarbonyl)-4-(1-(2-methanesulfonyloxyethyl)-1H-benzimidazol-2-yl)-[1,4]diazepane (0.1.33 g, 3.03 mmol, Preparation 28) and dimethylformamide (7 mL). Heat at 100° C. for 6 hours. Cool, add ethyl acetate (50 mL) and wash with saturated NaHCO$_3$ (3×25 mL) and brine (3×50 mL). Dry (MgSO$_4$) the organic phase, filter and concentrate in vacuo. Purify the residue by chromatography (silica gel, 3.5×50 cm) eluting with ethyl acetate:hexane (1:1) to afford 4-{1-[2-(5-methyl-tetrazol-1-yl]-ethyl]-1H-benzoimidazol-2-yl}-[1,4]diazepane-1-carboxylic acid tert-butyl ester (0.45 g), $R_f$=0.21 (silica gel, methanol:dichloromethane, 1:1).

Reflux 4-{1-[2-(5-methyl-tetrazol-1-yl)-ethyl]-1H-benzoimidazol-2-yl}-[1,4]diazepane-1-carboxylic acid tert-butyl ester (0.42 g, 0.98 mmol) in ethanol (15 mL) with 57% hydroiodic acid (5 mL) for one hour. Cool, treat with sodium hydroxide solution (final pH 13) and extract with dichloromethane (10×50 mL). Dry the combined organic phases (Na$_2$SO$_4$), filter and concentrate the filtrate in vacuo to afford 2-[1,4]diazepan-1-yl-1-[2-(5-methyl-tetrazol-1-yl)-ethyl]-1H-benzoimidazole (0.27 g), $R_f$=0.60 (silica gel, dichloromethane:methanol:ammonium hydroxide solution, 80:20:0.2).

Reflux a mixture of 2-[1,4]diazepan-1-yl-1-[2-(5-methyl-tetrazol-1-yl)-ethyl]-1H-benzoimidazole (0.27 g, 0.83 mmol), methanesulfonic acid 2-{(S)-1-[1-(2-methoxy-5-tetrazol-1-yl-phenyl)-methanoyl]-3-phenyl-pyrrolidin-3-yl}-ethyl ester (0.40 g, 0.84 mmol, example 47.2), diisopropylethylamine (1.0 mL, 1.27 mmol), potassium iodide (0.21 g, 1.27 mmol) and acetonitrile (20 mL) overnight. Concentrate in vacuo to remove the solvent and purify the residue by silica gel chromatography (3.5×30 cm) eluting with dichloromethane:methanol:30% ammonium hydroxide solution, (95:5:0.5). Combine and concentrate the appropriate fractions to afford 0.19 g of the title compound, $R_f$=0.36 (silica gel, dichloromethane:methanol:30% ammonium hydroxide solution, 90:10:0.1). The compound may be converted to the dihydrochloride salt by methods well known in the art.

EXAMPLE 118

Methanesulfonic acid 3-{1-[(R)-3-(2-{4-[1-(2-ethoxy-ethyl)-1H-benzoimidazol-2-yl]-[1,4]diazepan-1-yl}-ethyl)-3-phenyl-pyrrolidin-1-yl]-methanoyl}-4-methoxy-phenyl ester

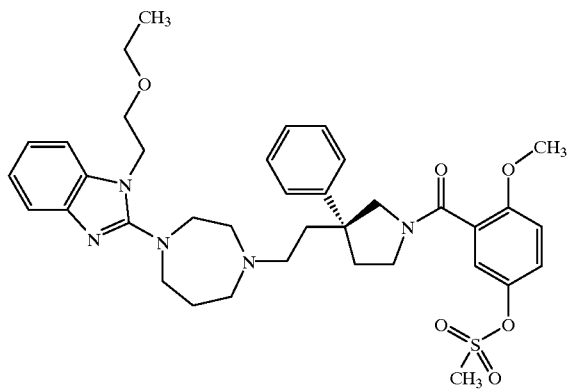

Stir a mixture of methyl 4-hydroxy-2-methoxybenzoate (Danishefsky et al., J. Med. Chem. 1979, 101, 7001–7008, 0.37 g, 2 mmol) and 1N NaOH for two hours at room temperature. Acidify with 1N HCl and extract with dichloromethane. Dry (MgSO$_4$) the organic phase, filter and concentrate the filtrate in vacuo. Vacuum dry the residue at room temperature overnight to afford 4-hydroxy-2-methoxybenzoic acid (0.34 g).

Stir a mixture of 1-(2-ethoxy-ethyl)-2-{4-[2-((S)-3-phenyl-pyrrolidin-3-yl)-ethyl]-[1,4]diazepan-1-yl}-1H-benzoimidazole dihydrochloride (0.53 g, 1 mmol, Preparation 12.1, named as 3-(2-(4-(1-(2-ethoxyethyl)-1H-benzimidazol-2-yl) [1,4]diazepan-1-yl)ethyl)-3-phenylpyrrolidine), 4-hydroxy-2-methoxybenzoic acid (0.34 g), 1-(3-dimethylaminopropyl)-3-ethylcarbodiimide (0.19 g, 1 mmol, Aldrich Chemical Company), 1-hydroxybenzotriazole hydrate (0.14 g, 1 mmol, Aldrich Chemical Company), diisopropyoethylamine (3.4 mL) and dichloromethane (10 mL) overnight at room temperature. Dilute the reaction mixture with dichloromethane, wash with saturated brine, dry (MgSO$_4$) the organic phase, filter and concentrate the filtrate in vacuo. Purify the residue by column chromatography on silica gel eluting sequentially with ethyl acetate, 3% methanol in dichloromethane and 10% methanol in dichloromethane. Concentrate the appropriate fractions to afford 1-[(R)-3-(2-{4-[1-(2-ethoxy-ethyl)-1H-benzoimidazol-2-yl]-[1,4]diazepan-1-yl}-ethyl)-3-phenyl-pyrrolidin-1-yl]-1-(5 -hydroxy-2-methoxy-phenyl)-methanone (0.19 g), R$_f$=0.38 (silica gel, 10% methanol in dichloromethane).

Treat a stirred solution of 1-[(R)-3-(2-{4-[1-(2-ethoxy-ethyl)-1H-benzoimidazol-2-yl]-[1,4]diazepan-1-yl}-ethyl)-3-phenyl-pyrrolidin-1-yl]-1-(5-hydroxy-2-methoxy-phenyl)-methanone (0.25 g, 0.22 mmol) and dichloromethane (5 mL) at 0° C. with diisopropylethylamine (0.14 mL, 0.84 mmol) and methane sulfonyl chloride (0.04 mL, 0.5 mmol). Stir the reaction mixture at 0° C. for two hours, dilute with dichloromethane and wash with water. Dry (MgSO$_4$) the organic phase, filter and concentrate the filtrate in vacuo. Purify the product by column chromatography (silica gel, elute sequentially with 3% methanol in dichloromethane then with 5% methanol in dichloromethane) and concentrate the appropriate fractions to afford 0.19 g of the title compound, R$_f$=0.28 (silica gel, 5% methanol in dichloromethane). The compound may be converted to the dihydrochloride salt by methods swell known in the art.

EXAMPLE 119

1-[(R)-3-(2-{4-[1-(2-Ethoxy-ethyl)-1H-benzoimidazol-2-yl]-[1,4]diazepan-1-yl}-ethyl)-3-phenyl-pyrrolidin-1-yl]-1-[2-methoxy-5-(2-methoxy-ethoxy)-phenyl]-methanone

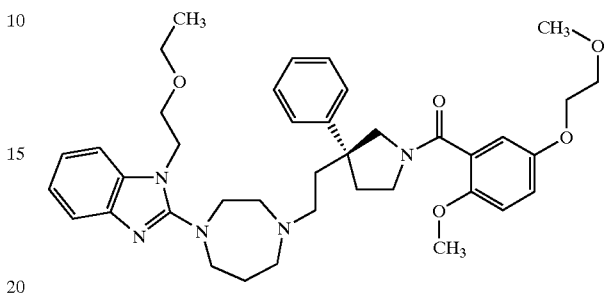

Stir a mixture of methyl 4-hydroxy-2-methoxybenzoate (Danishefsky et al., J. Med. Chem. 1979, 101, 7001–7008, 0.73 g, 4 mmol), 2-chloroethyl methy ether (1 mL, 12 mmol, Aldrich Chemical Company), potassium carbonate (0.55 g, 4.8 mmol) and dimethylformamide (20 mL) at 50° C. overnight. Cool to room temperature, add 2-chloroethyl methy ether (1 mL) and potassium carbonate (1.36 g), and heat with stirring at 70° C. for six hours. Cool and dilute with ethyl acetate, wash with saturated brine, dry (Na$_2$SO$_4$) the organic phase, filter and concentrate the filtrate in vacuo. Vacuum dry the residue overnight at room temperature to afford 0.94 g of 2-methoxy-5-(2-methoxy-ethoxy)-benzoic acid methyl ester.

Stir a mixture of 2-methoxy-5-(2-methoxy-ethoxy)-benzoic acid methyl ester (0.87 g, 3.6 mmol), methanol (20 mL) and 1N NaOH solution (20 mL) for two hours at room temperature. Acidify the reaction with 1N HCl and extract with dichloromethane. Dry (MgSO$_4$) the organic phase, filter and concentrate the filtrate in vacuo. Vacuum dry the residue at room temperature over 48 hours to afford 0.82 g of 2-methoxy-5-(2-methoxy-ethoxy)-benzoic acid as an oil, R$_f$=0.84 (silica gel, dichloromethane:methanol:acetic acid, 85:10:5).

Stir a mixture of 1-(2-ethoxy-ethyl)-2-{4-[2-((S)-3-phenyl-pyrrolidin-3-yl)-ethyl]-[1,4]diazepan-1-yl}-1H-benzoimidazole dihydrochloride (0.32 g, 0.6 mmol, Preparation 12.1), 2-methoxy-5-(2-methoxy-ethoxy)-benzoic acid (0.16 g, 0.72 mmol), 1-(3-dimethylaminopropyl)-3-ethylcarbodiimide (0.14 g, 0.72 mmol), 1-hydroxybenzotriazole hydrate (0.097 g, 0.72 mmol), diisopropyoethylamine (0.2 mL, 1.2 mmol) and dichloromethane (20 mL) overnight at room temperature. Dilute the reaction mixture with dichloromethane, wash with saturated brine, dry (MgSO$_4$) the organic phase, filter and concentrate the filtrate in vacuo. Purify the residue by column chromatography on silica gel eluting sequentially with ethyl acetate, 5% methanol in dichloromethane and 10% methanol in dichloromethane. Concentrate the appropriate fractions to afford 0.32 g of the title compound, R$_f$=0.46 (silica gel, 10% methanol in dichloromethane). The compound may be converted to the dihydrochloride salt by methods well known in the art.

EXAMPLE 120

1-(3-{1-[(R)-3-(2-{4-[1-(2-Ethoxy-ethyl)-1H-benzoimidazol-2-yl]-[1,4]diazepan-1-yl}-ethyl)-3-phenyl-pyrrolidin-1-yl]-methanoyl}-4-methoxy-phenoxy)-propan-2-one

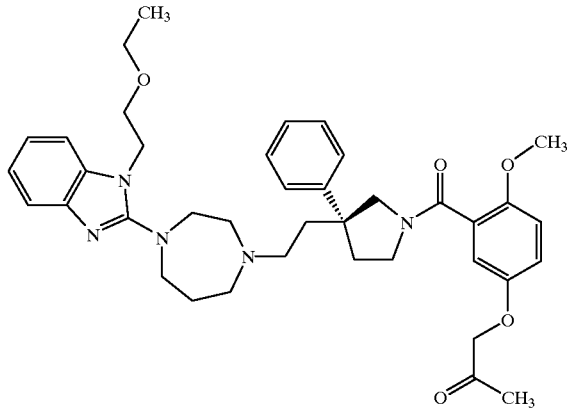

Stir a mixture of methyl 4-hydroxy-2-methoxybenzoate (Danishefsky et al., J. Med. Chem. 1979, 101, 7001–7008, 0.54 g, 3 mmol), chloroacetone (6 mmol, Aldrich Chemical Company), potassium carbonate (9 mmol) and dimethylformamide at 50° C. overnight. Cool the reaction to room temperature, dilute with ethyl acetate, wash with saturated NaHCO₃ solution and saturated brine. Dry (MgSO₄) the organic phase, filter and concentrate the filtrate in vacuo. Purify the residue by column chromatography (silica gel, step gradient elution with 10% ethyl acetate in hexane to 30% ethyl acetate in hexane) and concentrate the appropriate fractions to afford 0.73 g of 2-methoxy-5-(2-oxo-propoxy)-benzoic acid methyl ester.

Stir a mixture of 2-methoxy-5-(2-oxo-propoxy)-benzoic acid methyl ester (0.49 g, 2.1 mmol), methanol (20 mL) and 1N NaOH (20 mL, 20 mmol) for two hours at room temperatue. Acidify the reaction with 1N HCl (to pH 2) and extract with dichloromethane. Dry (MgSO₄) the organic phase, filter and concentrate the filtrate in vacuo. Purify the residue by column chromatography (silica gel, step gradient elution with 3% methanol in dichloromethane to 10% methanol in dichloromethane and concentrate the appropriate fractions to afford 0.38 g of 2-methoxy-5-(2-oxo-propoxy)-benzoic acid, $R_f$=0.82 (silica gel, dichloromethane:methanol:acetic acid, 85:10:5).

Stir a mixture of 1-(2-ethoxy-ethyl)-2-{4-[2-((S)-3-phenyl-pyrrolidin-3-yl)-ethyl]-[1,4]diazepan-1-yl}-1H-benzoimidazole dihydrochloride (0.33 g, 0.61 mmol, Preparation 12.1), 2-methoxy-5-(2-oxo-propoxy)-benzoic acid (0.14 g, 0.61 mmol), 1-(3-dimethylaminopropyl)-3-ethylcarbodiimide (0.14 g, 0.73 mmol), 1-hydroxybenzotriazole hydrate (0.099 g, 0.73 mmol), diisopropylethylamine (0.25 mL, 1.2 mmol) and dichloromethane (10 mL) overnight at room temperature. Dilute the reaction mixture with dichloromethane, wash with saturated brine, dry (MgSO₄) the organic phase, filter and concentrate the filtrate in vacuo. Purify the residue by column chromatography on silica gel eluting sequentially with ethyl acetate, 3% methanol in dichloromethane and 5% methanol in dichloromethane. Concentrate the appropriate fractions to afford 0.35 g of the title compound, $R_f$=0.48 (silica gel, 10% methanol in dichloromethane). The compound may be converted to the dihydrochloride salt by methods well known in the art.

EXAMPLE 121

1-(2-Methoxy-5-tetrazol-1-yl-phenyl)-1-[(R)-3-phenyl-3-(2-{4-[1-(4,4,4-trifluoro-butyl)-1H-benzoimidazol-2-yl]-[1,4]diazepan-1-yl} -ethyl)-pyrrolidin-1-yl]-methanone

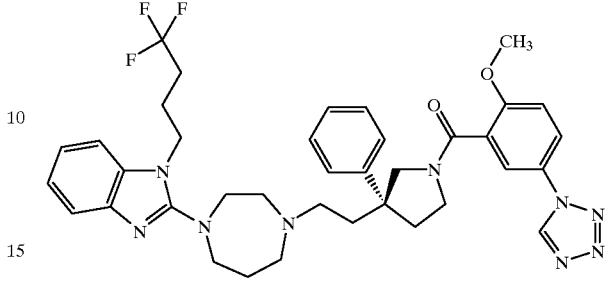

Treat a stirred solution of 1-(t-butoxycarbonyl)-4-(1H-benzimidazol-2-yl)[1,4]diazepan (1.50 g, 4.74 mmol, Preparation 9), tetrahydrofuran (45 mL) and dimethylformamide (5 mL) at 0° C. with sodium hydride (0.228 g, 5.69 mmol, 60% oil dispersion) under an argon atmosphere. Stir at room temperatue for 30 minutes, cool to 0° C. and treat with 1-iodo-4,4,4-trifluorobutane (1.35 g, 5.69 mmol, Lancaster Synthesis). Allow to warm slowly to room temperature and stir overnight at room temperature. Cool to 5° C., quench by addition of ice and saturated ammonium chloride solution (5 mL) and concentrate in vacuo to remove the tetrahydrofuran. Dissolve the residue in ethyl acetate (150 mL), wash the organic phase with water (3×40 mL), dry (Na₂SO₄), filter and concentrate to afford a yellow oil. Purify by flash chromatography (silica gel, 7×40 cm) eluting with 60% ethyl acetate in hexane. Concentrate the appropriate fractions in vacuo and dry the residue (1.2 Torr, 50° C., 2 hours) to afford 1.93 g of 4-[1-(4,4,4-trifluoro-butyl)-1H-benzoimidazol-2-yl]-[1,4]diazepane-1-carboxylic acid tert-butyl ester as an oil, $R_f$=0.40 (silica gel, ethyl acetate).

Treat a solution of 4-[1-(4,4,4-trifluoro-butyl)-1H-benzoimidazol-2-yl]-[1,4]diazepane-1-carboxylic acid tert-butyl ester (1.80 g, 4.22 mmol) and methanol (15 mL) at 0° C. with 57% hydroiodic acid (3.79 g, 16.9 mmol). Stir at room temperature for 30 minutes, heat to 50° C. for two hours and then stir at room temperature overnight. Thin layer analysis (silica gel, ethyl acetate) indicates the presence of starting material. Add 57% hydroiodic acid (1.12 mL) and heat at 50° C. for two hours. Concentrate in vacuo to remove the methanol, dissolve the residue in methanol (10 mL) and add ether (total of 200 mL) to afford a white tacky precipitate. Decant the supernatant, add ether (200 mL) and stir to afford a cream colored solid. Collect the solid by vacuum filtration under nitrogen and dry in vacuo at 82° C. (0.2 Torr) overnight to afford 2.25 g of 2-[1,4]diazepan-1-yl-1-(4,4,4-trifluoro-butyl)-1H-benzoimidazole dihydroiodide, m.p. 206–208° C. Elemental Analysis: Calculated for $C_{16}H_{21}F_3N_4 \cdot 2HI$: 33.01%C, 3.98%H, 9.62%N; Found 33.15%C, 3.87%H, 9.41%N.

Reflux a solution of 2-[1,4]diazepan-1-yl-1-(4,4,4-trifluoro-butyl)-1H-benzoimidazole dihydroiodide (0.65 g, 1.12 immol), methanesulfonic acid 2-{(S)-1-[1-(2-methoxy-5-tetrazol-1-yl-phenyl)-methanoyl]-3-phenyl-pyrrolidin-3-yl}-ethyl ester (0.50 g, 1.06 mmol, example 47.2), triethylamine (3.58 mmol) and acetonitrile (15 mL) for 20 hours. Cool and concentrate in vacuo. Dilute with dichloromethane (150 mL), wash the organic phase with NaHCO₃ solution (3×30 mL), dry (Na₂SO₄) the organic phase, filter and evaporate. Purify the residue by flash chromatography (silica gel, 7×15 cm) eluting with 10% methanol/0.1% ammonium hydroxide solution in dichloromethane and concentrate the appropriate fractions to afford 0.79 g of the title compound as a cream colored foam, $R_f$=0.46 (silica gel, 1.0% methanol/0.1% ammonium hydroxide solution in dichloromethane). The compound may be converted to the dihydrochloride salt by methods well known in the art.

EXAMPLE 122

1-(2-Methoxy-5-tetrazol-1-yl-phenyl)-1-[(R)-3-phenyl-3-(2-{4-[1-(2,2,2-trifluoro-ethyl)-1H-benzoimidazol-2-yl]-[1,4]diazepan-1-yl}-ethyl)-pyrrolidin-1-yl]-methanone

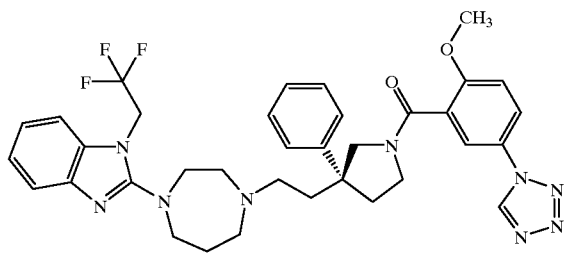

Treat a solution of 2,2,2-trifluoroethanol (170 mmol), pyridine (13.5 mL, 170 mmol) nd dichloromethane at 0° C. dropwise over 45 minutes with a solution of triflic anhydride (196 mmol) and dichloromethane (170 mL). Quench the reaction with water, wash the organic hase with water, dry (MgSO$_4$), filter and concentrate by fractional distillation to afford 1,1,1-trifluoro-methanesulfonic acid 2,2,2-trifluoro-ethyl ester.

Add to a suspension of sodium hydrdide (0.029 g, 1.21 mmol) in anhydrous dimethylformamide (5 mL) a suspension of 1-(t-butoxycarbonyl)-4-(1H-benzimidazol-2-yl)[1,4]diazepan (0.38 g, 1.2 mmol, Preparation 9) in anhydrous dimethylformamide (7 mL). Stir for 3 hours at room temperature and add a large excess of 1,1,1-trifluoro-methanesulfonic acid 2,2,2-trifluoro-ethyl ester. Stir overnight at room temperature, quench the reaction with water, wash the organic phase with water, dry (MgSO$_4$), filter and concentrate in vacuo to afford 4-[1-(2,2,2-trifluoro-ethyl)-1H-benzoimidazol-2-yl]-[1,4]diazepane-1-carboxylic acid tert-butyl ester. Repeat this preparation using 2.88 mmol of 1-(t-butoxycarbonyl)-4-(1H-benzimidazol-2-yl)[1,4]diazepan. Combine the product from both reactions and purify by column chromatography on silica gel eluting with 30% ethyl acetate in hexane and concentrate the appropriate fractions to afford 0.48 g of 4-[1-(2,2,2-trifluoro-ethyl)-1H-benzoimidazol-2-yl]-[1,4]diazepane-1-carboxylic acid tert-butyl ester.

Stir a solution of 4-[1-(2,2,2-trifluoro-ethyl)-1H-benzoimidazol-2-yl]-[1,4]diazepane-1-carboxylic acid tert-butyl ester (0.43 g, 1.07 mmol), methanol (10 mL) and 57% hydroiodic acid overnight at room temperature, and then heat for two hours at 50° C. Cool, add 57% hydroiodic acid (1 mL) and heat for two hours. Concentrate in vacuo to remove the solvents, dilute the residue with methanol (150 mL), concentrate in vacuo, and triturate the residual oil with ether (300 mL) to afford a tan solid. Stir the mixture for one hour, collect the solid by vacuum filtration under nitrogen, and dry in vacuo (0.2 Torr) at 82° C. to afford 0.54 g of 2-[1,4]diazepan-1-yl-1-(2,2,2-trifluoro-ethyl)-1H-benzoimidazole dihydroiodide, m.p. >225° C. Elemental Analysis: Calculated for $C_{14}H_{19}F_3N_4 \cdot 2HI$: 30.35%C, 3.46%H, 10.11%N; Found 30.46%C, 3.33%H, 9.79%N.

Reflux a stirred solution of 2-[1,4]diazepan-1-yl-1-(2,2,2-trifluoro-ethyl)-1H-benzoimidazole dihydroiodide (0.44 g, 0.79 mmol), methanesulfonic acid 2-{(S)-1-[1-(2-methoxy-5-tetrazol-1-yl-phenyl)-methanoyl]-3-phenyl-pyrrolidin-3-yl}-ethyl ester (0.38 g, 0.79 mmol, example 47.2), triethylamine (2.54 mmol) and acetonitrile (11 mL) under argon for 20 hours. Cool and concentrate in vacuo. Dilute with dichloromethane (100 mL), wash the organic phase with NaHCO$_3$ solution (2×20 mL), dry (Na$_2$SO$_4$) the organic phase, filter and evaporate in vacuo. Purify the residue by flash chromatography (silica gel, 7×15 cm) eluting with 10% methanol/0.1% ammonium hydroxide solution in dichloromethane, concentrate the appropriate fractions, and dry the resultant material in vacuo (0.2 Torr) for 2 hours to afford 0.41 g of the title compound as a beige colored foam, $R_f$=0.39 (silica gel, 10% methanol/0.1% ammonium hydroxide solution in dichloromethane). The compound may be converted to the dihydrochloride salt by methods well known in the art.

EXAMPLE 123

1-(2-Methoxy-5-tetrazol-1-yl-phenyl)-1-((R)-3-phenyl-3-{2-[4-(1-vinyl-1H-benzoimidazol-2-yl)-[1,4]diazepan-1-yl]-ethyl}-pyrrolidin-1-yl)-methanone

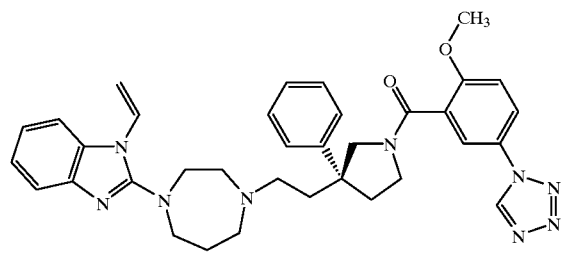

4-(1-Vinyl-1H-benzoimidazol-2-yl)-[1,4]diazepane-1-carboxylic acid tert-butyl ester is the major product obtained from an alternative synthesis of 1-(2,2,2-trifluoroethoxy)ethyl)-1H-benzoimidazol-2-yl)-[1,4]diazepane (Preparation 44.2). Treat a stirred solution of 1-(t-butoxycarbonyl)-4-(1-(2-methanesulfonyloxyethyl)-1H-benzimidazol-2-yl)-[1,4]diazepane (1.21 g, 2.77 mmol, Preparation 9), 2,2,2-trifluoroethanol (2.75 g, 27.4 numol, Aldrich Chemical Company), anhydrous tetrahydrofuran (20 mL) and dimethylformamide (2 mL) at 0–5° C. with sodium hydride (0.44 g, 11 mmol, 60% oil dispersion) under an argon atmosphere. Stir overnight at room temperature, heat at 50° C. for four hours, and stir at room temperature for two hours. Cool to 0° C., quench by addition of saturated ammonium chloride solution (5 mL) and concentrate in vacuo. Dissolve the residue in ethyl acetate (100 mL), wash with water (2×20 mL) and brine (20 mL), dry (Na$_2$SO$_4$) the organic phase, filter and concentrate to afford an oil. Purify the oil by flash chromatography (silica gel, 7×15 cm, ethyl acetate) to afford 0.97 g of 4-(1-vinyl-1H-benzoimidazol-2-yl)-[1,4]diazepane-1-carboxylic acid tert-butyl ester as an oil, $R_f$=0.52 (silica gel, ethyl acetate).

Treat a stirred solution of 4-(1-vinyl-1H-benzoimidazol-2-yl)-[1,4]diazepane-1-carboxylic acid tert-butyl ester (0.97 g, 2.8 mmol) and methanol (20 mL) at 0° C. with 57% hydroiodic acid (467 microliters, 6.21 mmol) solution. Stir at room temperatue for two hours, add 57% hydroiodic acid (934 microliters) and reflux for 30 minutes. Cool to room temperature, concentrate in vacuo to approximately 5 mL final volume, and add ether (total of 200 mL) to afford a tacky solid. Stir the suspension overnight, collect the solid by filtration under nitrogen and dry in vacuo for two hours. Dry in vacuo (0.2 Torr) at room temperature overnight to afford 1.33 g of 2-[1,4]diazepan-1-yl-1-vinyl-1H-benzoimidazole dihydroiodide.

Reflux a stirred solution of 2-[1,4]diazepan-1-yl-1-vinyl-1H-benzoimidazole dihydroiodide (0.70 g, 1.40 mmol), 1-(2-methoxy-5-(1H-tetrazol-1-yl)benzoyl-3-phenyl-3-(2-methanesulfonyloxyethyl)-pyrrolidine (0.61 g, 1.3 mmol, example 47.2), triethylamine (4.48 mmol) and acetonitrile (18 mL) under argon for 48 hours. Cool and concentrate in vacuo. Thin layer analysis (silica gel, 10% methanol/0.1% ammonium hydroxide solution in acetonitrile) indicates a mixture with a major component $R_f$=0.40. Dilute with dichloromethane (150 mL), wash the organic phase with NaHCO$_3$ solution (50 mL), dry (Na$_2$SO$_4$) the organic phase, filter and evaporate in vacuo. Purify the residue by flash chromatography (silica gel, 7×15 cm) eluting with 10% methanol/0.1% ammonium hydroxide solution in dichloromethane, concentrate the appropriate fractions to afford a tan solid. Purify the solid (in three separate injections of 110 mg, 250 mg and 250 mg) by reverse phase chromatography (PrepPak 40×100 mm μBondapak C$_{18}$, 10 μm, 125 A°, Waters 037684, flow rate 35 mL/minute using the following gradients: 5 minutes with 10% acetonitrile/90% water with 0.1% trifluoroacetic acid, increase over 30 minutes to 50/50 water/acetonitrile, hold 5 minutes at 50/50 water/acetonitrile, increase over 5 minutes to 100% acetonitrile, hold 15 minutes at 100% acetonitrile). Combine the desired fractions to afford 0.17 g of the title compound.

PREPARATION 59

2-Methoxy-5-(3-methylsulfanyl-[1,2,4]triazol-4-yl)-benzoic acid

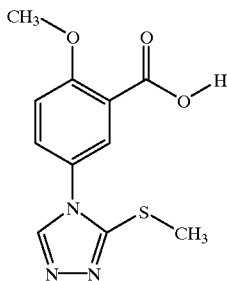

Prepare 5-amino-2-methoxy-benzoic acid methyl ester by catalytic hydrogenation of 1-methoxy-5-nitrobenzoic acid methyl ester (103.2 g, 0.49 mole, Wychem) over 10%Pd/C (5 g) in methanol (3.1 liters) at 119 pounds per square inch pressure. After the uptake of hydrogen ceases, filter the mixture and concentrate the filtrate. Dissolve the residue in ethyl acetate (1 liter), wash with saturated brine solution, dry (MgSO$_4$), filter and concentrate to afford 5-amino-2-methoxy-benzoic acid methyl ester.

Treat a solution of 5-amino-2-methoxy-benzoic acid methyl ester (7.70 g, 42.5 mmol) and dichloromethane (50 mL) portionwise with a solution of di-2-pyridyl thionocarbonate (10.0 g, 43.1 mmol; Aldrich Chemical Company) and dichloromethane (70 mL) at room temperature under an argon atmosphere. After 3.5 hours, concentrate in vacuo and purify the residue by flash chromatography (silica gel, 5.5×17.8 cm) eluting with dichloromethane. Combine the appropriate fractions and concentrate to afford 5-isothiocyanato-2-methoxy-benzoic acid methyl ester (6.9 g).

Treat a mixture of 5-isothiocyanato-2-methoxy-benzoic acid methyl ester (6.90 g, 30.91 mmol) and formic hydrazide (2.04 g, 34.0 mmol, Aldrich Chemical Company) under an argon atmosphere via syringe with anhydrous tetrahydrofuran (40 mL). After three hours, concentrate in vacuo to remove the solvent, mix the residue with 1 M NaHCO$_3$ solution (total of 300 mL employed) in portions and transfer to a 500 mL round bottom flask. Reflux for 3 days under an argon atmosphere. Filter the hot solution, acidify with concentrated hydrochloric acid (25 mL), chill the mixture in an ice bath and collect the precipitate by vacuum filtration. Wash the filter cake with dichloromethane and dry in vacuo to afford 7.12 g of 2-methoxy-5-(5-thioxo-1,5-dihydro-[1,2,4]triazol-4-yl)-benzoic acid. Combine the filtrates and concentrate in vacuo to afford another crop of 2-methoxy-5-(5-thioxo-1,5-dihydro-[1,2,4]triazol-4-yl)-benzoic acid (1.24 g).

Treat a solution of 2-methoxy-5-(5-thioxo-1,5-dihydro-[1,2,4]triazol-4-yl)-benzoic acid (6.66 g, 26.5 mmol) and methanol (80 mL) under argon via syringe dropwise with thionyl chloride (2.9 mL, 40 mmol). Stir for three days and remove the methanol in vacuo. Purify the residue by flash chromatography (silica gel, 9.5×12.7 cm) eluting with 40% ethyl acetate in dichloromethane and then with ethyl acetate. Concentrate the desired fractions in vacuo to afford 4.55 g of 2-methoxy-5-(5-thioxo-1,5-dihydro-[1,2,4]triazol-4-yl)-benzoic acid methyl ester.

Treat a stirred mixture of 2-methoxy-5-(5-thioxo-1,5-dihydro-[1,2,4]triazol-4-yl)-benzoic acid methyl ester (3.80 g, 14.38 mmol), potassium carbonate (2.19 g, 15.8 mmol) and anhydrous acetone (60 mL) with methyl iodide (1.07 mL, 17.25 mmol) added dropwise via syringe. Reflux the stirred mixture for 2.5 hours, cool, filter and wash the filter cake twice with acetone. Combine the acetone phases, concentrate in vacuo, dissolve the residue in ethyl acetate and wash with NaHCO$_3$ solution. Extract the combined aqueous phases three times with ethyl acetate. Combine the ethyl acetate phases, wash with saturated NaHCO$_3$ and brine, dry (MgSO$_4$), filter and concentrate in vacuo to afford an oil. Purify the oil by flash chromatography (silica gel, 5.5×15.2 cm) eluting with ethyl acetate and then with 5% methanol in dichloromethane after elution of the starting material. Concentrate the appropriate fractions to afford 2.89 g of 2-methoxy-5-(3-methylsulfanyl-[1,2,4]triazol-4-yl)-benzoic acid methyl ester as a colorless solid.

Stir a mixture of 2-methoxy-5-(3-methylsulfanyl-[1,2,4]triazol-4-yl)-benzoic acid methyl ester (0.28 g, 3.5 mmol), lithium hydroxide (0.041 g, 3.8 mmol), and 25% water in tetrahydrofuran (20 mL) overnight. Add 1N hydrochloric acid (3.9 mL) dropwise to pH 3. Concentrate to remove the tetrahydrofuran and collect the precipitate by vacuum filtration. Wash the filter cake twice with water and hexane, and dry in vacuo overnight to give 0.89 g of 2-methoxy-5-(3-methylsulfanyl-[1,2,4]triazol-4-yl)-benzoic acid as a solid.

EXAMPLE 124

1-[(R)-3-(2-{4-[1-(2-Ethoxy-ethyl)-1H-benzoimidazol-2-yl]-[1,4]diazepan-1-yl}-ethyl)-3-phenyl-pyrrolidin-1-yl]-1-[2-methoxy-5-(3-methylsulfanyl-[1,2,4]triazol-4-yl)-phenyl]-methanone

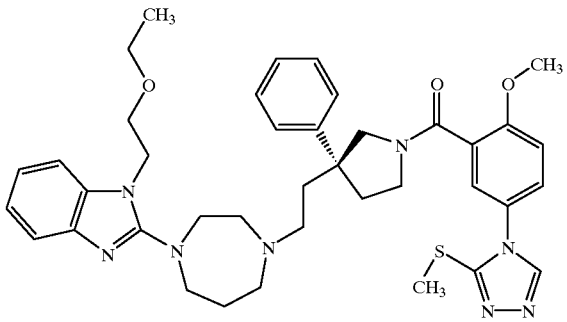

To a mixture of 2-methoxy-5-(3-methylsulfanyl-[1,2,4]triazol-4-yl)-benzoic acid (0.27 g, 0.42 mmol), 1-(2-ethoxy-ethyl)-2-{4-[2-((S)-3-phenyl-pyrrolidin-3-yl)-ethyl]-[1,4]diazepan-1-yl}-1H-benzoimidazole dihydrochloride (0.23 g, 0.42 mmol), 1-hydroxybenzotriazole hydrate (0.068 g, 0.51 mmol), and 1-(3-dimethylaminopropyl)-3-ethylcarbodiimide (0.97 g, 0.51 mmol), add via syringe under argon anhydrous dichloromethane (15 mL). Add diisopropylethylamine (0.22 mL, 1.26 mmol) and stir at room temperature for 20 hours. Dilute with dichloromethane and wash twice with water. Wash with saturated $NaHCO_3$ solution, dry ($MgSO_4$) the organic phase, filter and concentrate to an oil. Purify the oil by flash chromatography (silica gel, 3.5×15.2 cm) eluting with dichloromethane and then with 10% methanol in dichloromethane. Concentrate the appropriate fractions to afford 0.051 g of the title compound, $R_f$=0.26 (silica gel, 10% methanol in dichloromethane). The compound may be converted to the dihydrochloride salt by methods well known in the art.

PREPARATION 60

5-(3-Methanesulfonyl-[1,2,4]triazol-4-yl)-2-methoxy-benzoic acid

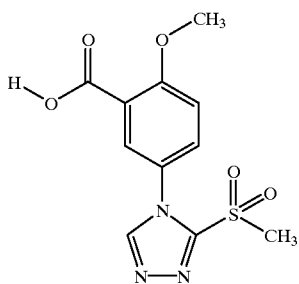

Treat a stirred, chilled (0° C.) solution of 2-methoxy-5-(3-methylsulfanyl-[1,2,4]triazol-4-yl)-benzoic acid methyl ester (1.50 g, 5.4 mmol) and dichloromethane (20 mL) dropwise with a solution of m-chloroperbenzoic acid (2.32 g, 13.5 mmol) and dichloromethane (10 mL). Stir at 0° C. for 30 minutes, then stir at room temperature for 64 hours. Concentrate and purify the residue by flash chromatography (silica gel, 5.5×15.2 cm) eluting with ethyl acetate. Combine the appropriate fractions and concentrate in vacuo. Dissolve the residue in dichloromethane, wash with $NaHCO_3$ solution, dry ($MgSO_4$) the organic phase, filter and concentrate to afford 1.37 g of 5-(3-methanesulfonyl-[1,2,4]triazol-4-yl)-2-methoxy-benzoic acid methyl ester.

Stir a mixture of 5-(3-methanesulfonyl-[1,2,4]triazol-4-yl)-2-methoxy-benzoic acid methyl ester (1.0 g, 3.2 mmol), lithium hydroxide (0.042 g, 3.6 mmol), and 25% water in tetrahydrofuran (30 mL) at reflux overnight. Cool and add 1N hydrochloric acid (3.6 mL) dropwise via syringe. Concentrate to remove the tetrahydrofuran and collect the precipitate by vacuum filtration. Wash the filter cake twice with water and hexane, and dry in vacuo overnight to give 0.79 g of 5-(3-methanesulfonyl-[1,2,4]triazol-4-yl)-2-methoxy-benzoic acid as a solid.

EXAMPLE 125

1-[(R)-3-(2-{4-[1-(2-Ethoxy-ethyl)-1H-benzoimidazol-2-yl]-[1,4]diazepan-1-yl}-ethyl)-3-phenyl-pyrrolidin-1-yl]-1-[5-(3-methanesulfonyl-[1,2,4]triazol-4-yl)-2-methoxy-phenyl]-methanone

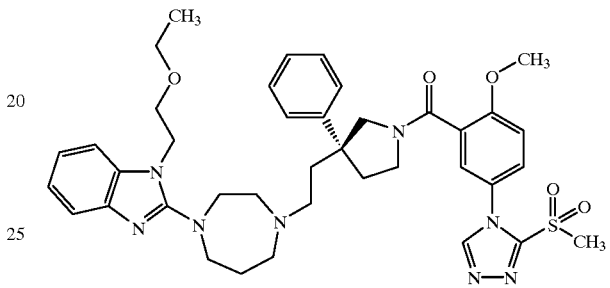

Condense 5-(3-methanesulfonyl-[1,2,4]triazol-4-yl)-2-methoxy-benzoic acid (0.125 g, 0.42 mmol) and 1-(2-ethoxy-ethyl)-2-{4-[2-((S)-3-phenyl-pyrrolidin-3-yl)-ethyl]-[1,4]diazepan-1-yl}-1H-benzoimidazole dihydrochloride (0.23 g, 0.42 mmol) in the presence of 1-hydroxybenzotriazole hydrate (0.062 g, 0.51 mmol), 1-(3-dimethylaminopropyl)-3-ethylcarbodiimide (0.97 g, 0.51 mmol), diisopropylethylamine (0.22 mL, 1.26 mmol), and dichloromethane (15 mL) as described for the preparation of Example 124 to afford 0.065 g of the title compound, $R_f$=0.28 (silica gel, 10% methanol in dichloromethane). The compound may be converted to the dihydrochloride salt by methods well known in the art.

The tachykinins are a class of neuropeptides which share a common C-terminus sequence, Phe-Xaa-Gly-Leu-Met-$NH_2$. The tachykinins are widely distributed in the peripheral and central nervous systems where they bind to at least three receptors types. Among the tachykinin receptors, the $NK_1$, $NK_2$, and $NK_3$ receptors are defined by the preferred binding affinity of substance P, neurokinin A (NKA), and neurokinin B (NKB), respectively.

The use of tachykinin antagonists is indicated as therapy for a variety of tachykinin-mediated diseases and conditions, including: hypersensitivity reactions; adverse immunological reactions; asthma; bronchitis; allergic rhinitis, including seasonal rhinitis and sinusitis; allergies; contact dermatitis; atopic dermatitis; inflammatory bowel diseases, including Crohn's disease and ulcerative colitis; and emesis.

It is understood that tachykinin-mediated diseases and conditions are those diseases and conditions in which the tachykinins are involved, either in whole or in part, in their clinical manifestation(s). Moreover, the tachykinins involvement is not necessarily causative of a particular tachykinin-mediated disease and condition. Tachykinin antagonists are useful in controlling or providing therapeutic relief of those tachykinin-mediated diseases and conditions.

The present invention provides new and useful tachykinin antagonists of formula (1) or stereoisomers or pharmaceutically acceptable salts thereof.

In a further embodiment, as tachykinin antagonists the present invention provides a method of treating tachykinin-mediated diseases and conditions, including: hypersensitivity reactions; adverse immunological reactions; asthma; bronchitis; allergic rhinitis, including seasonal rhinitis and sinusitis; allergies; contact dermatitis; atopic dermatitis; inflammatory bowel diseases, including Crohn's disease and ulcerative colitis; and emesis in a patient in need thereof comprising administering to said patient a therapeutically effective amount of a compound of formula (1).

Immediate hypersensitivity can occur when an IgE antibody response is directed against innocuous antigens, such as pollen. During such a response there is generally a subsequent release of pharmacological mediators, such as histamine, by IgE-sensitized mast cells resulting in an acute inflammatory reaction. The characteristics of the response are determined by the tissue in which the reaction occurs and gives rise to allergic diseases including: allergic rhinitis, including seasonal rhinitis and sinusitis; pulmonary diseases, such as asthma; allergic dermatosis, such as urticaria, angioedema, eczema, atopic dermatitis, and contact dermatitis; gastrointestinal allergies, such as those caused by food or drugs; cramping; nausea; vomiting; diarrhea; and ophthalmic allergies, and uveitis.

Histamine, producing its effects via activation of the $H_1$ receptor, is an important mediator of the above responses involved in immediate hypersensitivity. In the acute phase of allergic rhinitis, histamine $H_1$ receptor antagonists have been shown to effectively inhibit the nasal itchiness, rhinorrhea, and sneezing associated with that condition. However, histamine $H_1$ receptor antagonists are less effective in relieving nasal congestion. The acute response to allergen in rhinitis is often followed by a chronic inflammatory response during which the inflamed mucosa becomes hypersensitive to both antigens and nonspecific irritants. Histamine HI receptor antagonists are also ineffective in attenuating the symptoms of the chronic phase of the response.

The present invention provides new and useful histamine antagonists of formula (1) or stereoisomers or pharmaceutically acceptable salts thereof.

In a further embodiment, as histamine antagonists the present invention provides a method of treating allergic diseases, including: allergic rhinitis, including seasonal rhinitis and sinusitis; pulmonary diseases, such as asthma; allergic dermatosis, such as urticaria, angioedema, eczema, atopic dermatitis, and contact dermatitis; allergic conjuctivitis; gastrointestinal allergies, such as those caused by food or drugs; cramping; nausea; vomiting; diarrhea; and ophthalmic allergies and uveitis; in a patient in need thereof comprising administering to said patient a therapeutically effective amount of a compound of formula (1).

In addition to histamine, the tachykinins, particularly substance P, are also important contributors to the allergic response and produce some symptoms distinct from those produced by a histamine response. This occurs because sensory nerves of trigeminal origin, located around blood vessels and within the nasal mucosal lining, upon stimulation by irritants or inflammatory mediators, such as histamine, will release tachykinins.

Patients with allergic rhinitis have been shown to have higher nasal levels of substance P when their rhinitis symptoms are present. Mosimann et al. *J. Allergy Clin. Immunol.* 92, 95 (1993); Takeyama et al., *J. Pharm. Pharmacol.* 46, 41 (1994); and Wantanabe et al., *Ann. Otol. Rhinol. and Laryngol.*, 102, 16 (1993). Also see Wang, *Br. J. Pharmacol.*, 120, 1491–1496 (1997). In addition, substance P is elevated in the tears of patients suffering form allergic conjuctivitis. Fujishima, *Clin. Exp. Allergy,* 27, 372–378 (1997). In humans, topical or intravenous administration of tachykinins induces nasal obstruction, recruitment of inflammatory cells, glandular secretion, and microvascular leakage in allergic rhinitis. The nasal obstruction produced by substance P was found to be $NK_1$ receptor mediated. Braunstein et al., *Am. Rev. Respir. Dis.,* 144, 630 (1991); Devillier et al., *Eur. Respir. J.* 1, 356 (1988). Furthermore, sensory nerve-mediated effects, such as nasal irritability and hyperresponsivenesss which occurs in late phase allergic reactions, also result from tachykinin release. Anggard, *Acta Otolaryngol.* 113, 394 (1993). Depletion of tachykinins from nasal sensory nerves after chronic capsaicin administration improved rhinitic symptoms in affected individuals. Lacroix et al., *Clin. and Exper. Allergy,* 21, 595 (1991).

Antagonism of the effects of histamine on the $H_1$ receptor is useful in the treatment of allergic diseases, such as rhinitis. Likewise, antagonism of the effects of the tachykinins, particularly substance P on its preferred receptor, is useful in the treatment of symptoms which are concurrent with allergic diseases. Therefore, the potential benefits of an antagonist with affinity at both the $H_1$ and $NK_1$ receptors would be to reduce or prevent clinical manifestations of allergic diseases which are mediated through both receptors.

More particularly, the present invention provides new and useful compounds of formula (1) or stereoisomers or pharmaceutically acceptable salts thereof which are both tachykinin antagonists and histamine antagonists.

In a further embodiment, as both tachykinin antagonists and histamine antagonists the present invention provides a method of treating allergic diseases, including: allergic rhinitis, including seasonal rhinitis and sinusitis; contact dermatitis; allergic conjuctivitis; gastrointestinal allergies, such as those caused by food or drugs; cramping; nausea; vomiting; diarrhea; and ophthalmic allergies and uveitis; and inflammatory bowel diseases, including Crohn's diseases and ulcerative colitis; in a patient in need thereof comprising administering to said patient a therapeutically effective amount of a compound of formula (1).

Various diseases and conditions described to be treated herein, are well known and appreciated by those skilled in the art. It is also recognized that one skilled in the art may affect the associated diseases by treating a patient presently afflicted with the diseases or by prophylactically treating a patient afflicted with the diseases with a therapeutically effective amount of the compounds of formula (1).

As used herein, the term "patient" refers to a warm blooded animal such as a mammal which is afflicted with a particular allergic disease. It is understood that guinea pigs, dogs, cats, rats, mice, horses, cattle, sheep, and humans are examples of animals within the scope of the meaning of the term.

As used herein, the term "therapeutically effective amount" of a compound of formula (1) refers to an amount which is effective in controlling the diseases described herein. The term "controlling" is intended to refer to all processes wherein there may be a slowing, interrupting, arresting, or stopping of the progression of the diseases described herein, but does not necessarily indicate a total elimination of all disease symptoms, and is intended to include prophylactic treatment of the diseases.

A therapeutically effective amount can be readily determined by the attending diagnostician, as one skilled in the art, by the use of conventional techniques and by observing results obtained under analogous circumstances. In determining the therapeutically effective amount, the dose, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the use of concomitant medication; and other relevant circumstances.

A therapeutically effective amount of a compound of formula (1) is expected to vary from about 0.1 milligram per kilogram of body weight per day (mg/kg/day) to about 100 mg/kg/day. Preferred amounts are able to be determined by one skilled in the art.

In effecting treatment of a patient afflicted with diseases described above, a compound of formula (1) can be administered in any form or mode which makes the compound bioavailable in an effective amount, including oral, inhalation, and parenteral routes. For example, compounds of formula (1) can be administered orally, by inhalation of an aerosol or dry powder, subcutaneously, intramuscularly, intravenously, transdermally, intranasally, rectally, occularly, topically, and the like. Oral, inhalation, topical, or occular administration is generally preferred for treatment of allergic diseases. Oral, inhalation, or occular administration is more preferred for treatment of allergic diseases. One skilled in the art of preparing formulations can readily select the proper form and mode of administration depending upon the particular characteristics of the compound selected, the disease or condition to be treated, the stage of the disease or condition, and other relevant circumstances. (Remington's Pharmaceutical Sciences, 18th Edition, Mack Publishing Co. (1990)).

The compounds of the present invention can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice. The compounds of the present invention, while effective themselves, may be formulated and administered in the form of their pharmaceutically acceptable salts, such as acid addition salts or base addition salts, for purposes of stability, convenience of crystallization, increased solubility, and the like.

In another embodiment, the present invention provides pharmaceutical compositions comprising a therapeutically effective amount of a compound of formula (1) in admixture or otherwise in association with one or more pharmaceutically acceptable carriers or excipients.

The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solution, suspensions, ointments, or the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the present invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention may be determined by someone skilled in the art.

The tablets, pills, capsules, troches and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of a compound of the invention, but may be varied to be between 0.1 and about 50% of the weight thereof. The amount of the compound of formula (1) present in such compositions is such that a suitable dosage will be obtained. Preferred compositions and preparations are able to be determined by one skilled in the art.

The compounds of the present invention may also be administered by inhalation, such as by aerosol or dry powder. Delivery may be by a liquefied or compressed gas or by a suitable pump system which dispenses the compounds of the present invention or a formulation thereof.

Formulations for administration by inhalation of compounds of formula (1) may be delivered in single phase, bi-phasic, or tri-phasic systems. A variety of systems are available for the administration by aerosol of the compounds of formula (1). Dry powder formulations are prepared by either pelletizing or milling the compound of formula (1) to a suitable particle size or by admixing the pelletized or milled compound of formula (1) with a suitable carrier material, such as lactose and the like. Delivery by inhalation includes the necessary container, activators, valves, subcontainers, and the like. Preferred aerosol and dry powder formulations for administration by inhalation can be determined by one skilled in the art.

The compounds of the present invention may also be administered topically, and when done so the carrier may suitably comprise a solution, suspension, ointment, or gel base. The base, for example, may comprise one or more of the following: petrolatum, lanolin, polyethylene glycols, bee wax, mineral oil, diluents such as water and alcohol, and emulsifiers and stabilizers. Topical formulations may contain a concentration of the formula (1) or its pharmaceutical salt from about 0.1 to about 10% w/v (weight per unit volume).

The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

EXAMPLE A
Antagonism of [$^3$H]-pyrilamine binding to histamine $H_1$ receptors by putative antagonists One skilled in the art can measure the $H_1$ receptor affinity of proposed histamine antagonists as evaluated in rat brains or Chinese hamster ovary cells transfected with the human histamine $H_1$ receptor gene (CHOpcDNA3H1R cells).

For the studies in rat brain, young male rats are sacrificed by decapitation and the brains are immediately removed. The cortici are dissected and used immediately or stored at −20° C. For the studies in Chinese hamster ovary cells, confluent cells are freshly scraped from culture flasks. The tissues or cells are homogenized with a Polytron (setting no. 6 for 15 seconds) in 20 mL of 50 mM potassium sodium phosphate (pH 7.4, at 4° C.). The homogenate is centrifuged at 48,000×g for 12 minutes at 4° C. The pellet is resuspended using a Polytron (setting no. 6 for 15 seconds) in incubation buffer (50 mM potassium sodium phosphate, pH 7.4, at ambient temperature, containing 0.1% bovine serum albumin) to a concentration of 40 mg/mL and is immediately added to tubes to start the assay. The protein content of the crude membrane suspension can be determined by the method of O. H. Lowery et al., *J. Biol. Chem.*, 193 265 (1951).

The binding assay is carried out in duplicate or triplicate in 12×75 mm polypropylene tubes in 50 mM potassium sodium phosphate (pH 7.4, at ambient temperature) containing 0.1% bovine serum albumin. The radioligand, [$^3$H]-pyrilamine, is diluted in incubation buffer to a concentration of 2 nM and added to each tube (50 μL). The test compound is diluted in incubation buffer ($10^{-10}$ M to $10^{-5}$ M) and is added to the appropriate tubes (50 μL). The assay is started by the addition of 250 μL of well mixed tissue suspension. The final incubation volume is 0.5 mL. The assay is carried out at ambient temperature for 30 minutes. The incubation is terminated by the addition of 3.5 mL of 0.9% sodium chloride solution (4° C.) and filtration through GF/B filters that have been presoaked overnight in 0.1% polyethyleneimine, using a Brandel cell harvester. The filters are rapidly washed with two 3.5 mL portions of incubation buffer and transferred to scintillation vials. Ecolume (9 mL) is added the the vials. the vials are shaken and allowed to set for 4 hours before being counted by liquid scintillation spectrometry. Specific binding is determined bas the difference between tubes containing no test compound and the the tubes containing 10 μM pyrilamine. Total membrane bound radioactivity is generally about 5% of that added the the tubes. Specific binding is generally 75% to 90% of total binding as determined by the method of M. D. DeBacker et al., *Biochem. and Biophys. Res. Commun.*, 197(3) 1601 (1991).

The molar concentration of compound that causes 50% inhibition of radioligand binding. The $IC_{50}$ value is generated for each test compound by nonlinear regression using an iterative curve fitting program (Graph PAD Inplot, San Diego, Calif.).

EXAMPLE B
Antagonism of iodinated tachykinin binding to $NK_1$ receptors by putative antagonists One skilled in the art can measure the $NK_1$ receptor affinity of proposed tachykinin antagonists as evaluated in guinea pig lungs (Keystone Biologicals, Cleveland, Ohio). Tissues are homogenized with a Polytron in 15 volumes of 50 mM Tris-HCl buffer (pH 7.4, 4° C.) and centrifuged. The pellet is resuspended in Tris-HCl buffer and centrifuged; the pellet is washed twice by resuspension. The final pellet is resuspended at a concentration of 40 mg/ml incubation buffer and remains at room temperature for at least 15 min prior to use.

Receptor binding is initiated by addition of 250 μl membrane preparation in duplicate to 0.1 nM of $^{125}$I-Bolton Hunter Lys-3 labeled substance P in a final volume of 500 μl of buffer containing 50 mM Tris-HCl (pH 7.4 at room temperature), 0.1% bovine serum albumin, 2 mM $MnCl_2$, 40 μg/ml bacitracin, 4 μg/ml leupeptin and chymostatin, 1 μM thiorphan and various doses of the putative tachykinin antagonists. Incubations are performed at room temperature for 90 min; binding is terminated by addition of 50 mM Tris-HCl buffer (pH 7.4, 4° C.) and filtration under vacuum through GF/B filters presoaked with 0.1% polyethyleneimine. Filter bound radioactivity is quantitated in a gamma counter. Nonspecific binding is defined as binding in the presence of 1 μM substance P.

Specific binding is calculated by subtracting nonspecific binding from total binding. Competition of iodinated substance P binding by test compounds or standards is expressed as a percentage of this maximum competition. $IC_{50}$ values (concentration required to inhibit 50% of receptor binding) are generated for each of the test compounds by nonlinear regression using an iterative curve fitting program (GraphPAD Inplot, San Diego, Calif.).

EXAMPLE C
Histamine ($H_1$) antagonism in guinea pig ileum

One skilled in the art can determine that the compounds of the present invention are $H_1$ receptor antagonists in vitro by evaluating the compound's ability to inhibit histamine mediated smooth muscle contraction. Male Hartley guinea pigs, weighing 200–450 grams, are sacrificed by $CO_2$ asphyxiation. A piece of ileum, about 20 cm in length, is removed and cut into 2 cm pieces. Each ileum piece is placed in an organ bath at 37° C. containing Tyrode's solution and is constantly aerated with 95% $O_2$/5% $CO_2$. Tyrode's solution has the composition: sodium chloride 136.9 mM, potassium chloride 2.68 nM, calcium chloride 1.8 mM, sodium dihydrogen phosphate 0.42 mM, sodium bicarbonate 11.9 mM, and dextrose 5.55 mM. Contractions are measured with an isometric transducer (Grass FTO3C), and are recorded on a polygraph recorder and/or a computer. The ileum strips are loaded with 1.0 grams of tension and allowed to equilibrate for a minimum of 30 minutes before starting the experiments. Tissue are preincubated with vehicle or varying concentrations of test compound followed by histamine challenge.

A competitive $H_1$ receptor antagonist produces a parallel shift of the histamine dose-response curve to the right without a depression of the maximal response.

The potency of the antagonism is determined by the magnitude of the shift and is expressed as a $pA_2$ value which is the negative logarithm of the molar concentration of antagonist which produces a two-fold shift of the dose response curve to the right. The $pA_2$ value is calculated by using Schild analysis. O. Arunlakshana and H. O. Schild, *Br. J. Pharmacol Chemother.* 14, 48–58 (1958). When the slope of the lines obtained by a Schild analysis are not significantly different from one (1) the compound is acting as a competitive antagonist.

EXAMPLE D
Antagonism of Tachykinin-induced phosphatidylinositol (PI) turnover in vitro by putative antagonists One skilled in the art can determine $NK_1$ receptor antagonism by measuring the substance P-induced phosphatidylinositol (PI, inositol phosphate) accumulation in UC11 cells in the presence and absence of $NK_1$ or $NK_2$ receptor antagonists. Cells are seeded onto 24-well plates at 125,000 cells/well, two or three days prior to the assay. Cells are loaded with 0.5 mL of 0.2 $\mu$M myo-[2-$^3$H(N)]inositol (American Radiolabeled Chemicals Inc., specific activity; 20 $\mu$Ci/mmol) 20–24 hours prior to the assay. Cultured cells are maintained at 37° C. in 5% $CO_2$ environment.

On the day of the assay, media is aspirated and the cells incubated in RPMI-1640 media containing 40 $\mu$g/ml bacitracin, 4 $\mu$g/ml each of leupeptin and chymostatin, 0.1% bovine serum albumin, 10 $\mu$M thiorphan, and 10 mM lithium chloride. After 15 minutes, the test compound is added to the cells in a volume of 0.1 mL. After another 15 min, substance P is added to UC11 cells at various concentrations to start the reaction followed by incubation for 60 min at 37° C. in 5% $CO_2$ environment in a final volume of 1 mL. To terminate the reaction, the media is aspirated and methanol (0.1 mL) is added to each well. Two aliquots of methanol (0.5 mL) are added to the wells to harvest the cells into chloroform resistant tubes. Chloroform (1 mL) is added to each tube followed by doubly distilled water (0.5 mL). Samples are vortexed for 15 seconds and centrifuged at 1700×g for 10 minutes. An aliquot (0.9 mL) of the aqueous (top) phase is removed and added to doubly distilled water (2 mL). The mixture is vortexed and loaded onto a 50% Bio-Rad AG 1-X8 (formate form, 100–200 mesh) exchange column (Bio-Rad Laboratories, Hercules, Calif.). The columns are washed, in order, with: 1) 10 ml doubly distilled water, 2) 5 mL of 5 mM disodium tetraborate/60 mM sodium formate, and 3) 2 mL of 1 M ammonium formate/0.1 M formic acid. The third elution is collected and counted in 9 mL scintillation fluid. A 50 $\mu$l aliquot of the organic (bottom) phase is removed, dried in a scintillation vial and counted in 7 mL scintillation fluid.

The ratio of DPM in the aqueous phase aliquot (total inositol phosphates) to the DPM in the 50 $\mu$l organic phase aliquot (total [$^3$H]inositol incorporated) is calculated for each sample. Data are expressed as a percent of agonist-induced accumulation of [$^3$H]-inositol phosphates over basal levels. The ratios in the presence of test compound and/or standards are compared to the ratios for control samples (i.e. no stimulating agonist).

Dose-response graphs are constructed and the ability of the test compounds to inhibit tachykinin-induced phosphatidyinositol turnover determined with the aid of a computer program. Data is expressed as percent stimulation of total inositol phosphate accumulation over basal levels and normalized to the maximum response produced by substance P. Schild analysis is performed using dose response curves to obtain a value indicative of the strength of a competitive antagonist and is expressed as the $pA_2$, which is the negative logarithm of the molar concentration of antagonist which reduces the effect of a dose of agonist to one-half of that expected at the dose of agonist. When the slope of the lines obtained by a Schild analysis are not significantly different from one (1) the compound is acting as a competitive antagonist.

EXAMPLE E
Evaluation of $H_1$ (or $NK_1$) antagonism in vivo

One skilled in the art can determine that the compounds of the present invention mediate the immediate hypersensitivity response in vivo by evaluating the ability of the compounds to inhibit the formation of histamine (or substance P) induced wheals in guinea pigs. Animals are anesthetized with pentobarbital (i.p.). Dorsal skin is shaved and intradermal injections of histamine (or substance P) are given in the shaved area at appropriate times after the administration of the test compounds. Doses, routes, and times of administration may vary according to experimental design. The design of such experiments is well known and appreciated in the art. Immediately after the intradermal challenges, the animal is given an intravenous injection of 1% Evan's blue dye to make the wheals visible. At an appropriate time after the challenge the animals are sacrificed by $CO_2$ inhalation. The skin is removed and the diameter of each wheal is measured in two perpendicular directions.

The wheal response is used an the index of the edema response. The percent of inhibition of the wheal response is calculated by comparing the drug-treated group to a vehicle treated group. Linear regression of the dose-response inhibition curve is used to determine an $ED_{50}$ value, expressed in mg/kg.

EXAMPLE F
Evaluation of $NK_1$ antagonism in vivo

One skilled in the art can also determine that the compounds of the present invention are $NK_1$ receptor antagonists in vivo by evaluating the compound's ability to inhibit substance P-induced plasma protein extravasation in guinea pig trachea. Substance P-induced protein leakage through postcapillary venules is assessed by measuring Evans Blue dye accumulation in guinea pig trachea. Animals are anesthetized with pentobarbitol then injected with Evans Blue dye (20 mg/kg, i.v., prepared in 0.9% sodium chloride solution). One minute after dye administration, the antagonist is administered (i.v.) followed by substance P (0.3 mmole/kg, i.v.) and, after 5 min, excess dye removed from the circulation by transcardiac perfusion with 50 ml 0.9% sodium chloride solution. The trachea and primary bronchi are removed, blotted dry and weighed.

Dye quantitation is performed spectrophotometrically (620 nm) after extracting tissues in formamide for 24 hr at 50° C. Values are subtracted from background (dye only, no agonist). $ED_{50}$ (dose of compound which inhibits substance P-induced plasma protein extravasation by 50%) is calculated from linear regression analysis.

What is claimed is:

1. A compound, including enantiomers, stereoisomers, rotomers and tautomers of said compound and pharmaceutically acceptable salts, solvates or derivatives thereof, with said compound having the general structure shown in the formula:

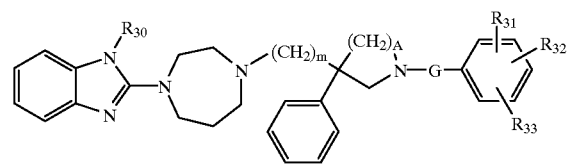

wherein m is 2 or 3;

A is 1 or 2;

G is —C(O)—, —C(O)—CH$_2$—, or —SO$_2$—;

R$_{30}$ is selected from the group consisting of:

—C$_5$–C$_8$ alkyl, —(CH$_2$)$_p$CF$_3$, vinyl,

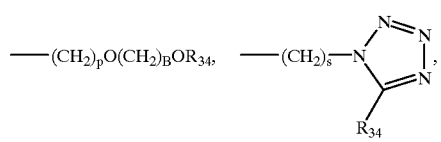

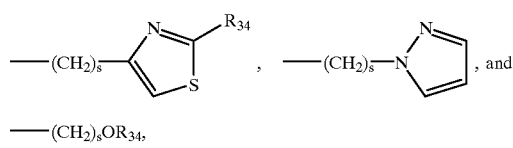

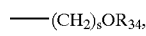

wherein p is an integer from 1 to 4;

B is an integer from 1 to 4;

D is an integer from 1 to 4;

s is an integer from 1 to 4; and

R$_{34}$ is C$_1$–C$_4$ alkyl;

R$_{31}$ and R$_{32}$ are the same or different and are independently selected from hydrogen or C$_1$–C$_4$ alkoxy; and R$_{33}$ is selected from the group consisting of:

hydrogen, C$_1$–C$_4$ alkoxy,

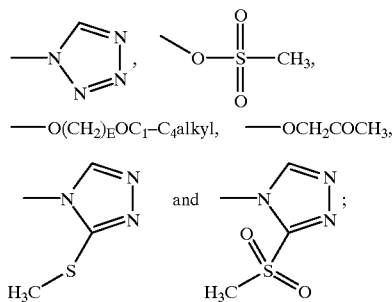

wherein

E is an integer from 2 to 4.

2. The compound as set forth in claim 1 which is 1-((R)-3-(2-(4-(1-(2-cyclopropylmethoxyethyl)-1H-benzoimidazol-2-yl)-(1,4)diazepan-1-yl)-ethyl)-3-phenyl-pyrrolidin-1-yl)-1-(2-methoxy-5-tetrazol-1-yl-phenyl)-methanone having the formula:

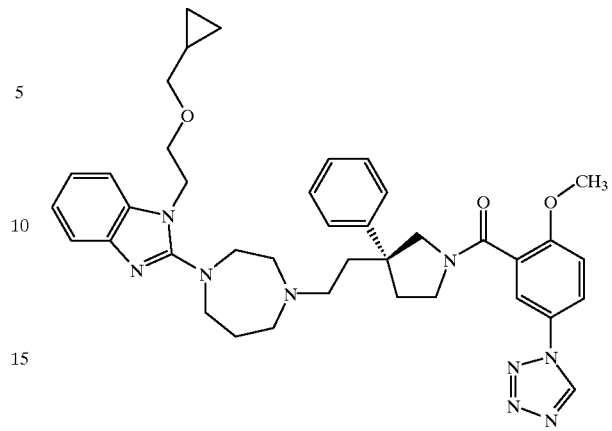

or a pharmaceutically acceptable acid addition salt thereof.

3. The compound as set forth in claim 1 which is 1-((R)-3-(2-(4-(1-cyclopropylmethyl-1H-benzoimidazol-2-yl)-(1,4)diazepan-1-yl)-ethyl)-3-phenyl-pyrrolidin-1-yl)-1-(2-methoxy-5-tetrazol-1-yl-phenyl)-methanone having the formula:

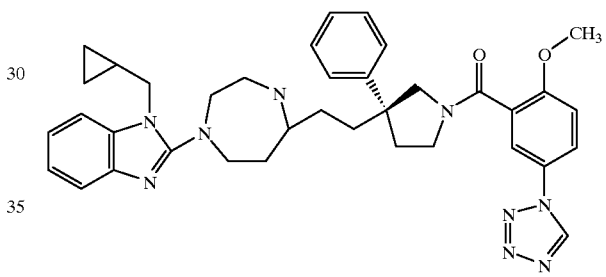

or a pharmaceutically acceptable acid addition salt thereof.

4. The compound as set forth in claim 1 which is 1-(2-methoxy-5-tetrazol-1-yl-phenyl)-1-((R)-3-(2-(4-(1-(2-(5-methyl-tetrazol-1-yl)-ethyl)-1H-benzoimidazol-2-yl)-(1,4)diazepan-1-yl)-ethyl)-3-phenyl-pyrrolidin-1-yl)-methanone having the formula:

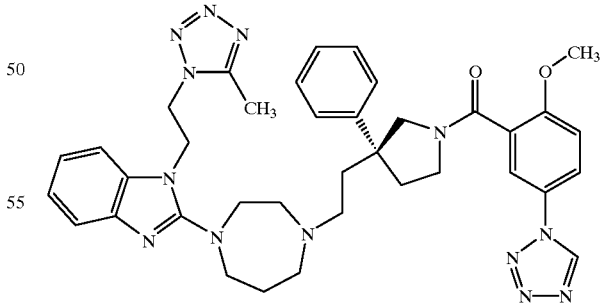

or a pharmaceutically acceptable acid addition salt thereof.

5. The compound as set forth in claim 1 which is 1-((R)-3-(2-(4-(1-(2-(2-methoxy-ethoxy)ethyl)-1H-benzoimidazol-2-yl)-(1,4)diazepan-1-yl)-ethyl)-3-phenyl-pyrrolidin-1-yl)-1-(2-methoxy-5-tetrazol-1-yl-phenyl)-methanone having the formula:

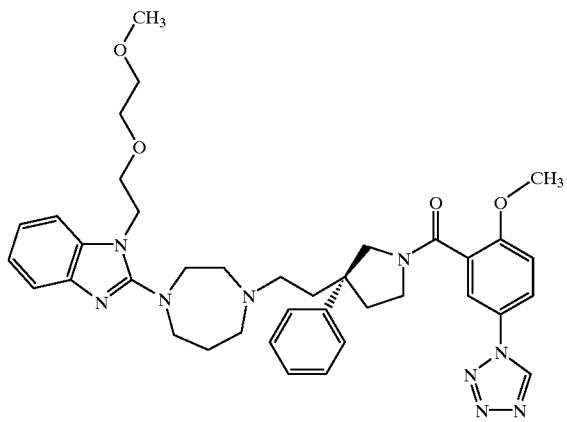

or a pharmaceutically acceptable acid addition salt thereof.

6. The compound as set forth in claim 1 which is 1-(2-methoxy-5-tetrazol-1-yl-phenyl)-1-((R)-3-(2-(4-(1-(2-methyl-thiazol-4-ylmethyl)-1H-benzoimidazol-2-yl)-(1,4)diazepan-1-yl)-ethyl)-3-phenyl-pyrrolidin-1-yl)-methanone having the formula:

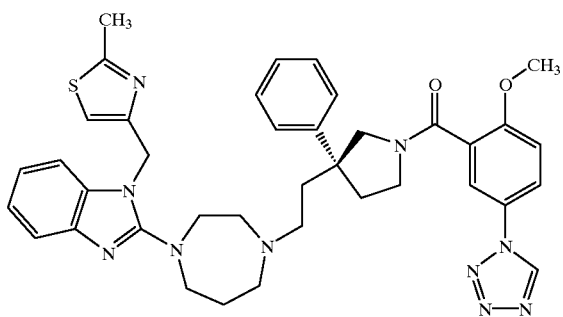

or a pharmaceutically acceptable acid addition salt thereof.

7. The compound as set forth in claim 1 which is 1-(2-methoxy-5-tetrazol-1-yl-phenyl)-1-((R)-3-phenyl-3-(2-(4-(1-(2-pyrazol-1-yl-ethyl)-1H-benzoimidazol-2-yl)-(1,4)diazepan-1-yl)-ethyl)-pyrrolidin-1-yl)-methanone having the formula:

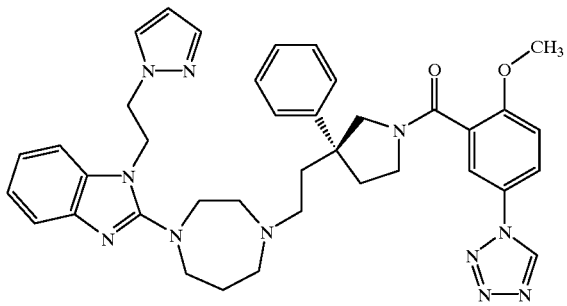

or a pharmaceutically acceptable acid addition salt thereof.

8. The compound as set forth in claim 1 which is methanesulfonic acid 3-(1-((R)-3-(2-(4-(1-(2-ethoxy-ethyl)-1H-berizoimidazol-2-yl)-(1,4)diazepan-1-yl)-ethyl)-3-phenyl-pyrrolidin-1-yl)-methanoyl)-4-methoxy-phenyl ester having the formula:

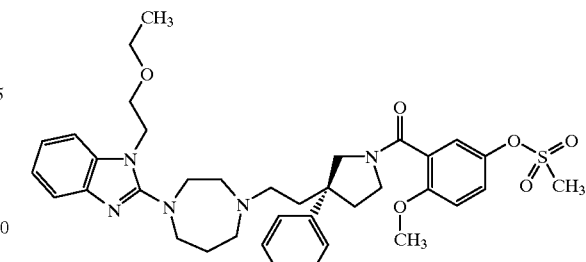

or a pharmaceutically acceptable acid addition salt thereof.

9. The compound as set forth in claim 1 which is 1-((R)-3-(2-(4-(1-(2-ethoxy-ethyl)-1H-benzoimidazol-2-yl)-(1,4)diazepan-1-yl)-ethyl)-3-phenyl-pyrrolidin-1-yl)-1-(2-methoxy-5-(2-methoxy-ethoxy)-phenyl)-methanone having the formula:

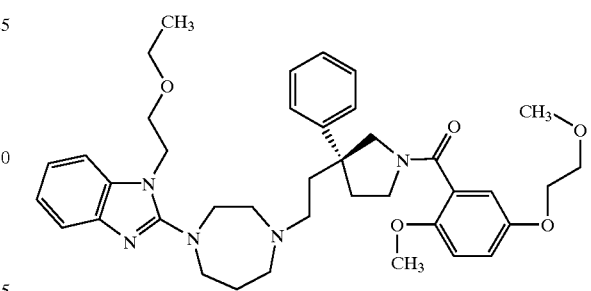

or a pharmaceutically acceptable acid addition salt thereof.

10. The compound as set forth in claim 1 which is 1-(2-methoxy-5-tetrazol-1-yl-phenyl)-1-((R)-3-(2-)4-(1-pentyl-1H-benzoimidazol-2-yl)-(1,4)diazepan-1-yl)-ethyl)-3-phenyl-pyrrolidin-1-yl)-methanone having the formula:

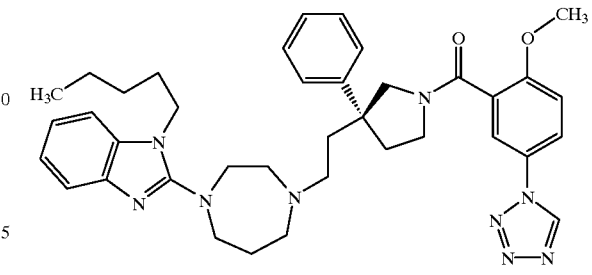

or a pharmaceutically acceptable acid addition salt thereof.

11. The compound as set forth in claim 1 which is 1-(3-(1-((R)-3-(2-(4-(1-(2-ethoxy-ethyl)-1H-benzoimidazol-2-yl)-(1,4)diazepan-1-yl)-ethyl)-3-phenyl-pyrrolidin-1-yl)methanoyl)-4-methoxy-phenoxy)-propan-2-one having the formula:

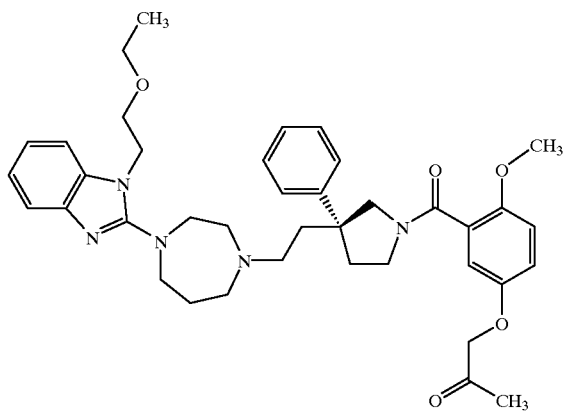

or a pharmaceutically acceptable acid addition salt thereof.

12. The compound as set forth in claim 1 which is 1-(2-methoxy-5-tetrazol-1-yl-phenyl)-1-((R)-3-phenyl-3-(2-(4-(1-(2,2,2-trifluoro-ethyl)-H-benzoimidazol-2-yl)-(1,4)diazepan-1-yl)-ethyl)-pyrrolidin-1-yl)-methanone having the formula:

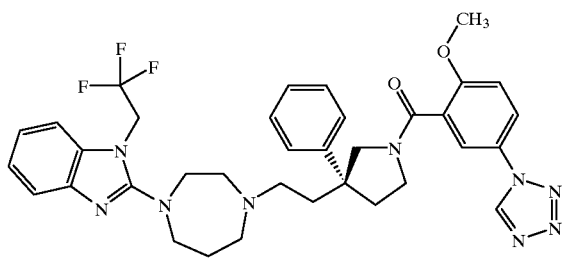

or a pharmaceutically acceptable acid addition salt thereof.

13. The compound as set forth in claim 1 which is 1-(2-methoxy-5-tetrazol-1-yl-phenyl)-1-((R)-3-phenyl-3-(2-(4-(1-(4,4,4-trifluoro-butyl)-1H-benzoimidazol-2-yl)-(1,4)diazepan-1-yl)-ethyl)-pyrrolidin-1-yl)-methanone having the formula:

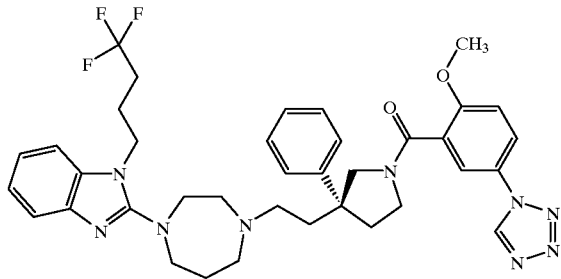

or a pharmaceutically acceptable acid addition salt thereof.

14. The compound as set forth in claim 1 which is 1-(2-methoxy-5-tetrazol-1-yl-phenyl)-1-((R)-3-phenyl-3-(2-(4-(1-vinyl-1H-benzoimidazol-2-yl)-(1,4)diazepan-1-yl(-ethyl)-pyrrolidin-1-yl)-methanone having the formula:

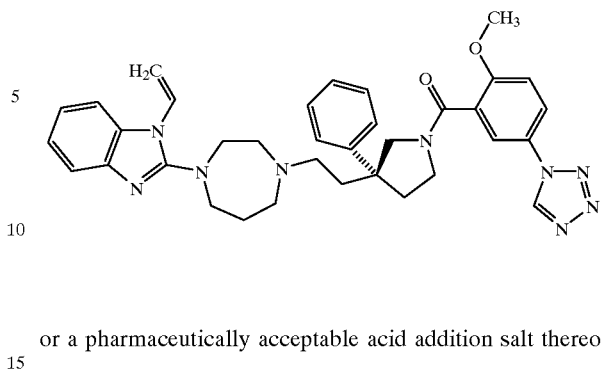

or a pharmaceutically acceptable acid addition salt thereof.

15. The compound as set forth in claim 1 which is methanesulfonic acid 4-(1-((R)-3-(2-(4-(1-2(ethoxy-ethyl)-1H-benzoimidazol-2-yl)-(1,4)diazepan-1-yl)-ethyl)-3-phenyl-pyrrolidin-1-yl)-methanoyl)-2,6-dimethoxy-phenyl ester hydrochloride having the formula:

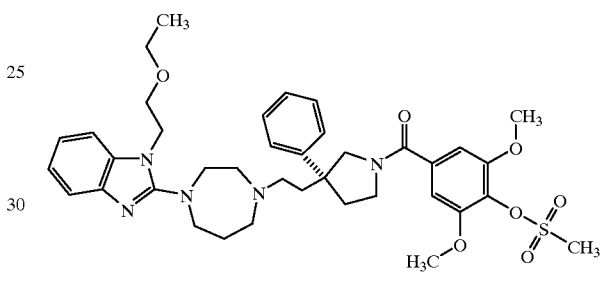

or a pharmaceutically acceptable acid addition salt thereof.

16. The compound as set forth in claim 1 which is 1-((R)-3-(2-(4-(1-(2-ethoxy-ethyl)-1H-benzoimidazol-2-yl)-(1,4)diazepan-1-yl)-ethyl)-3-phenyl-pyrrolidin-1-yl)-1-(2-methoxy-5-(3-methylsulfanyl-(1,2,4)triazol-4-yl)-phenyl)-methanone having the formula:

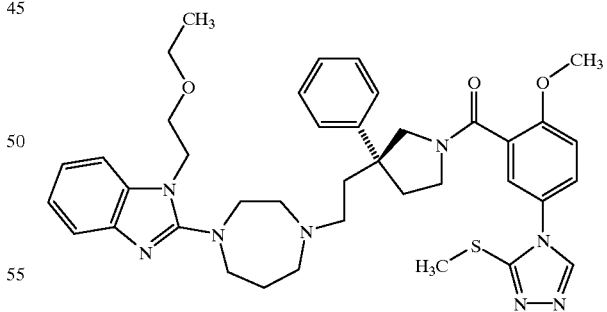

or a pharmaceutically acceptable acid addition salt thereof.

17. The compound as set forth in claim 1 which is 1-((R)-3-(2-(4-(1-(2-ethoxy-ethyl)-1H-benzoimidazol-2-yl)-(1,4)diazepan-1-yl)-ethyl)-3-phenyl-pyrrolidin-1-yl)-1-(5-(3-methanesulfonyl-(1,2,4)triazol-4-yl)-2-methoxy-phenyl)-methanone having the formula:

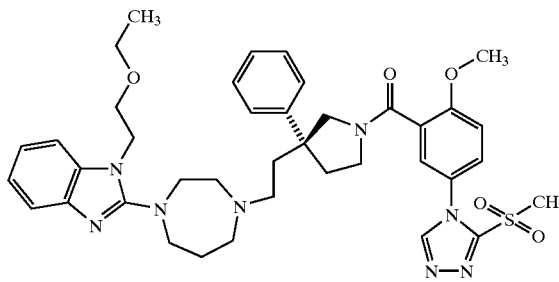

or a pharmaceutically acceptable acid addition salt thereof.

18. The compound as set forth in claim 1 which is 2-(4-(2-((R)-1-(2,5-dimethoxy-benzenesulfonyl)-3-phenyl-pyrrolidin-3-yl)-ethyl)-(1,4)dizaepan-1-yl)-1-(2-ethoxy-ethyl)-1H-benzoimidazole hydrochloride having the formula:

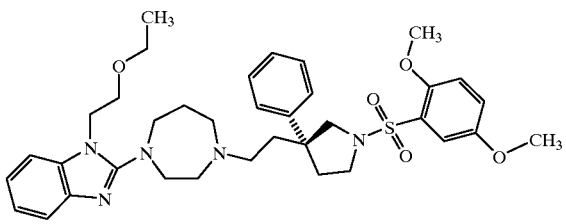

or a pharmaceutically acceptable acid addition salt thereof.

19. The compound as set forth in claim 1 which is 1-(3-(2-(4-(1-(2-ethoxy-ethyl)-1H-benzoimidazol-2-yl)-(1,4)diazepan-1-yl)-ethyl)-3-phenyl-azetidin-1-yl)-2-(3,4,5-trimethoxy-phenyl)-ethanone hydrochloride having the formula:

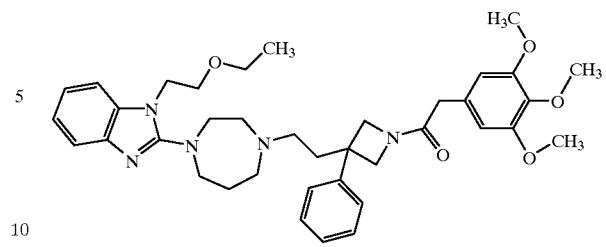

or a pharmaceutically acceptable acid addition salt thereof.

20. A pharmaceutical composition comprising a compound of claim 1 and a pharmaceutically acceptable carrier.

21. A method for treating allergic rhinitis in a patient in need thereof comprising administering to said patient a therapeutically effective amount of a compound of claim 1.

22. A method for treating asthma in a patient in need thereof comprising administering to said patient a therapeutically effective amount of a compound of claim 1.

23. A method for treating emesis in a patient in need thereof comprising administering to said patient a therapeutically effective amount of a compound of claim 1.

24. A method for treating uieitis in a patient in need thereof comprising administering to said patient a therapeutically effective amount of a compound of claim 1.

25. A method for treating allergic conjuctivitis in a patient in need thereof comprising administering to said patient a therapeutically effective amount of a compound of claim 1.

26. A method for treating ophthalmic allergies in a patient in need thereof comprising administering to said patient a therapeutically effective amount of a compound of claim 1.

27. A method for treating inflammatory bowel disease in a patient in need thereof comprising administering to said patient a therapeutically effective amount of a compound of claim 1.

* * * * *